(12) United States Patent
Kotian et al.

(10) Patent No.: US 10,562,850 B2
(45) Date of Patent: Feb. 18, 2020

(54) HUMAN PLASMA KALLIKREIN INHIBITORS

(71) Applicant: BioCryst Pharmaceuticals, Inc., Durham, NC (US)

(72) Inventors: Pravin L. Kotian, Hoover, AL (US); Yarlagadda S. Babu, Birmingham, AL (US); V. Satish Kumar, Birmingham, AL (US); Weihe Zhang, Vestavia, AL (US); Lakshminarayana Vogeti, Lawrence, KS (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 15/764,071

(22) PCT Filed: Sep. 30, 2016

(86) PCT No.: PCT/US2016/054619
§ 371 (c)(1),
(2) Date: Mar. 28, 2018

(87) PCT Pub. No.: WO2017/059178
PCT Pub. Date: Apr. 6, 2017

(65) Prior Publication Data
US 2018/0362458 A1    Dec. 20, 2018

Related U.S. Application Data

(60) Provisional application No. 62/235,754, filed on Oct. 1, 2015.

(51) Int. Cl.
| | |
|---|---|
| *C07D 401/14* | (2006.01) |
| *C07D 207/12* | (2006.01) |
| *A61K 31/444* | (2006.01) |
| *A61K 31/40* | (2006.01) |
| *C07D 207/16* | (2006.01) |
| *C07D 401/12* | (2006.01) |
| *C07D 409/14* | (2006.01) |
| *C07D 207/24* | (2006.01) |
| *A61P 17/00* | (2006.01) |

(52) U.S. Cl.
CPC ............ *C07D 207/16* (2013.01); *A61P 17/00* (2018.01); *C07D 207/24* (2013.01); *C07D 401/12* (2013.01); *C07D 401/14* (2013.01); *C07D 409/14* (2013.01)

(58) Field of Classification Search
CPC .. C07D 401/14; C07D 207/12; A61K 31/444; A61K 31/40
USPC ...... 546/256, 276.4; 548/538; 514/333, 343, 514/423
See application file for complete search history.

(56) References Cited

U.S. PATENT DOCUMENTS

| | | | |
|---|---|---|---|
| 7,407,972 B2 | 8/2008 | Edmunds | |
| 8,129,373 B2 | 3/2012 | Tsaklakidis et al. | |
| 2005/0107361 A1 | 5/2005 | Han et al. | |
| 2005/0267118 A1 | 12/2005 | Edmunds | |
| 2014/0221338 A1 | 8/2014 | Pinto et al. | |
| 2016/0039752 A1 | 2/2016 | Allan et al. | |

FOREIGN PATENT DOCUMENTS

| | | |
|---|---|---|
| CA | 2977993 A1 | 9/2016 |
| EP | 1217000 A1 | 6/2002 |
| EP | 1427415 A1 | 6/2004 |
| EP | 3095786 A1 | 11/2016 |
| EP | 3224256 A1 | 10/2017 |
| WO | WO-98/06694 A1 | 2/1998 |
| WO | WO-2004/083174 A2 | 9/2004 |
| WO | WO-2015/107724 A1 | 7/2015 |
| WO | WO-2015/134998 A1 | 9/2015 |

OTHER PUBLICATIONS

International Search Report and Written Opinion for International Application No. PCT/US16/54619 dated Jan. 24, 2017.
Pinto et al., "Factor Xa inhibitors: next-generation antithrombotic agents," J Med Chem, 53(17):6243-6274 (2010).
Van Huis et al., "Exploration of 4, 4-disubstituted pyrrolidine-1, 2-dicarboxamides as potent, orally active Factor Xa inhibitors with extended duration of action," Bioorg Med Chem, 17(6):2501-2511 (2009).
Extended European Search Report for EP Application No. 16852664.8 dated Feb. 26, 2019.
Maleev et al., "New (S)-proline derivatives as catalysts for the enantioselective aldol reaction," Russian Chemical Bulletin, 58(9):1903-1907 (2009).
Vishnumaya et al., "Highly efficient small organic molecules for enantioselective direct aldol reaction in organic and aqueous media," Journal of Organic Chemistry, 74(11):4289-4297 (2009).

(Continued)

*Primary Examiner* — Charanjit Aulakh
(74) *Attorney, Agent, or Firm* — Dana M. Gordon; Foley Hoag LLP

(57) ABSTRACT

Disclosed are compounds of formula I, and pharmaceutically acceptable salts thereof. The compounds are inhibitors of plasma kallikrein. Also provided are pharmaceutical compositions comprising at least one compound of the invention, and methods involving use of the compounds and compositions of the invention in the treatment and prevention of diseases and conditions characterized by unwanted plasma kallikrein activity.

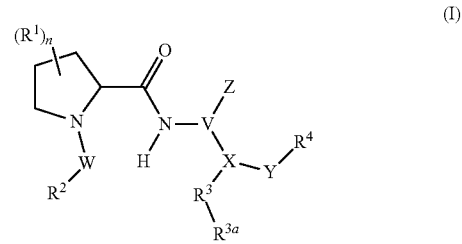

23 Claims, No Drawings

(56) References Cited

OTHER PUBLICATIONS

CAS Registry No. 1100143-53-0 (Entered STN: Feb. 3, 2009).
CAS Registry No. 1385222-72-9 (Entered STN: Aug. 1, 2012).
CAS Registry No. 1623094-22-3 (Entered STN: Sep. 17, 2014).
CAS Registry No. 1623318-56-8 (Entered STN: Sep. 18, 2014).
CAS Registry No. 1648027-12-6 (Entered STN: Feb. 16, 2015).
CAS Registry No. 1786248-79-0 (Entered STN: Jun. 22, 2015).
CAS Registry No. 346447-61-8 (Entered STN: Jul. 17, 2001).

HUMAN PLASMA KALLIKREIN INHIBITORS

CROSS-REFERENCES TO RELATED APPLICATIONS

This application is the U.S. national stage of International Patent Application No. PCT/US2016/054619, filed Sep. 30, 2016, which claims the benefit of priority to U.S. Provisional Patent Application Ser. No. 62/235,754, filed Oct. 1, 2015, the contents of both of which are hereby incorporated by reference in their entireties.

BACKGROUND OF THE INVENTION

Serine proteases make up the largest and most extensively studied group of proteolytic enzymes. Their critical roles in physiological processes extend over such diverse areas as blood coagulation, fibrinolysis, complement activation, reproduction, digestion, and the release of physiologically active peptides. Many of these vital processes begin with cleavage of a single peptide bond or a few peptide bonds in precursor protein or peptides. Sequential limited proteolytic reactions or cascades are involved in blood clotting, fibrinolysis, and complement activation. The biological signals to start these cascades can be controlled and amplified as well. Similarly, controlled proteolysis can shut down or inactivate proteins or peptides through single bond cleavages.

Kallikreins are a subgroup of serine proteases. In humans, plasma kallikrein (KLKB1) has no known homologue, while tissue kallikrein-related peptidases (KLKs) encode a family of fifteen closely related serine proteases. Plasma kallikrein participates in a number of pathways relating to the intrinsic pathway of coagulation, inflammation, and the complement system.

Coagulation is the process by which blood forms clots, for example to stop bleeding. The physiology of coagulation is somewhat complex insofar as it includes two separate initial pathways, which converge into a final common pathway leading to clot formation. In the final common pathway, prothrombin is converted into thrombin, which in turn converts fibrinogen into fibrin, the latter being the principal building block of cross-linked fibrin polymers which form a hemostatic plug. Of the two initial pathways upstream of the final common pathway, one is known as the contact activation or intrinsic pathway, and the other is known as the tissue factor or extrinsic pathway.

The intrinsic pathway begins with formation of a primary complex on collagen by high-molecular-weight kininogen (HMWK), prekallikrein, and FXII (Factor XII; Hageman factor). Prekallikrein is converted to kallikrein, and FXII is activated to become FXIIa. FXIIa then converts Factor XI (FXI) into FXIa, and FXIa in turn activates Factor IX (FIX), which with its co-factor FVIIIa form the "tenase" complex, which activates Factor X (FX) to FXa. It is FXa which is responsible for the conversion of prothrombin into thrombin within the final common pathway.

Prekallikrein, the inactive precursor of plasma kallikrein, is synthesized in the liver and circulates in the plasma bound to HMWK or as a free zymogen. Prekallikrein is cleaved by activated factor XII (FXIIa) to release activated plasma kallikrein (PK). Activated plasma kallikrein displays endopeptidase activity towards peptide bonds after arginine (preferred) and lysine. PK then generates additional FXIIa in a feedback loop which in turn activates factor XI (FXI) to FXIa to connect to the common pathway. Although the initial activation of the intrinsic pathway is through a small amount of FXIIa activating a small amount of PK, it is the subsequent feedback activation of FXII by PK that controls the extent of activation of the intrinsic pathway and hence downstream coagulation. Hathaway, W. E., et al. (1965) Blood 26:521-32.

Activated plasma kallikrein also cleaves HMWK to release the potent vasodilator peptide bradykinin. It is also able to cleave a number of inactive precursor proteins to generate active products, such as plasmin (from plasminogen) and urokinase (from prourokinase). Plasmin, a regulator of coagulation, proteolytically cleaves fibrin into fibrin degradation products that inhibit excessive fibrin formation.

Patients who have suffered acute myocardial infarction (MI) show clinical evidence of being in a hypercoagulable (clot-promoting) state. This hypercoagulability is paradoxically additionally aggravated in those receiving fibrinolytic therapy. Increased generation of thrombin, as measured by thrombin-antithrombin III (TAT) levels, is observed in patients undergoing such treatment compared to the already high levels observed in those receiving heparin alone. Hoffmeister, H. M. et al. (1998) Circulation 98:2527-33. The increase in thrombin has been proposed to result from plasmin-mediated activation of the intrinsic pathway by direct activation of FXII by plasmin.

Not only does the fibrinolysis-induced hypercoagulability lead to increased rates of reocclusion, but it is also probably responsible, at least in part, for failure to achieve complete fibrinolysis of the clot (thrombus), a major shortcoming of fibrinolytic therapy (Keeley, E. C. et al. (2003) Lancet 361: 13-20). Another problem in fibrinolytic therapy is the accompanying elevated risk of intracranial hemorrhage. Menon, V. et al. (2004) Chest 126:549S-575S; Fibrinolytic Therapy Trialists' Collaborative Group (1994) Lancet 343: 311-22. Hence, an adjunctive anti-coagulant therapy that does not increase the risk of bleeding, but inhibits the formation of new thrombin, would be greatly beneficial.

Therefore, a need exists to develop additional inhibitors of PK that can tip the balance of fibrinolysis/thrombosis at the occluding thrombus toward dissolution, thereby promoting reperfusion and attenuating the hypercoagulable state, thus preventing the thrombus from reforming and reoccluding the vessel.

SUMMARY OF THE INVENTION

In certain aspects, the invention provides compounds of formula (I), and pharmaceutically acceptable salts thereof:

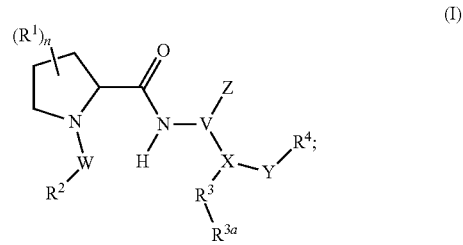

wherein, independently for each occurrence:
$R^1$ represents —OH, —$OR^c$, —$NH_2$, —$NHR^c$, —$NR^cR^d$, alkyl, aryl, aralkyl, heteroaryl, heteroaralkyl, halo, haloalkyl, cycloalkyl, (cycloalkyl)alkyl, —$C(O)R^c$, —C(O)OH, —$C(O)OR^c$, —$OC(O)R^c$, —$C(O)NH_2$, —$C(O)NHR^c$, —$C(O)NR^cR^d$, —$NHC(O)R^c$, or —$NR^cC(O)R^d$; or two geminal occurrences of $R^1$ taken together with the carbon to which they are attached represent —C(O)—; or two vicinal or geminal occurrences of $R^1$ taken together form an optionally substituted fused or spirocyclic carbocyclic or heterocyclic ring;

W is a bond, —C(O)NH—, —C(O)N($R^c$)—, —C(O)O—, —CH$_2$—, or —C(O)—;

$R^2$ represents optionally substituted aryl, heteroaryl, aralkyl, heteroaralkyl, cycloalkyl, heterocycloalkyl, (cycloalkyl)alkyl), or (heterocycloalkyl)alkyl;

V represents optionally substituted aryl or heteroaryl;

Z is absent or represents one or more substituents independently selected from the group consisting of halo, haloalkyl, —NO$_2$, —CN, —C(O)$R^c$, —C(O)OH, —C(O)O$R^c$, —OC(O)$R^c$, —C(O)NH$_2$, —C(O)NH$R^c$, —C(O)N$R^cR^d$, —NHC(O)$R^c$, —N($R^c$)C(O)$R^d$, —OS(O)$_p$($R^c$), —NHS(O)$_p$($R^c$), and —N$R^c$S(O)$_p$($R^c$);

X represents —C(NH$_2$)—, —C(NH($R^c$))—, —C(N$R^cR^d$)—, —C(NHS(O)$_p$$R^c$)—, —C(NHC(O)$R^c$)—, —C(NHC(O)NH$_2$)—, —C(NHC(O)NH$R^c$)—, —C(NHC(O)N$R^cR^d$)—, —C(OH)—, —C(O(alkyl))-, —C(N$_3$)—, —C(CN)—, —C(NO$_2$)—, —C(S(O)$_n$$R^a$)—, —C[—C(=O)$R^c$]—, —C[—C(=O)N$R^cR^d$]—, —C[—C(=O)S$R^c$]—, —C[—S(O)$R^c$]—, —C[—S(O)$_2R^c$]—, —C[S(O)(O$R^c$)]—, —C[—S(O)$_2$(O$R^c$)]—, —C[—SO$_2$N$R^cR^d$]—, —C(halogen)-, —C(alkyl), —C((cycloalkyl)alkyl), —C(alkenyl)-, —C(alkynyl)-, or —C(aralkyl)-;

$R^3$ represents optionally substituted aryl, heteroaryl, cycloalkyl, or heterocycloalkyl;

$R^{3a}$ is absent or represents one or more substituents independently selected from the group consisting of halo, hydroxy, alkyl, —CF$_3$, —OCF$_3$, alkoxy, aryl, heteroaryl, aryloxy, amino, aminoalkyl, —C(O)NH$_2$, cyano, —NHC(O)alkyl, —SO$_2$alkyl, —SO$_2$NH$_2$, cycloalkyl, —(CH$_2$)$_r$O$R^a$, —NO$_2$, —(CH$_2$)$_r$N$R^aR^b$, —(CH$_2$)$_r$C(O)$R^a$, —N$R^a$C(O)$R^b$, —C(O)N$R^cR^d$, —N$R^a$C(O)N$R^cR^d$, —C(=N$R^a$)N$R^cR^d$, —NHC(=N$R^a$)N$R^cR^d$, —N$R^aR^b$, —SO$_2$N$R^cR^d$, —N$R^a$SO$_2$N$R^cR^d$, —N$R^a$SO$_2$alkyl, —N$R^a$SO$_2$$R^a$, —S(O)$_p$$R^a$, —(CF$_2$)$_r$CF$_3$, —NHCH$_2R^a$, —OCH$_2R^a$, —SCH$_2R^a$, —NH(CH$_2$)$_2$(CH$_2$)$_r$$R^a$, —O(CH$_2$)$_2$(CH$_2$)$_r$$R^a$, or —S(CH$_2$)$_2$(CH$_2$)$_r$$R^a$;

Y represents a bond; or —Y—$R^4$ represents optionally substituted -alkylene-$R^4$, —CH$_2$C(O)—$R^4$, —CH$_2$NH—$R^4$, —CH$_2$N(alkyl)-$R^4$, —C$R^aR^b$—$R^4$, —NH—$R^4$, —NHCH$_2$—$R^4$, —NHC(O)—$R^4$, —N(alkyl)-$R^4$, —N(alkyl)CH$_2$—$R^4$, —N((CH$_2$)$_2$OH)—$R^4$, —N((cycloalkyl)alkyl)$R^4$, -heterocyclyl-$R^4$, —O$R^4$, —OCH$_2$—$R^4$, —OC(O)—$R^4$, —OC(O)N$R^aR^b$, —SCH$_2$R4, or —S$R^4$;

$R^4$ represents hydrogen, hydroxy, optionally substituted alkyl, cycloalkyl, (heterocycloalkyl)alkyl, (cycloalkyl)alkyl, —CH$_2$OH, —CH(alkyl)OH, —CH(NH$_2$)CH(alkyl)$_2$, aryl, aralkyl, heteroaryl, heteroaralkyl, —CH$_2$S(alkyl), amino, or cyano; or —(C$R^aR^b$)$_r$(C$R^aR^b$)$_p$— fused to the 4-position of the ring bearing Z to form a 5- to 7-membered heterocyclic ring with optional substituents; or, when $R^3$ is phenyl, $R^4$ can represent —N$R^a$— fused to the position ortho to X on that phenyl;

each $R^a$ and $R^b$ is independently H, alkyl, alkenyl, alkynyl, aralkyl, (cycloalkyl)alkyl, —C(=O)$R^c$, —C(=O)O$R^c$, —C(=O)N$R^cR^d$, —C(=O)S$R^c$, —S(O)$R^c$, —S(O)$_2R^c$, —S(O)(O$R^c$), or —SO$_2$N$R^cR^d$;

$R^c$ and $R^d$ represent, independently for each occurrence, optionally substituted alkyl, alkenyl, alkynyl, haloalkyl, aryl, aralkyl, heteroaryl, heteroaralkyl, cycloalkyl, (cycloalkyl)alkyl, heterocycloalkyl, (heterocycloalkyl)alkyl, —C(O)alkyl, or —S(O)$_p$(alkyl); or $R^c$ and $R^d$ can be taken together to form an optionally substituted heterocyclic ring;

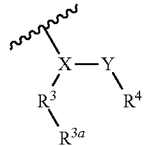

can represent

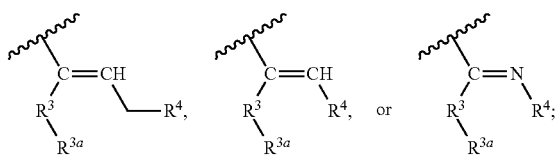

r is 0, 1, 2, or 3;
n is an integer from 0 to 6; and
p is 0, 1, or 2.

In certain aspects, the invention provides a pharmaceutical composition, comprising a compound of the invention, or a pharmaceutically acceptable salt thereof; and a pharmaceutically acceptable carrier.

In certain aspects, the invention provides a method of treating or preventing a disease or condition characterized by unwanted plasma kallikrein activity. The method comprises the step of administering to a subject in need thereof a therapeutically effective amount of a compound of the invention, or a pharmaceutically acceptable salt thereof, thereby treating or preventing the disease or condition characterized by unwanted plasma kallikrein activity. In one embodiment, the disease or condition characterized by unwanted plasma kallikrein activity is selected from the group consisting of stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

DETAILED DESCRIPTION

Inhibitors of plasma kallikrein have been reported and are useful in therapeutic methods and compositions suitable for use in eliminating or reducing various forms of ischemia, including but not limited to perioperative blood loss, cerebral ischemia, the onset of systemic inflammatory response, and/or reperfusion injury, e.g., reperfusion injury associated with cerebral ischemia or a focal brain ischemia. Perioperative blood loss results from invasive surgical procedures that lead to contact activation of complement components and the coagulation/fibrinolysis systems. Kallikrein inhibitors can be used to reduce or prevent perioperative blood loss and a systemic inflammatory response in patients subjected to invasive surgical procedures, especially cardiothoracic surgeries. Kallikrein inhibitors can also be used to reduce or prevent cerebral ischemia and stroke, and/or reperfusion injury associated with cerebral ischemia. They can also prevent neurological and cognitive deficits associated with stroke, blood loss, and cerebral ischemia, e.g., events that are not associated with surgical intervention. Further examples of applications for kallikrein inhibitors include pediatric cardiac surgery, lung transplantation, total hip replacement, and orthotopic liver transplantation, to reduce or prevent stroke during these procedures, as well as to reduce or prevent stroke during coronary artery bypass grafting (CABG) and extracorporeal membrane oxygenation (ECMO).

Definitions

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium, and alternatively oxygen, nitrogen or sulfur.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ straight-chain alkyl group. In certain embodiments, the term "alkyl" refers to a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "cycloalkylalkyl" as used herein refers to an alkyl group substituted with one or more cycloalkyl groups. An example of cycloalkylalkyl is cyclohexylmethyl group.

The term "heterocyclyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group is optionally substituted by one or more substituents as described below.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

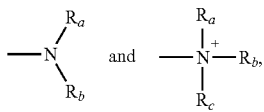

wherein $R_a$, $R_b$, and $R_c$ each independently represent a hydrogen, an alkyl, an alkenyl, $—(CH_2)_x—R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or $—(CH_2)_x—R^d$. In certain embodiments, the term "amino" refers to $—NH_2$.

The term "amido", as used herein, means —NHC(=O)—, wherein the amido group is bound to the parent molecular moiety through the nitrogen. Examples of amido include alkylamido such as $CH_3C(=O)N(H)—$ and $CH_3CH_2C(=O)N(H)—$.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

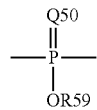

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

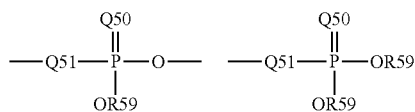

wherein Q50 and R59, each independently, are defined above, and Q51 represents O, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an —N$_3$ group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—.

The term "carboxy", as used herein, means a —CO$_2$H group.

The term "aryl" is a term of art and as used herein refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group. In certain embodiments, "aryl" has from 6 to 10 carbon atoms.

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH-CH_2-O-$) and vinyloxy (i.e., $CH_2=CH-O-$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si-$) group (i.e., (hydrocarbyl)$_3Si-$), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethyl silyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

The present invention provides compounds of Formula (I), or pharmaceutically acceptable salts thereof:

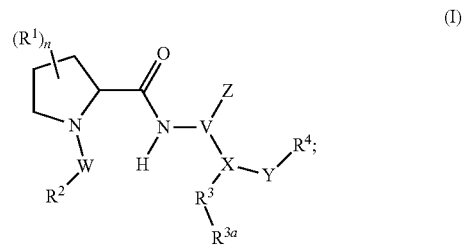

(I)

wherein, independently for each occurrence:

$R^1$ represents —OH, —OR$^c$, —NH$_2$, —NHR$^c$, —NR$^c$R$^d$, alkyl, aryl, aralkyl, heteroaryl, heteroaralkyl, halo, haloalkyl, cycloalkyl, (cycloalkyl)alkyl, —C(O)R$^c$, —C(O)OH, —C(O)OR$^c$, —OC(O)R$^c$, —C(O)NH$_2$, —C(O)NHR$^c$, —C(O)NR$^c$R$^d$, —NHC(O)R$^c$, or —NR$^c$C(O)R$^d$; or two geminal occurrences of R$^1$ taken together with the carbon to which they are attached represent —C(O)—; or two vicinal or geminal occurrences of R$^1$ taken together form an optionally substituted fused or spirocyclic carbocyclic or heterocyclic ring;

W is a bond, —C(O)NH—, —C(O)N(R$^c$)—, —C(O)O—, —CH$_2$—, or —C(O)—;

$R^2$ represents optionally substituted aryl, heteroaryl, aralkyl, heteroaralkyl, cycloalkyl, heterocycloalkyl, (cycloalkyl)alkyl), or (heterocycloalkyl)alkyl;

V represents optionally substituted aryl or heteroaryl;

Z is absent or represents one or more substituents independently selected from the group consisting of halo, haloalkyl, —NO$_2$, —CN, —C(O)R$^c$, —C(O)OH, —C(O)OR$^c$, —OC(O)R$^c$, —C(O)NH$_2$, —C(O)NHR$^c$, —C(O)NR$^c$R$^d$, —NHC(O)R$^c$, —N(R$^c$)C(O)R$^d$, —OS(O)$_p$(R$^c$), —NHS(O)$_p$(R$^c$), and —NR$^c$S(O)$_p$(R$^c$);

X represents —C(NH$_2$)—, —C(NH(R$^c$))—, —C(NR$^c$R$^d$)—, —C(NHS(O)$_p$R$^c$)—, —C(NHC(O)R$^c$)—, —C(NHC(O)NH$_2$)—, —C(NHC(O)NHR$^c$)—, —C(NHC(O)NR$^c$R$^d$)—, —C(OH)—, —C(O(alkyl))-, —C(N$_3$)—, —C(CN)—, —C(NO$_2$)—, —C(S(O)$_n$R$^a$)—, —C[—C(=O)R$^c$]—, —C[—C(=O)NR$^c$R$^d$]—, —C[—C(=O)SR$^c$]—, —C[—S(O)R$^c$]—, —C[—S(O)$_2$R$^c$]—, —C[S(O)(OR$^c$)]—, —C[—S(O)$_2$(OR$^c$)]—, —C[—SO$_2$NR$^c$R$^d$]—, —C(halogen)-, —C(alkyl), —C((cycloalkyl)alkyl), —C(alkenyl)-, —C(alkynyl)-, or —C(aralkyl)-;

$R^3$ represents optionally substituted aryl, heteroaryl, cycloalkyl, or heterocycloalkyl;

$R^{3a}$ is absent or represents one or more substituents independently selected from the group consisting of halo, hydroxy, alkyl, —CF$_3$, —OCF$_3$, alkoxy, aryl, heteroaryl, aryloxy, amino, aminoalkyl, —C(O)NH$_2$, cyano, —NHC(O)alkyl, —SO$_2$alkyl, —SO$_2$NH$_2$, cycloalkyl, —(CH$_2$)$_r$OR$^a$, —NO$_2$, —(CH$_2$)$_r$NR$^a$R$^b$, —(CH$_2$)$_r$C(O)R$^a$, —NR$^a$C(O)R$^b$, —C(O)NR$^d$, —NR$^a$C(O)NR$^c$R$^d$, —C(=NR$^a$)NR$^c$R$^d$, —NHC(=NR$^a$)NR$^c$R$^d$, —NR$^a$R$^b$, —SO$_2$NR$^c$R$^d$, —NR$^a$SO$_2$NR$^c$R$^d$, —NR$^a$SO$_2$alkyl, —NR$^a$SO$_2$R$^a$, —S(O)$_p$R$^a$, —(CF$_2$)$_r$CF$_3$, —NHCH$_2$R$^a$, —OCH$_2$R$^a$, —SCH$_2$R$^a$, —NH(CH$_2$)$_2$(CH$_2$)$_r$R$^a$, —O(CH$_2$)$_2$(CH$_2$)$_r$R$^a$, or —S(CH$_2$)$_2$(CH$_2$)$_r$R$^a$;

Y represents a bond; or —Y—R$^4$ represents optionally substituted -alkylene-R$^4$, —CH$_2$C(O)—R$^4$, —CH$_2$NH—R$^4$, —CH$_2$N(alkyl)-R$^4$, —CR$^a$R$^b$—R$^4$, —NH—R$^4$, —NHCH$_2$—R$^4$, —NHC(O)—R$^4$, —N(alkyl)-R$^4$, —N(alkyl)CH$_2$—R$^4$, —N((CH$_2$)$_2$OH)—R$^4$, —N((cycloalkyl)alkyl)R$^4$, -heterocyclyl-R$^4$, —OR$^4$, —OCH$_2$—R$^4$, —OC(O)—R$^4$, —OC(O)NR$^a$R$^b$, —SCH$_2$R4, or —SR$^4$;

R$^4$ represents hydrogen, hydroxy, optionally substituted alkyl, cycloalkyl, (heterocycloalkyl)alkyl, (cycloalkyl)alkyl, —CH$_2$OH, —CH(alkyl)OH, —CH(NH$_2$)CH(alkyl)$_2$, aryl, aralkyl, heteroaryl, heteroaralkyl, —CH$_2$S(alkyl), amino, or cyano; or —(CR$^a$R$^b$)$_r$(CR$^a$R$^b$)$_p$— fused to the 4-position of the ring bearing Z to form a 5- to 7-membered heterocyclic ring with optional substituents; or, when R$^3$ is phenyl, R$^4$ can represent —NR$^a$— fused to the position ortho to X on that phenyl;

each R$^a$ and R$^b$ is independently H, alkyl, alkenyl, alkynyl, aralkyl, (cycloalkyl)alkyl, —C(=O)R$^c$, —C(=O)OR$^c$, —C(=O)NR$^c$R$^d$, —C(=O)SR$^c$, —S(O)R$^c$, —S(O)$_2$R$^c$, —S(O)(OR$^c$), or —SO$_2$NR$^c$R$^d$;

R$^c$ and R$^d$ represent, independently for each occurrence, optionally substituted alkyl, alkenyl, alkynyl, haloalkyl, aryl, aralkyl, heteroaryl, heteroaralkyl, cycloalkyl, (cycloalkyl)alkyl, heterocycloalkyl, (heterocycloalkyl)alkyl, —C(O)alkyl, or —S(O)$_p$(alkyl); or R$^c$ and R$^d$ can be taken together to form an optionally substituted heterocyclic ring;

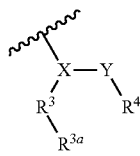

can represent

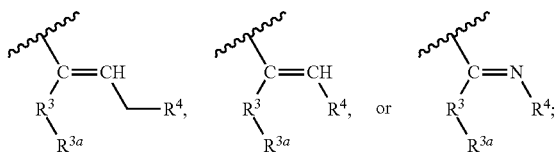

r is 0, 1, 2, or 3;
n is an integer from 0 to 6; and
p is 0, 1, or 2.

In certain embodiments, R$^1$ represents —OH, —OR$^c$, —NH$_2$, —NHR$^c$, —NR$^c$R$^d$, alkyl, aryl, heteroaryl, halo, haloalkyl, cycloalkyl, —OC(O)R$^c$, —NHC(O)R$^c$, or —NR$^c$C(O)R$^d$; or two geminal occurrences of R$^1$ taken together with the carbon to which they are attached represent —C(O)—; or two vicinal or geminal occurrences of R$^1$ taken together form an optionally substituted fused or spirocyclic carbocyclic or heterocyclic ring.

In certain embodiments, R$^1$ represents —OH, —OR$^c$, —NH$_2$, alkyl, aryl, halo, haloalkyl, cycloalkyl, or —OC(O)R$^c$.

In certain embodiments, n is 1.

In certain such embodiments, R$^1$ represents —OH or —OR$^c$.

In certain embodiments wherein n is 1, R$^1$ represents —OR$^c$, for example R$^1$ may represent —O((C$_1$-C$_6$)alkyl).

In certain embodiments wherein n is 1, R$^1$ represents —OC(O)R$^c$, for example R$^1$ may represent —OC(O)((C$_1$-C$_6$)alkyl).

In certain embodiments, R$^1$ represents —NH$_2$.

In certain embodiments, R$^1$ represents (C$_1$-C$_6$)alkyl.

In certain embodiments, n is 2.

In certain such embodiments, the two occurrences of R$^1$ are geminal, i.e., the two occurrences of R$^1$ are attached to the same carbon atom.

In certain such embodiments, one occurrence of R$^1$ represents —OH or —OR$^c$; and the other occurrence of R$^1$ represents aryl or heteroaryl.

Alternatively, in other certain such embodiments, one occurrence of R$^1$ represents —OH or —OR$^c$; and the other occurrence of R$^1$ represents haloalkyl.

In yet another alternative embodiment, both of the two geminal occurrences of R$^1$ are halo.

In certain embodiments, the two geminal occurrences of R$^1$ taken together with the carbon to which they are attached represent —C(O)—.

In certain embodiments wherein n is 2, the two occurrences of R$^1$ are vicinal, i.e., the two occurrences of R$^1$ are attached to two adjacent carbon atoms.

In certain such embodiments, the two vicinal occurrences of R$^1$ taken together form an optionally substituted fused carbocyclic ring.

In certain embodiments, n is 0.

In certain embodiments, W is —C(O)NH— or —C(O)N(R$^c$)—.

In certain such embodiments, R$^2$ represents optionally substituted aryl or heteroaryl.

In certain embodiments, R$^2$ represents aryl or heteroaryl, substituted by one or more substituents selected from the group consisting of —OH, halo, —NH$_2$, —NH((C$_1$-C$_6$)alkyl), —N((C$_1$-C$_6$)alkyl)$_2$, —CN, —NO$_2$, (C$_1$-C$_6$)alkyl, (C$_1$-C$_6$)haloalkyl, (C$_1$-C$_6$)alkoxy, —C(O)OH, —C(O)O(C$_1$-C$_6$)alkyl, —C(O)NH$_2$, —C(O)NH(C$_1$-C$_6$)alkyl, and —C(O)N((C$_1$-C$_6$)alkyl)$_2$.

In certain embodiments wherein W is —C(O)NH— or —C(O)N(R$^c$)—, R$^2$ represents (halo)aryl or (halo)heteroaryl.

In certain embodiments, W is —C(O)—.

In certain such embodiments, R$^2$ represents optionally substituted aralkyl or heteroaralkyl.

In certain embodiments, V represents optionally substituted aryl.

In certain embodiments, Z represents one or more substituents independently selected from the group consisting of halo, haloalkyl, —NO$_2$, and —CN.

In certain embodiments, Z represents one instance of halo.

In certain embodiments, Z represents one instance of fluoro.

In certain embodiments, Z is absent.

In certain embodiments, X represents —C(NH$_2$)—, —C(NH(R$^c$))—, —C(NR$^c$R$^d$)—, —C(NHS(O)$_p$R$^c$)—, —C(NHC(O)R$^c$)—, —C(NHC(O)NH$_2$)—, —C(NHC(O)NHR$^c$)—, or —C(NHC(O)NR$^c$R$^d$)—.

In certain embodiments, X represents —C(NH$_2$)—, —C(NH(R$^c$))—, —C(NR$^c$R$^d$)—, —C(NHS(O)$_p$R$^c$)—, —C(NHC(O)R$^c$)—, or —C(NHC(O)NHR$^c$)—.

In certain embodiments, X represents —C(NH$_2$)—.

In certain embodiments, X represents —C(NH(R$^c$))—.

In certain such embodiments, X represents —C(NH(cycloalkyl)alkyl)-. In alternative such embodiments, X represents —C(NH(C$_1$-C$_6$)alkyl)-.

In certain embodiments, X represents —C(NHS(O)$_p$R$^c$)—.

In certain such embodiments, X represents —C(NHS(O)$_p$(C$_1$-C$_6$)alkyl)-, wherein p is 1 or 2.

In certain embodiments, X represents —C(NHC(O)NHR$^c$)—.

In certain such embodiments, X represents optionally substituted —C(NHC(O)NH(aryl))- or C(NHC(O)NH(heteroaryl))-.

In certain embodiments, X represents —C(NHC(O)R$^c$)—.

In certain such embodiments, X represents —C(NHC(O)((C$_1$-C$_6$)alkyl))-.

In certain embodiments, R$^3$ represents optionally substituted aryl or heteroaryl.

In certain embodiments, R$^3$ represents optionally substituted heteroaryl.

In certain such embodiments, R$^3$ represents pyridyl.

In certain embodiments, R$^3$ represents optionally substituted aryl.

In certain such embodiments, R$^3$ represents phenyl, optionally substituted by one or more substituents selected from the group consisting of —CN, halo, —NO$_2$, (C$_1$-C$_6$) alkyl, and (C$_1$-C$_6$)haloalkyl.

In certain embodiments, R$^{3a}$ is absent or represents halo, alkyl, —CF$_3$, —OCF$_3$, aryl, heteroaryl, —C(O)NH$_2$, cyano, —NHC(O)alkyl, —SO$_2$alkyl, —SO$_2$NH$_2$, —NO$_2$, —NR$^a$C(O)R$^b$, —C(O)NR$^c$R$^d$, —NR$^a$C(O)NR$^c$R$^d$, —C(=NR$^a$)NR$^c$R$^d$, —NHC(=NR$^a$)NR$^c$R$^d$, —SO$_2$NR$^c$R$^d$, —NR$^a$SO$_2$NR$^c$R$^d$, —NR$^a$SO$_2$alkyl, —NR$^a$SO$_2$R$^a$, —S(O)$_p$R$^a$, or —(CF$_2$)$_r$CF$_3$.

In certain embodiments, Y represents a bond.

In certain embodiments, R$^4$ represents H.

In certain embodiments, R$^4$ represents (cycloalkyl)alkyl. For examples, R$^4$ may represent (cyclopropyl)(C$_1$-C$_6$)alkyl.

In certain embodiments, the compound of the invention is selected from the following table of compounds, or a pharmaceutically acceptable salt thereof:

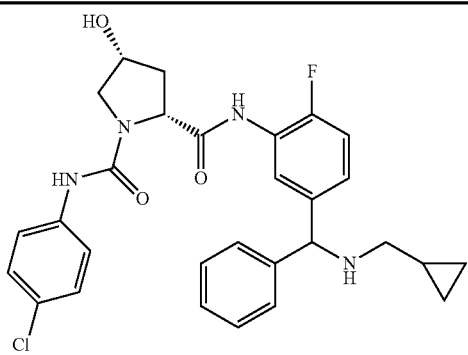

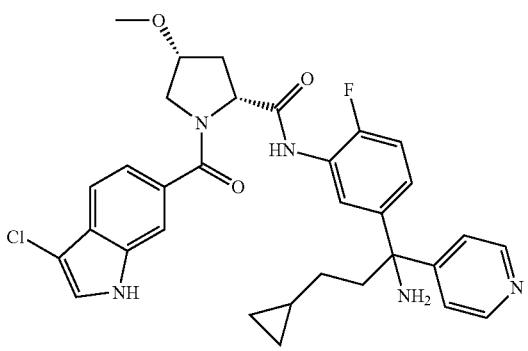 [SMILES: CO[C@@H]1C[C@H](C(=O)Nc2cc(C(N)(CCC3CC3)c3ccncc3)ccc2F)N(C(=O)c2ccc3c(Cl)c[nH]c3c2)C1]

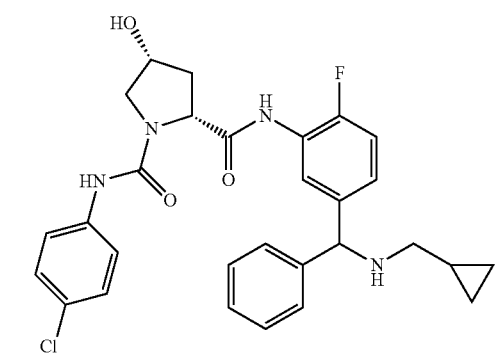 [SMILES: O=C(Nc1cc(C(NCC2CC2)c2ccccc2)ccc1F)[C@H]1C[C@@H](O)CN1C(=O)Nc1ccc(Cl)cc1]

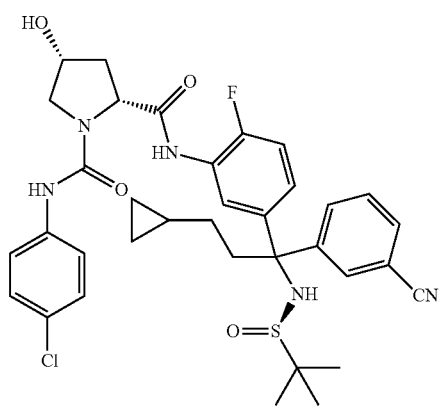 [SMILES: CC(C)(C)[S@@](=O)NC(CCC1CC1)(c1cccc(C#N)c1)c1ccc(F)c(NC(=O)[C@H]2C[C@@H](O)CN2C(=O)Nc2ccc(Cl)cc2)c1]

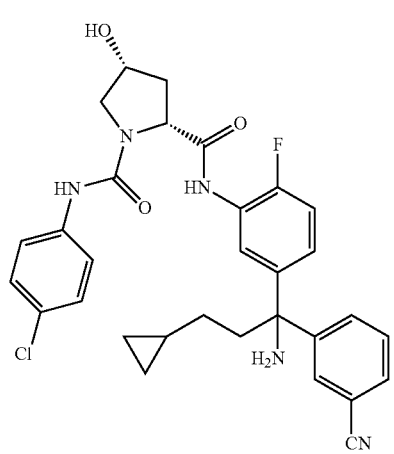 [SMILES: N#Cc1cccc(C(N)(CCC2CC2)c2ccc(F)c(NC(=O)[C@H]3C[C@@H](O)CN3C(=O)Nc3ccc(Cl)cc3)c2)c1]

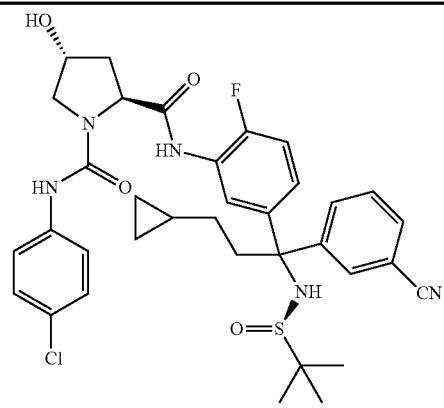
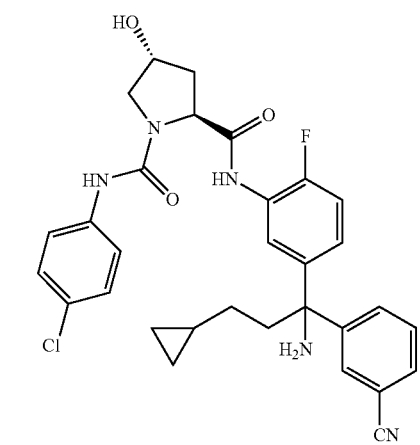 [SMILES: N#Cc1cccc(C(N)(CCC2CC2)c2ccc(F)c(NC(=O)[C@@H]3C[C@@H](O)CN3C(=O)Nc3ccc(Cl)cc3)c2)c1]
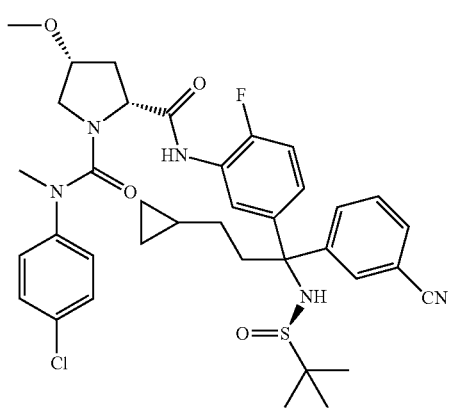 [SMILES: CO[C@@H]1C[C@H](C(=O)Nc2cc(C(CCC3CC3)(N[S@](=O)C(C)(C)C)c3cccc(C#N)c3)ccc2F)N(C(=O)N(C)c2ccc(Cl)cc2)C1]
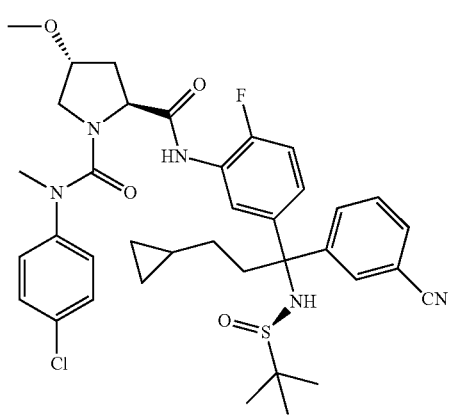 [SMILES: CO[C@@H]1C[C@@H](C(=O)Nc2cc(C(CCC3CC3)(N[S@](=O)C(C)(C)C)c3cccc(C#N)c3)ccc2F)N(C(=O)N(C)c2ccc(Cl)cc2)C1]
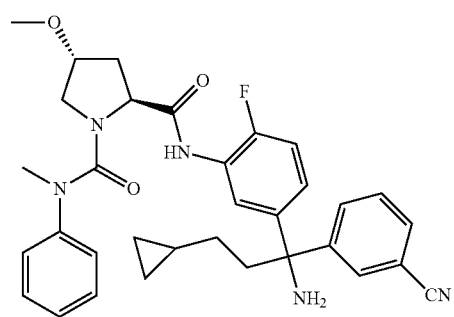
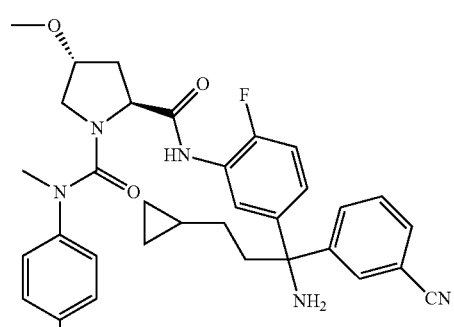
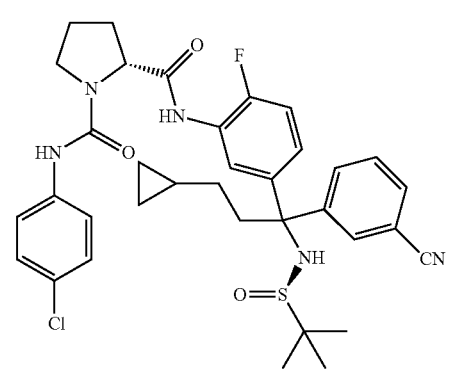 [SMILES: CC(C)(C)[S@@](=O)NC(CCC1CC1)(c1cccc(C#N)c1)c1ccc(F)c(NC(=O)[C@H]2CCCN2C(=O)Nc2ccc(Cl)cc2)c1]
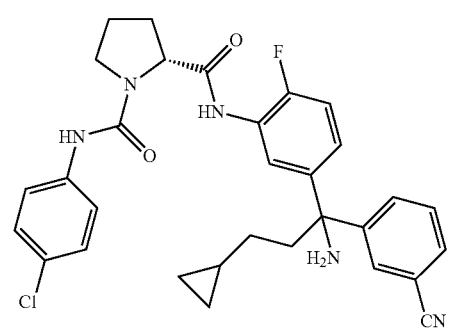 [SMILES: N#Cc1cccc(C(N)(CCC2CC2)c2ccc(F)c(NC(=O)[C@H]3CCCN3C(=O)Nc3ccc(Cl)cc3)c2)c1]

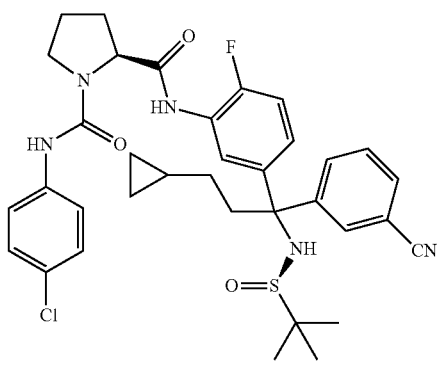 [SMILES: CC(C)(C)[S@@](=O)NC(CCC1CC1)(c1cccc(C#N)c1)c1ccc(F)c(NC(=O)[C@@H]2CCCN2C(=O)Nc2ccc(Cl)cc2)c1]
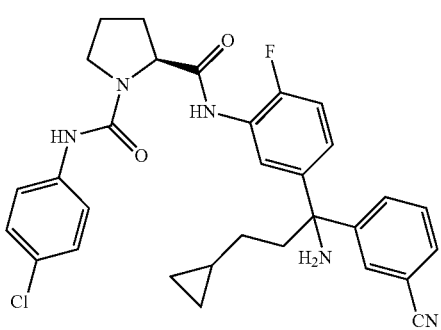 [SMILES: N#Cc1cccc(C(N)(CCC2CC2)c2ccc(F)c(NC(=O)[C@@H]3CCCN3C(=O)Nc3ccc(Cl)cc3)c2)c1]
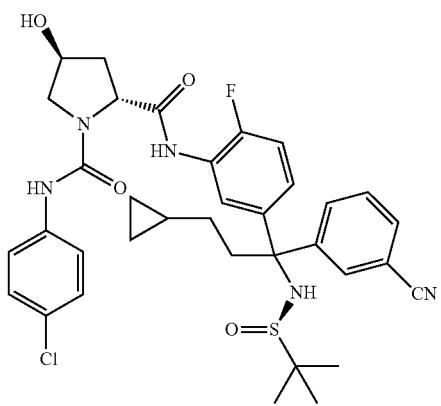 [SMILES: CC(C)(C)[S@@](=O)NC(CCC1CC1)(c1cccc(C#N)c1)c1ccc(F)c(NC(=O)[C@H]2C[C@H](O)CN2C(=O)Nc2ccc(Cl)cc2)c1]
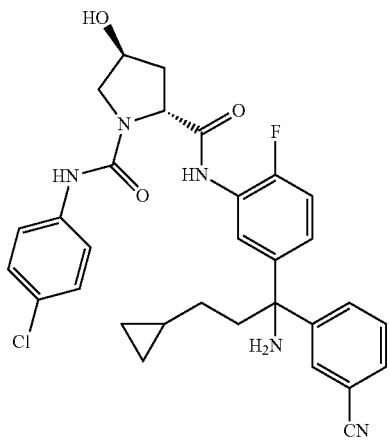 [SMILES: N#Cc1cccc(C(N)(CCC2CC2)c2ccc(F)c(NC(=O)[C@H]3C[C@H](O)CN3C(=O)Nc3ccc(Cl)cc3)c2)c1]
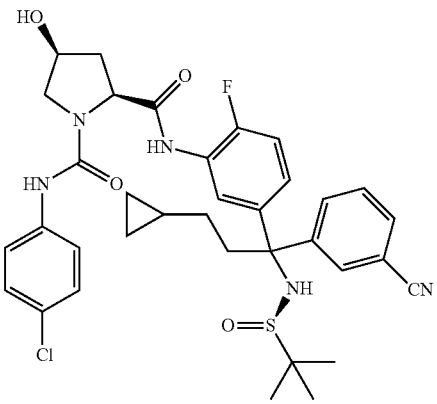 [SMILES: CC(C)(C)[S@@](=O)NC(CCC1CC1)(c1cccc(C#N)c1)c1ccc(F)c(NC(=O)[C@@H]2C[C@H](O)CN2C(=O)Nc2ccc(Cl)cc2)c1]
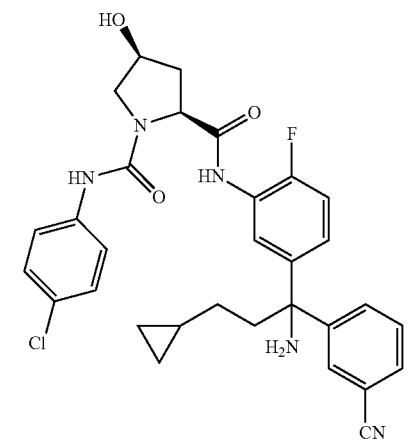 [SMILES: N#Cc1cccc(C(N)(CCC2CC2)c2ccc(F)c(NC(=O)[C@@H]3C[C@H](O)CN3C(=O)Nc3ccc(Cl)cc3)c2)c1]
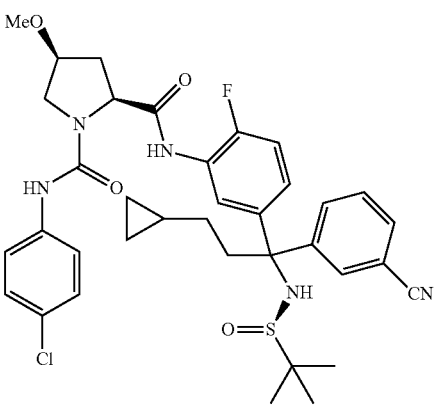 [SMILES: CO[C@H]1C[C@@H](C(=O)Nc2cc(C(CCC3CC3)(N[S@](=O)C(C)(C)C)c3cccc(C#N)c3)ccc2F)N(C(=O)Nc2ccc(Cl)cc2)C1]

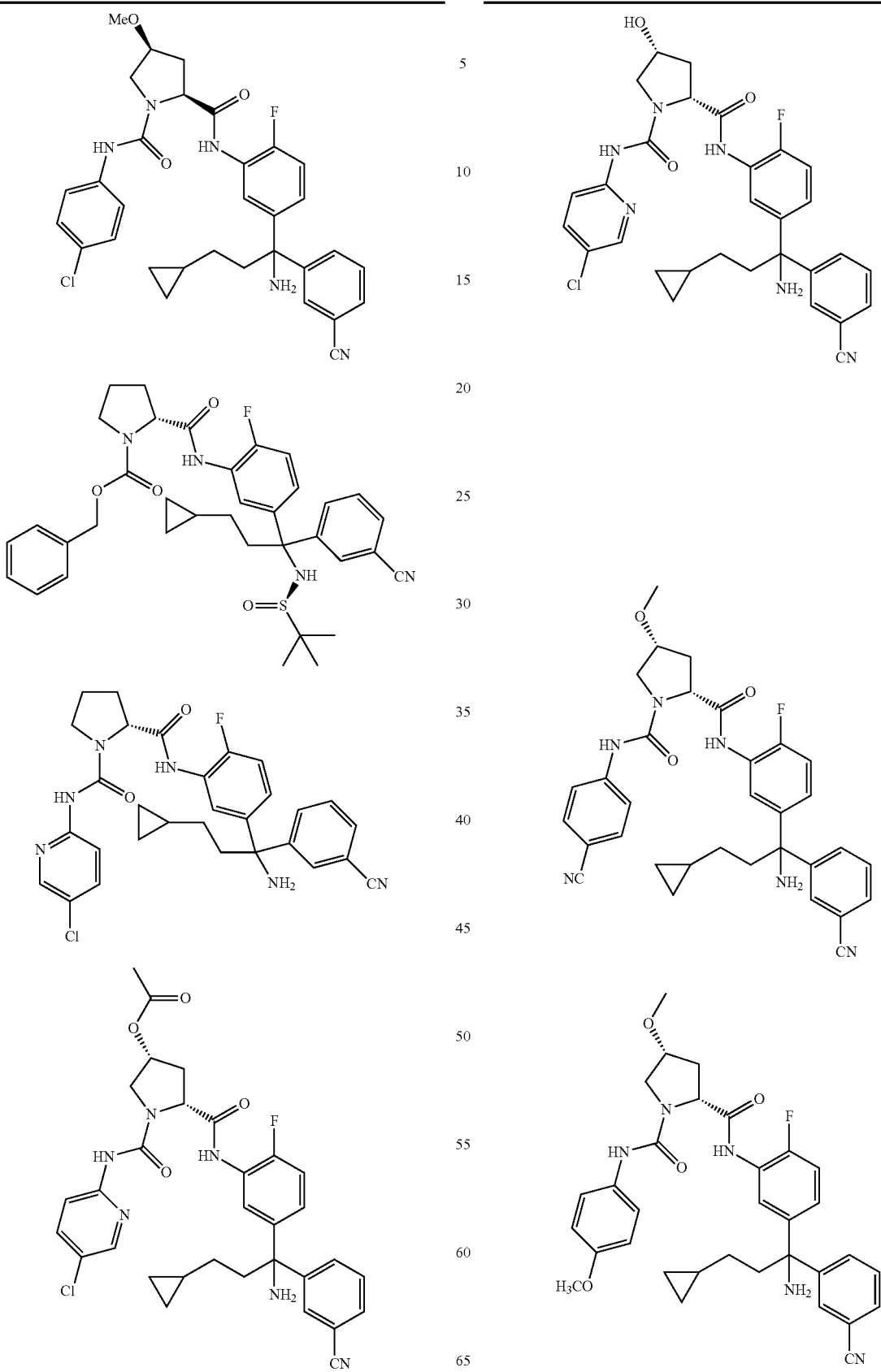

23
-continued
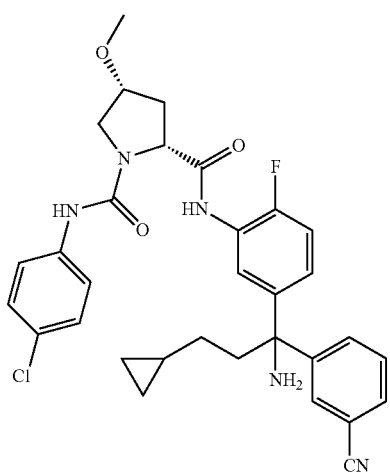 [SMILES: CO[C@@H]1C[C@H](C(=O)Nc2cc(C(N)(CCC3CC3)c3cccc(C#N)c3)ccc2F)N(C(=O)Nc2ccc(Cl)cc2)C1]
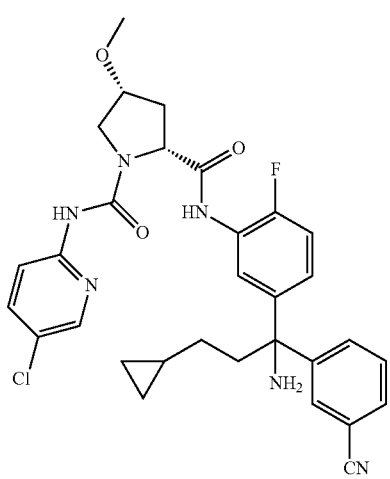 [SMILES: CO[C@@H]1C[C@H](C(=O)Nc2cc(C(N)(CCC3CC3)c3cccc(C#N)c3)ccc2F)N(C(=O)Nc2ccc(Cl)cn2)C1]
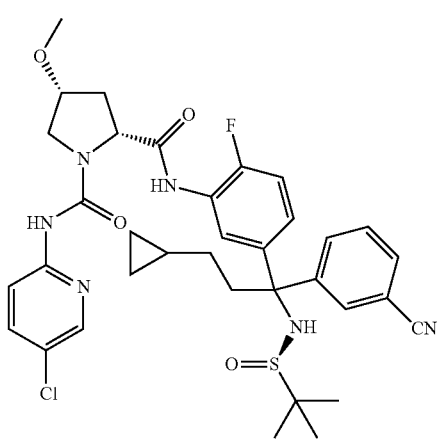 [SMILES: CO[C@@H]1C[C@H](C(=O)Nc2cc(C(CCC3CC3)(N[S@](=O)C(C)(C)C)c3cccc(C#N)c3)ccc2F)N(C(=O)Nc2ccc(Cl)cn2)C1]
24
-continued
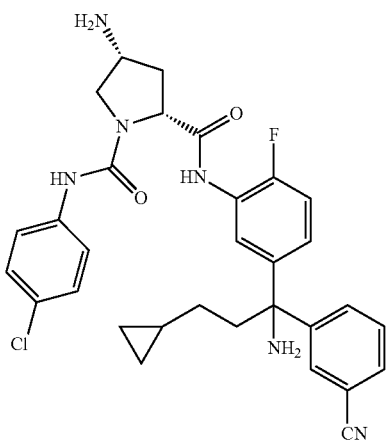 [SMILES: N#Cc1cccc(C(N)(CCC2CC2)c2ccc(F)c(NC(=O)[C@H]3C[C@@H](N)CN3C(=O)Nc3ccc(Cl)cc3)c2)c1]
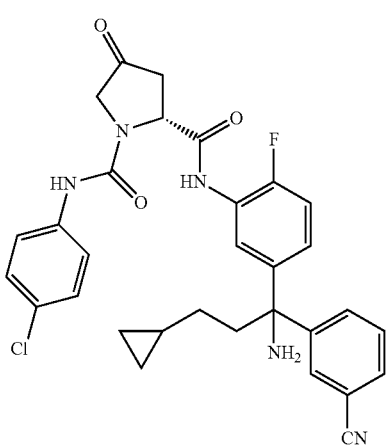 [SMILES: N#Cc1cccc(C(N)(CCC2CC2)c2ccc(F)c(NC(=O)[C@H]3CC(=O)CN3C(=O)Nc3ccc(Cl)cc3)c2)c1]
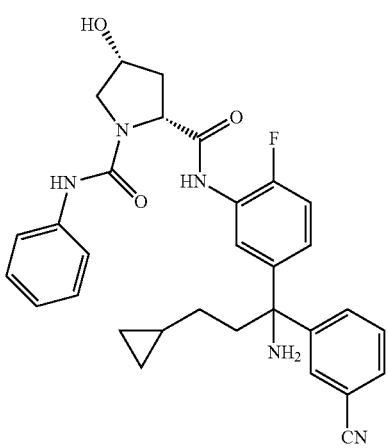 [SMILES: N#Cc1cccc(C(N)(CCC2CC2)c2ccc(F)c(NC(=O)[C@H]3C[C@@H](O)CN3C(=O)Nc3ccccc3)c2)c1]

25
-continued
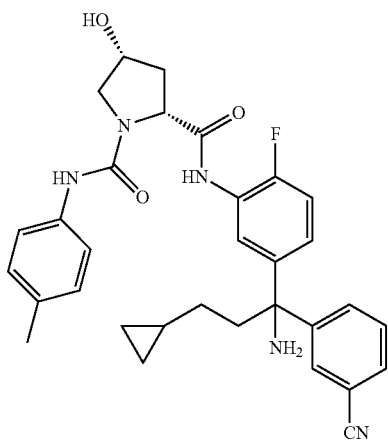 [SMILES: Cc1ccc(NC(=O)N2C[C@H](O)C[C@@H]2C(=O)Nc2cc(C(N)(CCC3CC3)c3cccc(C#N)c3)ccc2F)cc1]
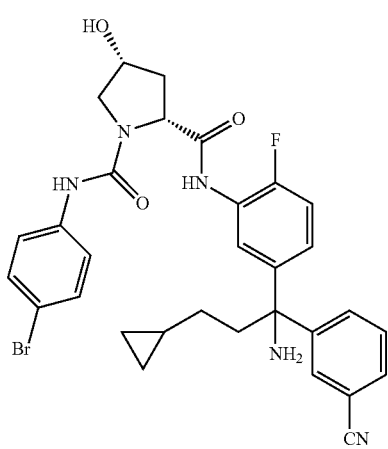 [SMILES: N#Cc1cccc(C(N)(CCC2CC2)c2ccc(F)c(NC(=O)[C@H]3C[C@@H](O)CN3C(=O)Nc3ccc(Br)cc3)c2)c1]
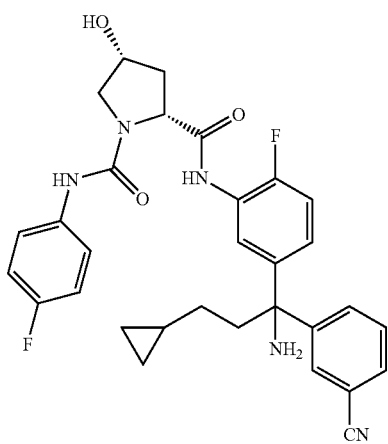 [SMILES: N#Cc1cccc(C(N)(CCC2CC2)c2ccc(F)c(NC(=O)[C@H]3C[C@@H](O)CN3C(=O)Nc3ccc(F)cc3)c2)c1]
26
-continued
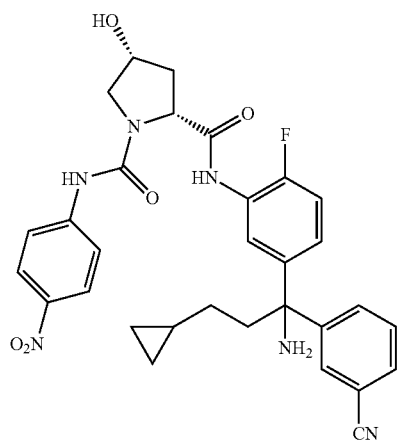
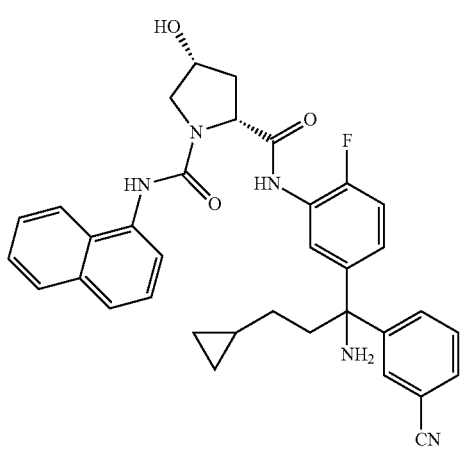 [SMILES: N#Cc1cccc(C(N)(CCC2CC2)c2ccc(F)c(NC(=O)[C@H]3C[C@@H](O)CN3C(=O)Nc3cccc4ccccc34)c2)c1]
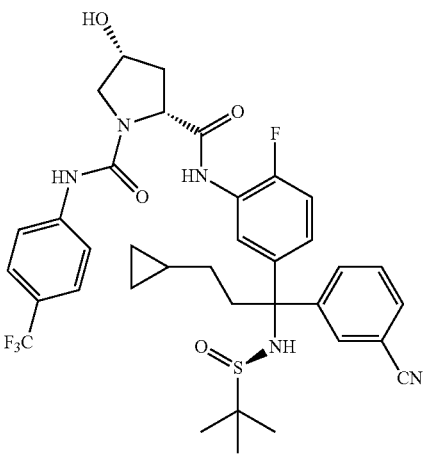 [SMILES: CC(C)(C)[S@@](=O)NC(CCC1CC1)(c1cccc(C#N)c1)c1ccc(F)c(NC(=O)[C@H]2C[C@@H](O)CN2C(=O)Nc2ccc(C(F)(F)F)cc2)c1]

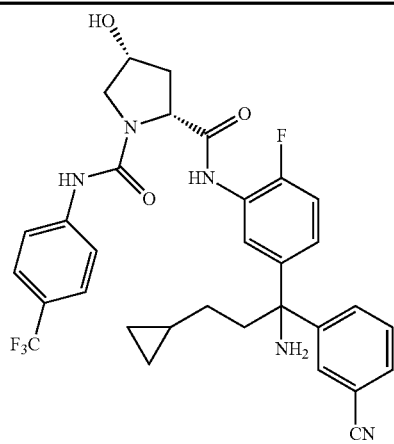
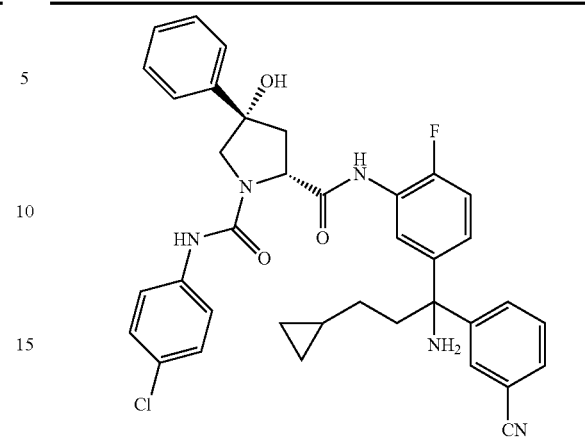
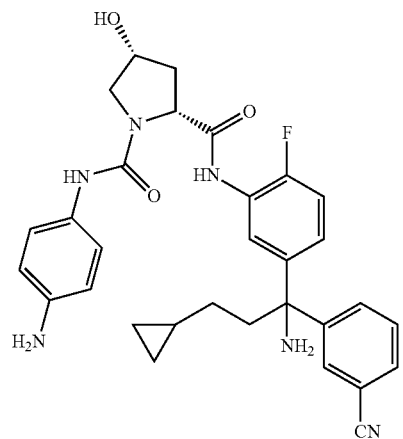
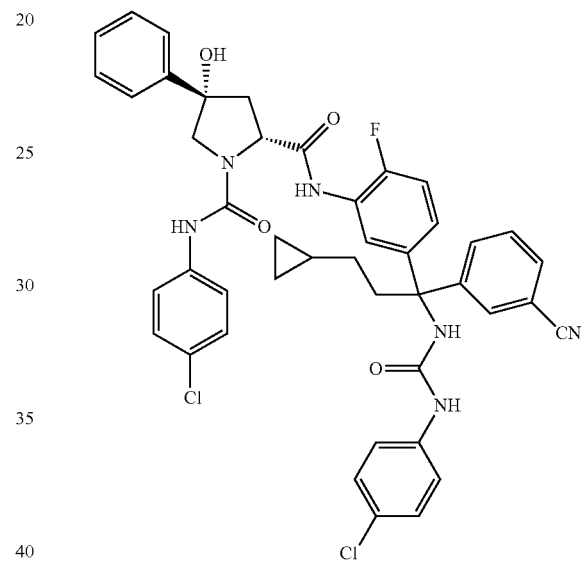
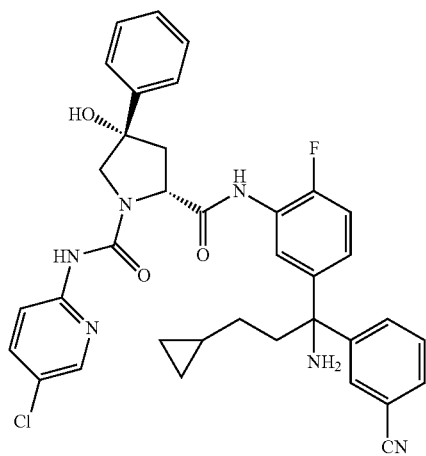 [SMILES: N#Cc1cccc(C(N)(CCC2CC2)c2ccc(F)c(NC(=O)[C@H]3C[C@](O)(c4ccccc4)CN3C(=O)Nc3ccc(Cl)cn3)c2)c1]
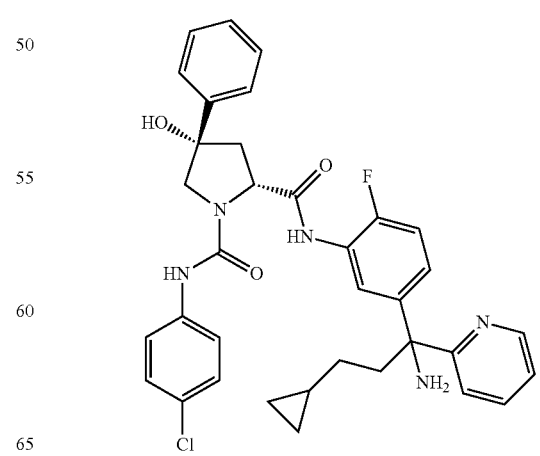

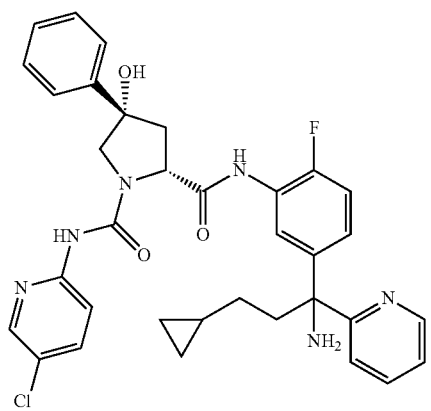 [SMILES: NC(CCC1CC1)(c1ccc(F)c(NC(=O)[C@H]2C[C@](O)(c3ccccc3)CN2C(=O)Nc2ccc(Cl)cn2)c1)c1ccccn1]
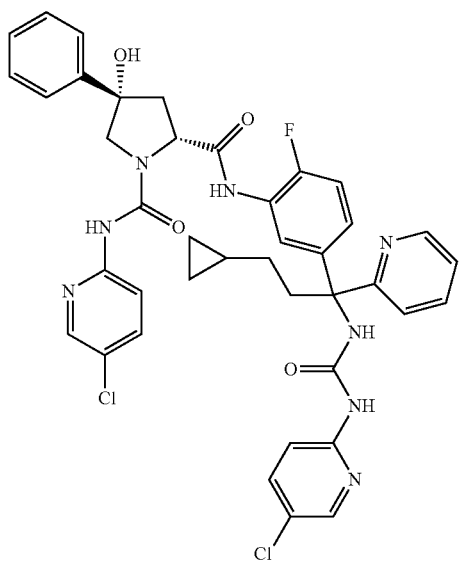 [SMILES: O=C(Nc1ccc(Cl)cn1)NC(CCC1CC1)(c1ccc(F)c(NC(=O)[C@H]2C[C@](O)(c3ccccc3)CN2C(=O)Nc2ccc(Cl)cn2)c1)c1ccccn1]
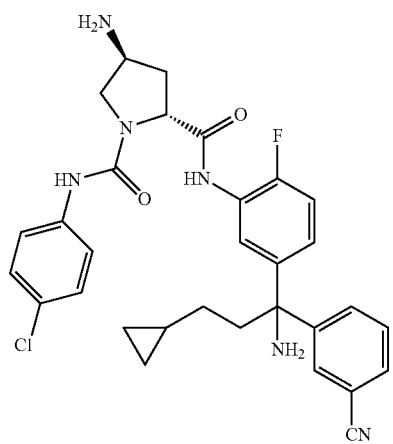 [SMILES: N#Cc1cccc(C(N)(CCC2CC2)c2ccc(F)c(NC(=O)[C@H]3C[C@H](N)CN3C(=O)Nc3ccc(Cl)cc3)c2)c1]
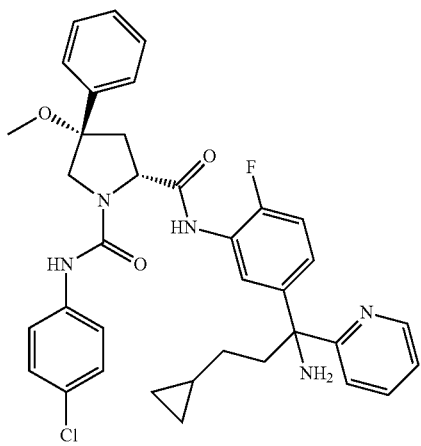 [SMILES: CO[C@]1(c2ccccc2)C[C@H](C(=O)Nc2cc(C(N)(CCC3CC3)c3ccccn3)ccc2F)N(C(=O)Nc2ccc(Cl)cc2)C1]
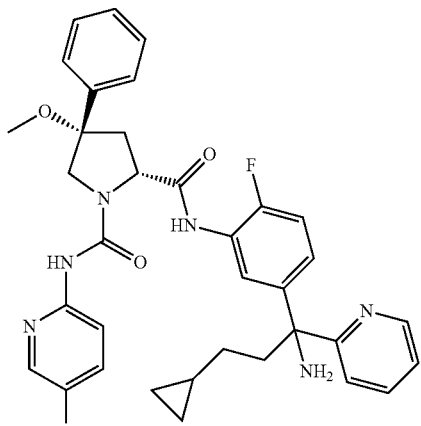

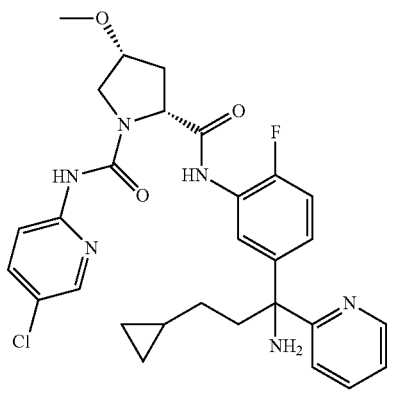 [SMILES: CO[C@@H]1C[C@H](C(=O)Nc2cc(C(N)(CCC3CC3)c3ccccn3)ccc2F)N(C(=O)Nc2ccc(Cl)cn2)C1]
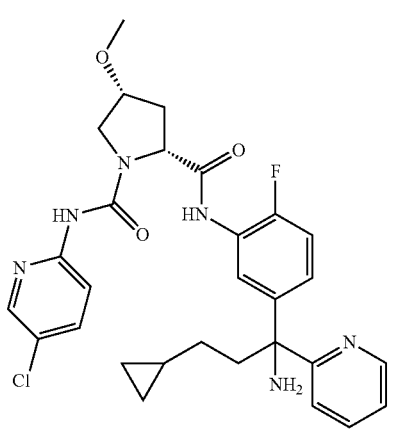 [SMILES: CO[C@@H]1C[C@H](C(=O)Nc2cc(C(N)(CCC3CC3)c3ccccn3)ccc2F)N(C(=O)Nc2ccc(Cl)cn2)C1]
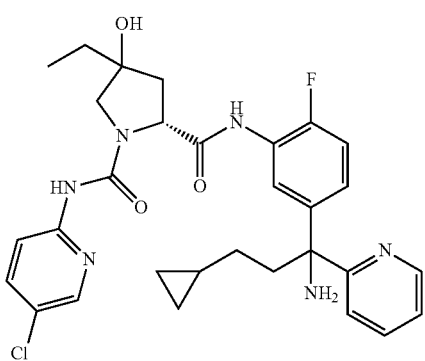 [SMILES: CCC1(O)C[C@H](C(=O)Nc2cc(C(N)(CCC3CC3)c3ccccn3)ccc2F)N(C(=O)Nc2ccc(Cl)cn2)C1]
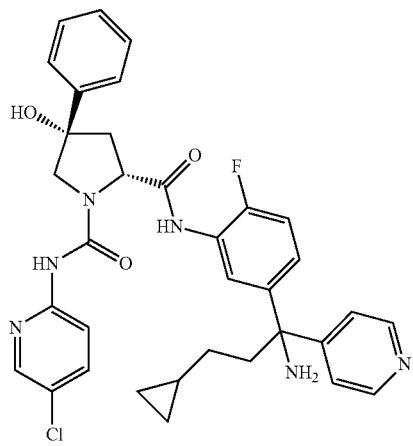 [SMILES: NC(CCC1CC1)(c1ccncc1)c1ccc(F)c(NC(=O)[C@H]2C[C@](O)(c3ccccc3)CN2C(=O)Nc2ccc(Cl)cn2)c1]
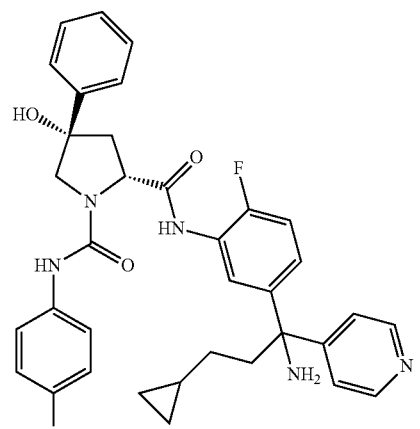
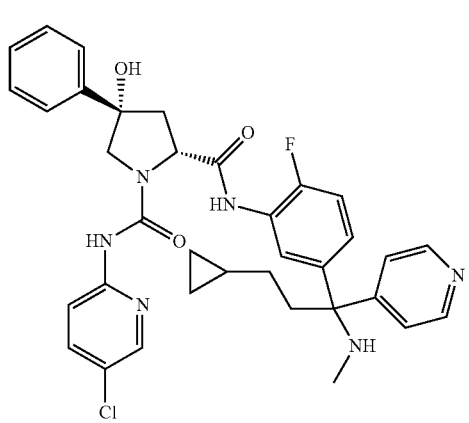 [SMILES: CNC(CCC1CC1)(c1ccncc1)c1ccc(F)c(NC(=O)[C@H]2C[C@](O)(c3ccccc3)CN2C(=O)Nc2ccc(Cl)cn2)c1]
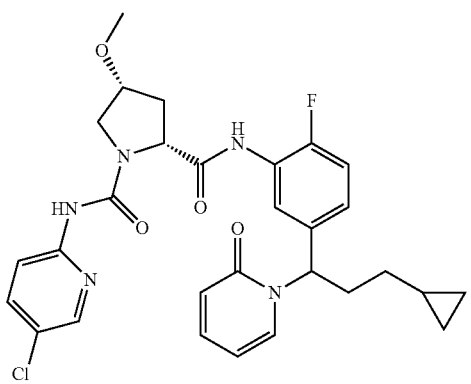 [SMILES: CO[C@@H]1C[C@H](C(=O)Nc2cc(C(CCC3CC3)n3ccccc3=O)ccc2F)N(C(=O)Nc2ccc(Cl)cn2)C1]
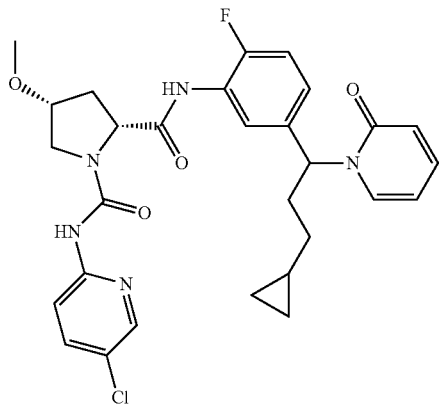 [SMILES: CO[C@@H]1C[C@H](C(=O)Nc2cc(C(CCC3CC3)n3ccccc3=O)ccc2F)N(C(=O)Nc2ccc(Cl)cn2)C1]

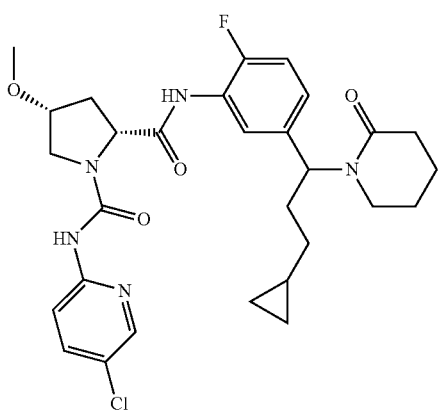 [SMILES: CO[C@@H]1C[C@H](C(=O)Nc2cc(C(CCC3CC3)N3CCCCC3=O)ccc2F)N(C(=O)Nc2ccc(Cl)cn2)C1]
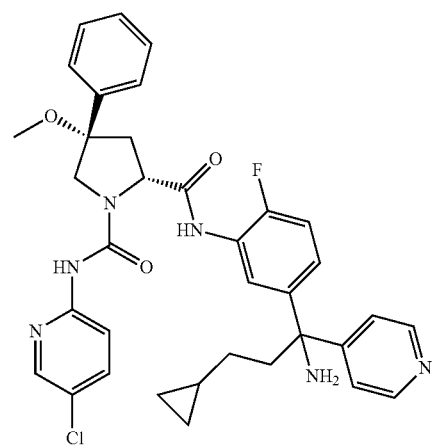 [SMILES: CO[C@]1(c2ccccc2)C[C@H](C(=O)Nc2cc(C(N)(CCC3CC3)c3ccncc3)ccc2F)N(C(=O)Nc2ccc(Cl)cn2)C1]
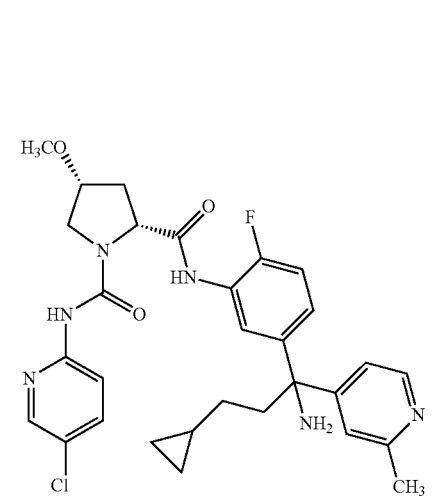 [SMILES: CO[C@@H]1C[C@H](C(=O)Nc2cc(C(N)(CCC3CC3)c3ccnc(C)c3)ccc2F)N(C(=O)Nc2ccc(Cl)cn2)C1]
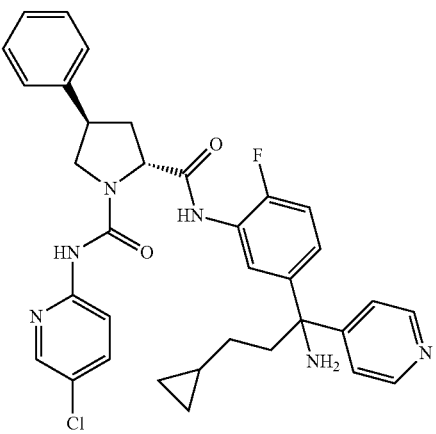 [SMILES: NC(CCC1CC1)(c1ccncc1)c1ccc(F)c(NC(=O)[C@H]2C[C@H](c3ccccc3)CN2C(=O)Nc2ccc(Cl)cn2)c1]
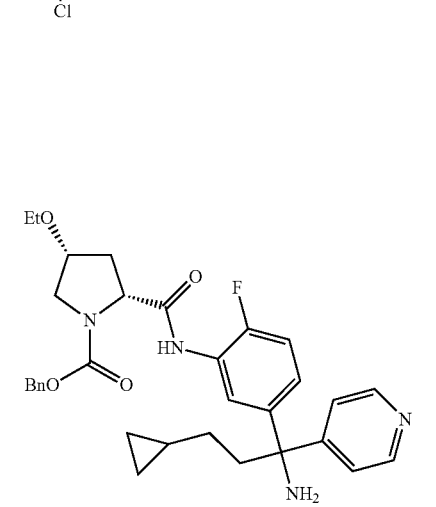

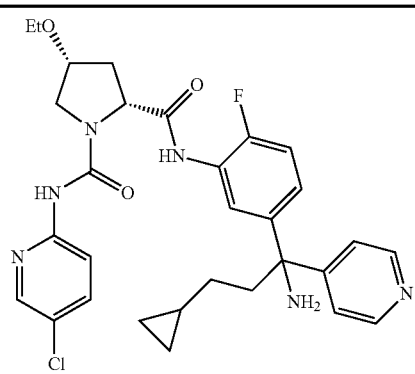
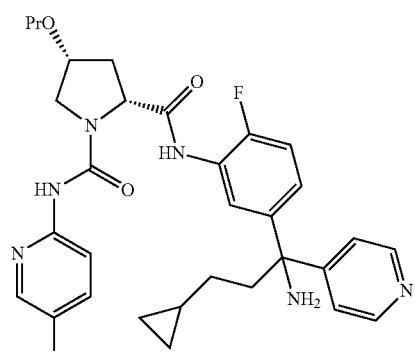
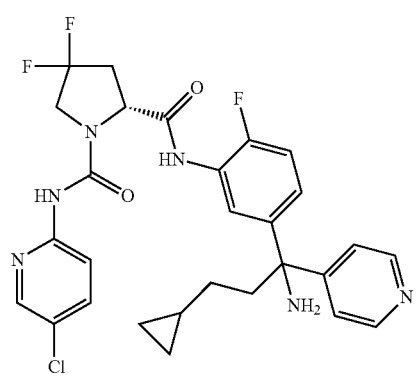 [SMILES: NC(CCC1CC1)(c1ccncc1)c1ccc(F)c(NC(=O)[C@H]2CC(F)(F)CN2C(=O)Nc2ccc(Cl)cn2)c1]
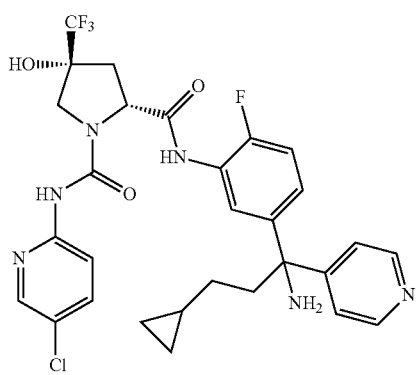 [SMILES: NC(CCC1CC1)(c1ccncc1)c1ccc(F)c(NC(=O)[C@H]2C[C@](O)(C(F)(F)F)CN2C(=O)Nc2ccc(Cl)cn2)c1]
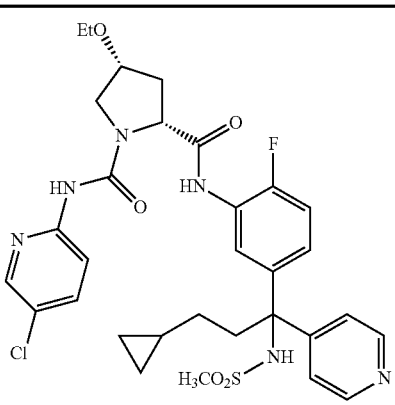
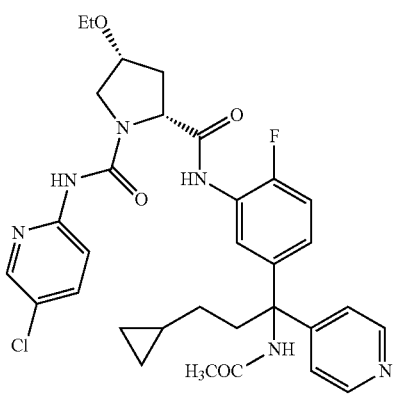
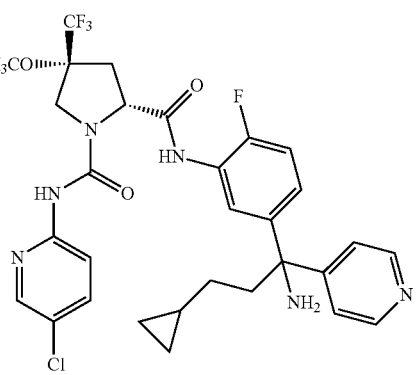
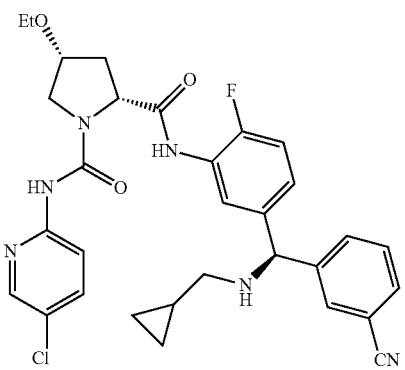 [SMILES: CCO[C@@H]1C[C@H](C(=O)Nc2cc([C@H](NCC3CC3)c3cccc(C#N)c3)ccc2F)N(C(=O)Nc2ccc(Cl)cn2)C1]

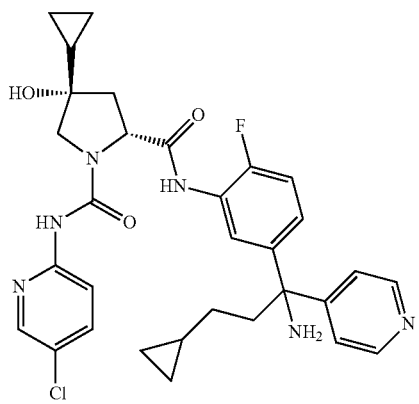 [SMILES: NC(CCC1CC1)(c1ccncc1)c1ccc(F)c(NC(=O)[C@H]2C[C@](O)(C3CC3)CN2C(=O)Nc2ccc(Cl)cn2)c1]
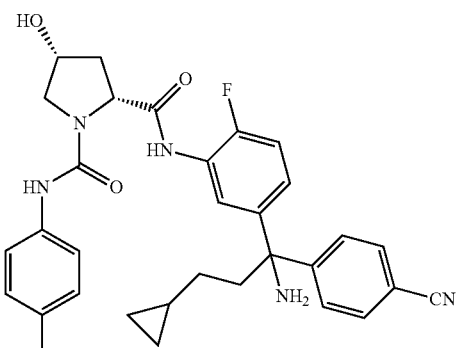
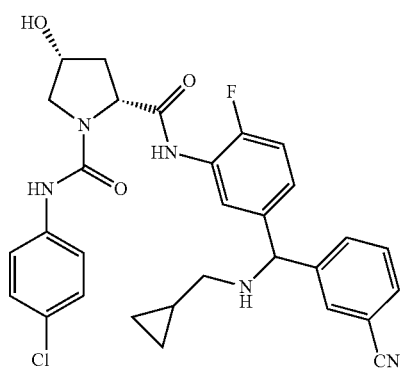 [SMILES: N#Cc1cccc(C(NCC2CC2)c2ccc(F)c(NC(=O)[C@H]3C[C@@H](O)CN3C(=O)Nc3ccc(Cl)cc3)c2)c1]
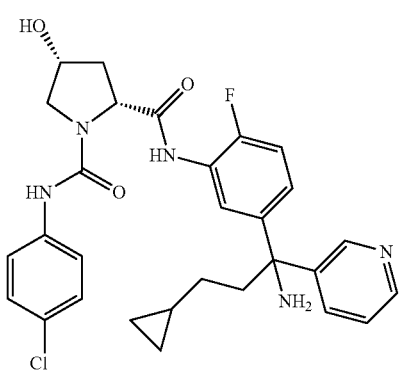
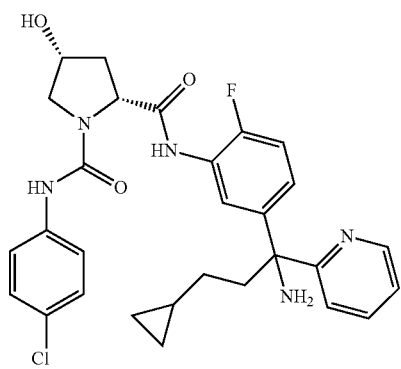 [SMILES: NC(CCC1CC1)(c1ccc(F)c(NC(=O)[C@H]2C[C@@H](O)CN2C(=O)Nc2ccc(Cl)cc2)c1)c1ccccn1]
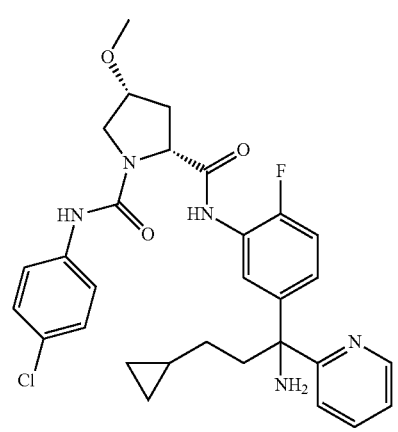
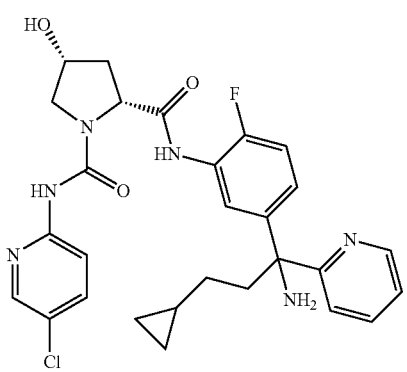 [SMILES: NC(CCC1CC1)(c1ccc(F)c(NC(=O)[C@H]2C[C@@H](O)CN2C(=O)Nc2ccc(Cl)cn2)c1)c1ccccn1]
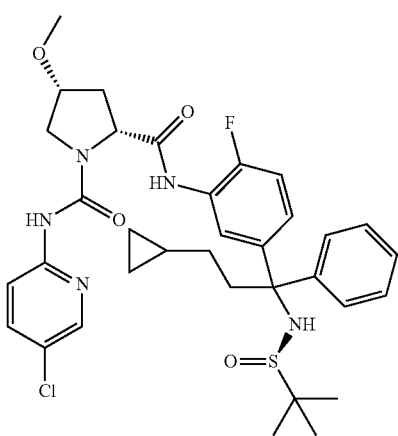 [SMILES: CO[C@@H]1C[C@H](C(=O)Nc2cc(C(CCC3CC3)(N[S@](=O)C(C)(C)C)c3ccccc3)ccc2F)N(C(=O)Nc2ccc(Cl)cn2)C1]

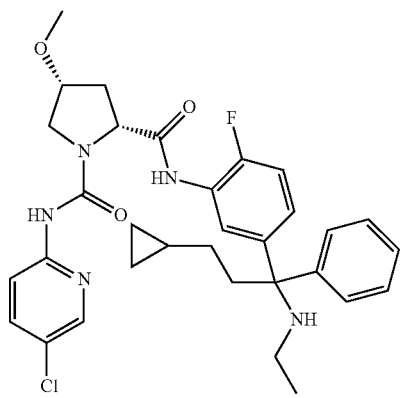 [SMILES: CCNC(CCC1CC1)(c1ccccc1)c1ccc(F)c(NC(=O)[C@H]2C[C@@H](OC)CN2C(=O)Nc2ccc(Cl)cn2)c1]
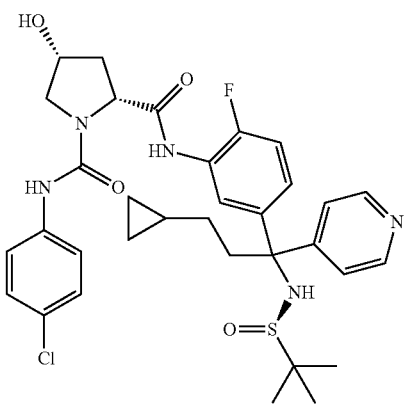 [SMILES: CC(C)(C)[S@@](=O)NC(CCC1CC1)(c1ccncc1)c1ccc(F)c(NC(=O)[C@H]2C[C@@H](O)CN2C(=O)Nc2ccc(Cl)cc2)c1]
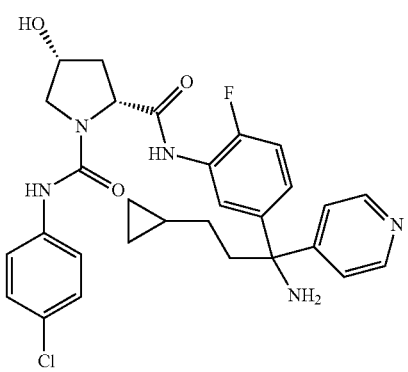 [SMILES: NC(CCC1CC1)(c1ccncc1)c1ccc(F)c(NC(=O)[C@H]2C[C@@H](O)CN2C(=O)Nc2ccc(Cl)cc2)c1]
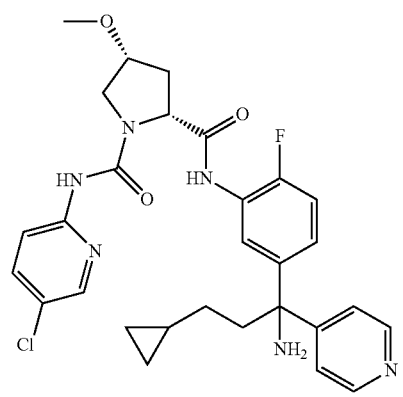
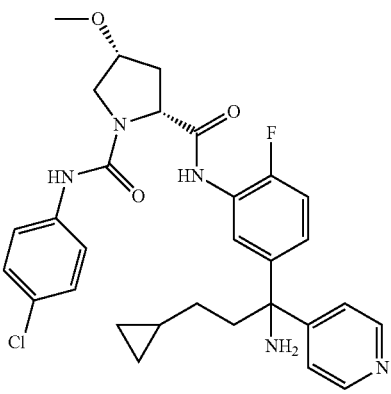 [SMILES: CO[C@@H]1C[C@H](C(=O)Nc2cc(C(N)(CCC3CC3)c3ccncc3)ccc2F)N(C(=O)Nc2ccc(Cl)cn2)C1]
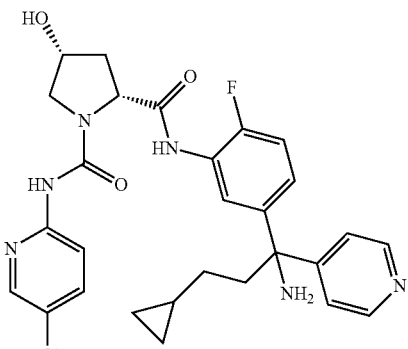
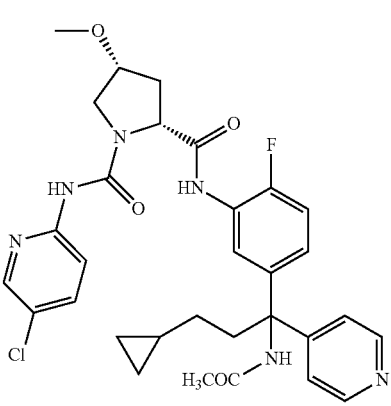
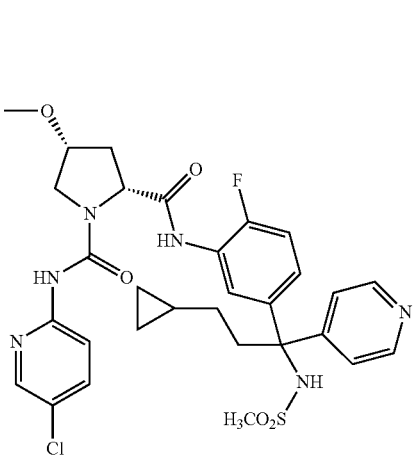

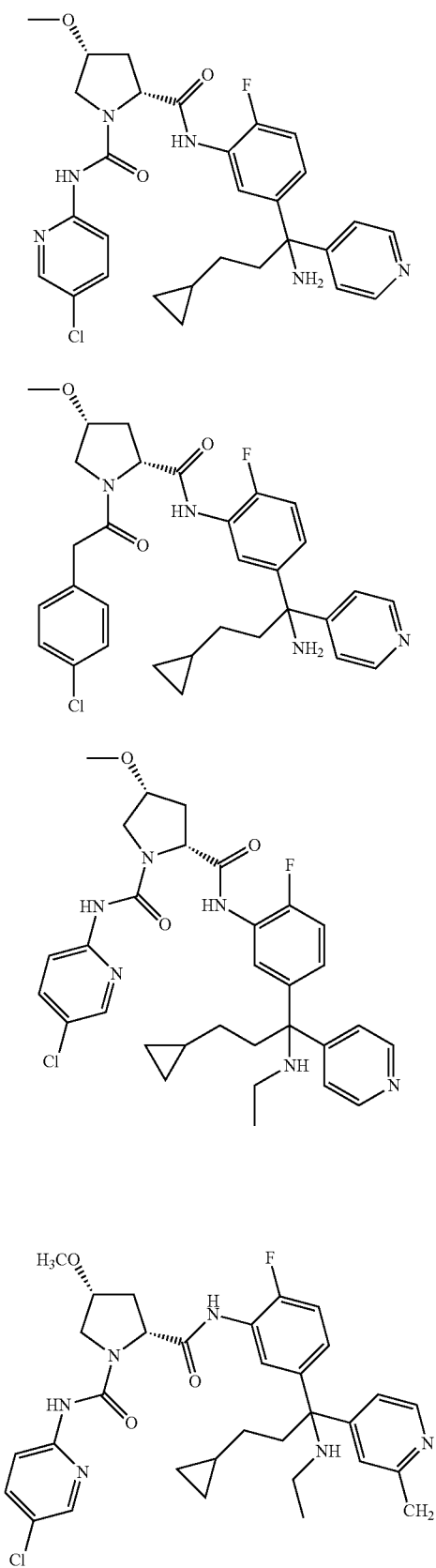
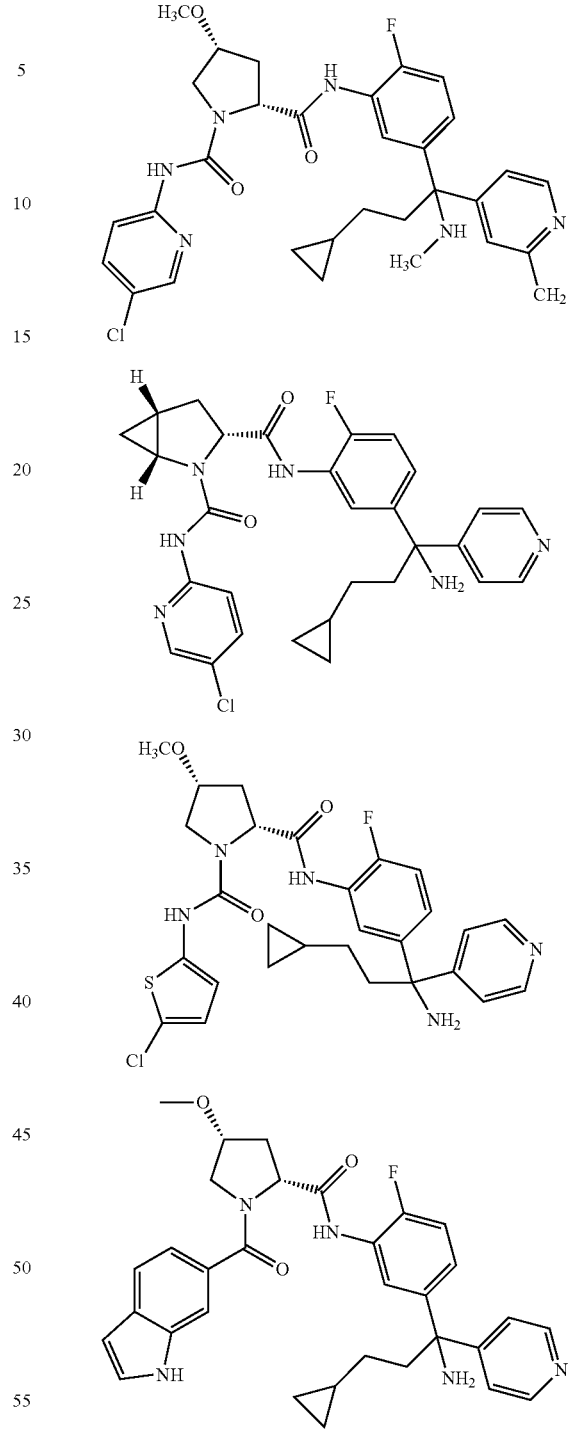

Pharmaceutical Compositions

The invention provides pharmaceutical compositions, each comprising one or more compounds of the invention and a pharmaceutically acceptable carrier. In certain embodiments, the pharmaceutical composition comprises a compound of the invention and a pharmaceutically acceptable carrier. In certain embodiments, the pharmaceutical composition comprises a plurality of compounds of the invention and a pharmaceutically acceptable carrier.

In certain embodiments, the pharmaceutical composition is formulated for parenteral administration.

In certain embodiments, the pharmaceutical composition is formulated for oral administration.

In certain embodiments, a pharmaceutical composition of the invention further comprises at least one additional pharmaceutically active agent other than a compound of the invention. The at least one additional pharmaceutically active agent can be an agent useful in the treatment of a disease or condition characterized by unwanted plasma kallikrein activity. For example, the at least one additional pharmaceutically active agent can be an anticoagulation agent, an anti-platelet agent, or a thrombolytic agent.

Anticoagulation agents prevent the coagulation of blood components and thus prevent clot formation, for example in atrial fibrillation. Anticoagulants include, but are not limited to, heparin, warfarin, coumadin, dicumarol, phenprocoumon, acenocoumarol, ethyl biscoumacetate, hirudin, bivalarutin, direct thrombin inhibitors, and indandione derivatives.

Anti-platelet agents inhibit platelet aggregation and are often used to prevent thromboembolic stroke in patients who have experienced a transient ischemic attack, stroke, or atrial fibrillation. Anti-platelet agents include, but are not limited to, aspirin, thienopyridine derivatives such as ticlopodine and clopidogrel, dipyridamole, and sulfinpyrazone, as well as RGD mimetics.

Thrombolytic agents lyse clots that cause thromboembolic phenomena such as stroke, myocardial infarction, and pulmonary thromboembolism. Thrombolytic agents include, but are not limited to, plasminogen, a2-antiplasmin, streptokinase, antistreplase, TNK, tissue plasminogen activator (tPA), and urokinase. Tissue plasminogen activator includes native tPA and recombinant tPA, as well as modified forms of tPA that retain the enzymatic or fibrinolytic activities of native tPA.

Pharmaceutical compositions of the invention can be prepared by combining one or more compounds of the invention with a pharmaceutically acceptable carrier and, optionally, one or more additional pharmaceutically active agents.

Methods of Use

The present invention provides compounds that inhibit the formation of thrombin via the intrinsic pathway and thus reduce the risk of new pathogenic thrombus formation (vessel occlusion or reocclusion) and also improve fibrinolytic-induced reperfusion when given as adjunctive therapy with a fibrinolytic regimen. Diseases and conditions that can be treated using the compounds of the present invention include, but are not limited to, stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

For example, in patients with angioedema conditions, small polypeptide PK inhibitor DX-88 (ecallantide) alleviates edema in patients with hereditary angioedema (HAE). Williams, A. et al. (2003) *Transfus. Apher. Sci.* 29:255-8; Schneider, L. et al. (2007) *J Allergy Clin Immunol.* 120:416-22; and Levy, J. H. et al. (2006) *Expert Opin. Invest. Drugs* 15:1077-90. A bradykinin B2 receptor antagonist, Icatibant, is also effective in treating HAE. Bork, K. et al. (2007) *J. Allergy Clin. Immunol.* 119:1497-1503. Because plasma kallikrein generates bradykinin, inhibition of plasma kallikrein is expected to inhibit bradykinin production.

For example, in coagulation resulting from fibrinolytic treatment (e.g., treatment with tissue plasminogen activator or streptokinase), higher levels of plasma kallikrein are found in patients undergoing fibrinolysis. Hoffmeister, H. M. et al. (1998) *J. Cardiovasc. Pharmacol.* 31:764-72. Plasmin-mediated activation of the intrinsic pathway has been shown to occur in plasma and blood and was markedly attenuated in plasma from individuals deficient in any of the intrinsic pathway components. Ewald, G. A. et al. (1995) *Circulation* 91:28-36.

Individuals who have had an acute MI were found to have elevated levels of activated plasma kallikrein and thrombin. Hoffmeister, H. M., et al. (1998) *Circulation* 98:2527-33.

DX-88 reduced brain edema, infarct volume, and neurological deficits in an animal model of ischemic stroke. Storini, C. et al. (2006) *J. Pharm. Exp. Ther.* 318:849-854. C1-inhibitor reduced infarct size in a mouse model of middle cerebral artery occlusion (MCAO). De Simoni, M. G. et al. (2004) *Am. J. Pathol.* 164:1857-1863; and Akita, N. et al. (2003) *Neurosurgery* 52:395-400). B2 receptor antagonists were found to reduce the infarct volume, brain swelling, and neutrophil accumulation and were neuroprotective in an MCAO animal model. Zausinger, S. et al. (2003) *Acta Neurochir. Suppl.* 86:205-7; Lumenta, D. B. et al. (2006) *Brain Res.* 1069:227-34; Ding-Zhou, L. et al. (2003) *Br. J Pharmacol.* 139:1539-47.

Regarding blood loss during cardiopulmonary bypass (CPB), it has been found that the kallikrein-kinin (i.e., contact) system is activated during CABG. Wachtfogel, Y. T. (1989) *Blood* 73:468. Activation of the contact system during CPB results in up to a 20-fold increase in plasma bradykinin. Cugno, M. et al. (2006) *Chest* 120:1776-82; and Campbell, D. J. et al. (2001) *Am. J. Physiol. Reg. Integr. Comp. Physiol.* 281:1059-70.

Plasma kallikrein inhibitors P8720 and PKSI-527 have also been found to reduce joint swelling in rat models of arthritis. De La Cadena, R. A. et al. (1995) *FASEB J.* 9:446-52; Fujimori, Y. (1993) *Agents Action* 39:42-8. It has also been found that inflammation in animal models of arthritis was accompanied by activation of the contact system. Blais, C. Jr. et al. (1997) *Arthritis Rheum.* 40:1327-33.

Additionally, plasma kallikrein inhibitor P8720 has been found to reduce inflammation in an acute and chronic rat model of inflammatory bowel disease (IBD). Stadnicki, A. et al. (1998) *FASEB J.* 12:325-33; Stadnicki, A. et al. (1996) *Dig. Dis. Sci.* 41:912-20; and De La Cadena, R. A., et al. (1995) *FASEB J.* 9:446-52. The contact system is activated during acute and chronic intestinal inflammation. Sartor, R. B. et al. (1996) *Gastroenterology* 110:1467-81. It has been found that B2 receptor antagonist, an antibody to high molecular weight kininogen, or reduction in levels of kininogen reduced clinicopathology in animal models of IBD. Ibid.; Arai, Y. et al. (1999) *Dig. Dis. Sci.* 44:845-51; and Keith, J. C. et al. (2005) *Arthritis Res. Therapy* 7:R769-76.

H-D-Pro-Phe-Arg-chloromethylketone (CMK), an inhibitor of PK and FXII and a physiological inhibitor (C1-inhibitor), has been found to reduce vascular permeability in multiple organs and reduce lesions in lipopolysaccharide (LPS)- or bacterial-induced sepsis in animals. Liu, D. et al. (2005) *Blood* 105:2350-5; Persson, K. et al. (2000) *J. Exp. Med.* 192:1415-24. Clinical improvement was observed in sepsis patients treated with C1-inhibitor. Zeerleder, S. et al.

(2003) *Clin. Diagnost. Lab. Immunol.* 10:529-35; Caliezi, C., et al. (2002) *Crit. Care Med.* 30:1722-8; and Marx, G. et al. (1999) *Intensive Care Med.* 25:1017-20. Fatal cases of septicemia are found to have a higher degree of contact activation. Martinez-Brotons, F. et al. (1987) *Thromb. Haemost.* 58:709-713; and Kalter, E. S. et al. (1985) *J. Infect. Dis.* 151:1019-27.

It has also been found that prePK levels are higher in diabetics, especially those with proliferative retinopathy, and correlate with fructosamine levels. Gao, B.-B., et al. (2007) *Nature Med.* 13:181-8; and Kedzierska, K. et al. (2005) *Archives Med. Res.* 36:539-43. PrePK is also found to be highest in those with a sensorimotor neuropathy. Christie, M. et al. (1984) *Thromb. Haemostas.* (Stuttgart) 52:221-3. PrePK levels are elevated in diabetics and are associated with increased blood pressure. PrePK levels independently correlate with the albumin excretion rate and are elevated in diabetics with macroalbuminuria, suggesting prePK may be a marker for progressive nephropathy. Jaffa, A. A. et al. (2003) *Diabetes* 52:1215-21. B1 receptor antagonists have been found to decrease plasma leakage in rats treated with streptozotocin. Lawson, S. R. et al. (2005) *Eur. J. Pharmacol.* 514:69-78. B1 receptor antagonists can also prevent streptozotocin-treated mice from developing hyperglycemia and renal dysfunction. Zuccollo, A. et al. (1996) *Can. J. Physiol. Pharmacol.* 74:586-9.

In certain aspects, the invention provides a compound of the invention, or a pharmaceutically acceptable salt thereof, for use as a medicament.

In certain aspects, the invention provides methods of treating or preventing a disease or condition characterized by unwanted plasma kallikrein activity. The method includes the step of administering to a subject in need thereof a therapeutically effective amount of a compound of the invention, or a pharmaceutically acceptable salt thereof, thereby treating or preventing the disease or condition characterized by unwanted plasma kallikrein activity. By reducing plasma kallikrein activity in the subject, the disease or condition characterized by unwanted plasma kallikrein activity is treated.

Alternatively, in certain aspects, the invention provides a compound of the invention, or a pharmaceutically acceptable salt thereof, for treatment of a disease or condition characterized by unwanted plasma kallikrein activity.

Alternatively, in certain aspects, the invention provides the use of a compound of the invention, or a pharmaceutically acceptable salt thereof, for the manufacture of a medicament for use in treatment of a disease or condition characterized by unwanted plasma kallikrein activity.

As used herein, a "disease or condition characterized by unwanted plasma kallikrein activity" refers to any disease or condition in which it is desirable to reduce plasma kallikrein activity. For example, it may be desirable to reduce plasma kallikrein activity in the setting of a hypercoagulable state. As another example, it may be desirable to reduce plasma kallikrein activity in the setting of tissue ischemia that is associated with the presence or formation of thrombus.

In certain embodiments, the disease or condition characterized by unwanted plasma kallikrein activity is selected from the group consisting of stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

In certain embodiments, the disease or condition characterized by unwanted plasma kallikrein activity is angioedema.

In certain embodiments, the disease or condition characterized by unwanted plasma kallikrein activity is hereditary angioedema (HAE).

In certain embodiments, the disease or condition characterized by unwanted plasma kallikrein activity is stroke.

In certain embodiments, the disease or condition characterized by unwanted plasma kallikrein activity is reperfusion injury.

In certain embodiments, the disease or condition characterized by unwanted plasma kallikrein activity is acute myocardial infarction.

In certain embodiments, the disease or condition characterized by unwanted plasma kallikrein activity is hemorrhage.

In certain embodiments, the disease or condition characterized by unwanted plasma kallikrein activity is blood loss during cardiopulmonary bypass.

In certain embodiments, the disease or condition characterized by unwanted plasma kallikrein activity is selected from the group consisting of retinopathy, diabetic retinopathy, diabetic macular edema, diabetic macular degeneration, age-related macular edema, age-related macular degeneration, and proliferative retinopathy.

Formulations, Routes of Administration, and Dosing

The compounds of the invention can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or an active salt thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention can be conveniently formulated in unit dosage form; for example, containing 5 to 1000 mg, 10 to 750 mg, or 50 to 500 mg of active ingredient per unit dosage form. In one embodiment, the invention provides a composition comprising a compound of the invention formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention can also be administered in combination with other therapeutic agents, for example, other agents that are useful for treating or preventing ischemia, blood loss, or reperfusion injury.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active ingredient for at least 30 days, and preferably 60 days.

In certain embodiments, a compound of the invention is formulated for intraocular administration, for example direct injection or insertion within or in association with an intraocular medical device.

The compounds of the invention may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention to the region of a body which has been treated by interventional technique.

In exemplary embodiment, a compound of the invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the compound is coated, adsorbed, placed, or otherwise incorporated into the device by methods known in the art. For example, the compound may be embedded and released from within ("matrix type") or surrounded by and released through ("reservoir type") polymer materials that coat or span the medical device. In the latter example, the compound may be entrapped within the polymer materials or coupled to the polymer materials using one or more the techniques for generating such materials known in the art. In other formulations, the compound may be linked to the surface of the medical device without the need for a coating, for example by means of detachable bonds, and release with time or can be removed by active mechanical or chemical processes. In other formulations, the compound may be in a permanently immobilized form that presents the compound at the implantation site.

In certain embodiments, the compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound is formulated for release from the polymer coating into the environment in which the medical device is placed. Preferably, the compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the compound from the polymer coating can be controlled. For example, the diffusion coefficient of the one or more polymer coatings can be modulated to control the release of the compound from the polymer coating. In a variation on this theme, the diffusion coefficient of the one or more polymer coatings can be controlled to modulate the ability of an analyte that is present in the environment in which the medical device is placed (e.g., an analyte that facilitates the breakdown or hydrolysis of some portion of the polymer) to access one or more components within the polymer composition (and for example, thereby modulate the release of the compound from the polymer coating). Yet another embodiment of the invention includes a device having a plurality of polymer coatings, each having a plurality of diffusion coefficients. In such embodiments of the invention, the release of the compound from the polymer coating can be modulated by the plurality of polymer coatings.

In yet another embodiment of the invention, the release of the compound from the polymer coating is controlled by modulating one or more of the properties of the polymer composition, such as the presence of one or more endogenous or exogenous compounds, or alternatively, the pH of the polymer composition. For example, certain polymer compositions can be designed to release a compound in response to a decrease in the pH of the polymer composition.

Kits

The invention also provides a kit, comprising a compound of the invention, or a pharmaceutically acceptable salt thereof: at least one other therapeutic agent, packaging material, and instructions for administering the compound of the invention or the pharmaceutically acceptable salt thereof and the other therapeutic agent or agents to a mammal to treat or prevent ischemia, blood loss, or reperfusion injury in the mammal. In one embodiment, the mammal is a human.

EXAMPLES

The present invention is further illustrated by the following examples, which in no way should be construed as limiting the scope of the claimed invention. The entire contents of all the references (including literature references, issued patents, published patent applications, and co-pending patent applications) cited throughout this application are hereby expressly incorporated by reference.

Scheme 1

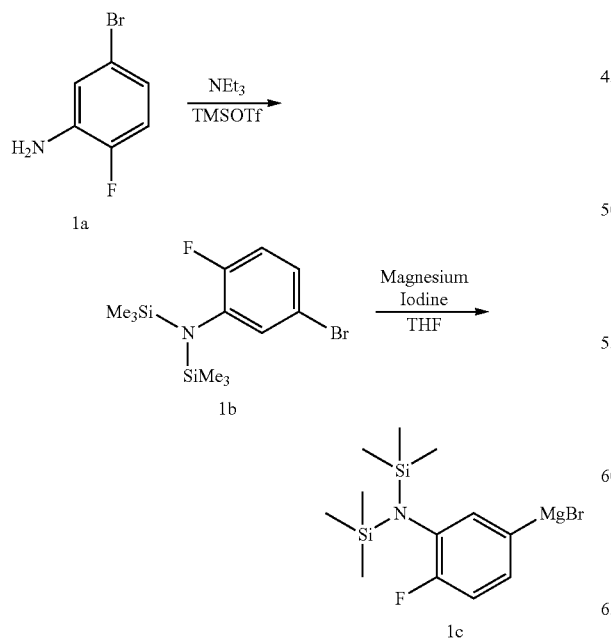

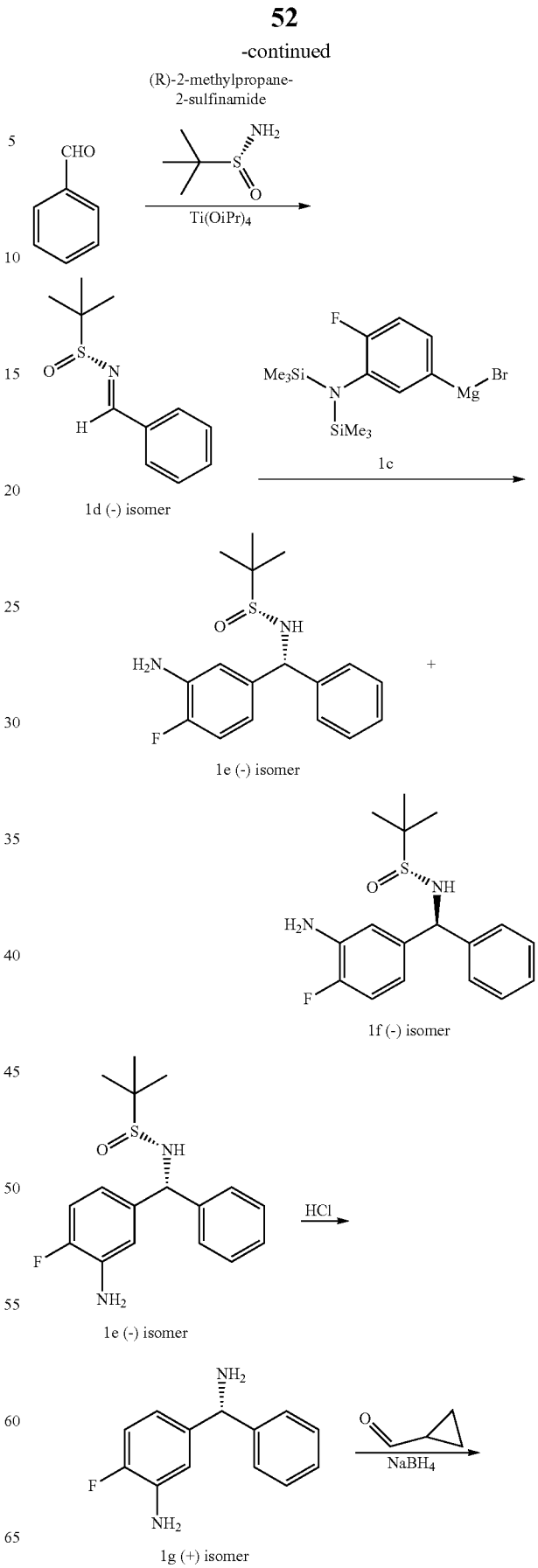

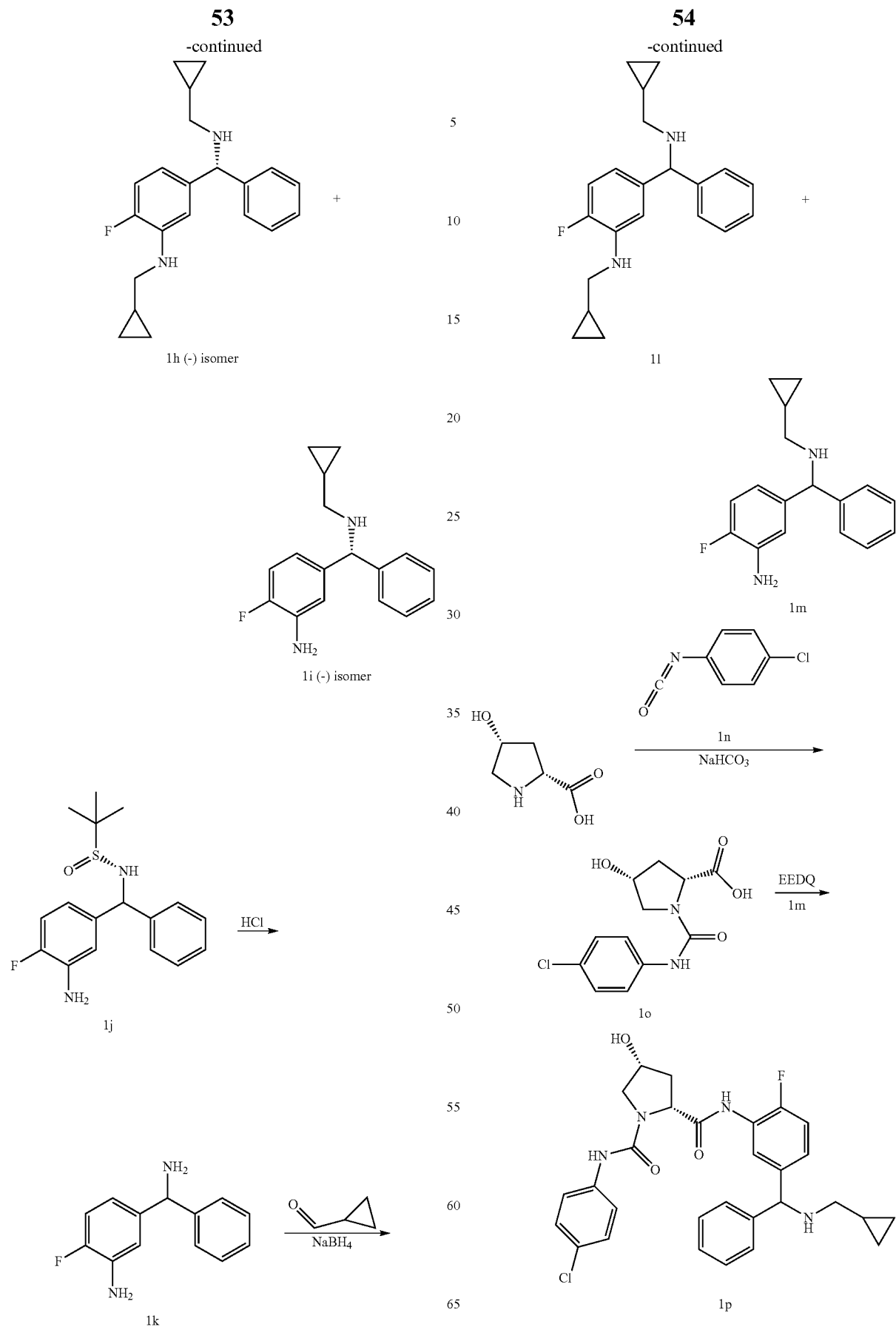

Preparation of (2R,4R)-N1-(4-chlorophenyl)-N2-(5-((((cyclopropylmethyl)amino)(phenyl)methyl)-2-fluorophenyl)-4-hydroxypyrrolidine-1,2-dicarboxamide (1p)

Step-1: Preparation of N-(5-bromo-2-fluorophenyl)-1,1,1-trimethyl-N-(trimethylsilyl)silanamine (1b)

To a stirred solution of 5-bromo-2-fluoroaniline (1a) (225 g, 1184 mmol) in triethylamine (3301 mL, 20 eq) was added trimethylsilyl trifluoromethanesulfonate (481 mL, 2664 mmol) at room temperature [Note: during the addition heat was generated but, was not needed to cool the flask]. The mixture was heated at reflux for 16 h and cooled to room temperature. The two layers were separated. [Note: try not to expose the solution to air or moisture during the separation]. Dark bottom solution was discarded and the upper layer was concentrated in vacuum to remove excess triethylamine. The oily residue was transferred to 1000 mL flask and distilled under high vacuum. The compound starts to distill at 100° C. at 0.5 mm/Hg. First fraction (about 15 mL) was discarded the second fraction was collected steadily at 100° C., 0.5 mm/Hg, to furnish N-(5-bromo-2-fluorophenyl)-1,1,1-trimethyl-N-(trimethylsilyl)silanamine (1b) (364 g, 1089 mmol, 92% yield). This was always freshly prepared for next step; $^1$H NMR (300 MHz, Chloroform-d) δ 7.17-7.11 (m, 1H), 7.09 (dd, J=7.5, 2.5 Hz, 1H), 6.89 (d, J=0.9 Hz, 1H), 0.08 (d, J=0.6 Hz, 18H).

Step-2: Preparation of (3-(bis(trimethylsilyl)amino)-4-fluorophenyl)magnesium bromide (1c)

To magnesium turnings (33.1 g, 1361 mmol) in tetrahydrofuran (15 mL) was added iodine (1.381 g, 5.44 mmol) followed by N-(5-bromo-2-fluorophenyl)-1,1,1-trimethyl-N-(trimethylsilyl)silanamine (1b) (4 g) to activate the reaction for about 5 minutes (Iodine color was decolorized). At this point rest of the solution of N-(5-bromo-2-fluorophenyl)-1,1,1-trimethyl-N-(trimethylsilyl)silanamine (1b) (364 g, 1089 mmol) in tetrahydrofuran (1000 mL) was added slowly in over a period of 3 h (reaction temperature was around 60° C. during the addition. The resulting dark grey solution was stirred overnight to furnish (3-(bis(trimethylsilyl)amino)-4-fluorophenyl)magnesium bromide (1c) (397 g, 1107 mmol, 102% yield, approximately 1M solution) which was used fresh in the next step.

Step-3: Preparation of (R)-(−)-N-benzylidene-2-methylpropane-2-sulfinamide (1d)

To a stirred solution of benzaldehyde (259 mL, 2541 mmol) in tetrahydrofuran (2500 mL) was added (R)-2-methylpropane-2-sulfinamide (280 g, 2310 mmol), tetraisopropoxytitanium (1382 mL, 4620 mmol) and stirred at room temperature for 36 h. The reaction mixture was diluted with 1 L of brine with vigorous stirring, followed by ethyl acetate (6 L) and stirred for 4 h. The reaction mixture was filtered washed with ethyl acetate (6×2 L). The organic layers were combined washed with a solution of sodium metabisulfite (329 mL, 1733 mmol), water (462 mL) dried over MgSO$_4$, filtered, evaporated to dryness. The crude residue was purified by flash column chromatography (silica gel 1.5 kg, eluting with 20% ethyl acetate in hexane) to furnish (R)-(−)-N-benzylidene-2-methylpropane-2-sulfinamide (1d) (472.51 g, 2257 mmol, 98% yield) as a pale yellow oil; $^1$H NMR (300 MHz, DMSO-d$_6$) δ 8.57 (s, 1H), 8.03-7.89 (m, 2H), 7.70-7.48 (m, 3H), 1.19 (s, 9H); MS (ES+) 232.18 (M+Na); Optical rotation: [α]$_D$=(−) 112.11 [4.155, CHCl$_3$].

Step-4: Preparation of (R)-N-((R)-(3-amino-4-fluorophenyl)(phenyl)methyl)-2-methylpropane-2-sulfinamide (1e) and (R)-N-((S)-(3-amino-4-fluorophenyl)(phenyl)methyl)-2-methylpropane-2-sulfinamide (1f)

Batch-1

To a solution of (R)-(−)-N-benzylidene-2-methylpropane-2-sulfinamide (1d) (475 g, 2269 mmol) in toluene (4 L) cooled to −11° C. was added dropwise freshly prepared Grignard reagent (3-(bis(trimethylsilyl)amino)-4-fluorophenyl)magnesium bromide (1c) (4.75 L, 3563 mmol) over a period of 70 minutes, maintaining internal between temp (−11.1 to −10° C.). Reaction mixture was stirred at the same temperature until complete (check TLC for reaction completion). Reaction was quenched with 1N KHSO$_4$ at −10° C. The reaction was warmed to room temperature over a 30 mins period and organic layer was separated. The aqueous layer was extracted with ethyl acetate (2×2 L). The organic layers were combined washed water (2×2 L), brine (3.5 L), dried filtered and concentrated in vacuum to afford crude oil containing mixture of diastereoisomers of (R)-N-((R)-(3-amino-4-fluorophenyl)(phenyl)methyl)-2-methylpropane-2-sulfinamide (1e) and (R)-N-((S)-(3-amino-4-fluorophenyl)(phenyl)methyl)-2-methylpropane-2-sulfinamide (1f) [(de=72/28) 727 g, 2269 mmol]. To crude in a 22 L flash was added IPA (2000 mL) and heated at reflux with stirring (30 mins to completely solubilize). The reaction mixture was cooled to 27° C. over a period of 5 h with gentle stirring. The solid obtained was collected by filtration washed with IPA (5×100 mL), air dried for 24 h to furnish (R)-N-((R)-(3-amino-4-fluorophenyl)(phenyl)methyl)-2-methylpropane-2-sulfinamide (1e) (351 g, 48.3% yield, de=94.63%.) as a white crystalline solid.

Batch-2

The above procedure was repeated using (R)-(−)-N-benzylidene-2-methylpropane-2-sulfinamide (1d) (0.500 kg, 2.389 mol) to furnish (R)-N-((R)-(3-amino-4-fluorophenyl)(phenyl)methyl)-2-methylpropane-2-sulfinamide (1e) (329 g, 43% yield, de=93.58%.) as a white crystalline solid.

Batch-3

The above procedure was repeated using (R)-(−)-N-benzylidene-2-methylpropane-2-sulfinamide (1d) (409 g, 1953 mmol) to furnish (R)-N-((R)-(3-amino-4-fluorophenyl)(phenyl)methyl)-2-methylpropane-2-sulfinamide (1e) (264 g, 42% yield, de=94.33%.) as a white crystalline solid.

Second crystallization: The above three batches were combined In a 22 L wide mouth rotary evaporator flash fitted with a mechanical stirrer containing mixture of diastereoisomers of (1e) and (1f) (batch-1, 351 g, 48.3% yield, de=94.63%), (batch-2, 329 g, 43% yield, de=93.58%) and (batch-3, 264 g, 42% yield, de=94.33%) was added IPA (4000 mL) and heated at reflux with stirring (50 mins to completely solubilize). The reaction mixture was cooled to room temperature overnight with gentle stirring (13° C.). The solid crystallized after about 1 h of cooling and stirring was continued overnight. The solid obtained was collected by filtration washed with IPA (1×100 mL and 2×200 mL), dried in high vacuum for 24 h to furnish (R)-N—((R)-(3-amino-4-fluorophenyl)(phenyl)methyl)-2-methylpropane-2-sulfinamide (1e) (872 g, 92% yield, de=99.2852%.) as a white crystalline solid; $^1$H NMR (300 MHz, DMSO-d$_6$) δ 7.40-7.26 (m, 4H), 7.25-7.15 (m, 1H), 6.90 (dd, J=11.5, 8.3 Hz, 1H), 6.75 (dd, J=8.9, 2.2 Hz, 1H), 6.57 (ddd, J=8.4, 4.4, 2.2 Hz, 1H), 5.77 (d, J=5.4 Hz, 1H), 5.33 (d, J=5.3 Hz, 1H), 5.11 (s, 2H), 1.13 (s, 9H); $^{19}$F NMR (282 MHz, DMSO) δ −137.36; $^{13}$C NMR (75 MHz, DMSO) δ 151.32, 148.19, 143.13, 139.74, 139.70, 128.22, 127.63, 126.93, 115.04, 114.98, 114.91, 114.82, 114.60, 114.35, 61.88, 55.42, 22.77; Optical rotation: $[α]_D$=(−) 70.70 (MeOH, 1.065); Analysis calculated for $C_{17}H_{21}FN_2OS$: C, 63.72; H, 6.61; N, 8.74. Found: C, 63.74; H, 6.74; N, 8.74.

Data for (R)-N-((S)-(3-amino-4-fluorophenyl)(phenyl)methyl)-2-methylpropane-2-sulfinamide (1f); $^1$H NMR (300 MHz, DMSO-d$_6$) δ 7.41-7.36 (m, 2H), 7.36-7.27 (m, 2H), 7.26-7.18 (m, 1H), 6.89 (dd, J=11.5, 8.3 Hz, 1H), 6.71 (dd, J=8.9, 2.2 Hz, 1H), 6.51 (ddd, J=8.4, 4.5, 2.2 Hz, 1H), 5.82 (d, J=5.5 Hz, 1H), 5.32 (d, J=5.5 Hz, 1H), 5.09 (s, 2H, 1H D$_2$O exchangeable), 1.14 (s, 9H); $^{19}$F NMR (282 MHz, DMSO-d$_6$) δ −137.32; MS (ES+) 321.3 (M+1), 343.3 (M+Na), 663.5 (2M+Na); MS (ES−) 319.3 (M−1). Optical rotation: $[α]_D$=(−) 73.21 (MeOH, 2.505).

Step-5: Preparation of (+)-5-(amino(phenyl)methyl)-2-fluoroaniline (1g)

To a mechanically stirred slurry of (R)-N-((R)-(3-amino-4-fluorophenyl)(phenyl)methyl)-2-methylpropane-2-sulfinamide (1e) (99.13 g, 309 mmol) in MTBE (600 mL) was added 4M HCl (dioxane) (162 mL, 650 mmol) and stirred at room temperature for 11 h. Solid starts forming as soon as HCl addition is started. TLC analysis shows unreacted starting material, additional 4M HCl (dioxane) (162 mL, 650 mmol) was added and stirred at room temperature for 16 h. Excess methanol was evaporated, mixture basified with 3N NaOH (455 mL) and compound was extracted with ethyl acetate (2×750 mL). The combined organic layers were dried over anhydrous MgSO4, filtered, evaporated to dryness. The solid was triturated with hexanes, stirred for 1 h and solid obtained was collected by filtration to afford (+)-5-(amino(phenyl)methyl)-2-fluoroaniline (1g) (38.0 g, 57% yield) as a pale yellow solid; $^1$H NMR (300 MHz, DMSO-d$_6$) δ 7.39-7.33 (m, 2H), 7.27 (ddd, J=7.6, 6.6, 1.2 Hz, 2H), 7.21-7.13 (m, 1H), 6.86 (dd, J=11.5, 8.3 Hz, 1H), 6.77 (dd, J=9.0, 2.2 Hz, 1H), 6.54 (ddd, J=8.3, 4.4, 2.2 Hz, 1H), 5.03 (s, 2H, D$_2$O exchangeable), 4.96 (s, 1H), 2.71 (s, 2H, D$_2$O exchangeable); $^{19}$F NMR (282 MHz, DMSO-d$_6$) δ −138.12; MS (ES+) 217.2 (M+1); 215.1 (M−1); Optical rotation: $[α]_D$=(+) 1.47 (0.545, MeOH).

Step-6: Preparation of (−)-N-(cyclopropylmethyl)-5-((cyclopropylmethylamino)(phenyl)methyl)-2-fluoroaniline (1h) and (−)-5-((cyclopropylmethylamino)(phenyl)methyl)-2-fluoroaniline (1i)

To a stirred solution of (+)-5-(amino(phenyl)methyl)-2-fluoroaniline (1g) (5.312 g, 24.56 mmol) in MeOH (80 mL) was added cyclopropanecarboxaldehyde (1.944 mL, 25.8 mmol) at 0° C. for a period of 10 min and stirred for 30 mins. To this sodium borohydride (1.859 g, 49.1 mmol) was added in multiple portions and stirred for 1 h at 0° C. Excess solvent was evaporated and residue was treated with water (100 mL), and extracted with ethyl acetate (2×100 mL). The organic layers were combined dried over anhydrous MgSO$_4$, filtered and evaporated to dryness. The residue was purified by flash column chromatography (silica gel 80 g, eluting with 0-100% ethyl acetate in hexanes) to furnish 1. (−)-N-(cyclopropylmethyl)-5-((cyclopropylmethylamino)(phenyl)methyl)-2-fluoroaniline (1h) (0.663 g, 8% yield) as an yellow oil as a yellow oil; $^1$H NMR (300 MHz, DMSO-d$_6$) δ 7.44-7.35 (m, 2H), 7.30-7.21 (m, 2H), 7.19-7.08 (m, 1H), 6.96-6.75 (m, 2H), 6.55 (ddd, J=8.3, 4.6, 2.0 Hz, 1H), 5.26 (td, J=6.0, 2.3 Hz, 1H, D$_2$O exchangeable), 4.71 (s, 1H), 2.93 (t, J=6.2 Hz, 2H), 2.27 (d, J=7.1 Hz, 3H, 1H, D$_2$O exchangeable), 1.09-0.84 (m, 2H), 0.39 (m, 4H), 0.25-0.15 (m, 2H), 0.09-−0.02 (m, 2H); $^{19}$F NMR (282 MHz, DMSO-d$_6$) δ −137.56; MS (ES+) 325.4 (M+1); Optical rotation: $[α]_D$=(−) 6.67 [0.27, methanol]

2. (−)-5-((cyclopropylmethylamino)(phenyl)methyl)-2-fluoroaniline (1i) (4.84 g, 73% yield) as a yellow oil; $^1$H NMR (300 MHz, DMSO-d$_6$) δ 7.42-7.34 (m, 2H), 7.32-7.23 (m, 2H), 7.22-7.11 (m, 1H), 6.92-6.78 (m, 2H), 6.55 (ddd, J=8.3, 4.5, 2.2 Hz, 1H), 5.04 (s, 2H, D$_2$O exchangeable), 4.67 (s, 1H), 2.25 (td, J=9.6, 5.3 Hz, 3H; 1H D$_2$O exchangeable), 1.04-0.80 (m, 1H), 0.50-0.28 (m, 2H), 0.11-0.02 (m, 2H); $^{19}$F NMR (282 MHz, DMSO-d$_6$) δ −137.92; MS (ES−) 269.3 (M−1); Optical rotation: $[α]_D$=(−) 12.24 [1.275, CHCl$_3$]; Chiral purity checked by performing chiral HPLC using chiral AD-H column, 1 mL/min, Solvent: 95% Hexane, 5% isopropanol, UV=260 nM, 25° C. (>99.99 ee).

Step-7: Preparation of 5-(amino(phenyl)methyl)-2-fluoroaniline (1k)

Compound (R)-N-((3-amino-4-fluorophenyl)(phenyl)methyl)-2-methylpropane-2-sulfinamide (1j) was obtained from the mother liquor from crystallization of mixture of diastereoisomers of (R)-N-((R)-(3-amino-4-fluorophenyl)(phenyl)methyl)-2-methylpropane-2-sulfinamide (1e) and (R)-N-((S)-(3-amino-4-fluorophenyl)(phenyl)methyl)-2-methylpropane-2-sulfinamide (1f). Compound 1k was prepared from (R)-N-((3-amino-4-fluorophenyl)(phenyl)methyl)-2-methylpropane-2-sulfinamide (1j) (27.8 g, 87 mmol) using procedure reported in step 5 of Scheme 1 to furnish 5-(amino(phenyl)methyl)-2-fluoroaniline (1k) (14 g, 75%) as a light brown solid; $^1$H NMR (300 MHz, DMSO-d$_6$) δ 7.40-7.32 (m, 2H), 7.27 (ddd, J=7.6, 6.7, 1.2 Hz, 2H), 7.21-7.11 (m, 1H), 6.86 (dd, J=11.5, 8.3 Hz, 1H), 6.78 (dd, J=9.0, 2.2 Hz, 1H), 6.54 (ddd, J=8.3, 4.5, 2.2 Hz, 1H), 5.00 (s, 2H), 4.93 (s, 1H), 2.13 (s, 2H); $^{19}$F NMR (282 MHz, DMSO) δ −138.30; MS (ES) 215.1 (M−1).

Step-8: Preparation of N-(cyclopropylmethyl)-5-((cyclopropylmethylamino)(phenyl)methyl)-2-fluoroaniline (1l) and 5-((cyclopropylmethylamino)(phenyl)methyl)-2-fluoroaniline (1m)

Compounds 1l and 1m was prepared from 5-(amino(phenyl)methyl)-2-fluoroaniline (1k) (1.081 g, 5.00 mmol) according to procedure reported in step 6 of Scheme 1 to furnish 1. N-(cyclopropylmethyl)-5-((cyclopropylmethylamino)(phenyl)methyl)-2-fluoroaniline (1l) (0.194 g, 0.598 mmol, 11.96% yield) as a colorless oil; $^1$H NMR (300 MHz, DMSO-d$_6$) δ 7.44-7.35 (m, 2H), 7.30-7.21 (m, 2H), 7.19-7.11 (m, 1H), 6.94-6.79 (m, 2H), 6.56 (ddd, J=8.2, 4.6, 2.1 Hz, 1H), 5.29 (td, J=5.9, 2.3 Hz, 1H), 4.72 (s, 1H), 2.94 (t, J=6.2 Hz, 2H), 2.38-2.20 (m, 3H), 1.10-0.97 (m, 1H), 0.91 (m, 1H), 0.40 (m, 4H), 0.21 (m, 2H), 0.03 (m, 2H); $^{19}$F NMR (282 MHz, DMSO) δ −137.78; MS (ES+) 325.3 (M+1); (ES−) 323.2 (M−1).

2. 5-((cyclopropylmethylamino)(phenyl)methyl)-2-fluoroaniline (1m) (0.795 g, 2.94 mmol, 58.8% yield) as a colorless oil; $^1$H NMR (300 MHz, DMSO-d$_6$) δ 7.40-7.33 (m, 2H), 7.27 (tt, J=6.6, 0.9 Hz, 2H), 7.20-7.12 (m, 1H), 6.90-6.78 (m, 2H), 6.54 (ddd, J=8.3, 4.5, 2.1 Hz, 1H), 5.04 (s, 2H), 4.67 (s, 1H), 2.34-2.22 (m, 3H), 0.91 (m, 1H), 0.44-0.30 (m, 2H), 0.09-0.00 (m, 2H); $^{19}$F NMR (282 MHz, DMSO) δ −137.95; MS (ES+) 271.2 (M+1).

Step-9: Preparation of (2R,4R)-1-(4-chlorophenylcarbamoyl)-4-hydroxypyrrolidine-2-carboxylic acid (1o)

To a stirred solution of Cis-hydroxy-D-proline (1 g, 7.63 mmol) in aqueous sodium bicarbonate (61.0 mL, 30.5 mmol, 0.5 molar) was added 4-chlorophenyl isocyanate (1n) (1.952 mL, 15.25 mmol) and heated at 80° C. for 5 h. The reaction was cooled to room temperature and solid obtained was filtered. The aqueous filtrate was washed with ethyl acetate, adjusted pH to 1 using conc. HCl and extracted with ethyl acetate (3×150 mL). The final extracted organic layers were combined washed with brine, dried and concentrated in vacuum to afford (2R,4R)-1-(4-chlorophenylcarbamoyl)-4-hydroxypyrrolidine-2-carboxylic acid (1o) (1.92 g, 6.74 mmol, 88% yield) as a colorless solid; $^1$H NMR (300 MHz, DMSO-d$_6$) δ 12.33 (s, 1H), 8.41 (s, 1H), 7.61-7.48 (m, 2H), 7.32-7.22 (m, 2H), 5.16 (bs, 1H), 4.32 (m, 2H), 3.65 (dd, J=10.2, 5.7 Hz, 1H), 3.31 (m, 1H), 2.32 (m, 1H), 1.90 (m, 1H); MS (ES+) 285.2 (M+1), 307.2 (M+Na), (ES−) 283.2 (M−1); Optical rotation: [α]$_D$=(+) 48.89 [0.27, MeOH].

Step-10: Preparation of (2R,4R)-N1-(4-chlorophenyl)-N2-(5-(((cyclopropylmethyl)amino)(phenyl)methyl)-2-fluorophenyl)-4-hydroxypyrrolidine-1,2-dicarboxamide (1p)

To a mixture of (2R,4R)-1-(4-chlorophenylcarbamoyl)-4-hydroxypyrrolidine-2-carboxylic acid (1o) (0.2 g, 0.703 mmol), 5-((cyclopropylmethylamino)(phenyl)methyl)-2-fluoroaniline (1m) (0.19 g, 0.703 mmol) in tetrahydrofuran (5 mL) was added ethyl 2-ethoxyquinoline-1(2H)-carboxylate (EEDQ, 0.174 g, 0.703 mmol) and stirred at room temperature overnight. The crude reaction mixture was concentrated in vacuum and the residue was purified by flash column chromatography (silica gel 24 g, eluting with 0-100% CMA 80 in chloroform) to afford (2R,4R)-N1-(4-chlorophenyl)-N2-(5-((cyclopropylmethylamino)(phenyl)methyl)-2-fluorophenyl)-4-hydroxypyrrolidine-1,2-dicarboxamide (1p) (65 mg, 0.121 mmol, 17.23% yield) as a white solid; $^1$H NMR (300 MHz, DMSO-d$_6$) δ 9.65-9.53 (m, 1H), 8.49 (s, 1H), 8.05 (d, J=7.5 Hz, 1H), 7.57-7.52 (m, 2H), 7.41-7.35 (m, 2H), 7.27 (dt, J=7.6, 3.2 Hz, 4H), 7.20-7.12 (m, 3H), 5.29 (d, J=4.7 Hz, 1H), 4.81 (s, 1H), 4.51 (dd, J=9.0, 4.6 Hz, 1H), 4.34 (q, J=4.8 Hz, 1H), 3.69 (dd, J=10.2, 5.6 Hz, 1H), 3.48 (dd, J=10.0, 3.9 Hz, 1H), 2.38 (ddd, J=18.8, 9.2, 4.7 Hz, 2H), 2.27 (d, J=6.6 Hz, 2H), 1.96-1.85 (m, 1H), 0.98-0.85 (m, 1H), 0.36 (dt, J=8.4, 2.8 Hz, 2H), 0.05 (dd, J=5.6, 4.0 Hz, 2H); $^{19}$F NMR (282 MHz, DMSO-d$_6$) δ −128.72 (d, J=2.9 Hz); MS (ES−) 535.4, 536.3, 537.4 (M, M−1, M−2); HPLC purity 93.5%.

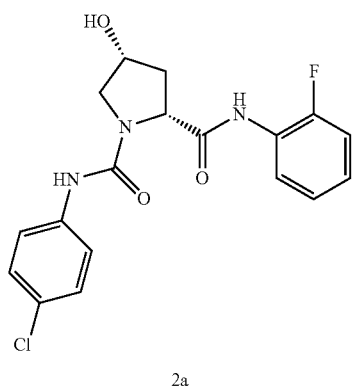

2a

Preparation of (2R,4R)-N1-(4-chlorophenyl)-N2-(2-fluorophenyl)-4-hydroxypyrrolidine-1,2-dicarboxamide (2a)

To a solution of (2R,4R)-1-(4-chlorophenylcarbamoyl)-4-hydroxypyrrolidine-2-carboxylic acid (1o) (0.2 g, 0.703 mmol), 2-fluoroaniline (0.078 g, 0.703 mmol) in tetrahydrofuran (5 mL) was added ethyl 2-ethoxyquinoline-1(2H)-carboxylate (0.174 g, 0.703 mmol) and stirred at room temperature overnight. The reaction mixture was concentrated in vacuum and the residue obtained was purified by flash column chromatography (silica gel 24 g, eluting with ethyl acetate in hexanes 0 to 100%) to afford (2R,4R)-N1-(4-chlorophenyl)-N2-(2-fluorophenyl)-4-hydroxypyrrolidine-1,2-dicarboxamide (2a) (140 mg, 0.371 mmol, 52.7% yield) as a colorless solid; $^1$H NMR (300 MHz, DMSO-d$_6$) δ 10.11 (s, 1H), 8.94 (s, 1H), 8.42 (m, 1H), 8.00 (m, 2H), 7.78-7.65 (m, 3H), 7.59 (m, 2H), 5.76 (d, J=4.4 Hz, 1H), 5.10-4.92 (m, 1H), 4.81 (m, 1H), 4.20-4.08 (m, 1H), 3.98 (m, 1H), 2.92-2.77 (m, 1H), 2.47-2.24 (m, 1H); $^{19}$F NMR (282 MHz, DMSO-d$_6$) δ −126.05; MS (ES+) 400.3 (M+Na), 777.4 (2M+Na), (ES−) 376.3 (M−1); HPLC purity 99.51%.

Scheme 2

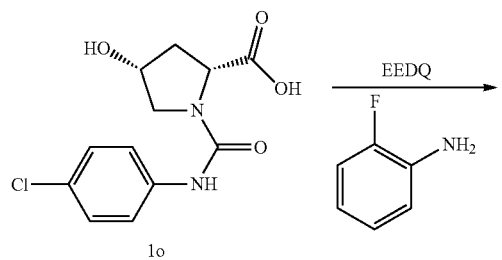

1o

Scheme 3

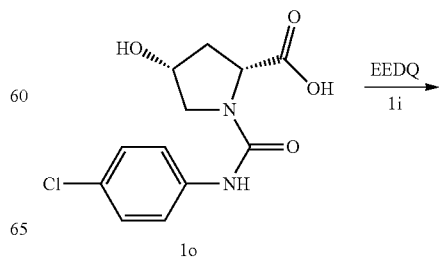

1o

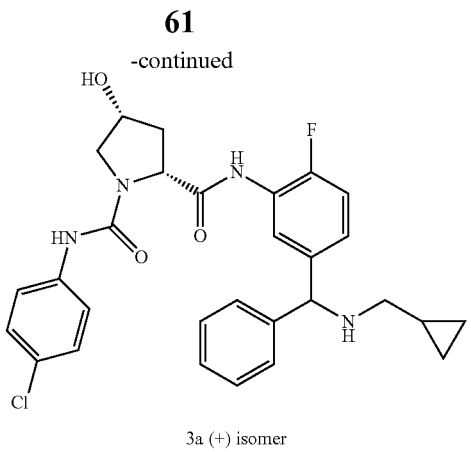

3a (+) isomer

Preparation of (2R,4R)-N1-(4-chlorophenyl)-N2-(5-((+)-(cyclopropylmethylamino)(phenyl) methyl)-2-fluorophenyl)-4-hydroxypyrrolidine-1,2-dicarboxamide (3a)

To a mixture of (2R,4R)-1-(4-chlorophenylcarbamoyl)-4-hydroxypyrrolidine-2-carboxylic acid (1o) (0.205 g, 0.721 mmol), (−)-5-((cyclopropylmethylamino)(phenyl)methyl)-2-fluoroaniline (1i) (0.195 g, 0.721 mmol) in tetrahydrofuran (5 mL) was added ethyl 2-ethoxyquinoline-1(2H)-carboxylate (0.178 g, 0.721 mmol) and stirred at room temperature overnight. The crude reaction mixture was concentrated in vacuum and the residue obtained was purified by flash column chromatography (silica gel 24 g, eluting with CMA 80 in chloroform afforded 0 to 100%) to afford (2R,4R)-N1-(4-chlorophenyl)-N2-(5-((+)-(cyclopropylmethylamino)(phenyl) methyl)-2-fluorophenyl)-4-hydroxypyrrolidine-1,2-dicarboxamide (3a) (25 mg, 0.047 mmol, 6.45% yield) as a white solid; $^1$H NMR (300 MHz, DMSO-$d_6$) δ 9.61 (s, 1H), 8.50 (s, 1H), 8.14-7.98 (m, 1H), 7.59-7.51 (m, 2H), 7.38 (m, 2H), 7.32-7.23 (m, 4H), 7.21-7.09 (m, 3H), 5.30 (d, J=4.8 Hz, 1H), 4.80 (s, 1H), 4.51 (dd, J=9.0, 4.7 Hz, 1H), 4.34 (q, J=4.8 Hz, 1H), 3.69 (dd, J=10.0, 5.2 Hz, 1H), 3.48 (dd, J=10.0, 4.1 Hz, 1H), 2.39 (m, 2H), 2.27 (d, J=6.7 Hz, 2H), 1.90 (m, 1H), 0.90 (m, 1H), 0.43-0.30 (m, 2H), 0.06-0.02 (m, 2H); $^{19}$F NMR (282 MHz, DMSO-d6) δ −128.88; Mass spec (ES+) 537.4, 539.5 (M,M+2), (ES−) 537.3, 535.4 (M, M−2); HPLC purity 96.99%; Optical rotation: $[\alpha]_D$=(+) 132 [0.2, MeOH].

Scheme 4

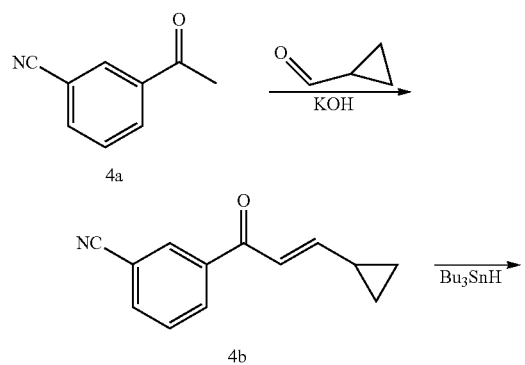

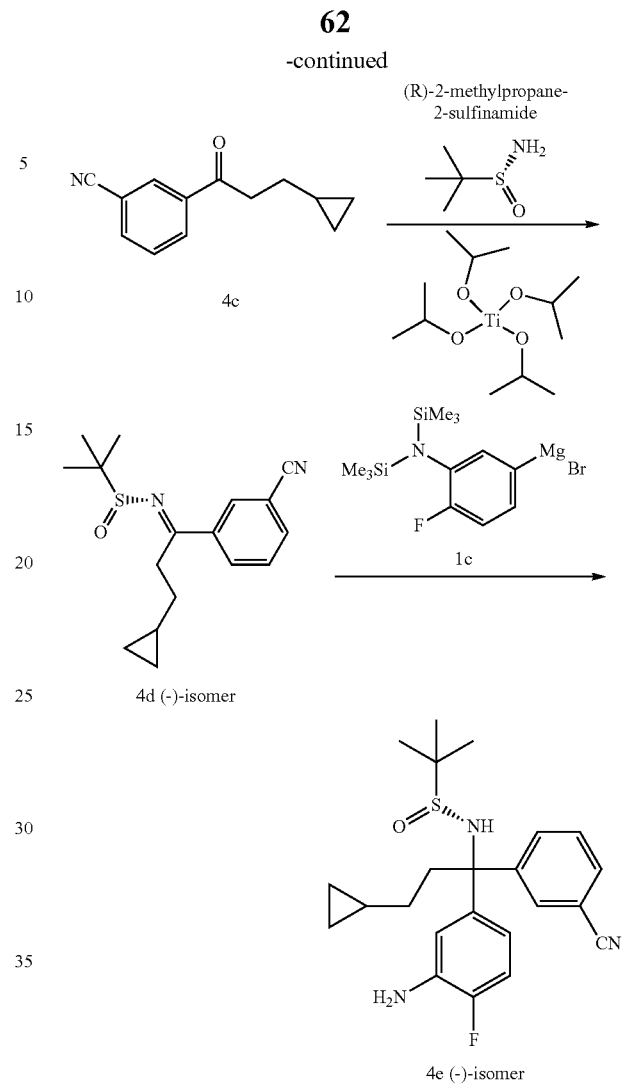

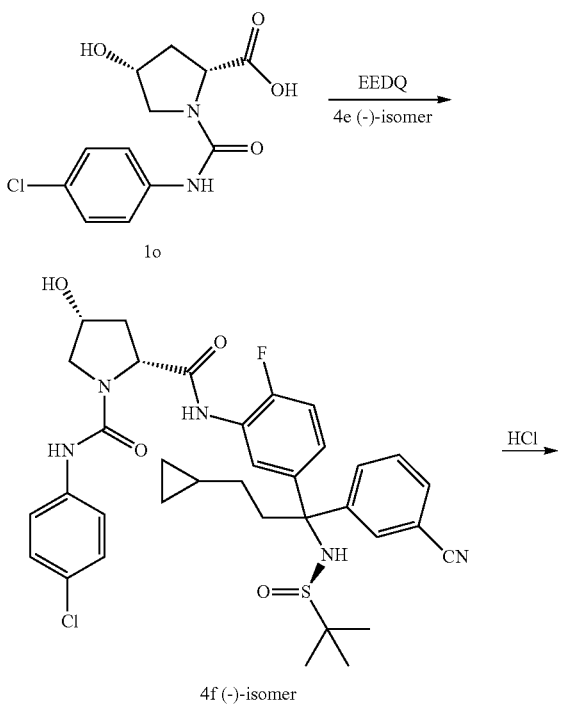

-continued

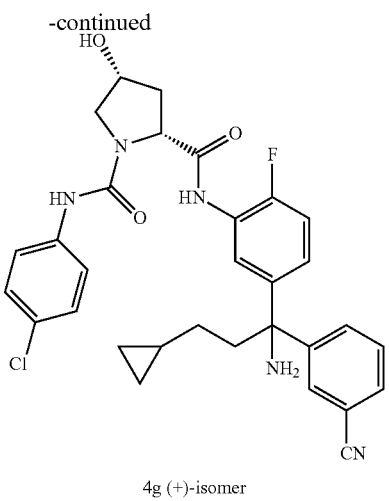

4g (+)-isomer

Preparation of (2R,4R)-N2-(5-((+)-1-amino-1-(3-cyanophenyl)-3-cyclopropylpropyl)-2-fluorophenyl)-N1-(4-chlorophenyl)-4-hydroxypyrrolidine-1,2-dicarboxamide (4g)

Step: 1 Preparation of 3-(3-cyclopropylacryloyl)benzonitrile (4b)

To a stirred solution of 3-acetylbenzonitrile (4a) (50 g, 344 mmol) in methanol (800 mL) at 0° C. was added cyclopropanecarboxaldehyde (41 mL, 549 mmol) followed by potassium hydroxide (1M aqueous solution, 67 mL, 67 mmol). The reaction mixture allowed to attain room temperature and stirred for 14 h. The reaction was acidified with HCl to pH-6 (75 mL, 1N) and concentrated in vacuum maintaining bath temperature below 35° C. The residue was diluted with ethyl acetate (1200 mL) and washed with water (800 mL). The aqueous layer was extracted with ethyl acetate (800 mL) and organic layers were combined washed with brine, dried, filtered and concentrated in vacuum to afford 3-(3-cyclopropylacryloyl)benzonitrile (4b) (72.42 gm) crude as a colorless liquid, which was used as such in next step; $^1$H NMR (300 MHz, DMSO-$d_6$) δ 8.19 (dp, J=7.8, 1.6 Hz, 1H), 8.11 (dddt, J=6.3, 3.7, 2.6, 1.4 Hz, 1H), 7.80-7.65 (m, 2H), 7.32 (dd, J=15.1, 7.6 Hz, 1H), 6.60 (ddd, J=15.0, 11.3, 10.4 Hz, 1H), 1.91-1.74 (m, 1H), 1.04 (m, 2H), 0.85-0.75 (m, 2H).

Step 2: Preparation of 3-(3-cyclopropylpropanoyl)benzonitrile (4c)

To a stirred solution of 3-(3-cyclopropylacryloyl)benzonitrile (4b) (65.7 g, 333 mmol) in benzene (750 mL) was added tri-n-butyltin hydride (185 mL, 666 mmol) and heated at reflux for 14 h. The reaction mixture was cooled to room temperature and concentrated in vacuum. The residue was purified by flash column chromatography (silica gel eluting with ethyl acetate in hexanes 0 to 100%) to afford 3-(3-cyclopropylpropanoyl)benzonitrile (4c) (23.3, 116.9 mmol, 34% yield) as a colorless oil; $^1$H NMR (300 MHz, DMSO-$d_6$) δ 8.41 (td, J=1.8, 0.6 Hz, 1H), 8.24 (ddd, J=7.9, 1.8, 1.2 Hz, 1H), 8.09 (dt, J=7.7, 1.4 Hz, 1H), 7.73 (td, J=7.8, 0.6 Hz, 1H), 3.15 (t, J=7.2 Hz, 2H), 1.52 (q, J=7.1 Hz, 2H), 0.81-0.64 (m, 1H), 0.46-0.26 (m, 2H), 0.13-0.00 (m, 2H); MS (ES−) 198.2 (M−1).

Step-3: Preparation of (−)-N-(1-(3-cyanophenyl)-3-cyclopropylpropylidene)-2-methylpropane-2-sulfinamide (4d)

Compound (4d) was prepared from 3-(3-cyclopropylpropanoyl)benzonitrile (4c) (22.8 g, 114 mmol) and (R)-2-methylpropane-2-sulfinamide (13.95 g, 114 mmol), using procedure as reported in step 3 of Scheme 1 to afford (−)-N-(1-(3-cyanophenyl)-3-cyclopropylpropylidene)-2-methylpropane-2-sulfinamide (4d) (21.8 g, 72.1 mmol, 63% yield) as a light yellow syrup;
$^1$H NMR (300 MHz, DMSO-$d_6$) δ 8.29 (s, 1H), 8.21-8.12 (m, 1H), 8.01 (d, J=7.7 Hz, 1H), 7.70 (t, J=7.9 Hz, 1H), 3.54-3.13 (m, 2H), 1.44 (q, J=7.5 Hz, 2H), 1.23 (s, 9H), 0.82-0.65 (m, 1H), 0.44-0.29 (m, 2H), 0.11-0.00 (m, 2H); MS (ES+) 303.3 (M+1); (ES−) 301.3 (M−1); Optical rotation: $[α]_D$ (−) 66.92 (0.26, MeOH).

Step-4: Preparation of (R)-N-((−)-1-(3-amino-4-fluorophenyl)-1-(3-cyanophenyl)-3-cyclopropylpropyl)-2-methylpropane-2-sulfinamide (4e)

To a stirred solution of (−)-N-(1-(3-cyanophenyl)-3-cyclopropylpropylidene)-2-methylpropane-2-sulfinamide (4d) (17.72 g, 58.6 mmol) in toluene (350 mL) at −20° C. was added dropwise a freshly prepared solution of (3-(bis(trimethylsilyl)amino)-4-fluorophenyl)magnesium bromide (1c) (160 mL, 120 mmol, 0.75N) over a period of 30 mins. The reaction mixture was stirred at −20° C. for 1 h and quenched with 1N aqueous KHSO$_4$ (275 mL). The reaction mixture was stirred for 1 h at room temperature, diluted with water (100 mL) basified with 2N NaOH to pH 8 and extracted with ethyl acetate (600 mL, 300 mL). The organic layers were combined washed with water (2×300 mL), brine (300 mL), dried and concentrated in vacuum to dryness. The crude residue was triturated with ethyl acetate and solid obtained was collected by filtration to obtain on drying under vacuum (R)-N-((−)-1-(3-amino-4-fluorophenyl)-1-(3-cyanophenyl)-3-cyclopropylpropyl)-2-methylpropane-2-sulfinamide (4e) (10.4 g, 42.91% yield) as a white solid. The filtrate was concentrated in vacuum and purified by flash column chromatography (silica gel, eluting with ethyl acetate in hexanes 0 to 50%) to (R)-N-((−)-1-(3-amino-4-fluorophenyl)-1-(3-cyanophenyl)-3-cyclopropylpropyl)-2-methylpropane-2-sulfinamide (4e) (4.11 g, 16.95% yield) as a white solid; $^1$H NMR (300 MHz, DMSO-$d_6$) δ 7.78 (t, J=1.6 Hz, 1H), 7.70 (dt, J=7.5, 1.4 Hz, 1H), 7.62 (dt, J=8.1, 1.5 Hz, 1H), 7.50 (t, J=7.8 Hz, 1H), 6.90 (dd, J=11.3, 8.5 Hz, 1H), 6.72 (dd, J=8.7, 2.4 Hz, 1H), 6.47 (ddd, J=8.5, 4.3, 2.4 Hz, 1H), 5.27 (s, 1H), 5.10 (s, 2H), 2.66-2.40 (m, 2H), 1.20-1.03 (m, 1H), 1.12 (s, 9H), 1.01-0.81 (m, 1H), 0.72-0.57 (m, 1H), 0.36 (m, 2H), 0.03-0.15 (m, 2H); 19F NMR (282 MHz, DMSO-$d_6$) δ −137.34; MS (ES+): 436.4 (M+Na); IR (KBr) 2235 cm$^1$; Optical rotation: $[α]_D$ (−) 107.95 (0.78, MeOH); Analysis calculated for $C_{23}H_{28}FN_3OS$: C, 66.80; H, 6.82; N, 10.16. Found: C, 67.06; H, 6.82; N, 10.28.

Step-5: Preparation of (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (4f)

To a mixture of (2R,4R)-1-(4-chlorophenylcarbamoyl)-4-hydroxypyrrolidine-2-carboxylic acid (1o) (0.2 g, 0.703 mmol), (R)-N-((−)-1-(3-amino-4-fluorophenyl)-1-(3-cyanophenyl)-3-cyclopropylpropyl)-2-methylpropane-2-sulfinamide (4e) (0.291 g, 0.703 mmol) in tetrahydrofuran (5 mL) was added ethyl 2-ethoxyquinoline-1(2H)-carboxylate (0.174 g, 0.703 mmol) and heated at reflux for 16 h. The reaction mixture was concentrated in vacuum and residue obtained was purified by flash column chromatography (silica gel 24 g, eluting with CMA 80 in chloroform afforded 0 to 100%) to afford (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (4f) (175 mg, 0.257 mmol, 36.6% yield) as a white solid; $^1$H NMR (300 MHz, DMSO-$d_6$) δ 9.66 (s, 1H), 8.52 (s, 1H), 8.07 (m, 1H), 7.79 (m, 1H), 7.71 (m, 1H), 7.61-7.47 (m, 4H), 7.31-7.24 (m, 2H), 7.19 (m, 1H), 7.08 (m, 1H), 5.50 (s, 1H), 5.33 (d, J=4.7 Hz, 1H), 4.51 (dd, J=9.0, 4.7 Hz, 1H), 4.34 (d, J=5.4 Hz, 1H), 3.68 (dd, J=10.0, 5.2 Hz, 1H), 3.49 (dd, J=10.0, 3.9 Hz, 1H), 2.78-2.53 (m, 2H), 2.38 (s, 1H), 1.90 (m, 1H), 1.13 (s, 10H), 0.90 (m, 1H), 0.63 (m, 1H), 0.34 (m, 2H), −0.03–−0.19 (m, 2H); $^9$F NMR (282 MHz, DMSO-$d_6$) δ −128.58; MS (ES+) 680.5 (M+1), 702.5, 704.5 (M+Cl), (ES−) 714.4, 716.5 (M+Cl); IR (KBr) 2231 cm-1; Optical rotation: $[α]_D$=(−) 19.4 [0.175, MeOH].

Step 6: Preparation of (2R,4R)-N2-(5-((+)-1-amino-1-(3-cyanophenyl)-3-cyclopropylpropyl)-2-fluorophenyl)-N1-(4-chlorophenyl)-4-hydroxypyrrolidine-1,2-dicarboxamide (4g)

To a stirred solution of (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (4f) (160 mg, 0.235 mmol) in Ethanol (10 mL) was added conc. HCl (0.098 mL, 1.176 mmol) and heated at reflux for 1 h. The reaction was concentrated in vacuum and residue obtained was purified by flash column chromatography (silica gel 12 g, eluting with 0-100% CMA 80 in chloroform) to afford (2R,4R)-N2-(5-((+)-1-amino-1-(3-cyanophenyl)-3-cyclopropylpropyl)-2-fluorophenyl)-N1-(4-chlorophenyl)-4-hydroxypyrrolidine-1,2-dicarboxamide (4g) (42 mg, 0.073 mmol, 31.0% yield) as a colorless solid; $^1$H NMR (300 MHz, DMSO-$d_6$) δ 9.61 (d, J=1.6 Hz, 1H), 8.50 (s, 1H), 8.08-7.99 (m, 1H), 7.86 (m, 1H), 7.63 (m, 2H), 7.59-7.51 (m, 2H), 7.46 (m, 1H), 7.32-7.23 (m, 2H), 7.12 (m, 2H), 5.30 (d, J=4.8 Hz, 1H), 4.50 (dd, J=9.1, 4.7 Hz, 1H), 4.34 (q, J=4.8 Hz, 1H), 3.68 (dd, J=10.1, 5.3 Hz, 1H), 3.48 (dd, J=10.1, 4.0 Hz, 1H), 2.46-2.28 (m, 3H), 2.27-2.16 (m, 2H), 1.90 (m, 1H), 1.02 (m, 2H), 0.70-0.56 (m, 1H), 0.34 (m, 2H), −0.08 (m, 2H); $^{19}$F NMR (282 MHz, DMSO-$d_6$) δ −129.29; MS (ES−) 575.3 (M−1); HPLC purity 94.3%; Analysis calculated for $C_{31}H_{31}ClFN_5O_3 \cdot 0.5H_2O$: C, 63.64; H, 5.51; N, 11.97. Found: C, 63.68; H, 5.75; N, 11.77; Optical rotation: $[α]_D$= (+) 93.53 [0.34, MeOH].

Scheme 5

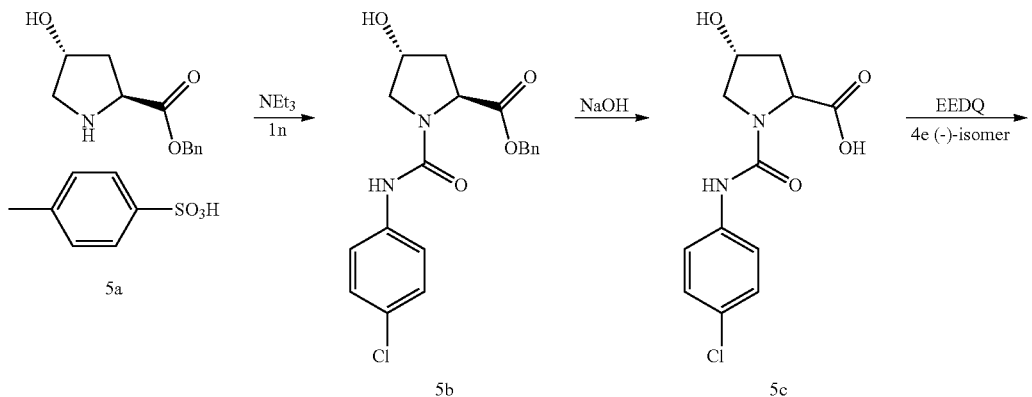

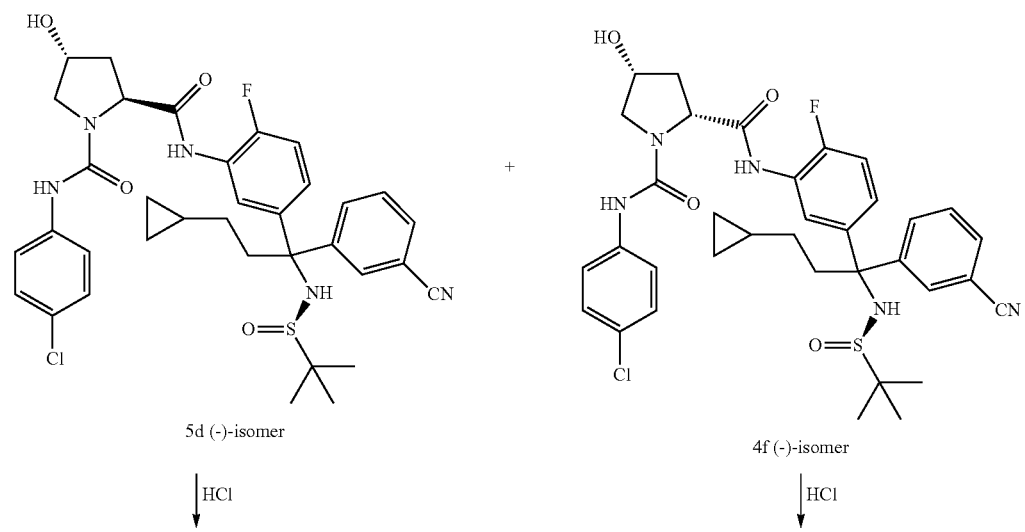

5d (−)-isomer 4f (−)-isomer

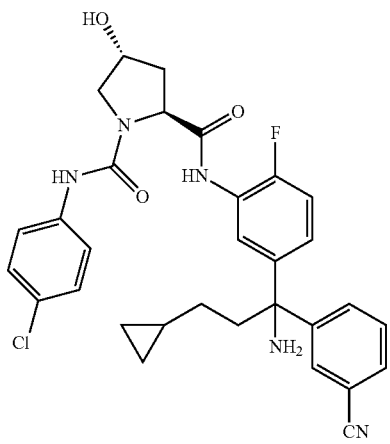

5e (−)-isomer

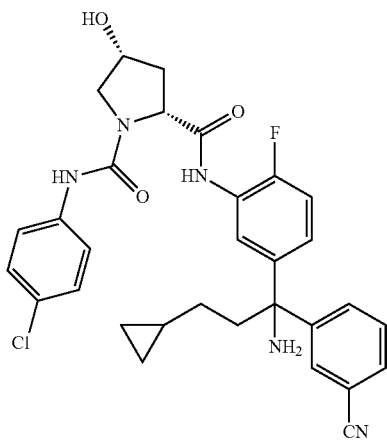

4g (+)-isomer

Preparation of (2S,4R)-N2-(5-((−)-1-amino-1-(3-cyanophenyl)-3-cyclopropylpropyl)-2-fluorophenyl)-N1-(4-chlorophenyl)-4-hydroxypyrrolidine-1,2-dicarboxamide (5e)

Step-1: Preparation of (2S,4R)-benzyl 1-(4-chlorophenylcarbamoyl)-4-hydroxypyrrolidine-2-carboxylate (5b)

Diisopropylethylamine (1.918 mL, 10.98 mmol) was dropped to a suspension of (2S,4R)-benzyl 4-hydroxypyrrolidine-2-carboxylate 4-methylbenzenesulfonate (5a) (4.32 g, 10.98 mmol) in anhydrous Dichloromethane (100 mL) stirred at room temperature for 10 mins followed by the addition of 1-chloro-4-isocyanatobenzene (1n) (1.686 g, 10.98 mmol). The reaction mixture was stirred at room temperature for 2 h and poured into water (50 mL). The solid separated was collected by filtration to furnish (2S,4R)-benzyl 1-(4-chlorophenylcarbamoyl)-4-hydroxypyrrolidine-2-carboxylate (5b) as a white solid. The filtrate was extracted with dichloromethane (3×50 mL), the organic layers was combined, washed with brine (50 mL), dried over anhydrous magnesium sulphate, filtered and concentrated in vacuum. The residue was combined with filtered solid to obtain (2S,4R)-benzyl 1-(4-chlorophenylcarbamoyl)-4-hydroxypyrrolidine-2-carboxylate (5b) (4.7 g, 12.54 mmol) as a white solid; $^1$H NMR (300 MHz, DMSO-$d_6$) δ 8.54 (s, 1H), 7.61-7.45 (m, 2H), 7.37-7.31 (m, 5H), 7.31-7.25 (m, 2H), 5.21 (d, J=4.0 Hz, 1H), 5.19-5.06 (m, 2H), 4.47 (t, J=7.8 Hz, 1H), 4.37 (m, 1H), 3.63 (dd, J=10.5, 4.6 Hz, 1H), 3.49-3.39 (m, 1H), 2.15 (m, 1H), 1.94 (m, 1H); MS (ES+) 375.4 (M+1), 397.4 (M+Na), 749.6 (2M+1), 771.6 (2M+Na), (ES−) 373.3 (M−1), 419.3 (M+Cl); Optical rotation: [α]$_D$=(−) 70.08 [0.625, MeOH].

Step-2: Preparation of (4R)-1-(4-chlorophenylcarbamoyl)-4-hydroxypyrrolidine-2-carboxylic acid (5c)

To a stirred solution of (2S,4R)-benzyl 1-(4-chlorophenylcarbamoyl)-4-hydroxypyrrolidine-2-carboxylate (5b) (3 g, 8.00 mmol) in methanol (30 mL) was added at room temperature sodium hydroxide (1.601 g, 40.0 mmol) and stirred for 2 h. The reaction was concentrated in vacuum to remove methanol. The residue was dissolved in water (10 mL) and washed with ethyl acetate (2×20 mL). The aqueous layer was acidified with conc HCl to pH 2, extracted with ethyl acetate (3×75 mL). The organic layers were combined washed with water (2×50 mL), brine (50 mL), dried, filtered and concentrated in vacuum to afford (4R)-1-(4-chlorophenylcarbamoyl)-4-hydroxypyrrolidine-2-carboxylic acid (5c) (1 g, 3.51 mmol, 43.9% yield) as a white solid; $^1$H NMR (300 MHz, DMSO-$d_6$) δ 12.21 (s, 1H), 8.45 (2s, 1H), 7.61-7.42 (m, 2H), 7.37-7.21 (m, 2H), 5.17 (d, J=3.9 Hz, 1H), 4.32 (m, 2H), 3.63 (m, 1H), 3.34-3.21 (m, 1H), 2.31 (m, 1H), 2.22-2.00 (m, 1H); MS (ES+) 285.2 (M+1), 307.1 (M+Na), (ES−) 283.1 (M−1).

Step-3: Preparation of (2S,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (5d) and (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (4f)

Reaction of (4R)-1-(4-chlorophenylcarbamoyl)-4-hydroxypyrrolidine-2-carboxylic acid (5c) (550 mg, 1.932 mmol) with (R)-N-((−)-1-(3-amino-4-fluorophenyl)-1-(3-cyanophenyl)-3-cyclopropylpropyl)-2-methylpropane-2-sulfinamide (4e) (799 mg, 1.932 mmol) in tetrahydrofuran (5 mL) using ethyl 2-ethoxyquinoline-1(2H)-carboxylate (478 mg, 1.932 mmol) as reported in step 5 of Scheme 4 gave after purification by flash column chromatography (silica gel 24 g, eluting with CMA 80 in chloroform afforded 0 to 100%)
1. (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (4f) (267 mg, 0.393 mmol, 20.32% yield) as a white solid, followed by.
2. (2S,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (5d) (203 mg, 0.298 mmol, 15.45% yield) as a light orange solid; $^1$H NMR (300 MHz, DMSO-$d_6$) δ 9.84 (s, 1H), 8.48 (s, 1H), 7.94 (d, J=7.4 Hz, 1H), 7.77 (d, J=1.9 Hz, 1H), 7.70 (dt, J=7.3, 1.5 Hz, 1H), 7.52 (m, 4H), 7.31-7.23 (m, 2H), 7.19 (m, 1H), 7.09 (m, 1H), 5.49 (s, 1H), 5.18 (d, J=3.7 Hz, 1H), 4.66 (t, J=7.5 Hz, 1H), 4.39 (s, 1H), 3.67 (m, 1H), 3.47-3.37 (m, 1H), 2.68-2.54 (m, 2H), 2.17-2.05 (m, 1H), 2.06-1.87 (m, 1H), 1.11 (s, 10H), 0.89 (m, 1H), 0.72-0.49 (m, 1H), 0.33 (m, 2H), −0.02−−0.20 (m, 2H); $^{19}$F NMR (282 MHz, DMSO-$d_6$) δ −127.00; MS (ES−) 678.4, 679.5 (M−1); Optical rotation $[α]_D$=(−) 190 [0.08, MeOH].

Step-4: Preparation of (2S,4R)-N2-(5-((−)-1-amino-1-(3-cyanophenyl)-3-cyclopropylpropyl)-2-fluorophenyl)-N1-(4-chlorophenyl)-4-hydroxypyrrolidine-1,2-dicarboxamide (5e)

Reaction of (2 S,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (5d) (183 mg, 0.269 mmol) in ethanol (5 mL) using Conc. HCl (0.224 mL, 2.69 mmol) as reported in Scheme 4 step 6 gave after purification by flash column chromatography (silica gel, 12 g eluting with 0 to 30% CMA 80 in chloroform) (2S,4R)-N2-(5-((−)-1-amino-1-(3-cyanophenyl)-3-cyclopropylpropyl)-2-fluorophenyl)-N1-(4-chlorophenyl)-4-hydroxypyrrolidine-1,2-dicarboxamide (5e) (100 mg, 0.174 mmol, 64.5% yield) as a colorless solid; $^1$H NMR (300 MHz, DMSO-$d_6$) δ 9.77 (s, 1H), 8.47 (s, 1H), 7.94 (d, J=7.5 Hz, 1H), 7.86 (t, J=1.7 Hz, 1H), 7.66-7.58 (m, 2H), 7.57-7.51 (m, 2H), 7.45 (t, J=7.8 Hz, 1H), 7.31-7.24 (m, 2H), 7.15-7.08 (m, 2H), 5.17 (d, J=3.8 Hz, 1H), 4.65 (t, J=7.5 Hz, 1H), 4.40 (s, 1H), 3.67 (dd, J=10.3, 4.6 Hz, 1H), 3.43 (m, 1H), 2.30 (m, 2H), 2.25-2.07 (m, 3H), 2.03-1.89 (m, 1H), 1.09-0.93 (m, 2H), 0.62 (m, 1H), 0.38-0.28 (m, 2H), −0.04−−0.14 (m, 2H); $^{19}$F NMR (282 MHz, DMSO-$d_6$) δ −127.76; MS (ES+) 598.4, 600.4 (M+Na); HPLC: 5.12 min. (93.86%); Optical rotation $[α]_D$=(−) 96.05 [0.86, MeOH].

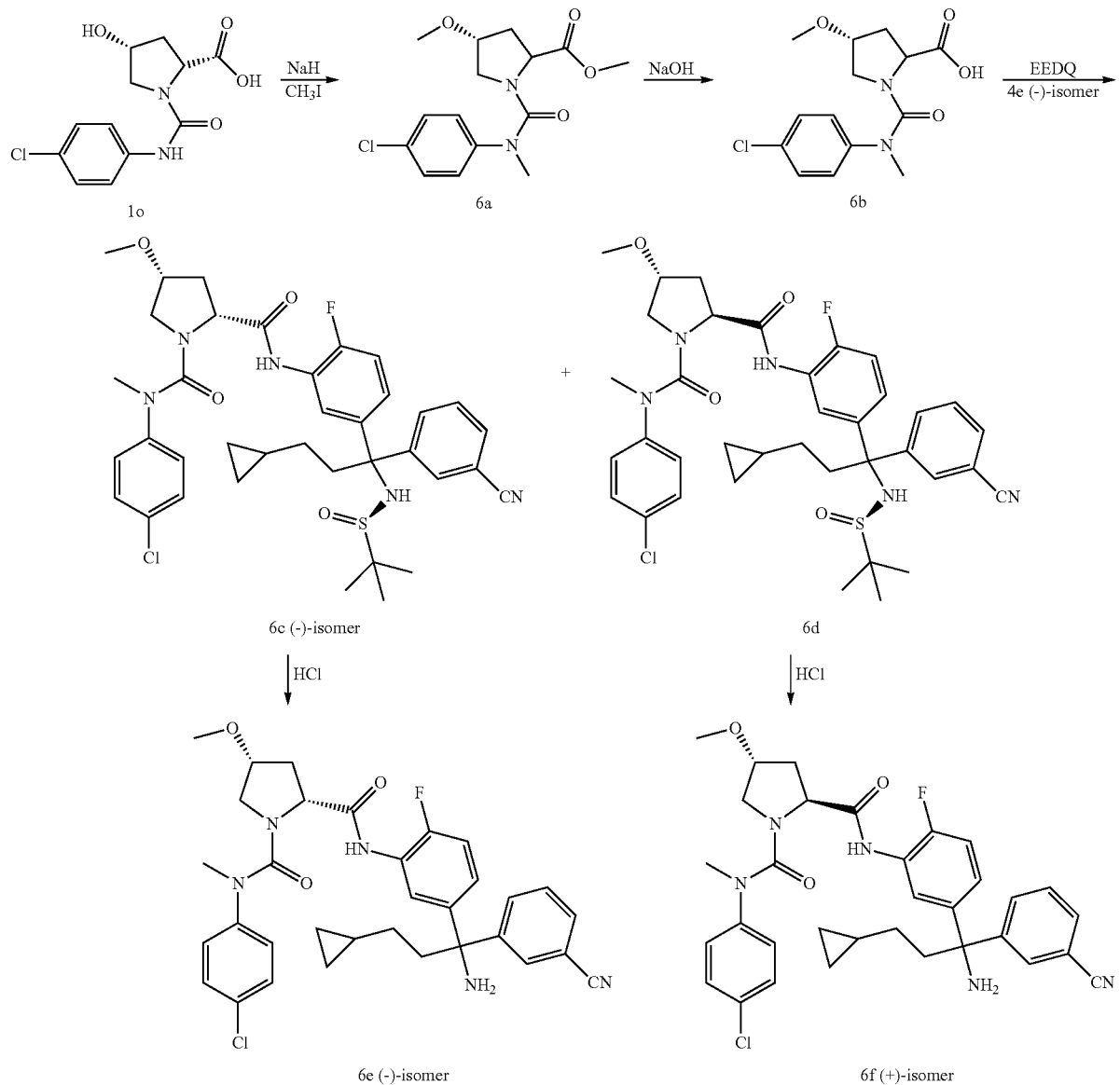

Scheme 6

Preparation of (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-methoxy-N1-methylpyrrolidine-1,2-dicarboxamide (6c) and (2S,4R)-N1-(4-chlorophenyl)-N2-(5-(1-(3-cyanophenyl)-3-cyclopropyl-1-((R)-1,1-dimethylethylsulfinamido)propyl)-2-fluorophenyl)-4-methoxy-N1-methylpyrrolidine-1,2-dicarboxamide (6d)

Step-1: Preparation of (4R)-methyl 1-((4-chlorophenyl)(methyl)carbamoyl)-4-methoxypyrrolidine-2-carboxylate (6a)

To a stirred solution of (2R,4R)-1-(4-chlorophenylcarbamoyl)-4-hydroxypyrrolidine-2-carboxylic acid (1o) (0.837 g, 2.94 mmol) in N,N-Dimethylformamide (20 mL) at 0° C. was added sodium hydride (60% dispersion in mineral oil, 0.941 g, 23.52 mmol) and stirred at 0° C. for 1 h. To the reaction mixture was added at 0° C. methyl iodide (1.471 mL, 23.52 mmol) and stirred for 2 h. The reaction was quenched by adding 1N aqueous $KHSO_4$ (15 mL), water (100 mL) and extracted with ethyl acetate (3×100 mL). The organic layers were combined washed with water (2×50 mL), brine (50 mL), dried, filtered and concentrated in vacuum. The crude residue was purified by flash column chromatography [silica gel 40 g, eluting with a (9:1) ethyl acetate and methanol in hexanes 0 to 40%] to afford ((4R)-methyl 1-((4-chlorophenyl)(methyl)carbamoyl)-4-methoxypyrrolidine-2-carboxylate (6a) (250 mg, 0.765 mmol, 26.0% yield) was used in the next reaction; $^1$H NMR (300 MHz, DMSO-$d_6$) δ 7.49-7.40 (m, 2H), 7.37-7.30 (m, 2H), 4.54-4.30 (m, 1H), 3.90-3.74 (m, 1H), 3.67 (d, J=4.7 Hz, 3H), 3.29-3.18 (m, 1H), 3.11 (2s, 3H), 3.06 (2s, 3H), 2.70-2.21 (m, 2H), 1.80-1.60 (m, 1H); MS (ES+) 349.3 (M+1).

Step-2: Preparation of ((4R)-1-((4-chlorophenyl)(methyl)carbamoyl)-4-methoxypyrrolidine-2-carboxylic acid (6b)

To a stirred solution of (4R)-methyl 1-((4-chlorophenyl)(methyl)carbamoyl)-4-methoxypyrrolidine-2-carboxylate (6a) (250 mg, 0.765 mmol) in methanol (10 mL) was added at room temperature sodium hydroxide (0.765 mL, 3.06 mmol, 4N aqueous), stirred at room temperature overnight and concentrated in vacuum to remove methanol. The residue was dissolved in water (30 mL), acidified with 1N $KHSO_4$ and extracted with ethyl acetate (3×50 mL). The organic layers were combined washed with water (20 mL), brine (20 mL), dried, filtered and concentrated in vacuum to afford ((4R)-1-((4-chlorophenyl)(methyl)carbamoyl)-4-methoxypyrrolidine-2-carboxylic acid (6b) (230 mg, 0.735 mmol, 96% yield) as white solid; $^1$H NMR (300 MHz, DMSO-$d_6$) δ 12.64 (s, 1H), 7.47-7.31 (m, 4H), 4.40-4.24 (m, 1H), 3.90-3.73 (m, 1H), 3.33-3.16 (m, 1H), 3.11 (2s, 3H), 3.08 (2s, 3H), 2.50-2.19 (m, 2H), 1.80-1.57 (m, 1H); MS (ES+) 313.3, (ES−) 311.2 (M−1).

Step-3: Preparation of (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-methoxy-N1-methylpyrrolidine-1,2-dicarboxamide (6c) and (2S,4R)-N1-(4-chlorophenyl)-N2-(5-(1-(3-cyanophenyl)-3-cyclopropyl-1-((R)-1,1-dimethylethylsulfinamido)propyl)-2-fluorophenyl)-4-methoxy-N1-methylpyrrolidine-1,2-dicarboxamide (6d)

To a mixture of ((4R)-1-((4-chlorophenyl)(methyl)carbamoyl)-4-methoxypyrrolidine-2-carboxylic acid (6b) (230 mg, 0.735 mmol), (R)-N-((−)-1-(3-amino-4-fluorophenyl)-1-(3-cyanophenyl)-3-cyclopropylpropyl)-2-methylpropane-2-sulfinamide (4e) (304 mg, 0.735 mmol) in tetrahydrofuran (5 mL) was added ethyl 2-ethoxyquinoline-1(2H)-carboxylate (EEDQ, 182 mg, 0.735 mmol) and heated at reflux for 16 h. The reaction mixture was concentrated in vacuum and the residue obtained was purified by flash column chromatography (silica gel 40 g, eluting with CMA 80 in chloroform, 0 to 100%) to obtain:

1. (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-methoxy-N1-methylpyrrolidine-1,2-dicarboxamide (6c) (279 mg, 0.394 mmol, 53.6% yield) as a white solid; $^1$H NMR (300 MHz, DMSO-$d_6$) δ 9.89 (s, 1H), 8.02 (d, J=7.1 Hz, 1H), 7.80 (d, J=1.8 Hz, 1H), 7.73 (dt, J=7.4, 1.3 Hz, 1H), 7.66-7.58 (m, 1H), 7.54 (d, J=7.7 Hz, 1H), 7.40 (s, 4H), 7.21 (dd, J=10.5, 8.8 Hz, 1H), 7.17-7.05 (m, 1H), 5.55 (s, 1H), 4.75-4.56 (m, 1H), 3.80 (s, 1H), 3.16 (s, 3H), 3.09 (s, 3H), 3.03 (d, J=11.2 Hz, 1H), 2.78-2.67 (m, 2H), 2.66-2.54 (m, 1H), 2.47-2.23 (m, 1H), 1.82-1.61 (m, 1H), 1.15 (d, J=1.4 Hz, 9H), 1.14-1.00 (m, 1H), 1.04-0.76 (m, 1H), 0.66 (m, 1H), 0.36 (m, 2H), 0.08--0.11 (m, 2H); $^{19}$F NMR (282 MHz, DMSO-$d_6$) δ −126.84; MS (ES+) 708.6 (M+1), 730.6, 732.6 (M+Cl), (ES−) 706.6, 708.6 (M−1).

2. (2S,4R)-N1-(4-chlorophenyl)-N2-(5-(1-(3-cyanophenyl)-3-cyclopropyl-1-((R)-1,1-dimethylethylsulfinamido)propyl)-2-fluorophenyl)-4-methoxy-N1-methylpyrrolidine-1,2-dicarboxamide (6d) (200 mg, 0.282 mmol, 38.4% yield) as a white solid: $^1$H NMR (300 MHz, DMSO-d6) δ 9.73 (s, 1H), 7.95 (d, J=7.3 Hz, 1H), 7.81 (t, J=1.7 Hz, 1H), 7.72 (dt, J=7.4, 1.3 Hz, 1H), 7.62 (d, J=8.3 Hz, 1H), 7.54 (d, J=7.7 Hz, 1H), 7.40 (s, 4H), 7.22 (dd, J=10.4, 8.7 Hz, 1H), 7.14 (m, 1H), 5.56 (s, 1H), 4.58 (t, J=8.4 Hz, 1H), 3.94-3.79 (m, 1H), 3.29 (m, 1H), 3.10 (s, 3H), 3.08 (s, 3H), 2.73 (m, 2H), 2.57 (m, 1H), 2.43 (m, 1H), 1.74-1.50 (m, 1H), 1.28-1.16 (m, 1H), 1.15 (2s, 9H), 0.99-0.78 (m, 1H), 0.66 (m, 1H), 0.37 (m, 2H), 0.10--0.11 (m, 2H); $^{19}$F NMR (282 MHz, DMSO-d6) δ −127.21; MS (ES+) 708.6 (M+1), 730.6, 732.6 (M+Cl), (ES−) 706.6, 708.6 (M−1).

Preparation of (2R,4R)-N2-(5-((−)-1-amino-1-(3-cyanophenyl)-3-cyclopropylpropyl)-2-fluorophenyl)-N1-(4-chlorophenyl)-4-methoxy-N1-methylpyrrolidine-1,2-dicarboxamide (6e)

Reaction of (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-methoxy-N1-methylpyrrolidine-1,2-dicarboxamide (6c) (170 mg, 0.240 mmol) in ethanol (5 mL) using conc. HCl (0.200 mL, 2.400 mmol) as reported in Scheme 4 step 6 for preparation of compound 4g gave after purification by flash column chromatography (silica gel, 12 g eluting with 0 to 30% CMA 80 in chloroform) (2R,4R)-N2-(5-((−)-1-amino-1-(3-cyanophenyl)-3-cyclopropylpropyl)-2-fluorophenyl)-N1-(4-chlorophenyl)-4-methoxy-N1-methylpyrrolidine-1,2-dicarboxamide (6e) (115 mg, 0.190 mmol, 79% yield) as a white solid; $^1$H NMR (300 MHz, DMSO-$d_6$) δ 9.65 (s, 1H), 7.94 (d, J=7.7 Hz, 1H), 7.89 (t, J=1.7 Hz, 1H), 7.66 (ddt, J=10.3, 7.7, 1.4 Hz, 2H), 7.49 (d, J=7.9 Hz, 1H), 7.46-7.34 (m, 4H), 7.19-7.12 (m, 2H), 4.56 (t, J=8.3 Hz, 1H), 3.93-3.77 (m, 1H), 3.10 (s, 3H), 3.08 (s, 3H), 2.61-2.39 (m, 2H), 2.36 (s, 2H), 2.31-2.14 (m, 2H), 1.72-1.52 (m, 1H), 1.13-0.97 (m, 2H), 0.77-0.57

(m, 1H), 0.42-0.27 (m, 2H), 3.42-3.19 (m, 1H), −0.00−−0.07 (m, 2H); $^{19}$F NMR (282 MHz, DMSO-$d_6$) δ −128.01; MS (ES+) 626.4, 628.4 (M+Na); HPLC purity 99.04%; Optical rotation $[α]_D$=(−) 142.49 [1.005, MeOH].

Preparation of (2S,4R)-N2-(5-((+)-1-amino-1-(3-cyanophenyl)-3-cyclopropylpropyl)-2-fluorophenyl)-N1-(4-chlorophenyl)-4-methoxy-N1-methylpyrrolidine-1,2-dicarboxamide (6f)

Reaction of (2S,4R)-N1-(4-chlorophenyl)-N2-(5-(1-(3-cyanophenyl)-3-cyclopropyl-1-((R)-1,1-dimethylethylsulfinamido)propyl)-2-fluorophenyl)-4-methoxy-N1-methylpyrrolidine-1,2-dicarboxamide (6d) (238 mg, 0.336 mmol) in ethanol (5 mL) using conc. HCl (0.280 mL, 3.36 mmol) as reported in Scheme 4 step 6 for preparation of compound 4g gave after purification by flash column chromatography (silica gel, 12 g eluting with 0 to 30% CMA 80 in chloroform) (2S,4R)-N2-(5-((+)-1-amino-1-(3-cyanophenyl)-3-cyclopropylpropyl)-2-fluorophenyl)-N1-(4-chlorophenyl)-4-methoxy-N1-methylpyrrolidine-1,2-dicarboxamide (6f) (106 mg, 0.175 mmol, 52.2% yield) as a white solid; $^1$H NMR (300 MHz, DMSO-$d_6$) δ 9.81 (s, 1H), 7.98-7.91 (m, 1H), 7.89 (t, J=1.7 Hz, 1H), 7.70-7.62 (m, 2H), 7.48 (t, J=7.8 Hz, 1H), 7.40 (d, J=1.5 Hz, 4H), 7.18-7.10 (m, 2H), 4.63 (dd, J=10.3, 7.0 Hz, 1H), 3.80 (t, J=3.5 Hz, 1H), 3.15 (s, 3H), 3.09 (s, 3H), 3.02 (m, 1H), 2.73 (m, 1H), 2.35 (s, 3H), 2.24 (m, 2H), 1.70 (m, 1H), 1.05 (m, 2H), 0.66 (m, 1H), 0.36 (m, 2H), −0.03 (s, 2H); $^{19}$F NMR (282 MHz, DMSO-$d_6$) δ −127.42; MS (ES+) 626.4, 627.5 (M+Na), (ES−) 602.5, 603.3 (M−1); HPLC purity 91.30%; Optical rotation $[α]_D$= (+) 189.77 [0.86, MeOH.

Scheme 7

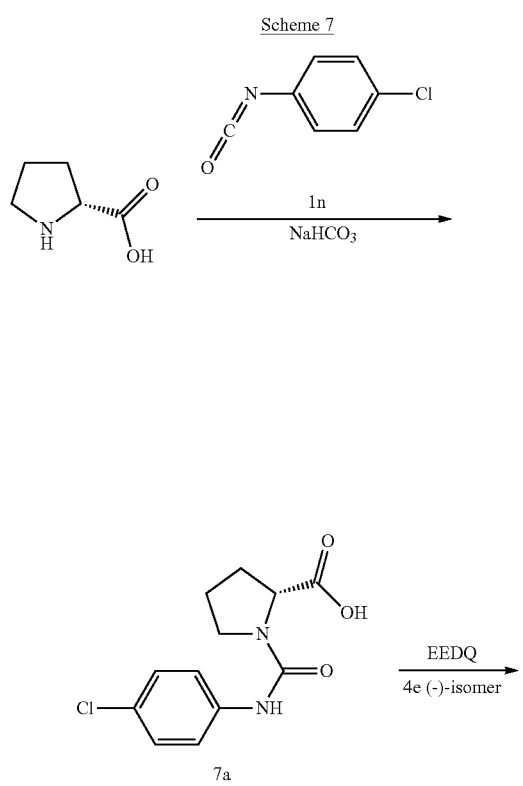

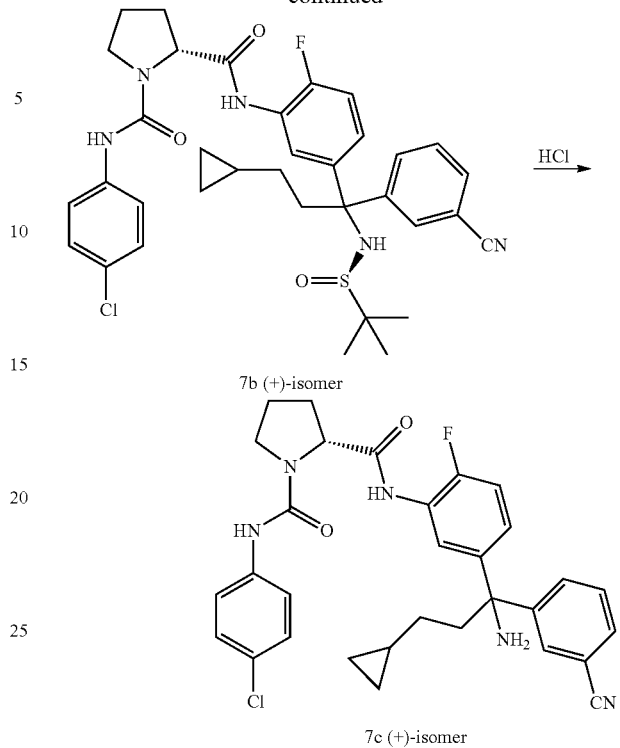

Preparation of (R)-N2-(5-((+)-1-amino-1-(3-cyanophenyl)-3-cyclopropylpropyl)-2-fluorophenyl)-N1-(4-chlorophenyl)pyrrolidine-1,2-dicarboxamide (7c)

Step-1: Preparation of (R)-1-(4-chlorophenylcarbamoyl)pyrrolidine-2-carboxylic acid (7a)

Reaction of D-Proline (1.0 g, 8.69 mmol) in aqueous sodium bicarbonate (69.5 mL, 34.7 mmol, 0.5M) with 4-chlorophenyl isocyanate (1n) (2.223 mL, 17.37 mmol) using the reaction and workup conditions as reported in step 9 of Scheme 1 gave (R)-1-(4-chlorophenylcarbamoyl)pyrrolidine-2-carboxylic acid (7a) (1.6 g, 5.95 mmol, 68.6% yield) as a white solid; $^1$H NMR (300 MHz, DMSO-$d_6$) δ 12.45 (s, 1H), 8.42 (s, 1H), 7.66-7.41 (m, 2H), 7.41-7.09 (m, 2H), 4.44-4.16 (m, 1H), 3.67-3.38 (m, 2H), 2.28-2.05 (m, 1H), 1.92 (m, 3H); MS (ES+) 269.1 (M+1), 291.2, 293.2 (M+Na), (ES−) 267.2, 269.1 (M−1); Optical rotation $[α]_D$= (+) 59.33 [0.3, MeOH].

Step-2: Preparation of (R)-N1-(4-chlorophenyl)-N2-(5-((+)-1-(3-cyanophenyl)-3-cyclopropyl-1-((R)-1,1-dimethylethylsulfinamido)propyl)-2-fluorophenyl) pyrrolidine-1,2-dicarboxamide (7b)

Reaction of (R)-1-(4-chlorophenylcarbamoyl)pyrrolidine-2-carboxylic acid (7a) (0.5 g, 1.861 mmol), (R)-N-((−)-1-(3-amino-4-fluorophenyl)-1-(3-cyanophenyl)-3-cyclopropylpropyl)-2-methylpropane-2-sulfinamide (4e) (0.770 g, 1.861 mmol) in tetrahydrofuran (25 mL) using ethyl 2-ethoxyquinoline-1(2H)-carboxylate (0.460 g, 1.861 mmol) using the reaction and workup conditions as reported in step 10 of Scheme 1 gave after purification by flash column chromatography (silica gel 25 g, eluting with CMA 80 in chloroform 0 to 100%) (R)-N1-(4-chlorophenyl)-N2-

(5-((+)-1-(3-cyanophenyl)-3-cyclopropyl-1-((R)-1,1-dimethylethylsulfinamido)propyl)-2-fluorophenyl)pyrrolidine-1,2-dicarboxamide (7b) (1.08 g, 1.626 mmol, 87% yield) as colorless solid; $^1$H NMR (300 MHz, DMSO-$d_6$) δ 9.84 (s, 1H), 8.45 (s, 1H), 7.92 (d, J=7.3 Hz, 1H), 7.78 (d, J=1.8 Hz, 1H), 7.71 (dt, J=7.3, 1.4 Hz, 1H), 7.65-7.44 (m, 4H), 7.32-7.24 (m, 2H), 7.19 (dd, J=10.4, 8.7 Hz, 1H), 7.16-7.03 (m, 1H), 5.53 (s, 1H), 4.68-4.45 (m, 1H), 3.71-3.55 (m, 2H), 3.56-3.42 (m, 1H), 2.77-2.55 (m, 1H), 2.22-2.04 (m, 1H), 1.95 (m, 4H), 1.12 (s, 9H), 1.00-0.75 (m, 1H), 0.74-0.50 (m, 1H), 0.41-0.26 (m, 2H), 0.10--0.25 (m, 2H); $^{19}$F NMR (282 MHz, DMSO-$d_6$) δ −127.07; MS (ES+) 686.5, 688.5 (M+Na); Optical rotation $[α]_D$=(+) 142.65 [0.415, MeOH].

Step 3: (R)-N2-(5-((+)-1-amino-1-(3-cyanophenyl)-3-cyclopropylpropyl)-2-fluorophenyl)-N1-(4-chlorophenyl)pyrrolidine-1,2-dicarboxamide (7c)

Reaction of (R)-N1-(4-chlorophenyl)-N2-(5-((+)-1-(3-cyanophenyl)-3-cyclopropyl-1-((R)-1,1-dimethylethylsulfinamido)propyl)-2-fluorophenyl)pyrrolidine-1,2-dicarboxamide (7b) (0.9 g, 1.355 mmol) in ethanol (20 mL) using conc. HCl (1.129 mL, 13.55 mmol) as reported in step 6 of Scheme 4 gave after purification by flash column chromatography (silica gel 25 g, eluting with CMA 80 in chloroform 0 to 30%) (R)-N2-(5-((+)-1-amino-1-(3-cyanophenyl)-3-cyclopropylpropyl)-2-fluorophenyl)-N1-(4-chlorophenyl)pyrrolidine-1,2-dicarboxamide (7c) (200 mg, 0.357 mmol, 26.4% yield) as a white solid; $^1$H NMR (300 MHz, DMSO-$d_6$) δ 9.76 (s, 1H), 8.43 (s, 1H), 7.94 (d, J=7.7 Hz, 1H), 7.86 (t, J=1.6 Hz, 1H), 7.63 (ddt, J=7.8, 6.1, 1.3 Hz, 2H), 7.59-7.51 (m, 2H), 7.46 (t, J=7.8 Hz, 1H), 7.33-7.23 (m, 2H), 7.19-7.05 (m, 2H), 4.64-4.52 (m, 1H), 3.61 (m, 1H), 3.49 (m, 1H), 2.31 (m, 2H), 2.22 (m, 2H), 2.14 (m, 1H), 1.96 (m, 3H), 1.04 (m, 2H), 0.63 (m, 1H), 0.33 (m, 2H), −0.07 (m, 2H); 19F NMR (282 MHz, DMSO-$d_6$) δ −127.97; MS (ES+) 582.4 (M+Na), (ES−) 558.5 (M−1), 594.3, 596.3 (M+Cl); IR(KBr) 3385, 2229, 1657, 1527, 1494, 1406 cm$^1$; Optical rotation $[α]_D$=(+) 23.57 [0.28, MeOH].

Scheme 8

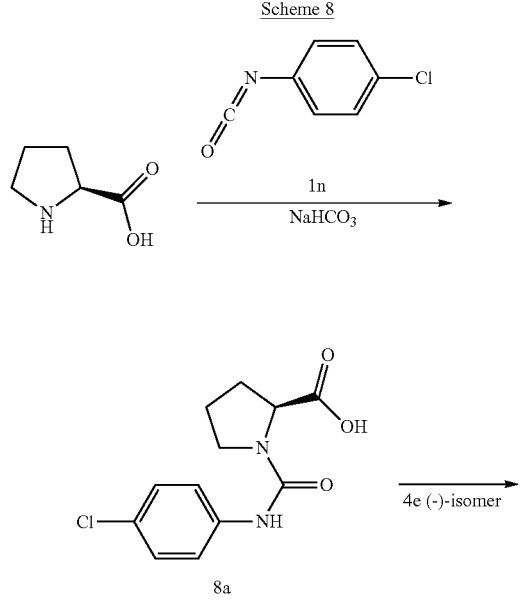

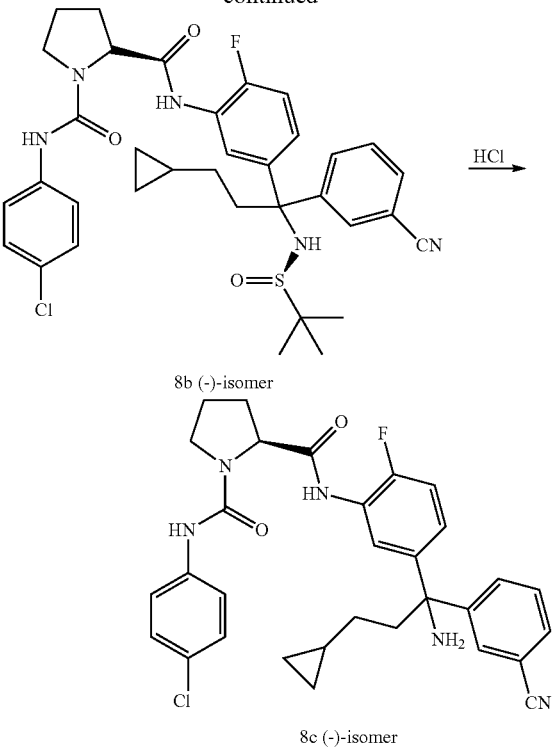

8b (−)-isomer 8c (−)-isomer

Preparation of (S)-N2-(5-((−)-1-amino-1-(3-cyanophenyl)-3-cyclopropylpropyl)-2-fluorophenyl)-N1-(4-chlorophenyl)pyrrolidine-1,2-dicarboxamide (8c)

Step-1: Preparation of (S)-1-(4-chlorophenylcarbamoyl)pyrrolidine-2-carboxylic acid (8a)

Reaction of L-Proline (1.0 g, 8.69 mmol) in aqueous sodium bicarbonate (69.5 mL, 34.7 mmol, 0.5M) with 4-chlorophenyl isocyanate (1n) (2.223 mL, 17.37 mmol) using the reaction and workup conditions as reported in step 9 of Scheme 1 gave (S)-1-(4-chlorophenylcarbamoyl)pyrrolidine-2-carboxylic acid (8a) (1.643 g, 6.11 mmol, 70.4% yield) as a white solid; $^1$H NMR (300 MHz, DMSO-$d_6$) δ 12.45 (s, 1H), 8.42 (s, 1H), 7.60-7.45 (m, 2H), 7.34-7.20 (m, 2H), 4.39-4.19 (m, 1H), 3.63-3.39 (m, 1H), 2.17 (m, 1H), 2.02-1.80 (m, 4H); MS (ES+) 269.3 (M+1), 291.3, 293.3 (M+Na); (ES−) 267.2 (M−1); Optical rotation $[α]_D$=(−) 51.85 [0.27, MeOH].

Step-2: Preparation of (S)-N1-(4-chlorophenyl)-N2-(5-((−)-1-(3-cyanophenyl)-3-cyclopropyl-1-((R)-1,1-dimethylethylsulfinamido)propyl)-2-fluorophenyl)pyrrolidine-1,2-dicarboxamide (8b)

Reaction of (S)-1-(4-chlorophenylcarbamoyl)pyrrolidine-2-carboxylic acid (8a) (0.5 g, 1.861 mmol), (R)-N-((−)-1-(3-amino-4-fluorophenyl)-1-(3-cyanophenyl)-3-cyclopropylpropyl)-2-methylpropane-2-sulfinamide (4e) (0.770 g, 1.861 mmol) in tetrahydrofuran (25 mL) using ethyl 2-ethoxyquinoline-1(2H)-carboxylate (0.46 g, 1.861 mmol) using the reaction and workup conditions as reported in step 10 of Scheme 1 gave after purification by flash column chromatography (silica gel 25 g, eluting with CMA 80 in chloroform 0 to 100%) (S)-N1-(4-chlorophenyl)-N2-(5-

((−)-1-(3-cyanophenyl)-3-cyclopropyl-1-((R)-1,1-dimethylethylsulfinamido)propyl)-2-fluorophenyl)pyrrolidine-1,2-dicarboxamide (8b) (1.002 g, 1.509 mmol, 81% yield) as colorless solid; $^1$H NMR (300 MHz, DMSO-d$_6$) δ 9.83 (s, 1H), 8.45 (s, 1H), 8.02-7.91 (m, 1H), 7.78 (d, J=1.8 Hz, 1H), 7.71 (dt, J=7.3, 1.5 Hz, 1H), 7.61-7.45 (m, 4H), 7.32-7.25 (m, 2H), 7.20 (dd, J=10.4, 8.7 Hz, 1H), 7.15-7.04 (m, 1H), 5.51 (s, 1H), 4.72-4.49 (m, 1H), 3.62 (m, 1H), 3.58-3.42 (m, 1H), 2.62 (m, 1H), 2.14 (m, 1H), 2.06-1.85 (m, 4H), 1.12 (s, 10H), 0.97-0.78 (m, 1H), 0.70-0.54 (m, 1H), 0.45-0.26 (m, 2H), 0.02--0.17 (m, 2H); $^{19}$F NMR (282 MHz, DMSO-d$_6$) δ −127.28; MS (ES+) 686.5, 688.5 (M+Na); Optical rotation [α]$_D$=(−) 208.15 [0.27, MeOH].

Step 3: (S)-N2-(5-((−)-1-amino-1-(3-cyanophenyl)-3-cyclopropylpropyl)-2-fluorophenyl)-N1-(4-chlorophenyl)pyrrolidine-1,2-dicarboxamide (8c)

Reaction of (S)-N1-(4-chlorophenyl)-N2-(5-((−)-1-(3-cyanophenyl)-3-cyclopropyl-1-((R)-1,1-dimethylethylsulfinamido)propyl)-2-fluorophenyl)pyrrolidine-1,2-dicarboxamide (8b) (0.9 g, 1.355 mmol) in ethanol (20 mL) using conc. HCl (1.129 mL, 13.55 mmol) as reported in step 6 of Scheme 4 gave after purification by flash column chromatography (silica gel 25 g, eluting with CMA 80 in chloroform 0 to 30%) (S)-N2-(5-((−)-1-amino-1-(3-cyanophenyl)-3-cyclopropylpropyl)-2-fluorophenyl)-N1-(4-chlorophenyl)pyrrolidine-1,2-dicarboxamide (8c) (300 mg, 0.536 mmol, 39.5% yield) as a white solid; $^1$H NMR (300 MHz, DMSO-d$_6$) δ 9.76 (s, 1H), 8.43 (s, 1H), 7.96 (d, J=7.3 Hz, 1H), 7.86 (t, J=1.7 Hz, 1H), 7.63 (ddt, J=7.8, 4.7, 1.3 Hz, 2H), 7.59-7.51 (m, 2H), 7.46 (t, J=7.8 Hz, 1H), 7.31-7.24 (m, 2H), 7.12 (d, J=9.0 Hz, 2H), 4.66-4.45 (m, 1H), 3.69-3.54 (m, 1H), 3.56-3.42 (m, 1H), 2.37-2.28 (m, 2H), 2.27-2.06 (m, 2H), 2.04-1.86 (m, 4H), 1.11-0.89 (m, 2H), 0.73-0.54 (m, 1H), 0.40-0.25 (m, 2H), −0.02--0.15 (m, 2H); $^{19}$F NMR (282 MHz, DMSO-d$_6$) δ −128.04; MS (ES+) 582.4; 584.5 (M+Na), (ES−) 558.4 (M−1); IR (KBr) 3386, 2229, 1655, 1594, 1526, 1494, 1405 cm-1; Optical Rotation [α]$_D$=(−) 102.42[1.035, MeOH]; Analysis calculated for C$_{31}$H$_{31}$ClFN$_5$O$_2$; C, 66.48; H, 5.58; N, 12.50. Found: C, 66.23; H, 5.71; N, 12.24.

Scheme 9

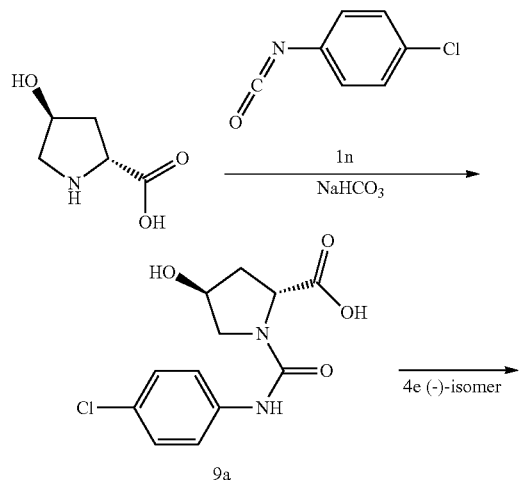

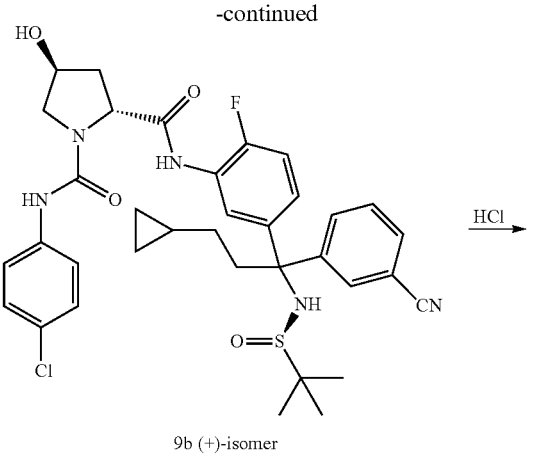

9b (+)-isomer

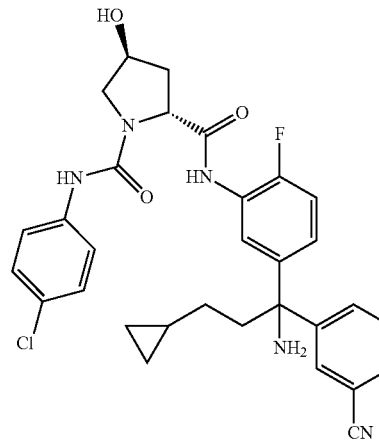

9c (+)-isomer

Preparation of (2R,4S)-N2-(5-((+)-1-amino-1-(3-cyanophenyl)-3-cyclopropylpropyl)-2-fluorophenyl)-N1-(4-chlorophenyl)-4-hydroxypyrrolidine-1,2-dicarboxamide (9c)

Step-1: Preparation of (2R,4S)-1-(4-chlorophenylcarbamoyl)-4 hydroxypyrrolidine-2-carboxylic acid (9a)

Reaction of (2S,4S)-4-hydroxypyrrolidine-2-carboxylic acid (trans-D-4-hydroxyproline, 1.0 g, 7.63 mmol) in aqueous sodium bicarbonate (61.0 mL, 30.5 mmol, 0.5M) with 4-chlorophenyl isocyanate (1n) (1.952 mL, 15.25 mmol) using the reaction and workup conditions as reported in step 9 of Scheme 1 gave (2R,4S)-1-(4-chlorophenylcarbamoyl)-4 hydroxypyrrolidine-2-carboxylic acid (9a) (1.643 g, 5.77 mmol, 76% yield) as a white solid; $^1$H NMR (300 MHz, DMSO-d$_6$) δ 12.43 (s, 1H), 8.47 (s, 1H), 7.57-7.48 (m, 2H), 7.31-7.22 (m, 2H), 5.16 (d, J=3.9 Hz, 1H), 4.34 (m, 2H), 3.60 (dd, J=10.4, 4.6 Hz, 1H), 3.45-3.35 (m, 1H), 2.12 (m, 1H), 1.92 (m, 1H); MS (ES+) 285.3 (M+1), 307.2, 309.3 (M+Na), (ES−) 283.2, 285.3 (M−1); Optical Rotation [α]$_D$= (+)54.375 [0.32, MeOH].

Step-2: Preparation of (2R,4S)-N1-(4-chlorophenyl)-N2-(5-((+)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (9b)

Reaction of (2R,4S)-1-(4-chlorophenylcarbamoyl)-4-hydroxypyrrolidine-2-carboxylic acid (9a) (0.7 g, 2.459 mmol), (R)-N-((−)-1-(3-amino-4-fluorophenyl)-1-(3-cyanophenyl)-3-cyclopropylpropyl)-2-methylpropane-2-sulfinamide (4e) (1.017 g, 2.459 mmol) in tetrahydrofuran (25 mL) using ethyl 2-ethoxyquinoline-1(2H)-carboxylate (0.608 g, 2.459 mmol) using the reaction and workup conditions as reported in step 10 of Scheme 1 gave after purification by flash column chromatography (silica gel 25 g, eluting with CMA 80 in chloroform 0 to 100%) (2R,4S)-N1-(4-chlorophenyl)-N2-(5-((+)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (9b) (1.37 g, 2.014 mmol, 82% yield) as a white solid; $^1$H NMR (300 MHz, DMSO-$d_6$) δ 9.86 (s, 1H), 8.49 (s, 1H), 7.91 (dd, J=7.5, 2.4 Hz, 1H), 7.78 (t, J=1.7 Hz, 1H), 7.71 (dt, J=7.4, 1.4 Hz, 1H), 7.63-7.45 (m, 4H), 7.31-7.23 (m, 2H), 7.19 (dd, J=10.3, 8.7 Hz, 1H), 7.14-7.03 (m, 1H), 5.53 (s, 1H), 5.19 (d, J=3.7 Hz, 1H), 4.66 (t, J=7.5 Hz, 1H), 4.39 (m, 1H), 3.67 (dd, J=10.4, 4.6 Hz, 1H), 3.44 (d, J=10.0 Hz, 1H), 2.80-2.53 (m, 1H), 2.10 (m, 1H), 2.04-1.84 (m, 1H), 1.12 (s, 10H), 1.05 (s, 1H), 0.90 (s, 1H), 0.63 (s, 1H), 0.39-0.27 (m, 2H), −0.03--0.16 (m, 2H); $^{19}$F NMR (282 MHz, DMSO-$d_6$) δ −126.81; MS (ES+) 702.5, 704.5 (M+Na); Optical Rotation [α]$_D$=(+) 20.71 [0.28, MeOH].

Step 3: (2R,4S)-N2-(5-((+)-1-amino-1-(3-cyanophenyl)-3-cyclopropylpropyl)-2-fluorophenyl)-N1-(4-chlorophenyl)-4-hydroxypyrrolidine-1,2-dicarboxamide (9c)

Reaction of (2R,4S)-N1-(4-chlorophenyl)-N2-(5-((+)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (9b) (0.725 g, 1.066 mmol) in ethanol (20 mL) using conc. HCl (0.888 mL, 10.66 mmol) as reported in step 6 of Scheme 4 gave after purification by flash column chromatography (silica gel 25 g, eluting with CMA 80 in chloroform 0 to 30%) (2R,4S)-N2-(5-((+)-1-amino-1-(3-cyanophenyl)-3-cyclopropylpropyl)-2-fluorophenyl)-N1-(4-chlorophenyl)-4-hydroxypyrrolidine-1,2-dicarboxamide (9c) (210 mg, 0.365 mmol, 34.2% yield) as a white solid; $^1$H NMR (300 MHz, DMSO-$d_6$) δ 9.77 (s, 1H), 8.46 (s, 1H), 7.92 (d, J=7.5 Hz, 1H), 7.86 (t, J=1.7 Hz, 1H), 7.63 (m, 2H), 7.59-7.50 (m, 2H), 7.45 (t, J=7.8 Hz, 1H), 7.32-7.22 (m, 2H), 7.18-7.08 (m, 2H), 5.17 (d, J=3.8 Hz, 1H), 4.64 (t, J=7.5 Hz, 1H), 4.39 (m, 1H), 3.67 (dd, J=10.3, 4.6 Hz, 1H), 3.47-3.36 (m, 2H), 2.31 (m, 2H), 2.21 (m, 2H), 2.11 (m, 1H), 1.11-0.91 (m, 2H), 0.62 (m, 1H), 0.41-0.22 (m, 2H), −0.08 (m, 2H); $^{19}$F NMR (282 MHz, DMSO-$d_6$) δ −127.52; MS (ES+) 598.4, 600.4 (M+Na), (ES−) 610.4, 612.4 (M+Cl); Optical rotation [α]$_D$=(+) 132.69 [0.82, MeOH].

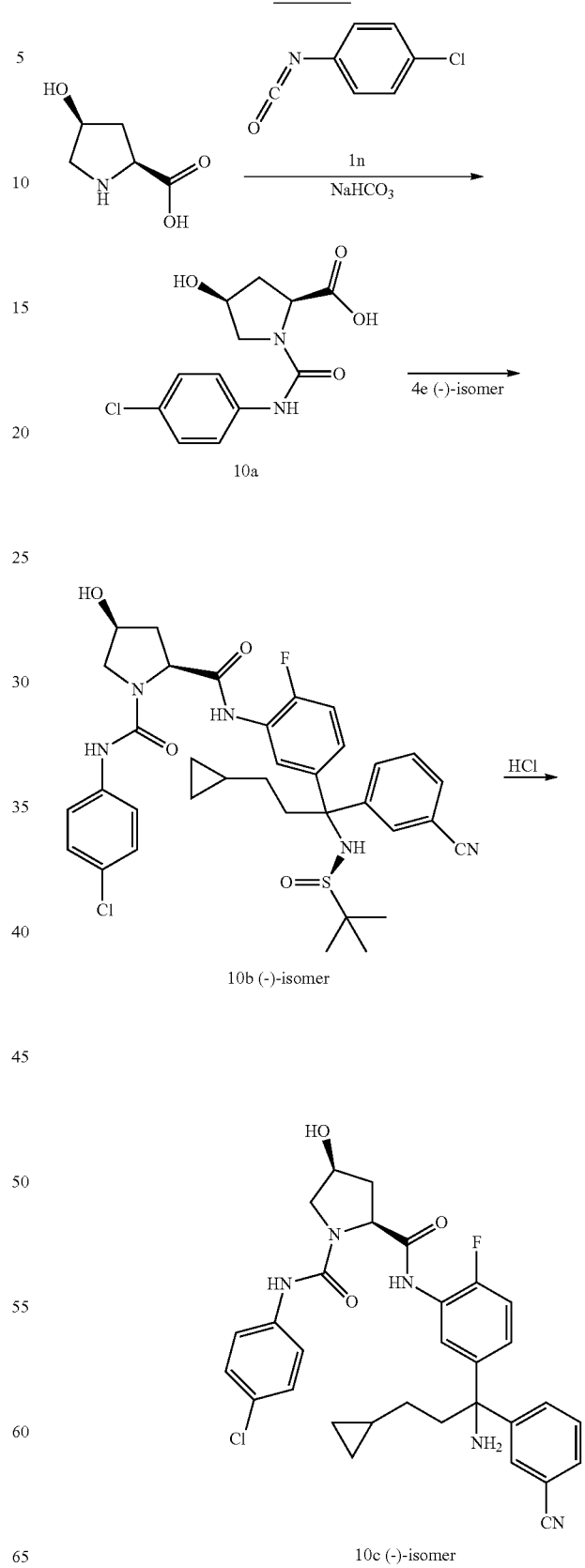

Scheme 10

Preparation of (2S,4S)-N2-(5-((−)-1-amino-1-(3-cyanophenyl)-3-cyclopropylpropyl)-2-fluorophenyl)-N1-(4-chlorophenyl)-4-hydroxypyrrolidine-1,2-dicarboxamide (10c)

Step-1: Preparation of (2S,4S)-1-(4-chlorophenylcarbamoyl)-4-hydroxypyrrolidine-2-carboxylic acid (10a)

Reaction of (2S,4S)-4-hydroxypyrrolidine-2-carboxylic acid (cis-L-4-hydroxyproline, 1.0 g, 7.63 mmol) in aqueous sodium bicarbonate (61.0 mL, 30.5 mmol, 0.5M) with 4-chlorophenyl isocyanate (1n) (1.952 mL, 15.25 mmol) using the reaction and workup conditions as reported in step 9 of Scheme 1 gave (2S,4S)-1-(4-chlorophenylcarbamoyl)-4-hydroxypyrrolidine-2-carboxylic acid (10a) (1.643 g, 5.77 mmol, 76% yield) as a white solid; $^1$H NMR (300 MHz, DMSO-$d_6$) δ 12.33 (s, 1H), 8.41 (s, 1H), 7.64-7.43 (m, 2H), 7.37-7.14 (m, 2H), 5.09 (s, 1H), 4.51-4.16 (m, 2H), 3.65 (dd, J=10.3, 5.6 Hz, 1H), 3.32 (m, 1H), 2.32 (m, 1H), 1.97-1.78 (m, 1H); MS (ES+) 307.2, 309.2 (M+Na), (ES−) 283.2, 285.2 (M−1); Optical Rotation $[α]_D$=(−) 37.74 [0.265, MeOH].

Step-2: Preparation of (2S,4S)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (10b)

Reaction of (2S,4S)-1-(4-chlorophenylcarbamoyl)-4-hydroxypyrrolidine-2-carboxylic acid (10a) (0.7 g, 2.459 mmol), (R)-N-((−)-1-(3-amino-4-fluorophenyl)-1-(3-cyanophenyl)-3-cyclopropylpropyl)-2-methylpropane-2-sulfinamide (4e) (1.017 g, 2.459 mmol) in tetrahydrofuran (25 mL) using ethyl 2-ethoxyquinoline-1(2H)-carboxylate (0.608 g, 2.459 mmol) using the reaction and workup conditions as reported in step 10 of Scheme 1 gave after purification by flash column chromatography (silica gel 25 g, eluting with CMA 80 in chloroform 0 to 100%) (2S,4S)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (10b) (0.961 g, 1.413 mmol, 57.5% yield) as a white solid; $^1$H NMR (300 MHz, DMSO-$d_6$) δ 9.66 (s, 1H), 8.52 (s, 1H), 8.06 (dd, J=7.6, 2.4 Hz, 1H), 7.79 (m, 1H), 7.71 (m, 1H), 7.62-7.45 (m, 4H), 7.34-7.24 (m, 2H), 7.20 (dd, J=10.5, 8.7 Hz, 1H), 7.14-7.03 (m, 1H), 5.49 (s, 1H), 5.32 (d, J=4.5 Hz, 1H), 4.51 (dd, J=9.0, 4.7 Hz, 1H), 4.39-4.25 (m, 1H), 3.68 (dd, J=10.1, 5.2 Hz, 1H), 3.49 (dd, J=9.9, 3.9 Hz, 1H), 2.75-2.51 (m, 2H), 2.49-2.20 (m, 1H), 1.97-1.81 (m, 1H), 1.13 (s, 9H), 1.07 (m, 1H), 0.90 (m, 1H), 0.64 (m, 1H), 0.40-0.26 (m, 2H), −0.06 (m, 2H); $^{19}$F NMR (282 MHz, DMSO-$d_6$) δ −128.68; MS (ES+) 702.5, 704.5 (M+Na), (ES−) 678.6, 680.5 (M−1); Optical Rotation $[α]_D$=(−) 153.33 [0.27, MeOH].

Step 3: Preparation of (2S,4S)-N2-(5-((−)-1-amino-1-(3-cyanophenyl)-3-cyclopropylpropyl)-2-fluorophenyl)-N1-(4-chlorophenyl)-4-hydroxypyrrolidine-1,2-dicarboxamide (10c)

Reaction of (2S,4S)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (10b) (0.5 g, 0.735 mmol) in ethanol (20 mL) using conc. HCl (0.613 mL, 7.35 mmol) as reported in step 6 of Scheme 4 gave after purification by flash column chromatography (silica gel 25 g, eluting with CMA 80 in chloroform 0 to 30%) (2S,4S)-N2-(5-((−)-1-amino-1-(3-cyanophenyl)-3-cyclopropylpropyl)-2-fluorophenyl)-N1-(4-chlorophenyl)-4-hydroxypyrrolidine-1,2-dicarboxamide (10c) (50 mg, 0.087 mmol, 11.81% yield) as a colorless solid; $^1$H NMR (300 MHz, DMSO-$d_6$) δ 9.62 (s, 1H), 8.50 (s, 1H), 8.05 (d, J=7.3 Hz, 1H), 7.86 (t, J=1.7 Hz, 1H), 7.63 (m, 2H), 7.59-7.50 (m, 2H), 7.46 (t, J=7.8 Hz, 1H), 7.34-7.24 (m, 2H), 7.19-7.04 (m, 2H), 5.30 (d, J=4.9 Hz, 1H), 4.51 (dd, J=9.0, 4.7 Hz, 1H), 4.34 (d, J=5.2 Hz, 1H), 3.69 (dd, J=10.1, 5.3 Hz, 1H), 3.54-3.43 (m, 1H), 2.40-2.08 (m, 5H), 1.90 (m, 1H), 1.02 (m, 2H), 0.63 (m, 1H), 0.34 (m, 2H), −0.07 (s, 2H); $^{19}$F NMR (282 MHz, DMSO-$d_6$) δ −129.13; MS (ES+) 598.4, 600.4 (M+Na); Optical Rotation $[α]_D$=(−) 51.85 [0.7, MeOH]; Analysis calculated for $C_{31}H_{31}ClFN_5O_3 \cdot 0.75H_2O$: C, 63.15; H, 5.56; N, 11.88. Found: C, 63.02; H, 5.89; N, 10.83.

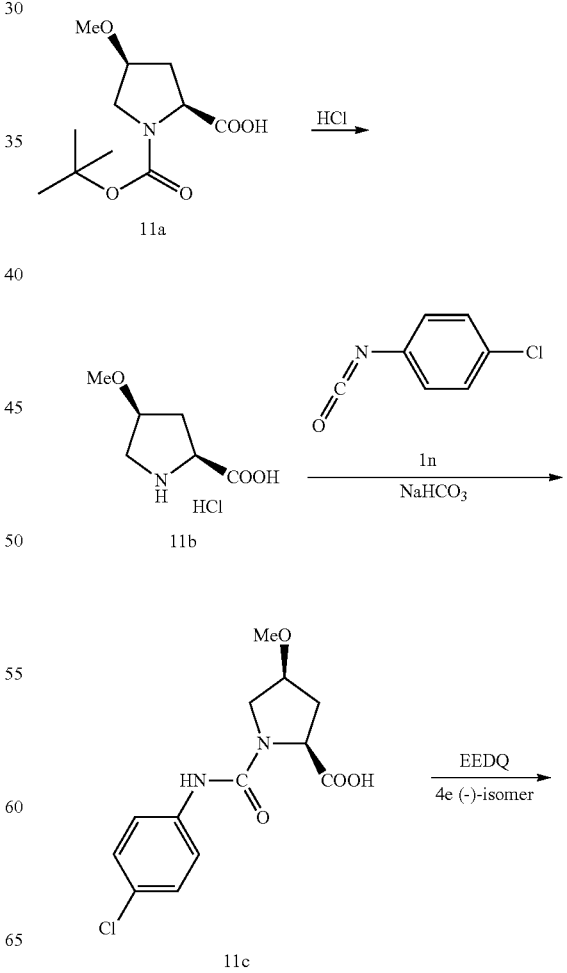

Scheme 11

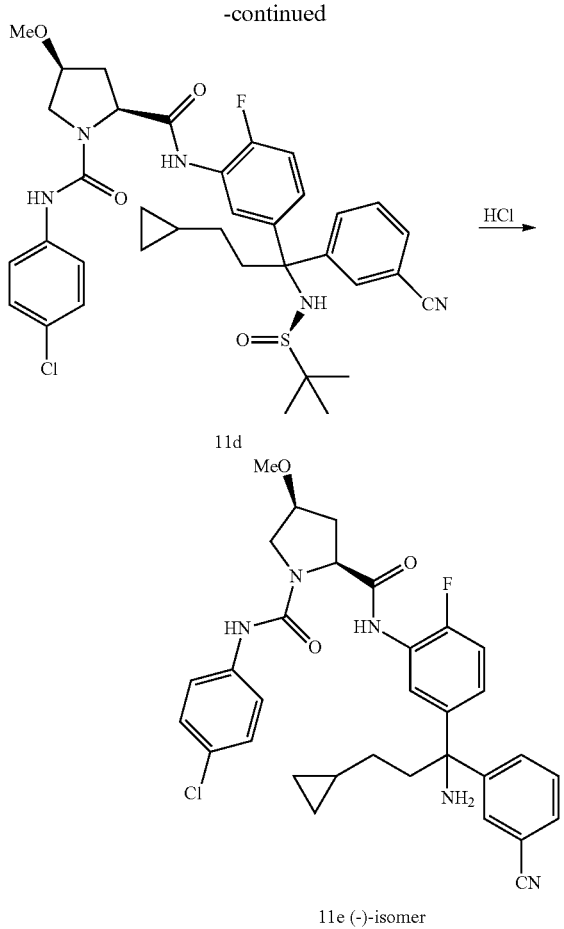

11d 11e (-)-isomer

Preparation of (2S,4S)-N2-(5-((−)-1-amino-1-(3-cyanophenyl)-3-cyclopropylpropyl)-2-fluorophenyl)-N1-(4-chlorophenyl)-4-methoxypyrrolidine-1,2-dicarboxamide (11e)

Step-1: Preparation of (2S,4S)-4-methoxypyrrolidine-2-carboxylic acid hydrochloride (11b)

To a stirred solution of (2S,4S)-1-(tert-butoxycarbonyl)-4-methoxypyrrolidine-2-carboxylic acid (11a) (Prepared according to the procedure reported in Benzimidazole-proline derivatives as orexin receptor antagonists and their preparation; By Boss, Christoph et al; From PCT Int. Appl., 2013182972, 12 Dec. 2013; 0.25 g, 1.019 mmol) in tetrahydrofuran (10 mL) was added 6N aqueous HCl (0.680 mL, 4.08 mmol) and stirred at room temperature overnight. The reaction was concentrated and dried in vacuum to afford (2S,4S)-4-methoxypyrrolidine-2-carboxylic acid hydrochloride (11b) (0.185 g, 1.019 mmol, 100% yield) as a white solid which was used as such in next step; $^1$H NMR (300 MHz, DMSO-$d_6$/$D_2$O) δ 4.42 (t, J=6.7 Hz, 1H), 4.06 (m, 1H), 3.38 (d, J=12.4 Hz, 1H), 3.25-3.18 (m, 1H), 3.16 (s, 3H), 2.30 (dd, J=7.3, 3.2 Hz, 2H).

Step-2: Preparation of (2S,4S)-1-(4-chlorophenyl-carbamoyl)-4-methoxypyrrolidine-2-carboxylic acid (11c)

Reaction of (2S,4S)-4-methoxypyrrolidine-2-carboxylic acid hydrochloride (11b) (182 mg, 1.0 mmol) in aqueous sodium bicarbonate (10 mL, 20 mmol, 0.5M) with 4-chlorophenyl isocyanate (1n) (10.256 mL, 2.0 mmol) using the reaction and workup conditions as reported in step 9 of Scheme 1 gave (2S,4S)-1-(4-chlorophenylcarbamoyl)-4-methoxypyrrolidine-2-carboxylic acid (11c) (133 mg, 0.445 mmol, 44.5% yield) MS (ES+) 321.3, 323.3 (M+Na), (ES−) 297.3, 299.3 (M−1).

Step-3: Preparation of (2S,4S)-N1-(4-chlorophenyl)-N2-(5-(1-(3-cyanophenyl)-3-cyclopropyl-1-((R)-1,1-dimethylethylsulfinamido)propyl)-2-fluorophenyl)-4-methoxypyrrolidine-1,2-dicarboxamide (11d)

Reaction of (2S,4S)-1-(4-chlorophenylcarbamoyl)-4-methoxypyrrolidine-2-carboxylic acid (11c) (120 mg, 0.402 mmol), (R)-N-((−)-1-(3-amino-4-fluorophenyl)-1-(3-cyanophenyl)-3-cyclopropylpropyl)-2-methylpropane-2-sulfinamide (4e) (166 mg, 0.402 mmol) in tetrahydrofuran (20 mL) using ethyl 2-ethoxyquinoline-1(2H)-carboxylate (99 mg, 0.402 mmol) using the reaction and workup conditions as reported in step 10 of Scheme 1 gave after purification by flash column chromatography (silica gel 25 g, eluting with CMA 80 in chloroform 0 to 100%) (2S,4S)-N1-(4-chlorophenyl)-N2-(5-((1-(3-cyanophenyl)-3-cyclopropyl-1-((R)-1,1-dimethylethylsulfinamido)propyl)-2-fluorophenyl)-4-methoxypyrrolidine-1,2-dicarboxamide (11d) (156 mg, 0.225 mmol, 55.9% yield) as a white solid; $^1$H NMR (300 MHz, DMSO-$d_6$) δ 9.51 (s, 1H), 8.53 (s, 1H), 7.92 (d, J=7.3 Hz, 1H), 7.79 (s, 1H), 7.71 (d, J=7.5 Hz, 1H), 7.64-7.46 (m, 4H), 7.35-7.25 (m, 2H), 7.24-7.14 (m, 1H), 7.10 (s, 1H), 5.48 (s, 1H), 4.54 (dd, J=9.2, 3.9 Hz, 1H), 4.07 (m, 1H), 3.72 (dd, J=10.6, 5.0 Hz, 1H), 3.61 (dd, J=10.0, 2.4 Hz, 1H), 3.22 (s, 3H), 2.69-2.51 (m, 2H), 2.43-2.24 (m, 1H), 2.23-2.06 (m, 1H), 1.12 (s, 10H), 0.99-0.79 (m, 1H), 0.63 (s, 1H), 0.42-0.27 (m, 2H), 0.06-−0.16 (m, 2H); $^{19}$F NMR (282 MHz, DMSO-$d_6$) δ −128.19; MS (ES+) 716.6, 718.5 (M+Na).

Step 4: Preparation of (2S,4S)-N2-(5-((−)-1-amino-1-(3-cyanophenyl)-3-cyclopropylpropyl)-2-fluorophenyl)-N1-(4-chlorophenyl)-4-methoxypyrrolidine-1,2-dicarboxamide (11e)

Reaction of (2S,4S)-N1-(4-chlorophenyl)-N2-(5-(1-(3-cyanophenyl)-3-cyclopropyl-1-((R)-1,1-dimethylethylsulfinamido)propyl)-2-fluorophenyl)-4-methoxypyrrolidine-1,2-dicarboxamide (11d) (0.143 g, 0.206 mmol) in ethanol (20 mL) using conc. HCl (0.172 mL, 2.060 mmol) as reported in step 6 of Scheme 4 gave after purification by flash column chromatography (silica gel 25 g, eluting with CMA 80 in chloroform 0 to 30%) (2S,4S)-N2-(5-((−)-1-amino-1-(3-cyanophenyl)-3-cyclopropylpropyl)-2-fluorophenyl)-N1-(4-chlorophenyl)-4-methoxypyrrolidine-1,2-dicarboxamide (11e) (80 mg, 0.136 mmol, 65.8% yield) as a white solid; $^1$H NMR (300 MHz, DMSO-$d_6$) δ 9.45 (d, J=1.3 Hz, 1H), 8.51 (s, 1H), 7.90 (d, J=7.7 Hz, 1H), 7.86 (m, 1H), 7.63 (m, 2H), 7.58-7.52 (m, 2H), 7.46 (t, J=7.8 Hz, 1H), 7.32-7.25 (m, 2H), 7.14 (s, 1H), 7.11 (s, 1H), 4.53 (dd, J=9.1, 3.9 Hz, 1H), 4.07 (m, 1H), 3.73 (dd, J=10.6, 5.1 Hz, 1H), 3.61 (dd, J=10.4, 3.3 Hz, 1H), 3.22 (s, 3H), 2.47-1.98 (m, 6H), 1.11-0.92 (m, 2H), 0.63 (m, 1H), 0.33 (m, 2H), −0.07 (m, 2H); $^{19}$F NMR (282 MHz, DMSO-$d_6$) δ −128.86; MS (ES+) 612.4, 614.4 (M+Na); IR (KBr) 2229 cm$^{-1}$; Optical rotation $[α]_D$=(−)56.57 [0.495, MeOH]

Scheme 12

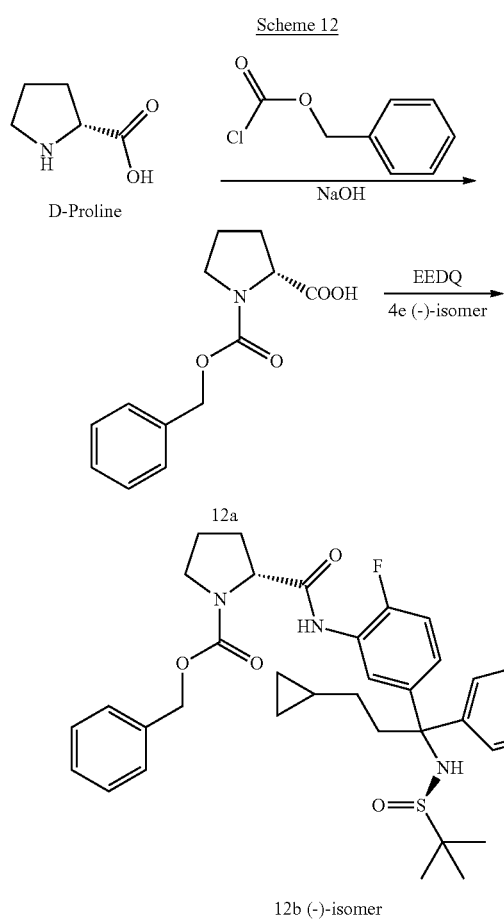

Preparation of (R)-benzyl 2-(5-((−)-1-(3-cyanophenyl)-3-cyclopropyl-1-((R)-1,1-dimethylethylsulfinamido)propyl)-2-fluorophenylcarbamoyl)pyrrolidine-1-carboxylate (12b)

Step-1: Preparation of (R)-1-(benzyloxycarbonyl)pyrrolidine-2-carboxylic acid (12a)

To a stirred solution of D-Proline (1.2 g, 10.42 mmol) in 2N aqueous NaOH solution (20.85 mL, 41.7 mmol) at 0° C. was added benzyl chloroformate (1.488 mL, 10.42 mmol) and allowed to warm to room temperature overnight. The reaction was washed with MTBE (2×25 mL), acidified with conc HCl and extracted with ethyl acetate (2×200 mL). The ethyl acetate layers were combined washed with water (50 mL), brine (25 mL) dried and concentrated in vacuum to afford (R)-1-(benzyloxycarbonyl)pyrrolidine-2-carboxylic acid (12a) (2.41 g, 9.67 mmol, 93% yield) which was used as such in next step; $^1$H NMR (300 MHz, DMSO-$d_6$) δ 12.66 (s, 1H), 7.42-7.25 (m, 5H), 5.14-4.97 (m, 2H), 4.20 (ddd, J=22.7, 8.8, 3.5 Hz, 1H), 3.50-3.25 (m, 2H), 2.32-2.08 (m, 1H), 1.97-1.75 (m, 3H); MS (ES+) 250.2 (M+1), 272.2 (M+Na), (ES−) 248.2 (M−1), 284.2 (M+Cl), 497.4 (2M−1).

Step-2: Preparation of (R)-benzyl 2-(5-((−)-1-(3-cyanophenyl)-3-cyclopropyl-1-((R)-1,1-dimethylethylsulfinamido)propyl)-2-fluorophenylcarbamoyl)pyrrolidine-1-carboxylate (12b)

Reaction of (R)-1-(benzyloxycarbonyl)pyrrolidine-2-carboxylic acid (12a) (1 g, 4.01 mmol), (R)-N-((−)-1-(3-amino-4-fluorophenyl)-1-(3-cyanophenyl)-3-cyclopropylpropyl)-2-methylpropane-2-sulfinamide (4e) (1.659 g, 4.01 mmol) in tetrahydrofuran (50 mL) using ethyl 2-ethoxyquinoline-1(2H)-carboxylate (0.992 g, 4.01 mmol) using the reaction and workup conditions as reported in step 10 of Scheme 1 gave after purification by flash column chromatography (silica gel 25 g, eluting with CMA 80 in chloroform 0 to 100%) (R)-benzyl 2-(5-((−)-1-(3-cyanophenyl)-3-cyclopropyl-1-((R)-,1,1-dimethylethylsulfinamido)propyl)-2-fluorophenylcarbamoyl)pyrrolidine-1-carboxylate (12b) (2.4 g, 3.72 mmol, 93% yield) as a white solid; $^1$H NMR (300 MHz, DMSO-$d_6$) δ 9.86 (d, J=11.1 Hz, 1H), 7.92 (t, J=9.0 Hz, 1H), 7.78 (d, J=1.7 Hz, 1H), 7.72 (d, J=7.4 Hz, 1H), 7.65-7.56 (m, 1H), 7.51 (m, 1H), 7.37 (m, 2H), 7.29-7.06 (m, 5H), 5.52 (d, J=10.5 Hz, 1H), 5.14-4.93 (m, 2H), 4.62-4.38 (m, 1H), 3.58-3.33 (m, 2H), 2.72-2.57 (m, 1H), 2.33-2.08 (m, 1H), 1.97-1.73 (m, 4H), 1.12 (2s, 9H for rotamers), 1.11-1.00 (m, 1H), 0.86 (m, 1H), 0.62 (m, 1H), 0.34 (m, 2H), 0.01-−0.18 (m, 2H); $^{19}$F NMR (282 MHz, DMSO-$d_6$) δ −126.74; MS (ES+) 645.6 (M+1), 667.6 (M+Na), (ES−) 643.6 (M−1); Optical rotation $[α]_D$=(−) 21.18 [0.255, MeOH].

Scheme 13

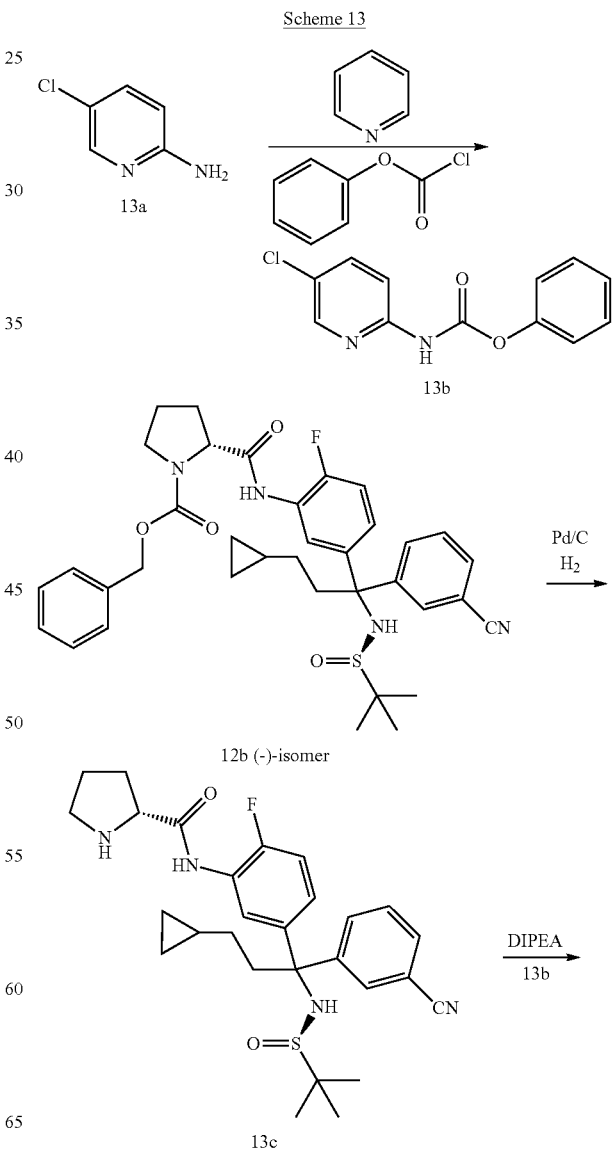

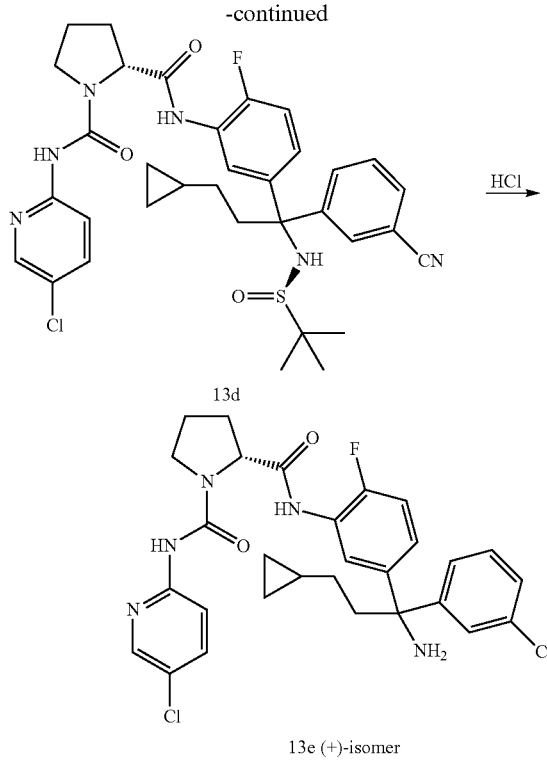

Preparation of (R)-N2-(5-((+)-1-amino-1-(3-cyanophenyl)-3-cyclopropylpropyl)-2-fluorophenyl)-N1-(5-chloropyridin-2-yl)pyrrolidine-1,2-dicarboxamide (13e)

Step 1: Preparation of phenyl 5-chloropyridin-2-ylcarbamate (13b)

To an ice-water bath cooled solution of 2-amino-5-chloropyridine (13a) (5 g, 38.9 mmol) in dichloromethane (100 mL) was added pyridine (4.72 mL, 58.3 mmol) and phenyl chloroformate (4.88 mL, 38.9 mmol). The resulting mixture was stirred in ice-water bath for 2 h, diluted with water (100 mL) and dichloromethane (50 mL). The solid obtained was collected by filtration dried at 50° C. under vacuum to give phenyl 5-chloropyridin-2-ylcarbamate (13b) (9.519 g, 38.3 mmol, 98% yield) as a white solid; $^1$H NMR (300 MHz, DMSO-$d_6$) δ 10.97 (s, 1H), 8.38 (dd, J=2.6, 0.8 Hz, 1H), 7.93 (dd, J=9.0, 2.6 Hz, 1H), 7.84 (dd, J=8.9, 0.8 Hz, 1H), 7.51-7.37 (m, 2H), 7.36-7.17 (m, 3H).

Step 2: Preparation of (R)-N-(5-(1-(3-cyanophenyl)-3-cyclopropyl-1-((R)-1,1-dimethylethylsulfinamido)propyl)-2-fluorophenyl)pyrrolidine-2-carboxamide (13c)

To a suspension of palladium on carbon 10% (0.165 g, 0.155 mmol) in ethanol (75 mL) was added a solution of (R)-benzyl 2-(5-((−)-1-(3-cyanophenyl)-3-cyclopropyl-1-((R)-1,1-dimethylethylsulfinamido)propyl)-2-fluorophenylcarbamoyl)pyrrolidine-1-carboxylate (12b) (1 g, 1.551 mmol) in ethanol and hydrogenated in a parr shaker at 50 psi for 5 h. The reaction was filtered through a small pad of celite and concentrated to give (R)-N-(5-(1-(3-cyanophenyl)-3-cyclopropyl-1-((R)-1,1-dimethylethylsulfinamido)propyl)-2-fluorophenyl)pyrrolidine-2-carboxamide (13c) (815 mg, 1.596 mmol, 103% yield) which was used in the next step without further purification; $^1$H NMR (300 MHz, DMSO-$d_6$) δ 10.13 (s, 1H), 8.29 (dd, J=7.6, 2.4 Hz, 1H), 7.79 (t, J=1.8 Hz, 1H), 7.72 (dt, J=7.4, 1.4 Hz, 1H), 7.60 (dt, J=8.3, 1.5 Hz, 1H), 7.51 (t, J=7.8 Hz, 1H), 7.22 (m, 1H), 7.06 (m, 1H), 5.46 (s, 1H), 3.74 (dd, J=9.1, 5.2 Hz, 1H), 3.43 (m, 2H), 2.87 (m, 2H), 2.71-2.53 (m, 2H), 2.05 (m, 1H), 1.79 (dq, J=12.4, 6.5 Hz, 1H), 1.72-1.56 (m, 2H), 1.14 (s, 9H), 0.99-0.82 (m, 1H), 0.74-0.54 (m, 1H), 0.35 (m, 2H), 0.04-0.15 (m, 2H); $^{19}$F NMR (282 MHz, DMSO-$d_6$) δ −131.82; MS (ES+) 511.4 (M+1), 533.5 (M+Na), (ES−) 509.4 (M−1).

Step 3: Preparation of (R)-N1-(5-chloropyridin-2-yl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (13d)

To a solution of (R)-N-(5-(1-(3-cyanophenyl)-3-cyclopropyl-1-((R)-1,1-dimethylethylsulfinamido)propyl)-2-fluorophenyl)pyrrolidine-2-carboxamide (13c) (0.763 g, 1.494 mmol) in tetrahydrofuran (50 mL) was added phenyl 5-chloropyridin-2-ylcarbamate (13b) (0.446 g, 1.793 mmol) and N-ethyl-N-isopropylpropan-2-amine (1.041 mL, 5.98 mmol). The reaction mixture was heated to reflux for 16 h. The reaction was cooled to room temperature, diluted with ethylacetate (100 mL), washed with water (2×50 mL), brine (50 mL), dried and concentrated in vacuum. The crude residue was purified by flash column chromatography to afford (R)-N1-(5-chloropyridin-2-yl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (13d) (773 mg, 1.162 mmol, 78% yield) as a white solid; $^1$H NMR (300 MHz, DMSO-$d_6$) δ 9.82 (s, 1H), 9.07 (s, 1H), 8.28 (dd, J=2.7, 0.8 Hz, 1H), 7.96-7.86 (m, 2H), 7.83-7.76 (m, 2H), 7.71 (dt, J=7.4, 1.5 Hz, 1H), 7.58 (d, J=8.0 Hz, 1H), 7.50 (m, 1H), 7.27-7.05 (m, 2H), 5.52 (s, 1H), 4.62 (d, J=7.7 Hz, 1H), 3.78-3.62 (m, 1H), 3.62-3.46 (m, 1H), 2.73-2.40 (m, 2H), 2.26-2.10 (m, 1H), 1.93 (m, 3H), 1.12 (s, 10H), 0.85 (m, 1H), 0.72-0.54 (m, 1H), 0.33 (m, 2H), 0.00-−0.16 (m, 2H); $^{19}$F NMR (282 MHz, DMSO-$d_6$) δ −126.74.

Step-4: Preparation of (R)-N2-(5-((+)-1-amino-1-(3-cyanophenyl)-3-cyclopropylpropyl)-2-fluorophenyl)-N1-(5-chloropyridin-2-yl)pyrrolidine-1,2-dicarboxamide (13e)

Reaction of (R)-N1-(5-chloropyridin-2-yl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (13d) (554 mg, 0.833 mmol) in ethanol (100 mL) using conc. HCl (0.694 mL, 8.33 mmol) as reported in step 6 of Scheme 4 gave after purification by flash column chromatography (silica gel 25 g, eluting with 9:1 mixture of ethyl acetate and methanol in hexanes 0 to 60%) (R)-N2-(5-((+)-1-amino-1-(3-cyanophenyl)-3-cyclopropylpropyl)-2-fluorophenyl)-N1-(5-chloropyridin-2-yl)pyrrolidine-1,2-dicarboxamide (13e) (219 mg, 0.390 mmol, 46.9% yield) as a colorless solid; $^1$H NMR (300 MHz, DMSO-$d_6$) δ 9.76 (s, 1H), 9.05 (s, 1H), 8.28 (d, J=2.6 Hz, 1H), 7.96-7.88 (m, 2H), 7.86 (m, 1H), 7.79 (dd, J=9.0, 2.6 Hz, 1H), 7.63 (ddt, J=7.6, 5.9, 1.3 Hz, 2H), 7.46 (t, J=7.8 Hz, 1H), 7.14 (d, J=2.0 Hz, 1H), 7.12 (d, J=1.3 Hz, 1H), 4.61 (d, J=7.7 Hz, 1H), 3.66 (m, 1H), 3.56 (m, 1H), 3.33-3.27 (m, 1H), 2.40-2.06 (m, 4H), 1.94 (m, 3H), 1.13-0.85 (m, 2H), 0.62 (m, 1H), 0.41-0.26 (m, 2H), −0.03-−0.17 (m, 2H); $^{19}$F NMR (282 MHz, DMSO-$d_6$) δ −127.82; MS(ES+) 561.4, 562.4 (M+1), 583.4, 585.5 (M+Na); IR (KBr) 2229 cm$^{-1}$; Optical rotation [α]$_D$= (+) 160.49 [0.82, MeOH].

Scheme 14
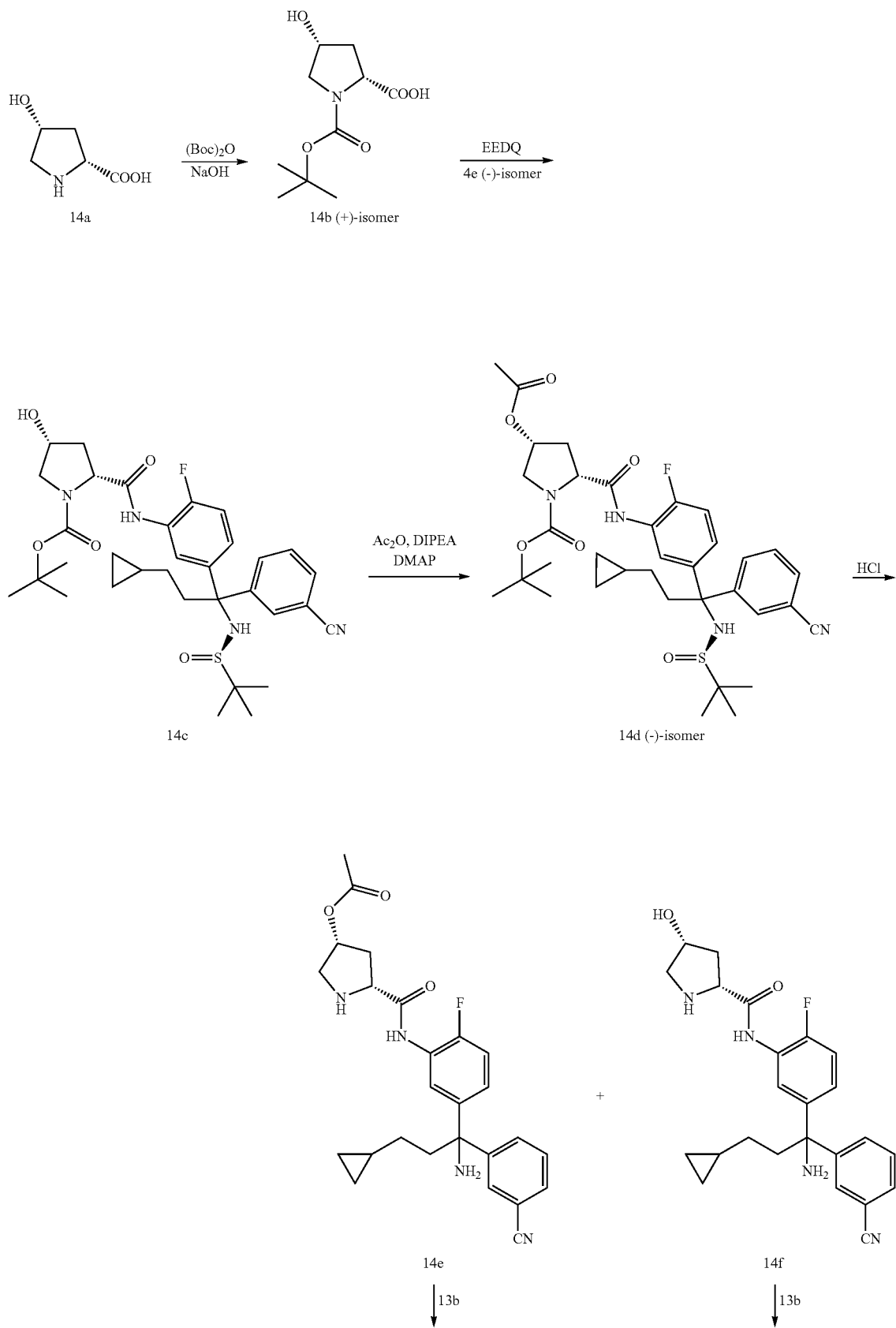

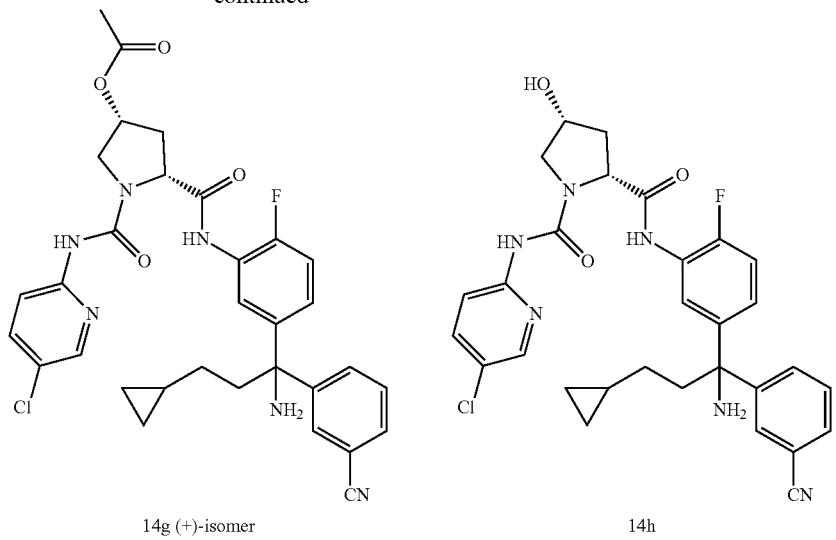

14g (+)-isomer      14h

Preparation of (2R,4R)-N2-(5-(1-amino-1-(3-cyanophenyl)-3-cyclopropylpropyl)-2-fluorophenyl)-N1-(5-chloropyridin-2-yl)-4-hydroxypyrrolidine-1,2-dicarboxamide (14h)

Step 1: Preparation of (2R,4R)-1-(tert-butoxycarbonyl)-4-hydroxypyrrolidine-2-carboxylic acid (14b)

To a solution of (2R,4R)-4-hydroxypyrrolidine-2-carboxylic acid (14a) (10 g, 76 mmol) in THF:H$_2$O (125 mL, 2:1) was added 2.5M aqueous sodium hydroxide (42.1 mL, 105 mmol) followed by a solution of di-tert-butyl dicarbonate (22.80 g, 104 mmol) in THF:H$_2$O (125 mL, 2:1) and stirred at room temperature for 32 h. The mixture was concentrated in vacuum to remove the THF and aqueous layer was added acidified with 10% aqueous potassium hydrogen sulfate solution (150 mL). The resulting mixture was extracted with ethyl acetate, washed with water, brine, dried, filtered, and evaporated to dryness. The resulting semi-solid was crystallized from hot ethyl acetate to afford (2R,4R)-1-(tert-butoxycarbonyl)-4-hydroxypyrrolidine-2-carboxylic acid (14b) (13.58 g, 58.7 mmol, 77% yield) as a white solid; $^1$H NMR (300 MHz, DMSO-d$_6$) δ 12.41 (s, 1H, D$_2$O exchangeable), 4.95 (s, 1H, D$_2$O exchangeable), 4.20 (q, J=5.1 Hz, 1H), 4.14-4.02 (m, 1H), 3.48 (dt, J=10.8, 5.4 Hz, 1H), 3.09 (ddd, J=10.6, 6.2, 4.2 Hz, 1H), 2.41-2.20 (m, 1H), 1.81 (dt, J=12.8, 5.0 Hz, 1H), 1.37 (d, J=15.9 Hz, 9H); $^1$H NMR (300 MHz, MeOH-d$_4$) δ 4.34 (ddd, J=5.8, 4.0, 1.5 Hz, 1H), 4.30-4.22 (m, 1H), 3.61 (dd, J=11.1, 5.6 Hz, 1H), 3.38-3.33 (m, 1H), 2.54-2.32 (m, 1H), 2.15-1.97 (m, 1H), 1.45 (d, J=12.0 Hz, 9H); MS (ES+) 254.3 (M+Na); MS (ES−) 230.2 (M−1), 461.5 (2M−1); Optical rotation [α]$_D$=(+) 52.96 [1.065, MeOH].

Step 2: Preparation of (2R,4R)-tert-butyl 2-(5-(1-(3-cyanophenyl)-3-cyclopropyl-1-((R)-1,1-dimethylethylsulfinamido)propyl)-2-fluorophenylcarbamoyl)-4-hydroxypyrrolidine-1-carboxylate (14c)

Reaction of (2R,4R)-1-(tert-butoxycarbonyl)-4-hydroxypyrrolidine-2-carboxylic acid (14b) (0.752 g, 3.25 mmol), (R)-N-((−)-1-(3-amino-4-fluorophenyl)-1-(3-cyanophenyl)-3-cyclopropylpropyl)-2-methylpropane-2-sulfinamide (4e) (1.345 g, 3.25 mmol) in tetrahydrofuran (50 mL) using ethyl 2-ethoxyquinoline-1(2H)-carboxylate (0.804 g, 3.25 mmol) using the reaction and workup conditions as reported in step 10 of Scheme 1 gave after purification by flash column chromatography (silica gel 25 g, eluting with CMA 80 in chloroform 0 to 100%) (2R,4R)-tert-butyl 2-(5-(1-(3-cyanophenyl)-3-cyclopropyl-1-((R)-1,1-dimethylethylsulfinamido) propyl)-2-fluorophenylcarbamoyl)-4-hydroxypyrrolidine-1-carboxylate (14c) (0.84 g, 1.340 mmol, 41.2% yield) as a white solid; $^1$H NMR (300 MHz, DMSO-d$_6$) δ 9.79 (s, 1H), 7.78 (d, J=1.9 Hz, 1H), 7.75-7.67 (m, 1H), 7.62 (m, 1H), 7.51 (m, 1H), 7.20 (m, 1H), 6.90 (m, 1H), 6.72 (m, 1H), 6.48 (m, 1H), 5.28 (s, 1H), 5.11 (s, 1H), 4.38-4.14 (m, 1H), 3.47 (m, 1H), 3.31-3.19 (m, 1H), 2.76-2.23 (m, 3H), 1.99 (m, 1H), 1.12 (s, 18H), 1.00-0.79 (m, 2H), 0.76-0.56 (m, 1H), 0.35 (m, 2H), −0.00--0.16 (m, 2H); $^{19}$F NMR (282 MHz, DMSO-d$_6$) δ −137.33; MS (ES+) 649.5 (M+Na), (ES−) 625.5 (M−1).

Step 3: Preparation of (2R,4R)-tert-butyl 4-acetoxy-2-(5-((−)-1-(3-cyanophenyl)-3-cyclopropyl-1-((R)-1,1-dimethylethylsulfinamido)propyl)-2-fluorophenylcarbamoyl)pyrrolidine-1-carboxylate (14d)

To a solution of (2R,4R)-tert-butyl 2-(5-(1-(3-cyanophenyl)-3-cyclopropyl-1-((R)-1,1-dimethylethylsulfinamido) propyl)-2-fluorophenylcarbamoyl)-4-hydroxypyrrolidine-1-carboxylate (14c) (0.8 g, 1.276 mmol) in dichloromethane (30 mL) was added DIPEA (0.669 mL, 3.83 mmol), acetic anhydride (0.145 mL, 1.532 mmol), DMAP (7.80 mg, 0.064 mmol) and stirred at room temperature overnight. The reaction was diluted with dichloromethane (100 mL), washed with water (2×25 mL), brine (25 mL), dried and concentrated. The crude residue obtained was purified by flash column chromatography (silica gel 12 g, eluting with ethyl acetate in hexanes 0 to 50%) to afford (2R,4R)-tert-butyl 4-acetoxy-2-(5-((−)-1-(3-cyanophenyl)-3-cyclopropyl-1-((R)-1,1-dimethylethylsulfinamido)propyl)-2-fluorophenylcarbamoyl)pyrrolidine-1-carboxylate (14d) (324 mg, 0.484 mmol, 38.0% yield) as a white semi solid; 1H NMR (300 MHz, DMSO-d$_6$) δ 9.63 (s, 1H), 7.78 (m, 1H), 7.76-7.55 (m, 3H), 7.51 (m, 1H), 7.21 (m, 2H), 5.49 (s, 1H), 5.09 (t, J=7.2 Hz, 1H), 4.42 (2 sets of dd, J=32.7, 7.2 Hz, 1H for rotamers), 3.76-3.59 (m, 1H), 3.49-3.35 (m, 1H), 2.75-2.38 (m, 2H), 2.09-1.95 (m, 1H), 1.87 (2S, 3H for rotamers), 1.36 (2s, 9H for rotamers), 1.12 (s, 10H), 1.08-1.00 (m, 1H), 1.00-0.80 (m, 1H), 0.72-0.51 (m, 1H), 0.44-0.24 (m, 2H), −0.06 (m, 2H); $^{19}$F NMR (282 MHz, DMSO-d$_6$) δ −125.32; MS (ES+) 691.6 (M+Na), (ES−) 667.6 (M−1); Optical rotation [α]$_D$=(−) 48.0 [0.125, MeOH].

Step-4: Preparation of (3R,5R)-5-(5-(1-amino-1-(3-cyanophenyl)-3-cyclopropylpropyl)-2-fluorophenylcarbamoyl)pyrrolidin-3-yl acetate (14e) and (2R,4R)-N-(5-(1-amino-1-(3-cyanophenyl)-3-cyclopropylpropyl)-2-fluorophenyl)-4-hydroxypyrrolidine-2-carboxamide (14f)

Reaction of (2R,4R)-tert-butyl 4-acetoxy-2-(5-((−)-1-(3-cyanophenyl)-3-cyclopropyl-1-((R)-1,1-dimethylethylsulfinamido)propyl)-2-fluorophenylcarbamoyl)pyrrolidine-1-carboxylate (14d) (0.32 g, 0.478 mmol) in ethanol (10 mL) using conc. HCl (0.399 mL, 4.78 mmol) as reported in step 6 of Scheme 4 gave after purification by flash column chromatography (silica gel 12 g, eluting with CMA-80 in chloroform 0 to 60%) gave
1. (3R,5R)-5-(5-(1-amino-1-(3-cyanophenyl)-3-cyclopropylpropyl)-2-fluorophenylcarbamoyl)pyrrolidin-3-yl acetate (14e) (90 mg, 0.194 mmol, 40.5% yield); 1H NMR (300 MHz, DMSO-d6) δ 10.04 (d, J=2.0 Hz, 1H), 8.24-8.11 (m, 1H), 7.84 (t, J=1.6 Hz, 1H), 7.64 (tt, J=7.6, 1.3 Hz, 2H), 7.47 (t, J=7.8 Hz, 1H), 7.27-7.06 (m, 2H), 5.07 (m, 1H), 3.81 (d, J=9.4 Hz, 1H), 3.46 (m, 1H), 3.18 (m, 1H), 2.91 (m, 1H), 2.26 (m, 5H), 2.06 (m, 1H), 1.75 (s, 3H), 1.03 (m, 2H), 0.64 (m, 1H), 0.42-0.28 (m, 2H), −0.07 (m, 2H); 19F NMR (282 MHz, DMSO-d6) δ −132.66. MS(ES+) 465.4 (M+1), 487.4 (M+Na), (ES−) 463.4 (M−1), 499.5 (M+Cl).
2. (2R,4R)-N-(5-(1-amino-1-(3-cyanophenyl)-3-cyclopropylpropyl)-2-fluorophenyl)-4-hydroxypyrrolidine-2-carboxamide (14f) (100 mg, 0.237 mmol, 49.5% yield); $^1$H NMR (300 MHz, DMSO-d$_6$) δ 10.19 (s, 1H), 8.42-8.22 (m, 1H), 7.86 (t, J=1.7 Hz, 1H), 7.74-7.59 (m, 2H), 7.47 (m, 1H), 7.25-6.94 (m, 2H), 4.67 (d, J=3.3 Hz, 1H), 4.16 (m, 1H), 3.84-3.60 (m, 1H), 3.00 (m, 1H), 2.72 (dd, J=10.6, 3.0 Hz, 1H), 2.43-2.03 (m, 6H), 1.83 (dt, J=13.0, 3.9 Hz, 1H), 1.14-0.88 (m, 2H), 0.76-0.51 (m, 1H), 0.46-0.25 (m, 2H), −0.03-−0.10 (m, 2H); $^{19}$F NMR (282 MHz, DMSO-d$_6$) δ −133.44; MS (ES+) 423.4 (M+1), 445.4 (M+Na), (ES−) 457.4 (M+Cl).

Step 5: Preparation of Preparation of (2R,4R)-N2-(5-(1-amino-1-(3-cyanophenyl)-3-cyclopropylpropyl)-2-fluorophenyl)-N1-(5-chloropyridin-2-yl)-4-hydroxypyrrolidine-1,2-dicarboxamide (14h)

Reaction of (2R,4R)-N-(5-(1-amino-1-(3-cyanophenyl)-3-cyclopropylpropyl)-2-fluorophenyl)-4-hydroxypyrrolidine-2-carboxamide (14f) (92 mg, 0.218 mmol) in tetrahydrofuran (10 mL) with phenyl 5-chloropyridin-2-ylcarbamate (54.1 mg, 0.218 mmol) as reported in step 3 of Scheme 13 after purification by flash column chromatography (silica gel 12 g, eluting with 0-100% CMA-80 in chloroform) afforded (2R,4R)-N2-(5-(1-amino-1-(3-cyanophenyl)-3-cyclopropylpropyl)-2-fluorophenyl)-N1-(5-chloropyridin-2-yl)-4-hydroxypyrrolidine-1,2-dicarboxamide (14h) (34 mg, 0.059 mmol, 27.1% yield) as a white solid; $^1$H NMR (300 MHz, DMSO-d$_6$) δ 9.67 (s, 1H), 9.16 (s, 1H), 8.31-8.26 (m, 1H), 8.01 (d, J=7.5 Hz, 1H), 7.94-7.83 (m, 2H), 7.79 (dd, J=9.0, 2.7 Hz, 1H), 7.63 (m, 2H), 7.46 (t, J=7.8 Hz, 1H), 7.13 (dd, J=7.4, 2.0 Hz, 2H), 5.31 (d, J=4.7 Hz, 1H), 4.54 (m, 1H), 4.31 (q, J=4.9 Hz, 1H), 3.73 (m, 1H), 3.51 (dd, J=10.5, 4.2 Hz, 1H), 2.47-2.28 (m, 3H), 2.28-2.10 (m, 2H), 1.89 (m, 1H), 1.01 (m, 2H), 0.63 (m, 1H), 0.34 (m, 2H), −0.03-−0.17 (m, 2H); $^{19}$F NMR (282 MHz, DMSO-d$_6$) δ −128.70; MS (ES+) 577.5, 579.5 (M+1); IR (KBr) 2229 cm$^1$.

Preparation of (3R,5R)-5-(5-((+)-1-amino-1-(3-cyanophenyl)-3-cyclopropylpropyl)-2-fluorophenylcarbamoyl)-1-(5-chloropyridin-2-ylcarbamoyl)pyrrolidin-3-yl acetate (14g)

Reaction of (3R,5R)-5-(5-(1-amino-1-(3-cyanophenyl)-3-cyclopropylpropyl)-2-fluorophenylcarbamoyl)pyrrolidin-3-yl acetate (14e) (81 mg, 0.174 mmol) in tetrahydrofuran (10 mL) with phenyl 5-chloropyridin-2-ylcarbamate (43.4 mg, 0.174 mmol) as reported in step 3 of Scheme 13 after purification by flash column chromatography (silica gel 12 g, eluting with 0-100% CMA-80 in chloroform) afforded (3R,5R)-5-(5-((+)-1-amino-1-(3-cyanophenyl)-3-cyclopropylpropyl)-2-fluorophenylcarbamoyl)-1-(5-chloropyridin-2-ylcarbamoyl)pyrrolidin-3-yl acetate (14g) (24 mg, 0.039 mmol, 22.23% yield) as a white solid; $^1$H NMR (300 MHz, DMSO-d$_6$) δ 9.64 (s, 1H), 9.18 (s, 1H), 8.30 (d, J=2.6 Hz, 1H), 7.91 (dd, J=9.0, 0.8 Hz, 1H), 7.86-7.79 (m, 2H), 7.75 (dd, J=7.6, 2.2 Hz, 1H), 7.63 (m, 2H), 7.46 (m, 1H), 7.23-7.10 (m, 2H), 5.19 (q, J=4.6, 3.7 Hz, 1H), 4.72 (d, J=8.7 Hz, 1H), 3.88 (dd, J=11.7, 5.2 Hz, 1H), 3.75 (d, J=11.7 Hz, 1H), 2.48-2.40 (m, 1H), 2.32 (m, 2H), 2.22 (m, 3H), 1.87 (s, 3H), 1.12-0.91 (m, 2H), 0.72-0.50 (m, 1H), 0.42-0.28 (m, 2H), −0.03-−0.14 (m, 2H); $^{19}$F NMR (282 MHz, DMSO-d$_6$) δ −126.76; MS (ES−) 617.4 (M−1), 653.3, 655.3 (M+Cl); Optical rotation [α]$_D$=(+) 109.1 [0.165, MeOH].

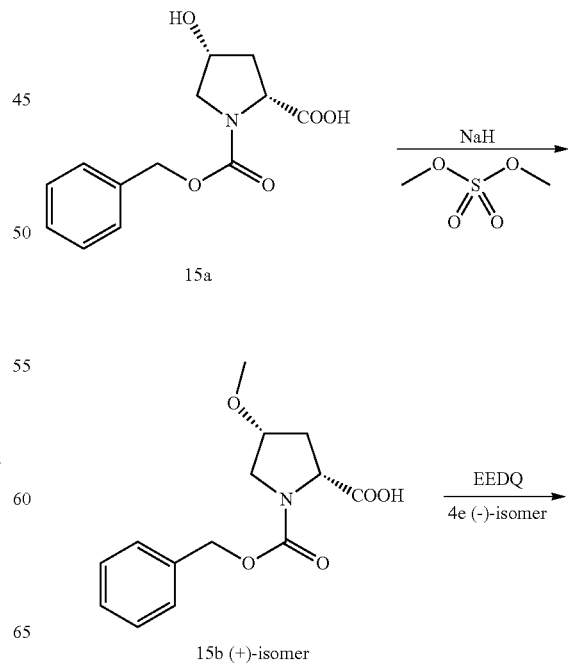

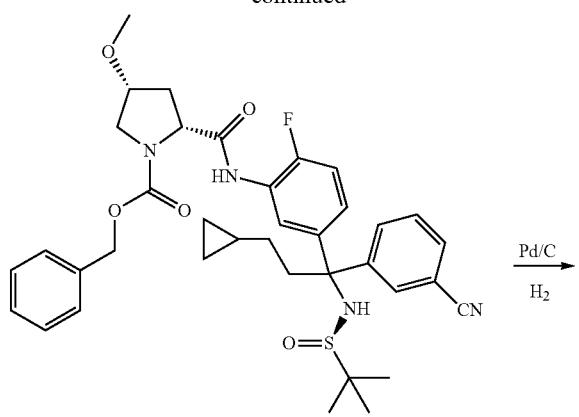

15c (−)-isomer

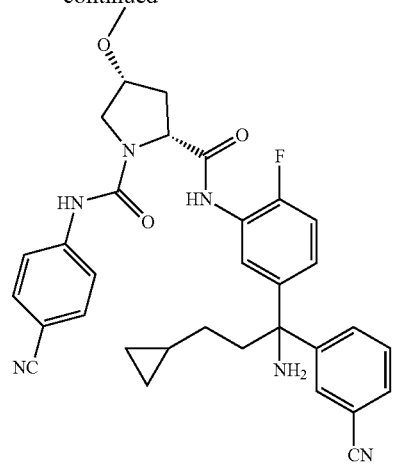

15f (+)-isomer

Preparation of (2R,4R)-N2-(5-((+)-1-amino-1-(3-cyanophenyl)-3-cyclopropylpropyl)-2-fluorophenyl)-N1-(4-cyanophenyl)-4-methoxypyrrolidine-1,2-dicarboxamide (15f)

Step 1: Preparation of (2R,4R)-1-(benzyloxycarbonyl)-4-methoxypyrrolidine-2-carboxylic acid (15b)

To a slurry of sodium hydride (60% dispersion in oil, 2.262 g, 56.5 mmol) in tetrahydrofuran (30 mL) at −10° C. was added a solution of (2R,4R)-1-(benzyloxycarbonyl)-4-hydroxypyrrolidine-2-carboxylic acid (15a) (2.5 g, 9.42 mmol) in THF (60 mL). The reaction was stirred for 30 min, followed by the addition of dimethyl sulfate (0.901 mL, 9.42 mmol) and stirred at room temperature for 16 h. The reaction mixture was quenched with saturated aqueous ammonium chloride and concentrated in vacuum to remove THF. The reaction mixture was basified, washed with ether, acidified and extracted with ethyl acetate (2×100 mL). The combined ethyl acetate layer was washed with water (50 mL), brine (50 mL), dried, filtered and evaporated in vacuum to obtain (2R,4R)-1-(benzyloxycarbonyl)-4-methoxypyrrolidine-2-carboxylic acid (15b) (2.138 g, 7.66 mmol, 81% yield) as a white solid; $^1$H NMR (300 MHz, DMSO-$d_6$) δ 12.56 (s, 1H), 7.55-7.12 (m, 5H), 5.23-4.88 (m, 2H), 4.29 (ddd, J=21.9, 9.4, 3.0 Hz, 1H), 3.95 (qt, J=5.3, 2.7 Hz, 1H), 3.61 (ddd, J=15.6, 11.5, 5.4 Hz, 1H), 3.31 (m, 1H), 3.17 (2s, 3H, for rotamers), 2.42-2.24 (m, 1H), 2.17-2.01 (m, 1H); MS (ES−) 278.2 (M−1); Optical rotation $[α]_D$=(+) 33.81 [0.775, MeOH].

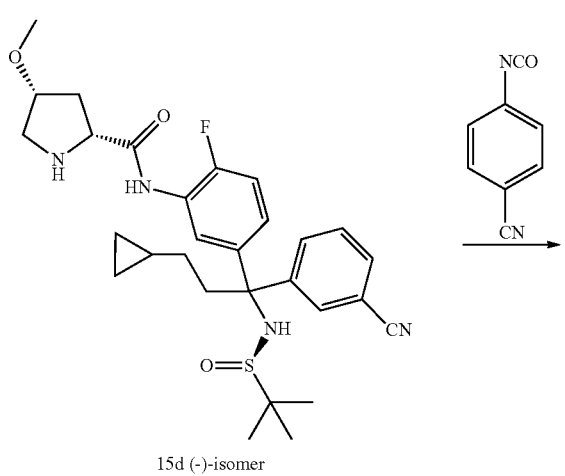

15d (−)-isomer

Step 2: Preparation of (2R,4R)-benzyl 2-(5-((−)-1-(3-cyanophenyl)-3-cyclopropyl-1-((R)-1,1-dimethylethylsulfinamido)propyl)-2-fluorophenylcarbamoyl)-4-methoxypyrrolidine-1-carboxylate (15c)

Reaction of (2R,4R)-1-(benzyloxycarbonyl)-4-methoxypyrrolidine-2-carboxylic acid (15b) (1.52 g, 5.44 mmol), (R)-N-((−)-1-(3-amino-4-fluorophenyl)-1-(3-cyanophenyl)-3-cyclopropylpropyl)-2-methylpropane-2-sulfinamide (4e) (2.251 g, 5.44 mmol) in tetrahydrofuran (75 mL) using ethyl 2-ethoxyquinoline-1(2H)-carboxylate (1.346 g, 5.44 mmol) using the reaction and workup conditions as reported in step 10 of Scheme 1 gave after purification by flash column chromatography (silica gel 25 g, eluting with CMA 80 in

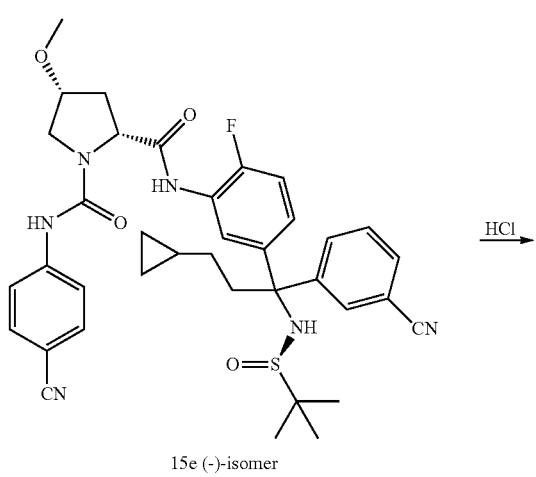

15e (−)-isomer chloroform 0 to 100%) (2R,4R)-benzyl 2-(5-((−)-1-(3-cyanophenyl)-3-cyclopropyl-1-((R)-1,1-dimethylethylsulfinamido)propyl)-2-fluorophenylcarbamoyl)-4-methoxypyrrolidine-1-carboxylate (15c) (3.15 g, 4.67 mmol, 86% yield) as a white solid; ¹H NMR (300 MHz, DMSO-d₆) δ 9.54 (2s, 1H, for rotamers), 7.86 (m, 1H), 7.79 (m, 1H), 7.71 (m, 1H), 7.65-7.56 (m, 1H), 7.52 (m, 1H), 7.38 (m, 2H), 7.19 (m, 5H), 5.50 (2s, 1H, for rotamers), 5.18-4.93 (m, 2H), 4.54-4.33 (m, 1H), 4.05-3.93 (m, 2H), 3.75-3.59 (m, 1H), 3.49-3.39 (m, 1H), 3.19 (2s, 3H, for rotamers), 2.51 (m, 2H), 2.12-2.00 (m, 1H), 1.17-1.01 (m, 10H), 0.98-0.81 (m, 1H), 0.71-0.55 (m, 1H), 0.42-0.25 (m, 2H), 0.01--0.13 (m, 2H); ¹⁹F NMR (282 MHz, DMSO-d₆) δ −126.94, −127.36; MS (ES+) 675.5 (M+1), 697.5, 698.5 (M+Na), (ES−) 673.5 (M−1), 709.4, 710.4 (M+Cl); Optical rotation [α]$_D$=(−) 58.2 [0.165, MeOH].

Step 3: Preparation of (2R,4R)-N-(5-((−)-1-(3-cyanophenyl)-3-cyclopropyl-1-((R)-1,1-dimethylethylsulfinamido)propyl)-2-fluorophenyl)-4-methoxypyrrolidine-2-carboxamide (15d)

Debenzylation by hydrogenation of (2R,4R)-benzyl 2-(5-((−)-1-(3-cyanophenyl)-3-cyclopropyl-1-((R)-1,1-dimethylethylsulfinamido)propyl)-2-fluorophenylcarbamoyl)-4-methoxypyrrolidine-1-carboxylate (15c) (3.05 g, 4.52 mmol) in ethanol (100 mL), using palladium on carbon 10% (0.265 g, 0.249 mmol) as catalyst according to procedure reported in step 2 of Scheme 13 gave (2R,4R)-N-(5-((−)-1-(3-cyanophenyl)-3-cyclopropyl-1-((R)-1,1-dimethylethylsulfinamido)propyl)-2-fluorophenyl)-4-methoxypyrrolidine-2-carboxamide (15d) (2.4 g, 4.44 mmol, 98% yield) as a white solid; ¹H NMR (300 MHz, DMSO-d₆) δ 10.09 (d, J=2.2 Hz, 1H), 8.29 (dd, J=7.7, 2.4 Hz, 1H), 7.80 (t, J=1.8 Hz, 1H), 7.71 (dt, J=7.4, 1.3 Hz, 1H), 7.62 (dt, J=8.3, 1.5 Hz, 1H), 7.51 (t, J=7.8 Hz, 1H), 7.21 (dd, J=10.8, 8.7 Hz, 1H), 7.10-7.01 (m, 1H), 5.47 (s, 1H), 3.95-3.81 (m, 1H), 3.74 (dd, J=8.1, 5.1 Hz, 1H), 3.11 (s, 3H), 3.08-2.97 (m, 1H), 2.89 (dd, J=11.1, 2.4 Hz, 1H), 2.75-2.56 (m, 2H), 2.13-2.01 (m, 2H), 1.14 (s, 10H), 1.12-1.04 (m, 1H), 0.96-0.80 (m, 1H), 0.72-0.53 (m, 1H), 0.43-0.27 (m, 2H), 0.00--0.15 (m, 2H); ¹⁹F NMR (282 MHz, DMSO-d₆) δ −132.45; MS (ES+) 541.5 (M+1), (ES−) 575.4 (M+Cl); Optical rotation [α]$_D$=(−) 67.1 [0.155, MeOH].

Step-4: Preparation of (2R,4R)-N1-(4-cyanophenyl)-N2-(5-((−)-1-(3-cyanophenyl)-3-cyclopropyl-1-((R)-1,1-dimethylethylsulfinamido)propyl)-2-fluorophenyl)-4-methoxypyrrolidine-1,2-dicarboxamide (15e)

Reaction of (2R,4R)-N-(5-((−)-1-(3-cyanophenyl)-3-cyclopropyl-1-((R)-1,1-dimethylethylsulfinamido)propyl)-2-fluorophenyl)-4-methoxypyrrolidine-2-carboxamide (15d) (0.5 g, 0.925 mmol) in tetrahydrofuran (20 mL), 4-isocyanatobenzonitrile (0.267 g, 1.849 mmol) using DIPEA (0.646 mL, 3.70 mmol) as base using reaction and workup conditions as reported in step 9 of Scheme 1 gave (2R,4R)-N1-(4-cyanophenyl)-N2-(5-((−)-1-(3-cyanophenyl)-3-cyclopropyl-1-((R)-1,1-dimethylethylsulfinamido)propyl)-2-fluorophenyl)-4-methoxypyrrolidine-1,2-dicarboxamide (15e)

(514 mg, 0.751 mmol, 81% yield) as a white solid; ¹H NMR (300 MHz, DMSO-d₆) δ 9.51 (d, J=1.3 Hz, 1H), 8.85 (s, 1H), 7.90-7.84 (m, 1H), 7.78 (t, J=1.6 Hz, 1H), 7.77-7.66 (m, 5H), 7.62-7.57 (m, 1H), 7.50 (t, J=7.8 Hz, 1H), 7.19 (dd, J=10.3, 8.7 Hz, 1H), 7.14-7.06 (m, 1H), 5.50 (s, 1H), 4.57 (dd, J=9.1, 4.1 Hz, 1H), 4.11-4.06 (m, 1H), 3.76 (dd, J=10.6, 5.2 Hz, 1H), 3.65 (dd, J=10.2, 2.9 Hz, 2H), 3.23 (s, 3H), 2.76-2.53 (m, 1H), 2.48-2.31 (m, 1H), 2.18-2.05 (m, 1H), 1.13 (s, 9H), 1.11-1.01 (m, 1H), 0.98-0.80 (m, 1H), 0.72-0.55 (m, 1H), 0.41-0.26 (m, 2H), −0.02--0.14 (m, 2H); ¹⁹F NMR (282 MHz, DMSO-d₆) δ −127.51; MS: (ES+) 685.5 (M+1), 707.5, 709.7 (M+Na), (ES−) 719.5, 721.1 (M+Cl); Optical rotation [α]$_D$=(−) 4.21 [0.19, MeOH].

Step 5: Preparation of (2R,4R)-N2-(5-((+)-1-amino-1-(3-cyanophenyl)-3-cyclopropylpropyl)-2-fluorophenyl)-N1-(4-cyanophenyl)-4-methoxypyrrolidine-1,2-dicarboxamide (15f)

Reaction of (2R,4R)-N1-(4-cyanophenyl)-N2-(5-((R)-1-(3-cyanophenyl)-3-cyclopropyl-1-((R)-1,1-dimethylethylsulfinamido)propyl)-2-fluorophenyl)-4-methoxypyrrolidine-1,2-dicarboxamide (15e) (445 mg, 0.650 mmol) in ethanol (20 mL) using conc. HCl (0.542 mL, 6.50 mmol) as reported in step 6 of Scheme 4 gave after purification by flash column chromatography (silica gel 12 g, eluting with CMA-80 in chloroform 0 to 60%) gave (2R,4R)-N2-(5-((+)-1-amino-1-(3-cyanophenyl)-3-cyclopropylpropyl)-2-fluorophenyl)-N1-(4-cyanophenyl)-4-methoxypyrrolidine-1,2-dicarboxamide (15f) (300 mg, 0.517 mmol, 80% yield) as a white solid; ¹H NMR (300 MHz, DMSO-d₆) δ 9.46 (s, 1H), 8.83 (s, 1H), 7.89-7.81 (m, 2H), 7.78-7.60 (m, 6H), 7.46 (t, J=7.8 Hz, 1H), 7.18-7.07 (m, 2H), 4.56 (dd, J=9.1, 4.1 Hz, 1H), 4.17-3.98 (m, 1H), 3.77 (dd, J=10.5, 5.2 Hz, 1H), 3.63 (dd, J=10.4, 3.4 Hz, 1H), 3.22 (s, 3H), 2.41-2.14 (m, 5H), 2.14-2.00 (m, 1H), 1.09-0.92 (m, 2H), 0.76-0.49 (m, 1H), 0.41-0.27 (m, 2H), −0.04--0.19 (m, 2H); 19F NMR (282 MHz, DMSO-d6) δ −128.39; MS (ES+) 603.5, 604.5 (M+Na), (ES−) 615.6, 617.4 (M+Cl); Optical rotation [α]$_D$= (+) 108.68 [0.265, MeOH].

Scheme 16

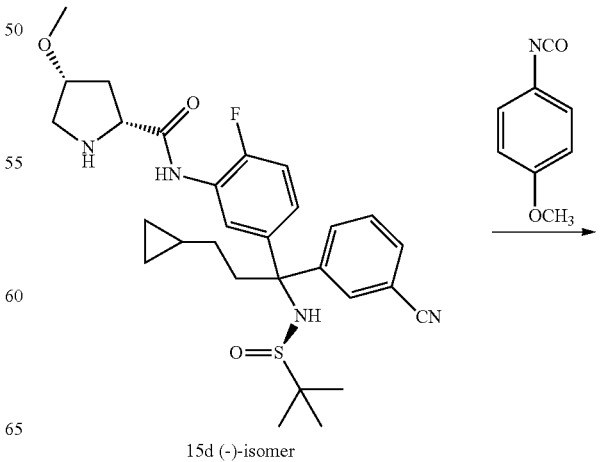

15d (−)-isomer

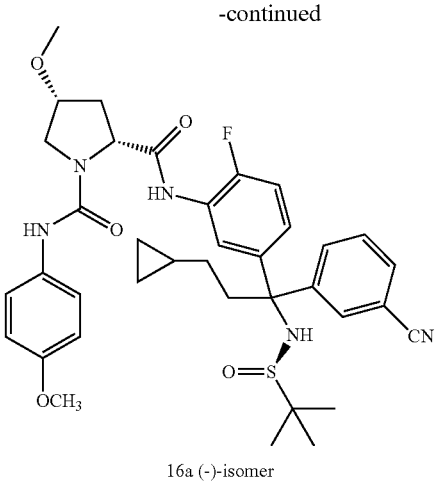

16a (−)-isomer

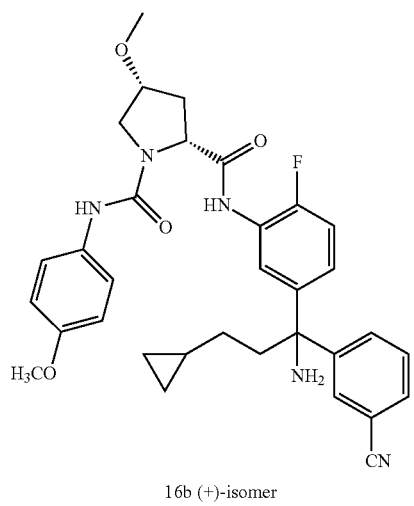

16b (+)-isomer

Preparation of (2R,4R)-N2-(5-((+)-1-amino-1-(3-cyanophenyl)-3-cyclopropylpropyl)-2-fluorophenyl)-4-methoxy-N1-(4-methoxyphenyl)pyrrolidine-1,2-dicarboxamide (16b)

Step 1: Preparation of (2R,4R)-N2-(5-((−)-1-(3-cyanophenyl)-3-cyclopropyl-1-((R)-1,1-dimethylethylsulfinamido)propyl)-2-fluorophenyl)-4-methoxy-N1-(4-methoxyphenyl)pyrrolidine-1,2-dicarboxamide (16a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-methoxypyrrolidine-2-carboxamide (15d) (0.5 g, 0.925 mmol) in tetrahydrofuran (20 mL), phenyl 1-isocyanato-4-methoxybenzene (0.240 mL, 1.849 mmol), DIPEA (0.646 mL, 3.70 mmol) using reaction and workup conditions as reported in step 9 of Scheme 1 gave (2R,4R)-N2-(5-((−)-1-(3-cyanophenyl)-3-cyclopropyl-1-((R)-1,1-dimethylethylsulfinamido)propyl)-2-fluorophenyl)-4-methoxy-N1-(4-methoxyphenyl)pyrrolidine-1,2-dicarboxamide (16a) (552 mg, 0.800 mmol, 87% yield) as a white solid; $^1$H NMR (300 MHz, DMSO-$d_6$) δ 9.50 (s, 1H), 8.28 (s, 1H), 8.00 (dd, J=7.7, 2.4 Hz, 1H), 7.79 (t, J=1.7 Hz, 1H), 7.71 (m, 1H), 7.60 (m, 1H), 7.50 (t, J=7.8 Hz, 1H), 7.43-7.34 (m, 2H), 7.19 (m, 1H), 6.87-6.79 (m, 2H), 5.50 (s, 1H), 4.52 (dd, J=9.2, 3.7 Hz, 1H), 4.07 (m, 1H), 3.70 (s, 3H), 3.65 (m, 2H), 3.22 (s, 3H), 2.75-2.48 (m, 2H), 2.32 (m, 1H), 2.23-2.11 (m, 1H), 1.13 (s, 10H), 1.00-0.79 (m, 1H), 0.43-0.25 (m, 2H), 0.63 (m, 1H), 0.43-0.25 (m, 2H), −0.01--0.15 (m, 2H); $^{19}$F NMR (282 MHz, DMSO-$d_6$) δ −127.51; MS (ES+) 690.5 (M+1), 712.5, 713.5 (M+Na), (ES−) 724.4, 726.6 (M+Cl); Optical rotation [α]$_D$=(−) 17.78 [0.36, MeOH].

Step 2: Preparation of (2R,4R)-N2-(5-((+)-1-amino-1-(3-cyanophenyl)-3-cyclopropylpropyl)-2-fluorophenyl)-4-methoxy-N1-(4-methoxyphenyl)pyrrolidine-1,2-dicarboxamide (16b)

Reaction of (2R,4R)-N2-(5-((−)-1-(3-cyanophenyl)-3-cyclopropyl-1-((R)-1,1-dimethylethylsulfinamido)propyl)-2-fluorophenyl)-4-methoxy-N1-(4-methoxyphenyl)pyrrolidine-1,2-dicarboxamide (16a) (485 mg, 0.703 mmol) in ethanol (20 mL) using conc. HCl (0.586 mL, 7.03 mmol) as reported in step 6 of Scheme 4 gave after purification by flash column chromatography (silica gel, eluting with CMA-80 in chloroform 0 to 100%) gave (2R,4R)-N2-(5-((+)-1-amino-1-(3-cyanophenyl)-3-cyclopropylpropyl)-2-fluorophenyl)-4-methoxy-N1-(4-methoxyphenyl)pyrrolidine-1,2-dicarboxamide (16b) (19 mg, 0.032 mmol, 4.61% yield) as a white solid; $^1$H NMR (300 MHz, DMSO-$d_6$) δ 9.44 (s, 1H), 8.26 (s, 1H), 7.97 (d, J=7.6 Hz, 1H), 7.86 (t, J=1.7 Hz, 1H), 7.71-7.57 (m, 2H), 7.46 (t, J=7.8 Hz, 1H), 7.41-7.32 (m, 2H), 7.13 (d, J=8.0 Hz, 2H), 6.88-6.75 (m, 2H), 4.51 (dd, J=9.3, 3.7 Hz, 1H), 4.11-3.99 (m, 1H), 3.70 (s, 3H), 3.67 (m, 1H), 3.64-3.56 (m, 1H), 3.22 (s, 3H), 2.38-2.11 (m, 6H), 1.11-0.94 (m, 2H), 0.73-0.55 (m, 1H), 0.40-0.24 (m, 2H), −0.01--0.21 (m, 2H); $^{19}$F NMR (282 MHz, DMSO-$d_6$) δ −129.61; MS (ES+) 586.5 (M+1), 608.5, 610.6 (M+Na), (ES−) 620.5, 622.5 (M+Cl); IR (KBr) 2228 cm$^1$; Analysis calculated for $C_{33}H_{36}FN_5O_4 \cdot 0.5H_2O$; C, 66.65; H, 6.27; N, 11.78. Found; C, 66.83; H, 6.19; N, 11.71; Optical rotation [α]$_D$=(+) 95.48 [0.155, MeOH].

Scheme 17

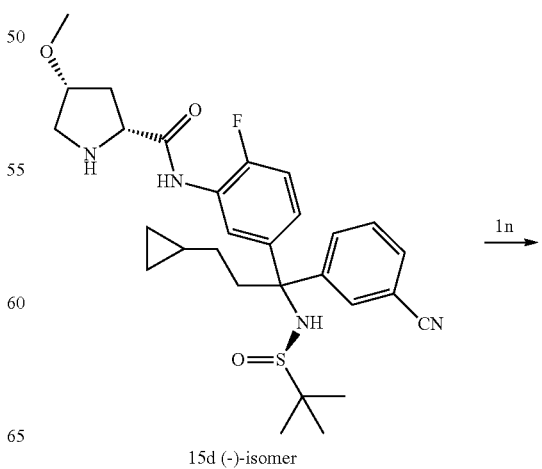

15d (−)-isomer

-continued

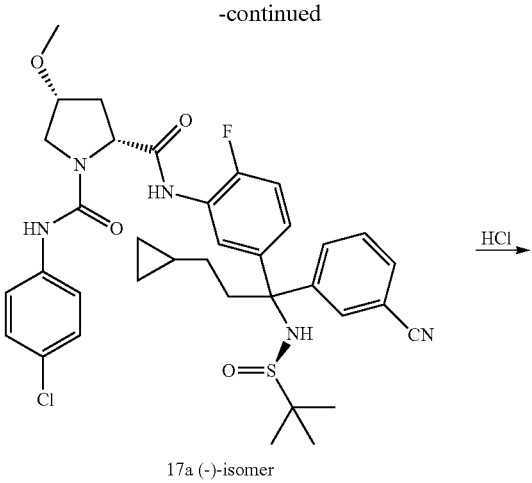

17a (−)-isomer

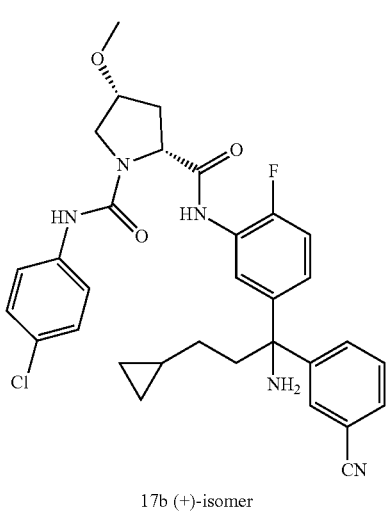

17b (+)-isomer

Preparation of (2R,4R)-N2-(5-((+)-1-amino-1-(3-cyanophenyl)-3-cyclopropylpropyl)-2-fluorophenyl)-4-methoxy-N1-(4-chlorophenyl)pyrrolidine-1,2-dicarboxamide (17b)

Step 1: Preparation of (2R,4R)-N2-(5-((−)-1-(3-cyanophenyl)-3-cyclopropyl-1-((R)-1,1-dimethylethylsulfinamido)propyl)-2-fluorophenyl)-4-methoxy-N1-(4-chlorophenyl)pyrrolidine-1,2-dicarboxamide (17a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-methoxypyrrolidine-2-carboxamide (15d) (0.5 g, 0.925 mmol) in tetrahydrofuran (20 mL), 4-chlorophenyl isocyanate (1n) (0.237 mL, 1.849 mmol), DIPEA (0.646 mL, 3.70 mmol) using reaction and workup conditions as reported in step 9 of Scheme 1 gave (2R,4R)-N2-(5-((−)-1-(3-cyanophenyl)-3-cyclopropyl-1-((R)-1,1-dimethylethylsulfinamido)propyl)-2-fluorophenyl)-4-methoxy-N1-(4-chlorophenyl)pyrrolidine-1,2-dicarboxamide (17a) (555 mg, 0.799 mmol, 86% yield) as a white solid; $^1$H NMR (300 MHz, DMSO-$d_6$) δ 9.52-9.44 (m, 1H), 8.53 (s, 1H), 7.96-7.88 (m, 1H), 7.79 (t, J=1.7 Hz, 1H), 7.71 (dt, J=7.5, 1.3 Hz, 1H), 7.63-7.46 (m, 4H), 7.33-7.25 (m, 2H), 7.19 (dd, J=10.4, 8.8 Hz, 1H), 7.11 (m, 1H), 5.50 (s, 1H), 4.54 (m, 1H), 4.10-4.05 (m, 1H), 3.72 (m, 1H), 3.68-3.57 (m, 1H), 3.22 (s, 3H), 2.63 (m, 2H), 2.42-2.26 (m, 1H), 2.12 (m, 1H), 1.13 (s, 9H), 1.12-1.01 (m, 1H), 0.98-0.76 (m, 1H), 0.72-0.56 (m, 1H), 0.43-0.22 (m, 2H), −0.02--0.16 (m, 2H); $^{19}$F NMR (282 MHz, DMSO-$d_6$) δ −128.06; MS: (ES+) 694.5 (M+H), 716.5, 718.5 (M+Na), (ES−) 728.5, 730.4 (M+Cl); Optical rotation $[α]_D$=(−) 17.31 [0.335, MeOH].

Step 2: Preparation of (2R,4R)-N2-(5-((+)-1-amino-1-(3-cyanophenyl)-3-cyclopropylpropyl)-2-fluorophenyl)-4-methoxy-N1-(4-chlorophenyl)pyrrolidine-1,2-dicarboxamide (17b)

Reaction of (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-methoxypyrrolidine-1,2-dicarboxamide (17a) (478 mg, 0.689 mmol) in ethanol (20 mL) using conc. HCl (0.574 mL, 6.89 mmol) as reported in step 6 of Scheme 4 gave after purification by flash column chromatography (silica gel, eluting with CMA-80 in chloroform 0 to 100%) (2R,4R)-N2-(5-((+)-1-amino-1-(3-cyanophenyl)-3-cyclopropylpropyl)-2-fluorophenyl)-N1-(4-chlorophenyl)-4-methoxypyrrolidine-1,2-dicarboxamide (17b) (52 mg, 8.3%) as a white solid; $^1$H NMR (300 MHz, DMSO-$d_6$) δ 9.67 (s, 1H), 9.21 (s, 3H), 8.56 (s, 1H), 7.89 (m, 2H), 7.84 (m, 1H), 7.70-7.58 (m, 2H), 7.58-7.52 (m, 2H), 7.36 (m, 1H), 7.32-7.26 (m, 2H), 7.09 (m, 1H), 4.56 (dd, J=9.2, 4.0 Hz, 1H), 4.13-4.04 (m, 1H), 3.74 (dd, J=10.5, 5.2 Hz, 1H), 3.62 (d, J=10.6 Hz, 1H), 3.22 (s, 3H), 2.60-2.53 (m, 1H), 2.47-2.32 (m, 1H), 2.08 (m, 1H), 1.15-0.99 (m, 2H), 0.78-0.57 (m, 1H), 0.45-0.17 (m, 2H), 0.17--0.10 (m, 2H); $^{19}$F NMR (282 MHz, DMSO-$d_6$) δ −125.67; MS (ES+) 612.5, 614.4 (M+Na), (ES−) 624.4, (M+Cl); Optical rotation $[α]_D$=(+) 71.88 [0.32, MeOH]; Analysis calculated for: $C_{32}H_{33}ClFN_5O_3 \cdot HCl \cdot 2H_2O$; C, 58.01; H, 5.78; N, 10.57. Found: C, 58.21; H, 5.41; N, 10.24; IR (KBr) 2233 cm$^1$.

Scheme 18

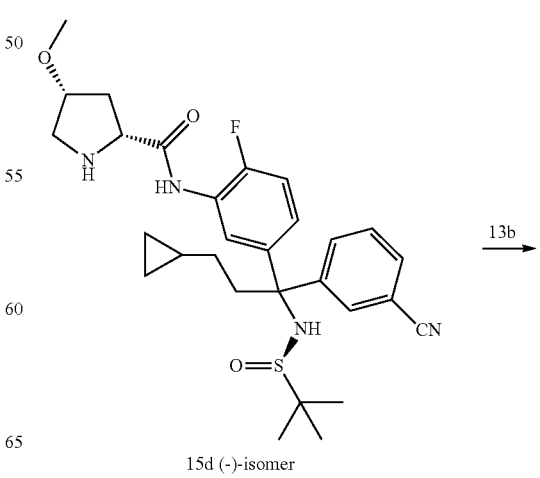

15d (−)-isomer

13b

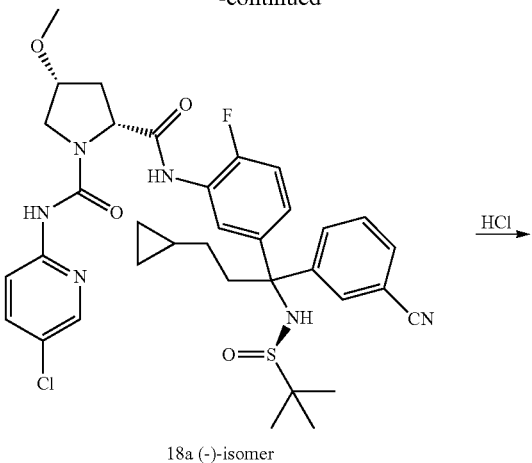

18a (-)-isomer

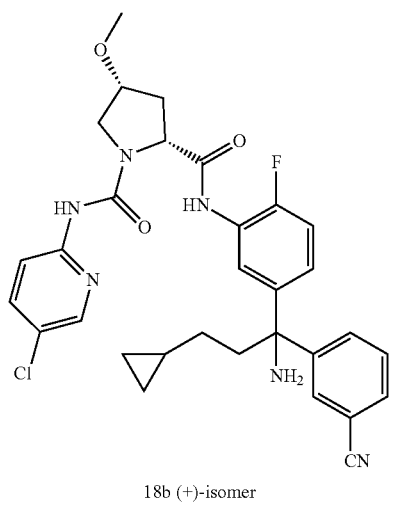

18b (+)-isomer

Preparation of (2R,4R)-N2-(5-((+)-1-amino-1-(3-cyanophenyl)-3-cyclopropylpropyl)-2-fluorophenyl)-N1-(5-chloropyridin-2-yl)-4-methoxypyrrolidine-1,2-dicarboxamide (18b)

Step 1: Preparation of ((2R,4R)-N1-(5-chloropyridin-2-yl)-N2-(5-((−)-1-(3-cyanophenyl)-3-cyclopropyl-1-((R)-1,1-dimethylethylsulfinamido)propyl)-2-fluorophenyl)-4-methoxypyrrolidine-1,2-dicarboxamide (18a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-methoxypyrrolidine-2-carboxamide (15d) (0.475 g, 0.879 mmol) in tetrahydrofuran (20 mL), phenyl 5-chloropyridin-2-ylcarbamate (13b) (0.437 g, 1.757 mmol), DIPEA (0.614 mL, 3.51 mmol) using reaction and workup conditions as reported in step 3 of Scheme 13 gave ((2R,4R)-N1-(5-chloropyridin-2-yl)-N2-(5-((−)-1-(3-cyanophenyl)-3-cyclopropyl-1-((R)-1,1-dimethylethylsulfinamido)propyl)-2-fluorophenyl)-4-methoxypyrrolidine-1,2-dicarboxamide (18a) (484 mg, 0.696 mmol, 79% yield) as white powder; $^1$H NMR (300 MHz, DMSO-$d_6$) δ 9.49 (s, 1H), 9.17 (s, 1H), 8.30 (d, J=2.7 Hz, 1H), 7.93-7.86 (m, 2H), 7.84-7.77 (m, 2H), 7.71 (dt, J=7.5, 1.3 Hz, 1H), 7.59 (dt, J=8.2, 1.6 Hz, 1H), 7.50 (t, J=7.8 Hz, 1H), 7.19 (dd, J=10.4, 8.7 Hz, 1H), 7.14-7.06 (m, 1H), 5.50 (s, 1H), 4.59 (dd, J=9.1, 3.9 Hz, 1H), 4.04 (m, 1H), 3.81-3.63 (m, 2H), 3.21 (s, 3H), 2.75-2.52 (m, 2H), 2.48-2.29 (m, 1H), 2.11 (m, 1H), 1.13 (s, 10H), 0.97-0.80 (m, 1H), 0.72-0.49 (m, 1H), 0.40-0.27 (m, 2H), −0.01-0.15 (m, 2H); $^{19}$F NMR (282 MHz, DMSO-$d_6$) δ −127.91; MS (ES+) 695.5 (M+1), 717.5, 719.5 (M+Na), (ES−) 729.5, 731.5 (M+Cl); IR (KBr) 2230 cm-; Optical rotation [α]$_D$=(−) 19.10 [0.335, MeOH]; CHN calculated for: $C_{35}H_{40}ClFN_6O_4S$. 0.5$H_2O$; C, 59.69; H, 5.87; N, 11.93. Found: C, 59.74; H, 5.75; N, 11.79.

Step 2: Preparation of (2R,4R)-N2-(5-((+)-1-amino-1-(3-cyanophenyl)-3-cyclopropylpropyl)-2-fluorophenyl)-N1-(5-chloropyridin-2-yl)-4-methoxypyrrolidine-1,2-dicarboxamide (18b)

Reaction of ((2R,4R)-N1-(5-chloropyridin-2-yl)-N2-(5-((−)-1-(3-cyanophenyl)-3-cyclopropyl-1-((R)-1,1-dimethylethylsulfinamido)propyl)-2-fluorophenyl)-4-methoxypyrrolidine-1,2-dicarboxamide (18a) (406 mg, 0.584 mmol) in ethanol (20 mL) using conc. HCl (0.487 mL, 5.84 mmol) as reported in step 6 of Scheme 4 gave after purification by flash column chromatography (silica gel, eluting with CMA-80 in chloroform 0 to 100%) (2R,4R)-N2-(5-((+)-1-amino-1-(3-cyanophenyl)-3-cyclopropylpropyl)-2-fluorophenyl)-N1-(5-chloropyridin-2-yl)-4-methoxypyrrolidine-1,2-dicarboxamide (18b) (60 mg, 10%) as a white solid; $^1$H NMR (300 MHz, DMSO-$d_6$) δ 9.45 (s, 1H), 9.15 (s, 1H), 8.30 (dd, J=2.6, 0.8 Hz, 1H), 7.93-7.84 (m, 3H), 7.81 (dd, J=9.0, 2.7 Hz, 1H), 7.63 (ddt, J=7.5, 5.7, 1.3 Hz, 2H), 7.46 (t, J=7.8 Hz, 1H), 7.15 (d, J=1.3 Hz, 1H), 7.13 (d, J=2.9 Hz, 1H), 4.57 (dd, J=9.2, 3.9 Hz, 1H), 4.10-3.97 (m, 1H), 3.82-3.62 (m, 2H), 3.21 (s, 3H), 2.41-2.18 (m, 5H), 2.17-2.00 (m, 1H), 1.08-0.94 (m, 2H), 0.72-0.53 (m, 1H), 0.42-0.25 (m, 2H), −0.03—0.16 (m, 2H); 19F NMR (282 MHz, DMSO-$d_6$) δ −128.61; MS (ES+) 591.5, 593.4 (M+1), (ES−) 625.3, 627.6 (M+Cl); Analysis calculated for: $C_{31}H_{32}ClFN_6O_3$.0.25$H_2O$: C, 62.52; H, 5.50; N, 14.11. Found: C, 62.53; H, 5.52; N, 13.89; Optical rotation [α]$_D$=(+) 95.38 [0.26, MeOH].

Scheme 19

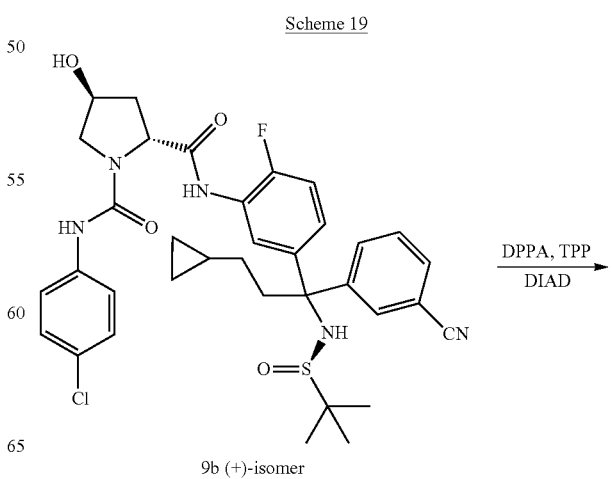

9b (+)-isomer

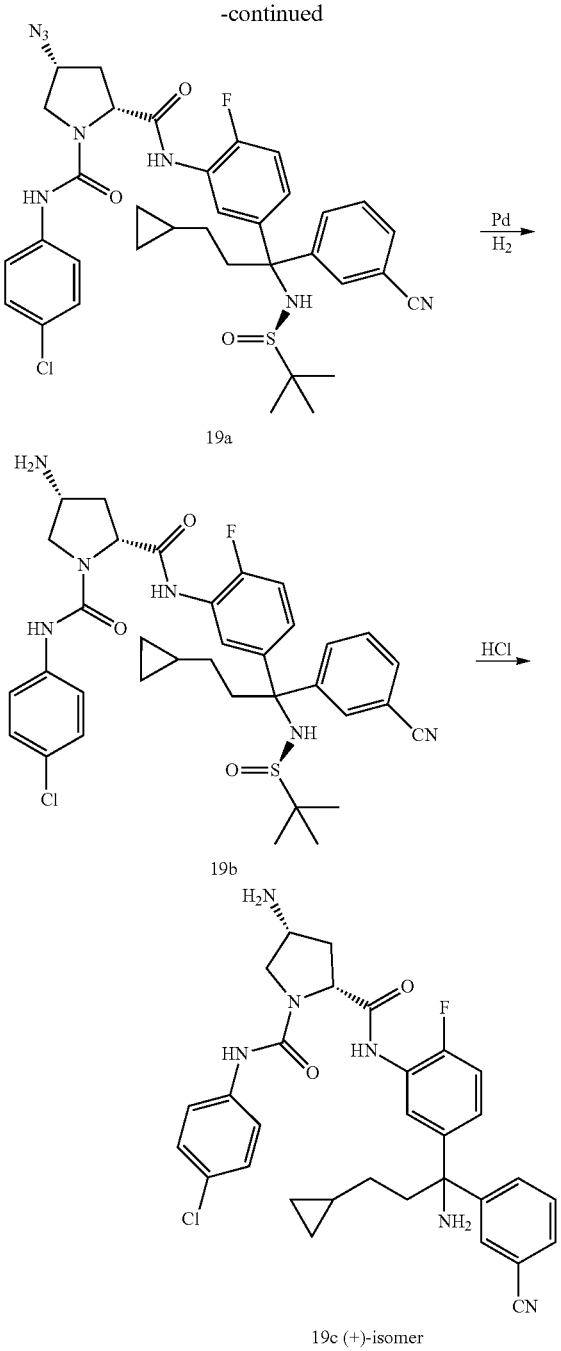

19a

19b 19c (+)-isomer

Preparation of (2R,4R)-4-amino-N2-(5-((+)-1-amino-1-(3-cyanophenyl)-3-cyclopropylpropyl)-2-fluorophenyl)-N1-(4-chlorophenyl)pyrrolidine-1,2-dicarboxamide (19c)

Step 1: Preparation of (2R,4R)-4-azido-N1-(4-chlorophenyl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (19a)

To a solution of (2R,4S)-N1-(4-chlorophenyl)-N2-(5-((+)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (9b) (0.502 g, 0.738 mmol) and triphenylphosphine (0.581 g, 2.214 mmol) in tetrahydrofuran (15 mL) at 0° C. was added a mixture of diphenyl phosphorazidate (0.477 mL, 2.214 mmol) and diisopropyl azodicarboxylate (0.430 mL, 2.214 mmol) in tetrahydrofuran (5 mL) over a period of 30 mins. Reaction was allowed to room temperature stirred for 24 h, diluted with ethyl acetate (150 mL), washed with water (2×25 mL), brine (25 mL), dried, filtered and concentrated in vacuum. The crude residue was purified by flash column chromatography (silica gel, 40 g eluting with (9:1) ethyl acetate and methanol in hexanes 0 to 100%) to afford (2R,4R)-4-azido-N1-(4-chlorophenyl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (19a) (88 mg, 0.125 mmol, 16.91% yield) as a white solid; $^1$H NMR (300 MHz, DMSO-$d_6$) δ 9.97 (s, 1H), 8.78 (s, 1H), 8.06 (s, 1H), 7.99 (m, 1H), 7.91 (m, 1H), 7.76 (m, 4H), 7.51 (m, 2H), 7.39 (m, 1H), 7.38-7.26 (m, 1H), 5.71 (s, 1H), 4.79 (m, 2H), 4.35-4.15 (m, 1H), 4.03 (m, 1H), 3.76 (d, J=10.2 Hz, 1H), 2.37-2.23 (m, 1H), 1.40-1.35 (m, 1H), 1.33 (s, 11H), 1.23-1.01 (m, 1H), 0.84 (m, 1H), 0.62-0.46 (m, 2H), 0.21-0.06 (m, 2H); $^{19}$F NMR (282 MHz, DMSO-$d_6$) δ −126.67.

Step 2: Preparation of (2R,4R)-4-amino-N1-(4-chlorophenyl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (19c)

Hydrogenation of (2R,4R)-4-azido-N1-(4-chlorophenyl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (19a) (0.08 g, 0.113 mmol) in ethanol (10 mL), using palladium on carbon 10% (0.012 g, 0.011 mmol) as catalyst for six hours according to procedure reported in step 2 of Scheme 13 gave (2R,4R)-4-amino-N1-(4-chlorophenyl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (19c) (60 mg, 0.088 mmol, 78% yield) as a white solid; $^1$H NMR (300 MHz, DMSO-$d_6$) δ 8.46 (s, 1H), 8.11 (d, J=7.3 Hz, 1H), 7.79 (m, 1H), 7.70 (m, 1H), 7.63-7.46 (m, 4H), 7.26 (m, 2H), 7.23-7.13 (m, 1H), 7.05 (m, 1H), 5.48 (s, 1H), 4.44 (dd, J=9.1, 5.1 Hz, 1H), 3.74-3.40 (m, 3H), 2.76-2.21 (m, 4H), 1.78 (m, 1H), 1.13 (s, 10H), 1.02-0.74 (m, 1H), 0.74-0.51 (m, 1H), 0.34 (m, 2H), −0.06 (m, 2H); MS (ES+) 679.6 (M+1); 702.5 (M+Na).

Step-3: Preparation of (2R,4R)-4-amino-N2-(5-((+)-1-amino-1-(3-cyanophenyl)-3-cyclopropylpropyl)-2-fluorophenyl)-N1-(4-chlorophenyl)pyrrolidine-1,2-dicarboxamide (19c)

Reaction of (2R,4R)-4-amino-N1-(4-chlorophenyl)-N2-(5-(1-(3-cyanophenyl)-3-cyclopropyl-1-((R)-1,1-dimethylethylsulfinamido)propyl)-2-fluorophenyl)pyrrolidine-1,2-dicarboxamide (19c) (0.052 g, 0.077 mmol) in ethanol (5 mL) using conc. HCl (0.064 mL, 0.766 mmol) as reported in step 6 of Scheme 4 gave after purification by flash column chromatography (silica gel, eluting with CMA-80 in chloroform 0 to 100%) (2R,4R)-4-amino-N2-(5-((+)-1-amino-1-(3-cyanophenyl)-3-cyclopropylpropyl)-2-fluorophenyl)-N1-(4-chlorophenyl)pyrrolidine-1,2-dicarboxamide (19c) (12 mg, 0.021 mmol, 27.3% yield) as a white solid; $^1$H NMR (300 MHz, DMSO-$d_6$) δ 8.45 (s, 1H), 8.15-7.99 (m, 1H), 7.86 (t, J=1.6 Hz, 1H), 7.67-7.60 (m, 2H), 7.57-7.42 (m, 3H), 7.32-7.23 (m, 2H), 7.15-7.06 (m, 2H), 4.43 (dd, J=9.0, 5.3 Hz, 1H), 3.64 (dd, J=9.6, 5.6 Hz, 1H), 3.58-3.47 (m, 1H), 2.41-2.27 (m, 4H), 2.25-2.18 (m, 2H), 1.84-1.63 (m, 1H), 1.12-0.93 (m, 2H), 0.72-0.55 (m, 1H), 0.34 (m, 2H), −0.01--0.14 (m, 2H); $^{19}$F NMR (282 MHz, DMSO-d$_6$) δ −128.51; MS (ES−) 573.5, 575.4 (M−1); Optical rotation [α]$_D$=(+) 85.0 [0.08, MeOH].

Scheme 20

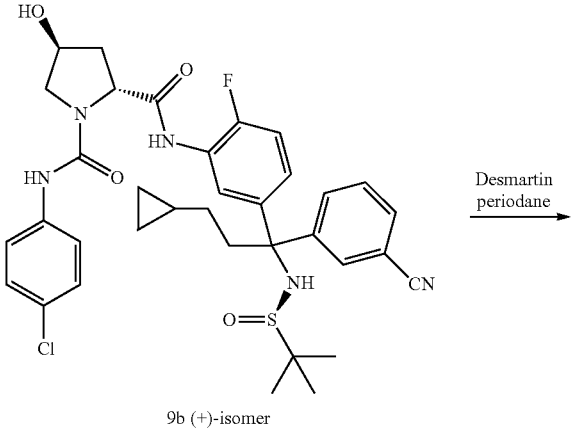

9b (+)-isomer

Desmartin periodane →

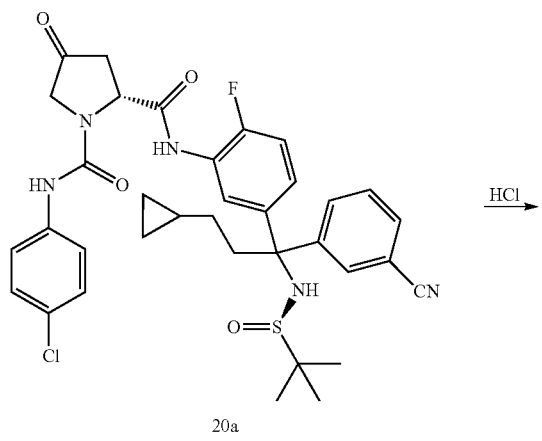

20a

HCl →

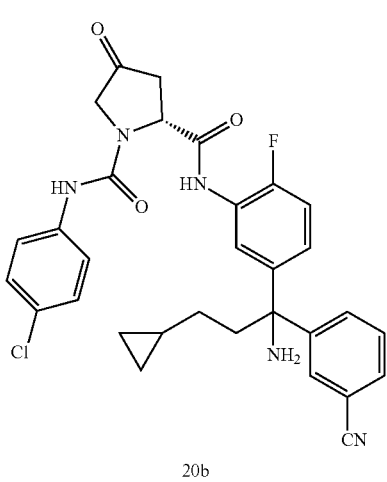

20b

Preparation of (R)-N2-(5-(1-amino-1-(3-cyanophenyl)-3-cyclopropylpropyl)-2-fluorophenyl)-N1-(4-chlorophenyl)-4-oxopyrrolidine-1,2-dicarboxamide (20b)

Step 1: Preparation of (R)-N1-(4-chlorophenyl)-N2-(5-(1-(3-cyanophenyl)-3-cyclopropyl-1-((R)-1,1-dimethylethylsulfinamido)propyl)-2-fluorophenyl)-4-oxopyrrolidine-1,2-dicarboxamide (20a)

To a solution of (2R,4S)-N1-(4-chlorophenyl)-N2-(5-((+)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (9b) (50 mg, 0.074 mmol) in dichloromethane (10 mL) at room temperature was added sodium bicarbonate (24.70 mg, 0.294 mmol), Dess-Martin Periodinane (100 mg, 0.235 mmol) and stirred for 30 mins. The reaction was diluted with dichloromethane (50 mL), washed with water (2×25 mL), brine (25 mL), dried, filtered and concentrated in vacuum to dryness. The crude residue obtained was purified by flash column chromatography (silica gel, 4 g eluting with CMA 80 in chloroform 0 to 100%) afford (R)-N1-(4-chlorophenyl)-N2-(5-(1-(3-cyanophenyl)-3-cyclopropyl-1-((R)-1,1-dimethylethylsulfinamido)propyl)-2-fluorophenyl)-4-oxopyrrolidine-1,2-dicarboxamide (20a) (40 mg, 0.059 mmol, 80% yield) as nearly colorless solid; $^1$H NMR (300 MHz, DMSO-d$_6$) δ 10.09 (s, 1H), 8.57 (s, 1H), 8.08-7.98 (m, 1H), 7.94 (m, 1H), 7.85-7.66 (m, 2H), 7.61-7.45 (m, 3H), 7.31 (m, 2H), 7.26-7.16 (m, 1H), 7.13 (m, 1H), 5.51 (s, 1H), 5.10 (d, J=9.7 Hz, 1H), 4.27-4.10 (m, 1H), 3.98 (d, J=17.4 Hz, 1H), 3.40 (m, 2H), 2.63-2.38 (m, 2H), 1.11 (s, 10H), 0.98-0.79 (m, 1H), 0.72-0.51 (m, 1H), 0.40-0.25 (m, 2H), −0.00--0.21 (m, 2H); $^{19}$F NMR (282 MHz, DMSO-d$_6$) δ −126.75; MS (ES+) 700.4 (M+23), (ES−) 676.4 (M−1); 712.4, 714.4 (M+Cl).

Step 2: Preparation of (R)-N2-(5-(1-amino-1-(3-cyanophenyl)-3-cyclopropylpropyl)-2-fluorophenyl)-N1-(4-chlorophenyl)-4-oxopyrrolidine-1,2-dicarboxamide (20b)

Reaction of (R)-N1-(4-chlorophenyl)-N2-(5-(1-(3-cyanophenyl)-3-cyclopropyl-1-((R)-1,1-dimethylethylsulfinamido)propyl)-2-fluorophenyl)-4-oxopyrrolidine-1,2-dicarboxamide (20a) (35 mg, 0.052 mmol) in ethanol (5 mL) using conc. HCl (0.043 mL, 0.516 mmol) as reported in step 6 of Scheme 4 gave after purification by flash column chromatography (silica gel, eluting with CMA-80 in chloroform 0 to 100%) (R)-N2-(5-(1-amino-1-(3-cyanophenyl)-3-cyclopropylpropyl)-2-fluorophenyl)-N1-(4-chlorophenyl)-4-oxopyrrolidine-1,2-dicarboxamide (20b) (20 mg, 0.035 mmol, 67.5% yield) as a white solid; $^1$H NMR (300 MHz, DMSO-d$_6$) δ 10.03 (s, 1H), 8.56 (s, 1H), 8.04-7.96 (m, 1H), 7.86 (t, J=1.8 Hz, 1H), 7.63 (ddt, J=7.6, 5.9, 1.4 Hz, 2H), 7.59-7.51 (m, 2H), 7.45 (t, J=7.8 Hz, 1H), 7.34-7.27 (m, 2H), 7.18-7.08 (m, 2H), 5.10 (dd, J=10.0, 2.2 Hz, 1H), 4.19 (d, J=17.6 Hz, 1H), 3.98 (d, J=17.5 Hz, 1H), 3.11 (m, 1H), 2.61-2.51 (m, 1H), 2.36-2.27 (m, 2H), 2.27-2.15 (m, 2H), 1.09-0.90 (m, 2H), 0.70-0.51 (m, 1H), 0.37-0.27 (m, 2H), −0.00--0.13 (m, 2H); $^{19}$F NMR (282 MHz, DMSO-d$_6$) δ −127.99; MS (ES+) 596.5 (M+Na), (ES−) 610.4 (M+Cl).

Scheme 21

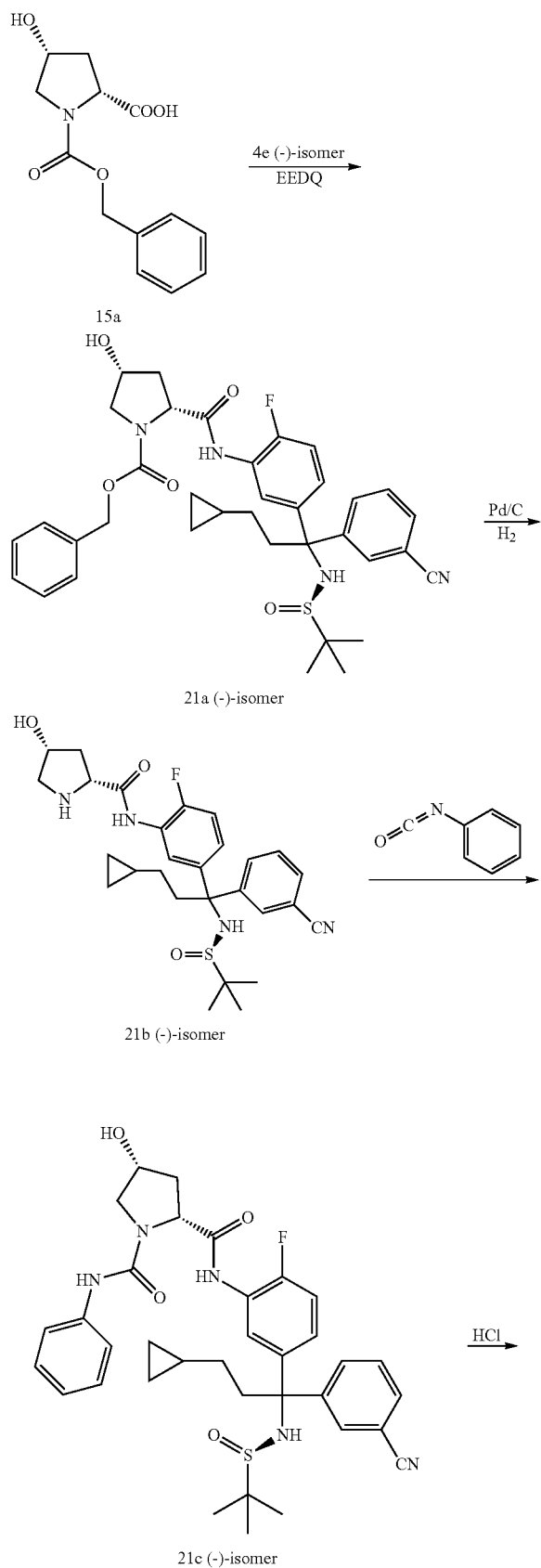

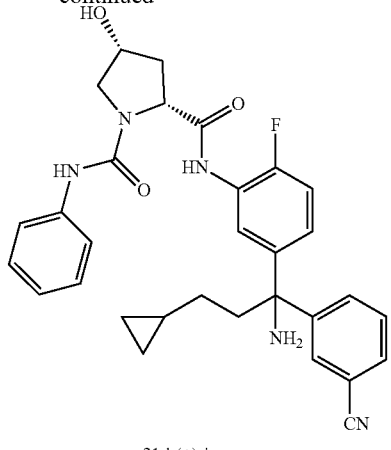

21d (+)-isomer

Preparation of (2R,4R)-N2-(5-((+)-1-amino-1-(3-cyanophenyl)-3-cyclopropylpropyl)-2-fluorophenyl)-4-hydroxy-N1-phenylpyrrolidine-1,2-dicarboxamide (21d)

Step 1: Preparation of (2R,4R)-benzyl 2-(5-((−)-1-(3-cyanophenyl)-3-cyclopropyl-1-((R)-1,1-dimethyl-ethylsulfinamido)propyl)-2-fluorophenylcarbamoyl)-4-hydroxypyrrolidine-1-carboxylate (21a)

Reaction of (2R,4R)-1-(benzyloxycarbonyl)-4-hydroxy-pyrrolidine-2-carboxylic acid (15a) (1.5 g, 5.65 mmol), (R)-N-((−)-1-(3-amino-4-fluorophenyl)-1-(3-cyanophenyl)-3-cyclopropylpropyl)-2-methylpropane-2-sulfinamide (4e) (2.339 g, 5.65 mmol) in tetrahydrofuran (50 mL) using ethyl 2-ethoxyquinoline-1(2H)-carboxylate (1.398 g, 5.65 mmol) using the reaction and workup conditions as reported in step 10 of Scheme 1 gave after purification by flash column chromatography (silica gel 25 g, eluting with CMA 80 in chloroform 0 to 100%) (2R,4R)-benzyl 2-(5-((−)-1-(3-cyanophenyl)-3-cyclopropyl-1-((R)-1,1-dimethylethylsulfinamido)propyl)-2-fluorophenylcarbamoyl)-4-hydroxypyrrolidine-1-carboxylate (21a) (2.396 g, 3.63 mmol, 64.1% yield) as a white solid; $^1$H NMR (300 MHz, DMSO-$d_6$) δ 9.79 (2s, 1H, rotamers), 8.04 (d, J=7.3 Hz, 1H), 7.79 (s, 1H), 7.71 (d, J=7.4 Hz, 1H), 7.60 (m, 1H), 7.51 (m, 1H), 7.37 (m, 2H), 7.26-7.04 (m, 5H), 5.50 (d, J=17.5 Hz, 1H), 5.29 (s, 1H), 5.14-4.89 (m, 2H), 4.53-4.34 (m, 1H), 4.27 (s, 1H), 3.71-3.47 (m, 2H), 3.47-3.24 (m, 1H), 2.77-2.26 (m, 2H), 1.88 (m, 1H), 1.16-1.01 (m, 10H, rotamers), 0.98-0.77 (m, 1H), 0.73-0.53 (m, 1H), 0.41-0.26 (m, 2H), −0.02-−0.16 (m, 2H); $^{19}$F NMR (282 MHz, DMSO-$d_6$) δ −127.76, −127.94; MS (ES+) 683.6 (M+Na), (ES−) 695.6 (M+Cl); Optical rotation $[\alpha]_D$=(−) 75.0 [0.16, MeOH].

Step 2: Preparation of (2R,4R)-N-(5-((−)-1-(3-cyanophenyl)-3-cyclopropyl-1-((R)-1,1-dimethylethylsulfinamido)propyl)-2-fluorophenyl)-4-hydroxypyrrolidine-2-carboxamide (21b)

Debenzylation by hydrogenation of (2R,4R)-benzyl 2-(5-((−)-1-(3-cyanophenyl)-3-cyclopropyl-1-((R)-1,1-dimethylethylsulfinamido)propyl)-2-fluorophenylcarbamoyl)-4-hydroxypyrrolidine-1-carboxylate (21a) (2.35 g, 3.56 mmol) in ethanol (100 mL), using palladium on carbon 10% (0.378 g, 0.356 mmol) as catalyst according to procedure reported in step 2 of Scheme 13 gave (2R,4R)-N-(5-((−)-1-(3-cyanophenyl)-3-cyclopropyl-1-((R)-1,1-dimethylethylsulfinamido) propyl)-2-fluorophenyl)-4-hydroxypyrrolidine-2-carboxamide (21b) (1.61 g, 3.06 mmol, 86% yield) as a white solid; $^1$H NMR (300 MHz, DMSO-d$_6$) δ 10.24 (s, 1H), 8.36 (dd, J=7.8, 2.4 Hz, 1H), 7.79 (t, J=1.7 Hz, 1H), 7.72 (m, 1H), 7.60 (m, 1H), 7.51 (m, 1H), 7.21 (dd, J=10.8, 8.7 Hz, 1H), 7.09-6.99 (m, 1H), 5.46 (s, 1H), 4.70 (d, J=3.3 Hz, 1H), 4.22-4.10 (m, 1H), 3.84-3.64 (m, 1H), 3.00 (m, 1H), 2.79-2.68 (m, 2H), 2.68-2.52 (m, 2H), 2.21-2.07 (m, 1H), 1.84 (m, 1H), 1.14 (s, 10H), 1.01-0.76 (m, 1H), 0.75-0.54 (m, 1H), 0.44-0.25 (m, 2H), −0.02--0.23 (m, 2H); $^{19}$F NMR (282 MHz, DMSO-d$_6$) δ −132.73; MS (ES+) 527.5 (M+1), 549.5 (M+Na), (ES−) 525.5 (M−1), 561.5 (M+Cl); Optical rotation [α]$_D$=(−) 0.44 [0.15, MeOH].

Step 3: Preparation of (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-phenylpyrrolidine-1,2-dicarboxamide (21c)

Reaction of (2R,4R)-N-(5-((−)-1-(3-cyanophenyl)-3-cyclopropyl-1-((R)-1,1-dimethylethylsulfinamido)propyl)-2-fluorophenyl)-4-hydroxypyrrolidine-2-carboxamide (21b) (160 mg, 0.304 mmol) and phenyl isocyanate (0.040 mL, 0.365 mmol) in tetrahydrofuran (10 mL) using reaction and workup conditions as reported in step 9 of Scheme 1 gave (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-phenylpyrrolidine-1,2-dicarboxamide (21c) (176 mg, 0.273 mmol, 90% yield) as a white solid; $^1$H NMR (300 MHz, DMSO-d$_6$) δ 9.67 (s, 1H), 8.37 (s, 1H), 8.14-8.02 (m, 1H), 7.79 (t, J=1.7 Hz, 1H), 7.70 (dt, J=7.4, 1.3 Hz, 1H), 7.59 (dt, J=8.1, 1.6 Hz, 1H), 7.55-7.44 (m, 3H), 7.29-7.10 (m, 3H), 7.12-7.02 (m, 1H), 6.94 (tt, J=7.3, 1.2 Hz, 1H), 5.50 (s, 1H), 5.34 (d, J=4.4 Hz, 1H), 4.51 (dd, J=9.1, 4.5 Hz, 1H), 4.42-4.27 (m, 1H), 3.67 (dd, J=10.1, 5.1 Hz, 1H), 3.52 (m, 1H), 2.74-2.52 (m, 2H), 2.44-2.29 (m, 1H), 1.93 (dd, J=11.0, 6.5 Hz, 1H), 1.13 (s, 10H), 1.00-0.79 (m, 1H), 0.71-0.55 (m, 1H), 0.42-0.26 (m, 2H), 0.02--0.15 (m, 2H); $^{19}$F NMR (282 MHz, DMSO-d$_6$) δ −128.67; MS: (ES+) 646.5 (M+1), 668.5 (M+Na), (ES−) 644.5 (M−1), 680.5 (M+Cl); Optical rotation [α]$_D$=(−) 37.42 [0.155, MeOH].

Step-4: Preparation of (2R,4R)-N2-(5-((+)-1-amino-1-(3-cyanophenyl)-3-cyclopropylpropyl)-2-fluorophenyl)-4-hydroxy-N1-phenylpyrrolidine-1,2-dicarboxamide (21d)

Reaction of (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-phenylpyrrolidine-1,2-dicarboxamide (21c) (160 mg, 0.248 mmol) in ethanol (10 mL) using conc. HCl (0.206 mL, 2.478 mmol) as reported in step 6 of Scheme 4 gave (2R,4R)-N2-(5-((+)-1-amino-1-(3-cyanophenyl)-3-cyclopropylpropyl)-2-fluorophenyl)-4-hydroxy-N1-phenylpyrrolidine-1,2-dicarboxamide (21d) (50 mg, 0.092 mmol, 37.3% yield) as a colorless solid; $^1$H NMR (300 MHz, DMSO-d$_6$) δ 9.61 (s, 1H), 8.36 (s, 1H), 8.07 (d, J=7.6 Hz, 1H), 7.86 (t, J=1.7 Hz, 1H), 7.68-7.58 (m, 2H), 7.55-7.39 (m, 3H), 7.29-7.17 (m, 1H), 7.12 (d, J=9.5 Hz, 2H), 6.99-6.85 (m, 1H), 5.30 (d, J=4.5 Hz, 1H), 4.50 (dd, J=9.1, 4.5 Hz, 1H), 4.34 (s, 1H), 3.68 (dd, J=10.1, 5.1 Hz, 1H), 3.50 (m, 1H), 2.38-2.19 (m, 6H), 1.98-1.84 (m, 1H), 1.10-0.94 (m, 2H), 0.70-0.55 (m, 1H), 0.39-0.18 (m, 2H), −0.02--0.12 (m, 2H); $^{19}$F NMR (282 MHz, DMSO-d$_6$) δ −129.38; MS (ES+) 564.4 (M+Na); Analysis calculated for C$_{31}$H$_{32}$FN$_5$O$_3$·0.25H$_2$O: C, 67.62; H, 6.04; N, 12.72. Found: C, 67.72; H, 6.10; N, 12.60; Optical rotation [α]$_D$=(+) 90.3 [0.32, MeOH].

Scheme 22

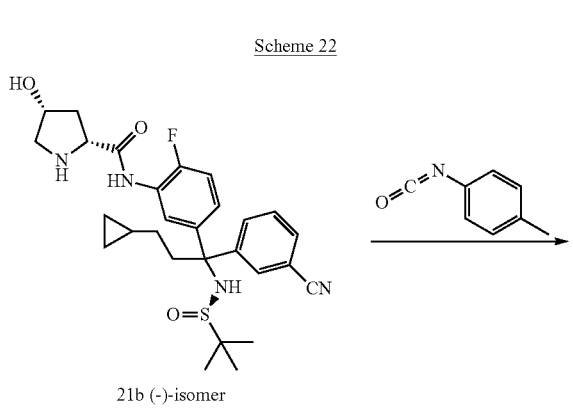

21b (−)-isomer

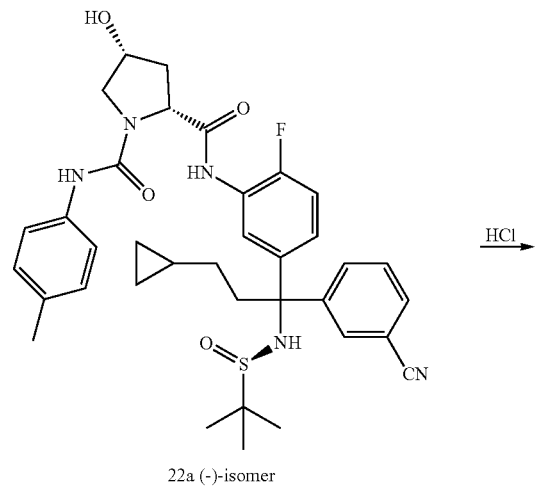

22a (−)-isomer

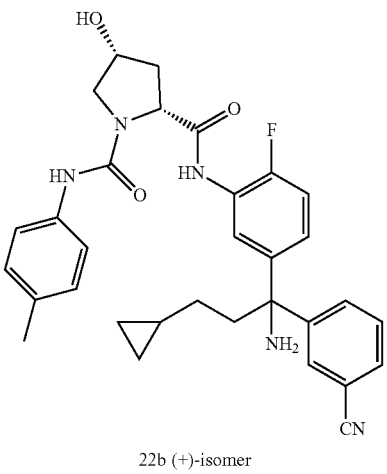 [SMILES: N#Cc1cccc(C(N)(CCC2CC2)c2ccc(F)c(NC(=O)[C@H]3C[C@@H](N)CN3C(=O)Nc3ccc(Cl)cc3)c2)c1]

22b (+)-isomer

Preparation of (2R,4R)-N2-(5-((+)-1-amino-1-(3-cyanophenyl)-3-cyclopropylpropyl)-2-fluorophenyl)-4-hydroxy-N1-p-tolylpyrrolidine-1,2-dicarboxamide (22b)

Step 1: Preparation of (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-p-tolylpyrrolidine-1,2-dicarboxamide (22a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-hydroxypyrrolidine-2-carboxamide (21b) (160 mg, 0.304 mmol) and p-tolyl isocyanate (0.046 mL, 0.365 mmol) in tetrahydrofuran (10 mL) using reaction and workup conditions as reported in step 9 of Scheme 1 gave (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-p-tolylpyrrolidine-1,2-dicarboxamide (22a) (154 mg, 0.233 mmol, 77% yield) as a white solid; $^1$H NMR (300 MHz, DMSO-$d_6$) δ 9.65 (s, 1H), 8.29 (s, 1H), 8.10 (dd, J=7.7, 2.4 Hz, 1H), 7.79 (t, J=1.7 Hz, 1H), 7.70 (dt, J=7.4, 1.4 Hz, 1H), 7.59 (dt, J=8.1, 1.6 Hz, 1H), 7.55-7.45 (m, 1H), 7.42-7.31 (m, 2H), 7.19 (dd, J=10.6, 8.7 Hz, 1H), 7.10-6.98 (m, 3H), 5.51 (s, 1H), 5.32 (d, J=3.7 Hz, 1H), 4.50 (d, J=4.7 Hz, 1H), 4.41-4.27 (m, 1H), 3.63 (d, J=5.1 Hz, 1H), 3.55-3.46 (m, 1H), 2.64 (m, 1H), 2.61-2.51 (m, 1H), 2.42-2.28 (m, 1H), 2.22 (m, 3H), 1.92 (m, 1H), 1.14 (d, 9H, rotamers), 1.12-1.00 (m, 1H), 0.98-0.81 (m, 1H), 0.72-0.55 (m, 1H), 0.44-0.29 (m, 2H), −0.01-−0.13 (m, 2H); $^{19}$F NMR (282 MHz, DMSO-$d_6$) δ −128.93; MS: (ES+) 682.5 (M+Na), (ES−) 658.6 (M−1), 694.6 (M+Cl); Optical rotation $[α]_D$=(−)14.66 [0.15, MeOH].

Step 2: Preparation of (2R,4R)-N2-(5-((+)-1-amino-1-(3-cyanophenyl)-3-cyclopropylpropyl)-2-fluorophenyl)-4-hydroxy-N1-p-tolylpyrrolidine-1,2-dicarboxamide (22b)

Reaction of (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-p-tolylpyrrolidine-1,2-dicarboxamide (22a) (140 mg, 0.212 mmol) in ethanol (10 mL) using conc. HCl (0.177 mL, 2.122 mmol) as reported in step 6 of Scheme 4 gave (2R,4R)-N2-(5-((+)-1-amino-1-(3-cyanophenyl)-3-cyclopropylpropyl)-2-fluorophenyl)-4-hydroxy-N1-p-tolylpyrrolidine-1,2-dicarboxamide (22b) (39 mg, 0.070 mmol, 33.1% yield) as a white solid; $^1$H NMR (300 MHz, DMSO-$d_6$) δ 9.60 (s, 1H), 8.27 (s, 1H), 8.07 (d, J=7.5 Hz, 1H), 7.87 (t, J=1.7 Hz, 1H), 7.73-7.57 (m, 2H), 7.46 (t, J=7.8 Hz, 1H), 7.40-7.34 (m, 2H), 7.15-7.09 (m, 2H), 7.03 (d, J=8.3 Hz, 2H), 5.29 (d, J=4.3 Hz, 1H), 4.49 (dd, J=9.1, 4.5 Hz, 1H), 4.33 (m, 1H), 3.66 (dd, J=10.1, 5.1 Hz, 1H), 3.48 (dd, J=10.0, 3.9 Hz, 1H), 2.44-2.27 (m, 3H), 2.22 (m, 5H), 1.98-1.84 (m, 1H), 1.10-0.93 (m, 2H), 0.72-0.54 (m, 1H), 0.40-0.26 (m, 2H), −0.06 (m, 2H); $^{19}$F NMR (282 MHz, DMSO-$d_6$) δ −129.66; MS (ES+) 578.5 (M+Na), (ES−) 554.6 (M−1), 590.5 (M+Cl); Optical rotation $[α]_D$=(+) 92.5 [0.24, MeOH]; Analysis calculated for $C_{32}H_{34}FN_5O_3 \cdot 0.25H_2O$: C, 68.61; H, 6.21; N, 12.50. Found, 68.68; H, 6.26; N, 12.30; Optical rotation $[α]_D$=(+) 90.0 [0.32, MeOH].

Scheme 23

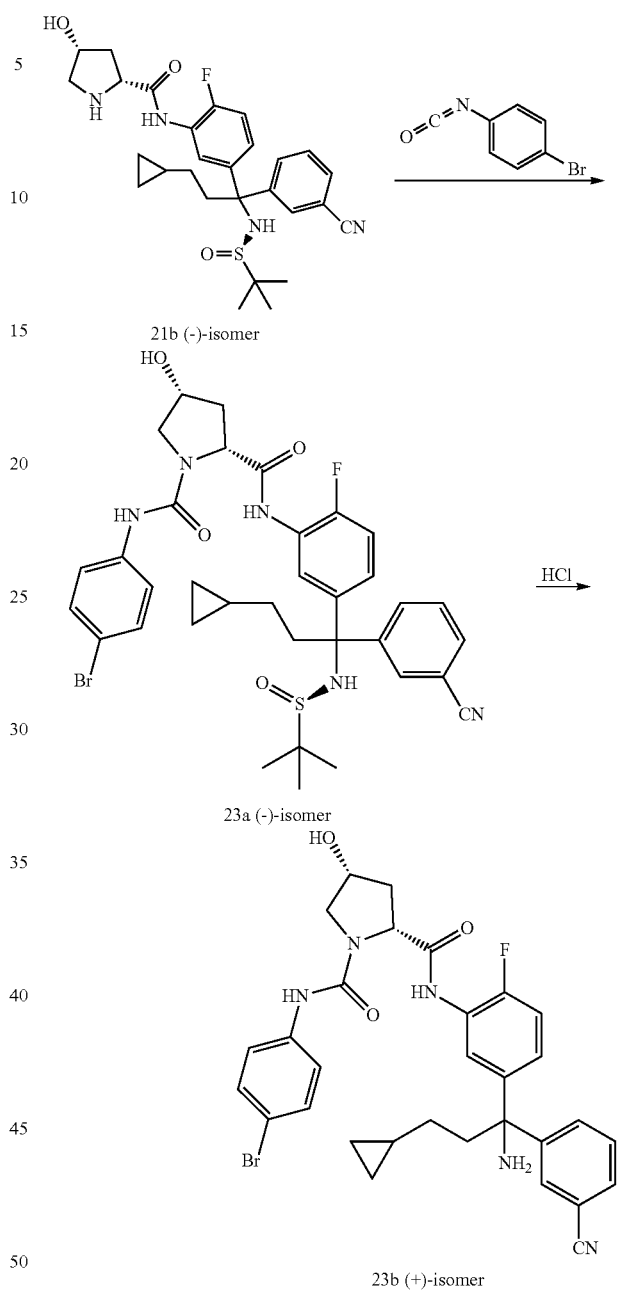

Preparation of (2R,4R)-N2-(5-((+)-1-amino-1-(3-cyanophenyl)-3-cyclopropylpropyl)-2-fluorophenyl)-N1-(4-bromophenyl)-4-hydroxypyrrolidine-1,2-dicarboxamide (23b)

Step 1: Preparation of (2R,4R)-N1-(4-bromophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (23a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-hydroxypyrrolidine-2-carboxamide (21b)

(160 mg, 0.304 mmol) and 4-Bromophenyl isocyanate (72.2 mg, 0.365 mmol) in tetrahydrofuran (10 mL) using reaction and workup conditions as reported in step 9 of Scheme 1 gave (2R,4R)-N1-(4-bromophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (23a) (192 mg, 0.265 mmol, 87% yield) as a white solid; $^{1}$H NMR (300 MHz, DMSO-d$_6$) δ 9.66 (s, 1H), 8.52 (s, 1H), 8.06 (dd, J=7.4, 2.3 Hz, 1H), 7.79 (t, J=1.6 Hz, 1H), 7.71 (dt, J=7.5, 1.3 Hz, 1H), 7.59 (dt, J=8.2, 1.6 Hz, 1H), 7.54-7.46 (m, 3H), 7.45-7.37 (m, 2H), 7.23-7.14 (m, 1H), 7.11-7.03 (m, 1H), 5.50 (s, 1H), 5.33 (d, J=4.4 Hz, 1H), 4.51 (dd, J=9.0, 4.7 Hz, 1H), 4.41-4.27 (m, 1H), 3.68 (dd, J=10.1, 5.2 Hz, 1H), 3.49 (dd, J=9.9, 3.8 Hz, 1H), 2.77-2.60 (m, 1H), 2.64-2.51 (m, 1H), 2.47-2.24 (m, 1H), 1.97-1.78 (m, 1H), 1.13 (s, 10H), 0.98-0.77 (m, 1H), 0.63 (m, 1H), 0.41-0.22 (m, 2H), −0.02--0.17 (m, 2H); $^{19}$F NMR (282 MHz, DMSO-d$_6$) δ −128.38; MS: (ES+) 746.5, 748.5 (M+Na), (ES−) 722.5 (M−1), 758.5, 760.4 (M+Cl); Optical rotation [α]$_D$=(−) 12.9 [0.155, MeOH].

Step 2: Preparation of (2R,4R)-N2-(5-((+)-1-amino-1-(3-cyanophenyl)-3-cyclopropylpropyl)-2-fluorophenyl)-N1-(4-bromophenyl)-4-hydroxypyrrolidine-1,2-dicarboxamide (23b)

Reaction of (2R,4R)-N1-(4-bromophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (23a) (180 mg, 0.248 mmol) in ethanol (10 mL) using conc. HCl (0.207 mL, 2.484 mmol) as reported in step 6 of Scheme 4 gave (2R,4R)-N2-(5-((+)-1-amino-1-(3-cyanophenyl)-3-cyclopropylpropyl)-2-fluorophenyl)-N1-(4-bromophenyl)-4-hydroxypyrrolidine-1,2-dicarboxamide (23b) (41 mg, 0.066 mmol, 26.6% yield) as a white solid; $^{1}$H NMR (300 MHz, DMSO-d$_6$) δ 9.61 (s, 1H), 8.50 (s, 1H), 8.04 (d, J=7.6 Hz, 1H), 7.86 (t, J=1.7 Hz, 1H), 7.67-7.59 (m, 2H), 7.53-7.45 (m, 3H), 7.44-7.37 (m, 2H), 7.12 (d, J=8.9 Hz, 2H), 5.30 (d, J=4.7 Hz, 1H), 4.50 (dd, J=9.1, 4.8 Hz, 1H), 4.41-4.28 (m, 1H), 3.68 (dd, J=10.2, 5.4 Hz, 1H), 3.47 (dd, J=9.8, 4.0 Hz, 1H), 2.40-2.14 (m, 5H), 2.01-1.79 (m, 1H), 1.13-0.88 (m, 2H), 0.63 (m, 1H), 0.42-0.27 (m, 2H), −0.02--0.12 (m, 2H); $^{19}$F NMR (282 MHz, DMSO-d$_6$) δ −129.26; MS (ES+) 642.4, 644.5 (M+Na); IR (KBr) 2229 cm$^{-1}$; Optical rotation [α]$_D$=(+) 101.54 [0.325, MeOH]; Analysis calculated for C$_{31}$H$_{31}$BrFN$_5$O$_3$.0.5H$_2$O: C, 59.15; H, 5.12; N, 11.12. Found: C, 59.11; H, 5.18; N, 10.95.

Scheme 24

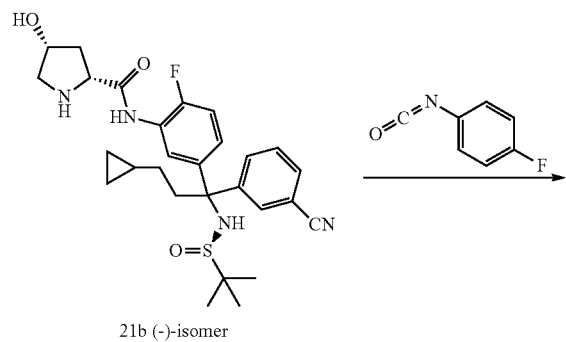

21b (−)-isomer

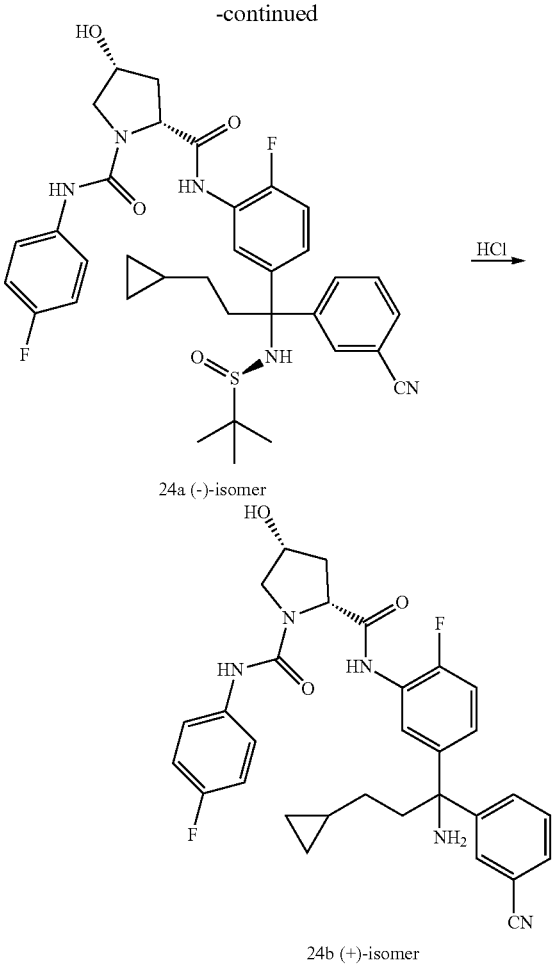

24a (−)-isomer 24b (+)-isomer

Preparation of (2R,4R)-N2-(5-((+)-1-amino-1-(3-cyanophenyl)-3-cyclopropylpropyl)-2-fluorophenyl)-N1-(4-fluorophenyl)-4-hydroxypyrrolidine-1,2-dicarboxamide (24b)

Step 1: Preparation of (2R,4R)-N2-(5-((−)-1-(3-cyanophenyl)-3-cyclopropyl-1-((R)-1,1-dimethylethylsulfinamido)propyl)-2-fluorophenyl)-N1-(4-fluorophenyl)-4-hydroxypyrrolidine-1,2-dicarboxamide (24a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-hydroxypyrrolidine-2-carboxamide (21b) (160 mg, 0.304 mmol) and 4-fluorophenyl isocyanate (0.041 mL, 0.365 mmol) in tetrahydrofuran (10 mL) using reaction and workup conditions as reported in step 9 of Scheme 1 gave (2R,4R)-N2-(5-((−)-1-(3-cyanophenyl)-3-cyclopropyl-1-((R)-1,1-dimethylethylsulfinamido)propyl)-2-fluorophenyl)-N1-(4-fluorophenyl)-4-hydroxypyrrolidine-1,2-dicarboxamide (24a) (138 mg, 0.208 mmol, 68.4% yield) as a white solid; $^{1}$H NMR (300 MHz, DMSO-d$_6$) δ 9.64 (d, J=7.0 Hz, 1H), 8.43 (s, 1H), 8.08 (dd, J=7.6, 2.5 Hz, 1H), 7.91-7.75 (m, 1H), 7.71 (dt, J=7.4, 1.4 Hz, 1H), 7.59 (dt, J=8.2, 1.6 Hz, 1H), 7.50 (m, 3H), 7.12-7.01 (m, 3H), 5.50 (m, 1H), 5.32 (d, J=4.5 Hz, 1H), 4.50 (dd, J=9.1, 4.5 Hz, 1H), 4.41-4.28 (m, 1H), 3.66 (dd, J=10.0, 5.1 Hz, 1H), 3.49 (dd, J=10.2, 3.8 Hz, 1H), 2.74-2.51 (m, 2H), 2.49-2.23 (m, 2H), 1.98-1.81 (m, 1H), 1.13 (d, J=2.2 Hz, 10H), 0.98-0.76 (m, 1H), 0.70-0.52 (m, 1H), 0.38-0.27 (m, 2H), 0.01--0.16 (m, 2H); $^{19}$F NMR (282 MHz, DMSO-d$_6$) δ −121.20, −128.61; MS: (ES+) 664.5 (M+1), 686.5 (M+Na), (ES−) 662.5 (M−1), 698.5 (M+Cl); Optical rotation [α]$_D$=(−) 10.52 [0.095, MeOH].

Step 2: Preparation of (2R,4R)-N2-(5-((+)-1-amino-1-(3-cyanophenyl)-3-cyclopropylpropyl)-2-fluorophenyl)-N1-(4-fluorophenyl)-4-hydroxypyrrolidine-1,2-dicarboxamide (24b)

Reaction of (2R,4R)-N2-(5-((−)-1-(3-cyanophenyl)-3-cyclopropyl-1-((R)-1,1-dimethylethylsulfinamido)propyl)-2-fluorophenyl)-N1-(4-fluorophenyl)-4-hydroxypyrrolidine-1,2-dicarboxamide (24a) (125 mg, 0.188 mmol) in ethanol (10 mL) using conc. HCl (0.157 mL, 1.883 mmol) as reported in step 6 of Scheme 4 gave (2R,4R)-N2-(5-((+)-1-amino-1-(3-cyanophenyl)-3-cyclopropylpropyl)-2-fluorophenyl)-N1-(4-fluorophenyl)-4-hydroxypyrrolidine-1,2-dicarboxamide (24b) (35 mg, 0.063 mmol, 33.2% yield) as a white solid; $^1$H NMR (300 MHz, DMSO-d$_6$) δ 9.60 (s, 1H), 8.42 (s, 1H), 8.06 (d, J=7.6 Hz, 1H), 7.86 (t, J=1.8 Hz, 1H), 7.63 (m, 2H), 7.55-7.41 (m, 3H), 7.18-7.06 (m, 2H), 7.05 (d, J=7.0 Hz, 1H), 5.30 (d, J=4.7 Hz, 1H), 4.49 (dd, J=9.1, 4.6 Hz, 1H), 4.43-4.22 (m, 1H), 3.67 (dd, J=10.1, 5.3 Hz, 1H), 3.58-3.31 (m, 1H), 2.37-2.17 (m, 6H), 1.98-1.77 (m, 1H), 1.11-0.94 (m, 2H), 0.71-0.54 (m, 1H), 0.40-0.26 (m, 2H), −0.03--0.12 (m, 2H); $^{19}$F NMR (282 MHz, DMSO-d$_6$) δ −121.39, −129.49; MS (ES+) 582.5 (M+Na); Optical rotation [α]$_D$=(+) 85.93 [0.27, MeOH]

Scheme 25

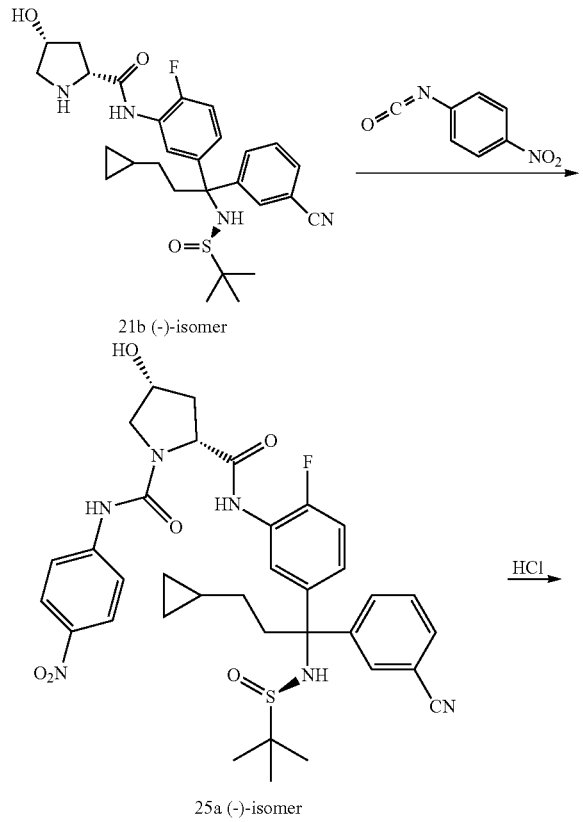

21b (−)-isomer 25a (−)-isomer

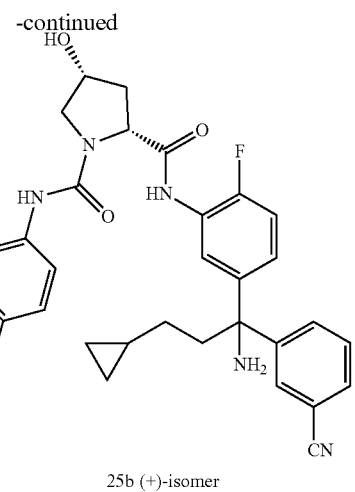

25b (+)-isomer

Preparation of (2R,4R)-N2-(5-((+)-1-amino-1-(3-cyanophenyl)-3-cyclopropylpropyl)-2-fluorophenyl)-4-hydroxy-N1-(4-nitrophenyl)pyrrolidine-1,2-dicarboxamide (25b)

Step 1: Preparation of (2R,4R)-N2-(5-((+)-1-(3-cyanophenyl)-3-cyclopropyl-1-((R)-1,1-dimethylethylsulfinamido)propyl)-2-fluorophenyl)-4-hydroxy-N1-(4-nitrophenyl)pyrrolidine-1,2-dicarboxamide (25a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-hydroxypyrrolidine-2-carboxamide (21b) (280 mg, 0.532 mmol) and 4-nitrophenyl isocyanate (105 mg, 0.638 mmol) in tetrahydrofuran (10 mL) using reaction and workup conditions as reported in step 9 of Scheme 1 gave (2R,4R)-N2-(5-((+)-1-(3-cyanophenyl)-3-cyclopropyl-1-((R)-1,1-dimethylethylsulfinamido)propyl)-2-fluorophenyl)-4-hydroxy-N1-(4-nitrophenyl)pyrrolidine-1,2-dicarboxamide (25a) (353 mg, 0.511 mmol, 96% yield) as a light yellow solid; $^1$H NMR (300 MHz, DMSO-d$_6$) δ 9.72 (s, 1H), 9.07 (s, 1H), 8.19-8.10 (m, 2H), 8.02 (d, J=7.1 Hz, 1H), 7.85-7.75 (m, 3H), 7.70 (m, 1H), 7.62-7.55 (m, 1H), 7.50 (t, J=7.8 Hz, 1H), 7.19 (dd, J=10.5, 8.7 Hz, 1H), 7.15-7.02 (m, 1H), 5.51 (s, 1H), 5.35 (s, 1H), 4.56 (dd, J=8.8, 5.1 Hz, 1H), 4.36 (m, 1H), 3.75 (dd, J=10.1, 5.4 Hz, 1H), 3.52 (dd, J=9.9, 4.2 Hz, 1H), 3.48-3.38 (m, 1H), 2.75-2.51 (m, 1H), 2.48-2.30 (m, 1H), 1.89 (m, 1H), 1.13 (s, 9H), 1.11-1.01 (m, 1H), 0.90 (m, 1H), 0.61 (m, 1H), 0.38-0.30 (m, 2H), −0.00--0.14 (m, 2H); $^{19}$F NMR (282 MHz, DMSO-d$_6$) δ −127.81; MS (ES+) 713.5 (M+Na), (ES−) 689.5 (M−1), 725.5 (M+Cl); Optical rotation [α]$_D$=(+) 18.66 [0.15, MeOH].

Step 2: Preparation of (2R,4R)-N2-(5-((+)-1-amino-1-(3-cyanophenyl)-3-cyclopropylpropyl)-2-fluorophenyl)-4-hydroxy-N1-(4-nitrophenyl)pyrrolidine-1,2-dicarboxamide (25b)

Reaction of (2R,4R)-N2-(5-((+)-1-(3-cyanophenyl)-3-cyclopropyl-1-((R)-1,1-dimethylethylsulfinamido)propyl)-2-fluorophenyl)-4-hydroxy-N1-(4-nitrophenyl)pyrrolidine-1,2-dicarboxamide (25a) (100 mg, 0.145 mmol) in ethanol (10 mL) using conc. HCl (0.121 mL, 1.448 mmol) as reported in step 6 of Scheme 4 gave (2R,4R)-N2-(5-((+)-1-amino-1-(3-cyanophenyl)-3-cyclopropylpropyl)-2-fluorophenyl)-4-hydroxy-N1-(4-nitrophenyl)pyrrolidine-1,2-dicarboxamide (25b) (61 mg, 0.104 mmol, 71.8% yield) as a light yellow solid; $^1$H NMR (300 MHz, DMSO-d$_6$) δ 9.66 (s, 1H), 9.05 (d, J=2.7 Hz, 1H), 8.15 (ddt, J=9.3, 4.3, 2.1 Hz, 2H), 7.99 (d, J=7.3 Hz, 1H), 7.89-7.75 (m, 3H), 7.69-7.56 (m, 2H), 7.47 (ddd, J=8.0, 3.9, 2.3 Hz, 1H), 7.18-7.07 (m, 2H), 5.32 (td, J=4.9, 4.2, 2.2 Hz, 1H), 4.63-4.45 (m, 1H), 4.41-4.25 (m, 1H), 3.85-3.65 (m, 1H), 3.58-3.43 (m, 1H), 2.49-2.37 (m, 1H), 2.36-2.26 (m, 1H), 2.29-2.13 (m, 3H), 1.89 (d, J=13.0 Hz, 1H), 1.12-0.92 (m, 2H), 0.71-0.53 (m, 1H), 0.40-0.26 (m, 2H), −0.02−−0.15 (m, 2H); $^{19}$F NMR (282 MHz, DMSO-d$_6$) δ −128.42; MS (ES+) 609.5 (M+Na), (ES−) 585.5 (M−1), 621.4 (M+Cl); Optical rotation [α]$_D$=(+) 124.90 [0.27, MeOH]; Analysis calculated for C$_{31}$H$_{31}$FN$_6$O$_5$·0.5H$_2$O: C, 62.51; H, 5.42; N, 14.11. Found: C, 62.58; H, 5.43; N, 13.89.

Scheme 26

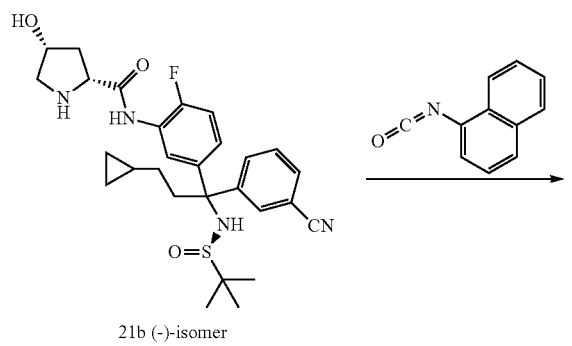

21b (−)-isomer

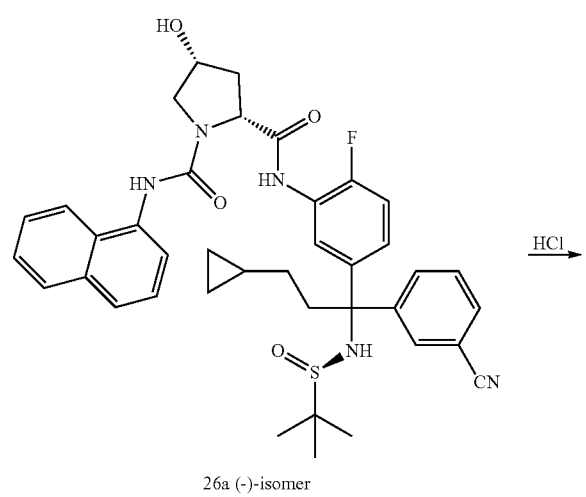

26a (−)-isomer

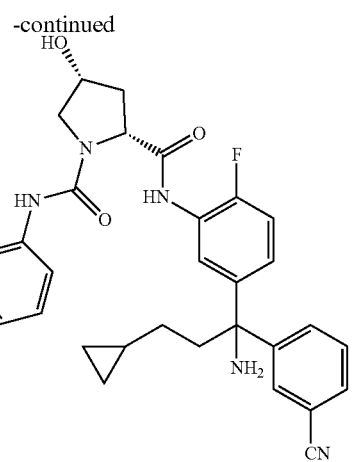

26b (+)-isomer

Preparation of (2R,4R)-N2-(5-((+)-1-amino-1-(3-cyanophenyl)-3-cyclopropylpropyl)-2-fluorophenyl)-4-hydroxy-N1-(naphthalen-1-yl)pyrrolidine-1,2-dicarboxamide (26b)

Step 1: Preparation of (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-(naphthalen-1-yl)pyrrolidine-1,2-dicarboxamide (26a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-hydroxypyrrolidine-2-carboxamide (21b) 160 mg, 0.304 mmol and 1-isocyanatonaphthalene (61.7 mg, 0.365 mmol) in tetrahydrofuran (10 mL) using reaction and workup conditions as reported in step 9 of Scheme 1 gave (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-(naphthalen-1-yl)pyrrolidine-1,2-dicarboxamide (26a) (196 mg, 0.282 mmol, 93% yield) as a white solid; $^1$H NMR (300 MHz, DMSO-d$_6$) δ 9.69 (s, 1H), 8.55 (s, 1H), 8.17 (dd, J=7.7, 2.4 Hz, 1H), 8.04-7.95 (m, 1H), 7.91 (dd, J=8.2, 1.4 Hz, 1H), 7.79 (t, J=1.7 Hz, 1H), 7.77-7.67 (m, 2H), 7.58 (m, 1H), 7.54-7.39 (m, 5H), 7.21 (dd, J=10.6, 8.7 Hz, 1H), 7.07 (m, 1H), 5.47 (s, 1H), 5.38 (s, 1H), 4.56 (dd, J=9.3, 3.9 Hz, 1H), 4.42 (s, 1H), 3.80 (dd, J=10.3, 4.9 Hz, 1H), 3.64 (dd, J=10.0, 3.1 Hz, 1H), 2.75-2.51 (m, 2H), 2.42 (m, 1H), 2.09-2.00 (m, 1H), 1.12 (s, 10H), 0.99-0.79 (m, 1H), 0.70-0.54 (m, 1H), 0.41-0.26 (m, 2H), −0.02−−0.14 (m, 2H); $^{19}$F NMR (282 MHz, DMSO-d6) δ −129.33; MS (ES+) 718.5 (M+Na), (ES−) 694.6 (M−1), 730.5 (M+Cl); Optical rotation [α]$_D$=(−) 61.3 [0.075, MeOH].

Step 2: Preparation of (2R,4R)-N2-(5-((+)-1-amino-1-(3-cyanophenyl)-3-cyclopropylpropyl)-2-fluorophenyl)-4-hydroxy-N1-(naphthalen-1-yl)pyrrolidine-1,2-dicarboxamide (26b)

Reaction of (2R,4R)-N2-(5-((−)-1-(3-cyanophenyl)-3-cyclopropyl-1-((R)-1,1-dimethylethylsulfinamido)propyl)-2-fluorophenyl)-4-hydroxy-N1-(naphthalen-1-yl)pyrrolidine-1,2-dicarboxamide (26a) (160 mg, 0.230 mmol) in ethanol (10 mL) using conc. HCl 0.192 mL, 2.299 mmol) as reported in step 6 of Scheme 4 gave (2R,4R)-N2-(5-((+)-1-amino-1-(3-cyanophenyl)-3-cyclopropylpropyl)-2-fluorophenyl)-4- hydroxy-N1-(naphthalen-1-yl)pyrrolidine-1,2-dicarboxamide (26b) (30 mg, 0.051 mmol, 22.05% yield) as a white solid; $^1$H NMR (300 MHz, DMSO-d$_6$) δ 9.63 (s, 1H), 8.53 (s, 1H), 8.13 (d, J=7.1 Hz, 1H), 8.00 (d, J=8.2 Hz, 1H), 7.91 (d, J=8.1 Hz, 1H), 7.87 (t, J=1.7 Hz, 1H), 7.77-7.69 (m, 1H), 7.66-7.62 (m, 1H), 7.51-7.40 (m, 5H), 7.20-7.07 (m, 2H), 5.34 (s, 1H), 4.55 (dd, J=9.3, 4.0 Hz, 1H), 4.46-4.28 (m, 1H), 3.81 (dd, J=10.3, 5.0 Hz, 1H), 3.68-3.55 (m, 1H), 2.48-2.35 (m, 2H), 2.30 (s, 2H), 2.22 (t, J=8.1 Hz, 2H), 2.08-1.96 (m, 1H), 1.12-0.94 (m, 2H), 0.71-0.55 (m, 1H), 0.39-0.28 (m, 2H), −0.03–−0.15 (m, 2H); $^{19}$F NMR (282 MHz, DMSO-d$_6$) δ −129.99; MS (ES+) 614.5 (M+Na), (ES−) 590.6 (M−1), 626.5 (M+Cl); Optical rotation [α]$_D$=(+) 81.2 [0.165, MeOH]; Analysis calculated for: C$_{35}$H$_{34}$FN$_5$O$_3$·0.5H$_2$O: C, 69.98; H, 5.87; N, 11.66. Found: C, 70.25; H, 5.99; N, 11.44.

Scheme 27

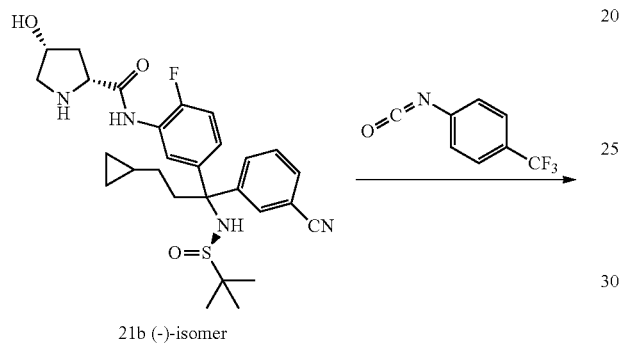

21b (−)-isomer

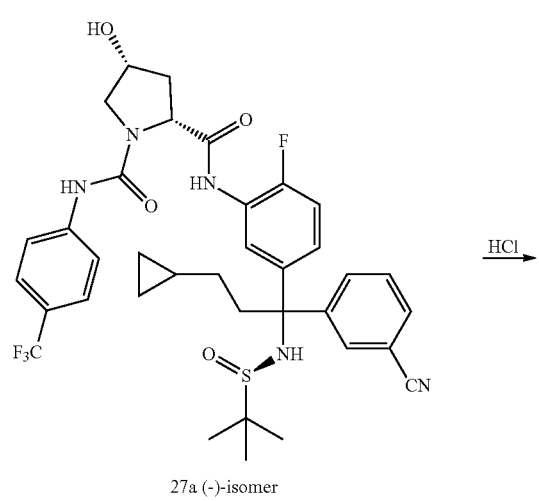

27a (−)-isomer

HCl →

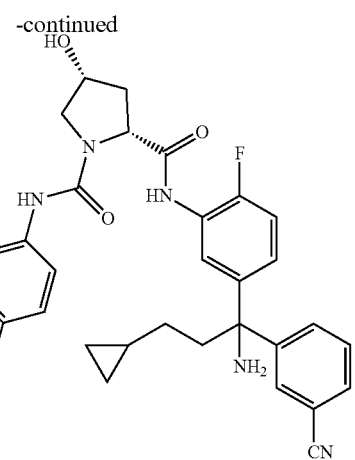

27b (+)-isomer

Preparation of (2R,4R)-N2-(5-((+)-1-amino-1-(3-cyanophenyl)-3-cyclopropylpropyl)-2-fluorophenyl)-4-hydroxy-N1-(4-(trifluoromethyl)phenyl)pyrrolidine-1,2-dicarboxamide (27b)

Step 1: Preparation of (2R,4R)-N2-(5-((+)-1-(3-cyanophenyl)-3-cyclopropyl-1-((R)-1,1-dimethylethylsulfinamido)propyl)-2-fluorophenyl)-4-hydroxy-N1-(4-(trifluoromethyl)phenyl)pyrrolidine-1,2-dicarboxamide (27a)

Reaction of (2R,4R)-N-(5-((−)-1-(3-cyanophenyl)-3-cyclopropyl-1-((R)-1,1-dimethylethylsulfinamido)propyl)-2-fluorophenyl)-4-hydroxypyrrolidine-2-carboxamide (21b) (160 mg, 0.304 mmol) and 1-isocyanato-4-(trifluoromethyl)benzene (0.043 mL, 0.304 mmol) in tetrahydrofuran (10 mL) using reaction and workup conditions as reported in step 9 of Scheme 1 gave (2R,4R)-N2-(5-((+)-1-(3-cyanophenyl)-3-cyclopropyl-1-((R)-1,1-dimethylethylsulfinamido)propyl)-2-fluorophenyl)-4-hydroxy-N1-(4-(trifluoromethyl)phenyl)pyrrolidine-1,2-dicarboxamide (27a) (161 mg, 0.226 mmol, 74.2% yield) as a colorless solid; $^1$H NMR (300 MHz, DMSO-d6) δ 9.69 (s, 1H), 8.76 (s, 1H), 8.04 (d, J=7.3 Hz, 1H), 7.89-7.62 (m, 4H), 7.60 (m, 2H), 7.50 (m, 1H), 7.25-7.11 (m, 1H), 7.04 (m, 1H), 5.50 (d, J=5.7 Hz, 1H), 5.35 (d, J=4.1 Hz, 1H), 4.54 (dd, J=9.0, 4.7 Hz, 1H), 4.41-4.28 (m, 2H), 3.72 (m, 1H), 3.52 (m, 1H), 2.75-2.54 (m, 1H), 2.48-2.24 (m, 1H), 1.99-1.80 (m, 1H), 1.13 (m, 10H), 1.11-1.00 (m, 1H), 0.97-0.76 (m, 1H), 0.71-0.56 (m, 1H), 0.42-0.26 (m, 2H), 0.00–−0.18 (m, 2H); $^{19}$F NMR (282 MHz, DMSO-d6) δ −59.80, −128.17; MS (ES+) 736.5 (M+Na), (ES−) 712.6 (M−1), 748.5 (M+Cl); Optical rotation [α]$_D$=(+) 14.19 [0.155, MeOH].

Step 2: Preparation of (2R,4R)-N2-(5-((+)-1-amino-1-(3-cyanophenyl)-3-cyclopropylpropyl)-2-fluorophenyl)-4-hydroxy-N1-(4-(trifluoromethyl)phenyl)pyrrolidine-1,2-dicarboxamide (27b)

Reaction of (2R,4R)-N2-(5-((+)-1-(3-cyanophenyl)-3-cyclopropyl-1-((R)-1,1-dimethylethylsulfinamido)propyl)-2-fluorophenyl)-4-hydroxy-N1-(4-(trifluoromethyl)phenyl)pyrrolidine-1,2-dicarboxamide (27a) (150 mg, 0.210 mmol) in ethanol (10 mL) using conc. HCl (0.175 mL, 2.101 mmol) as reported in step 6 of Scheme 4 gave (2R,4R)-N2-(5-((+)-1-amino-1-(3-cyanophenyl)-3-cyclopropylpropyl)-2-fluorophenyl)-4-hydroxy-N1-(4-(trifluoromethyl)phenyl)pyrrolidine-1,2-dicarboxamide (27b) (50 mg, 0.082 mmol, 39.0% yield) as a white solid; $^1$H NMR (300 MHz, DMSO-d6) δ 9.63 (s, 1H), 8.74 (s, 1H), 8.02 (d, J=7.6 Hz, 1H), 7.86 (t, J=1.8 Hz, 1H), 7.74 (d, J=8.5 Hz, 2H), 7.61 (m, 4H), 7.46 (t, J=7.8 Hz, 1H), 7.12 (d, J=8.0 Hz, 2H), 5.31 (d, J=4.7 Hz, 1H), 4.53 (dd, J=9.0, 4.9 Hz, 1H), 4.42-4.27 (m, 1H), 3.72 (dd, J=10.1, 5.3 Hz, 1H), 3.57-3.45 (m, 1H), 2.42-2.15 (m, 5H), 1.97-1.77 (m, 1H), 1.09-0.92 (m, 2H), 0.70-0.55 (m, 1H), 0.41-0.24 (m, 2H), −0.02−−0.14 (m, 2H); $^{19}$F NMR (282 MHz, DMSO-d6) δ −59.77, −128.84; MS(ES+) 632.5 (M+Na), (ES−) 608.4 (M−1), 644.5 (M+Cl); Optical rotation $[α]_D$=(+) 94.00 [0.3, MeOH]; Analysis calculated for $C_{32}H_{31}F_4N_5O_3 \cdot 0.5H_2O$: C, 62.13; H, 5.21; N, 11.32. Found: C, 62.54; H, 5.34; N, 11.15.

Scheme 28

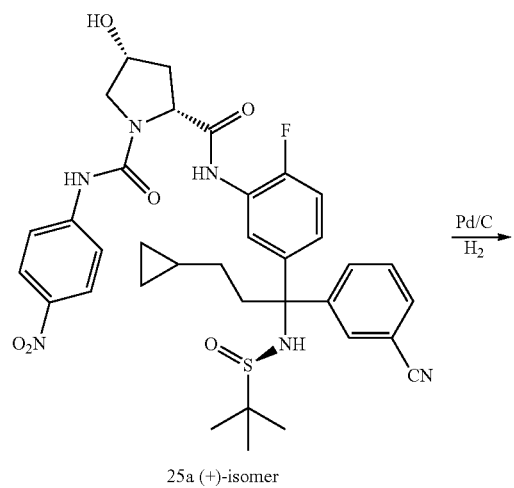

25a (+)-isomer

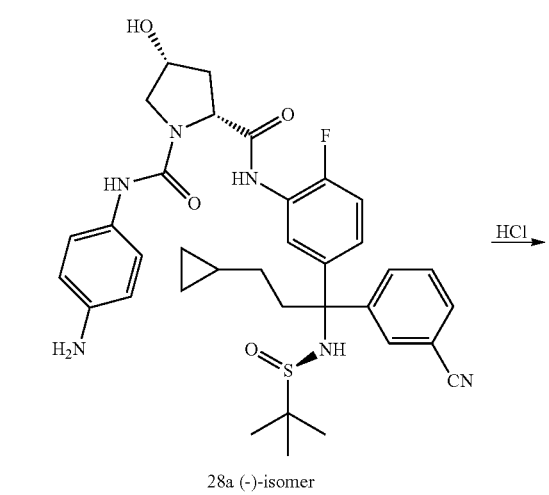

28a (−)-isomer

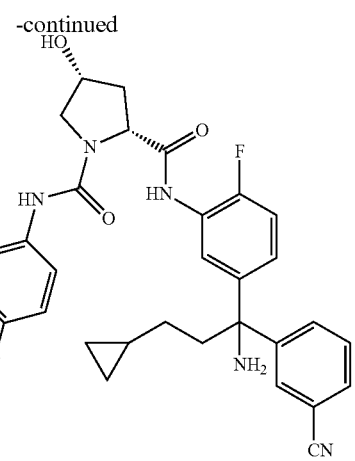

28b (+)-isomer

Preparation of (2R,4R)-N2-(5-((+)-1-amino-1-(3-cyanophenyl)-3-cyclopropylpropyl)-2-fluorophenyl)-N1-(4-aminophenyl)-4-hydroxypyrrolidine-1,2-dicarboxamide (28b)

Step 1: Preparation of (2R,4R)-N1-(4-aminophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (28a)

Reduction of nitro to amine by hydrogenation of (2R,4R)-N2-(5-((+)-1-(3-cyanophenyl)-3-cyclopropyl-1-((R)-1,1-dimethylethylsulfinamido)propyl)-2-fluorophenyl)-4-hydroxy-N1-(4-nitrophenyl)pyrrolidine-1,2-dicarboxamide (25a) (200 mg, 0.290 mmol) in ethanol (20 mL), using palladium on carbon 10% (30.8 mg, 0.029 mmol) as catalyst according to procedure reported in step 2 of Scheme 13 gave (2R,4R)-N1-(4-aminophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (28a) (160 mg, 0.242 mmol, 84% yield) as a light yellow solid; $^1$H NMR (300 MHz, DMSO-d$_6$) δ 9.62 (s, 1H), 8.32 (d, J=2.2 Hz, 1H), 8.15 (d, J=7.4 Hz, 1H), 7.98 (s, 1H), 7.79 (t, J=1.9 Hz, 1H), 7.70 (dd, J=7.2, 1.5 Hz, 1H), 7.63-7.55 (m, 1H), 7.50 (td, J=7.8, 2.3 Hz, 1H), 7.19 (ddd, J=10.6, 8.6, 2.0 Hz, 1H), 7.11-7.01 (m, 3H), 6.46 (dd, J=8.8, 2.2 Hz, 2H), 5.48 (d, J=1.8 Hz, 1H), 5.29 (dd, J=4.7, 2.0 Hz, 1H), 4.74 (s, 2H), 4.46 (dd, J=9.3, 4.0 Hz, 1H), 4.41-4.26 (m, 1H), 3.59 (m, 1H), 3.53-3.41 (m, 1H), 2.75-2.50 (m, 1H), 2.41-2.22 (m, 1H), 1.94 (d, J=13.4 Hz, 1H), 1.21-1.03 (m, 10H), 0.98-0.79 (m, 1H), 0.72-0.53 (m, 1H), 0.44-0.28 (m, 2H), −0.03−−0.11 (m, 2H); $^{19}$F NMR (282 MHz, DMSO-d$_6$) δ −129.01; MS (ES+) 661.5 (M+1), 683.5 (M+Na), (ES−) 659.5 (M−1), 695.6 (M+Cl); Optical rotation $[α]_D$=(−) 21.9 [0.155, MeOH].

Step 2: Preparation of (2R,4R)-N2-(5-((+)-1-amino-1-(3-cyanophenyl)-3-cyclopropylpropyl)-2-fluorophenyl)-N1-(4-aminophenyl)-4-hydroxypyrrolidine-1,2-dicarboxamide (28b)

Reaction of (2R,4R)-N1-(4-aminophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (28a) (0.15 g, 0.227 mmol) in ethanol (10 mL) using conc. HCl (0.208 mL, 2.497 mmol) as reported in step 6 of Scheme 4 gave (2R,4R)-N2-(5-((+)-1-amino-1-(3-cyanophenyl)-3-cyclopropylpropyl)-2-fluorophenyl)-N1-(4-aminophenyl)-4-hydroxypyrrolidine-1,2-dicarboxamide (28b) (65 mg, 0.117 mmol, 51.4% yield) as a white solid; $^1$H NMR (300 MHz, DMSO-d$_6$) δ 9.57 (d, J=1.8 Hz, 1H), 8.12 (dd, J=7.7, 2.1 Hz, 1H), 7.97 (s, 1H), 7.87 (t, J=1.8 Hz, 1H), 7.67-7.58 (m, 2H), 7.46 (t, J=7.8 Hz, 1H), 7.19-7.08 (m, 2H), 7.08-7.00 (m, 2H), 6.50-6.40 (m, 2H), 5.26 (d, J=4.7 Hz, 1H), 4.75 (s, 2H), 4.45 (dd, J=9.2, 4.1 Hz, 1H), 4.38-4.23 (m, 1H), 3.59 (dd, J=10.1, 4.9 Hz, 1H), 3.45 (dd, J=10.0, 3.3 Hz, 1H), 2.41-2.27 (m, 3H), 2.23 (t, J=8.1 Hz, 2H), 2.00-1.86 (m, 1H), 1.02 (m, 2H), 0.72-0.54 (m, 1H), 0.39-0.27 (m, 2H), −0.02−−0.14 (m, 2H); $^{19}$F NMR (282 MHz, DMSO-d$_6$) δ −130.17; MS (ES+) 579.5 (M+Na), (ES−) 555.5 (M−1), 593.6 (M+Cl); Optical rotation [α]$_D$= (+) 100.8 [0.25, MeOH]; Analysis Calculated for $C_{31}H_{33}FN_6O_3 \cdot 0.5H_2O$: C, 65.83; H, 6.06; N, 14.86. Found: C, 65.67; H, 5.98; N, 14.58.

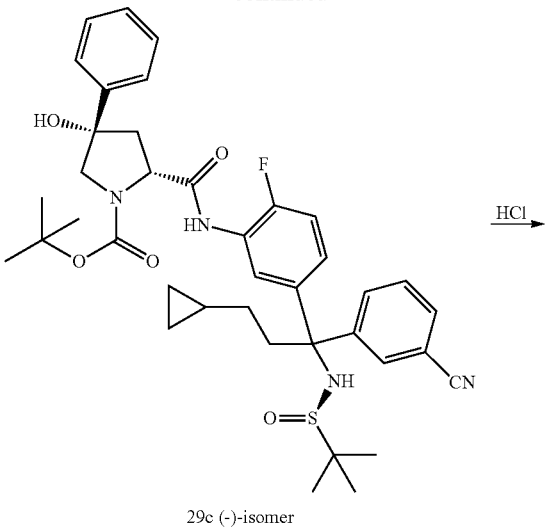

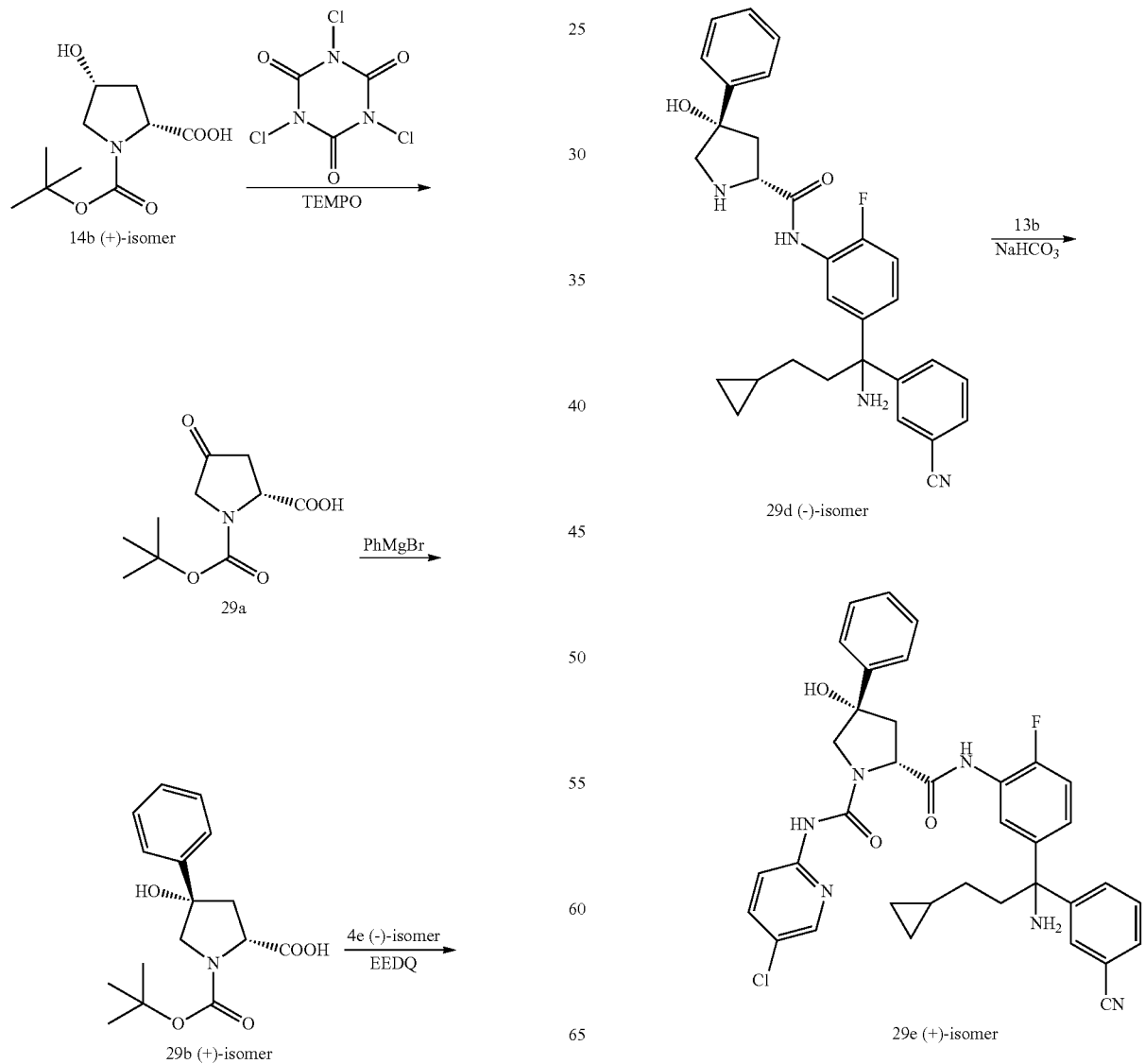

Preparation of (2R,4S)-N2-(5-((+)-1-amino-1-(3-cyanophenyl)-3-cyclopropylpropyl)-2-fluorophenyl)-N1-(5-chloropyridin-2-yl)-4-hydroxy-4-phenylpyrrolidine-1,2-dicarboxamide (29e)

Step 1: Preparation of (R)-1-(tert-butoxycarbonyl)-4-oxopyrrolidine-2-carboxylic acid (29a)

To a solution of (2R,4R)-1-(tert-butoxycarbonyl)-4-hydroxypyrrolidine-2-carboxylic acid (14b) (51 g, 221 mmol) in dichloromethane (2023 mL) at 0° C. containing trichloroisocyanuric acid (51.3 g, 221 mmol) was added TEMPO (1.723 g, 11.03 mmol), stirred at 0° C. for 30 min and allowed to warm to room temperature overnight. The reaction mixture was diluted with water (100 mL) stirred for 30 min and concentrated in vacuum to remove dichloromethane. The reaction mixture was diluted with 200 mL ethyl acetate, filtered through a plug of Celite. The filtrate was acidified with 8 mL of 1M HCl. The ethyl acetate layer was separated washed with water (4×200 mL), brine (100 mL), dried, filtered, and concentrated in vacuum to afford (R)-1-(tert-butoxycarbonyl)-4-oxopyrrolidine-2-carboxylic acid (29a) (38 g, 166 mmol, 75% yield) as a white solid; $^1$H NMR (300 MHz, DMSO-$d_6$) δ 13.00 (s, 1H), 4.53 (m, 1H), 3.82 (dd, J=18.6, 10.6 Hz, 1H), 3.66 (dd, J=18.4, 4.4 Hz, 1H), 3.44 (s, 1H), 3.12 (m, 1H), 1.40 (s, 9H); MS (ES−) 228.2 (M−1), 457.3 (2M−1).

Step 2: Preparation of (2R,4S)-1-(tert-butoxycarbonyl)-4-hydroxy-4-phenylpyrrolidine-2-carboxylic acid (29b)

A solution of (R)-1-(tert-butoxycarbonyl)-4-oxopyrrolidine-2-carboxylic acid (29a) (1.45 g, 6.33 mmol) in THF (20 mL) was added dropwise to a 1.0M solution of phenylmagnesium bromide (17.40 mL, 17.40 mmol) at 0° C. The reaction mixture was stirred at 0° C. for 20 min, quenched with saturated ammonium chloride (15 mL) and concentrated in vacuum to remove organic solvents. The reaction mixture was partitioned between ethyl acetate (50 mL) and 1M HCl (20 mL). The organic layer was separated washed with brine, dried, filtered and concentrated to a volume of 25 mL the solution was diluted with stirring with hexanes (70 mL). The solid obtained was collected by filtration washed with hexanes, dried in vacuum to yield (2R,4S)-1-(tert-butoxycarbonyl)-4-hydroxy-4-phenylpyrrolidine-2-carboxylic acid (29b) (900 mg, 2.93 mmol, 46.3% yield) as a light brown solid; $^1$H NMR (300 MHz, DMSO-$d_6$) δ 12.47 (s, 1H), 7.53 (d, J=7.7 Hz, 2H), 7.41 (t, J=7.5 Hz, 2H), 7.33 (q, J=7.1, 6.5 Hz, 1H), 5.59 (s, 1H), 4.47-4.29 (m, 1H), 3.76-3.55 (m, 2H), 2.74-2.61 (m, 1H), 2.31 (dd, J=12.8, 6.7 Hz, 1H), 1.56-1.40 (m, 9H); MS (ES+) 330.3 (M+Na), (ES−) 306.3 (M−1); Optical rotation $[α]_D$=(+) 38.43 [0.255, MeOH].

Step 3: Preparation of (2R,4S)-tert-butyl 2-(5-((−)-1-(3-cyanophenyl)-3-cyclopropyl-1-((R)-1,1-dimethylethylsulfinamido)propyl)-2-fluorophenylcarbamoyl)-4-hydroxy-4-phenylpyrrolidine-1-carboxylate (29c)

Reaction of (2R,4S)-1-(tert-butoxycarbonyl)-4-hydroxy-4-phenylpyrrolidine-2-carboxylic acid (29b) (500 mg, 1.627 mmol), (R)-N-((−)-1-(3-amino-4-fluorophenyl)-1-(3-cyanophenyl)-3-cyclopropylpropyl)-2-methylpropane-2-sulfinamide (4e) (673 mg, 1.627 mmol) in tetrahydrofuran (75 mL) using ethyl 2-ethoxyquinoline-1(2H)-carboxylate (402 mg, 1.627 mmol) using the reaction and workup conditions as reported in step 10 of Scheme 1 gave after purification by flash column chromatography (silica gel 25 g, eluting with CMA 80 in chloroform 0 to 100%) (2R,4S)-tert-butyl 2-(5-((−)-1-(3-cyanophenyl)-3-cyclopropyl-1-((R)-1,1-dimethylethylsulfinamido)propyl)-2-fluorophenylcarbamoyl)-4-hydroxy-4-phenylpyrrolidine-1-carboxylate (29c) (345 mg, 0.491 mmol, 30.2% yield) as a white solid; $^1$H NMR (300 MHz, DMSO-$d_6$) δ 9.78 (2s, 1H, rotamers), 8.40-7.98 (2m, 1H, rotamers), 7.77 (m, 1H), 7.72 (m, 1H), 7.64 (m, 1H), 7.58-7.46 (m, 3H), 7.37 (m, 2H), 7.33-6.99 (m, 4H), 6.00 (2s, 1H, rotamers), 5.48 (2s, 1H, rotamers), 4.66-4.30 (m, 1H), 3.82-3.53 (m, 2H), 2.80-2.55 (m, 2H), 2.33-2.14 (m, 1H), 1.32 (2s, 9H, rotamers), 1.14 (2s, 10H, rotamers), 1.00-0.75 (m, 1H), 0.71-0.52 (m, 1H), 0.44-0.26 (m, 2H), 0.01--0.17 (m, 2H); $^{19}$F NMR (282 MHz, DMSO-$d_6$) δ −128.69, −129.87; MS (ES+) 725.5 (M+Na), (ES−) 701.6 (M−1), 737.5 (M+Cl); Optical rotation $[α]_D$=(−) 71.10 [0.09, MeOH].

Step 4: Preparation of (2R,4S)-N-(5-((−)-1-amino-1-(3-cyanophenyl)-3-cyclopropylpropyl)-2-fluorophenyl)-4-hydroxy-4-phenylpyrrolidine-2-carboxamide (29d)

Reaction of (2R,4S)-tert-butyl 2-(5-((−)-1-(3-cyanophenyl)-3-cyclopropyl-1-((R)-1,1-dimethylethylsulfinamido)propyl)-2-fluorophenylcarbamoyl)-4-hydroxy-4-phenylpyrrolidine-1-carboxylate (29c) (335 mg, 0.477 mmol) in methanolic HCl (2.383 mL, 7.15 mmol) followed by workup and purification as reported in step 6 of Scheme 4 gave (2R,4S)-N-(5-((−)-1-amino-1-(3-cyanophenyl)-3-cyclopropylpropyl)-2-fluorophenyl)-4-hydroxy-4-phenylpyrrolidine-2-carboxamide (29d) (260 mg, 0.455 mmol, 95% yield) as a white solid; $^1$H NMR (300 MHz, DMSO-$d_6$) δ 10.56 (s, 1H), 10.26 (s, 1H), 9.45 (s, 3H), 8.78 (s, 1H), 7.90 (m, 2H), 7.86 (m, 1H), 7.72-7.63 (m, 2H), 7.57-7.51 (m, 2H), 7.49-7.24 (m, 5H), 5.88 (s, 1H), 4.72 (m, 1H), 3.60-3.41 (m, 3H), 2.79 (t, J=12.4 Hz, 1H), 1.26-1.14 (m, 1H), 1.14-1.01 (m, 3H), 0.82-0.59 (m, 1H), 0.48-0.32 (m, 2H), 0.11--0.06 (m, 2H); 19F NMR (282 MHz, DMSO-$d_6$) δ −123.49; MS (ES+) 521.5 (M+Na), (ES−) 533.5 (M+Cl); Optical rotation $[α]_D$=(−) 56.67 [0.18, MeOH].

Step 5: Preparation of (2R,4S)-N2-(5-((+)-1-amino-1-(3-cyanophenyl)-3-cyclopropylpropyl)-2-fluorophenyl)-N1-(5-chloropyridin-2-yl)-4-hydroxy-4-phenylpyrrolidine-1,2-dicarboxamide (29e)

Reaction of (2R,4S)-N-(5-((−)-1-amino-1-(3-cyanophenyl)-3-cyclopropylpropyl)-2-fluorophenyl)-4-hydroxy-4-phenylpyrrolidine-2-carboxamide (29d) (99 mg, 0.173 mmol) in tetrahydrofuran (20 mL) with phenyl 5-chloropyridin-2-ylcarbamate (43.1 mg, 0.173 mmol) using sodium bicarbonate (3.46 mL, 3.46 mmol) as base according to procedure reported in step 3 of Scheme 13 gave after purification by flash column chromatography (silica gel 12 g, eluting with 0-100% CMA-80 in chloroform) (2R,4S)-N2-(5-((+)-1-amino-1-(3-cyanophenyl)-3-cyclopropylpropyl)-2-fluorophenyl)-N1-(5-chloropyridin-2-yl)-4-hydroxy-4-phenylpyrrolidine-1,2-dicarboxamide (29e) (65 mg, 0.100 mmol, 57.5% yield) as an off white solid; 1H NMR (300 MHz, DMSO-$d_6$) δ 9.74 (s, 1H), 9.24 (s, 1H), 8.30 (dd, J=2.7, 0.8 Hz, 1H), 8.11 (d, J=7.6 Hz, 1H), 7.91 (dd, J=9.1, 0.8 Hz, 1H), 7.87 (t, J=1.7 Hz, 1H), 7.81 (dd, J=9.0, 2.6 Hz, 1H), 7.68-7.61 (m, 2H), 7.54 (dt, J=6.6, 1.3 Hz, 2H), 7.47 (t, J=7.8 Hz, 1H), 7.42-7.34 (m, 2H), 7.33-7.26 (m, 1H), 7.20-7.11 (m, 2H), 5.95 (s, 1H), 4.71 (d, J=8.5 Hz, 1H), 4.02-3.96 (m, 1H), 3.90 (d, J=10.5 Hz, 1H), 2.68 (dd, J=13.2, 9.7 Hz, 1H), 2.34 (s, 2H), 2.34-2.18 (m, 3H), 1.11-0.95 (m, 2H), 0.74-0.54 (m, 1H), 0.39-0.29 (m, 2H), −0.01−−0.11 (m, 2H); $^{19}$F NMR (282 MHz, DMSO-d$_6$) δ −129.26; MS (ES+) 653.5 (M+1) 675.4, 677.5 (M+Na), (ES−) 651.5, 653.7 (M−1), 689.5 (M+Cl); IR (KBr) 2229 cm$^1$; Optical rotation $[α]_D$=(+) 80 [0.295, MeOH].

Scheme 30

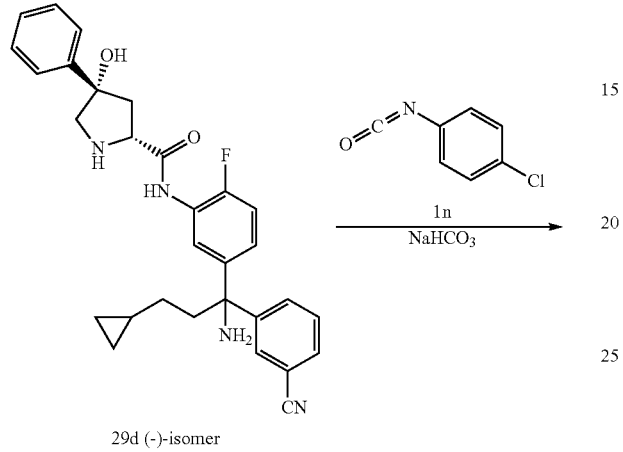

29d (−)-isomer

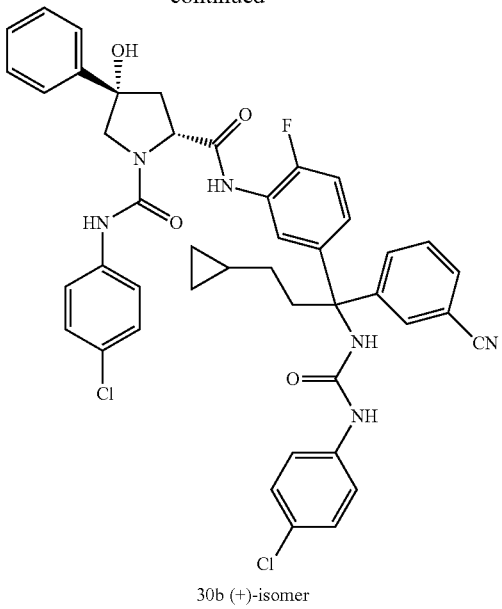

30b (+)-isomer

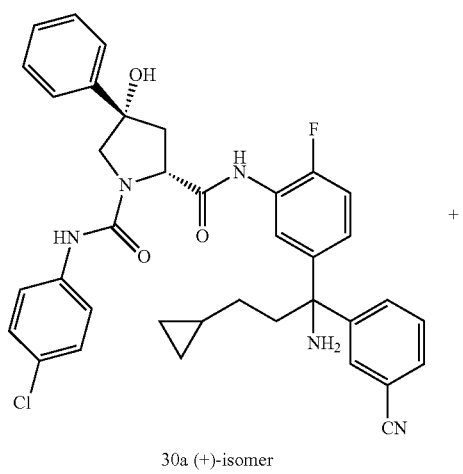

30a (+)-isomer

Preparation of (2R,4S)-N2-(5-((+)-1-amino-1-(3-cyanophenyl)-3-cyclopropylpropyl)-2-fluorophenyl)-N1-(4-chlorophenyl)-4-hydroxy-4-phenylpyrrolidine-1,2-dicarboxamide (30a) and (2R,4S)-N1-(4-chlorophenyl)-N2-(5-((+)-1-(3-(4-chlorophenyl)ureido)-1-(3-cyanophenyl)-3-cyclopropylpropyl)-2-fluorophenyl)-4-hydroxy-4-phenylpyrrolidine-1,2-dicarboxamide (30b)

Reaction of (2R,4S)-N-(5-((−)-1-amino-1-(3-cyanophenyl)-3-cyclopropylpropyl)-2-fluorophenyl)-4-hydroxy-4-phenylpyrrolidine-2-carboxamide (29d) (150 mg, 0.262 mmol) in dichloromethane (10 mL) with 4-chlorophenyl isocyanate (1n) (0.034 mL, 0.262 mmol) and sodium bicarbonate (5.25 mL, 5.25 mmol) according to procedure reported in step 9 Scheme 1 gave after purification 1. (2R,4S)-N2-(5-((+)-1-amino-1-(3-cyanophenyl)-3-cyclopropylpropyl)-2-fluorophenyl)-N1-(4-chlorophenyl)-4-hydroxy-4-phenylpyrrolidine-1,2-dicarboxamide (30a) (65 mg, 0.100 mmol, 38.0% yield) as a white solid; $^1$H NMR (300 MHz, DMSO-d$_6$) δ 9.69 (s, 1H), 8.53 (s, 1H), 8.14 (d, J=7.5 Hz, 1H), 7.88 (t, J=1.7 Hz, 1H), 7.64 (m, 2H), 7.60-7.53 (m, 4H), 7.48 (d, J=7.8 Hz, 1H), 7.45-7.35 (m, 2H), 7.33-7.25 (m, 3H), 7.18-7.10 (m, 2H), 5.97 (s, 1H), 4.76-4.60 (m, 1H), 3.93 (d, J=10.2 Hz, 1H), 3.83 (d, J=10.1 Hz, 1H), 2.72 (dd, J=13.2, 9.5 Hz, 1H), 2.35-2.21 (m, 5H), 1.10-0.96 (m, 2H), 0.71-0.56 (m, 1H), 0.40-0.28 (m, 2H), −0.00−−0.11 (m, 2H); $^{19}$F NMR (282 MHz, DMSO-d$_6$) δ −129.82; MS (ES+) 674.5, 677.5 (M+Na), (ES−) 650.5, 652.0 (M−1), 686.5, 688.6 (M+Cl); IR (KBr) 2229 cm-1; Optical rotation $[α]_D$=(+) 87.5 [0.32,MeOH]; Analysis calculated for $C_{37}H_{35}ClFN_5O_3 \cdot 0.25H_2O$; C, 67.68; H, 5.45; N, 10.67. Found: C, 67.73; H, 5.53; N, 10.51.

2. (2R,4S)-N1-(4-chlorophenyl)-N2-(5-((+)-1-(3-(4-chlorophenyl)ureido)-1-(3-cyanophenyl)-3-cyclopropylpropyl)-2-fluorophenyl)-4-hydroxy-4-phenylpyrrolidine-1,2-dicarboxamide (30b) (68 mg, 0.084 mmol, 32.2% yield) as a white solid; $^1$H NMR (300 MHz, DMSO-d$_6$) δ 9.73 (s, 1H), 8.85 (s, 1H), 8.55 (s, 1H), 8.20-8.10 (m, 1H), 7.80 (s, 1H), 7.67 (m, 2H), 7.58-7.49 (m, 5H), 7.43-7.18 (m, 10H), 7.14 (s, 1H), 7.08 (s, 1H), 5.96 (s, 1H), 4.68 (d, J=9.6 Hz, 1H), 3.93 (d, J=10.2 Hz, 1H), 3.83 (d, J=10.1 Hz, 1H), 2.80-2.61 (m, 3H), 2.30 (d, J=13.6 Hz, 1H), 1.11-0.91 (m, 2H), 0.74-0.57 (m, 1H), 0.42-0.29 (m, 2H), −0.01-−0.13 (m, 2H); $^{19}$F NMR (282 MHz, DMSO-d$_6$) δ −129.16; MS (ES+) 827.5, 828.6 (M+Na), (ES−) 803.5, 805.4 (M−1), 839.5, 840.6 (M+Cl); IR (KBr) 2229 cm-1; Optical rotation [α]$_D$=(+) 52.0 [0.25, MeOH]; Analysis calculated for C$_{44}$H$_{39}$Cl$_2$FN$_6$O$_4$·0.75H$_2$O: C, 64.51; H, 4.98; N, 10.26. Found: C, 64.49; H, 5.06; N, 9.99.
Scheme 31
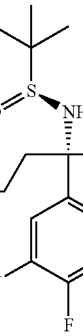
31a
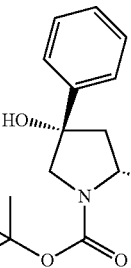
31b
31c
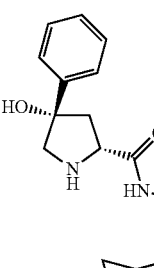
31d (+)-isomer
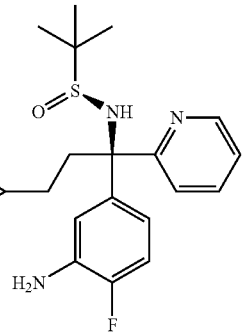
31e (+)-isomer     31f (−)-isomer
31g
31h -continued

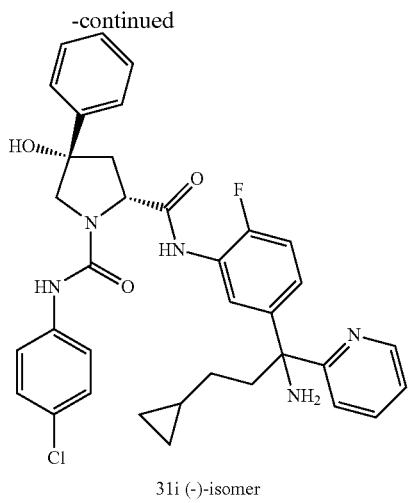

31i (-)-isomer

Preparation of (2R,4S)-N2-(5-((−)-1-amino-3-cyclo-propyl-1-(pyridin-2-yl)propyl)-2-fluorophenyl)-N1-(4-chlorophenyl)-4-hydroxy-4-phenylpyrrolidine-1, 2-dicarboxamide (31i)

Step-1: Preparation of (E)-3-cyclopropyl-1-(pyridin-2-yl)prop-2-en-1-one (31b)

To a stirred solution of 2-acetylpyridine (31a) (53 g, 438 mmol) in methanol (636 mL) cooled to 0° C. was added cyclopropanecarboxaldehyde (52.8 mL, 700 mmol) and aqueous potassium hydroxide (1N solution, 88 mL, 88 mmol). The reaction was allowed to warm to room temperature overnight. The reaction was concentrated in vacuum to remove methanol. The crude residue was dissolved in ethyl acetate (500 mL) washed with water (500 mL), brine (200 mL), dried, filtered and concentrated in vacuum to afford (E)-3-cyclopropyl-1-(pyridin-2-yl)prop-2-en-1-one (31b) (80 g, 462 mmol, 106% yield) which was used as such for next step. An analytical sample was prepared by purification of crude residue by flash column chromatography (silica gel, eluting with ethyl acetate in hexanes 0 to 100%); $^1$H NMR (300 MHz, DMSO-d$_6$) δ 8.80-8.68 (m, 1H), 8.07-7.98 (m, 2H), 7.74-7.63 (m, 2H), 6.63 (dd, J=15.5, 10.4 Hz, 1H), 1.93-1.76 (m, 1H), 1.08-0.98 (m, 2H), 0.84-0.71 (m, 2H).

Step-2: Preparation of 3-cyclopropyl-1-(pyridin-2-yl)propan-1-one (31c)

To a stirred solution of (E)-3-cyclopropyl-1-(pyridin-2-yl)prop-2-en-1-one (31b) (80 g, 462 mmol) in acetonitrile (829 mL) was added tributylstanane (256 mL, 924 mmol) and heated at reflux for 9 h. The reaction was cooled to room temperature and layers were separated. The acetonitrile layer was concentrated in vacuum and residue obtained was purified by flash column chromatography (silica gel, eluting with ethyl acetate in hexanes 0 to 100%) to afford 3-cyclopropyl-1-(pyridin-2-yl)propan-1-one (31c) (17.2 g, 98 mmol, 21.25% yield) as an oil $^1$H NMR (300 MHz, DMSO-d$_6$) δ 8.94 (dt, J=4.7, 1.5 Hz, 1H), 8.19 (m, 1H), 7.87 (m, 1H), 3.46 (td, J=7.2, 2.0 Hz, 2H), 1.74 (qd, J=7.2, 2.1 Hz, 2H), 1.03-0.87 (m, 1H), 0.59 (m, 2H), 0.30-0.20 (m, 2H).

Step-3: Preparation of (+)-N-(3-cyclopropyl-1-(pyridin-2-yl)propylidene)-2-methylpropane-2-sulfinamide (31d)

Reaction of 3-cyclopropyl-1-(pyridin-2-yl)propan-1-one (31c) (15.2 g, 87 mmol) in tetrahydrofuran (220 mL) with (S)-2-methylpropane-2-sulfinamide (12.62 g, 104 mmol) and tetraisopropoxytitanium (51.2 mL, 173 mmol) according to the procedure and workup reported in Step-3 of Scheme 1 gave (+)-N-(3-cyclopropyl-1-(pyridin-2-yl)propylidene)-2-methylpropane-2-sulfinamide (31d) (11.65 g, 41.8 mmol, 48.2% yield) as an yellow oil; $^1$H NMR (300 MHz, DMSO-d$_6$) δ 8.70 (dt, J=4.7, 1.4 Hz, 1H), 8.02 (d, J=8.0 Hz, 1H), 7.94 (td, J=7.6, 1.7 Hz, 1H), 7.56 (ddd, J=7.5, 4.7, 1.4 Hz, 1H), 3.53 (m, 1H), 3.41-3.35 (m, 1H), 1.49 (q, J=7.5 Hz, 2H), 1.25 (s, 9H), 0.81-0.65 (m, 1H), 0.44-0.28 (m, 2H), 0.03 (m, 2H); MS (ES+) 279.3 (M+1), 301.3 (M+Na); Optical rotation $[α]_D$=(+) 50.8 [2.64, MeOH].

Step-4: Preparation of (S)-N-((+)-1-(3-amino-4-fluorophenyl)-3-cyclopropyl-1-(pyridin-2-yl)propyl)-2-methylpropane-2-sulfinamide (31e) and (S)-N-((−)-1-(3-amino-4-fluorophenyl)-3-cyclopropyl-1-(pyridin-2-yl)propyl)-2-methylpropane-2-sulfinamide (31f)

Reaction of (+)-N-(3-cyclopropyl-1-(pyridin-2-yl)propylidene)-2-methylpropane-2-sulfinamide (31d) (12.665 g, 45.5 mmol) in toluene (400 mL) with freshly prepared solution of (3-(bis(trimethylsilyl)amino)-4-fluorophenyl)magnesium bromide (1c) (142 mL, 114 mmol) according to the procedure reported in step 4 of Scheme 1 gave after purification by flash column chromatography (silica gel, 120 g eluting with ethyl acetate in hexanes 0 to 60 to 100%)
1. (S)-N-((+)-1-(3-amino-4-fluorophenyl)-3-cyclopropyl-1-(pyridin-2-yl)propyl)-2-methylpropane-2-sulfinamide (31e) (10 g, 25.7 mmol, 56.4% yield) as a white solid; $^1$H NMR (300 MHz, DMSO-d$_6$) δ 8.52 (dt, J=4.6, 1.5 Hz, 1H), 7.73 (td, J=7.8, 1.9 Hz, 1H), 7.26 (ddd, J=7.5, 4.8, 1.0 Hz, 1H), 7.07 (dt, J=8.0, 1.1 Hz, 1H), 6.88 (dd, J=11.3, 8.5 Hz, 1H), 6.78 (dd, J=8.8, 2.4 Hz, 1H), 6.43 (ddd, J=8.6, 4.3, 2.3 Hz, 1H), 6.09 (s, 1H), 5.09 (s, 2H), 2.56 (m, 1H), 2.45 (m, 1H), 1.29-1.15 (m, 1H), 1.10 (s, 9H), 0.63-0.42 (m, 2H), 0.35-0.23 (m, 2H), −0.07 (m, 1H), −0.20 (m, 1H); $^{19}$F NMR (282 MHz, DMSO-d$_6$) δ −137.14; MS: (ES+) 412.4 (M+Na), (ES−) 388.4 (M−1), 424.4 (M+Cl); Optical rotation $[α]_D$=(+) 136.36 [0.55, MeOH].
2. (S)-N-((−)-1-(3-amino-4-fluorophenyl)-3-cyclopropyl-1-(pyridin-2-yl)propyl)-2-methylpropane-2-sulfinamide (31f) (300 mg, 0.770 mmol, 1.693% yield) as a white solid; $^1$H NMR (300 MHz, DMSO-d$_6$) δ 8.53 (ddd, J=4.9, 1.9, 0.9 Hz, 1H), 7.71 (td, J=7.7, 1.8 Hz, 1H), 7.35-7.09 (m, 2H), 6.85 (dd, J=11.3, 8.5 Hz, 1H), 6.71 (dd, J=8.8, 2.4 Hz, 1H), 6.41 (ddd, J=8.5, 4.3, 2.4 Hz, 1H), 5.82 (s, 1H), 5.06 (s, 2H), 2.55 (d, J=8.5 Hz, 2H), 1.13 (s, 9H), 1.08-0.96 (m, 1H), 0.81 (m, 1H), 0.61 (m, 1H), 0.38-0.29 (m, 2H), −0.10 (m, 2H); $^{19}$F NMR (282 MHz, DMSO-d$_6$) δ −137.42; MS (ES+) 390.4 (M+1), 412.4 (M+Na), (ES−) 388.4 (M−1), 424.4 (M+Cl); Optical rotation $[α]_D$=(−) 3.28 [0.305, MeOH].

Step-5: Preparation of (2R,4S)-tert-butyl 2-(5-(3-cyclopropyl-1-((S)-1,1-dimethylethylsulfinamido)-1-(pyridin-2-yl)propyl)-2-fluorophenylcarbamoyl)-4-hydroxy-4-phenylpyrrolidine-1-carboxylate (31g)

Reaction of (2R,4S)-1-(tert-butoxycarbonyl)-4-hydroxy-4-phenylpyrrolidine-2-carboxylic acid (29b) (158 mg, 0.513 mmol), (S)-N-((+)-1-(3-amino-4-fluorophenyl)-3-cyclopropyl-1-(pyridin-2-yl)propyl)-2-methylpropane-2-sulfinamide (31e) (200 mg, 0.513 mmol) in tetrahydrofuran (20 mL) using ethyl 2-ethoxyquinoline-1(2H)-carboxylate (127 mg, 0.513 mmol) using the reaction and workup conditions as reported in step 10 of Scheme 1 gave after purification by flash column chromatography (silica gel 25 g, eluting with CMA 80 in chloroform 0 to 100%) (2R,4S)-tert-butyl 2-(5-(3-cyclopropyl-1-((S)-1,1-dimethylethylsulfinamido)-1-(pyridin-2-yl)propyl)-2-fluorophenylcarbamoyl)-4-hydroxy-4-phenylpyrrolidine-1-carboxylate (31g) (130 mg, 0.191 mmol, 37.3% yield) as a white solid; $^1$H NMR (300 MHz, DMSO-$d_6$) δ 9.71 (2s, 1H, rotamers), 8.54 (2d, J=4.8 Hz, 1H, rotamers), 8.37-8.04 (m, 1H), 7.75 (m, 1H), 7.59-7.44 (m, 2H), 7.37 (m, 2H), 7.33-7.23 (m, 1H), 7.23-6.94 (m, 2H), 6.14 (m, 1H), 5.95 (2s, 1H, rotamers), 4.44 (m, 1H), 3.67 (s, 2H), 2.79-2.51 (m, 5H), 2.23 (m, 1H), 1.33 (2s, 9H, rotamers), 1.11 (s, 10H), 0.67-0.46 (m, 2H), 0.31 (m, 2H), 0.01 (m, 1H), −0.18 (m, 1H); $^{19}$F NMR (282 MHz, DMSO-$d_6$) δ −128.48, −129.79; MS (ES+) 679.6 (M+1), 701.6 (M+Na), (ES−) 677.7 (M−1), 713.6 (M+Cl).

Step-6: Preparation of (2R,4S)-N-(5-(1-amino-3-cyclopropyl-1-(pyridin-2-yl)propyl)-2-fluorophenyl)-4-hydroxy-4-phenylpyrrolidine-2-carboxamide (31h)

Reaction of (2R,4S)-tert-butyl 2-(5-(3-cyclopropyl-1-((S)-1,1-dimethylethylsulfinamido)-1-(pyridin-2-yl)propyl)-2-fluorophenylcarbamoyl)-4-hydroxy-4-phenylpyrrolidine-1-carboxylate (31g) (125 mg, 0.184 mmol) in methanolic HCl (0.614 mL, 1.841 mmol) followed by workup and purification as reported in step 6 of Scheme 4 gave (2R,4S)-N-(5-(1-amino-3-cyclopropyl-1-(pyridin-2-yl)propyl)-2-fluorophenyl)-4-hydroxy-4-phenylpyrrolidine-2-carboxamide (31h) (106 mg, 0.182 mmol, 99% yield) as a light brown solid; $^1$H NMR (300 MHz, DMSO-$d_6$) δ 10.61 (s, 1H), 10.29 (s, 1H), 9.06 (s, 3H), 8.96-8.78 (m, 1H), 8.74 (m, 1H), 8.10-8.02 (m, 1H), 7.96 (t, J=7.8 Hz, 1H), 7.65-7.56 (m, 2H), 7.56-7.35 (m, 5H), 7.31 (s, 1H), 4.77 (m, 1H), 3.94-3.50 (m, 5H), 2.97-2.75 (m, 1H), 1.39-1.20 (m, 1H), 1.16 (m, 2H), 1.14-1.06 (m, 2H), 0.75 (m, 1H), 0.46 (m, 2H), 0.27-−0.13 (m, 2H); $^{19}$F NMR (282 MHz, DMSO-$d_6$) δ −123.51; MS (ES+) 475.5 (M+1), 497.5 (M+Na), (ES−) 473.6 (M−1), 509.5 (M+Cl).

Step-7: Preparation of (2R,4S)-N2-(5-((−)-1-amino-3-cyclopropyl-1-(pyridin-2-yl)propyl)-2-fluorophenyl)-N1-(4-chlorophenyl)-4-hydroxy-4-phenylpyrrolidine-1,2-dicarboxamide (31i)

Reaction of (2R,4S)-N-(5-(1-amino-3-cyclopropyl-1-(pyridin-2-yl)propyl)-2-fluorophenyl)-4-hydroxy-4-phenylpyrrolidine-2-carboxamide (31h) (50 mg, 0.086 mmol) in dichloromethane (10 mL) with 4-chlorophenyl isocyanate (1n) (10.96 μL, 0.086 mmol) and sodium bicarbonate according to procedure reported in step 9 Scheme 1 gave after purification by flash column chromatography (silica gel, 12 g eluting with CMA 80 in chloroform) (2R,4S)-N2-(5-((−)-1-amino-3-cyclopropyl-1-(pyridin-2-yl)propyl)-2-fluorophenyl)-N1-(4-chlorophenyl)-4-hydroxy-4-phenylpyrrolidine-1,2-dicarboxamide (31i) (36 mg, 0.057 mmol, 66.9% yield) as a off white solid; $^1$H NMR (300 MHz, DMSO-$d_6$) δ 9.64 (s, 1H), 8.53 (s, 1H), 8.48 (dt, J=4.5, 1.5 Hz, 1H), 8.18 (dd, J=7.8, 2.2 Hz, 1H), 7.70 (td, J=7.7, 1.9 Hz, 1H), 7.60-7.51 (m, 5H), 7.39 (t, J=7.5 Hz, 2H), 7.33-7.26 (m, 3H), 7.21-7.06 (m, 3H), 5.98 (s, 1H), 4.68 (dd, J=9.6, 2.8 Hz, 1H), 3.93 (d, J=10.1 Hz, 1H), 3.82 (d, J=10.1 Hz, 1H), 2.72 (dd, J=13.1, 9.7 Hz, 1H), 2.40-2.21 (m, 5H), 1.04 (m, 2H), 0.70-0.55 (m, 1H), 0.40-0.26 (m, 2H), −0.01-−0.12 (m, 2H); $^{19}$F NMR (282 MHz, DMSO-$d_6$) δ −130.30; MS (ES+) 650.5, 651.4 (M+Na), (ES−) 626.5 (M−1), 662.6, 664.5 (M+Cl); Optical rotation $[α]_D$=(−) 56.25 [0.16, MeOH].

Scheme 32

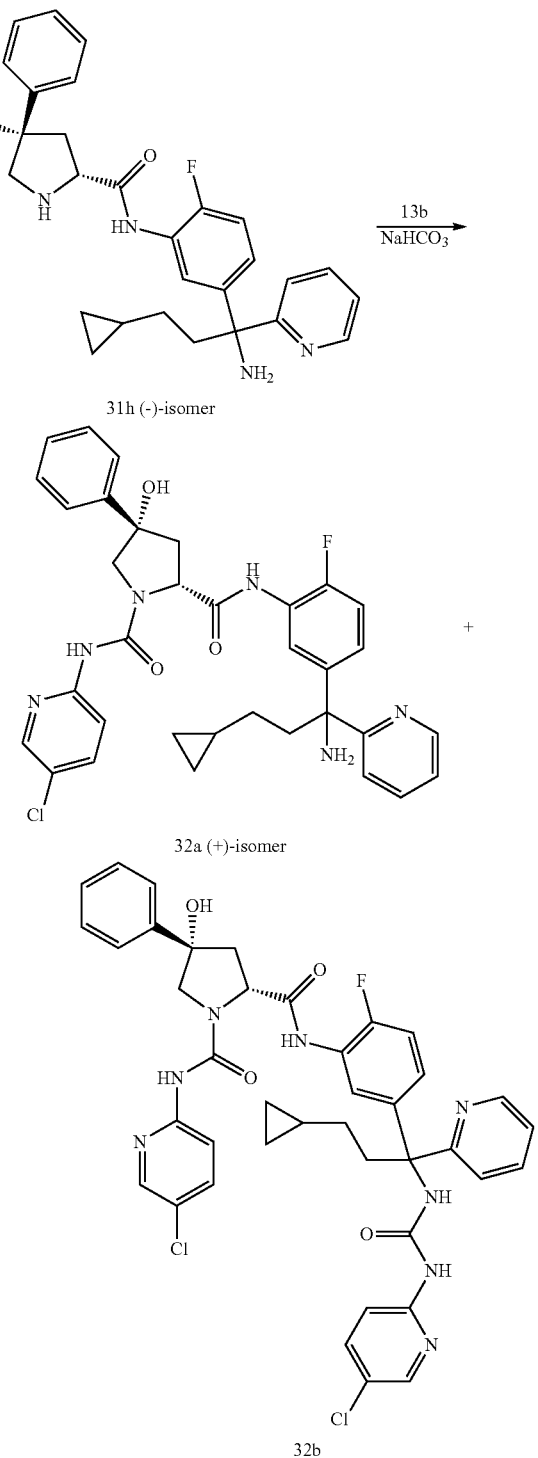

31h (−)-isomer 32a (+)-isomer

+

32b

Preparation of (2R,4S)-N2-(5-((+)-1-amino-3-cyclopropyl-1-(pyridin-2-yl)propyl)-2-fluorophenyl)-N1-(5-chloropyridin-2-yl)-4-hydroxy-4-phenylpyrrolidine-1,2-dicarboxamide (32a) and (2R,4S)-N1-(5-chloropyridin-2-yl)-N2-(5-(1-(3-(5-chloropyridin-2-yl)ureido)-3-cyclopropyl-1-(pyridin-2-yl)propyl)-2-fluorophenyl)-4-hydroxy-4-phenylpyrrolidine-1,2-dicarboxamide (32b)

Reaction of (2R,4S)-N-(5-((−)-1-amino-3-cyclopropyl-1-(pyridin-2-yl)propyl)-2-fluorophenyl)-4-hydroxy-4-phenylpyrrolidine-2-carboxamide (31h) (50 mg, 0.086 mmol) in tetrahydrofuran (10 mL) with phenyl 5-chloropyridin-2-ylcarbamate (13b) (21.29 mg, 0.086 mmol) using sodium bicarbonate as base according to procedure reported in step 3 of Scheme 13 gave after purification by flash column chromatography (silica gel 12 g, eluting with 0-100% CMA-80 in chloroform)

1. (2R,4S)-N2-(5-((+)-1-amino-3-cyclopropyl-1-(pyridin-2-yl)propyl)-2-fluorophenyl)-N1-(5-chloropyridin-2-yl)-4-hydroxy-4-phenylpyrrolidine-1,2-dicarboxamide (32a) (29 mg, 0.046 mmol, 53.8% yield) as off white solid; 1H NMR (300 MHz, DMSO-$d_6$) δ 9.70 (s, 1H), 9.23 (s, 1H), 8.56-8.41 (m, 1H), 8.30 (d, J=2.7 Hz, 1H), 8.21-8.07 (m, 1H), 7.92 (d, J=9.1 Hz, 1H), 7.81 (dd, J=9.0, 2.7 Hz, 1H), 7.70 (td, J=7.7, 1.9 Hz, 1H), 7.54 (d, J=7.8 Hz, 3H), 7.38 (t, J=7.5 Hz, 2H), 7.29 (m, 1H), 7.13 (m, 3H), 5.96 (s, 1H), 4.77-4.66 (m, 1H), 4.00 (d, J=10.5 Hz, 1H), 3.90 (d, J=10.4 Hz, 1H), 2.68 (dd, J=13.2, 9.6 Hz, 1H), 2.38-2.32 (m, 3H), 2.34-2.22 (m, 2H), 1.12-0.94 (m, 2H), 0.70-0.54 (m, 1H), 0.40-0.25 (m, 2H), 0.00--0.15 (m, 2H); $^{19}$F NMR (282 MHz, DMSO-$d_6$) δ −129.71; MS (ES+) 629.5 (M+1) 652.5 (M+Na), (ES−) 627.5, 628.5 (M−1); Optical rotation $[α]_D$=(+) 14.81 [0.27, MeOH].

2. (2R,4S)-N1-(5-chloropyridin-2-yl)-N2-(5-(1-(3-(5-chloropyridin-2-yl)ureido)-3-cyclopropyl-1-(pyridin-2-yl)propyl)-2-fluorophenyl)-4-hydroxy-4-phenylpyrrolidine-1,2-dicarboxamide (32b) (10 mg, 0.013 mmol, 14.90% yield) as off white solids; 1H NMR (300 MHz, DMSO-$d_6$) δ 9.88 (s, 1H), 9.69 (s, 2H), 9.24 (s, 1H), 8.62 (d, J=4.9 Hz, 1H), 8.34 (d, J=2.6 Hz, 1H), 8.29 (d, J=2.6 Hz, 1H), 8.25 (d, J=7.4 Hz, 1H), 7.92 (d, J=9.0 Hz, 1H), 7.85-7.67 (m, 3H), 7.53 (d, J=7.6 Hz, 2H), 7.37 (m, 3H), 7.26 (m, 3H), 7.14 (m, 2H), 5.92 (s, 1H), 4.71 (d, J=8.5 Hz, 1H), 4.00 (d, J=10.5 Hz, 1H), 3.90 (d, J=10.4 Hz, 1H), 2.76-2.64 (m, 1H), 2.67-2.54 (m, 2H), 2.40-2.20 (m, 1H), 1.13-0.93 (m, 2H), 0.70-0.53 (m, 1H), 0.30 (m, 2H), −0.07--0.26 (m, 2H); $^{19}$F NMR (282 MHz, DMSO-$d_6$) δ −129.58; MS (ES+) 783.6 (M+1) 805.5, 807.5 (M+Na).

Scheme 33

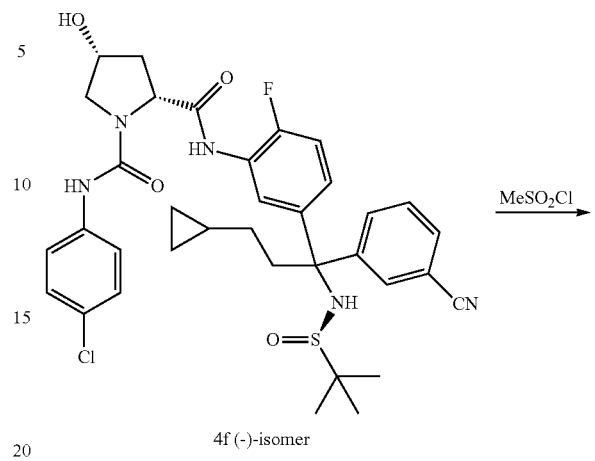

4f (−)-isomer

MeSO$_2$Cl →

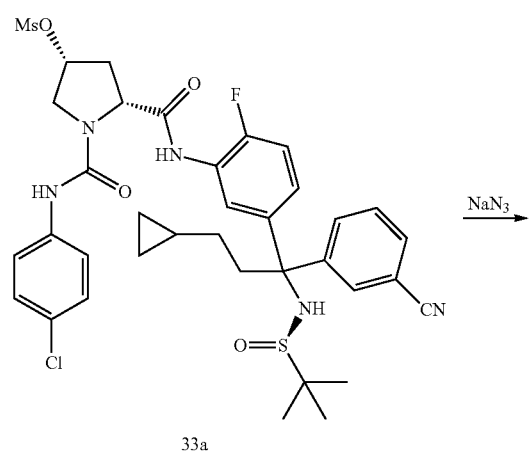

33a

NaN$_3$ →

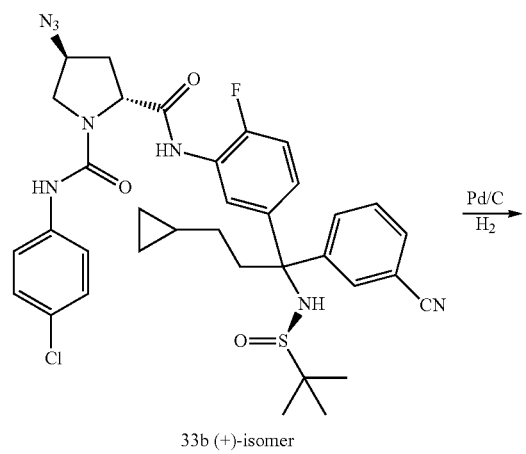

33b (+)-isomer

Pd/C H$_2$ →

-continued

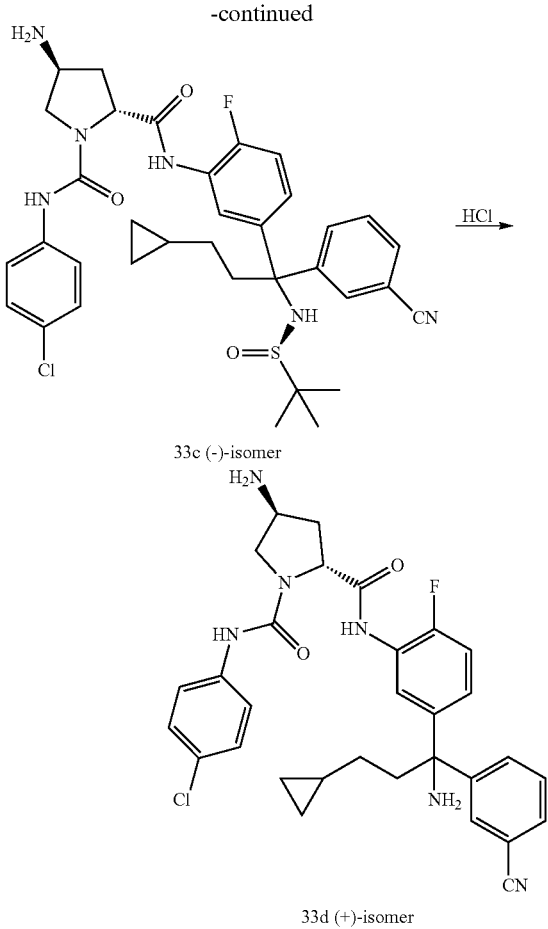

33c (−)-isomer 33d (+)-isomer

Preparation of (2R,4S)-4-amino-N2-(5-((+)-1-amino-1-(3-cyanophenyl)-3-cyclopropylpropyl)-2-fluorophenyl)-N1-(4-chlorophenyl)pyrrolidine-1,2-dicarboxamide (33d)

Step 1: Preparation of (3R,5R)-1-(4-chlorophenylcarbamoyl)-5-(5-(1-(3-cyanophenyl)-3-cyclopropyl-1-((R)-1,1-dimethylethylsulfinamido)propyl)-2-fluorophenylcarbamoyl)pyrrolidin-3-yl methanesulfonate (33a)

To a ice cold solution of (2R,4R)-N1-(4-chlorophenyl)-N2-(5-((−)-1-(3-cyanophenyl)-3-cyclopropyl-1-((R)-1,1-dimethylethylsulfinamido)propyl)-2-fluorophenyl)-4-hydroxypyrrolidine-1,2-dicarboxamide (4f) (110 mg, 0.162 mmol) in dichloromethane (10 mL) was added triethylamine (0.09 mL, 0.647 mmol), methanesulfonyl chloride (0.019 mL, 0.243 mmol) and stirred at room temperature overnight. The reaction was diluted with dichloromethane (100 mL), washed with water (2×20 mL), brine (2×20 mL), dried, filtered and concentrated in vacuum to afford (3R,5R)-1-(4-chlorophenylcarbamoyl)-5-(5-(1-(3-cyanophenyl)-3-cyclopropyl-1-((R)-1,1-dimethylethylsulfinamido)propyl)-2-fluorophenylcarbamoyl)pyrrolidin-3-yl methanesulfonate (33a) (136 mg, 0.179 mmol, 111% yield) which was used such for next step; $^1$H NMR (300 MHz, DMSO-d$_6$) δ 9.74 (s, 1H), 8.61 (s, 1H), 7.87-7.75 (m, 2H), 7.70 (dt, J=7.4, 1.4 Hz, 1H), 7.64-7.44 (m, 4H), 7.40-7.25 (m, 2H), 7.24-7.10 (m, 2H), 5.46 (s, 1H), 5.36 (d, J=6.6 Hz, 1H), 4.01-3.91 (m, 1H), 3.86 (m, 1H), 3.35 (m, 2H), 3.18 (s, 3H), 2.75-2.55 (m, 1H), 2.44-2.24 (m, 2H), 1.13 (s, 10H), 0.98-0.80 (m, 1H), 0.63 (s, 1H), 0.39-0.30 (m, 2H), 0.01−−0.14 (m, 2H); MS (ES+) 780.5, 782.4 (M+Na), (ES−) 792.5, 793.4 (M+Cl).

Step 2: Preparation of ((2R,4S)-4-azido-N1-(4-chlorophenyl)-N2-(5-((+)-1-(3-cyanophenyl)-3-cyclopropyl-1-((R)-1,1-dimethylethylsulfinamido)propyl)-2-fluorophenyl)pyrrolidine-1,2-dicarboxamide (33b)

To a stirred solution of 3R,5R)-1-(4-chlorophenylcarbamoyl)-5-(5-(1-(3-cyanophenyl)-3-cyclopropyl-1-((R)-1,1-dimethylethylsulfinamido)propyl)-2-fluorophenylcarbamoyl)pyrrolidin-3-yl methanesulfonate (33a) (120 mg, 0.158 mmol) in DMF (10 mL) was added sodium azide (41.1 mg, 0.633 mmol) and heated at 70° C. for 16 h.

The reaction was diluted with ethylacetate (100 mL), washed with water (2×25 mL), brine (25 mL), dried, filtered and concentrated in vacuum. The crude residue obtained was purified by flash column chromatography (silica gel, 12 g, eluting with CMA 80 In chloroform 0 to 100%) to afford ((2R,4S)-4-azido-N1-(4-chlorophenyl)-N2-(5-((+)-1-(3-cyanophenyl)-3-cyclopropyl-1-((R)-1,1-dimethylethylsulfinamido)propyl)-2-fluorophenyl)pyrrolidine-1,2-dicarboxamide (33b) (65 mg, 0.092 mmol, 58.2% yield) as a colorless solid; $^1$H NMR (300 MHz, DMSO-d$_6$) δ 9.92 (s, 1H), 8.60 (s, 1H), 7.97 (d, J=7.1 Hz, 1H), 7.77 (s, 1H), 7.74-7.67 (m, 1H), 7.62-7.44 (m, 3H), 7.31-7.25 (m, 2H), 7.24-7.16 (m, 1H), 7.12 (m, 1H), 5.51 (s, 1H), 4.70 (t, J=7.5 Hz, 1H), 4.45 (m, 1H), 3.77 (dd, J=11.0, 5.0 Hz, 1H), 3.62 (d, J=11.1 Hz, 1H), 2.44 (m, 2H), 2.41-2.22 (m, 1H), 2.16 (m, 1H), 1.12 (s, 11H), 0.97-0.80 (m, 1H), 0.70-0.53 (m, 1H), 0.39-0.27 (m, 2H), −0.01−−0.14 (m, 2H); 19F NMR (282 MHz, DMSO-d$_6$) δ −127.00; MS (ES+) 727.5, 729.5 (M+Na), (ES−) 739.5 (M+Cl); Optical rotation [α]$_D$=(+) 62.25 [0.71, MeOH].

Step 3: Preparation of (2R,4S)-4-amino-N1-(4-chlorophenyl)-N2-(5-((−)-1-(3-cyanophenyl)-3-cyclopropyl-1-((R)-1,1-dimethylethylsulfinamido)propyl)-2-fluorophenyl)pyrrolidine-1,2-dicarboxamide (33c)

Hydrogenation of ((2R,4S)-4-azido-N1-(4-chlorophenyl)-N2-(5-((+)-1-(3-cyanophenyl)-3-cyclopropyl-1-((R)-1,1-dimethylethylsulfinamido)propyl)-2-fluorophenyl)pyrrolidine-1,2-dicarboxamide (33b) (34 mg, 0.050 mmol) in ethanol (10 mL), using palladium on carbon 10% (9.05 mg, 8.51 µmol) as catalyst for 3 h according to procedure reported in step 2 of Scheme 13 gave (2R,4S)-4-amino-N1-(4-chlorophenyl)-N2-(5-((−)-1-(3-cyanophenyl)-3-cyclopropyl-1-((R)-1,1-dimethylethylsulfinamido)propyl)-2-fluorophenyl)pyrrolidine-1,2-dicarboxamide (33c) (34 mg, 0.050 mmol, 58.8% yield) as an off white solid; $^1$H NMR (300 MHz, DMSO-d$_6$) δ 9.81 (s, 1H), 8.43 (s, 1H), 7.91 (d, J=7.4 Hz, 1H), 7.78 (d, J=2.1 Hz, 1H), 7.75-7.68 (m, 1H), 7.64-7.44 (m, 4H), 7.35-7.24 (m, 2H), 7.23-7.06 (m, 1H), 5.51 (s, 1H), 4.65 (m, 1H), 3.81-3.70 (m, 1H), 3.69-3.55 (m, 1H), 3.23-3.10 (m, 1H), 2.80-2.40 (m, 4H), 2.06-1.73 (m, 3H), 1.12 (s, 10H), 0.99-0.78 (m, 1H), 0.71-0.54 (m, 1H), 0.43-0.25 (m, 2H), −0.00−−0.14 (m, 2H); 19F NMR (282 MHz, DMSO-d$_6$) δ −126.77; MS (ES+) 701.6, 703.5 (M+Na), (ES−) 713.5, 715.6 (M+Cl); Optical rotation [α]$_D$= (−) 5.07 [0.355, MeOH].

Step 4: Preparation of (2R,4S)-4-amino-N2-(5-((+)-1-amino-1-(3-cyanophenyl)-3-cyclopropylpropyl)-2-fluorophenyl)-N1-(4-chlorophenyl)pyrrolidine-1,2-dicarboxamide (33d)

Reaction of (2R,4S)-4-amino-N1-(4-chlorophenyl)-N2-(5-((−)-1-(3-cyanophenyl)-3-cyclopropyl-1-((R)-1,1-dimethylethylsulfinamido)propyl)-2-fluorophenyl)pyrrolidine-1,2-dicarboxamide (33c) (32 mg, 0.047 mmol) in ethanol (5 mL) using conc. HCl (0.039 mL, 0.471 mmol) as reported in step 6 of Scheme 4 gave after purification by flash column chromatography (silica gel, eluting with CMA-80 in chloroform 0 to 100%) (2R,4S)-4-amino-N2-(5-((+)-1-amino-1-(3-cyanophenyl)-3-cyclopropylpropyl)-2-fluorophenyl)-N1-(4-chlorophenyl)pyrrolidine-1,2-dicarboxamide (33d) (10 mg, 0.017 mmol, 36.9% yield) as a white solid; $^1$H NMR (300 MHz, DMSO-$d_6$) δ 9.76 (s, 1H), 8.44 (s, 1H), 7.92 (d, J=7.5 Hz, 1H), 7.86 (d, J=1.8 Hz, 1H), 7.69-7.40 (m, 4H), 7.30-7.25 (m, 2H), 7.13 (d, J=7.8 Hz, 2H), 4.64 (dd, J=8.3, 4.4 Hz, 1H), 3.74 (dd, J=9.4, 6.3 Hz, 1H), 3.62 (p, J=6.6 Hz, 1H), 3.17 (dd, J=9.4, 5.8 Hz, 1H), 2.43-2.31 (m, 5H), 2.22 (t, J=8.0 Hz, 2H), 2.10-1.87 (m, 2H), 1.11-0.91 (m, 2H), 0.71-0.54 (m, 1H), 0.40-0.26 (m, 2H), −0.00−−0.15 (m, 2H); $^{19}$F NMR (282 MHz, DMSO-$d_6$) δ −127.63; MS (ES+) 597.4, 599.8 (M+Na), (ES−) 609.5, 610.4 (M+Cl); Optical rotation $[α]_D$=(+) 136.0 [0.05, MeOH].

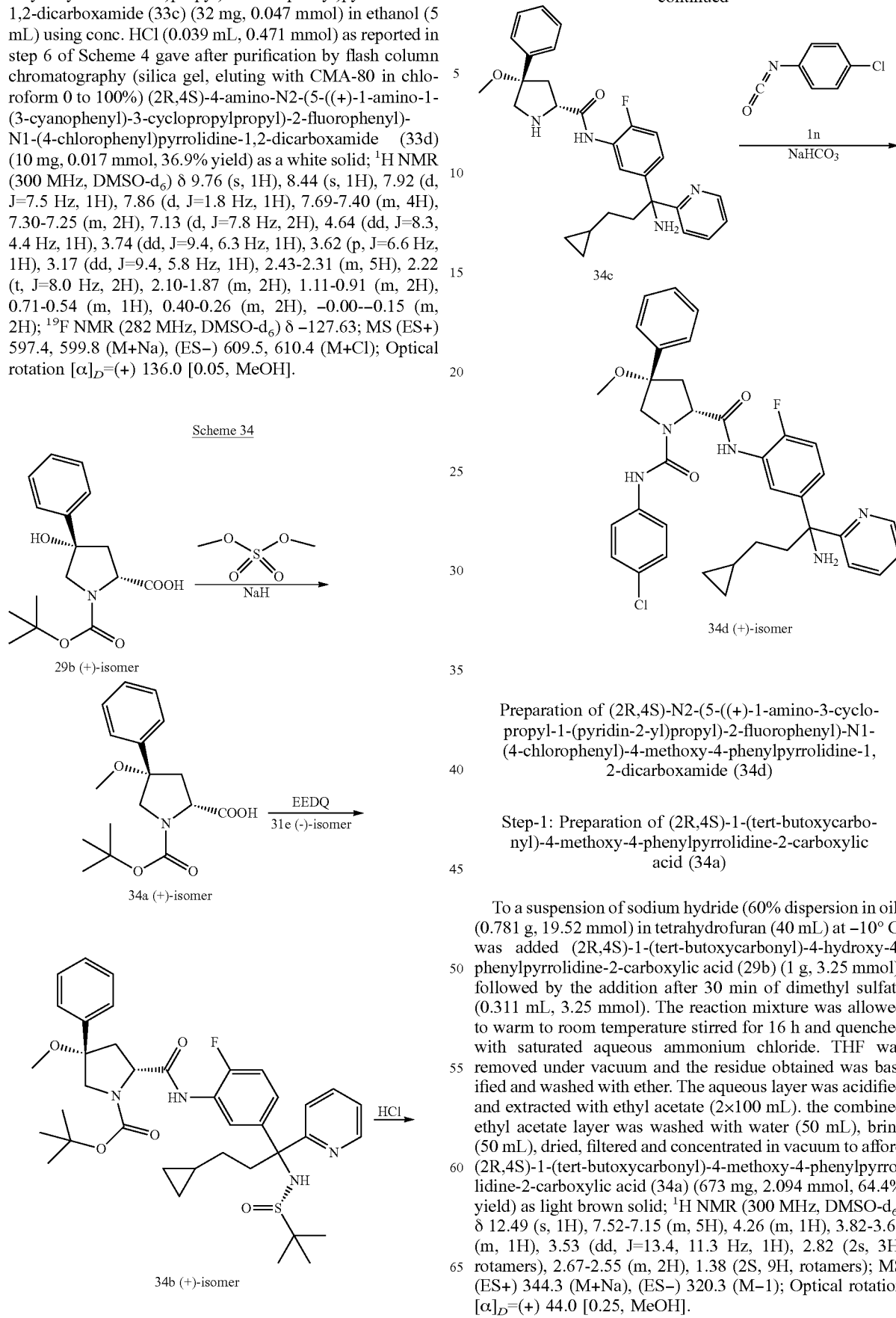

Preparation of (2R,4S)-N2-(5-((+)-1-amino-3-cyclopropyl-1-(pyridin-2-yl)propyl)-2-fluorophenyl)-N1-(4-chlorophenyl)-4-methoxy-4-phenylpyrrolidine-1,2-dicarboxamide (34d)

Step-1: Preparation of (2R,4S)-1-(tert-butoxycarbonyl)-4-methoxy-4-phenylpyrrolidine-2-carboxylic acid (34a)

To a suspension of sodium hydride (60% dispersion in oil) (0.781 g, 19.52 mmol) in tetrahydrofuran (40 mL) at −10° C. was added (2R,4S)-1-(tert-butoxycarbonyl)-4-hydroxy-4-phenylpyrrolidine-2-carboxylic acid (29b) (1 g, 3.25 mmol), followed by the addition after 30 min of dimethyl sulfate (0.311 mL, 3.25 mmol). The reaction mixture was allowed to warm to room temperature stirred for 16 h and quenched with saturated aqueous ammonium chloride. THF was removed under vacuum and the residue obtained was basified and washed with ether. The aqueous layer was acidified and extracted with ethyl acetate (2×100 mL). the combined ethyl acetate layer was washed with water (50 mL), brine (50 mL), dried, filtered and concentrated in vacuum to afford (2R,4S)-1-(tert-butoxycarbonyl)-4-methoxy-4-phenylpyrrolidine-2-carboxylic acid (34a) (673 mg, 2.094 mmol, 64.4% yield) as light brown solid; $^1$H NMR (300 MHz, DMSO-$d_6$) δ 12.49 (s, 1H), 7.52-7.15 (m, 5H), 4.26 (m, 1H), 3.82-3.65 (m, 1H), 3.53 (dd, J=13.4, 11.3 Hz, 1H), 2.82 (2s, 3H, rotamers), 2.67-2.55 (m, 2H), 1.38 (2S, 9H, rotamers); MS (ES+) 344.3 (M+Na), (ES−) 320.3 (M−1); Optical rotation $[α]_D$=(+) 44.0 [0.25, MeOH].

Step-2: Preparation of (2R,4S)-tert-butyl-2-(5-((+)-3-cyclopropyl-1-((S)-1,1-dimethylethylsulfinamido)-1-(pyridin-2-yl)propyl)-2-fluorophenylcarbamoyl)-4-methoxy-4-phenylpyrrolidine-1-carboxylate (34b)

Reaction of (2R,4S)-1-(tert-butoxycarbonyl)-4-methoxy-4-phenylpyrrolidine-2-carboxylic acid (34a) (111 mg, 0.347 mmol), (S)-N-((+)-1-(3-amino-4-fluorophenyl)-3-cyclopropyl-1-(pyridin-2-yl)propyl)-2-methylpropane-2-sulfinamide (31e) (86 mg, 0.347 mmol) in tetrahydrofuran (10 mL) using ethyl 2-ethoxyquinoline-1(2H)-carboxylate (127 mg, 0.513 mmol) using the reaction and workup conditions as reported in step 10 of Scheme 1 gave after purification by flash column chromatography (silica gel 25 g, eluting with CMA 80 in chloroform 0 to 100%) (2R,4S)-tert-butyl-2-(5-((+)-3-cyclopropyl-1-((S)-1,1-dimethylethylsulfinamido)-1-(pyridin-2-yl)propyl)-2-fluorophenylcarbamoyl)-4-methoxy-4-phenylpyrrolidine-1-carboxylate (34b) (141 mg, 0.203 mmol, 58.7% yield) as a solid; $^1$H NMR (300 MHz, DMSO-$d_6$) δ 9.66 (2s, 1H, rotamers), 8.73 (d, J=4.8 Hz, 1H), 8.36-8.12 (m, 1H), 7.94 (t, J=7.8 Hz, 1H), 7.60 (m, 4H), 7.52-7.19 (m, 4H), 6.34 (s, 1H), 4.57 (m, 1H), 3.96 (s, 2H), 3.02 (2s, 3H, rotamers), 2.95-2.73 (m, 3H), 2.74-2.53 (m, 2H), 1.52 (2s, 9H, rotamers), 1.31 (s, 9H), 1.24-0.94 (m, 1H), 0.88-0.66 (m, 2H), 0.57-0.43 (m, 2H), 0.30-−0.06 (m, 2H); $^{19}$F NMR (282 MHz, DMSO-$d_6$) δ −128.09, −129.22 (rotamers); MS (ES+) 693.7 (M+1), 715.7 (M+Na), (ES−) 691.7 (M−1), 727.7 (M+Cl); Optical rotation [α]$_D$=(+) 122.60 [0.075, MeOH].

Step-3: Preparation of (2R,4S)-N-(5-(1-amino-3-cyclopropyl-1-(pyridin-2-yl)propyl)-2-fluorophenyl)-4-methoxy-4-phenylpyrrolidine-2-carboxamide (34c)

Reaction of (2R,4S)-tert-butyl-2-(5-((+)-3-cyclopropyl-1-((S)-1,1-dimethylethylsulfinamido)-1-(pyridin-2-yl)propyl)-2-fluorophenylcarbamoyl)-4-methoxy-4-phenylpyrrolidine-1-carboxylate (34b) (131 mg, 0.189 mmol) in methanolic HCl (1.260 mL, 3.78 mmol) followed by workup and purification as reported in step 6 of Scheme 4 gave (2R,4S)-N-(5-(1-amino-3-cyclopropyl-1-(pyridin-2-yl)propyl)-2-fluorophenyl)-4-methoxy-4-phenylpyrrolidine-2-carboxamide (34c) (125 mg, 0.209 mmol, 111% yield) as a hydrochloride salt which was used directly as such in next step; MS (ES+) 511.5 (M+Na), (ES−) 523.5 (M+Cl).

Step-4: Preparation of (2R,4S)-N2-(5-((+)-1-amino-3-cyclopropyl-1-(pyridin-2-yl)propyl)-2-fluorophenyl)-N1-(4-chlorophenyl)-4-methoxy-4-phenylpyrrolidine-1,2-dicarboxamide (34d)

Reaction of (2R,4S)-N-(5-1-amino-3-cyclopropyl-1-(pyridin-2-yl)propyl)-2-fluorophenyl)-4-methoxy-4-phenylpyrrolidine-2-carboxamide (34c) (44 mg, 0.074 mmol) in dichloromethane (10 mL) with 4-chlorophenyl isocyanate (1n) (9.42 µL, 0.074 mmol) and sodium bicarbonate according to procedure reported in step 9 Scheme 1 gave after purification by flash column chromatography (silica gel, 12 g eluting with CMA 80 in chloroform) (2R,4S)-N2-(5-((+)-1-amino-3-cyclopropyl-1-(pyridin-2-yl)propyl)-2-fluorophenyl)-N1-(4-chlorophenyl)-4-methoxy-4-phenylpyrrolidine-1,2-dicarboxamide (34d) (36 mg, 0.056 mmol, 76% yield) as a white solid; $^1$H NMR (300 MHz, DMSO-$d_6$) δ 9.41 (s, 1H), 8.55 (s, 1H), 8.47 (m, 1H), 8.00-7.90 (m, 1H), 7.69 (d, J=1.9 Hz, 1H), 7.62-7.50 (m, 3H), 7.45 (d, J=5.0 Hz, 3H), 7.41-7.35 (m, 1H), 7.33-7.25 (m, 2H), 7.25-7.18 (m, 1H), 7.18-7.05 (m, 2H), 4.62 (t, J=6.0 Hz, 1H), 4.11 (d, J=10.4 Hz, 1H), 3.79 (d, J=10.5 Hz, 1H), 2.85 (s, 3H), 2.74-2.57 (m, 2H), 2.44-2.19 (m, 5H), 1.12-0.89 (m, 2H), 0.72-0.51 (m, 1H), 0.42-0.24 (m, 2H), −0.02-−0.14 (m, 2H); $^{19}$F NMR (282 MHz, DMSO-$d_6$) δ −129.42; MS (ES+) 664.5, 665.6 (M+Na), (ES−) 676.5 (M+Cl); Optical rotation [α]$_D$=(+) 89.0 [0.155, MeOH].

Scheme 35

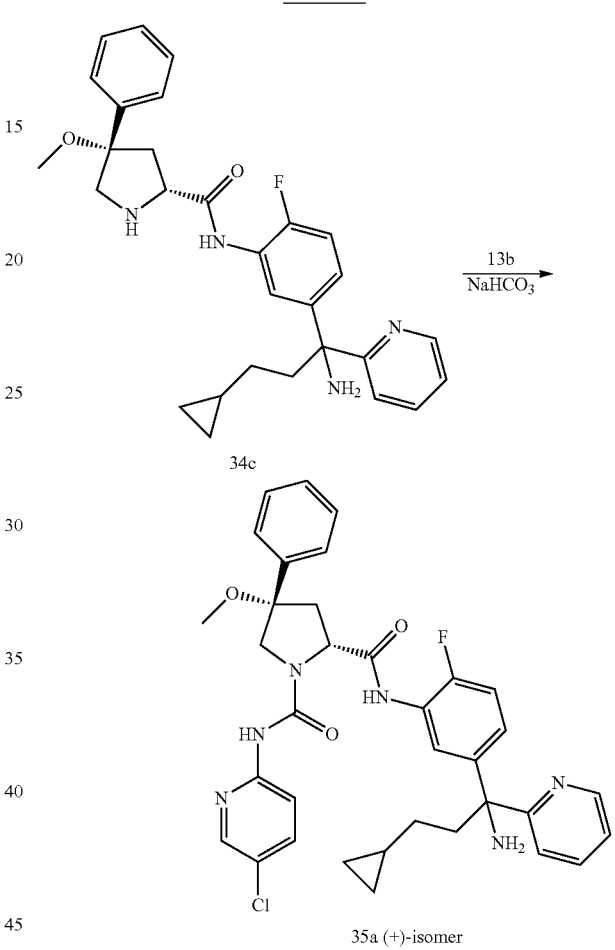

Preparation of (2R,4S)-N2-(5-((+)-1-amino-3-cyclopropyl-1-(pyridin-2-yl)propyl)-2-fluorophenyl)-N1-(5-chloropyridin-2-yl)-4-methoxy-4-phenylpyrrolidine-1,2-dicarboxamide Reaction of (2R,4S)-N-(5-1-amino-3-cyclopropyl-1-(pyridin-2-yl)propyl)-2-fluorophenyl)-4-methoxy-4-phenylpyrrolidine-2-carboxamide (34c) (50 mg, 0.084 mmol) in tetrahydrofuran (10 mL) with phenyl 5-chloropyridin-2-ylcarbamate (13b) (20.79 mg, 0.084 mmol) using sodium bicarbonate as base according to procedure reported in step 3 of Scheme 13 gave after purification by flash column chromatography (silica gel 12 g, eluting with 0-100% CMA-80 in chloroform) (2R,4S)-N2-(5-((+)-1-amino-3-cyclopropyl-1-(pyridin-2-yl)propyl)-2-fluorophenyl)-N1-(5-chloropyridin-2-yl)-4-methoxy-4-phenylpyrrolidine-1,2-dicarboxamide (35a) (36 mg, 0.056 mmol, 66.9% yield) as a white solid; $^1$H NMR (300 MHz, DMSO-$d_6$) δ 9.41 (s, 1H), 9.21 (s, 1H), 8.47 (dd, J=4.8, 1.9 Hz, 1H), 8.31 (d, J=2.6 Hz, 1H), 7.92 (m, 2H), 7.82 (dd, J=9.0, 2.7 Hz, 1H), 7.69 (td, J=7.7, 1.9 Hz, 1H), 7.54 (dt, J=8.1, 1.1 Hz, 1H), 7.43 (d, J=4.0 Hz, 4H), 7.37 (m, 1H), 7.22 (m, 1H), 7.19-7.04 (m, 2H), 4.64 (t, J=6.2 Hz, 1H), 4.24 (d, J=10.8 Hz, 1H), 3.89 (d, J=10.9 Hz, 1H), 2.84 (s, 3H), 2.61 (d, J=6.4 Hz, 2H), 2.43-2.24 (m, 4H), 1.12-0.95 (m, 2H), 0.68-0.53 (m, 1H), 0.38-0.26 (m, 2H), −0.02−−0.14 (m, 2H); $^{19}$F NMR (282 MHz, DMSO-$d_6$) δ −128.95; MS (ES+) 665.5 (M+Na), (ES−) 641.6, 642.3 (M−1); Optical rotation $[α]_D$=(+) 85.30 [0.075, MeOH].

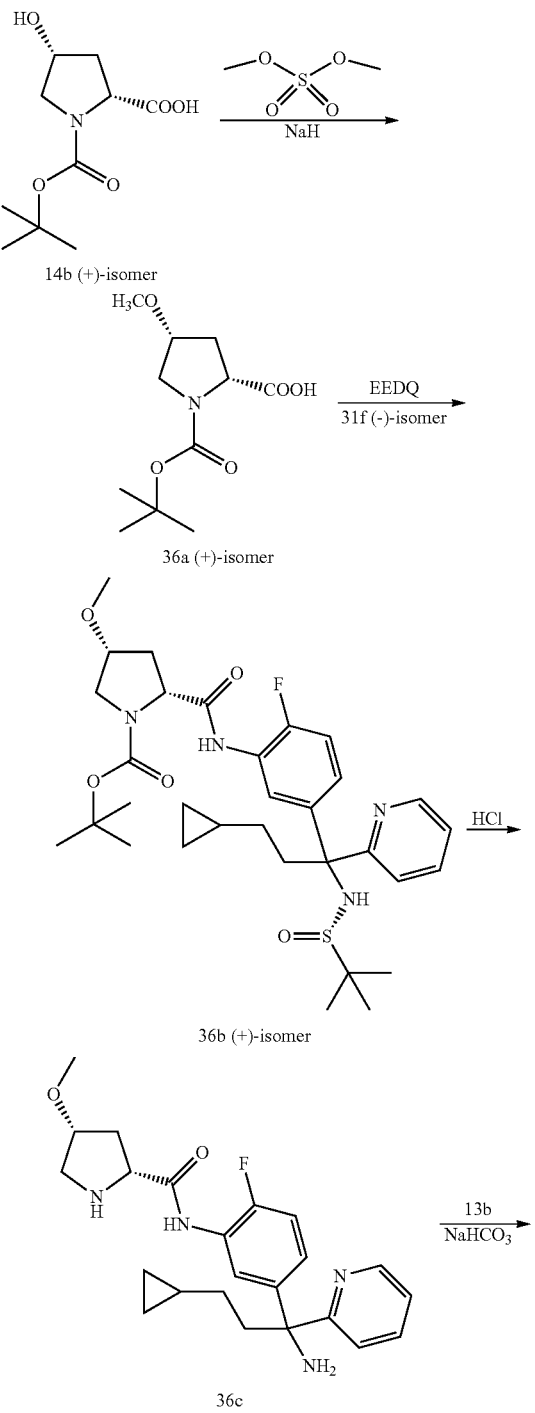

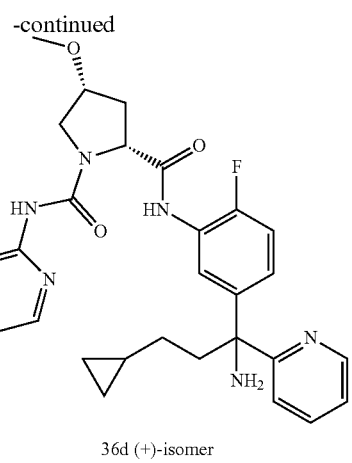

36d (+)-isomer

Preparation of (2R,4R)-N2-(5-((+)-1-amino-3-cyclopropyl-1-(pyridin-2-yl)propyl)-2-fluorophenyl)-N1-(5-chloropyridin-2-yl)-4-methoxypyrrolidine-1,2-dicarboxamide (36d)

Step-1: Preparation of (2R,4R)-1-(tert-butoxycarbonyl)-4-methoxypyrrolidine-2-carboxylic acid (36a)

Reaction of (2R,4R)-1-(tert-butoxycarbonyl)-4-hydroxypyrrolidine-2-carboxylic acid (14b) (6 g, 26 mmol) with NaH (6.24 g, 156 mmol; 60% suspension in oil) in THF (300 mL) and Dimethyl Sulfate (3.9 g, 31 mmol) according to the procedure reported in step 1 of Scheme 34 gave (2R,4R)-1-(tert-butoxycarbonyl)-4-methoxypyrrolidine-2-carboxylic acid (36a) (5.82 g, 91%) as a white solid; $^1$H NMR (300 MHz, DMSO-$d_6$) δ 4.14 (td, J=8.9, 3.7 Hz, 1H), 3.98-3.85 (m, 1H), 3.52 (m, 1H), 3.27-3.11 (m, 4H), 2.33 (m, 1H), 2.00 (dt, J=13.3, 3.8 Hz, 1H), 1.37 (2s, 9H); MS (ES+) 268.4 (M+Na), MS (ES−) 244.3 (M−1), 280.3 (M+Cl); Optical rotation $[α]_D$=(+) 45.28 [0.265, MeOH].

Step-2: Preparation of (2R,4R)-tert-butyl 2-(5-((+)-3-cyclopropyl-1-((S)-1,1-dimethylethylsulfinamido)-1-(pyridin-2-yl)propyl)-2-fluorophenylcarbamoyl)-4-methoxypyrrolidine-1-carboxylate (36b)

Reaction of (2R,4R)-1-(tert-butoxycarbonyl)-4-methoxypyrrolidine-2-carboxylic acid (36a) (95 mg, 0.388 mmol), (S)-N-((−)-1-(3-amino-4-fluorophenyl)-3-cyclopropyl-1-(pyridin-2-yl)propyl)-2-methylpropane-2-sulfinamide (31f) (151 mg, 0.388 mmol) in tetrahydrofuran (25 mL) using ethyl 2-ethoxyquinoline-1(2H)-carboxylate (96 mg, 0.388 mmol) using the reaction and workup conditions as reported in step 10 of Scheme 1 gave after purification by flash column chromatography (silica gel, eluting with CMA 80 in chloroform 0 to 100%) (2R,4R)-tert-butyl 2-(5-((+)-3-cyclopropyl-1-((S)-1,1-dimethylethylsulfinamido)-1-(pyridin-2-yl)propyl)-2-fluorophenylcarbamoyl)-4-methoxypyrrolidine-1-carboxylate (36b) (135 mg, 0.219 mmol, 56.5% yield) as a colorless solid; $^1$H NMR (300 MHz, DMSO-$d_6$) δ 9.43 (2s, 1H, rotamers), 8.61-8.45 (m, 1H), 7.89-7.66 (m, 2H), 7.33-7.23 (m, 2H), 7.15 (t, J=9.6 Hz, 1H), 7.06 (s, 1H), 5.91 (2s, 1H, rotamers), 4.39-4.17 (m, 1H), 4.01-3.91 (m, 1H), 3.56 (dd, J=11.0, 5.2 Hz, 1H), 3.21 (2s, 3H, rotamers), 2.70-2.52 (m, 2H), 2.50-2.37 (m, 1H), 2.16-1.86 (m, 1H), 1.34 (2s, 9H, rotamers), 1.14 (s, 10H), 1.11-0.94 (m, 1H), 0.97-0.79 (m, 1H), 0.71-0.54 (m, 1H), 0.42-0.26 (m, 2H), −0.01–−0.16 (m, 2H); ¹⁹F NMR (282 MHz, DMSO-$d_6$) δ −127.64, −128.92 rotamers; MS (ES+) 639.5 (M+Na), (ES−) 615.6 (M−1); Optical rotation $[α]_D$=(+) 11.42 [0.07, MeOH].

Step-3: Preparation of (2R,4R)-N-(5-(1-amino-3-cyclopropyl-1-(pyridin-2-yl)propyl)-2-fluorophenyl)-4-methoxypyrrolidine-2-carboxamide (36c)

Reaction of (2R,4R)-tert-butyl 2-(5-((+)-3-cyclopropyl-1-((S)-1,1-dimethylethylsulfinamido)-1-(pyridin-2-yl)propyl)-2-fluorophenylcarbamoyl)-4-methoxypyrrolidine-1-carboxylate (36b) (120 mg, 0.195 mmol) in 3N methanolic HCl (0.973 mL, 2.92 mmol) followed by workup and purification as reported in step 6 of Scheme 4 gave (2R,4R)-N-(5-(1-amino-3-cyclopropyl-1-(pyridin-2-yl)propyl)-2-fluorophenyl)-4-methoxypyrrolidine-2-carboxamide (36c) (100 mg, 0.192 mmol, 98% yield) hydrochloride salt which was used as such for next step; MS: (ES+) 413.5 (M+1), 435.5 (M+Na), (ES−) 447.5 (M+Cl).

Step-4: Preparation of (2R,4R)-N2-(5-((+)-1-amino-3-cyclopropyl-1-(pyridin-2-yl)propyl)-2-fluorophenyl)-N1-(5-chloropyridin-2-yl)-4-methoxypyrrolidine-1,2-dicarboxamide (36d)

Reaction of (2R,4R)-N-(5-(1-amino-3-cyclopropyl-1-(pyridin-2-yl)propyl)-2-fluorophenyl)-4-methoxypyrrolidine-2-carboxamide (36c) (95 mg, 0.182 mmol) in tetrahydrofuran (25 mL) with phenyl 5-chloropyridin-2-ylcarbamate (13b) (40.7 mg, 0.164 mmol) using sodium bicarbonate (306 mg, 3.64 mmol) as base according to procedure reported in step 3 of Scheme 13 gave after purification by flash column chromatography (2R,4R)-N2-(5-((+)-1-amino-3-cyclopropyl-1-(pyridin-2-yl)propyl)-2-fluorophenyl)-N1-(5-chloropyridin-2-yl)-4-methoxypyrrolidine-1,2-dicarboxamide (36d) (30 mg, 0.053 mmol, 29.1% yield) as a white solid; ¹H NMR (300 MHz, DMSO-$d_6$) δ 9.42 (s, 1H), 9.14 (s, 1H), 8.53-8.42 (m, 1H), 8.30 (d, J=2.6 Hz, 1H), 7.91 (dd, J=9.8, 2.5 Hz, 2H), 7.81 (dd, J=9.1, 2.6 Hz, 1H), 7.69 (td, J=7.7, 1.9 Hz, 1H), 7.53 (d, J=8.0 Hz, 1H), 7.17 (m, 2H), 7.08 (m, 1H), 4.57 (dd, J=9.1, 3.9 Hz, 1H), 4.12-3.98 (m, 1H), 3.81-3.61 (m, 2H), 3.22 (s, 3H), 2.45-2.23 (m, 5H), 2.10 (m, 1H), 1.11-0.93 (m, 2H), 0.69-0.53 (m, 1H), 0.39-0.23 (m, 2H), −0.05–−0.17 (m, 2H); ¹⁹F NMR (282 MHz, DMSO-$d_6$) δ −128.86; MS (ES+) 567.4, 569.4 (M+1), (ES−) 565.4, 567.4 (M−1); Optical rotation $[α]_D$=(+) 70.7 [0.065, MeOH].

Scheme 37

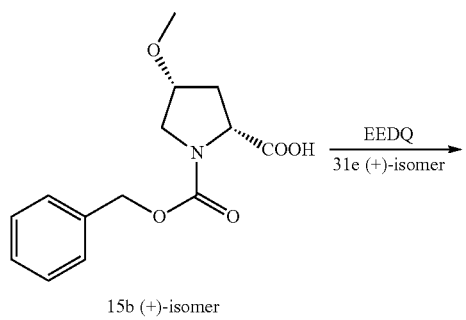

15b (+)-isomer

EEDQ
——————→
31e (+)-isomer

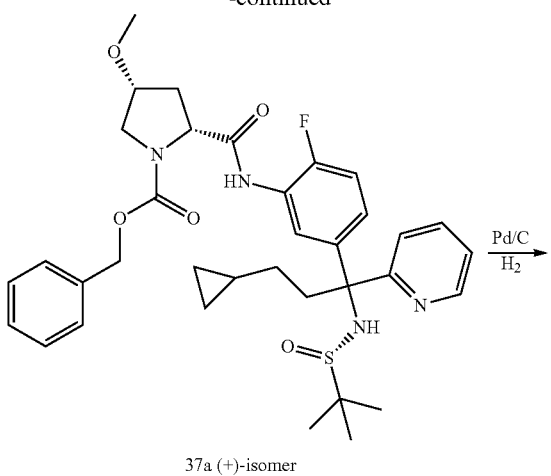

37a (+)-isomer

Pd/C
H₂
——→

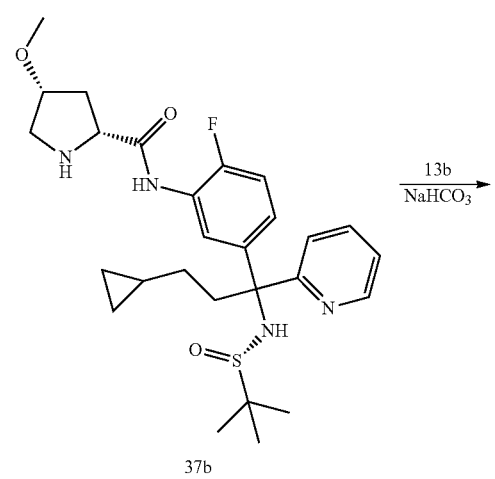

37b

13b
——————→
NaHCO₃

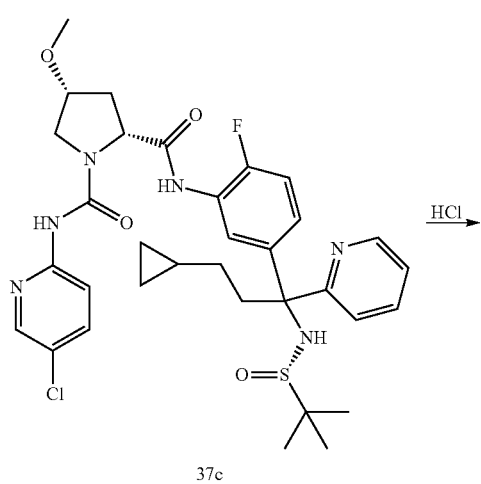

37c

HCl
——→

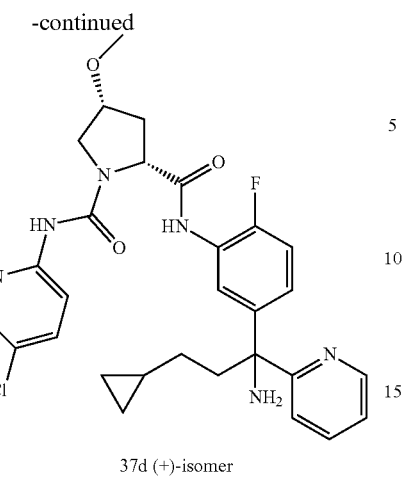

37d (+)-isomer

Preparation of (2R,4R)-N2-(5-((+)-1-amino-3-cyclopropyl-1-(pyridin-2-yl)propyl)-2-fluorophenyl)-N1-(5-chloropyridin-2-yl)-4-methoxypyrrolidine-1,2-dicarboxamide (37d)

Step-1: Preparation of benzyl (2R,4R)-2-((5-((+)-1-(((S)-tert-butylsulfinyl)amino)-3-cyclopropyl-1-(pyridin-2-yl)propyl)-2-fluorophenyl)carbamoyl)-4-methoxypyrrolidine-1-carboxylate (37a)

Reaction of (2R,4R)-1-(benzyloxycarbonyl)-4-methoxypyrrolidine-2-carboxylic acid (15b) (0.17 g, 0.6 mmol), (S)-N-((+)-1-(3-amino-4-fluorophenyl)-3-cyclopropyl-1-(pyridin-2-yl)propyl)-2-methylpropane-2-sulfinamide (31e) (0.2 g, 0.5 mmol) in tetrahydrofuran (5 mL) using ethyl 2-ethoxyquinoline-1(2H)-carboxylate (0.15 g, 0.6 mmol) using the reaction and workup conditions as reported in step 10 of Scheme 1 gave after purification by flash column chromatography benzyl (2R,4R)-2-((5-((+)-1-(((S)-tert-butylsulfinyl)amino)-3-cyclopropyl-1-(pyridin-2-yl)propyl)-2-fluorophenyl)carbamoyl)-4-methoxypyrrolidine-1-carboxylate (37a) (0.29 g, 86%) as a white solid; $^1$H NMR (300 MHz, DMSO-d$_6$) δ 9.54 (2s, 1H, rotamers), 8.58-8.50 (m, 1H), 7.97 (dd, J=7.6, 2.3 Hz, 1H), 7.74 (t, J=7.9 Hz, 1H), 7.37 (s, 2H), 7.31-6.99 (m, 7H), 6.16 (s, 1H), 5.16-4.91 (m, 2H), 4.51-4.34 (m, 1H), 4.05-3.91 (m, 1H), 3.74-3.58 (m, 1H), 3.47-3.37 (m, 1H), 3.19 (d, J=5.3 Hz, 3H), 2.58 (m, 2H), 1.09 (m, 9H, rotamers), 0.64-0.47 (m, 3H), 0.38-0.24 (m, 2H), −0.10--0.25 (m, 2H); MS (ES+) 651.6 (M+1), 673.5 (M+Na), MS (ES−) 685.6 (M+Cl); Optical rotation [α]$_D$=(+) 131.3 [0.23, MeOH].

Step 2: Preparation of (2R,4R)-N-(5-(1-(((S)-tert-butylsulfinyl)amino)-3-cyclopropyl-1-(pyridin-2-yl)propyl)-2-fluorophenyl)-4-methoxypyrrolidine-2-carboxamide (37b)

Debenzylation by hydrogenation of benzyl (2R,4R)-2-((5-((+)-1-(((S)-tert-butyl sulfinyl)amino)-3-cyclopropyl-1-(pyridin-2-yl)propyl)-2-fluorophenyl)carbamoyl)-4-methoxypyrrolidine-1-carboxylate (37a) (0.28 g, 0.43 mmol) in ethanol (20 mL), using palladium on carbon 10% as catalyst according to procedure reported in step 2 of Scheme 13 gave (2R,4R)-N-(5-(1-(((S)-tert-butylsulfinyl)amino)-3-cyclopropyl-1-(pyridin-2-yl)propyl)-2-fluorophenyl)-4-methoxypyrrolidine-2-carboxamide (37b) (0.21 g, 95% yield) as a gummy solid; $^1$H NMR (300 MHz, DMSO-d$_6$) δ 10.09 (s, 1H), 8.58-8.49 (m, 1H), 8.32 (dd, J=7.8, 2.3 Hz, 1H), 7.74 (td, J=7.8, 1.8 Hz, 1H), 7.31-7.14 (m, 2H), 7.11 (d, J=8.1 Hz, 2H), 7.04-6.96 (m, 1H), 6.14 (s, 1H), 3.91-3.75 (m, 1H), 3.74 (d, J=7.2 Hz, 1H), 3.04-2.98 (m, 1H), 2.90 (d, J=10.7 Hz, 1H), 2.66-2.54 (m, 5H), 2.18-1.95 (m, 2H), 1.08 (s, 9H), 0.68-0.46 (m, 3H), 0.31 (m, 2H), −0.10--0.25 (m, 2H); MS (ES+) 516.5 (M+1), 539.5 (M+Na), MS (ES−) 515.5 (M−1).

Step 3: Preparation of (2R,4R)-N2-(5-(1-(((S)-tert-butylsulfinyl)amino)-3-cyclopropyl-1-(pyridin-2-yl)propyl)-2-fluorophenyl)-N1-(5-chloropyridin-2-yl)-4-methoxypyrrolidine-1,2-dicarboxamide (37c)

Reaction of (2R,4R)-N-(5-(1-(((S)-tert-butylsulfinyl)amino)-3-cyclopropyl-1-(pyridin-2-yl)propyl)-2-fluorophenyl)-4-methoxypyrrolidine-2-carboxamide (37b) (0.1 g, 0.19 mmol) in THF (5 mL) with phenyl 5-chloropyridin-2-ylcarbamate (13b) (0.06 g, 0.23 mmol) using TEA (50 μL) as base according to procedure reported in step 3 of Scheme 13 gave after purification by flash column chromatography (2R,4R)-N2-(5-(1-(((S)-tert-butyl sulfinyl)amino)-3-cyclopropyl-1-(pyridin-2-yl)propyl)-2-fluorophenyl)-N1-(5-chloropyridin-2-yl)-4-methoxypyrrolidine-1,2-dicarboxamide (37c) (0.11 g, 84%) as a white solid; $^1$H NMR (300 MHz, DMSO-d$_6$) δ 9.50 (s, 1H), 9.15 (s, 1H), 8.53 (dd, J=4.9, 1.8, Hz, 1H), 8.29 (d, J=2.6 Hz, 1H), 7.96 (dd, J=7.6, 2.3 Hz, 1H), 7.89 (d, J=9.0 Hz, 1H), 7.81 (dd, J=9.0, 2.6 Hz, 1H), 7.73 (td, J=7.8, 1.8 Hz, 1H), 7.26 (m, 1H), 7.22-7.07 (m, 2H), 7.10-6.99 (m, 1H), 6.14 (s, 1H), 4.58 (dd, J=9.1, 3.9 Hz, 1H), 4.03 (d, J=4.3 Hz, 1H), 3.72 (m, 2H), 3.21 (s, 3H), 2.63-2.52 (m, 2H), 2.45-2.27 (m, 1H), 2.08 (m, 1H), 1.09 (s, 9H), 0.90-0.78 (m, 2H), 0.64-0.46 (m, 1H), 0.36-0.23 (m, 2H), −0.19 (m, 2H); MS (ES+) 671.5 (M+1), 693.5 (M+Na), MS (ES−) 669.5 (M−1), 705.5 (M+Cl).

Step 4: Preparation of (2R,4R)-N2-(5-((+)-1-amino-3-cyclopropyl-1-(pyridin-2-yl)propyl)-2-fluorophenyl)-N1-(5-chloropyridin-2-yl)-4-methoxypyrrolidine-1,2-dicarboxamide (37d)

Reaction of (2R,4R)-N2-(5-(1-(((S)-tert-butyl sulfinyl)amino)-3-cyclopropyl-1-(pyridin-2-yl)propyl)-2-fluorophenyl)-N1-(5-chloropyridin-2-yl)-4-methoxypyrrolidine-1,2-dicarboxamide (37c) (0.1 g, 0.15 mmol) in ethanol (5 mL) using conc. HCl (0.12 mL) as reported in step 6 of Scheme 4 gave after purification by flash column chromatography (2R,4R)-N2-(5-((+)-1-amino-3-cyclopropyl-1-(pyridin-2-yl)propyl)-2-fluorophenyl)-N1-(5-chloropyridin-2-yl)-4-methoxypyrrolidine-1,2-dicarboxamide (37d) (50 mg, 60% yield) as a white solid; $^1$H NMR (300 MHz, DMSO-d$_6$) δ 9.40 (d, J=1.4 Hz, 1H), 9.13 (s, 1H), 8.47 (ddd, J=4.9, 1.8, 0.9 Hz, 1H), 8.30 (dd, J=2.6, 0.8 Hz, 1H), 7.90 (dd, J=8.2, 1.5 Hz, 2H), 7.81 (dd, J=9.0, 2.6 Hz, 1H), 7.69 (td, J=7.7, 1.9 Hz, 1H), 7.53 (dt, J=8.1, 1.1 Hz, 1H), 7.23-7.03 (m, 3H), 4.56 (dd, J=9.2, 3.9 Hz, 1H), 4.11-3.96 (m, 1H), 3.81-3.64 (m, 2H), 3.21 (s, 3H), 2.43-2.20 (m, 4H), 2.09 (m, 1H), 1.02 (m, 2H), 0.71-0.54 (m, 1H), 0.40-0.30 (m, 2H), −0.08 (m, 2H); $^{19}$F NMR (282 MHz, DMSO-d$_6$) δ −128.01; MS (ES+) 567.5 (M+1), (ES−) 603.5 (M+Cl); Optical rotation [α]$_D$= (+) 70.7 [0.065, MeOH].

Scheme 38

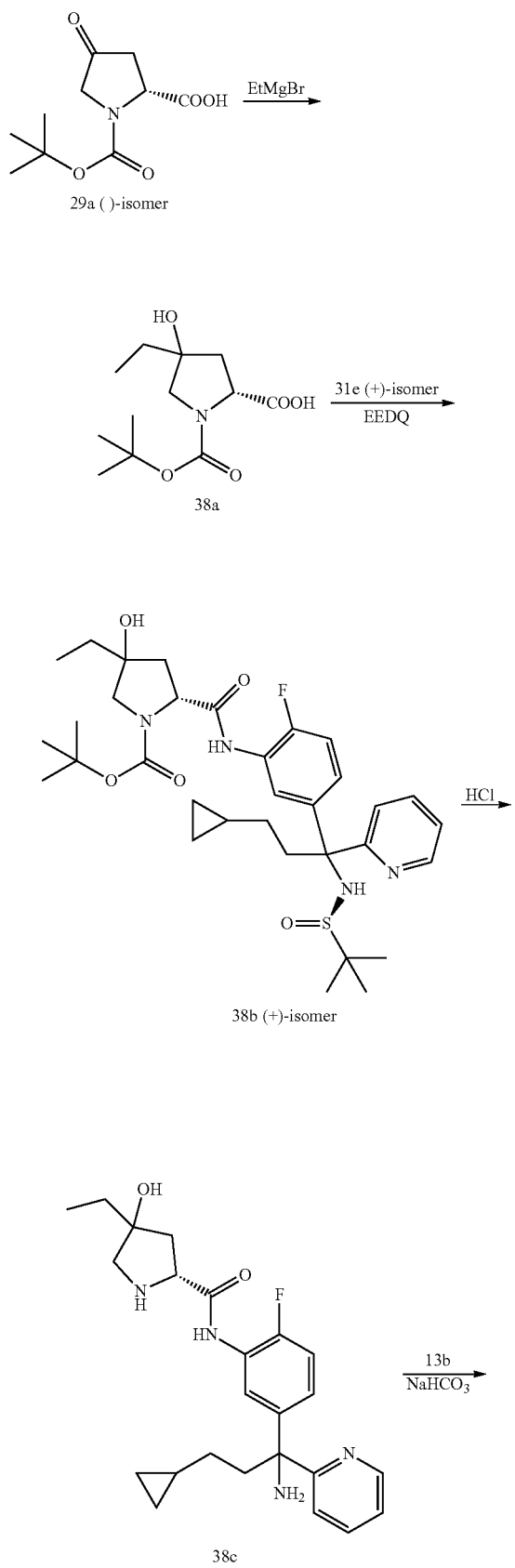

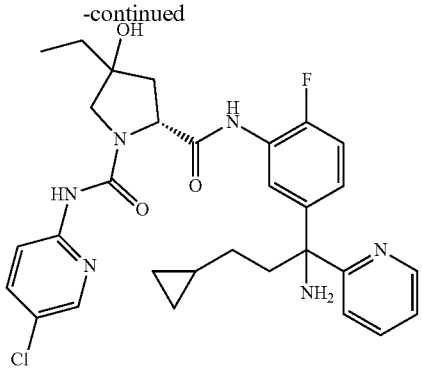

38d (+)-isomer

Preparation of (2R)-N2-(5-((+)-1-amino-3-cyclopropyl-1-(pyridin-2-yl)propyl)-2-fluorophenyl)-N1-(5-chloropyridin-2-yl)-4-ethyl-4-hydroxypyrrolidine-1,2-dicarboxamide (38d)

Step 1: Preparation of (2R)-1-(tert-butoxycarbonyl)-4-ethyl-4-hydroxypyrrolidine-2-carboxylic acid (38a)

Reaction of (R)-1-(tert-butoxycarbonyl)-4-oxopyrrolidine-2-carboxylic acid (29a) (0.502 g, 2.19 mmol) in THF (20 mL) with 1.0M solution of ethylmagnesiumbromide (6.02 mL, 6.02 mmol) using the reaction and workup conditions as reported in step 2 of Scheme 29 gave (2R)-1-(tert-butoxycarbonyl)-4-ethyl-4-hydroxypyrrolidine-2-carboxylic acid (38a) (330 mg, 1.273 mmol, 58.1% yield) as an oil which was used as such for next step; MS (ES+) 282.4 (M+Na), 541.6 (2M+Na), (ES−) 258.3 (M−1), 517.6 (2M−1).

Step 2: Preparation of (2R)-tert-butyl 2-(5-((+)-3-cyclopropyl-1-((S)-1,1-dimethylethylsulfinamido)-1-(pyridin-2-yl)propyl)-2-fluorophenylcarbamoyl)-4-ethyl-4-hydroxypyrrolidine-1-carboxylate (38b)

Reaction of (2R)-1-(tert-butoxycarbonyl)-4-ethyl-4-hydroxypyrrolidine-2-carboxylic acid (38a) (300 mg, 1.157 mmol), (S)-N-((+)-1-(3-amino-4-fluorophenyl)-3-cyclopropyl-1-(pyridin-2-yl)propyl)-2-methylpropane-2-sulfinamide (31e) (451 mg, 1.157 mmol) in tetrahydrofuran (25 mL) using ethyl 2-ethoxyquinoline-1(2H)-carboxylate (402 mg, 1.627 mmol) using the reaction and workup conditions as reported in step 10 of Scheme 1 gave after purification by flash column chromatography (2R)-tert-butyl 2-(5-((+)-3-cyclopropyl-1-((S)-1,1-dimethylethylsulfinamido)-1-(pyridin-2-yl)propyl)-2-fluorophenylcarbamoyl)-4-ethyl-4-hydroxypyrrolidine-1-carboxylate (38b) (97 mg, 0.154 mmol, 13.29% yield) as a white solid; 1H NMR (300 MHz, DMSO-$d_6$) δ 9.68 (2s, 1H, rotamers), 8.69-8.46 (m, 1H), 8.11 (2dd, 1H, rotamers), 7.74 (m, 1H), 7.41-6.95 (m, 3H), 6.14 (d, J=6.5 Hz, 1H), 5.08 (2s, 1H, rotamers), 4.41-4.21 (m, 1H), 3.30-3.17 (m, 1H), 2.67-2.54 (m, 4H), 2.32-2.11 (m, 1H), 1.98-1.80 (m, 1H), 1.52 (m, 2H), 1.31 (2s, 9H, rotamers), 1.10 (s, 9H), 0.88 (t, J=7.4 Hz, 3H), 0.57 (m, 3H), 0.38-0.26 (m, 2H), 0.05--0.28 (m, 2H); 19F NMR (282 MHz, DMSO-$d_6$) δ −128.40, −129.65 rotamers; MS (ES+) 631.7 (M+1), 653.7 (M+Na), (ES−) 629.7 (M−1), 665.7 (M+Cl); Optical rotation $[α]_D$=(+) 100.0 [0.07, MeOH].

Step 3: Preparation of (2R)-N-(5-(1-amino-3-cyclopropyl-1-(pyridin-2-yl)propyl)-2-fluorophenyl)-4-ethyl-4-hydroxypyrrolidine-2-carboxamide (38c)

Reaction of (2R)-tert-butyl 2-(5-((+)-3-cyclopropyl-1-((S)-1,1-dimethylethylsulfinamido)-1-(pyridin-2-yl)propyl)-2-fluorophenylcarbamoyl)-4-ethyl-4-hydroxypyrrolidine-1-carboxylate (38b) (87 mg, 0.138 mmol) in methanol (20 mL) using 3N methanolic HCl (0.919 mL, 2.76 mmol) using the reaction and workup conditions as reported in step 6 of Scheme 4 gave (2R)-N-(5-(1-amino-3-cyclopropyl-1-(pyridin-2-yl)propyl)-2-fluorophenyl)-4-ethyl-4-hydroxypyrrolidine-2-carboxamide (38c) (69 mg, 0.138 mmol, 100% yield) as a hydrochloride salt, which was used as such in next step without any further purification; MS (ES+) 449.4 (M+Na), (ES−) 461.2 (M+Cl).

Step 4: Preparation of (2R)-N2-(5-((+)-1-amino-3-cyclopropyl-1-(pyridin-2-yl)propyl)-2-fluorophenyl)-N1-(5-chloropyridin-2-yl)-4-ethyl-4-hydroxypyrrolidine-1,2-dicarboxamide (38d)

Reaction of (2R)-N-(5-(1-amino-3-cyclopropyl-1-(pyridin-2-yl)propyl)-2-fluorophenyl)-4-ethyl-4-hydroxypyrrolidine-2-carboxamide (38c) (65 mg, 0.130 mmol) in tetrahydrofuran (25 mL) with phenyl 5-chloropyridin-2-ylcarbamate (29.1 mg, 0.117 mmol) using sodium bicarbonate as base according to procedure reported in step 3 of Scheme 13 gave after purification by flash column chromatography (silica gel 12 g, eluting with 0-100% CMA-80 in chloroform) (2R)-N2-(5-((+)-1-amino-3-cyclopropyl-1-(pyridin-2-yl)propyl)-2-fluorophenyl)-N1-(5-chloropyridin-2-yl)-4-ethyl-4-hydroxypyrrolidine-1,2-dicarboxamide (38d) (28 mg, 0.048 mmol, 37.0% yield) as a white solid; $^1$H NMR (300 MHz, DMSO-d$_6$) δ 9.68 (s, 1H), 9.13 (s, 1H), 8.47 (dd, J=4.7, 1.9 Hz, 1H), 8.29 (d, J=2.6 Hz, 1H), 8.08 (dd, J=7.8, 2.3 Hz, 1H), 7.89 (d, J=9.1 Hz, 1H), 7.80 (dd, J=9.0, 2.6 Hz, 1H), 7.70 (m, 1H), 7.53 (m, 1H), 7.25-7.03 (m, 3H), 5.77 (s, 1H), 5.11 (s, 1H), 4.63-4.45 (m, 1H), 3.64 (d, J=10.3 Hz, 1H), 3.48 (d, J=10.4 Hz, 1H), 2.42-2.15 (m, 4H), 2.01-1.89 (m, 1H), 1.56 (q, J=7.4 Hz, 2H), 1.12-0.97 (m, 2H), 0.92 (t, J=7.3 Hz, 3H), 0.71-0.52 (m, 1H), 0.40-0.26 (m, 2H), −0.02−−0.14 (m, 2H); $^{19}$F NMR (282 MHz, DMSO-d6) δ −129.61; MS (ES+) 581.4 (M+1), 604.5, 606.4 (M+Na), (ES−) 579.4, 581.5 (M−1), 615.5, 616.5 (M+Cl); Optical rotation [α]$_D$=(+) 67.37 [0.19, MeOH].

Scheme 39

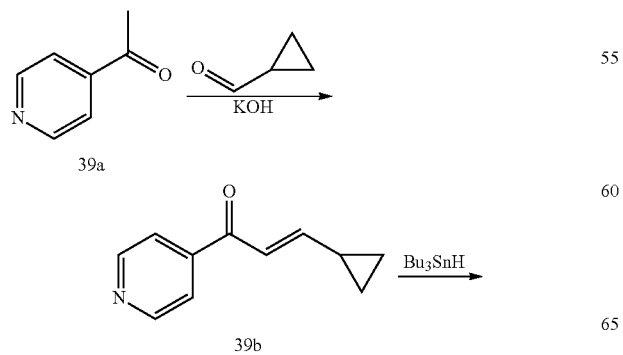

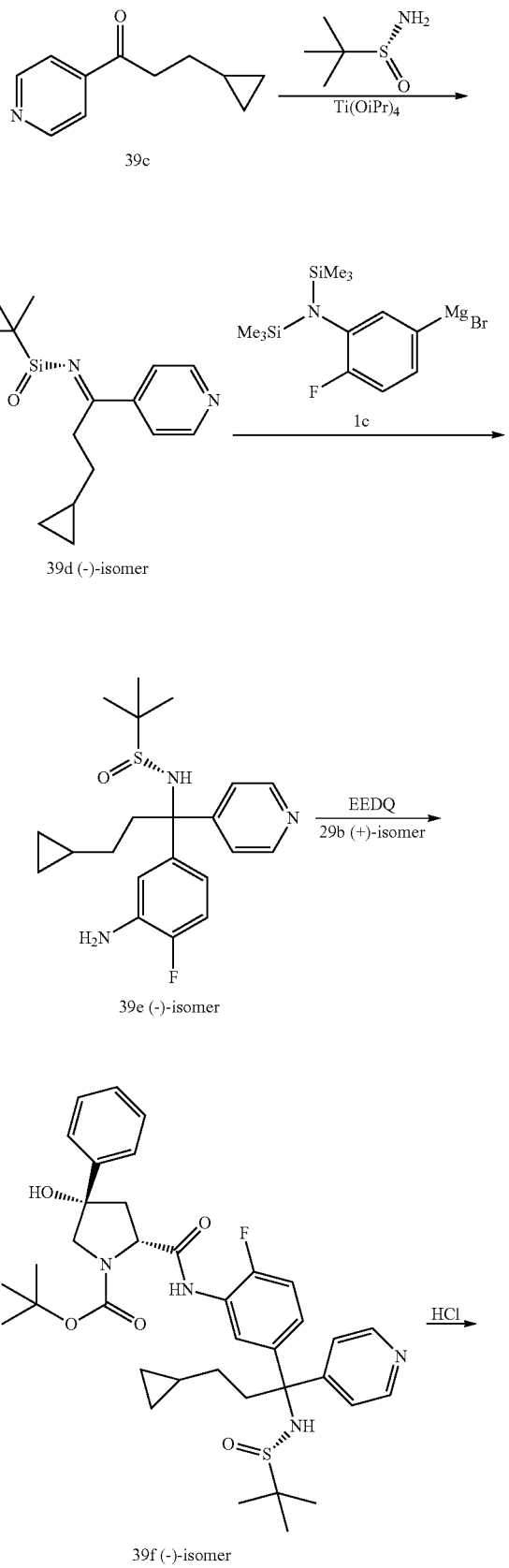

-continued

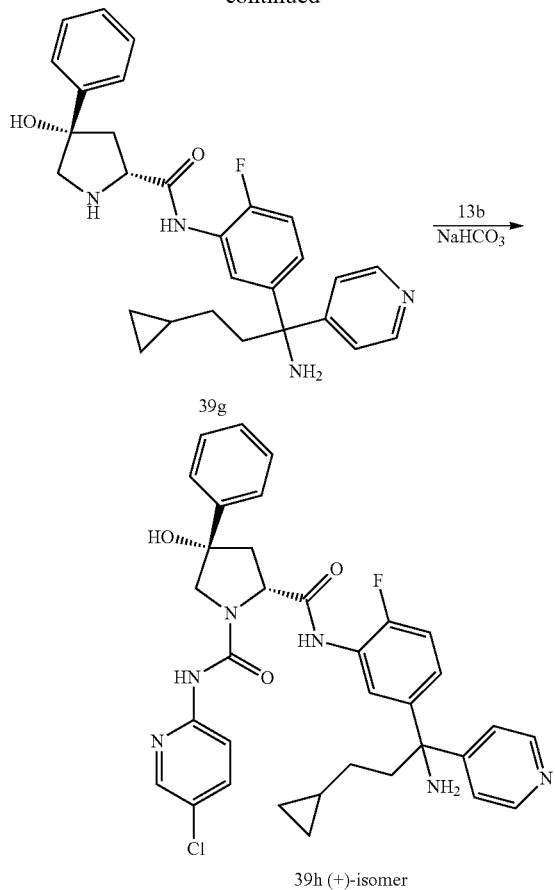

39g 39h (+)-isomer

Preparation of (2R,4S)-N2-(5-((+)-1-amino-3-cyclopropyl-1-(pyridin-4-yl)propyl)-2-fluorophenyl)-N1-(5-chloropyridin-2-yl)-4-hydroxy-4-phenylpyrrolidine-1,2-dicarboxamide (39h)

Step-1 Preparation of (E)-3-cyclopropyl-1-(pyridin-4-yl)prop-2-en-1-one (39b)

Reaction of 1-(pyridin-4-yl)ethanone (39a) (1.516 mL, 13.27 mmol) in methanol (100 mL) with cyclopropanecarboxaldehyde (1.5 mL, 19.90 mmol) and aqueous potassium hydroxide (1N, 2.65 mL, 2.65 mmol) using the reaction and workup procedure as reported in Scheme 31 step 1 gave (E)-3-cyclopropyl-1-(pyridin-4-yl)prop-2-en-1-one (39b) (479 mg, 20.85%); $^1$H NMR (300 MHz, DMSO-d$_6$) δ 8.89-8.59 (m, 2H), 7.91-7.71 (m, 2H), 7.19 (d, J=15.1 Hz, 1H), 6.58 (dd, J=15.1, 10.4 Hz, 1H), 1.88-1.71 (m, 1H), 1.10-0.96 (m, 2H), 0.87-0.72 (m, 2H).

Step-2: Preparation of 3-cyclopropyl-1-(pyridin-2-yl)propan-1-one (39c)

Reaction of (E)-3-cyclopropyl-1-(pyridin-4-yl)prop-2-en-1-one (39b) (18.35 g, 106 mmol) in acetonitrile (180 mL) and tributylstannane (60.0 mL, 216 mmol) using the procedure reported in step 2 of Scheme 31 gave after purification by flash column chromatography (silica gel, eluting with 0-30% ethyl acetate in hexane) 3-cyclopropyl-1-(pyridin-4-yl)propan-1-one (39c) (3.028 g, 15%) as an oil; $^1$H NMR (300 MHz, DMSO-d$_6$) δ 3.14 (t, J=7.2 Hz, 2H), 1.52 (q, J=7.1 Hz, 2H), 0.75 (dddd, J=12.0, 8.1, 7.0, 2.8 Hz, 1H), 0.47-0.28 (m, 2H), 0.14-0.02 (m, 2H).

Step-3: Preparation of (−)-N-(3-cyclopropyl-1-(pyridin-4-yl)propylidene)-2-methylpropane-2-sulfinamide (39d)

Compound (39d) was prepared from 3-cyclopropyl-1-(pyridin-4-yl)propan-1-one (39c) (1.8 g, 10.27 mmol) and (R)-2-methylpropane-2-sulfinamide (1.566 g, 12.84 mmol) using procedure as reported in step 3 of scheme 31 to afford (−)-N-(3-cyclopropyl-1-(pyridin-4-yl)propylidene)-2-methylpropane-2-sulfinamide (39d) (1.838 g, 6.57 mmol, 63.9% yield) as a yellow syrup; $^1$H NMR (300 MHz, DMSO-d$_6$) δ 8.76-8.69 (m, 2H), 7.80-7.73 (m, 2H), 3.49-3.15 (m, 2H), 1.45 (q, J=7.4 Hz, 2H), 1.24 (s, 9H), 0.84-0.65 (m, 1H), 0.43-0.30 (m, 2H), 0.10--0.03 (m, 2H); MS (ES+) 301.3, (M+Na); (ES−) 277.3 (M−1); Optical Rotation [α]$_D$=(−) 27.61 [0.355, MeOH].

Step-4: Preparation of (R)-N-((−)-1-(3-amino-4-fluorophenyl)-3-cyclopropyl-1-(pyridin-4-yl)propyl)-2-methylpropane-2-sulfinamide (39e)

Compound (39e) was prepared from (−)-N-(3-cyclopropyl-1-(pyridin-4-yl)propylidene)-2-methylpropane-2-sulfinamide (39d) (1.7 g, 6.11 mmol), using procedure as reported in step 4 of scheme 31 to afford (R)-N-((−)-1-(3-amino-4-fluorophenyl)-3-cyclopropyl-1-(pyridin-4-yl)propyl)-2-methylpropane-2-sulfinamide (39e) (1.443 g, 3.7 mmol, 60.7% yield) as a white solid; $^1$H NMR (300 MHz, DMSO-d$_6$) δ 8.77-8.68 (m, 2H), 7.62-7.53 (m, 2H), 7.15 (dd, J=11.3, 8.5 Hz, 1H), 7.00-6.94 (m, 1H), 6.77-6.70 (m, 1H), 5.50 (s, 1H), 5.35 (s, 2H), 2.90-2.60 (m, 2H), 1.47-1.27 (m, 1H), 1.38 (s, 9H), 1.25-1.05 (m, 1H), 0.97-0.80 (m, 1H), 0.65-0.55 (m, 2H), 0.32-0.10 (m, 2H); $^{19}$F NMR (282 MHz, DMSO-d$_6$) −137.30; MS (ES+): 390.4 (M+1); Chiral purity checked by performing chiral HPLC using chiral AD-H column, 1 mL/min, Solvent: 90% Hexane, 10% EtOH, 0.1% TEA, UV=260 nM, 25° C. (>99.99 ee); Optical Rotation [α]$_D$=(−) 78.49 [0.265, MeOH].

Step-5: Preparation of (2R,4S)-tert-butyl 2-(5-((−)-3-cyclopropyl-1-((R)-1,1-dimethylethylsulfinamido)-1-(pyridin-4-yl)propyl)-2-fluorophenylcarbamoyl)-4-hydroxy-4-phenylpyrrolidine-1-carboxylate (39f)

Compound 39f was prepared from (2R,4S)-1-(tert-butoxycarbonyl)-4-hydroxy-4-phenylpyrrolidine-2-carboxylic acid (29b) (225 mg, 0.732 mmol), (R)-N-((−)-1-(3-amino-4-fluorophenyl)-3-cyclopropyl-1-(pyridin-4-yl)propyl)-2-methylpropane-2-sulfinamide (39e) and ethyl 2-ethoxyquinoline-1(2H)-carboxylate (181 mg, 0.732 mmol) using the reaction and workup conditions as reported in step 10 of Scheme 1 to afford (2R,4S)-tert-butyl 2-(5-((−)-3-cyclopropyl-1-((R)-1,1-dimethylethylsulfinamido)-1-(pyridin-4-yl)propyl)-2-fluorophenylcarbamoyl)-4-hydroxy-4-phenylpyrrolidine-1-carboxylate (39f) (235 mg, 0.346 mmol, 47.3% yield) as a white solid; $^1$H NMR (300 MHz, DMSO-d$_6$) δ 9.78 (d, J=93.3 Hz, 1H), 8.59-8.47 (m, 2H), 8.32 (s, 1H), 8.29-8.06 (m, 1H), 7.51 (dt, J=6.6, 1.4 Hz, 2H), 7.43-7.07 (m, 6H), 5.99 (2s, 1H, rotamers), 5.51 (m, 1H), 4.44 (m, 1H), 3.68 (m, 2H), 2.78-2.51 (m, 2H), 2.35-2.15 (m, 1H), 1.33 (2s, 9H, rotamers), 1.15 (s, 10H), 0.92 (m, 2H), 0.73-0.57 (m, 1H), 0.42-0.30 (m, 2H), 0.00--0.13 (m, 2H); $^{19}$F NMR (282 MHz, DMSO-d$_6$) δ −128.66, −130.04 (rotamers); MS (ES+) 679.5 (M+1), 701.5 (M+Na), (ES−) 677.5 (M−1), 713.5 (M+Cl); Optical Rotation [α]$_D$=(−) 55.55 [0.18, MeOH].

Step-6: Preparation of (2R,4S)-N-(5-(1-amino-3-cyclopropyl-1-(pyridin-4-yl)propyl)-2-fluorophenyl)-4-hydroxy-4-phenylpyrrolidine-2-carboxamide (39g)

Reaction of (2R,4S)-tert-butyl 2-(5-((−)-3-cyclopropyl-1-((R)-1,1-dimethylethylsulfinamido)-1-(pyridin-4-yl)propyl)-2-fluorophenylcarbamoyl)-4-hydroxy-4-phenylpyrrolidine-1-carboxylate (39f) (200 mg, 0.295 mmol) in methanol (10 mL) with hydrochloric acid (1.964 mL, 5.89 mmol) gave after workup and purification as reported in step 6 of Scheme 4 (2R,4S)-N-(5-(1-amino-3-cyclopropyl-1-(pyridin-4-yl)propyl)-2-fluorophenyl)-4-hydroxy-4-phenylpyrrolidine-2-carboxamide (39g) (169 mg, 0.289 mmol, 98% yield) as a hydrochloride salt which was used as such for next step; MS (ES−) 509.4 (M+Cl).

Step-7: (2R,4S)-N2-(5-((+)-1-amino-3-cyclopropyl-1-(pyridin-4-yl)propyl)-2-fluorophenyl)-N1-(5-chloropyridin-2-yl)-4-hydroxy-4-phenylpyrrolidine-1,2-dicarboxamide (39h)

Reaction of (2R,4S)-N-(5-(1-amino-3-cyclopropyl-1-(pyridin-4-yl)propyl)-2-fluorophenyl)-4-hydroxy-4-phenylpyrrolidine-2-carboxamide (39g) (160 mg, 0.274 mmol) in tetrahydrofuran (25 mL) with phenyl 5-chloropyridin-2-ylcarbamate (13b) (61.3 mg, 0.247 mmol) using sodium bicarbonate as base according to procedure reported in step 3 of Scheme 13 gave after purification by flash column chromatography (2R,4S)-N2-(5-((+)-1-amino-3-cyclopropyl-1-(pyridin-4-yl)propyl)-2-fluorophenyl)-N1-(5-chloropyridin-2-yl)-4-hydroxy-4-phenylpyrrolidine-1,2-dicarboxamide (98 mg, 0.156 mmol, 56.9% yield) as a white solid; $^1$H NMR (300 MHz, DMSO-d$_6$) δ 9.74 (s, 1H), 9.25 (s, 1H), 8.47-8.41 (m, 2H), 8.30 (d, J=2.4 Hz, 1H), 8.12 (d, J=7.6 Hz, 1H), 7.91 (d, J=9.0 Hz, 1H), 7.81 (dd, J=8.9, 2.6 Hz, 1H), 7.54 (dt, J=6.5, 1.3 Hz, 2H), 7.41-7.33 (m, 4H), 7.33-7.25 (m, 1H), 7.15 (dd, J=7.3, 1.7 Hz, 2H), 5.95 (s, 1H), 4.80-4.65 (m, 1H), 4.00 (d, J=10.5 Hz, 1H), 3.90 (d, J=10.4 Hz, 1H), 2.68 (dd, J=13.1, 9.6 Hz, 1H), 2.31 (m, 3H), 2.21 (t, J=8.1 Hz, 2H), 1.12-0.96 (m, 2H), 0.70-0.53 (m, 1H), 0.45-0.26 (m, 2H), −0.01−−0.14 (m, 2H); $^{19}$F NMR (282 MHz, DMSO-d$_6$) δ −129.43; MS (ES+) 629.4 (M+1), 651.4, 653.4 (M+Na), (ES−) 627.4, 629.4 (M−1); Optical Rotation [α]$_D$= (+) 7.209 [0.265, MeOH]; Analysis calculated for C$_{34}$H$_{34}$ClFN$_6$O$_3$·0.5H$_2$O; C, 63.99; H, 5.53; N, 13.17. Found: C, 64.02; H, 5.63; N, 12.86.

Scheme 40

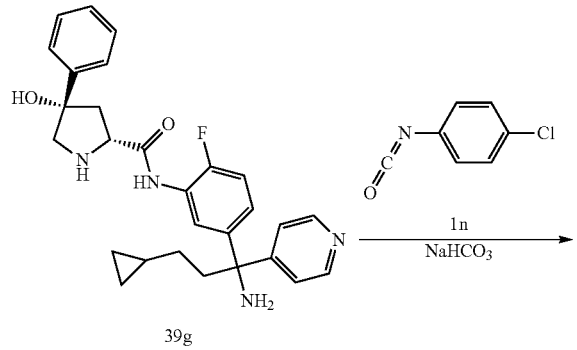

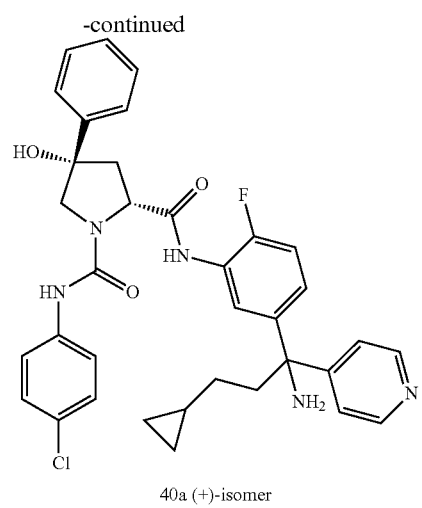

40a (+)-isomer

Preparation of (2R,4S)-N2-(5-((+)-1-amino-3-cyclopropyl-1-(pyridin-4-yl)propyl)-2-fluorophenyl)-N1-(4-chlorophenyl)-4-hydroxy-4-phenylpyrrolidine-1,2-dicarboxamide (40a)

Reaction of (2R,4S)-N-(5-(1-amino-3-cyclopropyl-1-(pyridin-4-yl)propyl)-2-fluorophenyl)-4-hydroxy-4-phenylpyrrolidine-2-carboxamide (39g) (250 mg, 0.428 mmol) in dichloromethane (20 mL) with 4-chlorophenyl isocyanate (1n) (0.049 mL, 0.385 mmol) and sodium bicarbonate (719 mg, 8.56 mmol) according to procedure reported in step 9 Scheme 1 gave after purification by flash column chromatography (silica gel, 12 g eluting with CMA 80 in chloroform) (2R,4S)-N2-(5-((+)-1-amino-3-cyclopropyl-1-(pyridin-4-yl)propyl)-2-fluorophenyl)-N1-(4-chlorophenyl)-4-hydroxy-4-phenylpyrrolidine-1,2-dicarboxamide (40a) (134 mg, 0.213 mmol, 49.8% yield) as an off white solid; $^1$H NMR (300 MHz, DMSO-d$_6$) δ 9.69 (s, 1H), 8.53 (s, 1H), 8.49-8.37 (m, 2H), 8.16 (d, J=7.8 Hz, 1H), 7.61-7.53 (m, 4H), 7.43-7.34 (m, 4H), 7.33-7.25 (m, 3H), 7.17 (s, 1H), 7.14 (d, J=1.3 Hz, 1H), 5.97 (s, 1H), 4.68 (dd, J=9.7, 2.7 Hz, 1H), 3.93 (d, J=10.1 Hz, 1H), 3.83 (d, J=10.0 Hz, 1H), 2.72 (dd, J=13.1, 9.8 Hz, 1H), 2.39-2.10 (m, 5H), 1.12-0.97 (m, 2H), 0.73-0.56 (m, 1H), 0.43-0.28 (m, 2H), −0.00−−0.10 (m, 2H); $^{19}$F NMR (282 MHz, DMSO-d$_6$) δ −129.82; MS (ES−), 626.5, 628.5 (M−1); Analysis calculated for C$_{35}$H$_{35}$ClFN$_5$O$_3$·0.5H$_2$O: C, 65.98; H, 5.70; N, 10.99. Found: C, 65.94; H, 5.86; N, 10.69; Optical Rotation [α]$_D$=(+) 65.14 [0.175, MeOH].

Scheme 41

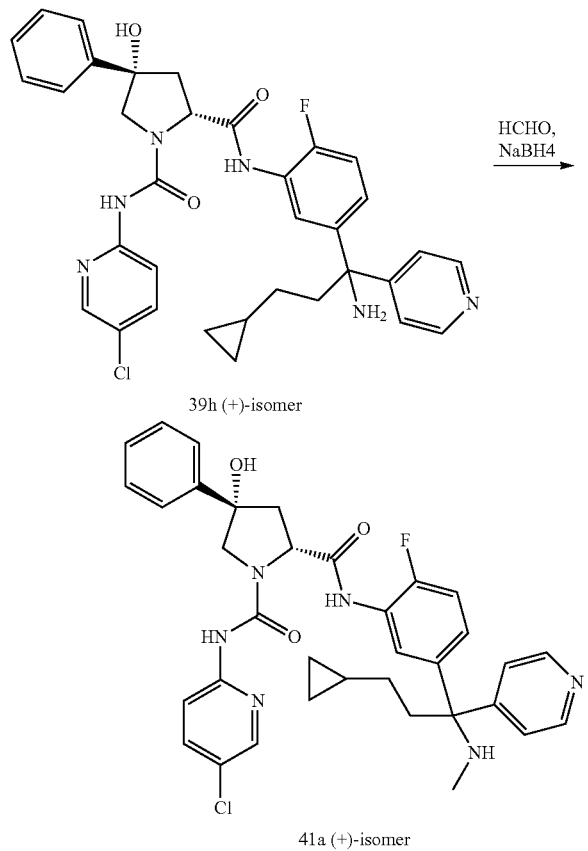

39h (+)-isomer 41a (+)-isomer

Preparation of (2R,4S)-N1-(5-chloropyridin-2-yl)-N2-(5-((+)-3-cyclopropyl-1-(methylamino)-1-(pyridin-4-yl)propyl)-2-fluorophenyl)-4-hydroxy-4-phenylpyrrolidine-1,2-dicarboxamide (41a)

To a solution of (2R,4S)-N2-(5-((+)-1-amino-3-cyclopropyl-1-(pyridin-4-yl)propyl)-2-fluorophenyl)-N1-(5-chloropyridin-2-yl)-4-hydroxy-4-phenylpyrrolidine-1,2-dicarboxamide (39h) (100 mg, 0.159 mmol) in methanol (10 mL) was added acetic acid (1 drop) paraformaldehyde (23.86 mg, 0.795 mmol), sodium borohydride (30.1 mg, 0.795 mmol) and stirred at room temperature for 8 h. Additional paraformaldehyde (23.86 mg, 0.795 mmol) and sodium borohydride (30.1 mg, 0.795 mmol) was added to the reaction and stirred at room temperature overnight. The reaction was concentrated in vacuum and the residue obtained was purified by flash column chromatography (silica gel, 12 g eluting with CMA 80 in chloroform) to afford ((2R,4S)-N1-(5-chloropyridin-2-yl)-N2-(5-((+)-3-cyclopropyl-1-(methylamino)-1-(pyridin-4-yl)propyl)-2-fluorophenyl)-4-hydroxy-4-phenylpyrrolidine-1,2-dicarboxamide (41a) (74 mg, 0.115 mmol, 72.4% yield) free base as a white solid; $^1$H NMR (300 MHz, DMSO-$d_6$) δ 9.73 (s, 1H), 9.25 (s, 1H), 8.50-8.41 (m, 2H), 8.34-8.27 (m, 1H), 8.10 (d, J=7.1 Hz, 1H), 7.91 (dd, J=9.1, 0.8 Hz, 1H), 7.82 (dd, J=9.0, 2.7 Hz, 1H), 7.59-7.48 (m, 2H), 7.43-7.34 (m, 3H), 7.35-7.26 (m, 2H), 7.16 (dd, J=10.5, 8.8 Hz, 1H), 7.11-7.00 (m, 1H), 5.94 (s, 1H), 4.71 (d, J=7.5 Hz, 1H), 4.10-3.85 (m, 2H), 2.75-2.63 (m, 1H), 2.25 (m, 3H), 1.94 (s, 4H, N-Me and NH), 1.05-0.74 (m, 2H), 0.70-0.56 (m, 1H), 0.40-0.24 (m, 2H), −0.06-−0.18 (m, 2H); $^{19}$F NMR (282 MHz, DMSO-$d_6$) δ −129.21; MS (ES+) 643.3 (M+1), 665.3, 667.3 (M+Na), (ES−) 641.4, 643.3 (M−1). The free base of compound 41a (100 mg, 0.159 mmol) was converted to HCl salt in methanol (10 mL) using conc. HCl (0.101 mL, 0.303 mmol) to afford on freeze drying (2R,4S)-N1-(5-chloropyridin-2-yl)-N2-(5-((+)-3-cyclopropyl-1-(methylamino)-1-(pyridin-4-yl)propyl)-2-fluorophenyl)-4-hydroxy-4-phenylpyrrolidine-1,2-dicarboxamide (41a) (64 mg, 0.089 mmol, 88% yield) as a white powder; $^1$H NMR (300 MHz, DMSO-$d_6$) δ 10.31 (s, 2H), 9.96 (s, 1H), 9.29 (s, 1H), 8.80 (d, J=5.3 Hz, 2H), 8.31 (d, J=2.5 Hz, 1H), 8.17 (d, J=6.7 Hz, 1H), 7.95-7.77 (m, 2H), 7.66 (d, J=5.3 Hz, 2H), 7.53 (d, J=7.6 Hz, 2H), 7.49-7.17 (m, 5H), 4.87-4.58 (m, 1H), 4.11-3.84 (m, 2H), 2.78-2.54 (m, 3H), 2.47-2.13 (m, 6H), 1.19-0.98 (m, 1H), 0.96-0.77 (m, 1H), 0.76-0.61 (m, 1H), 0.45-0.30 (m, 2H), −0.00-−0.10 (m, 2H); $^{19}$F NMR (282 MHz, DMSO-$d_6$) δ −124.81; MS (ES+) 665.4, 667.4 (M+Na), (ES−) 641.5, 643.5 (M−1), 677.3, 679.4 (M+Cl); Optical Rotation [α]$_D$=(+) 6.0 [0.19, MeOH].

Scheme 42

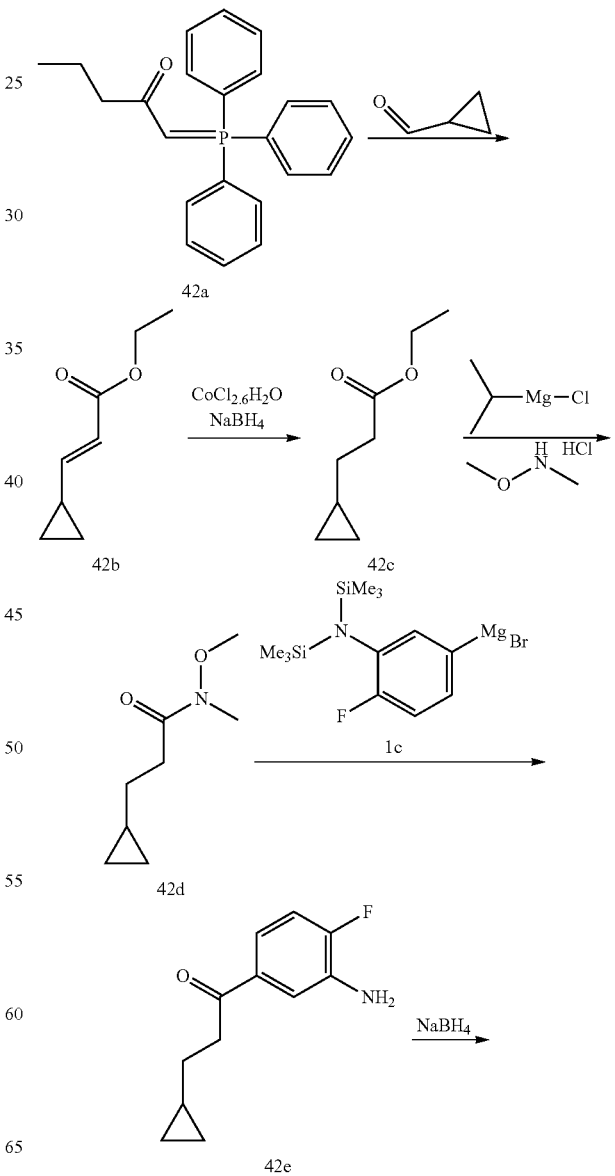

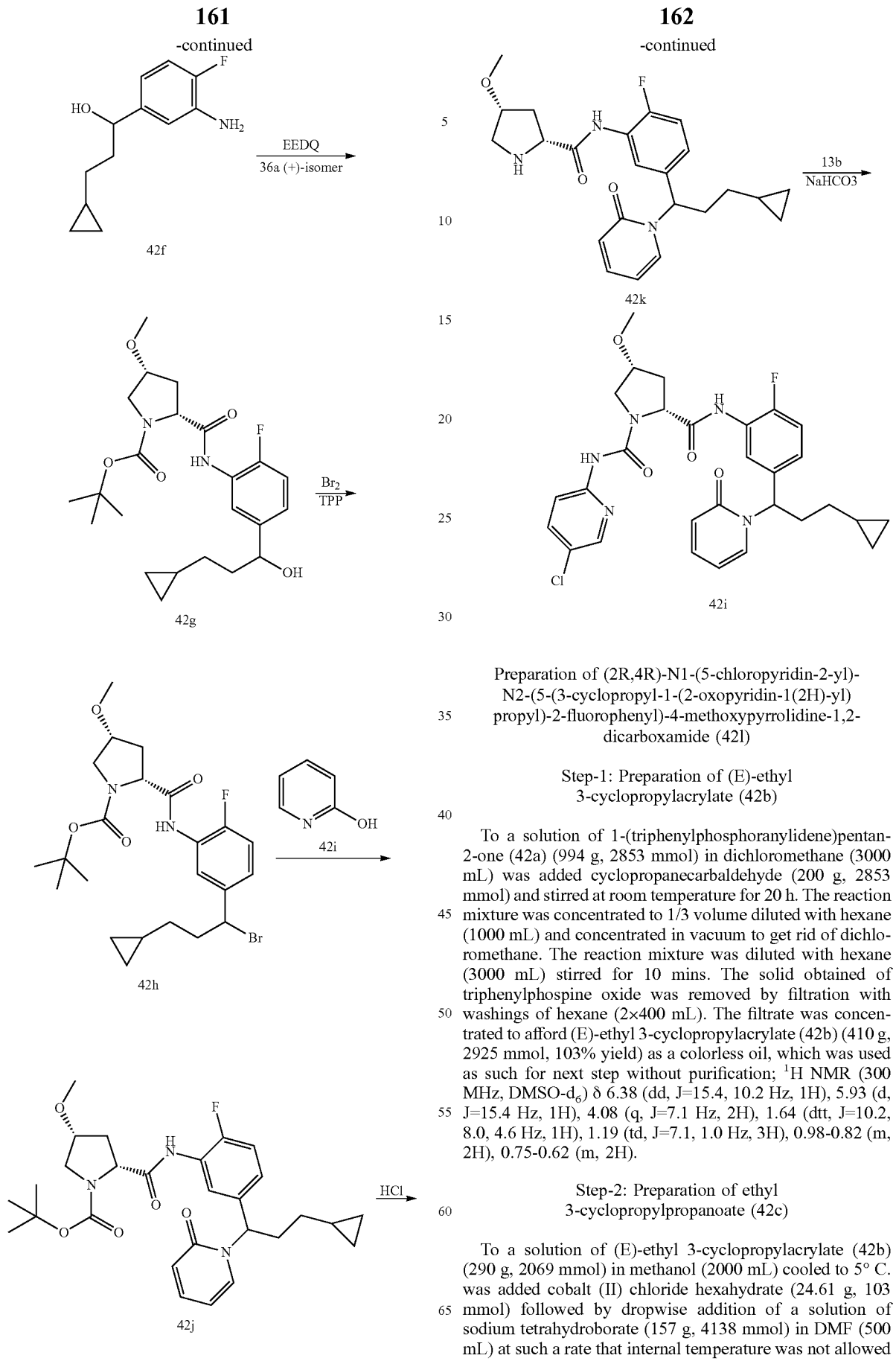

Preparation of (2R,4R)-N1-(5-chloropyridin-2-yl)-N2-(5-(3-cyclopropyl-1-(2-oxopyridin-1(2H)-yl)propyl)-2-fluorophenyl)-4-methoxypyrrolidine-1,2-dicarboxamide (42l)

Step-1: Preparation of (E)-ethyl 3-cyclopropylacrylate (42b)

To a solution of 1-(triphenylphosphoranylidene)pentan-2-one (42a) (994 g, 2853 mmol) in dichloromethane (3000 mL) was added cyclopropanecarbaldehyde (200 g, 2853 mmol) and stirred at room temperature for 20 h. The reaction mixture was concentrated to 1/3 volume diluted with hexane (1000 mL) and concentrated in vacuum to get rid of dichloromethane. The reaction mixture was diluted with hexane (3000 mL) stirred for 10 mins. The solid obtained of triphenylphospine oxide was removed by filtration with washings of hexane (2×400 mL). The filtrate was concentrated to afford (E)-ethyl 3-cyclopropylacrylate (42b) (410 g, 2925 mmol, 103% yield) as a colorless oil, which was used as such for next step without purification; $^1$H NMR (300 MHz, DMSO-d$_6$) δ 6.38 (dd, J=15.4, 10.2 Hz, 1H), 5.93 (d, J=15.4 Hz, 1H), 4.08 (q, J=7.1 Hz, 2H), 1.64 (dtt, J=10.2, 8.0, 4.6 Hz, 1H), 1.19 (td, J=7.1, 1.0 Hz, 3H), 0.98-0.82 (m, 2H), 0.75-0.62 (m, 2H).

Step-2: Preparation of ethyl 3-cyclopropylpropanoate (42c)

To a solution of (E)-ethyl 3-cyclopropylacrylate (42b) (290 g, 2069 mmol) in methanol (2000 mL) cooled to 5° C. was added cobalt (II) chloride hexahydrate (24.61 g, 103 mmol) followed by dropwise addition of a solution of sodium tetrahydroborate (157 g, 4138 mmol) in DMF (500 mL) at such a rate that internal temperature was not allowed to raise above 10° C. The reaction mixture was stirred for 1 h at 5° C., poured into water (5000 mL) and stirred for 15 mins. The resultant black suspended solution was filtered over celite pad, pad, washed with dichloromethane (3×800 mL). The aqueous layer was separated and extracted with dichloromethane (2×600 mL). The dichloromethane layers were combined washed with water (2×1500 mL), brine, dried over MgSO$_4$, filtered and concentrated under vacuum with bath temperature below 40° C. to afford ethyl 3-cyclopropylpropanoate (42c) (260 g, 88% yield) as colorless liquid; $^1$H NMR (300 MHz, DMSO-d$_6$) δ 4.03 (q, J=7.1 Hz, 2H), 2.33 (t, J=7.3 Hz, 2H), 1.41 (q, J=7.2 Hz, 2H), 1.16 (t, J=7.1 Hz, 3H), 0.75-0.59 (m, 1H), 0.40-0.31 (m, 2H), 0.06--0.06 (m, 2H).

Step-3: Preparation of 3-cyclopropyl-N-methoxy-N-methylpropanamide (42d)

To a solution of ethyl 3-cyclopropylpropanoate (42c) (260 g, 1828 mmol) in THF (2000 mL) cooled to −10° C. was added N,O-dimethylhydroxylamine hydrochloride (268 g, 2743 mmol), followed by drop-wise addition of isopropylmagnesiumchloride (2743 mL, 5485 mmol, 2M in THF). The mixture was stirred at −10° C. for 2 h, quenched with sat. NH$_4$Cl solution (4000 mL) and allowed to warm to room temperature. The THF layer was separated and aqueous layer was extracted with EtOAc (2×1000 mL). The organic layers were combined washed with brine, dried over MgSO$_4$, filtered and concentrated in vacuum to afford 3-cyclopropyl-N-methoxy-N-methylpropanamide (42d) (240 g, 1527 mmol, 83% yield) as an orange liquid; $^1$H NMR (300 MHz, DMSO-d$_6$) δ 3.66 (s, 3H), 3.07 (s, 3H), 2.44 (t, J=7.6 Hz, 2H), 1.39 (q, J=7.3 Hz, 2H), 0.76-0.62 (m, 1H), 0.42-0.31 (m, 2H), 0.08--0.09 (m, 2H).

Step-4: Preparation of 1-(3-amino-4-fluorophenyl)-3-cyclopropylpropan-1-one (42e)

To a solution of 3-cyclopropyl-N-methoxy-N-methylpropanamide (42d) (240 g, 1527 mmol) in THF (2000 mL) cooled to 5° C. was added drop-wise a freshly prepared solution of (3-(bis(trimethylsilyl)amino)-4-fluorophenyl) magnesium bromide (1c) (1908 mL, 1527 mmol, 1M in THF) maintaining internal temperature around 5° C. during addition. The reaction was stirred at 5° C. for 2 h, quenched with 3N HCl (1000 mL) and stirred for 2 h. The mixture was basified with solid NaHCO$_3$ and extracted with ethyl acetate (2×500 mL). The combined organic layers were washed with brine, dried over MgSO$_4$, filtered and concentrated in vacuum to afford crude 42e. The crude material was dissolved isopropanol (150 mL) and stirred over night. The solid obtained was collected by filtration, washed with isopropanol and dried to afford 1-(3-amino-4-fluorophenyl)-3-cyclopropylpropan-1-one (42e) (90 g, 28.46% first crop) as a white solid. The filtrate was concentrated, kept at room temperature for 6 h and the solid obtained was collected by filtration to afford 1-(3-amino-4-fluorophenyl)-3-cyclopropylpropan-1-one (42e) (50 g, 15.81%, second crop) as a white solid; $^1$H NMR (300 MHz, DMSO-d$_6$) δ 7.38 (dd, J=8.9, 2.2 Hz, 1H), 7.18 (ddd, J=8.4, 4.7, 2.2 Hz, 1H), 7.09 (dd, J=11.1, 8.4 Hz, 1H), 5.41 (s, 2H), 2.98 (t, J=7.3 Hz, 2H), 1.48 (q, J=7.2 Hz, 2H), 0.82-0.65 (m, 1H), 0.41-0.33 (m, 2H), 0.10--0.02 (m, 2H); MS (ES+) 208.2 (M+1), (ES−) 206.2 (M−1); $^{19}$F NMR (282 MHz, DMSO-d$_6$) δ −128.24;

Step-5: Preparation of 1-(3-amino-4-fluorophenyl)-3-cyclopropylpropan-1-ol (42f)

To a solution of 1-(3-amino-4-fluorophenyl)-3-cyclopropylpropan-1-one (42e) (13.63 g, 65.8 mmol) in THF (150 mL) and Methanol (300 mL) at 0° C. was added sodium borohydride (5.08 g, 132 mmol) and stirred at 0° C. for 1 h. The reaction mixture was allowed to warm to room temperature overnight. The reaction mixture was diluted with ethyl acetate (800 mL), neutralized with acetic acid, washed with water (2×300 mL), brine (300 mL), dried over MgSO4, filtered and concentrated in vacuum. The residue was purified by flash column chromatography [silica gel, eluting with hexanes/ethyl acetate (1:0 to 4:1)] to afford 1-(3-amino-4-fluorophenyl)-3-cyclopropylpropan-1-ol (42f) (11.47 g, 53.8 mmol, 83% yield) as a white solid; $^1$H NMR (300 MHz, DMSO-d$_6$) δ 6.86 (dd, J=11.5, 8.2 Hz, 1H), 6.72 (dd, J=9.1, 2.1 Hz, 1H), 6.42 (ddd, J=8.3, 4.5, 2.1 Hz, 1H), 5.03 (s, 2H), 4.98 (d, J=4.1 Hz, 1H), 4.40-4.30 (m, 1H), 1.71-1.48 (m, 2H), 1.26-1.01 (m, 2H), 0.73-0.54 (m, 1H), 0.45-0.24 (m, 2H), 0.02--0.14 (m, 2H); $^{19}$F NMR (282 MHz, DMSO) δ −138.16; MS (ES+) 210.1 (M+1); (ES−) 208.1 (M−1).

Step-6: Preparation of (2R,4R)-tert-butyl 2-(5-(3-cyclopropyl-1-hydroxypropyl)-2-fluorophenylcarbamoyl)-4-methoxypyrrolidine-1-carboxylate (42g)

Compound 42g was prepared from 1-(3-amino-4-fluorophenyl)-3-cyclopropylpropan-1-ol (42f) (700 mg, 3.35 mmol), (2R,4R)-1-(tert-butoxycarbonyl)-4-methoxypyrrolidine-2-carboxylic acid (36a) (820 mg, 3.35 mmol) and ethyl 2-ethoxyquinoline-1(2H)-carboxylate (827 mg, 3.35 mmol) using the reaction and workup conditions as reported in step 10 of Scheme 1 to afford (2R,4R)-tert-butyl 2-(5-(3-cyclopropyl-1-hydroxypropyl)-2-fluorophenylcarbamoyl)-4-methoxypyrrolidine-1-carboxylate (42g) (1.273 g, 2.92 mmol, 87% yield) as a colorless syrup; $^1$H NMR (300 MHz, DMSO-d$_6$) δ 9.42 (2s, 1H, rotamers), 7.87 (dd, J=35.9, 7.7 Hz, 1H, rotamers), 7.17 (dd, J=10.8, 8.4 Hz, 1H), 7.06 (s, 1H), 5.19 (d, J=4.4 Hz, 1H), 4.49 (q, J=5.9 Hz, 1H), 4.29 (m, 1H), 3.99 (m, 1H), 3.59 (dd, J=11.0, 5.5 Hz, 1H), 3.34-3.30 (m, 1H), 3.22 (2s, 3H, rotamers), 2.45-2.25 (m, 1H), 2.19-1.89 (m, 1H), 1.77-1.51 (m, 2H), 1.36 (2s, 9H, rotamers), 1.26-1.05 (m, 2H), 0.74-0.53 (m, 1H), 0.46-0.22 (m, 2H), −0.011--0.098 (m, 2H); $^{19}$F NMR (282 MHz, DMSO-d$_6$) δ −128.81, −130.11 rotamers.

Step-7: Preparation of (2R,4R)-tert-butyl 2-(5-(1-bromo-3-cyclopropylpropyl)-2-fluorophenylcarbamoyl)-4-methoxypyrrolidine-1-carboxylate (42h)

To a solution of triphenylphosphine (451 mg, 1.718 mmol) in dichloromethane (15 mL) at 0° C. was added bromine (70.8 µL, 1.374 mmol) and stirred for 15 mins. To the reaction at 0° C. was added a premixed solution containing (2R,4R)-tert-butyl 2-(5-(3-cyclopropyl-1-hydroxypropyl)-2-fluorophenylcarbamoyl)-4-methoxypyrrolidine-1-carboxylate (42g) (300 mg, 0.687 mmol) and imidazole (117 mg, 1.718 mmol) in dichloromethane (15 mL). The reaction was allowed to warm to room temperature over a period of 1 h and concentrated in vacuum. The residue obtained was purified by flash column chromatography (silica gel, eluting with ethyl acetate in hexanes 20 to 30%) to afford (2R,4R)-tert-butyl 2-(5-(1-bromo-3-cyclopropylpropyl)-2-fluorophenylcarbamoyl)-4-methoxypyrrolidine-1-carboxylate (42h) (279 mg, 0.559 mmol, 81% yield) as light brown semi solid; $^1$H NMR (300 MHz, DMSO-d$_6$) δ

9.56 (2s, 1H, rotamers), 8.05 (2m, 1H, rotamers), 7.37-7.04 (m, 2H), 5.30 (t, J=7.5 Hz, 1H), 4.32 (m, 1H), 4.07-3.90 (m, 1H), 3.59 (dd, J=11.1, 5.4 Hz, 1H), 3.43-3.28 (m, 1H), 3.23 (2s, 3H, rotamers), 2.62-2.23 (m, 2H), 2.20-1.89 (m, 1H), 1.37 (2s, 9H, rotamers), 1.30-1.02 (m, 3H), 0.79-0.63 (m, 1H), 0.48-0.29 (m, 2H), 0.03--0.049 (m, 2H). $^{19}$F NMR (282 MHz, DMSO-$d_6$) δ −126.1 rotamers. MS (ES+) 499.46, 501.47 (M+1), 521.45, 523.46 (M+Na), (ES−) 497.41, 499.37 (M−1).

Step-8: Preparation of (2R,4R)-tert-butyl 2-(5-(3-cyclopropyl-1-(2-oxopyridin-1(2H)-yl)propyl)-2-fluorophenylcarbamoyl)-4-methoxypyrrolidine-1-carboxylate (42j)

To a stirred solution of pyridin-2-ol (42i) (252 mg, 2.65 mmol) in acetonitrile (25 mL) was added potassium carbonate (381 mg, 2.76 mmol), heated at reflux for 1 h and cooled to room temperature. To the reaction mixture was added a solution of (2R,4R)-tert-butyl 2-(5-(1-bromo-3-cyclopropylpropyl)-2-fluorophenylcarbamoyl)-4-methoxypyrrolidine-1-carboxylate (42h) (265 mg, 0.531 mmol) in acetonitrile (15 mL) and heated at reflux overnight. The reaction mixture was concentrated in vacuum and the residue was suspended in water (25 mL), extracted with ethyl acetate (3×50 mL). The ethyl acetate layers were combined, washed with water (2×25 mL), brine (25 mL), dried and concentrated in vacuum.

The crude residue was purified by flash column chromatography (silica gel, 12 g eluting with 9:1 mixture of ethyl acetate and methanol in hexanes 0 to 60%) to afford (2R,4R)-tert-butyl 2-(5-(3-cyclopropyl-1-(2-oxopyridin-1(2H)-yl)propyl)-2-fluorophenylcarbamoyl)-4-methoxypyrrolidine-1-carboxylate (42j) (120 mg, 0.234 mmol, 44.0% yield) as an off white solid; $^{1}$H NMR (300 MHz, DMSO-$d_6$) δ 9.55 (2s, 1H, rotamers), 7.79 (s, 1H, rotamers), 7.62 (s, 1H), 7.42-7.31 (m, 1H), 7.25 (dd, J=10.5, 8.6 Hz, 1H), 7.18 (bs, 1H), 6.39 (dd, J=9.2, 1.4 Hz, 1H), 6.23 (tt, J=6.7, 1.6 Hz, 1H), 6.06 (t, J=8.2 Hz, 1H), 4.27 (m, 1H), 3.97 (m, 1H), 3.58 (m, 1H), 3.45-3.23 (m, 1H), 3.21 (2s, 3H, rotamers), 2.61-2.23 (m, 1H), 2.23-2.08 (m, 2H), 2.00-1.83 (m, 1H), 1.34 (2s, 9H, rotamers), 1.17-0.96 (m, 2H), 0.79-0.61 (m, 1H), 0.48-0.28 (m, 2H), 0.10--0.10 (m, 2H); $^{19}$F NMR (282 MHz, DMSO-$d_6$) δ −126.20, −127.58 rotamers; MS (ES+) 514.6 (M+1), 536.6 (M+Na), (ES−) 512.5 (M−1), 548.6 (M+Cl).

Step-9: Preparation of (2R,4R)-N-(5-(3-cyclopropyl-1-(2-oxopyridin-1(2H)-yl)propyl)-2-fluorophenyl)-4-methoxypyrrolidine-2-carboxamide (42k)

Compound 42k was prepared from (2R,4R)-tert-butyl 2-(5-(3-cyclopropyl-1-(2-oxopyridin-1(2H)-yl)propyl)-2-fluorophenylcarbamoyl)-4-methoxypyrrolidine-1-carboxylate (42j) (110 mg, 0.214) using 3N HCl in methanol (0.714 mL, 2.142 mmol) according to the procedure reported in step 6 of Scheme 4 for to furnish (2R,4R)-N-(5-(3-cyclopropyl-1-(2-oxopyridin-1(2H)-yl)propyl)-2-fluorophenyl)-4-methoxypyrrolidine-2-carboxamide (42k) (96 mg, 0.213 mmol, 100% yield) hydrochloride as a light brown solid; $^{1}$H NMR (300 MHz, DMSO-$d_6$) δ 10.46 (s, 1H), 10.08 (s, 1H), 8.79 (s, 1H), 7.89-7.56 (m, 2H), 7.50-7.11 (m, 2H), 6.40 (d, J=9.3 Hz, 1H), 6.25 (d, J=7.2 Hz, 1H), 6.07 (s, 1H), 4.49 (d, J=5.6 Hz, 1H), 4.09 (s, 1H), 3.39 (s, 1H), 3.35-3.21 (m, 1H), 3.19 (2s, 3H two diastereomers), 2.64-2.51 (m, 2H), 2.31-2.15 (m, 4H), 1.25-0.93 (m, 2H), 0.79-0.61 (m, 1H), 0.49-0.28 (m, 2H), 0.07--0.10 (m, 2H); $^{19}$F NMR (282 MHz, DMSO-$d_6$) δ −124.71, −124.73 (diastereomers); MS (ES+) 414.5 (M+1), 436.5 (M+Na), (ES−) 4112.5 (M−1), 448.5 (M+Cl).

Step-10: Preparation of (2R,4R)-N1-(5-chloropyridin-2-yl)-N2-(5-(3-cyclopropyl-1-(2-oxopyridin-1(2H)-yl)propyl)-2-fluorophenyl)-4-methoxypyrrolidine-1,2-dicarboxamide (421)

Reaction of (2R,4R)-N-(5-(3-cyclopropyl-1-(2-oxopyridin-1(2H)-yl)propyl)-2-fluorophenyl)-4-methoxypyrrolidine-2-carboxamide (42k) (96 mg, 0.213 mmol) in tetrahydrofuran (10 mL) with phenyl 5-chloropyridin-2-ylcarbamate (13b) (80 mg, 0.320 mmol) using 1N aqueous sodium bicarbonate (4.27 mL, 4.27 mmol) as base according to procedure reported in step 3 of Scheme 13 gave after purification by flash column chromatography (2R,4R)-N1-(5-chloropyridin-2-yl)-N2-(5-(3-cyclopropyl-1-(2-oxopyridin-1(2H)-yl)propyl)-2-fluorophenyl)-4-methoxypyrrolidine-1,2-dicarboxamide (42i) (113 mg, 0.199 mmol, 93% yield) as a white solid; $^{1}$H NMR (300 MHz, DMSO-$d_6$) δ 9.55 (s, 1H), 9.16 (s, 1H), 8.30 (dd, J=2.6, 0.7 Hz, 1H), 7.90 (dd, J=9.1, 0.8 Hz, 1H), 7.87-7.77 (m, 2H), 7.65 (d, J=6.9 Hz, 1H), 7.35 (ddd, J=8.8, 6.5, 2.0 Hz, 1H), 7.29-7.12 (m, 2H), 6.38 (dd, J=9.2, 1.3 Hz, 1H), 6.22 (t, J=6.7 Hz, 1H), 6.05 (t, J=8.0 Hz, 1H), 4.59 (dd, J=9.2, 3.8 Hz, 1H), 4.08-3.97 (m, 1H), 3.82-3.60 (m, 2H), 3.22 (2s, 3H, diastereomers), 2.42-2.32 (m, 1H), 2.29-2.04 (m, 3H), 1.18-0.93 (m, 2H), 0.78-0.62 (m, 1H), 0.44-0.29 (m, 2H), 0.04--0.11 (m, 2H); $^{19}$F NMR (282 MHz, DMSO-$d_6$) δ −126.35; MS (ES+) 568.6, 570.6 (M+1), 590.5, 592.5 (M+Na), (ES−) 566.5, 568.5 (M−1); IR (KBr) 3420, 3077, 2998, 2932, 1659, 1520 cm$^{-1}$; Analysis calculated for $C_{29}H_{31}ClFN_5O_4 \cdot 0.5H_2O$: C, 60.36; H, 5.59; N, 12.14. Found: C, 60.76; H, 5.66; N, 11.82.

Scheme 43

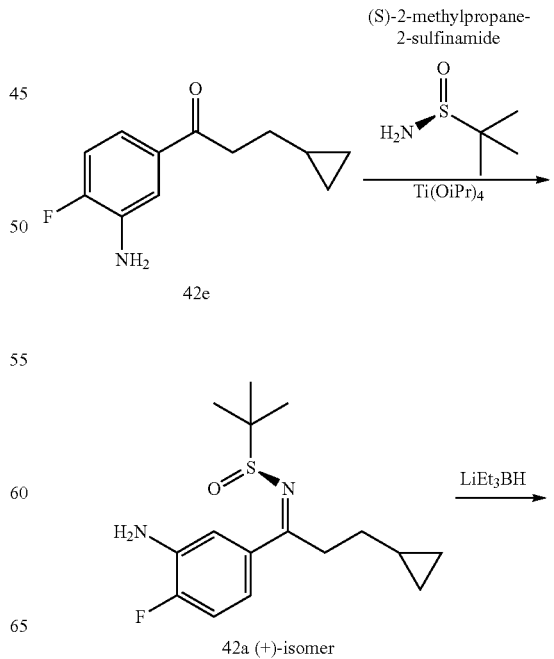

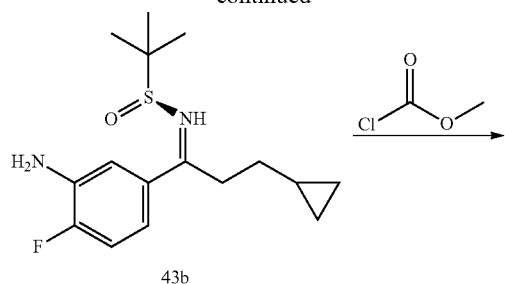
43b
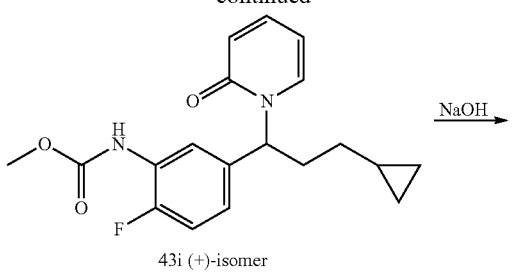
43i (+)-isomer
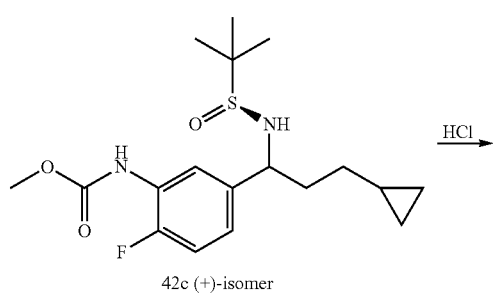
42c (+)-isomer
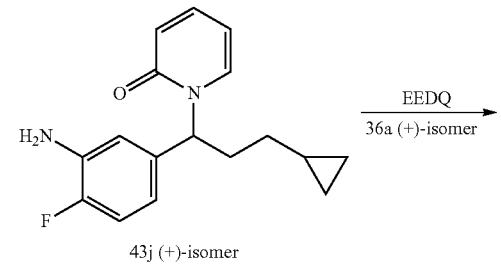
43j (+)-isomer
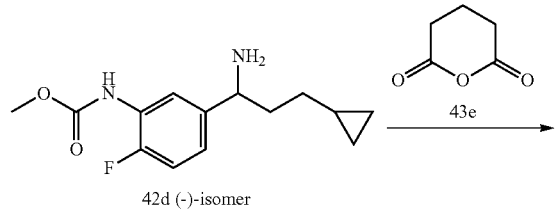
42d (−)-isomer
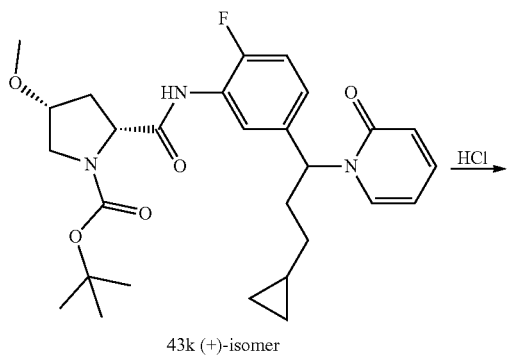
43k (+)-isomer
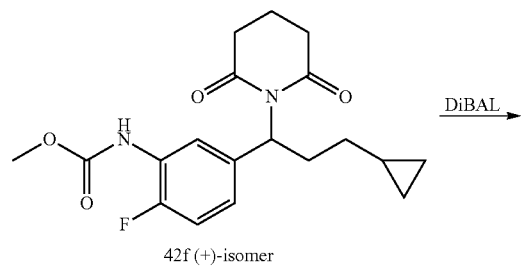
42f (+)-isomer
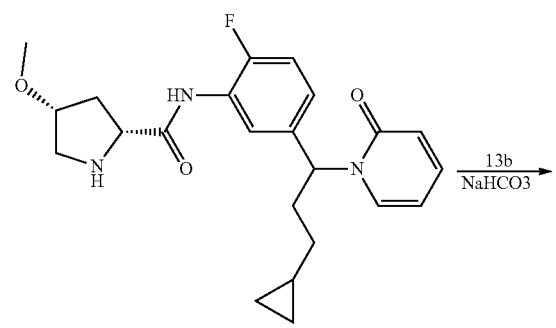
43l (+)-isomer
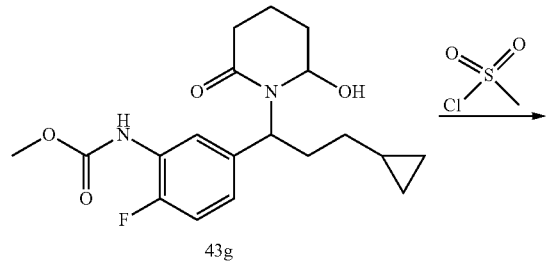
43g
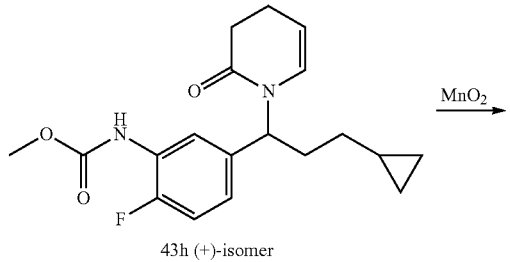
43h (+)-isomer
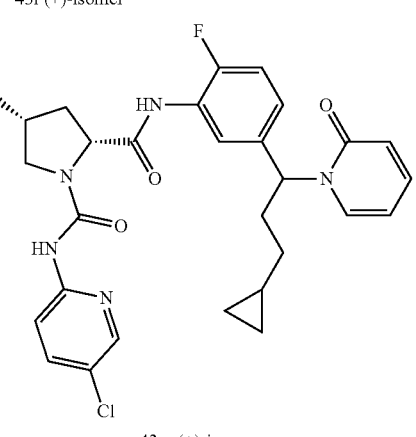
43m (+)-isomer Preparation of ((2R,4R)-N1-(5-chloropyridin-2-yl)-N2-(5-((+)-3-cyclopropyl-1-(2-oxopyridin-1(2H)-yl)propyl)-2-fluorophenyl)-4-methoxypyrrolidine-1,2-dicarboxamide (43m)

Step-1: Preparation of (S)(+)-N-(1-(3-amino-4-fluorophenyl)-3-cyclopropylpropylidene)-2-methylpropane-2-sulfinamide (43a)

Compound (43a) was prepared from 1-(3-amino-4-fluorophenyl)-3-cyclopropylpropan-1-one (42e) (100.865 g, 487 mmol), (S)-2-methylpropane-2-sulfinamide (86 g, 681 mmol) and tetraisopropoxytitanium (287 mL, 973 mmol) using procedure as reported in step 3 of scheme 31 to afford (S)(+)-N-(1-(3-amino-4-fluorophenyl)-3-cyclopropylpropylidene)-2-methylpropane-2-sulfinamide (43a) (64 g, 206 mmol, 42.4% yield) as a light brown solid; $^1$H NMR (300 MHz, DMSO-d$_6$) δ 7.33 (d, J=8.9 Hz, 1H), 7.07 (d, J=8.7 Hz, 2H), 5.39 (s, 2H), 3.33-3.05 (m, 2H), 1.54-1.37 (m, 2H), 1.21 (s, 9H), 0.85-0.63 (m, 1H), 0.46-0.32 (m, 2H), 0.15-0.02 (m, 2H); $^{19}$F NMR (282 MHz, DMSO-d$_6$) δ −129.79; MS (ES+) 311.4 (M+1), 333.4 (M+Na), (ES−) 309.4 (M−1), 345.3 (M+Cl); Optical rotation [α]$_D$=(+) 20.0 [0.18, MeOH].

Step-2: Preparation of (S)-N-(1-(3-amino-4-fluorophenyl)-3-cyclopropylpropyl)-2-methylpropane-2-sulfinamide (43b)

To a solution of (S)(+)-N-(1-(3-amino-4-fluorophenyl)-3-cyclopropylpropylidene)-2-methylpropane-2-sulfinamide (43a) (64 g, 206 mmol) in tetrahydrofuran (1.5 L) cooled to −78° C. was added Lithium triethylborohydride (618 mL, 618 mmol) slowly over a period of 2 h maintaining the reaction temperature below −75° C. The reaction was stirred at −78° C. for 3 h and allowed to warm to room temperature overnight. Reaction mixture was cooled to 0° C. quenched and with saturated aqueous NH4Cl (600 mL). The layers were separated and aqueous layer was extracted with ethyl acetate (2×1000 mL). The combined organic layers were washed with water (2×1000 mL), brine (500 mL), dried over MgSO4 filtered and concentrated in vacuum to afford (S)-N-(1-(3-amino-4-fluorophenyl)-3-cyclopropylpropyl)-2-methylpropane-2-sulfinamide (43b) (127 g, 203 mmol, 99% yield) which was used without purification in the next; MS (ES+) 313.4 (M+1), 335.4 (M+Na), (ES−) 311.4 (M−1), 347.3 (M+Cl).

Step-3: Preparation of methyl 5-((+)-3-cyclopropyl-1-((S)-1,1-dimethylethylsulfinamido)propyl)-2-fluorophenylcarbamate (43c)

To a biphasic solution of (S)-N-(1-(3-amino-4-fluorophenyl)-3-cyclopropylpropyl)-2-methylpropane-2-sulfinamide (43b) (127 g, 203 mmol) in ethyl acetate (635 mL) and saturated aqueous NaHCO$_3$ (635 mL) was added methyl chloroformate (23.61 mL, 305 mmol) and stirred vigorously at room temperature overnight. The layers were separated and aqueous layer was extracted with ethyl acetate (2×1 L). The combined organic layers were washed with brine, dried, filtered, concentrated in vacuum and purified by chromatography to afford methyl 5-((+)-3-cyclopropyl-1-((S)-1,1-dimethylethylsulfinamido)propyl)-2-fluorophenylcarbamate (43c) (75.344 g, 203 mmol, 100% yield) as a gummy solid; $^1$H NMR (300 MHz, DMSO-d$_6$) δ 9.29 (s, 1H), 7.56 (dd, J=7.9, 2.2 Hz, 1H), 7.15 (dd, J=10.6, 8.4 Hz, 1H), 7.05 (ddd, J=8.5, 4.8, 2.2 Hz, 1H), 5.31 (d, J=4.8 Hz, 1H), 4.28-4.09 (m, 1H), 3.65 (s, 3H), 2.06-1.88 (m, 1H), 1.78-1.61 (m, 1H), 1.25-1.11 (m, 1H), 1.06 (s, 9H), 1.06-0.88 (m, 1H), 0.74-0.55 (m, 1H), 0.42-0.29 (m, 2H), −0.01--0.09 (m, 2H); 19F NMR (282 MHz, DMSO-d$_6$) δ −126.77; MS (ES+) 371.5 (M+1), 393.5 (M+Na), (ES−) 369.4 (M−1), 405.4 (M+Cl); Optical rotation [α]$_D$=(+) 74.4 [0.18, MeOH].

Step-4: Preparation of (−)-methyl 5-(1-amino-3-cyclopropylpropyl)-2-fluorophenylcarbamate (43d)

To a solution of methyl 5-((+)-3-cyclopropyl-1-((S)-1,1-dimethylethylsulfinamido)propyl)-2-fluorophenylcarbamate (43c) (75 g, 202 mmol) in methanol (1000 mL) was added 3M HCl in Methanol (337 mL, 1012 mmol) stirred for 30 mins and concentrated in vacuum to dryness. The residue was dissolved in water (500 mL) basified with saturated sodium bicarbonate and extracted with ethyl acetate (3×1500 mL).

The combined organic layers were washed with water (2×300 mL), brine (500 mL), dried, filtered and concentrated in vacuum to afford (−)-methyl 5-(1-amino-3-cyclopropylpropyl)-2-fluorophenylcarbamate (43d) (63.5 g, 238 mmol, 118% yield) as a thick syrup; $^1$H NMR (300 MHz, DMSO-d$_6$) δ 9.26 (s, 1H), 7.55 (dd, J=8.0, 2.0 Hz, 1H), 7.20-7.06 (m, 1H), 3.77 (t, J=6.8 Hz, 1H), 3.65 (s, 3H), 3.50-3.14 (m, 2H), 2.50-2.28 (m, 1H), 1.60 (m, 2H), 1.24-0.94 (m, 2H), 0.72-0.53 (m, 1H), 0.41-0.27 (m, 2H), −0.02--0.11 (m, 2H); $^{19}$F NMR (282 MHz, DMSO-d$_6$) δ −127.37; MS (ES+) 267.4 (M+1), (ES−) 265.3 (M−1); Optical rotation [α]$_D$=(−) 3.0 [0.2, MeOH].

Step-5: Preparation of (+)-methyl 5-(3-cyclopropyl-1-(2,6-dioxopiperidin-1-yl)propyl)-2-fluorophenylcarbamate (43f)

To a solution of (−)-methyl 5-(1-amino-3-cyclopropylpropyl)-2-fluorophenylcarbamate (43d) (63 g, 237 mmol) in dichloromethane (1000 mL) was added dihydro-2H-pyran-2,6(3H)-dione (43e) (29.7 g, 260 mmol) at room temperature and stirred for 30 mins. To the reaction was added acetyl chloride (336 mL, 4731 mmol) heated at reflux 2 h and concentrated in vacuum to dryness. The solid separated was (crude weight 100 g) crystallized from isopropanol (250 mL) to afford (+)-methyl 5-(3-cyclopropyl-1-(2,6-dioxopiperidin-1-yl)propyl)-2-fluorophenylcarbamate (43f) (51.5 g, 142 mmol, 60.1% yield) as white solid; $^1$H NMR (300 MHz, DMSO-d$_6$) δ 9.29 (s, 1H), 7.65-7.41 (m, 1H), 7.19-6.86 (m, 2H), 5.71 (dd, J=9.2, 6.5 Hz, 1H), 3.65 (s, 3H), 2.61 (qd, J=7.6, 7.0, 3.2 Hz, 4H), 2.42-2.11 (m, 2H), 1.81 (p, J=6.5 Hz, 2H), 1.22-0.99 (m, 2H), 0.76-0.56 (m, 1H), 0.44-0.28 (m, 2H), 0.11--0.12 (m, 2H); $^{19}$F NMR (282 MHz, DMSO-d$_6$) δ −126.82; MS (ES+) 363.5 (M+1), 385.5 (M+Na), (ES−) 361.5; Optical rotation [α]$_D$=(+) 101.9 [0.21, MeOH].

Step-6: Preparation of methyl 5-(3-cyclopropyl-1-(2-hydroxy-6-oxopiperidin-1-yl)propyl)-2-fluorophenylcarbamate (43g)

To a solution of (+)-methyl 5-(3-cyclopropyl-1-(2,6-dioxopiperidin-1-yl)propyl)-2-fluorophenylcarbamate (43f) (51 g, 141 mmol) in dichloromethane (1407 mL) at −78° C. was added diisobutylaluminum hydride (422 mL, 422 mmol) and stirred at −78° C. for 1 h. Reaction was quenched with methanol (30 mL), saturated aqueous sodium potassium tartarate (1 L) and allowed to 0° C. The slurry was stirred for 2 h, layers were separated and aqueous layer was extracted with dichloromethane (2×500 mL). The combined organic layers were washed with water (2×500 mL), brine (200 mL) dried, filtered and concentrated in vacuum to afford methyl 5-(3-cyclopropyl-1-(2-hydroxy-6-oxopiperidin-1-yl)propyl)-2-fluorophenylcarbamate (43g) (51.3 g, 141 mmol, 100% yield,) which was used as such in next step without purification; MS (ES−) 363.5 (M−1).

Step-7: Preparation of (+)-methyl 5-(3-cyclopropyl-1-(2-oxo-3,4-dihydropyridin-1(2H)-yl)propyl)-2-fluorophenylcarbamate (43h)

To a stirred solution of methyl 5-(3-cyclopropyl-1-(2-hydroxy-6-oxopiperidin-1-yl)propyl)-2-fluorophenylcarbamate (43g) (52 g, 143 mmol) in dichloromethane (1586 mL) was added triethylamine (119 mL, 856 mmol), cooled to 0° C. and added methanesulfonyl chloride (22.24 mL, 285 mmol). The reaction was stirred at room temperature overnight, diluted with dichloromethane (100 mL) and water (500 mL). Layers were separated and aqueous layer was extracted with dichloromethane (2×500 mL). The organic layers were combined washed with water (2×250 mL), brine (250 mL), dried, filtered and concentrated in vacuum. The crude residue was purified by flash column chromatography (silica gel, eluting with ethyl acetate in hexanes 0 to 100%) to afford (+)-methyl 5-(3-cyclopropyl-1-(2-oxo-3,4-dihydropyridin-1(2H)-yl)propyl)-2-fluorophenylcarbamate (43h) (51.6 g, 149 mmol, 104% yield) as a colorless syrup; $^1$H NMR (300 MHz, DMSO-$d_6$) δ 9.35 (s, 1H), 7.66-7.50 (m, 1H), 7.18 (dd, J=10.7, 8.5 Hz, 1H), 7.06 (m, 1H), 6.15 (dt, J=7.9, 1.6 Hz, 1H), 5.64 (dd, J=9.8, 6.3 Hz, 1H), 5.17 (dt, J=8.2, 4.4 Hz, 1H), 3.66 (s, 4H, Me, NH), 2.50-2.36 (m, 2H), 2.26-2.14 (m, 1H), 2.06-1.87 (m, 1H), 1.43 (m, 1H), 1.28-0.99 (m, 2H), 0.72 (m, 1H), 0.44-0.30 (m, 2H), 0.11-−0.13 (m, 2H); 19F NMR (282 MHz, DMSO-$d_6$) δ −126.08; MS (ES+) 369.5 (M+Na), (ES−) 345.4 (M−1); Optical rotation $[α]_D$=(+) 123.9 [0.255, MeOH].

Step-8: Preparation of (+)-methyl 5-(3-cyclopropyl-1-(2-oxopyridin-1(2H)-yl)propyl)-2-fluorophenylcarbamate (43i)

To a stirred solution of (+)-methyl 5-(3-cyclopropyl-1-(2-oxo-3,4-dihydropyridin-1(2H)-yl)propyl)-2-fluorophenylcarbamate (43h) (5.95 g, 17.18 mmol) in dichloromethane (200 mL) was added manganese dioxide (7.47 g, 86 mmol) and heated to reflux for 10 h. Additional manganese dioxide (7.47 g, 86 mmol) was added in 7 installments over a period of 72 h. The reaction mixture was filtered washed with dichloromethane and concentrated in vacuum. The crude residue obtained was purified by flash column chromatography (silica gel, eluting with ethyl acetate in hexanes 0 to 100%) to afford (+)-methyl 5-(3-cyclopropyl-1-(2-oxopyridin-1(2H)-yl)propyl)-2-fluorophenylcarbamate (43i) (2.962 g, 8.60 mmol, 50.1% yield) as light black oil; $^1$H NMR (300 MHz, DMSO-$d_6$) δ 9.40 (s, 1H), 7.75-7.59 (m, 2H), 7.38 (ddd, J=8.8, 6.5, 2.0 Hz, 1H), 7.28-7.14 (m, 2H), 6.45-6.37 (m, 1H), 6.25 (td, J=6.7, 1.5 Hz, 1H), 6.08 (t, J=8.1 Hz, 1H), 3.67 (s, 3H), 2.22 (q, J=7.7 Hz, 2H), 1.28-0.93 (m, 2H), 0.84-0.62 (m, 1H), 0.47-0.31 (m, 2H), 0.11-−0.13 (m, 2H); $^{19}$F NMR (282 MHz, DMSO-$d_6$) δ −125.29; MS (ES+) 345.4 (M+1), 367.4 (M+Na), (ES−) 343.4 (M−1), 379.3 (M+Cl); Optical rotation $[α]_D$=(+) 240.0 [0.05, MeOH].

Step-9: Preparation of (+)-1-(1-(3-amino-4-fluorophenyl)-3-cyclopropylpropyl)pyridin-2(1H)-one (43j)

To a solution of (+)-methyl 5-(3-cyclopropyl-1-(2-oxopyridin-1(2H)-yl)propyl)-2-fluorophenylcarbamate (43i) (2.9 g, 8.42 mmol) in methanol (75 mL) was added aqueous sodium hydroxide (14.03 mL, 84 mmol, 6N), heated to reflux for 10 h and concentrated in vacuum. The residue was diluted with water (200 mL) extracted with ethyl acetate (3×200 mL). The organic layers were combined, washed with water (2×100 mL), brine (100 mL), dried, filtered and concentrated in vacuum. The crude residue was purified by flash column chromatography (silica gel, eluting with ethyl acetate in hexanes 0 to 60 to 100%) to afford of (+)-1-(1-(3-amino-4-fluorophenyl)-3-cyclopropylpropyl)pyridin-2 (1H)-one (43j) (2.173 g, 7.59 mmol, 90% yield) as a syrup; $^1$H NMR (300 MHz, DMSO-$d_6$) δ 7.58 (dd, J=6.9, 2.0 Hz, 1H), 7.35 (ddd, J=8.8, 6.5, 2.0 Hz, 1H), 6.94 (dd, J=11.5, 8.3 Hz, 1H), 6.75 (dd, J=8.7, 2.3 Hz, 1H), 6.53 (ddd, J=8.4, 4.3, 2.3 Hz, 1H), 6.39 (dd, J=9.1, 1.3 Hz, 1H), 6.21 (td, J=6.7, 1.5 Hz, 1H), 5.99 (dd, J=9.1, 7.0 Hz, 1H), 5.19 (s, 2H), 2.23-2.03 (m, 2H), 1.11 (m, 1H), 0.99 (m, 1H), 0.79-0.62 (m, 1H), 0.46-0.28 (m, 2H), 0.08-−0.12 (m, 2H); $^{19}$F NMR (282 MHz, DMSO-$d_6$) δ −136.31; MS (ES+) 287.4 (M+1), 309.4 (M+Na), 573.7 (2M+1), 595.7 (2M+Na), (ES−) 285.3 (M−1), 321.3 (M+Cl); Optical rotation $[α]_D$=(+) 296.25 [0.16, MeOH].

Step-10: Preparation of (2R,4R)-tert-butyl 2-(5-((+)-3-cyclopropyl-1-(2-oxopyridin-1(2H)-yl)propyl)-2-fluorophenylcarbamoyl)-4-methoxypyrrolidine-1-carboxylate (43k)

Reaction of (2R,4R)-1-(tert-butoxycarbonyl)-4-methoxypyrrolidine-2-carboxylic acid (36a) (158 mg, 0.513 mmol), (+)-1-(1-(3-amino-4-fluorophenyl)-3-cyclopropylpropyl)pyridin-2(1H)-one (43j) (286 mg, 1.0 mmol) in tetrahydrofuran (20 mL) with ethyl 2-ethoxyquinoline-1(2H)-carboxylate (247 mg, 1.0 mmol) using the reaction and workup conditions as reported in step 10 of Scheme 1 gave after purification by flash column chromatography (silica gel 25 g, eluting with ethyl acetate in hexanes 0 to 100%) afforded (2R,4R)-tert-butyl 2-(5-((+)-3-cyclopropyl-1-(2-oxopyridin-1(2H)-yl)propyl)-2-fluorophenylcarbamoyl)-4-methoxypyrrolidine-1-carboxylate (43k) (462 mg, 0.900 mmol, 90% yield) as a white solid; $^1$H NMR (300 MHz, DMSO-$d_6$) δ 9.51 (2s, 1H, rotamers), 7.87 (m, 1H), 7.71-7.56 (m, 1H), 7.36 (ddd, J=8.8, 6.5, 2.0 Hz, 1H), 7.25 (dd, J=10.5, 8.5 Hz, 1H), 7.17 (d, J=8.1 Hz, 1H), 6.39 (d, J=9.1, 1.4 Hz, 1H), 6.23 (td, J=6.7, 1.4 Hz, 1H), 6.07 (t, J=8.0 Hz, 1H), 4.42-4.21 (m, 1H), 4.00-3.92 (m, 1H), 3.59 (dd, J=11.1, 5.5 Hz, 1H), 3.35-3.26 (m, 1H), 3.21 (2s, 3H, rotamers), 2.51-2.28 (m, 1H), 2.20 (m, 2H), 2.11-1.85 (m, 1H), 1.34 (2s, 9H, rotamers), 1.26-0.93 (m, 2H), 0.72 (m, 1H), 0.37 (m, 2H), 0.10-−0.10 (m, 2H); $^{19}$F NMR (282 MHz, DMSO-$d_6$) δ −125.99, −127.39; MS (ES+) 514.6 (M+1), 536.6 (M+Na), (ES−) 512.6 (M−1), 548.5 (M+Cl); Optical rotation $[α]_D$=(+) 248 [0.115, MeOH].

Step-11: Preparation of (2R,4R)-N-(5-((+)-3-cyclopropyl-1-(2-oxopyridin-1(2H)-yl)propyl)-2-fluorophenyl)-4-methoxypyrrolidine-2-carboxamide (43l)

Compound 43l was prepared from (2R,4R)-tert-butyl 2-(5-((+)-3-cyclopropyl-1-(2-oxopyridin-1(2H)-yl)propyl)-2-fluorophenylcarbamoyl)-4-methoxypyrrolidine-1-carboxylate (43k) (450 mg, 0.876 mmol) using 3N HCl in methanol (2.92 mL, 8.76 mmol) according to the procedure reported in step 6 of Scheme 4 for to furnish (2R,4R)-N-(5-((+)-3-cyclopropyl-1-(2-oxopyridin-1(2H)-yl)propyl)-2-fluorophenyl)-4-methoxypyrrolidine-2-carboxamide (43l) (394 mg, 0.876 mmol, 100% yield) hydrochloride salt as a as light brown syrup; 1H NMR (300 MHz, DMSO-$d_6$) δ 10.45 (s, 1H), 10.17-9.94 (m, 1H), 8.95-8.64 (m, 2H), 7.73 (ddd, J=32.9, 7.3, 2.1 Hz, 2H), 7.37 (ddd, J=8.8, 6.5, 2.0 Hz, 1H), 7.33-7.25 (m, 2H), 6.40 (dd, J=9.1, 1.3 Hz, 1H), 6.24 (td, J=6.8, 1.5 Hz, 1H), 6.07 (t, J=8.1 Hz, 1H), 4.63-4.35 (m, 1H), 4.09 (d, J=3.8 Hz, 1H), 3.50-3.21 (m, 1H), 3.19 (s, 3H), 2.63-2.52 (m, 1H), 2.22 (m, 3H), 1.11 (m, 2H), 0.71 (m, 1H), 0.38 (m, 2H), 0.06--0.11 (m, 2H); 19F NMR (282 MHz, DMSO-$d_6$) δ −124.56; MS (ES+) 414.5 (M+1), 436.5 (M+Na), 827.8 (2M+1), (ES−) 412.5 (M−1), 448.4 (M+Cl); Optical rotation $[α]_D$=(+) 170.9 [0.055, MeOH].

Step-12: Preparation of ((2R,4R)-N1-(5-chloropyridin-2-yl)-N2-(5-((+)-3-cyclopropyl-1-(2-oxopyridin-1(2H)-yl)propyl)-2-fluorophenyl)-4-methoxypyrrolidine-1,2-dicarboxamide (43m)

Reaction of (2R,4R)-N-(5-((+)-3-cyclopropyl-1-(2-oxopyridin-1(2H)-yl)propyl)-2-fluorophenyl)-4-methoxypyrrolidine-2-carboxamide (43l) (394 mg, 0.876 mmol) in tetrahydrofuran (50 mL) with phenyl 5-chloropyridin-2-ylcarbamate (13b) (327 mg, 1.314 mmol) using 1N aqueous sodium bicarbonate (17.52 mL, 17.52 mmol) as base according to procedure reported in step 3 of Scheme 13 gave after purification by flash column chromatography ((2R,4R)-N1-(5-chloropyridin-2-yl)-N2-(5-((+)-3-cyclopropyl-1-(2-oxopyridin-1(2H)-yl)propyl)-2-fluorophenyl)-4-methoxypyrrolidine-1,2-dicarboxamide (43m) (245 mg, 0.431 mmol, 49.2% yield) as white solid; 1H NMR (300 MHz, DMSO-$d_6$) δ 9.55 (s, 1H), 9.17 (s, 1H), 8.30 (dd, J=2.7, 0.7 Hz, 1H), 7.90 (dd, J=9.0, 0.8 Hz, 1H), 7.88-7.78 (m, 2H), 7.65 (dd, J=7.0, 2.0 Hz, 1H), 7.35 (ddd, J=8.9, 6.5, 2.0 Hz, 1H), 7.24 (dd, J=10.5, 8.6 Hz, 1H), 7.19-7.12 (m, 1H), 6.38 (dd, J=9.2, 1.4 Hz, 1H), 6.22 (td, J=6.7, 1.5 Hz, 1H), 6.05 (t, J=8.0 Hz, 1H), 4.59 (dd, J=9.2, 4.0 Hz, 1H), 4.12-3.96 (m, 1H), 3.83-3.62 (m, 2H), 3.22 (s, 3H), 2.44-2.30 (m, 1H), 2.29-2.04 (m, 3H), 1.24-0.91 (m, 2H), 0.79-0.61 (m, 1H), 0.45-0.29 (m, 2H), 0.04--0.09 (m, 2H); 19F NMR (282 MHz, DMSO-$d_6$) δ −126.21; MS (ES+) 568.5, 570.6 (M+1), 590.5, 592 (M+Na), (ES−) 566.5, 568.5 (M−1); Optical rotation $[α]_D$=(+) 229.54 [0.325, MeOH]; Analysis calculated for $C_{29}H_{31}ClFN_5O_4$: C, 61.32; H, 5.50; Cl, 6.24; N, 12.33. Found: C, 61.06; H, 5.53; Cl, 6.02; N, 12.27.

Scheme 44

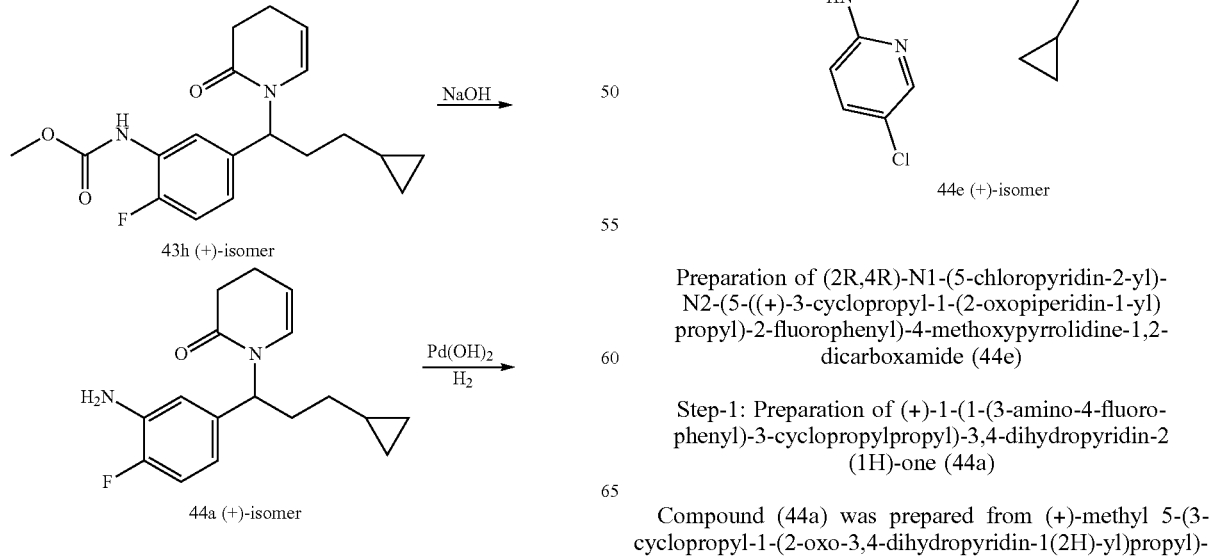

Preparation of (2R,4R)-N1-(5-chloropyridin-2-yl)-N2-(5-((+)-3-cyclopropyl-1-(2-oxopiperidin-1-yl)propyl)-2-fluorophenyl)-4-methoxypyrrolidine-1,2-dicarboxamide (44e)

Step-1: Preparation of (+)-1-(1-(3-amino-4-fluorophenyl)-3-cyclopropylpropyl)-3,4-dihydropyridin-2(1H)-one (44a)

Compound (44a) was prepared from (+)-methyl 5-(3-cyclopropyl-1-(2-oxo-3,4-dihydropyridin-1(2H)-yl)propyl)-

2-fluorophenylcarbamate (43h) (4 g, 11.55 mmol) and aqueous NaOH (19.25 mL, 115 mmol 6N) using procedure as reported in step 9 of scheme 43 to afford (+)-1-(1-(3-amino-4-fluorophenyl)-3-cyclopropylpropyl)-3,4-dihydropyridin-2 (1H)-one (44a) (3.22 g, 11.17 mmol, 97% yield) as a syrup; $^1$H NMR (300 MHz, DMSO-$d_6$) δ 6.91 (dd, J=11.5, 8.3 Hz, 1H), 6.69 (dd, J=8.8, 2.3 Hz, 1H), 6.44 (ddd, J=8.5, 4.4, 2.3 Hz, 1H), 6.09 (dt, J=7.7, 1.6 Hz, 1H), 5.56 (dd, J=10.1, 5.9 Hz, 1H), 5.21-5.04 (m, 3H), 2.48-2.36 (m, 2H), 2.27-2.12 (m, 2H), 1.98-1.80 (m, 2H), 1.21-0.94 (m, 2H), 0.81-0.61 (m, 1H), 0.45-0.28 (m, 2H), 0.07-0.01 (m, 1H), −0.01-−0.08 (m, 1H); $^{19}$F NMR (282 MHz, DMSO-$d_6$) δ −136.82; MS (ES+) 289.4 (M+1), 311.4 (M+Na), (ES−) 287.4 (M−1); Optical rotation $[α]_D$=(+) 144.4 [0.205, MeOH].

Step-2: Preparation of (+)-1-(1-(3-amino-4-fluorophenyl)-3-cyclopropylpropyl)piperidin-2-one (44b)

Compound 44b was prepared by reduction of (+)-1-(1-(3-amino-4-fluorophenyl)-3-cyclopropylpropyl)-3,4-dihydropyridin-2(1H)-one (44a) (3.2 g, 11.10 mmol) for 1 h according to the reaction and work procedure reported in step 2 of Scheme 13 using palladium hydroxide (0.779 g, 1.11 mmol) in ethyl acetate (50 mL) to afford (+)-1-(1-(3-amino-4-fluorophenyl)-3-cyclopropylpropyl)piperidin-2-one (44b) (2.846 g, 9.80 mmol, 88% yield) as a light yellow oil; 1H NMR (300 MHz, DMSO-$d_6$) δ 6.91 (dd, J=11.5, 8.3 Hz, 1H), 6.70 (dd, J=8.9, 2.2 Hz, 1H), 6.42 (ddd, J=8.4, 4.3, 2.2 Hz, 1H), 5.68 (dd, J=9.3, 6.7 Hz, 1H), 5.11 (s, 2H), 3.12-2.93 (m, 1H), 2.82-2.63 (m, 1H), 2.28 (m, 2H), 1.95-1.75 (m, 2H), 1.75-1.42 (m, 4H), 1.25-0.95 (m, 2H), 0.82-0.67 (m, 1H), 0.42-0.35 (m, 2H), 0.11-−0.05 (m, 2H); $^{19}$F NMR (282 MHz, DMSO-$d_6$) δ −137.07; MS (ES+) 291.4, 313.4 (M+Na), ES−) 289.4 (M−1), 325.4 (M+Cl); Optical rotation $[α]_D$=(+) 164.0 [0.15, MeOH].

Step-3: Preparation of methyl (2R,4R)-tert-butyl 2-(5-((+)-3-cyclopropyl-1-(2-oxopiperidin-1-yl)propyl)-2-fluorophenylcarbamoyl)-4-methoxypyrrolidine-1-carboxylate (44c)

Reaction of (2R,4R)-1-(tert-butoxycarbonyl)-4-methoxypyrrolidine-2-carboxylic acid (36a) (245 mg, 1 mmol), (+)-1-(1-(3-amino-4-fluorophenyl)-3-cyclopropylpropyl)piperidin-2-one (44b) (290 mg, 1.0 mmol) in tetrahydrofuran (20 mL) using ethyl 2-ethoxyquinoline-1(2H)-carboxylate (247 mg, 1.0 mmol) using the reaction and workup conditions as reported in step 10 of Scheme 1 gave after purification by flash column chromatography (silica gel 25 g, eluting with ethyl acetate in hexanes 0 to 100%) methyl (2R,4R)-tert-butyl 2-(5-((+)-3-cyclopropyl-1-(2-oxopiperidin-1-yl)propyl)-2-fluorophenylcarbamoyl)-4-methoxypyrrolidine-1-carboxylate (44c) (453 mg, 0.875 mmol, 88% yield) as a colorless syrup; $^1$H NMR (300 MHz, DMSO-$d_6$) δ 9.50 (2s, 1H, rotamers), 8.04-7.66 (m, 1H), 7.22 (dd, J=10.8, 8.5 Hz, 1H), 7.10-6.99 (m, 1H), 5.78 (t, J=8.0 Hz, 1H), 4.48-4.20 (m, 1H), 4.06-3.91 (m, 1H), 3.59 (dd, J=11.1, 5.6 Hz, 1H), 3.41 (s, 1H), 3.22 (2s, 3H, rotamers), 3.14-3.01 (m, 1H), 2.82-2.67 (m, 1H), 2.50-2.04 (m, 2H), 2.01-1.79 (m, 4H), 1.77-1.56 (m, 3H), 1.60-1.46 (m, 1H), 1.36 (2s, 9H, rotamers), 1.29-0.98 (m, 2H), 0.85-0.64 (m, 1H), 0.47-0.30 (m, 2H), 0.14-−0.08 (m, 2H); $^{19}$F NMR (282 MHz, DMSO-$d_6$) δ −127.42, −128.68 rotamers; MS (ES+) 518.6 (M+1), 540.6 (M+Na), (ES−) 516.5 (M−1), 552.5 (M+Cl); Optical rotation $[α]_D$=(+)126.6 [0.15, MeOH].

Step-4: Preparation of (2R,4R)-N-(5-(3-cyclopropyl-1-(2-oxopiperidin-1-yl)propyl)-2-fluorophenyl)-4-methoxypyrrolidine-2-carboxamide (44d)

Compound 44d was prepared from methyl (2R,4R)-tert-butyl 2-(5-((+)-3-cyclopropyl-1-(2-oxopiperidin-1-yl)propyl)-2-fluorophenylcarbamoyl)-4-methoxypyrrolidine-1-carboxylate (44c) (400 mg, 0.773 mmol) using 3N HCl in methanol (2.58 mL, 7.73 mmol) according to the procedure reported in step 6 of Scheme 4 to furnish (2R,4R)-N-(5-(3-cyclopropyl-1-(2-oxopiperidin-1-yl)propyl)-2-fluorophenyl)-4-methoxypyrrolidine-2-carboxamide (44d) (351 mg, 0.773 mmol, 100% yield) as a light brown syrup; $^1$H NMR (300 MHz, DMSO-$d_6$) δ 10.51 (s, 1H), 10.37 (s, 1H), 8.78 (s, 1H), 7.73 (dd, J=7.6, 2.2 Hz, 1H), 7.27 (dd, J=10.6, 8.5 Hz, 1H), 7.14 (ddd, J=8.1, 4.8, 2.2 Hz, 1H), 5.79 (dd, J=9.5, 6.5 Hz, 1H), 4.71-4.35 (m, 1H), 4.22-4.02 (m, 1H), 3.47-3.35 (m, 1H), 3.36-3.20 (m, 1H), 3.20 (s, 3H), 3.14-3.04 (m, 1H), 2.82-2.67 (m, 1H), 2.65-2.52 (m, 1H), 2.39-2.18 (m, 3H), 2.06-1.85 (m, 2H), 1.79-1.44 (m, 4H), 1.31-0.98 (m, 2H), 0.84-0.64 (m, 1H), 0.48-0.31 (m, 2H), 0.12-−0.07 (m, 2H); $^{19}$F NMR (282 MHz, DMSO-$d_6$) δ −125.55; MS (ES+) 418.6 (M+1), 440.5 (M+Na), (ES−) 416.5 (M−1), 452.5 (M+Cl).

Step-5: Preparation of (2R,4R)-N1-(5-chloropyridin-2-yl)-N2-(5-((+)-3-cyclopropyl-1-(2-oxopiperidin-1-yl)propyl)-2-fluorophenyl)-4-methoxypyrrolidine-1,2-dicarboxamide (44e)

Reaction of (2R,4R)-N-(5-(3-cyclopropyl-1-(2-oxopiperidin-1-yl)propyl)-2-fluorophenyl)-4-methoxypyrrolidine-2-carboxamide (44d) (340 mg, 0.749 mmol) in tetrahydrofuran (50 mL) with phenyl 5-chloropyridin-2-ylcarbamate (13b) (280 mg, 1.125 mmol) using 1N aqueous sodium bicarbonate (15 mL, 15.00 mmol) as base according to procedure reported in step 3 of Scheme 13 gave after purification by flash column chromatography (silica gel, 12 g eluting with CMA 80 in chloroform 0-100%) pure (2R,4R)-N1-(5-chloropyridin-2-yl)-N2-(5-((+)-3-cyclopropyl-1-(2-oxopiperidin-1-yl)propyl)-2-fluorophenyl)-4-methoxypyrrolidine-1,2-dicarboxamide (44e) (210 mg, 0.367 mmol, 48.9% yield) as a white solid; $^1$H NMR (300 MHz, DMSO-$d_6$) δ 9.53 (s, 1H), 9.18 (s, 1H), 8.30 (dd, J=2.6, 0.8 Hz, 1H), 7.91 (dd, J=9.0, 0.8 Hz, 1H), 7.87-7.73 (m, 2H), 7.21 (dd, J=10.7, 8.5 Hz, 1H), 7.10-6.99 (m, 1H), 5.85-5.68 (m, 1H), 4.60 (dd, J=9.1, 3.9 Hz, 1H), 4.12-3.98 (m, 2H), 3.83-3.65 (m, 2H), 3.24 (s, 3H), 3.14-3.00 (m, 1H), 2.83-2.64 (m, 1H), 2.47-2.32 (m, 1H), 2.35-2.20 (m, 1H), 2.18-2.03 (m, 1H), 2.01-1.81 (m, 2H), 1.75-1.56 (m, 3H), 1.61-1.44 (m, 1H), 1.27-0.97 (m, 2H), 0.83-0.64 (m, 1H), 0.47-0.30 (m, 2H), 0.10-−0.07 (m, 2H); $^{19}$F NMR (282 MHz, DMSO-$d_6$) δ −127.47; MS (ES+) 572.6 (M+1), 594.5, 596.5 (M+Na), (ES−) 570.5, 572.5 (M−1); Optical rotation $[α]_D$=(+) 174.3 [0.21, MeOH].

Scheme 45

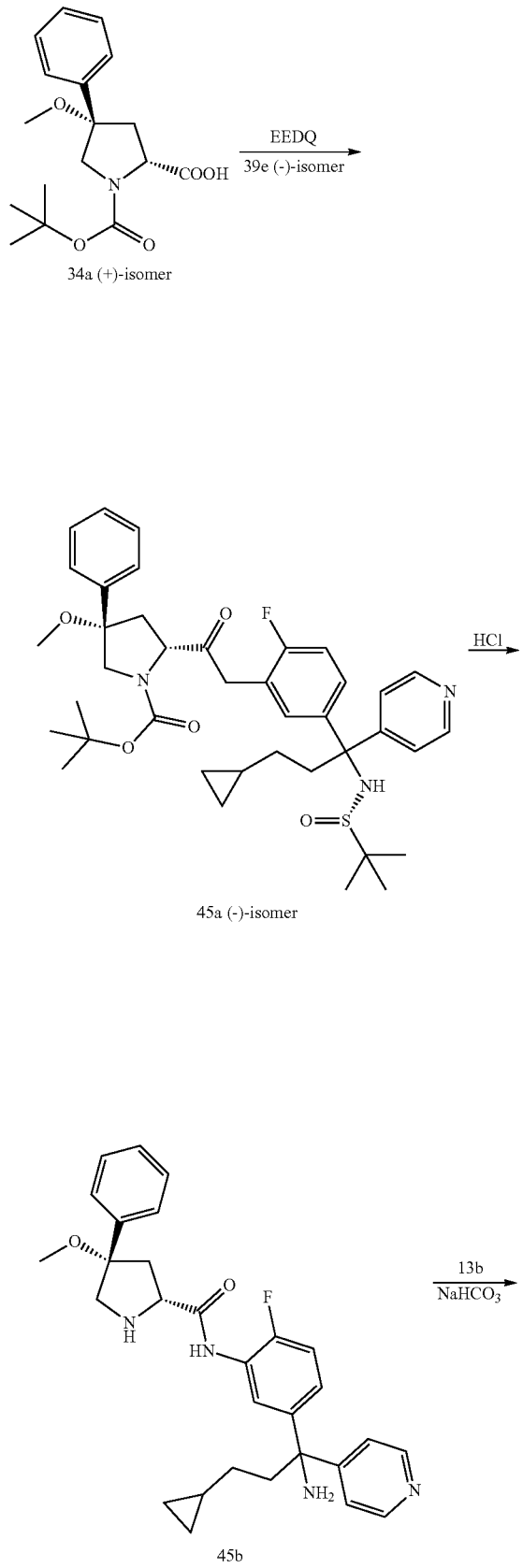

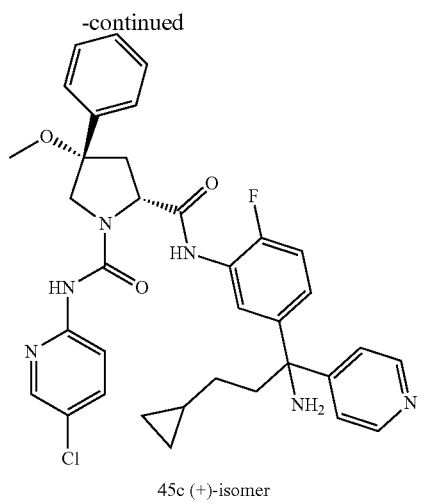

45c (+)-isomer

Preparation of (2R,4S)-N2-(5-((+)-1-amino-3-cyclopropyl-1-(pyridin-4-yl)propyl)-2-fluorophenyl)-N1-(5-chloropyridin-2-yl)-4-methoxy-4-phenylpyrrolidine-1,2-dicarboxamide (45c)

Step-1: Preparation of (2R,4S)-tert-butyl 2-(5-((−)-3-cyclopropyl-1-((S)-1,1-dimethylethylsulfinamido)-1-(pyridin-4-yl)propyl)-2-fluorophenylcarbamoyl)-4-methoxy-4-phenylpyrrolidine-1-carboxylate (45a)

Reaction of (2R,4S)-1-(tert-butoxycarbonyl)-4-methoxy-4-phenylpyrrolidine-2-carboxylic acid (34a) (160 mg, 0.498 mmol), (R)-N-((−)-1-(3-amino-4-fluorophenyl)-3-cyclopropyl-1-(pyridin-4-yl)propyl)-2-methylpropane-2-sulfinamide (39e) (194 mg, 0.498 mmol) in tetrahydrofuran (10 mL) using ethyl 2-ethoxyquinoline-1(2H)-carboxylate (123 mg, 0.498 mmol) using the reaction and workup conditions as reported in step 10 of Scheme 1 gave after purification by flash column chromatography (silica gel 25 g, eluting with CMA 80 in chloroform 0 to 100%) (2R,4S)-tert-butyl 2-(5-((−)-3-cyclopropyl-1-((S)-1,1-dimethylethylsulfinamido)-1-(pyridin-4-yl)propyl)-2-fluorophenylcarbamoyl)-4-methoxy-4-phenylpyrrolidine-1-carboxylate (45a) (287 mg, 0.414 mmol, 83% yield) as a white solid; $^1$H NMR (300 MHz, DMSO-$d_6$) δ 9.49 (2s, 1H, rotamers), 8.77-8.28 (m, 2H), 8.04 (m, 1H), 7.53-7.08 (m, 8H), 5.48 (m, 1H), 4.35 (m, 1H), 3.77 (s, 1H), 3.41 (s, 2H), 2.85 (2s, 3H, rotamers), 2.78-2.35 (m, 3H), 1.33 (2s, 9H, rotamers), 1.15 (m, 10H), 1.02-0.82 (m, 2H), 0.64 (m, 1H), 0.36 (m, 2H), 0.04-−0.15 (m, 2H); 19F NMR (282 MHz, DMSO-$d_6$) δ −128.09, −129.50 rotamers; MS (ES+) 693.7 (M+1), 715.7 (M+Na), (ES−) 691.7 (M−1), 727.7 (M+Cl); Optical rotation [α]$_D$= (−) 8.0 [0.075, MeOH].

Step-2: Preparation of (2R,4S)-N-(5-(1-amino-3-cyclopropyl-1-(pyridin-4-yl)propyl)-2-fluorophenyl)-4-methoxy-4-phenylpyrrolidine-2-carboxamide (45b)

Reaction of (2R,4S)-tert-butyl 2-(5-((−)-3-cyclopropyl-1-((S)-1,1-dimethylethylsulfinamido)-1-(pyridin-4-yl)propyl)-2-fluorophenylcarbamoyl)-4-methoxy-4-phenylpyrrolidine-1-carboxylate (45a) (280 mg, 0.404 mmol) in methanolic HCl (2.694 mL, 8.08 mmol) followed by workup and purification as reported in step 6 of Scheme 4 gave (2R,4S)-N-(5-(1-amino-3-cyclopropyl-1-(pyridin-4-yl)propyl)-2-fluorophenyl)-4-methoxy-4-phenylpyrrolidine-2-carboxamide (45b) (227 mg, 0.404 mmol, 100% yield) hydrochloride salt which was used as such for next step; MS (ES+) 489.5 (M+1), (ES−) 487.4 (M−1), 523.5 (M+Cl).

Step-3: Preparation of (2R,4S)-N2-(5-((+)-1-amino-3-cyclopropyl-1-(pyridin-4-yl)propyl)-2-fluorophenyl)-N1-(5-chloropyridin-2-yl)-4-methoxy-4-phenylpyrrolidine-1,2-dicarboxamide (45c)

Reaction of (2R,4S)-N-(5-(1-amino-3-cyclopropyl-1-(pyridin-4-yl)propyl)-2-fluorophenyl)-4-methoxy-4-phenylpyrrolidine-2-carboxamide (45b) (111 mg, 0.444 mmol) in tetrahydrofuran (50 mL) with phenyl 5-chloropyridin-2-ylcarbamate (13b) (227 mg, 0.404 mmol) using 1N aqueous sodium bicarbonate (8.08 mL, 8.08 mmol) as base according to procedure reported in step 3 of Scheme 13 gave after purification by flash column chromatography (silica gel, 12 g eluting with CMA 80 in chloroform 0-100%) (2R,4S)-N2-(5-((+)-1-amino-3-cyclopropyl-1-(pyridin-4-yl)propyl)-2-fluorophenyl)-N1-(5-chloropyridin-2-yl)-4-methoxy-4-phenylpyrrolidine-1,2-dicarboxamide (45c) (50 mg, 0.078 mmol, 19.24% yield) as white solid; $^1$H NMR (300 MHz, DMSO-$d_6$) δ 9.46 (s, 1H), 9.23 (s, 1H), 8.59-8.36 (m, 2H), 8.31 (d, J=2.6 Hz, 1H), 7.97-7.88 (m, 2H), 7.81 (dd, J=9.0, 2.6 Hz, 1H), 7.43 (d, J=4.2 Hz, 4H), 7.40-7.32 (m, 3H), 7.21-7.09 (m, 2H), 4.65 (t, J=6.2 Hz, 1H), 4.23 (d, J=10.8 Hz, 1H), 3.90 (d, J=10.8 Hz, 1H), 2.84 (s, 3H), 2.62 (d, J=6.4 Hz, 2H), 2.40-2.25 (m, 2H), 2.26-2.12 (m, 2H), 1.12-0.94 (m, 2H), 0.73-0.54 (m, 1H), 0.43-0.27 (m, 2H), 0.01-−0.17 (m, 2H); $^{19}$F NMR (282 MHz, DMSO-$d_6$) δ −128.48; MS (ES+) 643.6, 645.7 (M+1), (ES−) 641.6, 643.6 (M−1); Optical rotation [α]$_D$=(+) 99.23 [0.26, MeOH].

Scheme 46

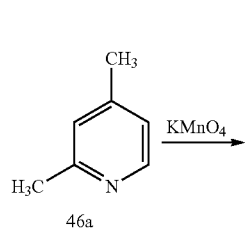
46a

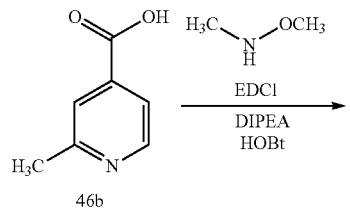
46b

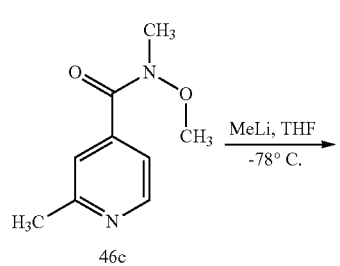
46c

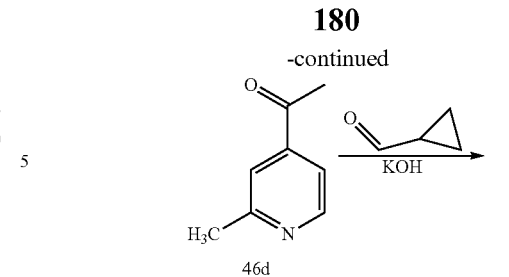
46d

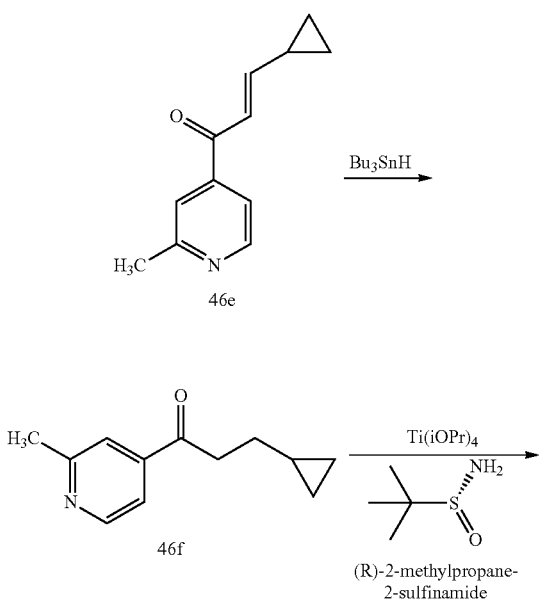
46e

46f (R)-2-methylpropane-2-sulfinamide

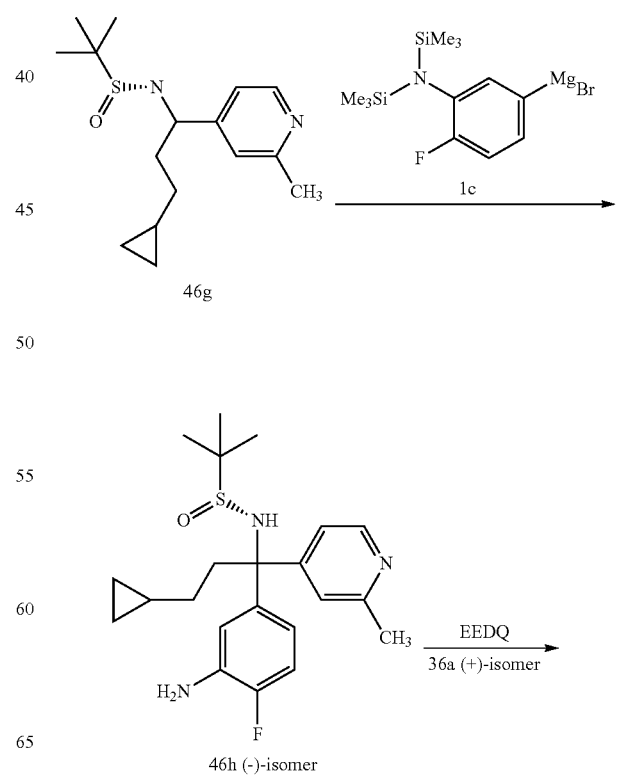
46g

1c 46h (−)-isomer 36a (+)-isomer

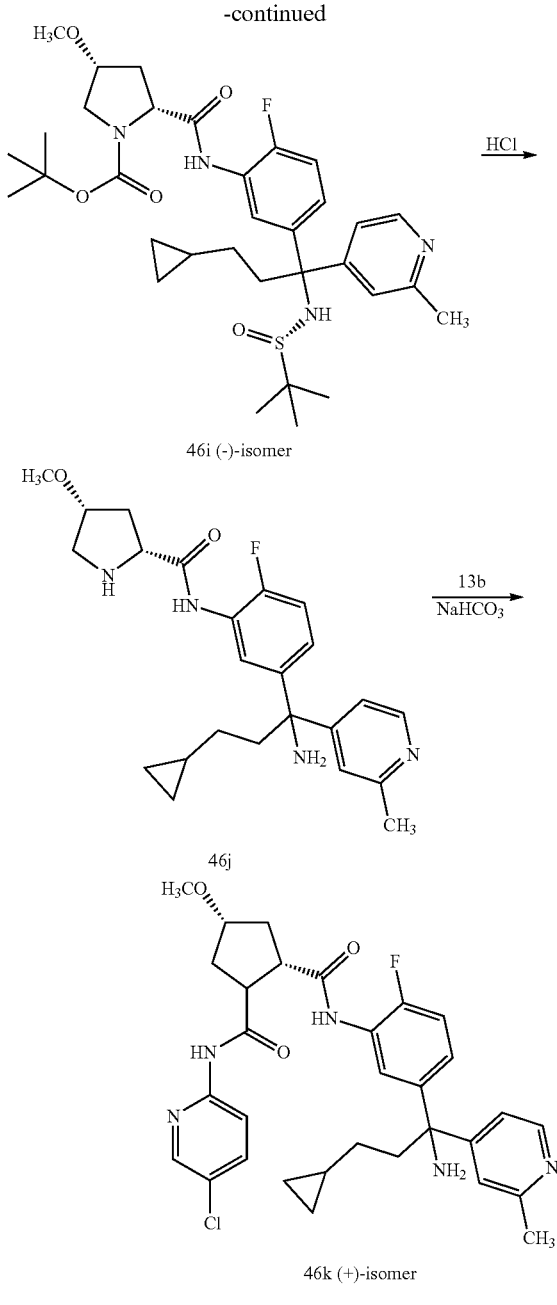

46i (-)-isomer

46j 46k (+)-isomer

Preparation of ((2R,4R)-N2-(5-((+)-1-amino-3-cyclopropyl-1-(2-methylpyridin-4-yl)propyl)-2-fluorophenyl)-N1-(5-chloropyridin-2-yl)-4-methoxypyrrolidine-1,2-dicarboxamide (46k)

Step-1: Preparation of 2-methyl-isonicotinic acid (46b)

To a solution of 2, 4-dimethyl-pyridine (46a) (100 g, 933.245 mmol) in water (1000 mL) was added potassium permanganate (294.97 g, 1866.489 mmol) portion-wise over a period of 2 h. The resulting reaction mixture was heated at 80° C. for 12 h. The reaction mixture was cooled to room temperature, filtered through celite bed and filtrate was concentrated under reduced pressure to a volume of 250 mL at 50° C. The obtained solution was cooled to 0° C. and pH was adjusted to 3 using 1N HCl (temperature between 0° C. to 5° C.). The solid obtained was collected by filtration washed with chilled water and dried to afford 2-methylisonicotinic acid (46b) (22.3 g, yield: 17.42%); $^1$H NMR (D$_2$O) δ 8.52 (s, 1H), 7.94-7.90 (m, 2H), 2.69 (s, 3H); MS (+) 138.1 (M+1).

Step-2: Preparation of N-methoxy-N,2-dimethylisonicotinamide (46c)

To a stirred solution of 2-methylisonicotinic acid (46b) (17.8 g, 129.798 mmol) in N,N-dimethylformamide (180 mL) was added N,N-diisopropylethylamine (67.105 gm, 519.192 mmol) and 1-ethyl-3-(3-dimethylaminopropyl)carbodiimide hydrochloride (EDCI, 40.299 g, 259.596 mmol) and hydroxybenzotriazole (HOBt, 39.753 g, 259.596 mmol) at room temperature. The resulting reaction mixture was stirred for 0.5 h at room temperature followed by the addition of N, O dimethyl hydroxyl amine hydrochloride (13.8 g, 141,479 mmol). The reaction mixture was stirred at room temperature for 12 h, quenched with water (500 mL), extracted with ethyl acetate (5×500 mL). The combined organic layers were dried over sodium sulfate, filtered and concentrated. The residue obtained was purified by column chromatography to afford N-methoxy-N,2-dimethylisonicotinamide (46c) (23 g, 98.4% yield) as a reddish thick solid; $^1$H NMR (CDCl$_3$) δ 8.29-8.27 (s, 1H), 7.08-7.01 (m, 2H), 3.27 (s, 3H), 3.07 (s, 3H), 2.32 (s, 3H); MS (ES+) 181.1 (M+1).

Step-3: Preparation of 1-(2-methylpyridin-4-yl)ethanone (46d)

To a stirred solution of N-methoxy-N,2-dimethylisonicotinamide (46c) (26 g, 144.281 mmol) in THF (520 mL) was added MeLi (6.342 g, 288.562 mmol, 1M solution in THF) under nitrogen atmosphere at −78° C. The reaction mixture was warmed to room temperature over a period of 1 h, quenched with saturated NH$_4$Cl solution at 0° C. The resulting reaction mixture was extracted with ethyl acetate and the organic layer was washed with water and brine, dried over sodium sulfate, filtered and concentrated. The residue obtained was purified by column chromatography to afford 1-(2-methylpyridin-4-yl)ethanone (46d) (11 g, 56.4% yield) as a reddish thick liquid; $^1$H NMR (CDCl$_3$) δ 8.61-8.59 (d, 1H), 7.51-7.45 (d, 1H), 7.45-7.44 (m, 1H), 4.05-4.02 (s, 3H); MS (ES+) 136.1 (M+1).

Step-4: Preparation of 3-cyclopropyl-1-(2-methyl-pyridin-4-yl)prop-2-en-1-one (46e)

Compound 46e was prepared from 1-(2-methylpyridin-4-yl)ethanone (46d) (11.g, 81.383 mmol) according to the procedure reported in step 1 of scheme 31 gave after purification by column chromatography 3-cyclopropyl-1-(2-methylpyridin-4-yl)prop-2-en-1-one (46e) (4.5 g, 29.5% yield) as a reddish liquid; MS (ES+) 188.1 (M+1).

Step-5: Preparation of 3-cyclopropyl-1-(2-methyl-pyridin-4-yl)propan-1-one (46f)

Compound 46f was prepared from 3-cyclopropyl-1-pyridin-4-yl-propenone (46e) (8 g, 42.726 mmol) according to the procedure reported in step 2 of scheme 31 gave after purification by column chromatography 3-cyclopropyl-1-(2-methylpyridin-4-yl)propan-1-one (46f) (5.5 g 68.1% yield) as yellow liquid; $^1$H NMR (CDCl$_3$) δ 8.61-8.59 (d, 1H), 7.53-7.48 (m, 1H), 7.46-7.20 (m, 1H), 3.02-2.97 (m, 2H), 2.58 (s, 3H), 1.60-1.53 (m, 2H), 0.85-0.71 (m, 1H), 0.71-0.67 (m, 2H), 0.42-0.37 (m, 2H); MS (ES+) 190.2 (M+1).

Step-6: Preparation of (R)-N-(3-cyclopropyl-1-(2-methylpyridin-4-yl)propylidene)-2-methylpropane-2-sulfinamide (46g)

Compound 46g was prepared from 3-cyclopropyl-1-(2-methylpyridin-4-yl)propan-1-one (46f) (5.5 g, 29.062 mmol) and R-2-methyl propane-2-sulfinamide (4.209 g, 34.729 mmol) according to the procedure reported in step 3 of scheme 31 gave after purification by column chromatography (R)-N-(3-cyclopropyl-1-(2-methylpyridin-4-yl)propylidene)-2-methylpropane-2-sulfinamide (46g) (7 g, 82.44% yield) as a yellow liquid; $^1$H NMR (CDCl$_3$) δ 8.59-8.49 (m, 1H), 7.51-7.33 (m, 2H), 3.32-2.98 (m, 2H), 2.54 (s, 3H), 1.54-1.49 (m, 2H), 1.42-1.13 (m, 9H), 0.85-0.71 (m, 1H), 0.71-0.67 (m, 2H), 0.42-0.37 (m, 2H); MS (ES+) 293.2 (M+1).

Step-7: Preparation of (R)-N-((−)-1-(3-amino-4-fluorophenyl)-3-cyclopropyl-1-(2-methylpyridin-4-yl)propyl)-2-methylpropane-2-sulfinamide (46h)

Compound 46h was prepared from (R)-N-(3-cyclopropyl-1-(2-methylpyridin-4-yl)propylidene)-2-methylpropane-2-sulfinamide (46g) (5.5 g, 29.062 mmol) and R-2-methyl propane-2-sulfinamide (2 g, 6.839 mmol) and freshly prepared (3-(bis(trimethylsilyl)amino)-4-fluorophenyl)magnesium bromide (1c) (19.10 mL, 15.28 mmol) according to the procedure reported in step 4 of scheme 31 gave after purification by column chromatography (R)-N-((−)-1-(3-amino-4-fluorophenyl)-3-cyclopropyl-1-(2-methylpyridin-4-yl)propyl)-2-methylpropane-2-sulfinamide (46h) (0.8 g, 29.0% yield) as a reddish thick liquid; $^1$H NMR (DMSO-d$_6$) δ 8.36-8.34 (d, 1H), 7.24 (s, 1H), 7.12-7.10 (d, 1H), 6.95-6.88 (m, 1H), 6.76-6.73 (m, 1H), 5.38-5.32 (s, 1H), 5.17-5.11 (s, 2H), 2.58-2.45 (s, 3H), 2.05-2.01 (m, 2H), 1.55-1.51 (m, 2H), 1.28-1.10 (m, 9H), 0.67-0.45 (m, 1H), 0.39-0.37 (m, 2H), 0.03-0.00 (m, 2H); MS (ES+) 404.3 (M+1); Optical rotation [α]$_D$=(−) 55.0 [0.28,MeOH]

Step-8: Preparation of (2R,4R)-tert-butyl 2-(5-((−)-3-cyclopropyl-1-((R)-1,1-dimethylethylsulfinamido)-1-(2-methylpyridin-4-yl)propyl)-2-fluorophenylcarbamoyl)-4-methoxypyrrolidine-1-carboxylate (46i)

Reaction of (2R,4R)-1-(tert-butoxycarbonyl)-4-methoxypyrrolidine-2-carboxylic acid (36a) (245 mg, 1.0 mmol), (R)-N-((−)-1-(3-amino-4-fluorophenyl)-3-cyclopropyl-1-(2-methylpyridin-4-yl)propyl)-2-methylpropane-2-sulfinamide (46h) (404 mg, 1.0 mmol) in tetrahydrofuran (50 mL) using ethyl 2-ethoxyquinoline-1(2H)-carboxylate (247 mg, 1.0 mmol) using the reaction and workup conditions as reported in step 10 of Scheme 1 gave after purification by flash column chromatography (2R,4R)-tert-butyl 2-(5-((−)-3-cyclopropyl-1-((R)-1,1-dimethylethylsulfinamido)-1-(2-methylpyridin-4-yl)propyl)-2-fluorophenylcarbamoyl)-4-methoxypyrrolidine-1-carboxylate (46i) (485 mg, 0.769 mmol, 77% yield) as a colorless solid; $^1$H NMR (300 MHz, DMSO-d6) δ 9.47 (2s, 1H, rotamers), 8.33 (d, J=5.4 Hz, 1H), 8.09-7.77 (m, 1H), 7.26-7.15 (m, 3H), 7.08 (dd, J=5.3, 1.7 Hz, 1H), 5.41 (2s, 1H, rotamers), 4.46-4.16 (m, 1H), 3.97 (dd, J=9.1, 4.1 Hz, 1H), 3.57 (dd, J=11.0, 5.4 Hz, 1H), 3.36-3.24 (m, 1H), 3.21 (m, 3H), 2.65-2.53 (m, 1H), 2.45-2.39 (m, 4H), 2.01-1.84 (m, 1H), 1.33 (2s, 9H, rotamers), 1.14 (m, 10H), 0.90 (m, 2H), 0.71-0.54 (m, 1H), 0.42-0.32 (m, 2H), −0.00--0.17 (m, 2H); $^{19}$F NMR (282 MHz, DMSO-d6) δ −127.87 (q, J=8.1, 7.2 Hz), −128.88 rotamers; MS (ES+) 631.7 (M+1), 653.7 (M+Na), (ES−) 629.6 (M−1); Optical rotation [α]$_D$=(−) 50.2 [0.175, MeOH].

Step-9: Preparation of (2R,4R)-N-(5-(-1-amino-3-cyclopropyl-1-(2-methylpyridin-4-yl)propyl)-2-fluorophenyl)-4-methoxypyrrolidine-2-carboxamide (46j)

Reaction of (2R,4R)-tert-butyl 2-(5-((−)-3-cyclopropyl-1-((R)-1,1-dimethylethylsulfinamido)-1-(2-methylpyridin-4-yl)propyl)-2-fluorophenylcarbamoyl)-4-methoxypyrrolidine-1-carboxylate (46i) (475 mg, 0.753 mmol) in 3N methanolic HCl (5.020 mL, 15.06 mmol) followed by workup and purification as reported in step 6 of Scheme 4 gave (2R,4R)-N-(5-(-1-amino-3-cyclopropyl-1-(2-methylpyridin-4-yl)propyl)-2-fluorophenyl)-4-methoxypyrrolidine-2-carboxamide (46j) (376 mg, 0.753 mmol, 100% yield) hydrochloride salt as on off white solid; $^1$H NMR (300 MHz, DMSO-d$_6$) δ 10.69 (s, 1H), 10.40 (s, 1H), 9.76 (s, 3H), 9.55 (bs, 1H), 8.90-8.67 (m, 2H), 7.89-7.76 (m, 2H), 7.76-7.62 (m, 1H), 7.53-7.28 (m, 2H), 4.61-4.43 (m, 1H), 4.22-3.98 (m, 1H), 3.49-3.33 (m, 1H), 3.33-3.22 (m, 1H), 3.17 (s, 3H), 2.69 (d, J=6.8 Hz, 3H), 2.66-2.50 (m, 1H), 2.50-2.39 (m, 1H), 2.31-2.12 (m, 1H), 1.34-1.15 (m, 1H), 1.16-0.94 (m, 1H), 0.79-0.60 (m, 1H), 0.46-0.33 (m, 2H), 0.10-0.00 (m, 2H); $^{19}$F NMR (282 MHz, DMSO-d$_6$) δ −122.19; MS (ES+) 427.5 (M+1), (ES−) 425.5 (M−1), 461.4 (M+Cl).

Step-10: Preparation of ((2R,4R)-N2-(5-((+)-1-amino-3-cyclopropyl-1-(2-methylpyridin-4-yl)propyl)-2-fluorophenyl)-N1-(5-chloropyridin-2-yl)-4-methoxypyrrolidine-1,2-dicarboxamide (46k)

Reaction of gave (2R,4R)-N-(5-(-1-amino-3-cyclopropyl-1-(2-methylpyridin-4-yl)propyl)-2-fluorophenyl)-4-methoxypyrrolidine-2-carboxamide (46j) (370 mg, 0.741 mmol) in tetrahydrofuran (55 mL) with phenyl 5-chloropyridin-2-ylcarbamate (13b) (203 mg, 0.815 mmol) using sodium bicarbonate (14.82 mL, 14.82 mmol, 1N aqueous) as base according to procedure reported in step 3 of Scheme 13 gave after purification by flash column chromatography ((2R,4R)-N2-(5-((+)-1-amino-3-cyclopropyl-1-(2-methylpyridin-4-yl)propyl)-2-fluorophenyl)-N1-(5-chloropyridin-2-yl)-4-methoxypyrrolidine-1,2-dicarboxamide (46k) (190 mg, 0.327 mmol, 44.1% yield) as white solid; $^1$H NMR (300 MHz, DMSO-d$_6$) δ 9.45 (s, 1H), 9.15 (s, 1H), 8.33-8.24 (m, 2H), 7.95-7.82 (m, 2H), 7.81 (dd, J=9.0, 2.6 Hz, 1H), 7.24 (d, J=1.7 Hz, 1H), 7.16-7.09 (m, 3H), 4.57 (dd, J=9.2, 3.9 Hz, 1H), 4.11-3.97 (m, 1H), 3.85-3.63 (m, 2H), 3.20 (s, 3H), 2.48-2.38 (m, 1H), 2.40 (s, 3H), 2.35-2.21 (m, 2H), 2.24-2.03 (m, 3H), 1.11-0.93 (m, 2H), 0.73-0.51 (m, 1H), 0.41-0.25 (m, 2H), −0.02--0.14 (m, 2H); $^{19}$F NMR (282 MHz, DMSO-d$_6$) δ −128.45; MS (ES+) 581.6, 583.6 (M+1), 603.6 (M+Na), 579.5 (M−1), 615.5, 617.5 (M+Cl); Optical rotation [α]$_D$=(+) 92.12 [0.33,MeOH]; Analysis calculated for $C_{30}H_{34}ClFN_6O_3 \cdot 0.75H_2O$: C, 60.60; H, 6.02; N, 14.13. Found: C, 60.90; H, 6.00; N, 14.17.

Scheme 47

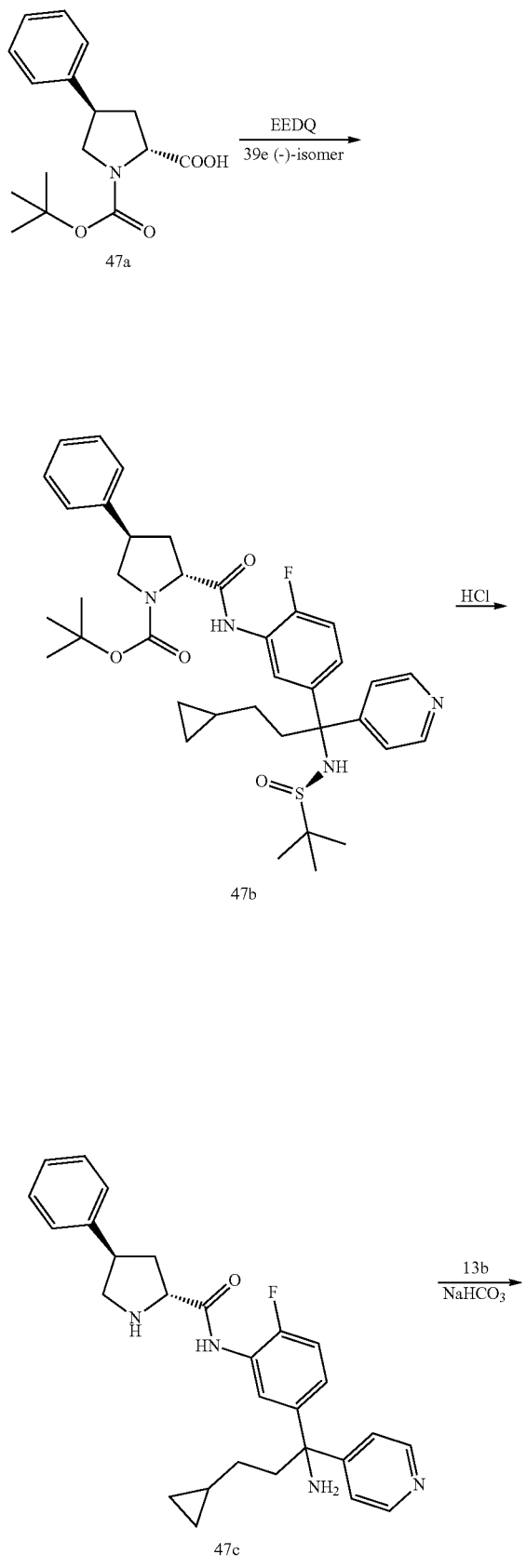

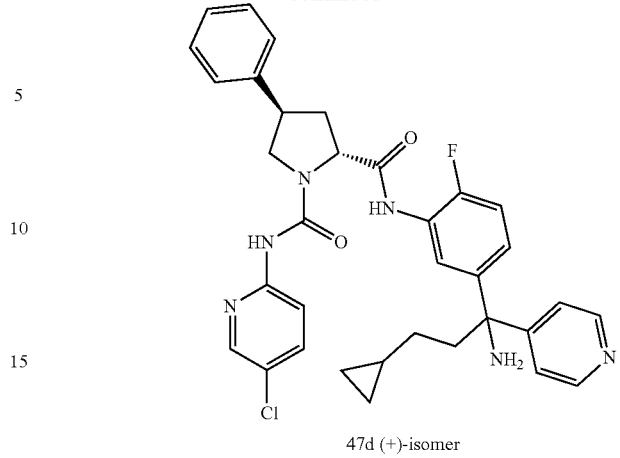

Preparation of (2R,4R)-N2-(5-((+)-1-amino-3-cyclopropyl-1-(pyridin-4-yl)propyl)-2-fluorophenyl)-N1-(5-chloropyridin-2-yl)-4-phenylpyrrolidine-1,2-dicarboxamide (47d)

Step-1: Preparation of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-phenylpyrrolidine-1-carboxylate (47b)

Reaction of (2R,4R)-1-(tert-butoxycarbonyl)-4-phenylpyrrolidine-2-carboxylic acid (47a) (230 mg, 0.789 mmol), (R)-N-((−)-1-(3-amino-4-fluorophenyl)-3-cyclopropyl-1-(pyridin-4-yl)propyl)-2-methylpropane-2-sulfinamide (39e) (308 mg, 0.789 mmol) in tetrahydrofuran (10 mL) using ethyl 2-ethoxyquinoline-1(2H)-carboxylate (195 mg, 0.789 mmol) using the reaction and workup conditions as reported in step 10 of Scheme 1 gave after purification by flash column chromatography (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-phenylpyrrolidine-1-carboxylate (47b) (255 mg, 0.385 mmol, 48.7% yield) as a clear oil. MS (ES+) 663.7 (M+1).

Step-2: Preparation of (2R,4R)-N-(5-(1-amino-3-cyclopropyl-1-(pyridin-4-yl)propyl)-2-fluorophenyl)-4-phenylpyrrolidine-2-carboxamide (47c)

Reaction of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-phenylpyrrolidine-1-carboxylate (47b) (255 mg, 0.385 mmol) in methanol (10 mL) using 4N HCl in dioxane (1.282 mL, 3.85 mmol) followed by workup and purification as reported in step 6 of Scheme 4 gave (2R,4R)-N-(5-(1-amino-3-cyclopropyl-1-(pyridin-4-yl)propyl)-2-fluorophenyl)-4-phenylpyrrolidine-2-carboxamide (47c) (95 mg, 0.207 mmol, 53.9% yield) as a clear oil. $^1$H NMR (300 MHz, CDCl$_3$) δ 10.26 (s, 1H), 8.65-8.57 (m, 1H), 8.54 (d, J=6.0 Hz, 2H), 7.41-7.30 (m, 4H), 7.30-7.21 (m, 3H), 7.12-6.95 (m, 2H), 4.15 (dd, J=9.8, 2.8 Hz, 1H), 3.56-3.44 (m, 1H), 3.42-3.25 (m, 1H), 3.17 (t, J=9.3 Hz, 1H), 2.67-2.52 (m, 4H), 2.42-2.30 (m, 3H), 1.29-1.03 (m, 2H), 0.80-0.59 (m, 1H), 0.53-0.34 (m, 2H), −0.00 (m, 2H); $^{19}$F NMR (282 MHz, CDCl$_3$) δ −132.94; MS (ES+) 459.4 (M+1).

187

Step-3: Preparation of (2R,4R)-N2-(5-((+)-1-amino-3-cyclopropyl-1-(pyridin-4-yl)propyl)-2-fluorophenyl)-N1-(5-chloropyridin-2-yl)-4-phenylpyrrolidine-1,2-dicarboxamide (47d)

Reaction of (2R,4R)-N-(5-(1-amino-3-cyclopropyl-1-(pyridin-4-yl)propyl)-2-fluorophenyl)-4-phenylpyrrolidine-2-carboxamide (47c) (95 mg, 0.207 mmol) in tetrahydrofuran (10 mL) with phenyl 5-chloropyridin-2-ylcarbamate (13b) (46.4 mg, 0.186 mmol) using potassium carbonate (71.6 mg, 0.518 mmol) as base according to procedure reported in step 3 of Scheme 13 gave after purification by flash column chromatography (silica gel, 12 g eluting with CMA 80 in chloroform 0-50%) (2R,4R)-N2-(5-((+)-1-amino-3-cyclopropyl-1-(pyridin-4-yl)propyl)-2-fluorophenyl)-N1-(5-chloropyridin-2-yl)-4-phenylpyrrolidine-1,2-dicarboxamide (47d) (68 mg, 0.111 mmol, 53.5% yield) free base as a white solid, which was converted into hydrochloride salt (72 mg, 0.105 mmol, 50.7% yield) with HCl (3N in MeOH, 3 mL). $^1$H NMR (300 MHz, DMSO-d6) δ 10.23-10.13 (m, 1H), 9.79 (s, 3H), 9.26 (s, 1H), 9.01-8.88 (m, 2H), 8.30 (dd, J=2.6, 0.8 Hz, 1H), 8.10 (dd, J=7.2, 2.5 Hz, 1H), 7.97-7.77 (m, 4H), 7.46-7.19 (m, 7H), 4.95-4.76 (m, 1H), 4.28-4.02 (m, 1H), 3.63-3.58 (m, 1H), 2.62-2.53 (m, 2H), 2.32 (td, J=15.7, 12.5, 6.1 Hz, 3H), 1.31-1.00 (m, 2H), 0.69 (m, 1H), 0.48-0.31 (m, 2H), 0.09-0.01 (m, 2H); $^{19}$F NMR (282 MHz, DMSO) δ −123.88; MS (ES+) 613.5 (M+1); Optical rotation [α]$_D$=(+) 101.4 [0.28, MeOH].

Scheme 48

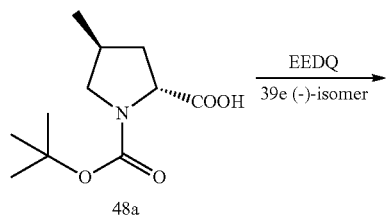

48a

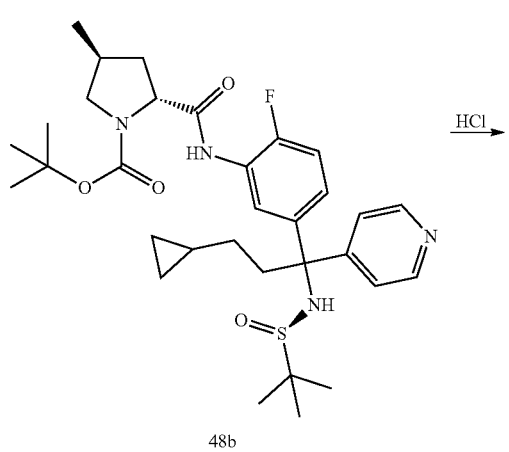

48b

188

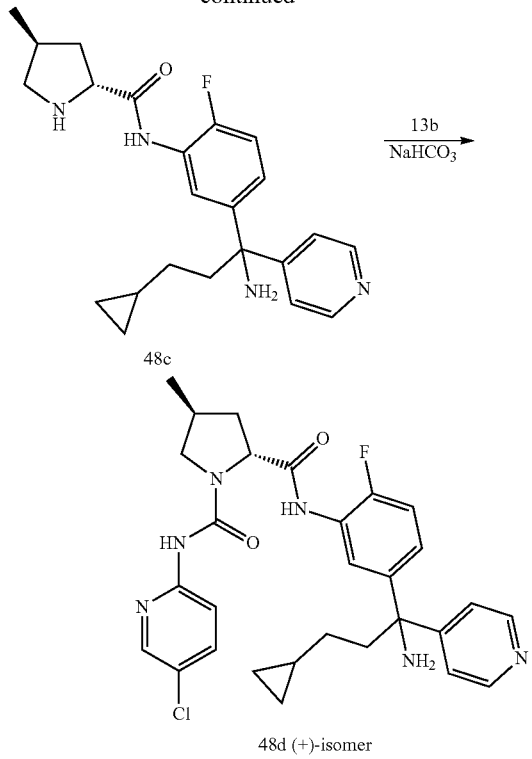

48c 48d (+)-isomer

Preparation of (2R,4S)-N2-(5-((+)-1-amino-3-cyclopropyl-1-(pyridin-4-yl)propyl)-2-fluorophenyl)-N1-(5-chloropyridin-2-yl)-4-methylpyrrolidine-1,2-dicarboxamide (48d)

Step-1: Preparation of (2R,4S)-tert-butyl 2-(5-(3-cyclopropyl-1-((R)-1,1-dimethylethylsulfinamido)-1-(pyridin-4-yl)propyl)-2-fluorophenylcarbamoyl)-4-methylpyrrolidine-1-carboxylate (48b)

Reaction of (2R,4S)-1-(tert-butoxycarbonyl)-4-methylpyrrolidine-2-carboxylic acid (48a) (145 mg, 0.632 mmol), (R)-N-((−)-1-(3-amino-4-fluorophenyl)-3-cyclopropyl-1-(pyridin-4-yl)propyl)-2-methylpropane-2-sulfinamide (39e) (246 mg, 0.632 mmol) in tetrahydrofuran (10 mL) using ethyl 2-ethoxyquinoline-1(2H)-carboxylate (156 mg, 0.632 mmol) using the reaction and workup conditions as reported in step 10 of Scheme 1 gave after purification by flash column chromatography (silica gel, eluting with 0-60% EtOAc in Hexane) (2R,4S)-tert-butyl 2-(5-(3-cyclopropyl-1-((R)-1,1-dimethylethylsulfinamido)-1-(pyridin-4-yl)propyl)-2-fluorophenylcarbamoyl)-4-methylpyrrolidine-1-carboxylate (48b) (248 mg, 0.413 mmol, 65.3% yield) as a clear oil. MS (ES+) 601.7 (M+1).

Step-2: Preparation of (2R,4S)-N-(5-(1-amino-3-cyclopropyl-1-(pyridin-4-yl)propyl)-2-fluorophenyl)-4-methylpyrrolidine-2-carboxamide (48c)

Reaction of (2R,4S)-tert-butyl 2-(5-(3-cyclopropyl-1-((R)-1,1-dimethylethylsulfinamido)-1-(pyridin-4-yl)propyl)-2-fluorophenylcarbamoyl)-4-methylpyrrolidine-1-carboxylate (48b) (246 mg, 0.409 mmol) in methanol (10 mL) using 4N HCl in dioxane (1.365 mL, 4.09 mmol) followed by workup and purification as reported in step 6 of Scheme 4 gave (2R,4S)-N-(5-(1-amino-3-cyclopropyl-1-(pyridin-4-yl)propyl)-2-fluorophenyl)-4-methylpyrrolidine-2-carboxamide (48c) (100 mg, 0.252 mmol, 61.6% yield) as a clear oil. 1H NMR (300 MHz, CDCl$_3$) δ 10.22 (s, 1H), 8.61-8.44 (m, 3H), 7.43-7.25 (m, 3H), 7.13-6.91 (m, 2H), 4.13-4.01 (m, 1H), 3.31-3.13 (m, 1H), 2.79-2.67 (m, 1H), 2.44-2.32 (m, 3H), 2.32-2.17 (m, 2H), 1.96-1.76 (m, 1H), 1.27-0.95 (m, 6H), 0.80-0.71 (m, 1H), 0.71-0.60 (m, 1H), 0.54-0.31 (m, 2H), 0.00 (s, 2H); 19F NMR (282 MHz, CDCl$_3$) δ −132.78; MS (ES+) 551.5 (M+1).

Step-3: Preparation of (2R,4S)-N2-(5-((+)-1-amino-3-cyclopropyl-1-(pyridin-4-yl)propyl)-2-fluorophenyl)-N1-(5-chloropyridin-2-yl)-4-methylpyrrolidine-1,2-dicarboxamide (48d)

Reaction of (2R,4S)-N-(5-(1-amino-3-cyclopropyl-1-(pyridin-4-yl)propyl)-2-fluorophenyl)-4-methylpyrrolidine-2-carboxamide (48c) (95 mg, 0.207 mmol) in tetrahydrofuran (10 mL) with phenyl 5-chloropyridin-2-ylcarbamate (13b) (46.4 mg, 0.186 mmol) using potassium carbonate (71.6 mg, 0.518 mmol) as base according to procedure reported in step 3 of Scheme 13 gave after purification by flash column chromatography (silica gel, 12 g eluting with CMA 80 in chloroform 0-50%) (2R,4S)-N2-(5-((+)-1-amino-3-cyclopropyl-1-(pyridin-4-yl)propyl)-2-fluorophenyl)-N1-(5-chloropyridin-2-yl)-4-methylpyrrolidine-1,2-dicarboxamide (48d) (68 mg, 0.111 mmol, 53.5% yield) free base as a white solid, which was converted into hydrochloride salt (72 mg, 0.105 mmol, 50.7% yield) with HCl (3N in MeOH, 3 mL). $^1$H NMR (300 MHz, DMSO-d$_6$) δ 10.23-10.13 (m, 1H), 9.79 (s, 3H), 9.26 (s, 1H), 9.01-8.88 (m, 2H), 8.30 (dd, J=2.6, 0.8 Hz, 1H), 8.10 (dd, J=7.2, 2.5 Hz, 1H), 7.97-7.77 (m, 4H), 7.46-7.19 (m, 7H), 4.95-4.76 (m, 1H), 4.28-4.02 (m, 1H), 3.63-3.58 (m, 1H), 2.62-2.53 (m, 2H), 2.32 (td, J=15.7, 12.5, 6.1 Hz, 3H), 1.31-1.00 (m, 2H), 0.69 (m, 1H), 0.48-0.31 (m, 2H), 0.09-0.01 (m, 2H); $^{19}$F NMR (282 MHz, DMSO-d$_6$) δ −123.88; MS (ES+) 613.5 (M+1); Optical rotation [α]$_D$=(+) 144.4 [0.29, MeOH].

Scheme 49

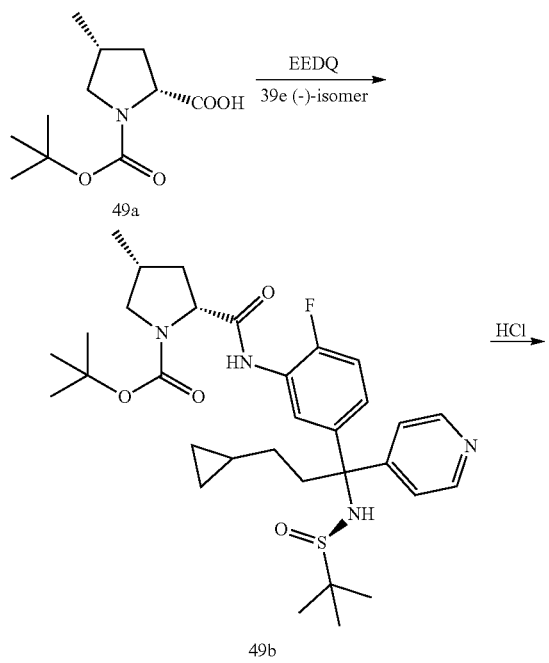

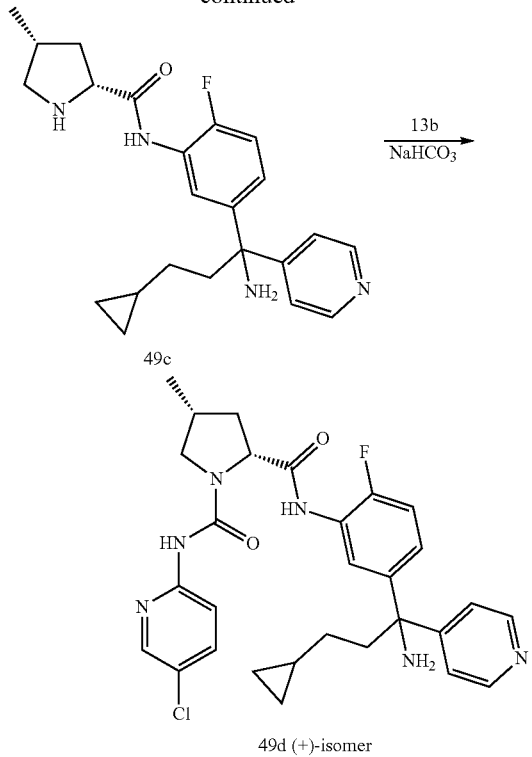

49d (+)-isomer

Preparation of (2R,4R)-N2-(5-((+)-1-amino-3-cyclopropyl-1-(pyridin-4-yl)propyl)-2-fluorophenyl)-N1-(5-chloropyridin-2-yl)-4-methylpyrrolidine-1,2-dicarboxamide (49d)

Step-1: Preparation of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methylpyrrolidine-1-carboxylate (49b)

Reaction of (2R,4R)-1-(tert-butoxycarbonyl)-4-methylpyrrolidine-2-carboxylic acid (49a) (90 mg, 0.393 mmol), (R)-N-((−)-1-(3-amino-4-fluorophenyl)-3-cyclopropyl-1-(pyridin-4-yl)propyl)-2-methylpropane-2-sulfinamide (39e) (153 mg, 0.393 mmol) in tetrahydrofuran (10 mL) using ethyl 2-ethoxyquinoline-1(2H)-carboxylate (97 mg, 0.393 mmol) using the reaction and workup conditions as reported in step 10 of Scheme 1 gave (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methylpyrrolidine-1-carboxylate (49b) crude (160 mg, 67.8%), which was used as such in next step without further purification. MS (ES+) 601.7 (M+1).

Step-2: Preparation of (2R,4R)-N-(5-(1-amino-3-cyclopropyl-1-(pyridin-4-yl)propyl)-2-fluorophenyl)-4-methylpyrrolidine-2-carboxamide (49c)

Reaction of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methylpyrrolidine-1-carboxylate (49b) (160 mg, 0.266 mmol) in methanol (10 mL) using 4N HCl in dioxane (0.888 mL, 2.66 mmol) followed by workup and purification as reported in step 6 of Scheme 4 gave (2R,4R)-N-(5-(1-amino-3-cyclopropyl-1-(pyridin-4- yl)propyl)-2-fluorophenyl)-4-methylpyrrolidine-2-carboxamide (49c) crude (66 mg, 62.5% yield), which was used as such in next step without further purification. MS (ES+) 419.4 (M+Na).

Step-3: Preparation of (2R,4R)-N2-(5-((+)-1-amino-3-cyclopropyl-1-(pyridin-4-yl)propyl)-2-fluorophenyl)-N1-(5-chloropyridin-2-yl)-4-methylpyrrolidine-1,2-dicarboxamide (49d)

Reaction of (2R,4R)-N-(5-(1-amino-3-cyclopropyl-1-(pyridin-4-yl)propyl)-2-fluorophenyl)-4-methylpyrrolidine-2-carboxamide (49c) (66 mg, 0.166 mmol) in tetrahydrofuran (10 mL) with phenyl 5-chloropyridin-2-ylcarbamate (13b) (37.3 mg, 0.150 mmol) using potassium carbonate (57.5 mg, 0.416 mmol) as base according to procedure reported in step 3 of Scheme 13 gave after purification by flash column chromatography (silica gel, 12 g eluting with CMA 80 in chloroform 0-50%) (2R,4R)-N2-(5-((+)-1-amino-3-cyclopropyl-1-(pyridin-4-yl)propyl)-2-fluorophenyl)-N1-(5-chloropyridin-2-yl)-4-methylpyrrolidine-1,2-dicarboxamide (49d) free base as a white solid, which was converted into hydrochloride salt (12 mg, 0.019 mmol, 11.55% yield) with HCl (3N in MeOH, 3 mL); $^1$H NMR (300 MHz, DMSO-$d_6$) δ 9.99 (s, 1H), 9.38 (s, 3H), 9.14 (s, 1H), 8.75 (d, J=5.9 Hz, 2H), 8.28 (dd, J=2.6, 0.9 Hz, 1H), 8.03 (dd, J=7.3, 2.5 Hz, 1H), 7.87-7.68 (m, 2H), 7.51 (d, J=5.5 Hz, 2H), 7.38 (dd, J=10.5, 8.8 Hz, 1H), 7.13 (d, J=8.0 Hz, 1H), 4.60 (t, J=8.1 Hz, 1H), 3.90-3.74 (m, 1H), 3.10 (t, J=9.9 Hz, 1H), 2.67-2.20 (m, 4H), 1.44 (m, 1H), 1.30-1.08 (m, 2H), 1.03 (d, J=6.3 Hz, 3H), 0.68 (m, 1H), 0.37 (m, 2H), 0.01 (m, 2H); $^{19}$F NMR (282 MHz, DMSO) δ -124.26; MS (ES+) 551.5 (M+1); Optical rotation [α]$_D$=(+) 130.9 [0.055, MeOH].

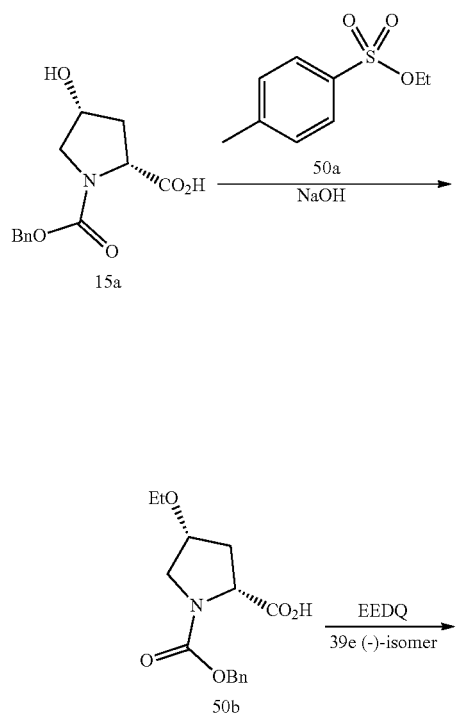

Scheme 50

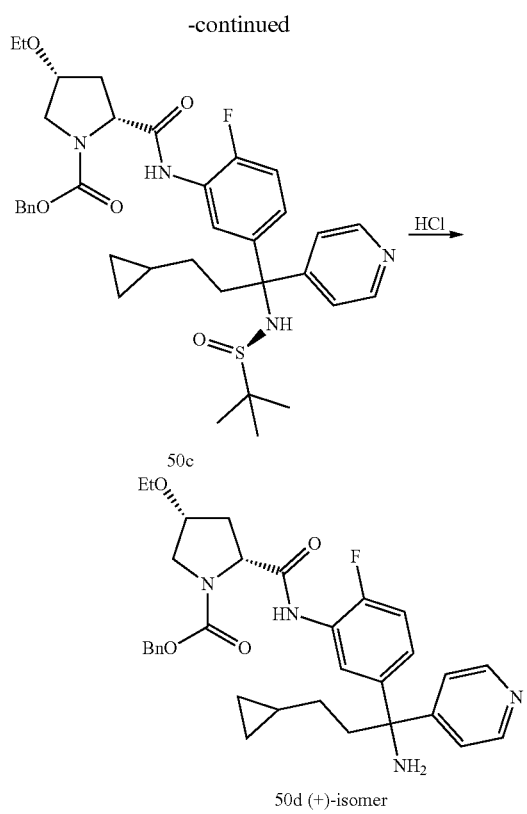

Preparation of (2R,4R)-benzyl 2-(5-((+)-1-amino-3-cyclopropyl-1-(pyridin-4-yl)propyl)-2-fluorophenylcarbamoyl)-4-ethoxypyrrolidine-1-carboxylate (50d)

Step-1: Preparation of (2R,4R)-1-(benzyloxycarbonyl)-4-ethoxypyrrolidine-2-carboxylic acid (50b)

To a solution of (2R,4R)-1-(benzyloxycarbonyl)-4-hydroxypyrrolidine-2-carboxylic acid (15a) (1.14 g, 4.30 mmol) in THF (20 mL) was added a solution of ethyl 4-methylbenzenesulfonate (50a) (1.721 g, 8.60 mmol) in THF (2 mL), followed by NaOH (0.688 g, 17.19 mmol) and water (5 mL). The resulting mixture was heated to 55° C. overnight and concentrated in vacuum to dryness. The residue was dissolved in water (10 mL), washed with dichloromethane (3×25 mL) and acidified to pH 2 with HCl (1.5N). The reaction mixture was extracted with dichloromethane (3×25 mL) and organic layers were combined, dried over MgSO4, filtered and concentrated in vacuum. The residue was purified by flash chromatography (silica gel, eluting with 0-20% MeOH in chloroform) to obtain (2R,4R)-1-(benzyloxycarbonyl)-4-ethoxypyrrolidine-2-carboxylic acid (50b) (301 mg, 1.026 mmol, 23.88% yield) as a clear oil. MS (ES+) 316.3 (M+Na).

Step-2: Preparation of (2R,4R)-benzyl 2-(5-(3-cyclopropyl-1-((R)-1,1-dimethylethylsulfinamido)-1-(pyridin-4-yl)propyl)-2-fluorophenylcarbamoyl)-4-ethoxypyrrolidine-1-carboxylate (50c)

Reaction of (2R,4R)-1-(benzyloxycarbonyl)-4-ethoxypyrrolidine-2-carboxylic acid (50b) (300 mg, 1.023 mmol), (R)-N-((-)-1-(3-amino-4-fluorophenyl)-3-cyclopropyl-1-(pyridin-4-yl)propyl)-2-methylpropane-2-sulfinamide (39e)

(398 mg, 1.023 mmol) in tetrahydrofuran (10 mL) using ethyl 2-ethoxyquinoline-1(2H)-carboxylate (253 mg, 1.023 mmol) using the reaction and workup conditions as reported in step 10 of Scheme 1 gave (2R,4R)-benzyl 2-(5-(3-cyclopropyl-1-((R)-1,1-dimethylethylsulfinamido)-1-(pyridin-4-yl)propyl)-2-fluorophenylcarbamoyl)-4-ethoxypyrrolidine-1-carboxylate (50c) (240 mg, 0.361 mmol, 35.3% yield) as a clear oil. $^1$H NMR (300 MHz, DMSO-$d_6$) δ 9.51 (d, J=24.2 Hz, 1H), 8.49 (d, J=4.4 Hz, 2H), 7.87 (s, 1H), 7.45-7.27 (m, 5H), 7.27-7.07 (m, 5H), 5.52 (d, J=12.7 Hz, 1H), 5.06 (dd, J=21.2, 3.4 Hz, 2H), 4.45 (d, J=4.0 Hz, 1H), 4.07 (s, 1H), 3.67 (d, J=6.0 Hz, 1H), 3.38 (d, J=6.5 Hz, 2H), 2.05 (s, 1H), 1.13 (s, 11H), 1.04-0.94 (m, 3H), 0.83 (m, 2H), 0.62 (s, 1H), 0.34 (s, 2H), −0.08 (s, 2H); MS (ES+) 665.5 (M+1).

Step-3: (2R,4R)-benzyl 2-(5-((+)-1-amino-3-cyclopropyl-1-(pyridin-4-yl)propyl)-2-fluorophenylcarbamoyl)-4-ethoxypyrrolidine-1-carboxylate (50d)

Reaction of (2R,4R)-benzyl 2-(5-(3-cyclopropyl-1-((R)-1,1-dimethylethylsulfinamido)-1-(pyridin-4-yl)propyl)-2-fluorophenylcarbamoyl)-4-ethoxypyrrolidine-1-carboxylate (50c) (50 mg, 0.075 mmol) in methanol (5 mL) using 3N HCl in methanol (0.15 mL, 0.451 mmol) followed by workup and purification as reported in step 6 of Scheme 4 gave (2R,4R)-benzyl 2-(5-((+)-1-amino-3-cyclopropyl-1-(pyridin-4-yl)propyl)-2-fluorophenylcarbamoyl)-4-ethoxypyrrolidine-1-carboxylate (50d) (24 mg, 0.043 mmol, 56.9% yield) as a white solid; $^1$H NMR (300 MHz, DMSO-$d_6$) δ 9.73 (d, J=17.2 Hz, 1H), 9.64-9.53 (m, 6H), 8.82 (d, J=5.4 Hz, 2H), 7.99-7.82 (m, 1H), 7.65 (m, 3H), 7.42-7.32 (m, 3H), 7.29-7.12 (m, 3H), 5.15-4.97 (m, 2H), 4.47 (m, 1H), 4.09 (s, 1H), 3.71 (s, 1H), 3.39 (q, J=7.0 Hz, 3H), 2.01 (m, 1H), 1.27-1.04 (m, 2H), 1.00 (t, J=7.0 Hz, 3H), 0.69 (m, 1H), 0.39 (m, 2H), 0.08--0.00 (m, 2H); $^{19}$F NMR (282 MHz, DMSO-$d_6$) δ −124.55; MS (ES+) 561.5 (M+1); 559.5 (M−1); Analysis calculated for $C_{32}H_{37}FN_4O_4$·2HCl·2$H_2O$: C, 57.40; H, 6.47; N, 8.37. Found: C, 57.37; H, 6.25; N, 8.32; Optical rotation $[α]_D$=(+) 43.6 [0.165, MeOH].

Scheme 51

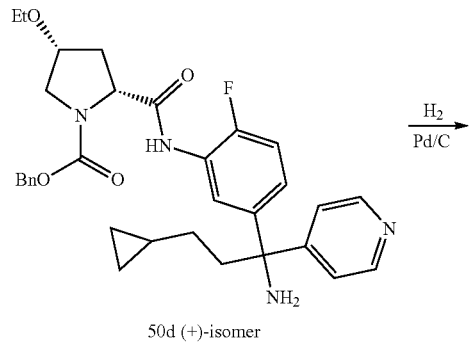

50d (+)-isomer

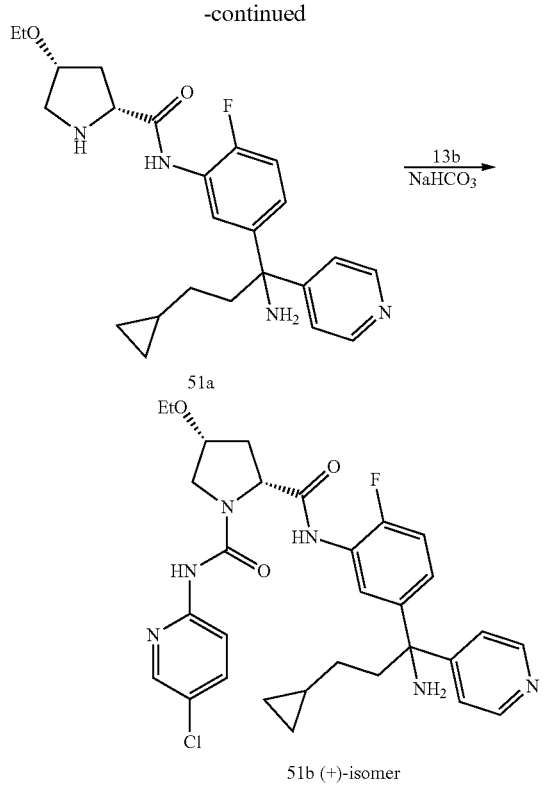

51a 51b (+)-isomer

Preparation of (2R,4R)-N2-(5-((+)-1-amino-3-cyclopropyl-1-(pyridin-4-yl)propyl)-2-fluorophenyl)-N1-(5-chloropyridin-2-yl)-4-ethoxypyrrolidine-1,2-dicarboxamide (51b)

Step-1: Preparation of (2R,4R)-N-(5-(1-amino-3-cyclopropyl-1-(pyridin-4-yl)propyl)-2-fluorophenyl)-4-ethoxypyrrolidine-2-carboxamide (51a)

Debenzylation by hydrogenation of (2R,4R)-benzyl 2-(5-((+)-1-amino-3-cyclopropyl-1-(pyridin-4-yl)propyl)-2-fluorophenylcarbamoyl)-4-ethoxypyrrolidine-1-carboxylate (50d) (190 mg, 0.286 mmol) in methanol (5 mL), using palladium on carbon 10% (15.21 mg, 0.086 mmol) as catalyst according to procedure reported in step 2 of Scheme 13 gave (2R,4R)-N-(5-(1-amino-3-cyclopropyl-1-(pyridin-4-yl)propyl)-2-fluorophenyl)-4-ethoxypyrrolidine-2-carboxamide (51a) (105 mg, 0.198 mmol, 69.2% yield), which was used as such in next step without further purification. MS (ES+) 531.4 (M+1).

Step-2: Preparation of (2R,4R)-N2-(5-((+)-1-amino-3-cyclopropyl-1-(pyridin-4-yl)propyl)-2-fluorophenyl)-N1-(5-chloropyridin-2-yl)-4-ethoxypyrrolidine-1,2-dicarboxamide (51b)

Reaction of (2R,4R)-N-(5-(1-amino-3-cyclopropyl-1-(pyridin-4-yl)propyl)-2-fluorophenyl)-4-ethoxypyrrolidine-2-carboxamide (51a) (105 mg, 0.198 mmol) in tetrahydrofuran (10 mL) with phenyl 5-chloropyridin-2-ylcarbamate (13b) (49.2 mg, 0.198 mmol) using potassium carbonate (68.4 mg, 0.495 mmol) as base according to procedure reported in step 3 of Scheme 13 gave after purification by flash column chromatography (silica gel, 12 g eluting with CMA 80 in chloroform 0-50%) (2R,4R)-N2-(5-((+)-1-amino-3-cyclopropyl-1-(pyridin-4-yl)propyl)-2-fluorophenyl)-N1-(5-chloropyridin-2-yl)-4-ethoxypyrrolidine-1,2-dicarboxamide (51b) free base as a white solid, which was converted into hydrochloride salt (60 mg, 0.092 mmol, 46.4% yield) with HCl (3N in MeOH, 3 mL); $^1$H NMR (300 MHz, DMSO-$d_6$) δ 9.74 (s, 4H), 9.71-9.68 (m, 1H), 9.28 (s, 1H), 8.97-8.86 (m, 2H), 8.30 (dd, J=2.5, 0.9 Hz, 1H), 7.96 (dd, J=7.3, 2.5 Hz, 1H), 7.90-7.80 (m, 4H), 7.39 (dd, J=10.4, 8.7 Hz, 1H), 7.26 (ddd, J=8.7, 4.4, 2.4 Hz, 1H), 4.61 (dd, J=8.9, 4.4 Hz, 1H), 4.13 (p, J=4.9 Hz, 1H), 3.79 (dd, J=10.7, 5.3 Hz, 1H), 3.64 (dd, J=10.7, 3.8 Hz, 1H), 3.46-3.35 (m, 2H), 2.65-2.48 (m, 2H), 2.40 (ddd, J=14.0, 9.0, 5.1 Hz, 1H), 2.07-1.98 (m, 1H), 1.34-1.15 (m, 1H), 1.14-1.02 (m, 1H), 1.01 (t, J=7.0 Hz, 3H), 0.76-0.59 (m, 1H), 0.45-0.31 (m, 2H), 0.07-0.00 (m, 2H); $^{19}$F NMR (282 MHz, DMSO-$d_6$) δ −124.72; Optical rotation $[α]_D$=(+) 7.209 [0.54, MeOH]; Analysis calculated for $C_{30}H_{34}ClFN_6O_3 \cdot 3HCl \cdot 1.5H_2O$: C, 50.22; H, 5.62; Cl, 19.77; N, 11.71. Found: C, 50.55; H, 5.63; Cl, 19.51; N, 11.49.

Scheme 52

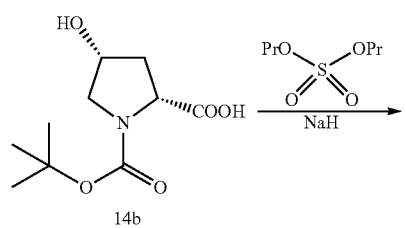

14b

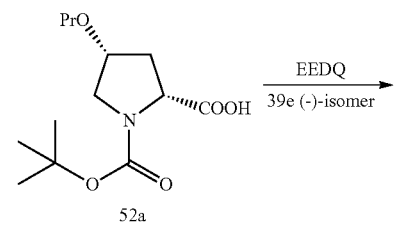

52a

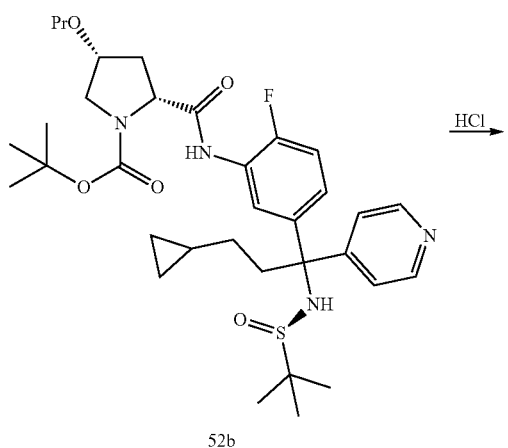

52b

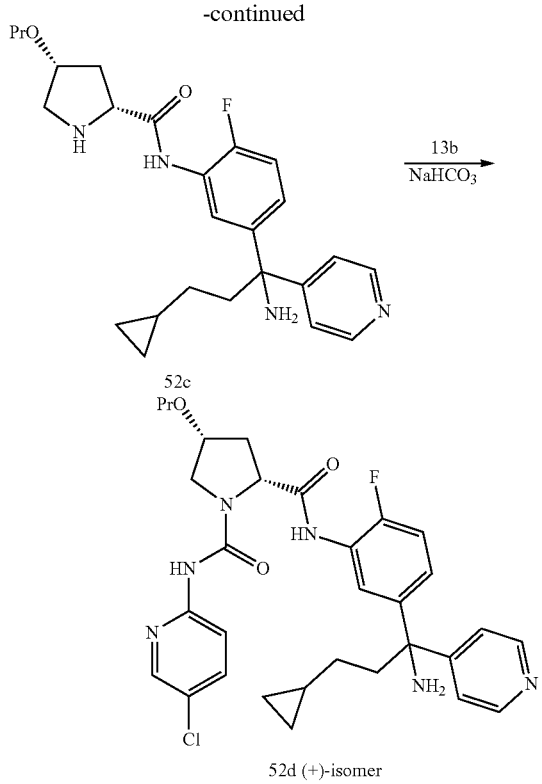

52c 52d (+)-isomer

Preparation of (2R,4R)-N2-(5-((+)-1-amino-3-cyclopropyl-1-(pyridin-4-yl)propyl)-2-fluorophenyl)-N1-(5-chloropyridin-2-yl)-4-propoxypyrrolidine-1,2-dicarboxamide (52d)

Step-1: Preparation of (2R,4R)-1-(tert-butoxycarbonyl)-4-propoxypyrrolidine-2-carboxylic acid (52a)

Alkylation of (2R,4R)-1-(tert-butoxycarbonyl)-4-hydroxypyrrolidine-2-carboxylic acid (14b) (30.5 g, 132 mmol) with diisopropyl sulfate (33.4 mL, 203 mmol) using NaH (60% dispersion in oil) (32.5 g, 813 mmol) as base according to the procedure reported in scheme 15 step 1 gave (2R,4R)-1-(tert-butoxycarbonyl)-4-propoxypyrrolidine-2-carboxylic acid (52a) (23 g, 84 mmol, 63.7% yield) as a clear oil, which was used as such in the next step without further purification. $^1$H NMR (300 MHz, DMSO-$d_6$) δ 12.41 (s, 1H), 4.23-4.04 (m, 1H), 4.05-3.93 (m, 1H), 3.62-3.44 (m, 1H), 3.37-3.22 (m, 2H), 3.23-3.11 (m, 1H), 2.43-2.21 (m, 1H), 2.04-1.91 (m, 1H), 1.56-1.23 (m, 11H), 0.82 (t, J=7.4 Hz, 3H); MS (ES−) 272.3 (M−1).

Step-2: Preparation of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-propoxypyrrolidine-1-carboxylate (52b)

Reaction of (2R,4R)-1-(tert-butoxycarbonyl)-4-propoxypyrrolidine-2-carboxylic acid (52a) (20 g, 73.0 mmol), (R)-N-((−)-1-(3-amino-4-fluorophenyl)-3-cyclopropyl-1-(pyridin-4-yl)propyl)-2-methylpropane-2-sulfinamide (39e) (26.5 g, 68.1 mmol) in tetrahydrofuran (300 mL) using ethyl 2-ethoxyquinoline-1(2H)-carboxylate (18.09 g, 73.2 mmol) using the reaction and workup conditions as reported in step 10 of Scheme 1 gave (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-propoxypyrrolidine-1-carboxylate (52b) (43 g, 66.7 mmol, 98% yield), which was used as such in the next step without further purification. MS (ES+) 667.7 (M+Na).

Step-3: Preparation of (2R,4R)-N-(5-(1-amino-3-cyclopropyl-1-(pyridin-4-yl)propyl)-2-fluorophenyl)-4-methylpyrrolidine-2-carboxamide (52c)

Reaction of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-propoxypyrrolidine-1-carboxylate (52b) (43 g, 66.7 mmol) in methanol (600 mL) using 4N HCl in dioxane (133 mL, 533 mmol) followed by workup and purification as reported in step 6 of Scheme 4 gave (2R,4R)-N-(5-(1-amino-3-cyclopropyl-1-(pyridin-4-yl)propyl)-2-fluorophenyl)-4-methylpyrrolidine-2-carboxamide (52c) (24.5 g, 55.6 mmol, 83% yield) as a yellow oil, which was used as such in next step without further purification. MS (ES+) 441.6 (M+1).

Step-4: Preparation of (2R,4R)-N2-(5-((+)-1-amino-3-cyclopropyl-1-(pyridin-4-yl)propyl)-2-fluorophenyl)-N1-(5-chloropyridin-2-yl)-4-propoxypyrrolidine-1,2-dicarboxamide (52d)

Reaction of (2R,4R)-N-(5-(1-amino-3-cyclopropyl-1-(pyridin-4-yl)propyl)-2-fluorophenyl)-4-methylpyrrolidine-2-carboxamide (52c) (24.5 g, 55.6 mmol) in tetrahydrofuran (550 mL) with phenyl 5-chloropyridin-2-ylcarbamate (13b) 12.45 g, 50.1 mmol) using sodium bicarbonate (28.0 g, 334 mmol) as base according to procedure reported in step 3 of Scheme 13 gave after purification by flash column chromatography (silica gel, eluting with ethyl acetate/MeOH (9:1) in hexane 0-50%) followed by reverse-phase column (eluting with methanol in water 0-100%) (2R,4R)-N2-(5-((+)-1-amino-3-cyclopropyl-1-(pyridin-4-yl)propyl)-2-fluorophenyl)-N1-(5-chloropyridin-2-yl)-4-propoxypyrrolidine-1,2-dicarboxamide (52d) as a free base, which was converted into HCl salt with 3N HCl in MeOH (30 mL) to afford compound 52d (13.2 g, 39.5% yield) hydrochloride salt as a white solid; $^1$H NMR (300 MHz, DMSO-$d_6$) δ 9.89 (s, 2H), 9.73 (s, 1H), 9.37 (s, 1H), 8.97 (d, J=6.6 Hz, 2H), 8.31 (dd, J=2.5, 0.8 Hz, 1H), 8.05-7.91 (m, 3H), 7.90-7.80 (m, 2H), 7.46-7.22 (m, 2H), 4.68-4.57 (m, 1H), 4.18-4.06 (m, 1H), 3.81 (dd, J=10.6, 5.4 Hz, 1H), 3.64 (dd, J=10.5, 3.5 Hz, 1H), 3.32 (t, J=6.6 Hz, 2H), 2.65-2.52 (m, 2H), 2.49-2.33 (m, 1H), 2.12-1.99 (m, 1H), 1.41 (q, J=6.8 Hz, 2H), 1.30-1.02 (m, 2H), 0.77 (t, J=7.4 Hz, 3H), 0.76-0.60 (m, 1H), 0.43-0.30 (m, 2H), 0.09--0.02 (m, 2H); $^{19}$F NMR (282 MHz, DMSO-$d_6$) δ -124.57; MS (ES+) 595.6 (M+1); Optical rotation $[α]_D$=(+) 87.31 [0.52, MeOH]; Analysis calculated for $C_{31}H_{36}ClFN_6O_3 \cdot 2HCl \cdot 3H_2O$: C, 51.56; H, 6.14; Cl, 14.73; N, 11.64. Found: C, 51.25; H, 5.82; Cl, 14.94; N, 11.53.

Scheme 53

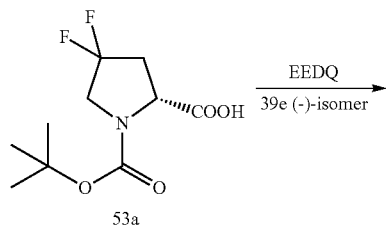

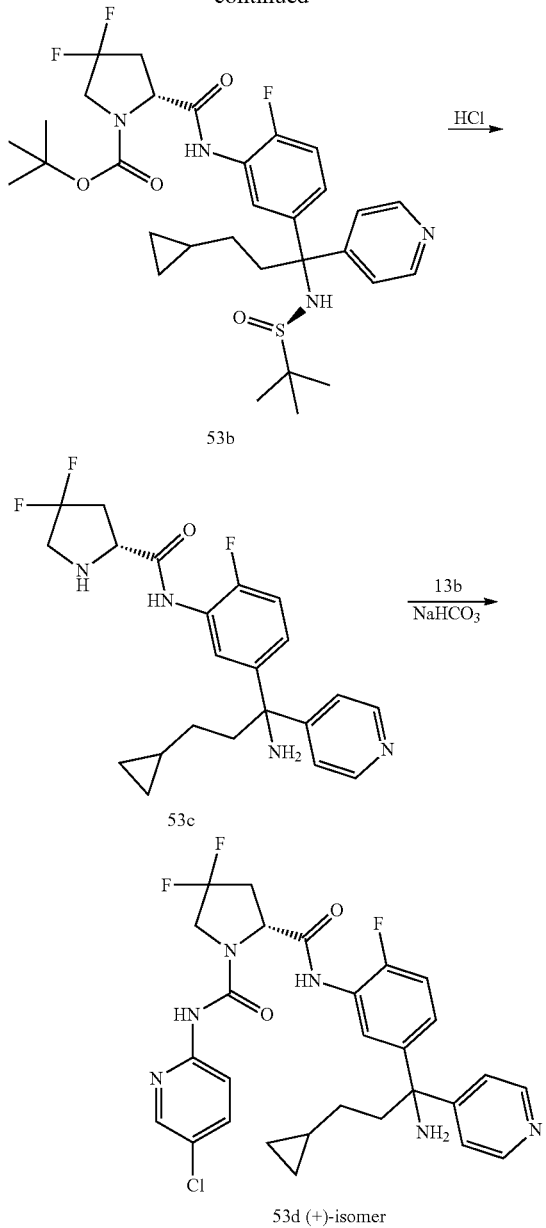

Preparation of (R)-N2-(5-((+)-1-amino-3-cyclopropyl-1-(pyridin-4-yl)propyl)-2-fluorophenyl)-N1-(5-chloropyridin-2-yl)-4,4-difluoropyrrolidine-1,2-dicarboxamide (53d)

Step-1: Preparation of (R)-tert-butyl 2-(5-(3-cyclopropyl-1-((R)-1,1-dimethylethylsulfinamido)-1-(pyridin-4-yl)propyl)-2-fluorophenylcarbamoyl)-4,4-difluoropyrrolidine-1-carboxylate (53b)

Reaction of (R)-1-(tert-butoxycarbonyl)-4,4-difluoropyrrolidine-2-carboxylic acid (53a) (225 mg, 0.896 mmol), (R)-N-((−)-1-(3-amino-4-fluorophenyl)-3-cyclopropyl-1-(pyridin-4-yl)propyl)-2-methylpropane-2-sulfinamide (39e) (349 mg, 0.896 mmol) in tetrahydrofuran (10 mL) using ethyl 2-ethoxyquinoline-1(2H)-carboxylate (221 mg, 0.896 mmol) using the reaction and workup conditions as reported in step 10 of Scheme 1 gave (R)-tert-butyl 2-(5-(3-cyclopropyl-1-((R)-1,1-dimethylethylsulfinamido)-1-(pyridin-4-yl)propyl)-2-fluorophenylcarbamoyl)-4,4-difluoropyrrolidine-1-carboxylate (53b) which was used as such for next step; MS (ES+) 623.6 (M+1).

Step-2: Preparation of (R)-N-(5-(1-amino-3-cyclopropyl-1-(pyridin-4-yl)propyl)-2-fluorophenyl)-4,4-difluoropyrrolidine-2-carboxamide (53c)

Reaction of (R)-tert-butyl 2-(5-(3-cyclopropyl-1-((R)-1,1-dimethylethylsulfinamido)-1-(pyridin-4-yl)propyl)-2-fluorophenylcarbamoyl)-4,4-difluoropyrrolidine-1-carboxylate (53b) (243 mg, 0.39 mmol) in methanol (10 mL) using 4N HCl in dioxane (1.301 mL, 3.9 mmol) followed by workup and purification as reported in step 6 of Scheme 4 gave (R)-N-(5-(1-amino-3-cyclopropyl-1-(pyridin-4-yl)propyl)-2-fluorophenyl)-4,4-difluoropyrrolidine-2-carboxamide (53c) which was used as such in next step without further purification. MS (ES+) 441.4 (M+Na).

Step-3: Preparation of (R)-N2-(5-((+)-1-amino-3-cyclopropyl-1-(pyridin-4-yl)propyl)-2-fluorophenyl)-N1-(5-chloropyridin-2-yl)-4,4-difluoropyrrolidine-1,2-dicarboxamide (53d)

Reaction of (R)-N-(5-(1-amino-3-cyclopropyl-1-(pyridin-4-yl)propyl)-2-fluorophenyl)-4,4-difluoropyrrolidine-2-carboxamide (53c) (90 mg, 0.215 mmol) in tetrahydrofuran (10 mL) with phenyl 5-chloropyridin-2-ylcarbamate (13b) (48.1 mg, 0.194 mmol) using potassium carbonate (74.3 mg, 0.538 mmol) as base according to procedure reported in step 3 of Scheme 13 gave after purification by flash column chromatography (silica gel, 12 g eluting with CMA 80 in chloroform 0-50%) (R)-N2-(5-((+)-1-amino-3-cyclopropyl-1-(pyridin-4-yl)propyl)-2-fluorophenyl)-N1-(5-chloropyridin-2-yl)-4,4-difluoropyrrolidine-1,2-dicarboxamide (53d) free base as a white solid, which was converted into hydrochloride salt using HCl (3N in MeOH, 3 mL) to obtain compound 53d (16 mg, 0.025 mmol, 11.52% yield) hydrochloride salt as a white solid; $^1$H NMR (300 MHz, DMSO-$d_6$) δ 10.24-10.15 (m, 1H), 9.61 (s, 3H), 9.51 (s, 1H), 8.84 (d, J=5.8 Hz, 2H), 8.32 (dd, J=2.1, 1.3 Hz, 1H), 8.01 (dd, J=7.3, 2.5 Hz, 1H), 7.84 (dd, J=1.7, 1.1 Hz, 2H), 7.70 (d, J=5.5 Hz, 2H), 7.40 (dd, J=10.4, 8.8 Hz, 1H), 7.22 (q, J=5.4, 4.6 Hz, 1H), 4.92 (dd, J=9.0, 5.1 Hz, 1H), 4.11 (dq, J=26.3, 12.5 Hz, 2H), 3.05-2.78 (m, 1H), 2.59-2.54 (m, 2H), 2.46-2.41 (m, 1H), 1.14 (m, 2H), 0.81-0.55 (m, 1H), 0.47-0.31 (m, 2H), 0.02 (m, 2H); $^{19}$F NMR (282 MHz, DMSO-$d_6$) δ -97.03, -123.95; MS (ES+) 573.4 (M+1); Optical rotation [α]$_D$=(+) 72.3 [0.155, MeOH]; Analysis calculated for $C_{28}H_{28}ClF_3N_6O_2 \cdot 4HCl \cdot 2H_2O$: C, 44.55; H, 4.81; N, 11.13. Found: C, 44.49; H, 4.92; N, 11.07.

Scheme 54

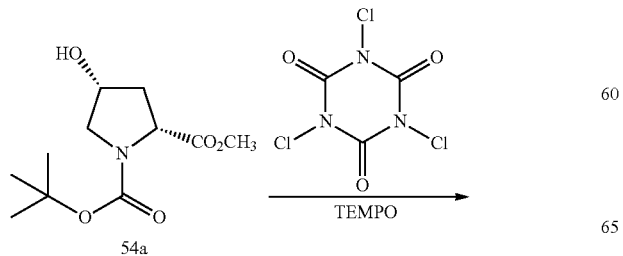

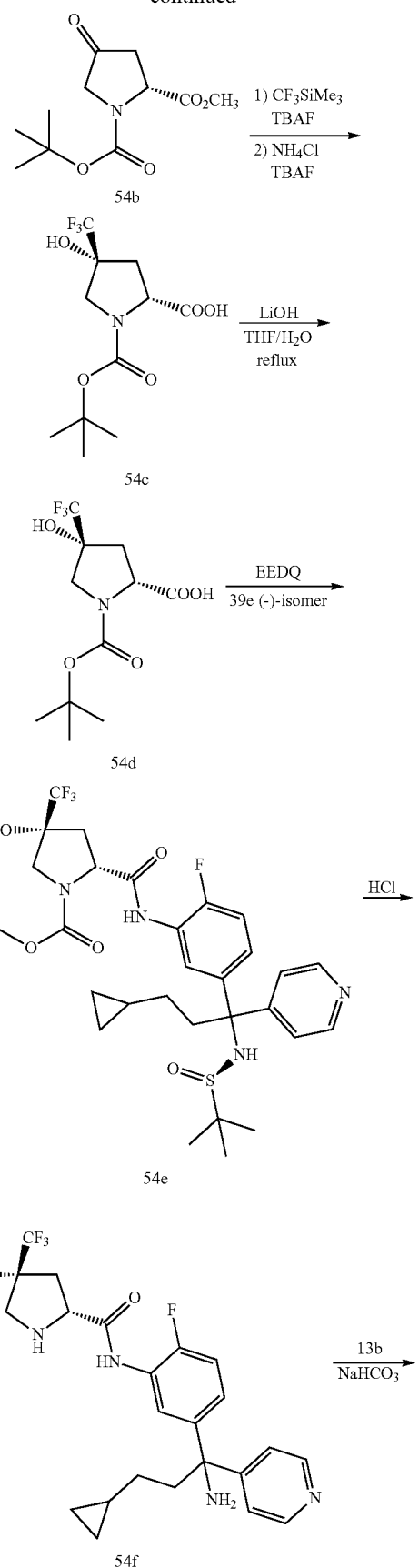

-continued

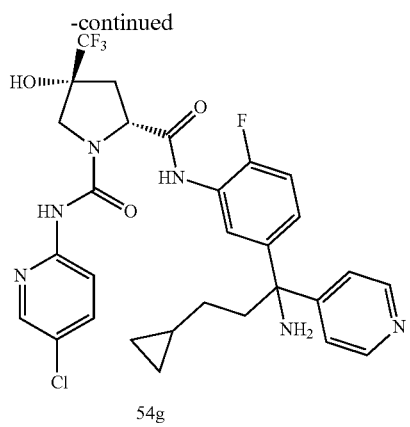

54g

Preparation of (2R,4R)-N2-(5-(1-amino-3-cyclopropyl-1-(pyridin-4-yl)propyl)-2-fluorophenyl)-N1-(5-chloropyridin-2-yl)-4-hydroxy-4-(trifluoromethyl)pyrrolidine-1,2-dicarboxamide (54g)

Step-1: Preparation of (R)-1-tert-butyl 2-methyl 4-oxopyrrolidine-1,2-dicarboxylate (54b)

Oxidation of (2R,4R)-1-tert-butyl 2-methyl 4-hydroxy-pyrrolidine-1,2-dicarboxylate (54a) (9.5 g, 38.7 mmol) in anhydrous DCM (50 mL) using trichloroisocyanuric acid (9.45 g, 40.7 mmol) and TEMPO (0.303 g, 1.937 mmol) according to the procedure reported in step 1 of Scheme 29 gave (R)-1-tert-butyl 2-methyl 4-oxopyrrolidine-1,2-dicarboxylate (54b) (9.197 g, 98% yield) as a yellow oil. $^1$H NMR (300 MHz, DMSO-$d_6$) δ 4.70-4.56 (m, 1H), 3.91-3.75 (m, 1H), 3.68 (m, 4H), 3.19-3.01 (m, 1H), 2.67-2.50 (m, 1H), 1.39 (2s, 9H, rotamers).

Step-2: Preparation of (2R,4R)-1-(tert-butoxycarbonyl)-4-hydroxy-4-(trifluoromethyl)pyrrolidine-2-carboxylic acid (54c)

To a solution of (R)-1-tert-butyl 2-methyl 4-oxopyrrolidine-1,2-dicarboxylate (54b) (3.5 g, 14.39 mmol) in THF (100 mL) cooled to 0° C. was added trimethyl(trifluoromethyl)silane (2.189 g, 15.40 mmol), TBAF (0.113 g, 0.432 mmol) and stirred at room temperature overnight. The reaction was quenched with saturated aqueous NH$_4$Cl (75 mL), stirred for 20 min added tetrabutylammonium fluoride (6.02 g, 23.02 mmol) and stirred at room temperature for 3 h. The organic layer was separated and the aqueous layer was extracted with ethyl acetate (3×100 mL). The combined organic phases were washed with water, brine, dried over anhydrous MgSO4, filtered and concentrated in vacuum to dryness. The residue obtained was purified by flash chromatography (silica gel, eluting with 0-40% ethyl acetate in hexanes) to afford (2R,4R)-1-tert-butyl 2-methyl 4-hydroxy-4-(trifluoromethyl)pyrrolidine-1,2-dicarboxylate (54c) (2.818 g, 9.0 mmol, 62.5% yield) as a clear oil. $^1$H NMR (300 MHz, DMSO-$d_6$) δ 6.59 (s, 1H), 4.70-4.38 (m, 1H), 3.76-3.61 (m, 3H, rotamers), 3.63-3.47 (m, 2H), 2.66-2.53 (m, 1H), 2.11 (dd, J=13.2, 5.4 Hz, 1H), 1.47-1.27 (m, 9H, rotamers); MS (ES+) 336.3 (M+Na).

Step-3: Preparation of (2R,4R)-1-(tert-butoxycarbonyl)-4-hydroxy-4-(trifluoromethyl)pyrrolidine-2-carboxylic acid (54d)

To a solution of (2R,4R)-1-tert-butyl 2-methyl 4-hydroxy-4-(trifluoromethyl)pyrrolidine-1,2-dicarboxylate (54c) (850 mg, 2.71 mmol) in THF/H$_2$O (1:1, 20 mL) was added lithium hydroxide (325 mg, 13.57 mmol) and heated at reflux for 1 h. The reaction mixture was filtered and concentrated in vacuum to afford (2R,4R)-1-(tert-butoxycarbonyl)-4-hydroxy-4-(trifluoromethyl)pyrrolidine-2-carboxylic acid (54d) (842 mg, 2.81 mmol, 104% yield), which was used as such in next step without further purification. MS (ES−), 298.3 (M−1).

Step-4: Preparation of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-hydroxy-4-(trifluoromethyl)pyrrolidine-1-carboxylate (54e)

Reaction of (2R,4R)-1-(tert-butoxycarbonyl)-4-hydroxy-4-(trifluoromethyl)pyrrolidine-2-carboxylic acid (54d) (842 mg, 2.82 mmol), (R)-N-((−)-1-(3-amino-4-fluorophenyl)-3-cyclopropyl-1-(pyridin-4-yl)propyl)-2-methylpropane-2-sulfinamide (39e) (850 mg, 2.71 mmol) in tetrahydrofuran (20 mL) using ethyl 2-ethoxyquinoline-1(2H)-carboxylate (695 mg, 2.82 mmol) using the reaction and workup conditions as reported in step 10 of Scheme 1 gave (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-hydroxy-4-(trifluoromethyl)pyrrolidine-1-carboxylate (54e) (420 mg, 23.08% yield); MS (E+), 693.4 (M+23).

Step-5: Preparation of (2R,4R)-N-(5-(1-amino-3-cyclopropyl-1-(pyridin-4-yl)propyl)-2-fluorophenyl)-4-hydroxy-4-(trifluoromethyl)pyrrolidine-2-carboxamide (54f)

Reaction of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-hydroxy-4-(trifluoromethyl)pyrrolidine-1-carboxylate (54e) (420 mg, 0.626 mmol) in ethanol (20 mL) using 4N HCl in dioxane (1.565 mL, 6.26 mmol) followed by workup and purification as reported in step 6 of Scheme 4 gave (2R,4R)-N-(5-(1-amino-3-cyclopropyl-1-(pyridin-4-yl)propyl)-2-fluorophenyl)-4-hydroxy-4-(trifluoromethyl)pyrrolidine-2-carboxamide (54f) (113 mg, 38.7% yield). MS (E+), 467.4 (M+1).

Step-6: Preparation of (2R,4R)-N2-(5-(1-amino-3-cyclopropyl-1-(pyridin-4-yl)propyl)-2-fluorophenyl)-N1-(5-chloropyridin-2-yl)-4-hydroxy-4-(trifluoromethyl)pyrrolidine-1,2-dicarboxamide (54g)

Reaction of (2R,4R)-N-(5-(1-amino-3-cyclopropyl-1-(pyridin-4-yl)propyl)-2-fluorophenyl)-4-hydroxy-4-(trifluoromethyl)pyrrolidine-2-carboxamide (54f) (113 mg, 242 mmol) in tetrahydrofuran (10 mL) with phenyl 5-chloropyridin-2-ylcarbamate (13b) (60.2 mg, 242 mmol) using potassium carbonate (100 mg, 727 mmol) as base according to procedure reported in step 3 of Scheme 13 gave after purification by flash column chromatography (silica gel, 12 g eluting with CMA 80 in chloroform 0-50%) followed by reverse phase column chromatography (C-18 column, eluting with 0-100% MeOH in water) (2R,4R)-N2-(5-(1-amino-3-cyclopropyl-1-(pyridin-4-yl)propyl)-2-fluorophenyl)-N1-(5-chloropyridin-2-yl)-4-hydroxy-4-(trifluoromethyl)pyrrolidine-1,2-dicarboxamide (54g) as a free base, which was converted into HCl salt using HCl (3N in MeOH, 2 mL) to afford compound 54g hydrochloride salt (42 mg, 28% yield) as a white solid. $^1$H NMR (300 MHz, DMSO-$d_6$) δ

10.00 (s, 1H), 9.69 (s, 3H), 9.46 (s, 1H), 9.00-8.79 (m, 2H), 8.31 (dd, J=2.4, 1.0 Hz, 1H), 8.06 (dd, J=7.2, 2.5 Hz, 1H), 7.92-7.74 (m, 4H), 7.39 (dd, J=10.1, 8.5 Hz, 1H), 7.29-7.04 (m, 2H), 4.84 (dd, J=9.1, 4.6 Hz, 1H), 4.05 (d, J=11.6 Hz, 1H), 3.77 (d, J=11.7 Hz, 1H), 2.65 (m, 1H), 2.51 (m, 2H), 2.26-2.14 (m, 1H), 1.23 (m, 1H), 1.08 (m, 1H), 0.67 (m, 1H), 0.36 (m, 2H), 0.02 (m, 2H); $^{19}$F NMR (282 MHz, DMSO) δ −75.03, −80.20, −124.32. MS (ES+): 521.3 (M+1); 519.3 (M−1).

Scheme 55

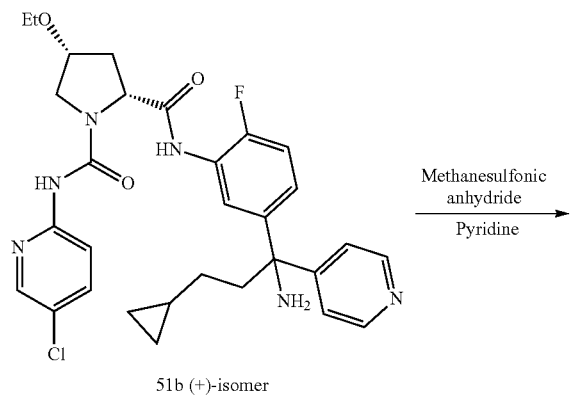

51b (+)-isomer

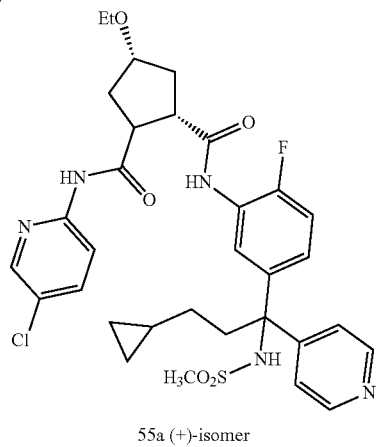

55a (+)-isomer

Preparation of (2R,4R)-N1-(5-chloropyridin-2-yl)-N2-(5-((+)-3-cyclopropyl-1-(methylsulfonamido)-1-(pyridin-4-yl)propyl)-2-fluorophenyl)-4-ethoxypyrrolidine-1,2-dicarboxamide (55a)

To a solution of (2R,4R)-N2-(5-((+)-1-amino-3-cyclopropyl-1-(pyridin-4-yl)propyl)-2-fluorophenyl)-N1-(5-chloropyridin-2-yl)-4-ethoxypyrrolidine-1,2-dicarboxamide (51b) (240 mg, 0.413 mmol) at 0° C. in dichloromethane (10 mL) was added pyridine (163 mg, 2.065 mmol), methanesulfonic anhydride (144 mg, 0.826 mmol) and stirred at room temperature overnight. Additional pyridine (98 mg, 1.239 mmol) and methanesulfonic anhydride (71.9 mg, 0.413 mmol) were added and the mixture was stirred for 2 h at room temperature. The reaction mixture was quenched with water (10 mL) and extracted with DCM (3×20 mL). The organic layers were combined, dried, filtered and concentrated in vacuum. The residue was purified by flash column chromatography (silica gel, 12 g, eluting with 0-40% CMA80 in CHCl$_3$) to give (2R,4R)-N1-(5-chloropyridin-2-yl)-N2-(5-((+)-3-cyclopropyl-1-(methylsulfonamido)-1-(pyridin-4-yl)propyl)-2-fluorophenyl)-4-ethoxypyrrolidine-1,2-dicarboxamide (55a) (158 mg, 0.240 mmol, 58.0% yield) free base as a white solid. $^1$H NMR (300 MHz, DMSO-d$_6$) δ 9.52 (s, 1H), 9.16 (s, 1H), 8.51 (d, J=6.1 Hz, 2H), 8.29 (d, J=2.6 Hz, 1H), 7.92-7.78 (m, 4H), 7.30-7.18 (m, 3H), 7.14-7.03 (m, 1H), 4.59 (dd, J=9.0, 3.8 Hz, 1H), 4.12 (s, 1H), 3.76 (dd, J=10.8, 5.1 Hz, 1H), 3.65 (d, J=8.1 Hz, 1H), 3.40 (q, J=7.0 Hz, 2H), 2.40-2.35 (m, 1H), 2.27 (s, 3H), 2.19-2.06 (m, 1H), 1.34-1.20 (m, 2H), 0.99 (t, J=7.0 Hz, 3H), 0.91-0.78 (m, 2H), 0.63-0.44 (m, 1H), 0.37-0.21 (m, 2H), −0.09-−0.14 (m, 2H); $^{19}$F NMR (282 MHz, DMSO-d$_6$) δ −126.31; MS (ES+): 659.3 (M+1).

The free base (132 mg, 0.20 mmol) was converted to hydrochloride salt in MeOH (10 mL) using HCl (3N in MeOH) (0.03 mL, 1.001 mmol) to afford (136 mg, 0.196 mmol, 98% yield) hydrochloride salt of compound 55a as a yellow solid. $^1$H NMR (300 MHz, DMSO-d$_6$) δ 9.62 (s, 1H), 8.87 (d, J=6.6 Hz, 2H), 8.30 (d, J=2.0 Hz, 1H), 8.22 (s, 1H), 7.96 (d, J=6.5 Hz, 3H), 7.93-7.79 (m, 2H), 7.34-7.21 (m, 1H), 7.16-7.05 (m, 1H), 4.61 (dd, J=8.9, 3.9 Hz, 1H), 4.19-4.06 (m, 2H), 3.84-3.72 (m, 2H), 3.66 (dd, J=10.7, 3.2 Hz, 2H), 3.41 (q, J=7.0 Hz, 2H), 2.77-2.62 (m, 1H), 2.46-2.29 (m, 5H), 2.16-1.99 (m, 1H), 1.00 (t, J=7.0 Hz, 4H), 0.88-0.69 (m, 1H), 0.64-0.50 (m, 1H), 0.32 (d, J=7.9 Hz, 2H), −0.01-−0.15 (m, 2H); $^{19}$F NMR (282 MHz, DMSO) δ −125.42; MS (ES+): 659.3 (M+1); Optical rotation [α]$_D$=(+) 76.47 [0.17, MeOH].

Scheme 55

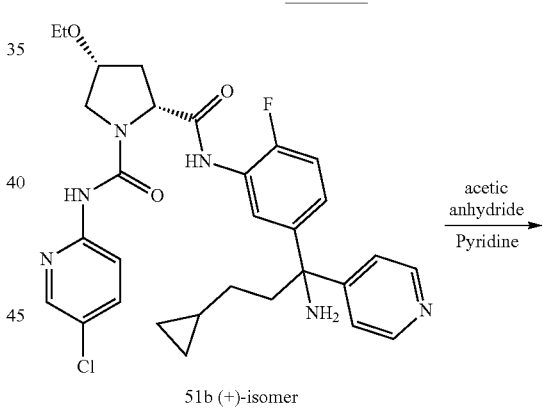

51b (+)-isomer

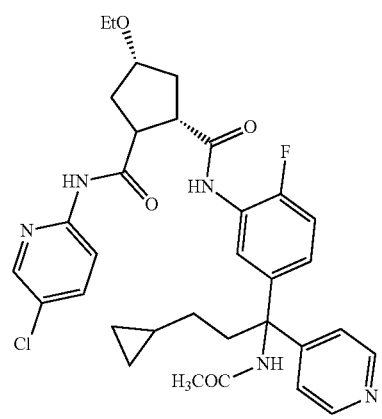

55a (+)-isomer

Preparation of (2R,4R)-N2-(5-((+)-1-acetamido-3-cyclopropyl-1-(pyridin-4-yl)propyl)-2-fluorophenyl)-N1-(5-chloropyridin-2-yl)-4-ethoxypyrrolidine-1,2-dicarboxamide (56a)

Reaction of (2R,4R)-N2-(5-((+)-1-amino-3-cyclopropyl-1-(pyridin-4-yl)propyl)-2-fluorophenyl)-N1-(5-chloropyridin-2-yl)-4-ethoxypyrrolidine-1,2-dicarboxamide (51b) (200 mg, 0.344 mmol) at 0° C. in dichloromethane using pyridine and acetic anhydride as reported in Scheme 55 gave (2R,4R)-N2-(5-((+)-1-acetamido-3-cyclopropyl-1-(pyridin-4-yl)propyl)-2-fluorophenyl)-N1-(5-chloropyridin-2-yl)-4-ethoxypyrrolidine-1,2-dicarboxamide (56a) (156 mg, 72.7% yield) free base as a white solid. $^1$H NMR (300 MHz, DMSO-$d_6$) δ 9.45 (s, 1H), 9.16 (s, 1H), 8.47-8.40 (m, 2H), 8.32-8.24 (m, 2H), 7.94-7.82 (m, 2H), 7.80 (dd, J=9.0, 2.6 Hz, 1H), 7.29-7.22 (m, 2H), 7.20-7.06 (m, 2H), 4.58 (dd, J=9.0, 3.9 Hz, 1H), 4.17-4.06 (m, 1H), 3.82-3.70 (m, 1H), 3.70-3.60 (m, 1H), 3.49-3.30 (m, 2H), 2.60-2.50 (m, 1H), 2.42-2.26 (m, 1H), 2.17-2.03 (m, 1H), 1.90 (s, 3H), 1.30-1.20 (m, 2H), 1.03 (t, J=7.0 Hz, 3H), 0.91-0.78 (m, 1H), 0.70-0.52 (m, 1H), 0.38-0.27 (m, 2H), −0.04-−0.18 (m, 2H); $^{19}$F NMR (282 MHz, DMSO-$d_6$) δ −127.98; Optical rotation [α]$_D$=(+) 70.59 [0.255, MeOH]. The free base was converted to hydrochloride salt in methanol (10 mL) using HCl (3N in MeOH) (2.5 mL, 82 mmol) to afford hydrochloride salt of compound 56a (148 mg, 0.224 mmol, 98% yield) as a white solid; $^1$H NMR (300 MHz, DMSO-$d_6$) δ 9.58 (s, 1H), 9.28 (s, 1H), 8.83-8.69 (m, 3H), 8.30 (d, J=1.9 Hz, 1H), 7.95 (m, 3H), 7.92-7.79 (m, 2H), 7.33-7.17 (m, 2H), 4.60 (dd, J=9.0, 4.3 Hz, 1H), 4.18-4.08 (m, 2H), 3.84-3.72 (m, 1H), 3.66 (dd, J=10.7, 3.2 Hz, 1H), 3.42 (q, J=7.0 Hz, 2H), 2.53 (m, 2H), 2.45-2.31 (m, 1H), 2.11-2.01 (m, 1H), 1.94 (s, 3H), 1.03 (t, J=7.0 Hz, 5H), 0.71-0.57 (m, 1H), 0.40-0.30 (m, 2H), −0.03-−0.14 (m, 2H); $^{19}$F NMR (282 MHz, DMSO-$d_6$) δ −126.67; MS (ES+): 623.3 (M+1); (ES−) 621.3 (M−1); Optical rotation [α]$_D$=(+) 70.59 [0.255, MeOH].

Scheme 57

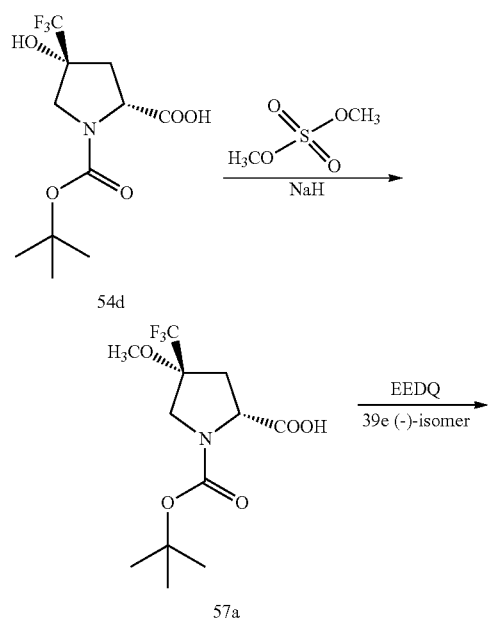

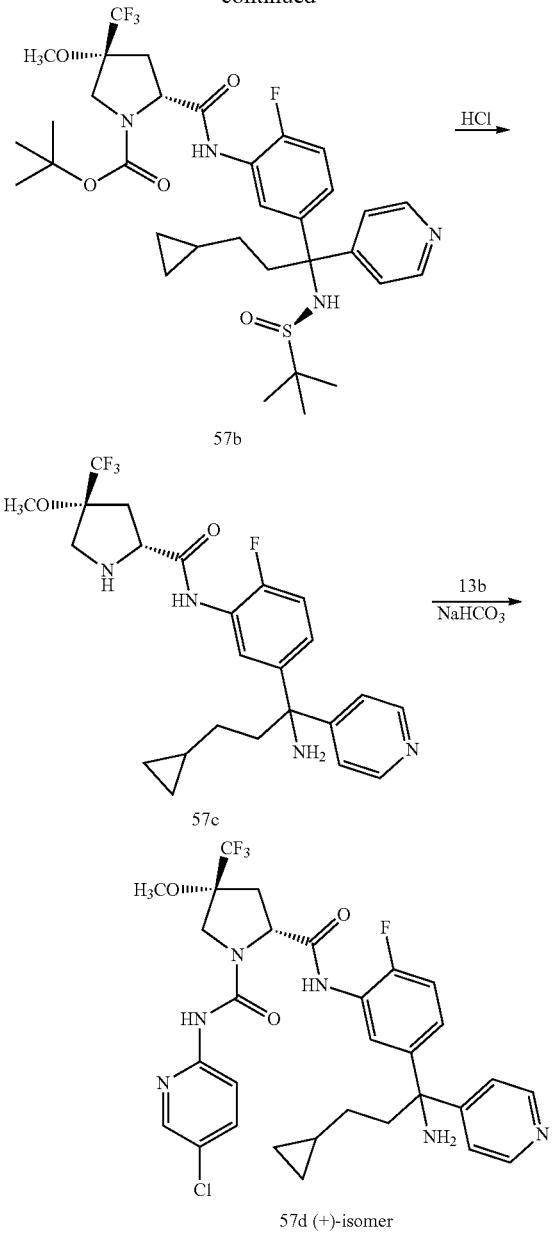

57d (+)-isomer

Preparation of (2R,4R)-N2-(5-((+)-1-amino-3-cyclopropyl-1-(pyridin-4-yl)propyl)-2-fluorophenyl)-N1-(5-chloropyridin-2-yl)-4-methoxy-4-(trifluoromethyl)pyrrolidine-1,2-dicarboxamide (57d)

Step-1: Preparation of (2R,4R)-1-(tert-butoxycarbonyl)-4-methoxy-4-(trifluoromethyl)pyrrolidine-2-carboxylic acid (57a)

Alkylation of (2R,4R)-1-(tert-butoxycarbonyl)-4-hydroxy-4-(trifluoromethyl)pyrrolidine-2-carboxylic acid (54d) (2.26 g, 7.55 mmol) in THF (50 mL) with dimethyl sulfate (1.905 g, 15.10 mmol) using sodium hydride (60% dispersion in mineral oil, 1.812 g, 45.3 mmol) as base according to the procedure reported in scheme 15 step 1 gave (2R,4R)-1-(tert-butoxycarbonyl)-4-methoxy-4-(trifluoromethyl)pyrrolidine-2-carboxylic acid (57a) (1.6 g, 5.11 mmol, 67.6% yield) as a white solid. $^1$H NMR (300 MHz, DMSO-d$_6$) δ 12.84 (s, 1H), 4.35 (t, J=9.3 Hz, 1H), 3.73-3.53 (m, 2H), 3.36 (s, 3H), 2.71-2.51 (m, 1H), 2.38-2.24 (m, 1H), 1.39 (2s, 9H, rotamers).

Step-2: Preparation of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methoxy-4-(trifluoromethyl)pyrrolidine-1-carboxylate (57b)

Reaction of (2R,4R)-1-(tert-butoxycarbonyl)-4-methoxy-4-(trifluoromethyl)pyrrolidine-2-carboxylic acid (57a) (400 mg, 1.277 mmol), (R)-N-((−)-1-(3-amino-4-fluorophenyl)-3-cyclopropyl-1-(pyridin-4-yl)propyl)-2-methylpropane-2-sulfinamide (39e) (497 mg, 1.277 mmol) in tetrahydrofuran (20 mL) using ethyl 2-ethoxyquinoline-1(2H)-carboxylate (316 mg, 1.277 mmol) using the reaction and workup conditions as reported in step 10 of Scheme 1 gave (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methoxy-4-(trifluoromethyl)pyrrolidine-1-carboxylate (57b) (640 mg, 0.935 mmol, 73.2% yield) as an off white solid.

Step-3: Preparation of (2R,4R)-N-(5-(1-amino-3-cyclopropyl-1-(pyridin-4-yl)propyl)-2-fluorophenyl)-4-methoxy-4-(trifluoromethyl)pyrrolidine-2-carboxamide (57c)

Reaction of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methoxy-4-(trifluoromethyl)pyrrolidine-1-carboxylate (57b) (640 mg, 0.935 mmol) in ethanol (200 mL) using 3N HCl in methanol (16 mL) followed by workup and purification as reported in step 6 of Scheme 4 gave (2R,4R)-N-(5-(1-amino-3-cyclopropyl-1-(pyridin-4-yl)propyl)-2-fluorophenyl)-4-methoxy-4-(trifluoromethyl)pyrrolidine-2-carboxamide (57c) (340 mg, 0.708 mmol, 76% yield) as a white solid. 1H NMR (300 MHz, DMSO-d$_6$) δ 9.92 (s, 1H), 8.47-8.38 (m, 2H), 8.20-8.11 (m, 1H), 7.39-7.31 (m, 2H), 7.20-7.11 (m, 2H), 3.93 (q, J=6.9 Hz, 1H), 3.70-3.56 (m, 1H), 3.24 (s, 4H), 3.23-3.09 (m, 1H), 2.36-2.25 (m, 4H), 2.25-2.16 (m, 2H), 1.11-1.02 (m, 2H), 0.69-0.57 (m, 1H), 0.39-0.30 (m, 2H), −0.01-−0.12 (m, 2H).

Step-4: Preparation of (2R,4R)-N2-(5-((+)-1-amino-3-cyclopropyl-1-(pyridin-4-yl)propyl)-2-fluorophenyl)-N1-(5-chloropyridin-2-yl)-4-methoxy-4-(trifluoromethyl)pyrrolidine-1,2-dicarboxamide (57d)

Reaction of (2R,4R)-N-(5-(1-amino-3-cyclopropyl-1-(pyridin-4-yl)propyl)-2-fluorophenyl)-4-methoxy-4-(trifluoromethyl)pyrrolidine-2-carboxamide (57c) (340 mg, 0.708 mmol) in tetrahydrofuran/water (60 mL, 5:1) with phenyl 5-chloropyridin-2-ylcarbamate (13b) (167 mg, 0.672 mmol) using potassium carbonate (489 mg, 3.54 mmol) as base according to procedure reported in step 3 of Scheme 13 gave after purification by flash column chromatography (silica gel, 12 g eluting with CMA 80 in chloroform 0-25%) (2R,4R)-N2-(5-((+)-1-amino-3-cyclopropyl-1-(pyridin-4-yl)propyl)-2-fluorophenyl)-N1-(5-chloropyridin-2-yl)-4-methoxy-4-(trifluoromethyl)pyrrolidine-1,2-dicarboxamide (57d) (35 mg, 0.055 mmol, 8.85% yield) as a free base, which was converted to hydrochloride salt in MeOH (10 mL) using HCl (3N in MeOH) (0.367 mL, 1.102 mmol) to obtain hydrochloride salt of compound 57d (34 mg, 87% yield) as a solid; $^1$H NMR (300 MHz, DMSO-d$_6$) δ 10.00 (s, 1H), 9.67 (s, 3H), 9.45 (s, 1H), 8.84 (d, J=5.7 Hz, 2H), 8.37-8.21 (m, 1H), 7.92-7.79 (m, 3H), 7.71 (d, J=5.8 Hz, 2H), 7.43 (d, J=1.6 Hz, 1H), 7.41-7.35 (m, 1H), 7.34-7.23 (m, 1H), 4.85 (dd, J=9.2, 3.8 Hz, 1H), 4.02 (q, J=12.1 Hz, 2H), 3.31 (s, 3H), 2.75-2.55 (m, 1H), 2.51 (m, 2H), 2.47-2.30 (m, 1H), 1.30-0.99 (m, 2H), 0.68 (m, 1H), 0.43-0.29 (m, 2H), 0.10-−0.05 (m, 2H); $^{19}$F NMR (282 MHz, DMSO-d$_6$) δ −75.82, −123.56; Optical rotation $[α]_D$=(+) 56.0 [0.05, MeOH].

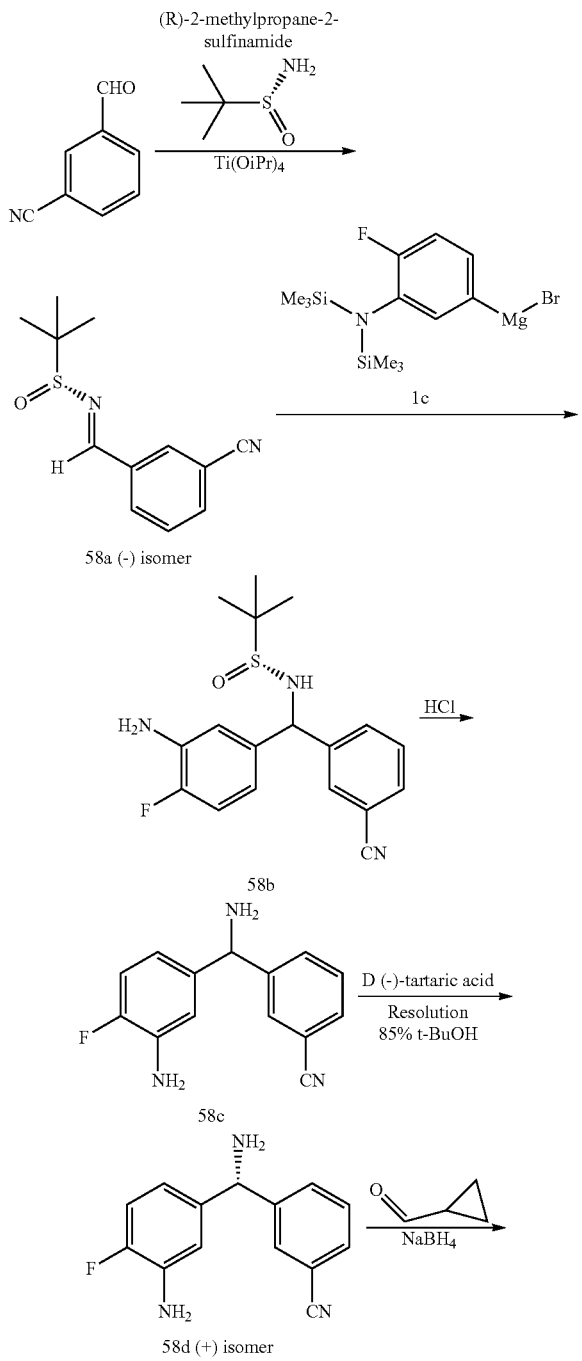

Scheme 58

209

-continued

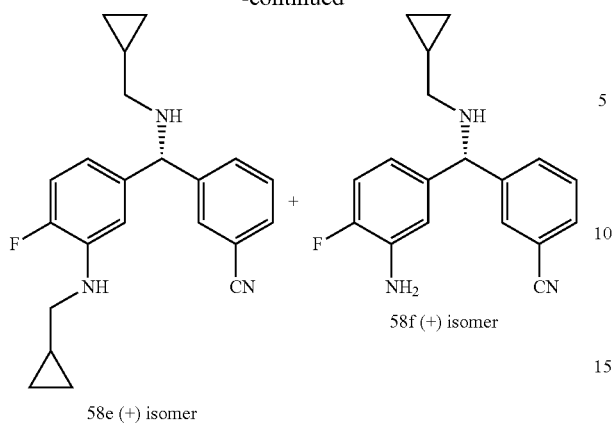

58e (+) isomer

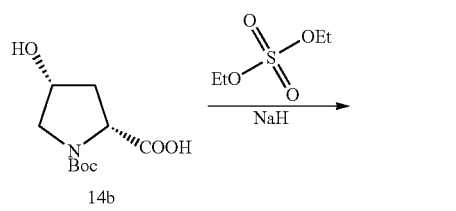

14b

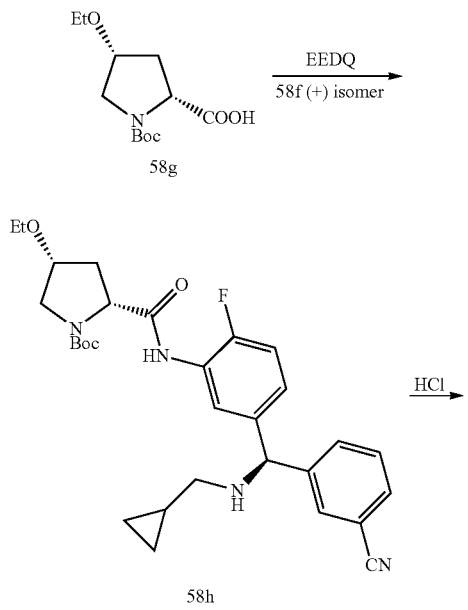

210

-continued

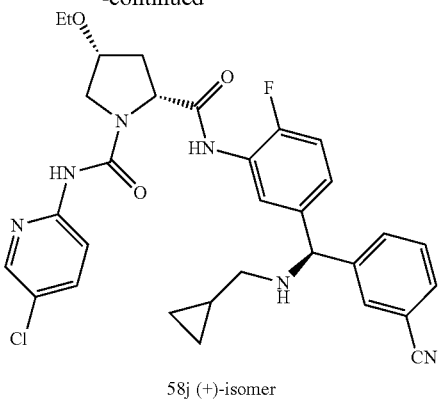

58j (+)-isomer

Preparation of (2R,4R)-N1-(5-chloropyridin-2-yl)-N2-(5-((+)-(3-cyanophenyl)(cyclopropylmethylamino)methyl)-2-fluorophenyl)-4-ethoxypyrrolidine-1,2-dicarboxamide (58j)

Step-1: Preparation of (−)-N-(3-cyanobenzylidene)-2-methylpropane-2-sulfinamide (58a)

To a stirred solution of 3-formylbenzonitrile (45.4 g, 347 mmol) in tetrahydrofuran (460 mL) was added (R)-2,4,6-triisopropylbenzenesulfinamide (35 g, 289 mmol), tetraisopropoxytitanium (173 mL, 578 mmol) and heated at reflux for 10 h. Work up was performed as reported in step 1 of Scheme 1 to furnish after column chromatography (silica gel 1.5 kg, eluting with 20% ethyl acetate in hexane) (−)-N-(3-cyanobenzylidene)-2-methylpropane-2-sulfinamide (58a) (37.4 g, 160 mmol, 55.3% yield) as a colorless solid; $^1$H NMR (300 MHz, DMSO-$d_6$) δ 8.63 (s, 1H), 8.42 (dd, J=1.9, 1.3 Hz, 1H), 8.28 (dt, J=7.9, 1.4 Hz, 1H), 8.07 (dt, J=7.7, 1.4 Hz, 1H), 7.76 (t, J=7.8 Hz, 1H), 1.21 (s, 9H); MS (ES+) 257.2 (M+Na); Optical rotation: $[α]_D$=(−) 83.21 [2.55, CHCl$_3$].

Step-2: Preparation of (R)-N-((3-amino-4-fluorophenyl)(3-cyanophenyl)methyl)-2-methylpropane-2-sulfinamide (58b)

Compound 58b was prepared from (−)-N-(3-cyanobenzylidene)-2-methylpropane-2-sulfinamide (58a) (72 g, 307 mmol) and 3-(bis(trimethylsilyl)amino)-4-fluorophenyl)magnesium bromide (1c) (430 mL, 430 mmol) as described in step 4 of Scheme 1 to afford (R)-N-((3-amino-4-fluorophenyl)(3-cyanophenyl)methyl)-2-methylpropane-2-sulfinamide (58b) (47.32 g, 137 mmol, 44.6% yield) thick yellow oil.

Step-3: Preparation of 3-(amino(3-amino-4-fluorophenyl)methyl)benzonitrile (58c)

To a stirred solution of (R)-N-((3-amino-4-fluorophenyl)(3-cyanophenyl)methyl)-2-methylpropane-2-sulfinamide (58b) (238.82 g, 691 mmol, ratio of diastereoisomers 55/45) in MTBE (1200 mL) was added hydrogen chloride in 1,4-Dioxane (363 mL, 1452 mmol) and stirred at room temperature for 7 h. Additional hydrogen chloride in dioxane (346 mL, 1383 mmol) was added and stirred until all starting material disappeared (24 h). The solid obtained was collected by filtration washed with MTBE (2×250 mL),

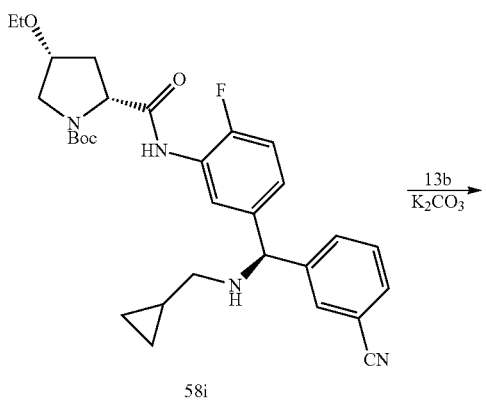

dried in air to furnish 3-(amino(3-amino-4-fluorophenyl) methyl)benzonitrile (58c) as an HCl salt (slightly hygroscopic); ¹H NMR (300 MHz, DMSO-d₆) δ 9.39-9.10 (m, 3H), 7.57-7.49 (m, 2H), 7.45-7.34 (m, 3H), 7.26 (d, J=5.8 Hz, 1H), 7.15 (dd, J=8.0, 2.0 Hz, 1H), 5.58 (d, J=5.5 Hz, 1H); ¹⁹F NMR (282 MHz, DMSO) δ −129.75; MS (ES−) 240.2 (M−1). The above solid was dissolved in water (500 mL), basified by addition of NaOH (3N, 922 mL, 2765 mmol). The mixture was extracted with ethyl acetate (2×1000 mL). The organic layers were combined washed with brine, dried, filtered and concentrated in vacuum to furnish racemic 3-(amino(3-amino-4-fluorophenyl)methyl) benzonitrile (58c) (194 g, 804 mmol, 116% yield) free base as a brown oil; ¹H NMR (300 MHz, DMSO-d₆) δ 7.38-7.35 (m, 2H), 7.30-7.24 (m, 2H), 6.86 (dd, J=11.5, 8.3 Hz, 1H), 6.79 (dd, J=9.0, 2.2 Hz, 1H), 6.55 (ddd, J=8.3, 4.5, 2.2 Hz, 1H), 5.03 (s, 2H), 4.94 (s, 1H), 2.13 (s, 2H); ¹⁹F NMR (282 MHz, DMSO) δ −138.23.

Step-4: Preparation of (+)-3-(amino(3-amino-4-fluorophenyl)methyl)benzonitrile (58d)

To a solution of racemic 3-(amino(3-amino-4-fluorophenyl)methyl)benzonitrile (58c) (ratio 55/45 for two disteroemers, 141.38 g, 586 mmol) in 85% tert-butanol (5600 mL, made from tert-butanol and water) was added D (−)-tartaric acid (88 g, 586 mmol) and heated to 80° C. The clear solution was allowed to cool to 29.8° C. (8 h). At this point the crystals obtained were collected by filtration, washed with 200 mL of 85% tert-butanol, dried in vacuum to obtain (+)-3-(amino(3-amino-4-fluorophenyl)methyl)benzonitrile (58d) (36.4 g, 93 mmol, 15.87% overall yield) as a 2,3-dihydroxysuccinate salt; MS (ES+) 225.2 (M+1); Chiral HPLC purity 96.077% ee. To (+)-3-(amino(3-amino-4-fluorophenyl)methyl)benzonitrile (58d) 2,3-dihydroxysuccinate salt (18 g, 46.0 mmol) in 85% tert-butanol (388 mL) was heated to 80° C. (internal temperature) until homogenous. The mixture was allowed to come to room temperature and the white crystals formed were collected by filtration and air dried to afford pure (+)-3-(amino(3-amino-4-fluorophenyl) methyl)benzonitrile (58d) (16.7 g, 42.7 mmol, 93% yield) 2,3-dihydroxysuccinate salt as a white solid; ¹H NMR (300 MHz, DMSO-d6) δ 7.90 (t, J=1.6 Hz, 1H), 7.78 (dt, J=7.6, 1.4 Hz, 1H), 7.72 (dt, J=8.0, 1.4 Hz, 1H), 7.59 (t, J=7.8 Hz, 1H), 6.99 (dd, J=11.5, 8.3 Hz, 1H), 6.74 (dd, J=8.7, 2.3 Hz, 1H), 6.59 (ddd, J=8.4, 4.4, 2.3 Hz, 1H), 5.34 (s, 1H), 5.24 (s, 2H), 4.02 (s, 2H); ¹⁹F NMR (282 MHz, DMSO-d₆) δ −135.95; MS (ES−) 240.2 (M−1); Chiral HPLC purity > 99.99%; Optical rotation: [α]_D=(+) 0.59 [1.025, MeOH].

Step-5: Preparation of (+)-3-((cyclopropylmethylamino)(3-(cyclopropylmethylamino)-4-fluorophenyl)methyl)benzonitrile (58e) and (+)-3-((3-amino-4-fluorophenyl)(cyclopropylmethylamino)methyl) benzonitrile (58f)

To a stirred solution of (+)-3-(amino(3-amino-4-fluorophenyl)methyl)benzonitrile (58d) (8.321 g, 34.5 mmol, which was converted to free base using aqueous NaOH and extracting with ethyl acetate) in MeOH (20 mL) was added cyclopropanecarboxaldehyde (3.25 mL, 43.1 mmol) at 0° C. and stirred for 30 mins. To this sodium borohydride (2.61 g, 69.0 mmol) was added and stirred at 0° C. for 1 hr. The reaction was concentrated in vacuum to remove methanol and residue was dissolved in ethyl acetate (200 mL), washed with water (2×50 mL), brine (50 mL), dried and concentrated. The crude residue was purified by flash column chromatography (silica gel 120 g, eluting with ethyl acetate in hexanes 0-100%) to afford (+)-3-((cyclopropylmethylamino)(3-(cyclopropylmethylamino)-4-fluorophenyl) methyl)benzonitrile (58e) (1.087 g, 3.11 mmol, 9.02% yield) as a colorless syrup; ¹H NMR (300 MHz, DMSO-d₆) δ 7.88 (t, J=1.7 Hz, 1H), 7.75 (dt, J=7.9, 1.5 Hz, 1H), 7.64 (dt, J=7.7, 1.4 Hz, 1H), 7.48 (t, J=7.7 Hz, 1H), 6.90 (dd, J=11.9, 8.2 Hz, 1H), 6.84 (dd, J=8.9, 2.1 Hz, 1H), 6.57 (ddd, J=8.2, 4.5, 2.0 Hz, 1H), 5.34 (td, J=6.0, 2.4 Hz, 1H), 4.81 (d, J=4.2 Hz, 1H), 2.96 (t, J=6.3 Hz, 2H), 2.59 (m, 1H), 2.27 (m, 2H), 1.03 (m, 1H), 0.98-0.84 (m, 1H), 0.40 (m, 4H), 0.26-0.17 (m, 2H), 0.05 (m, 2H); ¹⁹F NMR (282 MHz, DMSO-d₆) δ −137.04; MS (ES−) 348.4 (M−1); Optical rotation: [α]_D=(+) 17.96 [0.245, MeOH]. followed by (+)-3-((3-amino-4-fluorophenyl)(cyclopropylmethylamino)methyl)benzonitrile (58f) (7.891 g, 26.7 mmol, 77% yield) as colorless syrup; ¹H NMR (300 MHz, DMSO-d₆) δ 7.84 (t, J=1.6 Hz, 1H), 7.71 (dt, J=7.9, 1.5 Hz, 1H), 7.68-7.63 (m, 1H), 7.49 (t, J=7.7 Hz, 1H), 6.88 (dd, J=11.5, 8.3 Hz, 1H), 6.81 (dd, J=9.0, 2.2 Hz, 1H), 6.56 (ddd, J=8.3, 4.5, 2.1 Hz, 1H), 5.08 (s, 2H), 4.76 (d, J=2.8 Hz, 1H), 2.48 (m, 1H), 2.26 (m, 2H), 0.91 (m, 1H), 0.42-0.34 (m, 2H), 0.09-0.01 (m, 2H); ¹⁹F NMR (282 MHz, DMSO-d6) δ −137.18; MS (ES+) 296.3 (M+1), (ES−) 294.3 (M−1); Optical rotation: [α]_D=(+) 22.05 [0.88, CHCl₃].

Step-6: Preparation of (2R,4R)-1-(tert-butoxycarbonyl)-4-ethoxypyrrolidine-2-carboxylic acid (58g)

Alkylation of (2R,4R)-1-(tert-butoxycarbonyl)-4-hydroxypyrrolidine-2-carboxylic acid (14b) (26 g, 112 mmol)) in THF (600 mL) with diethyl sulfate (34.7 g, 225 mmol) using sodium hydride (60% dispersion in mineral oil, 27.0 g, 675 mmol) as base according to the procedure reported in scheme 15 step 1 gave (2R,4R)-1-(tert-butoxycarbonyl)-4-ethoxypyrrolidine-2-carboxylic acid (58g) (21.98 g, 85 mmol, 75% yield) as a white semisolid; ¹H NMR (300 MHz, DMSO-d₆) δ 12.45 (s, 1H), 4.20-4.05 (m, 1H), 4.00 (m, 1H), 3.61-3.47 (m, 1H), 3.47-3.27 (m, 1H), 3.23-3.10 (m, 1H), 2.44-2.21 (m, 1H), 2.02-1.85 (m, 2H), 1.39, 1.34 (2s, 9H, rotamers), 1.14-0.93 (m, 3H); MS (ES+) 282.3 (M+Na); 258.3 (M−1)

Step-7: Preparation of (2R,4R)-tert-butyl 2-(5-(3-cyanophenyl)(cyclopropylmethylamino)methyl)-2-fluorophenylcarbamoyl)-4-ethoxypyrrolidine-1-carboxylate (58h)

Reaction of (2R,4R)-1-(tert-butoxycarbonyl)-4-ethoxypyrrolidine-2-carboxylic acid (58g) (676 mg, 2.61 mmol), (+)-3-((3-amino-4-fluorophenyl)(cyclopropylmethylamino) methyl)benzonitrile (58f) (770 mg, 2.61 mmol) in tetrahydrofuran (20 mL) using ethyl 2-ethoxyquinoline-1(2H)-carboxylate (645 mg, 2.61 mmol) using the reaction and workup conditions as reported in step 10 of Scheme 1 gave (2R,4R)-tert-butyl 2-(5-(3-cyanophenyl)(cyclopropylmethylamino)methyl)-2-fluorophenylcarbamoyl)-4-ethoxypyrrolidine-1-carboxylate (58h) (1.21 gm, 86% yield) as a white solid, which was used as such for next step Step-8: Preparation of (2R,4R)-N-(5-(3-cyanophenyl)(cyclopropylmethylamino)methyl)-2-fluorophenyl)-4-ethoxypyrrolidine-2-carboxamide (58i)

Reaction of (2R,4R)-tert-butyl 2-(5-(3-cyanophenyl)(cyclopropylmethylamino)methyl)-2-fluorophenylcarbamoyl)-4-ethoxypyrrolidine-1-carboxylate (58h) (590 mg, 1.099 mmol) in methanol (20 mL) using 3N HCl in methanol

213

(1.832 mL, 5.50 mmol) followed by workup and purification as reported in step 6 of Scheme 4 gave (2R,4R)-N-(5-(3-cyanophenyl)(cyclopropylmethylamino)methyl)-2-fluorophenyl)-4-ethoxypyrrolidine-2-carboxamide (58i) (220 mg, 45.8% yield) as a clear oil. $^1$H NMR (300 MHz, DMSO-$d_6$) δ 10.09 (d, J=1.6 Hz, 1H), 8.34-8.21 (m, 1H), 7.85 (s, 1H), 7.77-7.67 (m, 1H), 7.66 (m, 1H), 7.49 (t, J=7.7 Hz, 1H), 7.23-7.09 (m, 2H), 4.90 (s, 1H), 3.99-3.87 (m, 1H), 3.73 (t, J=6.1 Hz, 1H), 3.29 (q, J=7.0 Hz, 2H), 3.02 (dd, J=10.5, 4.0 Hz, 1H), 2.86 (dd, J=11.0, 2.0 Hz, 1H), 2.62 (s, 1H), 2.26 (d, J=6.1 Hz, 2H), 2.13-2.01 (m, 3H), 0.88 (m, 4H), 0.43-0.28 (m, 2H), 0.12--0.00 (m, 2H); MS (E+) 437.3 (M+1).

Step-9: Preparation of (2R,4R)-N1-(5-chloropyridin-2-yl)-N2-(5-((+)-(3-cyanophenyl)(cyclopropylmethylamino)methyl)-2-fluorophenyl)-4-ethoxypyrrolidine-1,2-dicarboxamide (58j)

Reaction of (2R,4R)-N-(5-(3-cyanophenyl)(cyclopropylmethylamino)methyl)-2-fluorophenyl)-4-ethoxypyrrolidine-2-carboxamide (58i) (183 mg, 0.419 mmol) in tetrahydrofuran/water (10 mL, 5:1) with phenyl 5-chloropyridin-2-ylcarbamate (13b) (94 mg, 0.377 mmol) using sodium bicarbonate (264 mg, 3.14 mmol) as base according to procedure reported in step 3 of Scheme 13 gave after purification by flash column chromatography (silica gel, 12 g eluting with CMA 80 in chloroform 0-40%) (2R,4R)-N1-(5-chloropyridin-2-yl)-N2-(5-((+)-(3-cyanophenyl)(cyclopropylmethylamino)methyl)-2-fluorophenyl)-4-ethoxypyrrolidine-1,2-dicarboxamide (58j) (95 mg, 0.161 mmol, 43.6% yield) free base as a white solid. $^1$H NMR (300 MHz, DMSO-$d_6$) δ 9.45 (s, 1H), 9.16 (s, 1H), 8.30 (dd, J=2.6, 0.7 Hz, 1H), 7.93-7.84 (m, 3H), 7.81 (dd, J=9.0, 2.6 Hz, 1H), 7.75-7.68 (m, 1H), 7.66 (dt, J=7.6, 1.3 Hz, 1H), 7.49 (t, J=7.7 Hz, 1H), 7.26-7.12 (m, 2H), 4.89 (d, J=2.2 Hz, 1H), 4.58 (dd, J=9.0, 4.0 Hz, 1H), 4.17-4.06 (m, 1H), 3.81-3.71 (m, 1H), 3.71-3.59 (m, 1H), 3.41 (q, J=7.0 Hz, 2H), 2.66-2.57 (m, 1H), 2.25 (m, 2H), 2.16-2.04 (m, 1H), 1.04 (t, J=7.0 Hz, 3H), 0.95-0.82 (m, 1H), 0.41-0.32 (m, 2H), 0.07-0.01 (m, 2H); $^{19}$F NMR (282 MHz, DMSO) δ -127.31; MS (ES+) 591.3 (M+1). The free base of compound 58j (83 mg, 0.140 mmol) was converted to hydrochloride salt in MeOH (5 mL) using HCl (3N in MeOH) (0.234 mL, 0.14 mmol) to obtain hydrochloride salt of compound 58j (80 mg, 91% yield) as a white solid. $^1$H NMR (300 MHz, DMSO-$d_6$) δ 10.42 (2s, 2H), 9.70 (s, 1H), 9.40 (s, 1H), 8.30 (d, J=11.8 Hz, 2H), 8.18-7.99 (m, 2H), 7.99-7.81 (m, 3H), 7.65 (t, J=7.8 Hz, 1H), 7.39 (t, J=9.4 Hz, 1H), 6.68 (s, 2H), 5.77 (s, 1H), 4.70-4.55 (m, 1H), 4.15 (s, 1H), 3.90-3.75 (m, 1H), 3.71-3.55 (m, 1H), 3.42 (q, J=6.5 Hz, 2H), 2.71 (d, J=4.1 Hz, 2H), 2.47-2.35 (m, 1H), 2.06 (m, 1H), 1.28-1.10 (m, 1H), 1.03 (t, J=6.8 Hz, 3H), 0.62-0.50 (m, 2H), 0.36-0.25 (m, 2H); $^{19}$F NMR (282 MHz, DMSO) δ -124.07; MS (ES+) 591.3 (M+1); Analysis calculated for $C_{31}H_{32}ClFN_6O_3$·1.7HCl·2H$_2$O: C, 54.03; H, 5.51; Cl, 13.89; N, 12.20. Found: C, 53.71; H, 5.64; Cl, 13.58; N, 11.88; Optical rotation $[α]_D$=(+) 73.14 [0.175, MeOH].

Scheme 59

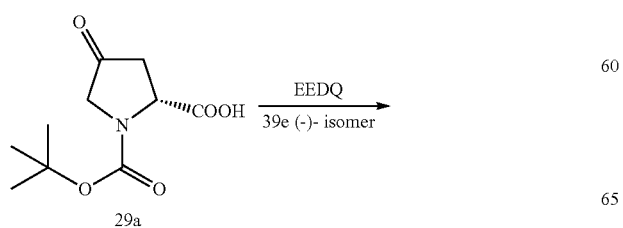

214

-continued

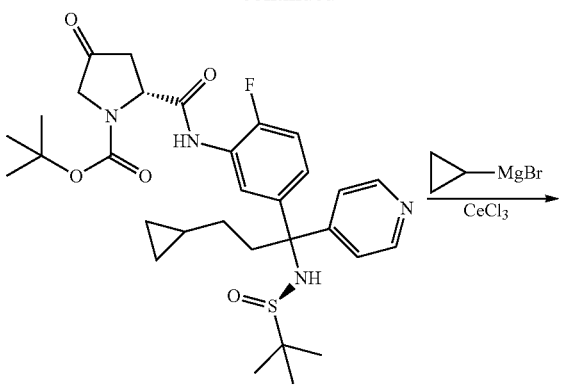

59a

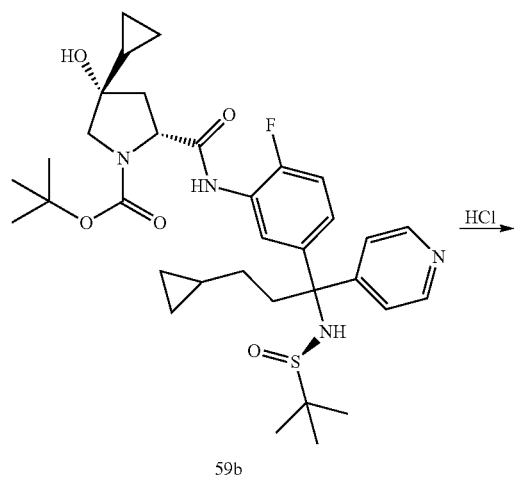

59b

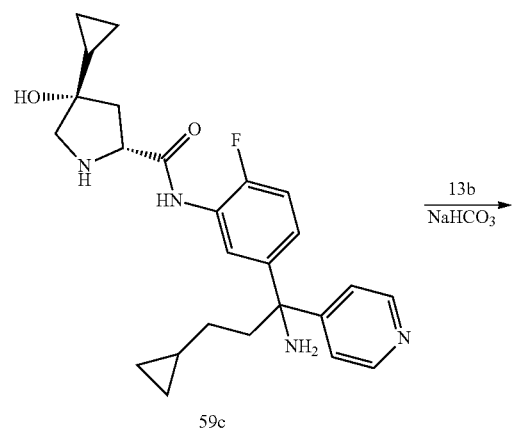

59c

-continued

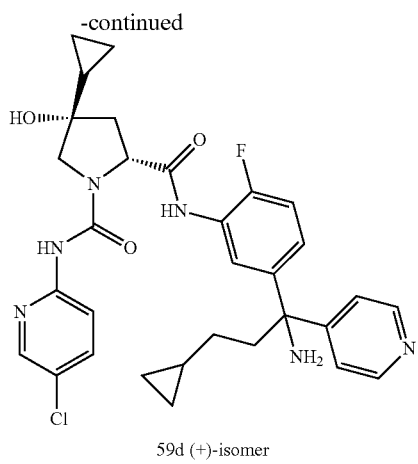

59d (+)-isomer

Preparation of (2R,4S)-N2-(5-((+)-1-amino-3-cyclopropyl-1-(pyridin-4-yl)propyl)-2-fluorophenyl)-N1-(5-chloropyridin-2-yl)-4-cyclopropyl-4-hydroxypyrrolidine-1,2-dicarboxamide (59d)

Step-1: Preparation of (R)-tert-butyl 2-(5-(3-cyclopropyl-1-((R)-1,1-dimethylethylsulfinamido)-1-(pyridin-4-yl)propyl)-2-fluorophenylcarbamoyl)-4-oxopyrrolidine-1-carboxylate (59a)

Reaction of (R)-1-(tert-butoxycarbonyl)-4-oxopyrrolidine-2-carboxylic acid (29a) (1.5 g, 6.54 mmol), (R)-N-((−)-1-(3-amino-4-fluorophenyl)-3-cyclopropyl-1-(pyridin-4-yl)propyl)-2-methylpropane-2-sulfinamide (39e) (2.55 g, 6.54 mmol) in tetrahydrofuran (50 mL) using ethyl 2-ethoxyquinoline-1(2H)-carboxylate (1.651 g, 6.54 mmol) using the reaction and workup conditions as reported in step 10 of Scheme 1 gave (R)-tert-butyl 2-(5-(3-cyclopropyl-1-((R)-1,1-dimethylethylsulfinamido)-1-(pyridin-4-yl)propyl)-2-fluorophenylcarbamoyl)-4-oxopyrrolidine-1-carboxylate (59a) (1.215 g, 2.022 mmol, 30.9% yield) as a light cream colored compound; $^1$H NMR (300 MHz, DMSO-$d_6$) δ 10.08 (s, 1H), 8.57-8.45 (m, 2H), 8.05-7.86 (m, 1H), 7.35-7.13 (m, 4H), 5.52 (s, 1H), 5.01-4.78 (m, 1H), 3.88-3.71 (m, 2H), 3.17-2.99 (m, 1H), 2.68-2.55 (m, 2H), 2.49-2.39 (m, 1H), 1.38 (2s, 9H, rotamers), 1.29-1.17 (m, 1H), 1.14 (s, 9H), 1.00-0.80 (m, 1H), 0.72-0.56 (m, 1H), 0.42-0.28 (m, 2H), −0.03--0.09 (m, 2H); $^{19}$F NMR (282 MHz, DMSO-$d_6$) δ −126.64, −126.84 (rotamers)

Step-2: Preparation of (2R,4S)-tert-butyl 4-cyclopropyl-2-(5-((S)-3-cyclopropyl-1-((R)-1,1-dimethylethylsulfinamido)-1-(pyridin-4-yl)propyl)-2-fluorophenylcarbamoyl)-4-hydroxypyrrolidine-1-carboxylate (59b)

To a suspension of cerium (III) chloride (2.462 g, 9.99 mmol) in tetrahydrofuran (40 mL) cooled to −78° C. was added dropwise cyclopropylmagnesium bromide (0.5M solution in THF, 18.64 mL, 9.32 mmol) maintaining internal temperature below −70° C. The reaction was stirred at −78° C. for 30 min followed by dropwise addition of a solution of (R)-tert-butyl 2-(5-(3-cyclopropyl-1-((R)-1,1-dimethylethylsulfinamido)-1-(pyridin-4-yl)propyl)-2-fluorophenylcarbamoyl)-4-oxopyrrolidine-1-carboxylate (59a) (1 g, 1.665 mmol) in THF maintaining internal temperature below −70° C. during addition. The reaction mixture was warmed to 0° C. over 2 h, diluted with ethyl acetate (50 mL) and filtered to remove insoluble material. The filtrate was diluted with water and organic layer was separated, washed with brine, dried, filtered and concentrated in vacuum to furnish (2R,4S)-tert-butyl 4-cyclopropyl-2-(5-((S)-3-cyclopropyl-1-((R)-1,1-dimethylethylsulfinamido)-1-(pyridin-4-yl)propyl)-2-fluorophenylcarbamoyl)-4-hydroxypyrrolidine-1-carboxylate (59b) which was used as such in next step without purification.

Step-3: Preparation of (2R,4S)-N-(5-(1-amino-3-cyclopropyl-1-(pyridin-4-yl)propyl)-2-fluorophenyl)-4-cyclopropyl-4-hydroxypyrrolidine-2-carboxamide (59c)

Reaction of crude (2R,4S)-tert-butyl 4-cyclopropyl-2-(5-((S)-3-cyclopropyl-1-((R)-1,1-dimethylethylsulfinamido)-1-(pyridin-4-yl)propyl)-2-fluorophenylcarbamoyl)-4-hydroxypyrrolidine-1-carboxylate (59b) obtained from step 2 above in methanol (10 mL) using 3N HCl in methanol (15 mL) followed by workup and purification as reported in step 6 of Scheme 4 gave after purification by flash column chromatography (silica gel, eluting with 0-60% CMA-80 in CHCl$_3$) (2R,4S)-N-(5-(1-amino-3-cyclopropyl-1-(pyridin-4-yl)propyl)-2-fluorophenyl)-4-cyclopropyl-4-hydroxypyrrolidine-2-carboxamide (59c) (163 mg, 22.33% yield for two steps), MS (439.5, M+1).

Step-4: Preparation of (2R,4S)-N2-(5-((+)-1-amino-3-cyclopropyl-1-(pyridin-4-yl)propyl)-2-fluorophenyl)-N1-(5-chloropyridin-2-yl)-4-cyclopropyl-4-hydroxypyrrolidine-1,2-dicarboxamide (59d)

Reaction of (2R,4S)-N-(5-(1-amino-3-cyclopropyl-1-(pyridin-4-yl)propyl)-2-fluorophenyl)-4-cyclopropyl-4-hydroxypyrrolidine-2-carboxamide (59c) (160 mg, 0.365 mmol) in tetrahydrofuran/water (10 mL, 5:1) with phenyl 5-chloropyridin-2-ylcarbamate (13b) (82 mg, 0.328 mmol) using sodium hydrogen carbonate (184 mg, 2.189 mmol) as base according to procedure reported in step 3 of Scheme 13 gave after purification by flash column chromatography (silica gel, 12 g eluting with 9:1 ethyl acetate/methanol in hexane 0-50%) (2R,4S)-N2-(5-((+)-1-amino-3-cyclopropyl-1-(pyridin-4-yl)propyl)-2-fluorophenyl)-N1-(5-chloropyridin-2-yl)-4-cyclopropyl-4-hydroxypyrrolidine-1,2-dicarboxamide (59d) as a free base which was converted to hydrochloride salt (3N HCl in MeOH) to give compound 59d (25 mg, 0.042 mmol, 12.84% yield) hydrochloride salt as a white solid. $^1$H NMR (300 MHz, DMSO-$d_6$) δ 9.94 (s, 1H), 9.83 (s, 2H), 9.31 (s, 1H), 8.96 (d, J=6.0 Hz, 2H), 8.31 (d, J=2.0 Hz, 1H), 8.12 (d, J=5.2 Hz, 1H), 7.99-7.88 (m, 2H), 7.88-7.76 (m, 2H), 7.46-7.32 (m, 1H), 4.68-4.60 (m, 3H), 3.63 (d, J=10.5 Hz, 1H), 3.50 (d, J=10.3 Hz, 1H), 2.57 (m, 2H), 2.28 (m, 1H), 1.95 (m, 1H), 1.32-1.19 (m, 1H), 1.15-0.94 (m, 2H), 0.82-0.61 (m, 1H), 0.47-0.20 (m, 5H), 0.13--0.02 (m, 4H); $^{19}$F NMR (282 MHz, DMSO) δ −124.96; MS (ES+): 593.6 (M+1); Optical rotation [α]$_D$=(+) 102.6 [0.15, MeOH].

Scheme 60

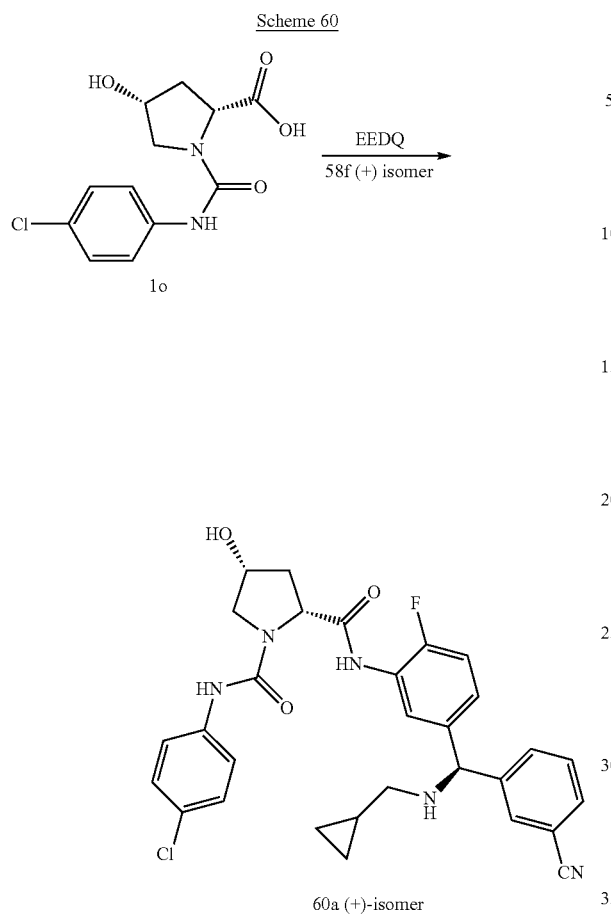

60a (+)-isomer

Preparation of (2R,4R)-N1-(4-chlorophenyl)-N2-(5-((R)-(3-cyanophenyl)(cyclopropylmethylamino)methyl)-2-fluorophenyl)-4-hydroxypyrrolidine-1,2-dicarboxamide (60a)

Reaction of (2R,4R)-1-(4-chlorophenylcarbamoyl)-4-hydroxypyrrolidine-2-carboxylic acid (1o) (0.14 g, 0.5 mmol), (+)-3-((3-amino-4-fluorophenyl)(cyclopropylmethylamino)methyl) benzonitrile (58f) (0.15 g, 0.5 mmol) in tetrahydrofuran (5 mL) using ethyl 2-ethoxyquinoline-1(2H)-carboxylate (0.12 g, 0.5 mmol) using the reaction and workup conditions as reported in step 10 of Scheme 1 gave after purification by flash chromatography (silica gel 24 g, eluting with CMA80 in chloroform 0 to 30%) (2R,4R)-N1-(4-chlorophenyl)-N2-(5-((R)-(3-cyanophenyl)(cyclopropylmethylamino)methyl)-2-fluorophenyl)-4-hydroxypyrrolidine-1,2-dicarboxamide (60a) (96 mg, 34% yield) as white solid; $^1$H NMR (300 MHz, DMSO-$d_6$) δ 9.65 (s, 1H), 8.51 (s, 1H), 8.05 (s, 1H), 7.89 (s, 1H), 7.69 (m 2H), 7.58-7.45 (m, 2H), 7.30-7.24 (m, 2H), 7.20 (m, 3H), 5.31 (d, J=4.8 Hz, 1H), 4.91 (s, 1H), 4.51 (dd, J=9.0, 4.7 Hz, 1H), 4.34 (q, J=4.8 Hz, 1H), 3.69 (m, 1H), 3.48 (m, 1H), 2.44-2.32 (m, 1H), 2.27 (s, 2H), 1.90 (m, 1H), 1.03-0.78 (m, 1H), 0.49-0.29 (m, 2H), 0.10-0.02 (m, 2H); $^{19}$F NMR (282 MHz, DMSO-$d_6$) δ −128.01; MS (ES+) 562.4 (M+1), 584.4 (M+Na), (ES−) 596.5, 598.4 (M+Cl); Optical rotation $[α]_D$=(+) 83.49 [0.355, MeOH].

Scheme 61

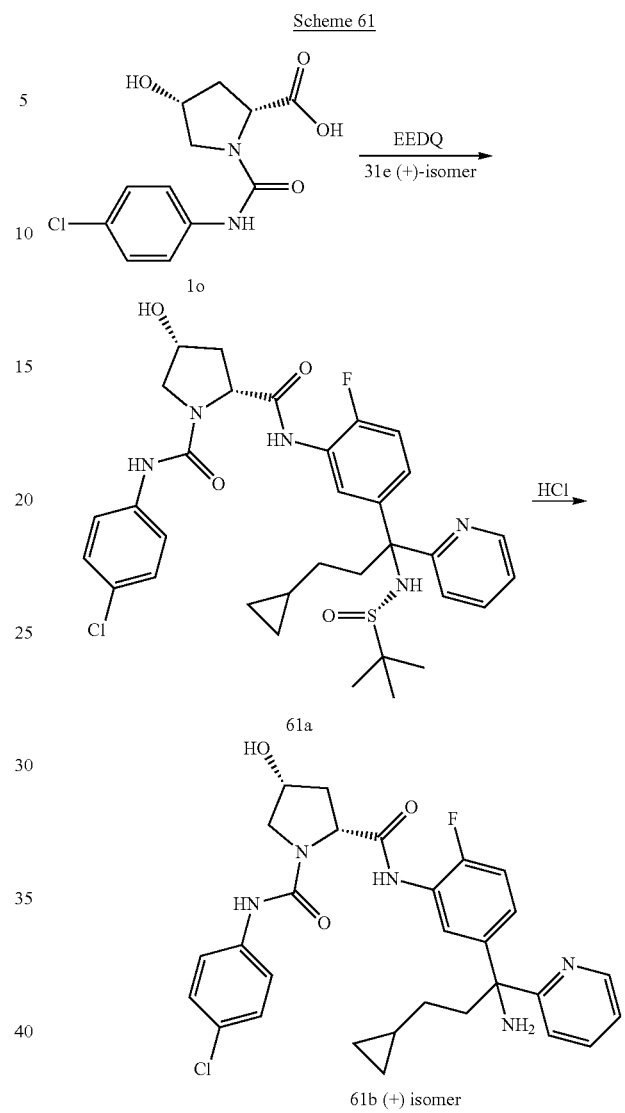

61b (+) isomer

Preparation of (2R,4R)-N1-(4-chlorophenyl)-N2-(5-((+)-3-cyclopropyl-1-((S)-1,1-dimethylethylsulfinamido)-1-(pyridin-2-yl)propyl)-2-fluorophenyl)-4-hydroxypyrrolidine-1,2-dicarboxamide (61b)

Step-1: Preparation of (2R,4R)-N1-(4-chlorophenyl)-N2-(5-(3-cyclopropyl-1-((S)-1,1-dimethylethylsulfinamido)-1-(pyridin-2-yl)propyl)-2-fluorophenyl)-4-hydroxypyrrolidine-1,2-dicarboxamide (61a)

Reaction of (2R,4R)-1-(4-chlorophenylcarbamoyl)-4-hydroxypyrrolidine-2-carboxylic acid (1o) (0.28 g, 1.0 mmol), (S)-N-((+)-1-(3-amino-4-fluorophenyl)-3-cyclopropyl-1-(pyridin-2-yl)propyl)-2-methylpropane-2-sulfinamide (31e) (0.39 g, 1.0 mmol) in tetrahydrofuran (10 mL) using ethyl 2-ethoxyquinoline-1(2H)-carboxylate (0.25 g, 1.0 mmol) using the reaction and workup conditions as reported in step 10 of Scheme 1 gave after purification by flash chromatography (silica gel 24 g, eluting with CMA80 in chloroform 0 to 30%) (2R,4R)-N1-(4-chlorophenyl)-N2-(5-(3-cyclopropyl-1-((S)-1,1-dimethylethylsulfinamido)-1-(pyridin-2-yl)

propyl)-2-fluorophenyl)-4-hydroxypyrrolidine-1,2-dicarboxamide (61a) (0.43 g, 65%) as a white solid; ¹H NMR (300 MHz, DMSO-d₆) δ 9.83 (s, 1H), 8.78-8.64 (m, 2H), 8.41-8.27 (m, 1H), 7.99-7.86 (m, 1H), 7.80-7.67 (m, 2H), 7.52-7.41 (m, 3H), 7.41-7.31 (m, 1H), 7.28 (d, J=8.1 Hz, 1H), 7.22 (m, 1H), 6.35 (s, 1H), 5.49 (d, J=4.6 Hz, 1H), 4.70 (dd, J=9.0, 4.6 Hz, 1H), 4.54 (d, J=4.6 Hz, 1H), 3.87 (dd, J=10.1, 5.2 Hz, 1H), 3.73-3.60 (m, 1H), 2.76 (m, 2H), 2.62-2.47 (m, 1H), 2.16-2.01 (m, 1H), 1.29 (s, 9H), 1.04 (m, 2H), 0.75 (m, 1H), 0.49 (m, 2H), 0.01 (m, 2H); MS (ES+) 656.5 (M+1), 678.5 (M+Na).

Step-2: Preparation of (2R,4R)-N1-(4-chlorophenyl)-N2-(5-((+)-3-cyclopropyl-1-((S)-1,1-dimethylethylsulfinamido)-1-(pyridin-2-yl)propyl)-2-fluorophenyl)-4-hydroxypyrrolidine-1,2-dicarboxamide (61b)

Reaction of crude (2R,4R)-N1-(4-chlorophenyl)-N2-(5-(3-cyclopropyl-1-((S)-1,1-dimethylethylsulfinamido)-1-(pyridin-2-yl)propyl)-2-fluorophenyl)-4-hydroxypyrrolidine-1,2-dicarboxamide (61a) (0.13 g, 0.2 mmol) in ethanol (5 mL) using conc. HCl (0.12 mL) followed by workup and purification as reported in step 6 of Scheme 4 gave after purification by flash column chromatography (silica gel 24 g, eluting with 0-30% CMA-80 in chloroform) (2R,4R)-N1-(4-chlorophenyl)-N2-(5-((+)-3-cyclopropyl-1-((S)-1,1-dimethylethylsulfinamido)-1-(pyridin-2-yl)propyl)-2-fluorophenyl)-4-hydroxypyrrolidine-1,2-dicarboxamide (61b) (95 mg, 86% yield) as white solid; ¹H NMR (300 MHz, DMSO-d₆) δ 9.56 (s, 1H), 8.55-8.42 (m, 2H), 8.07 (dd, J=7.9, 2.2 Hz, 1H), 7.69 (td, J=7.7, 1.9 Hz, 1H), 7.62-7.47 (m, 3H), 7.32-7.22 (m, 2H), 7.22-7.12 (m, 2H), 7.08 (dd, J=10.5, 8.7 Hz, 1H), 5.30 (d, J=4.9 Hz, 1H), 4.49 (dd, J=9.0, 4.7 Hz, 1H), 4.33 (d, J=5.0 Hz, 1H), 3.68 (dd, J=10.1, 5.2 Hz, 1H), 3.50-3.42 (m, 1H), 2.40-2.21 (m, 5H), 1.89 (m, 1H), 1.03 (m, 2H), 0.60 (m, 1H), 0.39-0.27 (m, 2H), -0.03--0.13 (m, 2H); ¹⁹F NMR (282 MHz, DMSO-d₆) δ -129.58; MS (ES+) 552.5 (M+), MS (ES-) 586.4 (M+Cl); Optical rotation [α]$_D$=(+) 91.1 [0.18, MeOH].

Scheme 62

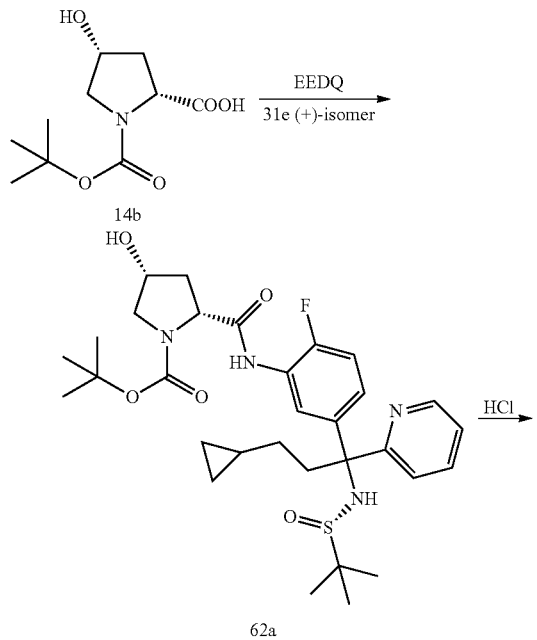

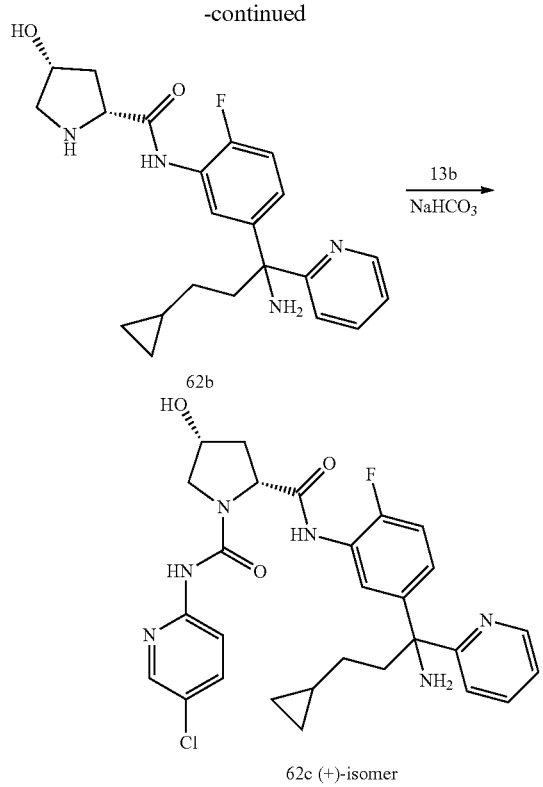

Preparation of (2R,4R)-N2-(5-((+)-1-amino-3-cyclopropyl-1-(pyridin-2-yl)propyl)-2-fluorophenyl)-N1-(5-chloropyridin-2-yl)-4-hydroxypyrrolidine-1,2-dicarboxamide (62c)

Step-1: Preparation of (2R,4R)-tert-butyl 2-(5-(3-cyclopropyl-1-((S)-1,1-dimethylethylsulfinamido)-1-(pyridin-2-yl)propyl)-2-fluorophenylcarbamoyl)-4-hydroxypyrrolidine-1-carboxylate (62a)

Reaction of (2R,4R)-1-(tert-butoxycarbonyl)-4-hydroxypyrrolidine-2-carboxylic acid (14b) (0.15 g, 0.65 mmol), (S)-N-((+)-1-(3-amino-4-fluorophenyl)-3-cyclopropyl-1-(pyridin-2-yl)propyl)-2-methylpropane-2-sulfinamide (31e) (0.25 g, 0.65 mmol) in tetrahydrofuran (50 mL) using ethyl 2-ethoxyquinoline-1(2H)-carboxylate (0.175 g, 0.71 mmol) using the reaction and workup conditions as reported in step 10 of Scheme 1 gave (2R,4R)-tert-butyl 2-(5-(3-cyclopropyl-1-((S)-1,1-dimethylethylsulfinamido)-1-(pyridin-2-yl)propyl)-2-fluorophenylcarbamoyl)-4-hydroxypyrrolidine-1-carboxylate (62a) (0.24 g, 61%) as a white solid; ¹H NMR (300 MHz, DMSO-d₆) δ 9.71 (s, 1H), 8.57-8.48 (m, 1H), 7.97 (d, J=7.4 Hz, 1H), 7.80-7.66 (m, 1H), 7.33-6.97 (m, 4H), 6.14 (s, 1H), 5.33-5.15 (m, 1H), 4.23 (m, 2H), 3.55-3.41 (m, 1H), 3.27-3.14 (m, 1H), 2.65-2.53 (m, 2H), 2.41-2.29 (m, 1H), 1.78 (m, 1H), 1.44-1.13 (m, 11H), 1.09 (s, 9H), 0.65-0.44 (m, 1H), 0.38-0.23 (m, 2H), -0.13--0.27 (m, 2H); MS (ES+) 603.6 (M+1), MS (ES-) 601.6 (M-1).

Step-2: Preparation of (2R,4R)-N-(5-(1-amino-3-cyclopropyl-1-(pyridin-2-yl)propyl)-2-fluorophenyl)-4-hydroxypyrrolidine-2-carboxamide (62b)

Reaction of (2R,4R)-tert-butyl 2-(5-(3-cyclopropyl-1-((S)-1,1-dimethylethylsulfinamido)-1-(pyridin-2-yl)propyl)-2-fluorophenylcarbamoyl)-4-hydroxypyrrolidine-1-carboxylate (62a) (0.24 g, 0.4 mmol) in methanol (5 mL) using conc HCl followed by workup and purification as reported in step 6 of Scheme 4 gave (2R,4R)-N-(5-(1-amino-3-cyclopropyl-1-(pyridin-2-yl)propyl)-2-fluorophenyl)-4-hydroxypyrrolidine-2-carboxamide (62b) as a yellow oil, which was used as such in next step without further purification.

Step-3: Preparation of (2R,4R)-N2-(5-((+)-1-amino-3-cyclopropyl-1-(pyridin-2-yl)propyl)-2-fluorophenyl)-N1-(5-chloropyridin-2-yl)-4-hydroxypyrrolidine-1,2-dicarboxamide (62c)

Reaction of (2R,4R)-N-(5-(1-amino-3-cyclopropyl-1-(pyridin-2-yl)propyl)-2-fluorophenyl)-4-hydroxypyrrolidine-2-carboxamide (62b) obtained in above step 2 in tetrahydrofuran/water (20 mL/1 mL) with phenyl 5-chloropyridin-2-ylcarbamate (13b) (0.09 g, 0.35 mmol) using sodium bicarbonate (0.33 g, 4 mmol) as base according to procedure reported in step 3 of Scheme 13 gave after purification by flash column chromatography (silica gel 12 g, eluting with CMA-80 in chloroform 0-30%) (2R,4R)-N2-(5-((+)-1-amino-3-cyclopropyl-1-(pyridin-2-yl)propyl)-2-fluorophenyl)-N1-(5-chloropyridin-2-yl)-4-hydroxypyrrolidine-1,2-dicarboxamide (62c) (0.11 g, 50%) as a white solid; $^1$H NMR (300 MHz, DMSO-$d_6$) δ 9.63 (s, 1H), 9.16 (s, 1H), 8.50-8.43 (m, 1H), 8.32-8.26 (m, 1H), 8.08-8.00 (m, 1H), 7.88 (dd, J=9.0, 0.8 Hz, 1H), 7.79 (dd, J=9.0, 2.7 Hz, 1H), 7.74-7.64 (m, 1H), 7.52 (dt, J=8.0, 1.0 Hz, 1H), 7.22-7.02 (m, 2H), 5.30 (d, J=5.0 Hz, 1H), 4.60-4.47 (m, 1H), 4.36-4.23 (m, 1H), 3.78-3.64 (m, 1H), 3.58-3.42 (m, 2H), 2.40-2.19 (m, 5H), 1.88 (m, 1H), 1.10-0.92 (m, 2H), 0.70-0.51 (m, 1H), 0.40-0.25 (m, 2H), −0.04-−0.17 (m, 2H); $^{19}$F NMR (282 MHz, DMSO-$d_6$) δ −129.34; MS (ES+) 553.4 (M+1), MS (ES−) 551.3 (M−1); Optical rotation [α]$_D$=(+) 74.44 [0.36, MeOH].

Scheme 63

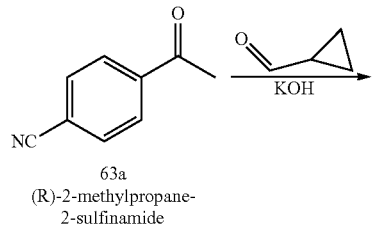

63a

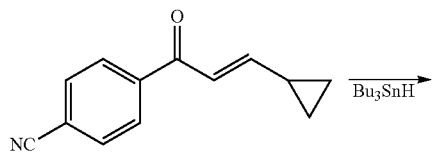

63b

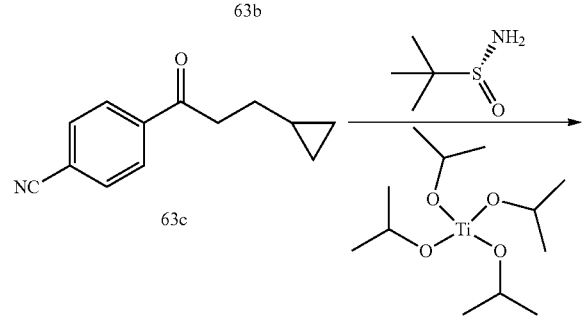

63c (R)-2-methylpropane-2-sulfinamide

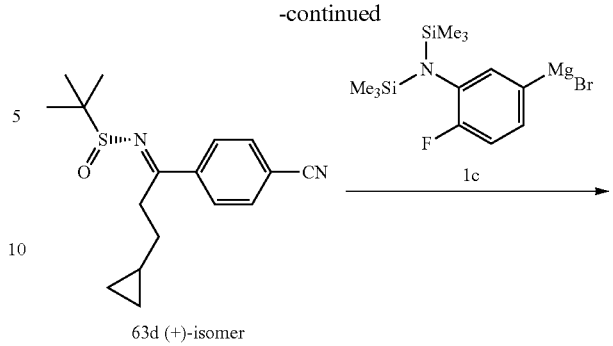

63d (+)-isomer

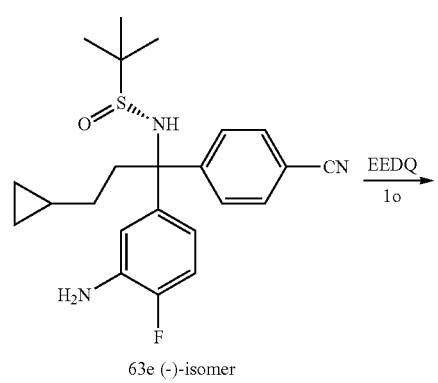

63e (−)-isomer

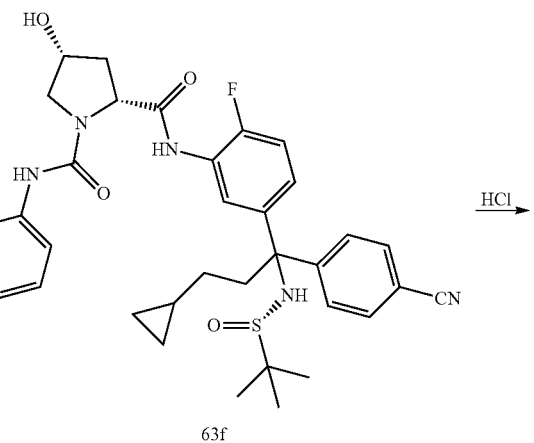

63f

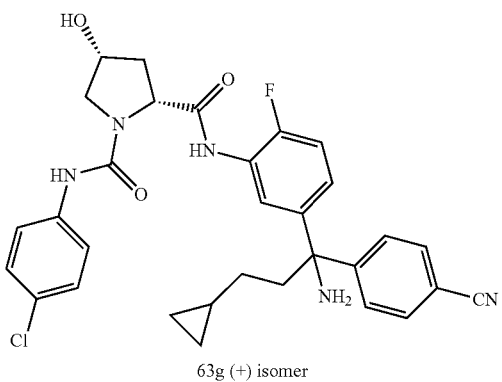

63g (+) isomer

Preparation of (2R,4R)-N2-(5-((+)-1-amino-1-(4-cyanophenyl)-3-cyclopropylpropyl)-2-fluorophenyl)-N1-(4-chlorophenyl)-4-hydroxypyrrolidine-1,2-dicarboxamide (63g)

Step: 1 Preparation of (E)-4-(3-cyclopropylacryloyl)benzonitrile (63b)

To a stirred solution of 4-acetylbenzonitrile (63a) (5 g, 34.4 mmol) in ethanol (100 mL) at 0° C. was added cyclopropanecarboxaldehyde (4.15 mL, 55.1 mmol) followed by potassium hydroxide (2M aqueous solution, 3.44 mL, 6.89 mmol). The reaction mixture allowed to attain room temperature and stirred for 24 h. The reaction was acidified with HCl to pH 6 and concentrated in vacuum maintaining bath temperature below 35° C. The residue obtained was purified by flash column chromatography (silica gel eluting with ethyl acetate in hexanes 0 to 20%) to afford (E)-4-(3-cyclopropylacryloyl)benzonitrile (63b) (512 mg, 2.60 mmol, 7.54% yield) as a colorless liquid; $^1$H NMR (300 MHz, DMSO-d$_6$) δ 8.12-8.08 (m, 2H), 8.02-7.99 (m, 2H), 7.25 (d, J=15.0 Hz, 1H), 6.57 (dd, J=15.1, 10.4 Hz, 1H), 1.80 (dddd, J=12.4, 10.4, 7.9, 4.5 Hz, 1H), 1.08-0.99 (m, 2H), 0.79 (tt, J=4.8, 2.4 Hz, 2H); MS (ES−) 196.1 (M−1).

Step 2: Preparation of 4-(3-cyclopropylpropanoyl)benzonitrile (63c)

To a stirred solution of (E)-4-(3-cyclopropylacryloyl) benzonitrile (63b) (1.1 g, 5.58 mmol) in acetonitrile (10 mL) was added tri-n-butyltin hydride (1.489 mL, 5.58 mmol) and heated at reflux for 6 h. The reaction mixture was cooled to room temperature and concentrated in vacuum. The residue obtained was purified by flash column chromatography (silica gel eluting with ethyl acetate in hexanes 0 to 100%) to afford 4-(3-cyclopropylpropanoyl)benzonitrile (63c) (457 mg, 2.294 mmol, 41.1% yield) as a colorless oil; $^1$H NMR (300 MHz, DMSO-d$_6$) δ 8.08-8.03 (m, 2H), 7.98-7.91 (m, 2H), 3.09 (t, J=7.2 Hz, 2H), 1.46 (q, J=7.1 Hz, 2H), 0.77-0.59 (m, 1H), 0.38-0.26 (m, 2H), 0.06-−0.04 (m, 2H); MS (ES−) 198.2 (M−1).

Step-3: Preparation of (+)-N-(1-(4-cyanophenyl)-3-cyclopropylpropylidene)-2-methylpropane-2-sulfinamide (63d)

Compound (63d) was prepared from 4-(3-cyclopropylpropanoyl)benzonitrile (63c) (0.814 g, 4.08 mmol) and (R)-2-methylpropane-2-sulfinamide (0.45 g, 3.71 mmol), using procedure as reported in step 3 of scheme 31 to afford (+)-N-(1-(4-cyanophenyl)-3-cyclopropylpropylidene)-2-methylpropane-2-sulfinamide (63d) (720 mg, 2.38 mmol, 64.1% yield) as a light yellow syrup; $^1$H NMR (300 MHz, DMSO-d$_6$) δ 8.11-7.93 (m, 4H), 3.34 (m, 2H), 1.44 (m, 1H), 1.24 (s, 10H), 0.73 (m, 1H), 0.45-0.29 (m, 2H), 0.03 (m, 2H); Optical rotation: $[α]_D$=(+) 16.55 [0.29, MeOH].

Step-4: Preparation of (R)-N-((−)-1-(3-amino-4-fluorophenyl)-1-(4-cyanophenyl)-3-cyclopropylpropyl)-2-methylpropane-2-sulfinamide (63e)

Compound (63e) was prepared from (+)-N-(1-(4-cyanophenyl)-3-cyclopropylpropylidene)-2-methylpropane-2-sulfinamide (63d) (0.5 g, 1.653 mmol), using procedure as reported in step 4 of scheme 31 to afford (R)-N-((−)-1-(3-amino-4-fluorophenyl)-1-(4-cyanophenyl)-3-cyclopropylpropyl)-2-methylpropane-2-sulfinamide (63e) (538 mg, 1.301 mmol, 79% yield) as a white solid; $^1$H NMR (300 MHz, DMSO-d$_6$) δ 7.83-7.66 (m, 2H), 7.61-7.44 (m, 2H), 6.90 (dd, J=11.3, 8.5 Hz, 1H), 6.70 (dd, J=8.7, 2.4 Hz, 1H), 6.47 (ddd, J=8.6, 4.3, 2.4 Hz, 1H), 5.27 (s, 1H), 5.11 (s, 2H), 2.62-2.55 (m, 1H), 2.46-2.39 (m, 1H), 1.12 (s, 9H), 1.06 (s, 1H), 0.99-0.80 (m, 1H), 0.64 (s, 1H), 0.36 (m, 2H), −0.02-−0.14 (m, 2H); $^{19}$F NMR (282 MHz, DMSO-d$_6$) δ −137.54; MS (ES+) 414.396 (M+1); Optical rotation: $[α]_D$=(−) 83.24 [0.185, MeOH].

Step-5: Preparation of (2R,4R)-N1-(4-chlorophenyl)-N2-(5-(1-(4-cyanophenyl)-3-cyclopropyl-1-((S)-1,1-dimethylethylsulfinamido)propyl)-2-fluorophenyl)-4-hydroxypyrrolidine-1,2-dicarboxamide (63f)

Reaction of (2R,4R)-1-(4-chlorophenylcarbamoyl)-4-hydroxypyrrolidine-2-carboxylic acid (1o) (0.14 g, 0.5 mmol), (R)-N-((−)-1-(3-amino-4-fluorophenyl)-1-(4-cyanophenyl)-3-cyclopropylpropyl)-2-methylpropane-2-sulfinamide (63e) (0.2 g, 0.5 mmol) in tetrahydrofuran (10 mL) using ethyl 2-ethoxyquinoline-1(2H)-carboxylate (0.12 g, 0.5 mmol) using the reaction and workup conditions as reported in step 10 of Scheme 1 gave after purification by flash chromatography (silica gel 24 g, eluting with CMA80 in chloroform 0 to 30%) (2R,4R)-N1-(4-chlorophenyl)-N2-(5-(1-(4-cyanophenyl)-3-cyclopropyl-1-((S)-1,1-dimethylethylsulfinamido)propyl)-2-fluorophenyl)-4-hydroxypyrrolidine-1,2-dicarboxamide (63f) (0.13 g, 38%) as a white solid; $^1$H NMR (300 MHz, DMSO-d$_6$) δ 9.85 (s, 1H), 8.71 (s, 1H), 8.28 (d, J=7.5 Hz, 1H), 7.97 (d, J=8.1 Hz, 2H), 7.80-7.64 (m, 4H), 7.48 (dd, J=8.9, 2.3 Hz, 2H), 7.38 (t, J=9.8 Hz, 1H), 7.28 (s, 1H), 5.68 (s, 1H), 5.52 (d, J=4.6 Hz, 1H), 4.71 (dd, J=9.2, 4.6 Hz, 1H), 4.54 (d, J=4.8 Hz, 1H), 3.88 (dd, J=9.9, 5.2 Hz, 1H), 3.70 (d, J=10.0 Hz, 1H), 2.79 (m, 1H), 2.61 (m, 1H), 1.42 (m, 2H), 1.33 (s, 9H), 1.14-0.98 (m, 2H), 0.83 (m, 1H), 0.54 (m, 2H), 0.17-0.04 (m, 2H); MS (ES+) 680.5 (M+1), 702.5 (M+Na), MS (ES−) 678.6 (M−1), 714.5 (M+Cl).

Step-6: Preparation of (2R,4R)-N2-(5-((+)-1-amino-1-(4-cyanophenyl)-3-cyclopropylpropyl)-2-fluorophenyl)-N1-(4-chlorophenyl)-4-hydroxypyrrolidine-1,2-dicarboxamide (63g)

Reaction of (2R,4R)-N1-(4-chlorophenyl)-N2-(5-(1-(4-cyanophenyl)-3-cyclopropyl-1-((S)-1,1-dimethylethylsulfinamido)propyl)-2-fluorophenyl)-4-hydroxypyrrolidine-1,2-dicarboxamide (63f) (0.13 g, 0.2 mmol) in ethanol (5 mL) using conc. HCl (0.12 mL) followed by workup and purification as reported in step 6 of Scheme 4 gave after purification by flash column chromatography (silica gel 24 g, eluting with 0-30% CMA-80 in chloroform) (2R,4R)-N2-(5-((+)-1-amino-1-(4-cyanophenyl)-3-cyclopropylpropyl)-2-fluorophenyl)-N1-(4-chlorophenyl)-4-hydroxypyrrolidine-1,2-dicarboxamide (63g) (70 mg, 61% yield) as white solid; $^1$H NMR (300 MHz, DMSO-d$_6$) δ 9.60 (s, 1H), 8.50 (s, 1H), 8.10-7.96 (m, 1H), 7.78-7.67 (m, 2H), 7.61-7.52 (m, 4H), 7.30-7.24 (m, 2H), 7.14-7.08 (m, 2H), 5.30 (d, J=4.9 Hz, 1H), 4.48 (td, J=9.2, 4.0 Hz, 1H), 4.33 (q, J=4.8 Hz, 1H), 3.68 (dd, J=10.0, 5.4 Hz, 1H), 3.50-3.41 (m, 1H), 2.23 (m, 5H), 1.95-1.83 (m, 1H), 1.13-0.91 (m, 2H), 0.80-0.53 (m, 1H), 0.40-0.27 (m, 2H), −0.04-−0.13 (m, 2H). $^{19}$F NMR (282 MHz, DMSO-d$_6$) δ −129.19; MS (ES+) 598.5 (M+Na), (ES−) 574.4 (M−1), 610.4 (M+Cl); Optical rotation: $[α]_D$= (+) 81.7 [0.225, CH$_3$OH].

Scheme 64

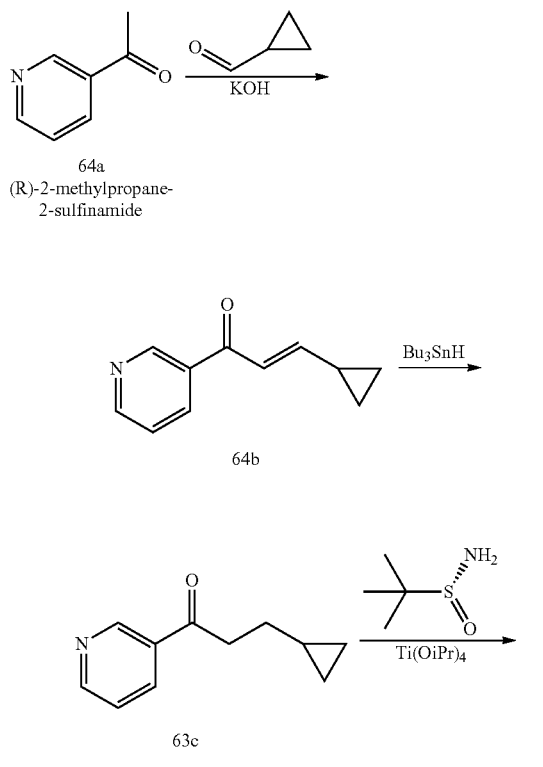

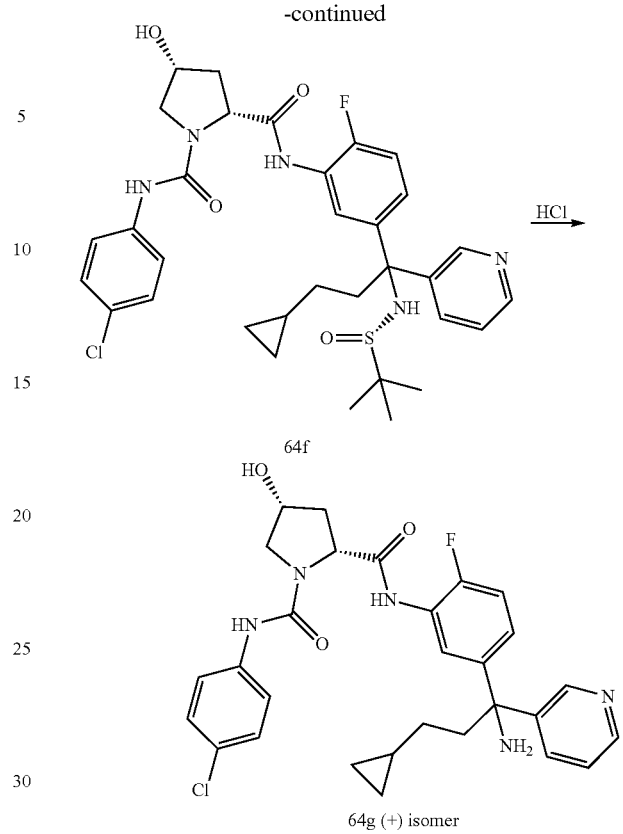

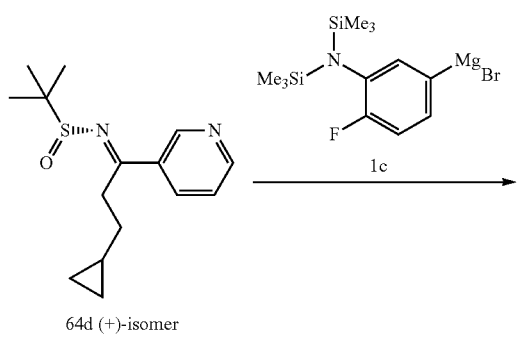

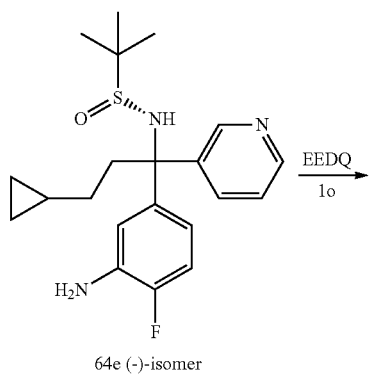

Preparation of (2R,4R)-N2-(5-((+)-1-amino-3-cyclopropyl-1-(pyridin-3-yl)propyl)-2-fluorophenyl)-N1-(4-chlorophenyl)-4-hydroxypyrrolidine-1,2-dicarboxamide (64g)

Step-1: Preparation of (E)-3-cyclopropyl-1-(pyridin-3-yl)prop-2-en-1-one (64b)

To a stirred solution of 3-acetylpyridine (64a) (9.07 mL, 83 mmol) in methanol (200 mL) cooled to 0° C. was added cyclopropanecarboxaldehyde (9.95 mL, 132 mmol) and aqueous potassium hydroxide (1N solution, 16.51 mL, 16.51 mmol). The reaction was allowed to warm to room temperature overnight. The reaction was acidified with 1N hydrochloric acid and concentrated in vacuum to remove methanol. The crude residue was dissolved in ethyl acetate (300 mL) washed with sodium carbonate solution, water (2×100 mL), brine (50 mL), dried, filtered and concentrated in vacuum. The crude residue was purified by flash column chromatography (silica gel, 80 g, eluting with ethyl acetate in hexanes 0 to 100%) to afford (E)-3-cyclopropyl-1-(pyridin-3-yl)prop-2-en-1-one (64b) (5.99 g, 41.9%); $^1$H NMR (300 MHz, DMSO-d6) δ 9.14 (td, J=2.7, 0.9 Hz, 1H), 8.80 (ddd, J=4.9, 3.3, 1.7 Hz, 1H), 8.36-8.27 (m, 1H), 7.57 (ddt, J=8.0, 4.8, 1.2 Hz, 1H), 7.28 (d, J=15.1 Hz, 1H), 6.58 (dd, J=15.1, 10.3 Hz, 1H), 1.80 (dddd, J=12.5, 10.4, 7.8, 4.5 Hz, 1H), 1.08-0.99 (m, 2H), 0.85-0.76 (m, 2H); MS (ES+) 196.1 (M+Na).

Step-2: Preparation of 3-cyclopropyl-1-(pyridin-3-yl)propan-1-one (64c)

To a stirred solution of (E)-3-cyclopropyl-1-(pyridin-3-yl)prop-2-en-1-one (64b) (5.93 g, 34.2 mmol) in benzene (150 mL) was added tributylstannane (18.42 mL, 68.5 mmol) and heated to reflux. The reaction was stirred at reflux for 5 h and cooled to room temperature. Benzene was evaporated and the residue was purified by flash column chromatography (silica gel, 80 g, eluting with ethyl acetate in hexanes 0 to 100%) to afford 3-cyclopropyl-1-(pyridin-3-yl)propan-1-one (64c) (5.29 g, 88%); $^1$H NMR (300 MHz, DMSO-$d_6$) δ 9.07 (dd, J=2.3, 0.9 Hz, 1H), 8.72 (dd, J=4.8, 1.7 Hz, 1H), 8.24 (ddd, J=8.0, 2.4, 1.8 Hz, 1H), 7.50 (ddd, J=8.0, 4.9, 0.9 Hz, 1H), 3.09 (t, J=7.2 Hz, 2H), 1.47 (q, J=7.1 Hz, 2H), 0.70 (dddd, J=12.0, 8.1, 5.1, 2.2 Hz, 1H), 0.40-0.21 (m, 2H), 0.06--0.05 (m, 2H).

Step-3: Preparation of (−)-N-(3-cyclopropyl-1-(pyridin-3-yl)propylidene)-2-methylpropane-2-sulfinamide (64d)

Compound (64d) was prepared from 3-cyclopropyl-1-(pyridin-3-yl)propan-1-one (64c) (3.98 g, 22.69 mmol) and (R)-2-methylpropane-2-sulfinamide (2.5 g, 20.63 mmol) using procedure as reported in step 3 of Scheme 31 to afford (−)-N-(3-cyclopropyl-1-(pyridin-3-yl)propylidene)-2-methylpropane-2-sulfinamide (64d) (2.5 g, 8.98 mmol, 43.5% yield) as a yellow syrup; $^1$H NMR (300 MHz, DMSO-$d_6$) δ 9.04 (s, 1H), 8.72 (dd, J=4.8, 1.6 Hz, 1H), 8.24 (d, J=8.1 Hz, 1H), 7.53 (dd, J=8.1, 4.8 Hz, 1H), 3.40 (m, 1H), 3.30 (m, 1H), 1.47 (q, J=7.4 Hz, 2H), 1.24 (s, 9H), 0.82-0.66 (m, 1H), 0.44-0.29 (m, 2H), 0.12-0.01 (m, 2H); Optical Rotation [α]$_D$=(−) 17.29 [0.59,MeOH].

Step-4: Preparation of (R)-N-((−)-1-(3-amino-4-fluorophenyl)-3-cyclopropyl-1-(pyridin-3-yl)propyl)-2-methylpropane-2-sulfinamide (64e)

To a stirred solution of (−)-N-(3-cyclopropyl-1-(pyridin-3-yl)propylidene)-2-methylpropane-2-sulfinamide (64d) (82 g, 295 mmol) in Toluene (1700 mL) at −20° C. was added dropwise a freshly prepared solution of (3-(bis(trimethylsilyl)amino)-4-fluorophenyl)magnesium bromide (1c) (920 mL, 736 mmol) over a period of 120 mins. The reaction mixture was stirred at −20° C. for 1 h and quenched with 1N aqueous KHSO$_4$ (1600 mL). The reaction mixture was stirred for 1 h at room temperature, basified with 2N NaOH to pH~8 and extracted with ethyl acetate (1500, 700 mL). The organic layers were combined washed with water (2×700 mL), brine (700 mL), dried and concentrated in vacuum. The crude residue was purified by flash column chromatography (silica gel, eluting with (9:1) ethyl acetate/methanol in hexanes 0 to 50%) to afford (R)-N-((−)-1-(3-amino-4-fluorophenyl)-3-cyclopropyl-1-(pyridin-3-yl)propyl)-2-methylpropane-2-sulfinamide (64e) (54.155 g, 139 mmol, 47.2% yield) as a white solid; $^1$H NMR (300 MHz, DMSO-$d_6$) δ 8.53-8.48 (m, 1H), 8.39 (dd, J=4.7, 1.5 Hz, 1H), 7.70 (dt, J=8.1, 2.0 Hz, 1H), 7.32 (dd, J=8.0, 4.7 Hz, 1H), 6.90 (dd, J=11.2, 8.5 Hz, 1H), 6.73 (dd, J=8.8, 2.4 Hz, 1H), 6.56-6.45 (m, 1H), 5.26 (s, 1H), 5.10 (s, 2H), 2.67-2.54 (m, 2H), 1.28-1.11 (m, 1H), 1.12 (s, 9H), 0.91 (m, 1H), 0.64 (m, 1H), 0.40-0.30 (m, 2H), −0.02--0.14 (m, 2H); 19F NMR (282 MHz, DMSO $d_6$) δ −137.67; MS (ES+) 390.4 (M+1); (ES−) 388.4 (M−1); Optical Rotation [α]$_D$=(−) 105.71 [0.28, MeOH].

Step-5: Preparation of (2R,4R)-N1-(4-chlorophenyl)-N2-(5-(3-cyclopropyl-1-((S)-1,1-dimethylethylsulfinamido)-1-(pyridin-3-yl)propyl)-2-fluorophenyl)-4-hydroxypyrrolidine-1,2-dicarboxamide (64f)

Reaction of (2R,4R)-1-(4-chlorophenylcarbamoyl)-4-hydroxypyrrolidine-2-carboxylic acid (1o) (0.14 g, 0.5 mmol), (R)-N-((−)-1-(3-amino-4-fluorophenyl)-3-cyclopropyl-1-(pyridin-3-yl)propyl)-2-methylpropane-2-sulfinamide (64e) (0.2 g, 0.5 mmol) in tetrahydrofuran (5 mL) using ethyl 2-ethoxyquinoline-1(2H)-carboxylate (0.12 g, 0.5 mmol) using the reaction and workup conditions as reported in step 10 of Scheme 1 gave after purification by flash chromatography (silica gel 24 g, eluting with CMA80 in chloroform 0 to 30%) (2R,4R)-N1-(4-chlorophenyl)-N2-(5-(3-cyclopropyl-1-((S)-1,1-dimethylethylsulfinamido)-1-(pyridin-3-yl)propyl)-2-fluorophenyl)-4-hydroxypyrrolidine-1,2-dicarboxamide (64f) (0.09 g, 27%) as a white solid; $^1$H NMR (300 MHz, DMSO-$d_6$) δ 9.97 (s, 1H), 8.83 (d, J=2.5 Hz, 2H), 8.72 (dd, J=4.5, 2.8 Hz, 1H), 8.40 (d, J=7.4 Hz, 1H), 8.01 (d, J=8.1 Hz, 1H), 7.92-7.81 (m, 2H), 7.70-7.56 (m, 3H), 7.54-7.38 (m, 2H), 5.81 (s, 1H), 5.64 (d, J=4.5 Hz, 1H), 4.82 (d, J=8.6 Hz, 1H), 4.66 (m, 1H), 3.99 (m, 1H), 3.82 (d, J=10.1 Hz, 1H), 2.42-2.32 (m, 3H), 2.23 (m, 1H), 1.45 (m, 10H), 1.31-1.10 (m, 1H), 0.96 (s, 1H), 0.65 (s, 2H), 0.33-0.24 (m, 2H); MS (ES+) 656.5 (M+1), 678.5 (M+Na), MS (ES−) 654.4 (M−1), 690.5 (M+Cl).

Step-6: Preparation of (2R,4R)-N2-(5-((+)-1-amino-3-cyclopropyl-1-(pyridin-3-yl)propyl)-2-fluorophenyl)-N1-(4-chlorophenyl)-4-hydroxypyrrolidine-1,2-dicarboxamide (64g)

Reaction of (2R,4R)-N1-(4-chlorophenyl)-N2-(5-(3-cyclopropyl-1-((S)-1,1-dimethylethylsulfinamido)-1-(pyridin-3-yl)propyl)-2-fluorophenyl)-4-hydroxypyrrolidine-1,2-dicarboxamide (64f) (0.08 g, 0.12 mmol) in ethanol (4 mL) using conc. HCl (0.12 mL) followed by workup and purification as reported in step 6 of Scheme 4 gave after purification by flash column chromatography (silica gel 24 g, eluting with 0-30% CMA-80 in chloroform) (2R,4R)-N2-(5-((+)-1-amino-3-cyclopropyl-1-(pyridin-3-yl)propyl)-2-fluorophenyl)-N1-(4-chlorophenyl)-4-hydroxypyrrolidine-1,2-dicarboxamide (64g) (35 mg, 50% yield) as white solid; $^1$H NMR (300 MHz, DMSO-$d_6$) δ 9.61 (s, 1H), 8.58 (d, J=2.3 Hz, 1H), 8.50 (s, 1H), 8.35 (dd, J=4.7, 1.5 Hz, 1H), 8.04 (d, J=7.6 Hz, 1H), 7.73 (dt, J=8.1, 2.0 Hz, 1H), 7.58-7.49 (m, 2H), 7.32-7.23 (m, 3H), 7.18-7.09 (m, 2H), 5.30 (d, J=4.9 Hz, 1H), 4.50 (dd, J=9.0, 4.7 Hz, 1H), 4.33 (d, J=5.0 Hz, 1H), 3.68 (dd, J=10.0, 5.3 Hz, 1H), 3.49 (s, 1H), 2.38 (m, 3H), 2.23 (m, 1H), 1.03 (m, 2H), 0.64 (m, 1H), 0.41-0.27 (m, 2H), −0.03--0.13 (m, 2H); $^{19}$F NMR (282 MHz, DMSO-$d_6$) δ −129.28; MS (ES+) 552.5 (M+1), 574.5, 576.5 (M+Na), (ES−) 550.5, 552.4 (M−1), 586.5, 588.5 (M+Cl); Optical rotation: [α]$_D$=(+) 68.0 [0.25, CH$_3$OH].

Scheme 65

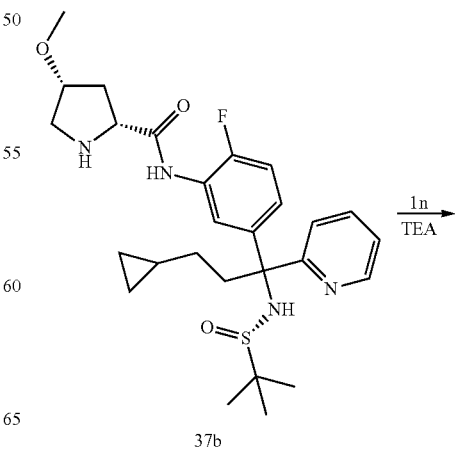

37b

229
-continued

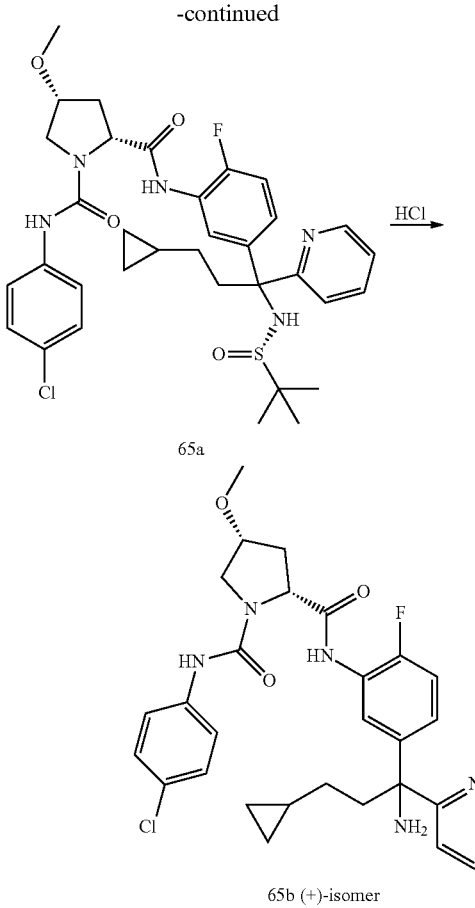

65a 65b (+)-isomer

Preparation of (2R,4R)-N2-(5-((+)-1-amino-3-cyclopropyl-1-(pyridin-2-yl)propyl)-2-fluorophenyl)-N1-(4-chlorophenyl)-4-methoxypyrrolidine-1,2-dicarboxamide (65b)

Step-1: Preparation of (2R,4R)-N1-(4-chlorophenyl)-N2-(5-(3-cyclopropyl-1-((S)-1,1-dimethylethylsulfinamido)-1-(pyridin-2-yl)propyl)-2-fluorophenyl)-4-methoxypyrrolidine-1,2-dicarboxamide (65a)

Reaction of (2R,4R)-N-(5-(3-cyclopropyl-1-((S)-1,1-dimethylethylsulfinamido)-1-(pyridin-2-yl)propyl)-2-fluorophenyl)-4-methoxypyrrolidine-2-carboxamide (37b) (0.1 g, 0.19 mmol), 4-Chlorophenyl isocyanate (0.045 g, 0.3 mmol) using TEA (80 µL) as base in THF (5 mL) according to the procedure reported in step 9 of Scheme 1 gave after purification by flash column chromatography (2R,4R)-N1-(4-chlorophenyl)-N2-(5-(3-cyclopropyl-1-((S)-1,1-dimethylethylsulfinamido)-1-(pyridin-2-yl)propyl)-2-fluorophenyl)-4-methoxypyrrolidine-1,2-dicarboxamide (65a) (0.105 g, 80%) as a white solid; $^1$H NMR (300 MHz, DMSO-$d_6$) δ 9.48 (s, 1H), 8.57-8.47 (m, 2H), 8.04-7.94 (m, 1H), 7.73 (td, J=7.7, 1.7 Hz, 1H), 7.54 (d, J=8.9 Hz, 2H), 7.27 (dd, J=10.5, 7.5 Hz, 3H), 7.23-7.05 (m, 2H), 6.14 (s, 1H), 4.53 (dd, J=9.2, 3.9 Hz, 1H), 4.06 (s, 1H), 3.78-3.55 (m, 2H), 3.21 (s, 3H), 2.68-2.52 (m, 2H), 2.42-2.24 (m, 1H), 2.15-2.02 (m, 1H), 1.21 (m, 1H), 1.09 (s, 9H), 0.91-0.65 (m, 2H), 0.62-0.47 (m, 1H), 0.29 (m, 2H), -0.16--0.21 (m, 2H); MS (ES+) 670.5 (M+1), 692.5 (M+Na), MS (ES-) 668.5 (M-1), 704.5 (M+Cl).

Step 2: Preparation of (2R,4R)-N2-(5-((+)-1-amino-3-cyclopropyl-1-(pyridin-2-yl)propyl)-2-fluorophenyl)-N1-(4-chlorophenyl)-4-methoxypyrrolidine-1,2-dicarboxamide (65b)

Reaction of (2R,4R)-N1-(4-chlorophenyl)-N2-(5-(3-cyclopropyl-1-((S)-1,1-dimethylethylsulfinamido)-1-(pyridin-2-yl)propyl)-2-fluorophenyl)-4-methoxypyrrolidine-1,2-dicarboxamide (65a) (0.1 g, 0.43 mmol) in ethanol (5 mL) using conc. HCl (0.12 mL) as reported in step 6 of Scheme 4 gave after purification by flash column chromatography (silica gel 12 g, eluting with CMA80 in chloroform 0 to 30%) (2R,4R)-N2-(5-((+)-1-amino-3-cyclopropyl-1-(pyridin-2-yl)propyl)-2-fluorophenyl)-N1-(4-chlorophenyl)-4-methoxypyrrolidine-1,2-dicarboxamide (65b) (65 mg, 65% yield) hydrochloride salt as white solid; $^1$H NMR (300 MHz, DMSO-$d_6$) δ 9.65 (s, 1H), 8.90 (s, 3H), 8.69-8.64 (m, 1H), 8.57 (s, 1H), 7.99 (dd, J=7.4, 2.5 Hz, 1H), 7.87 (td, J=7.8, 1.8 Hz, 1H), 7.61-7.52 (m, 2H), 7.47-7.41 (m, 1H), 7.38-7.25 (m, 4H), 7.17-7.08 (m, 1H), 4.55 (dd, J=9.2, 4.2 Hz, 1H), 4.15-4.04 (m, 1H), 3.75 (dd, J=10.5, 5.3 Hz, 1H), 3.61 (dd, J=10.4, 3.5 Hz, 1H), 3.23 (s, 3H), 2.52-2.33 (m, 3H), 2.14-2.00 (m, 1H), 1.10 (m, 2H), 0.67 (m, 1H), 0.45-0.34 (m, 2H), -0.01 (m, 2H); $^{19}$F NMR (282 MHz, DMSO-$d_6$) δ -125.63; MS (ES+) 566.5 (M+1), (ES-) 600.5 (M+Cl); Optical rotation: $[α]_D$=(+) 94.4 [0.25, MeOH].

Scheme 66

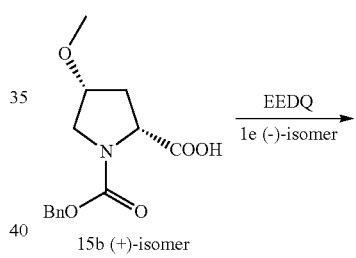

15b (+)-isomer

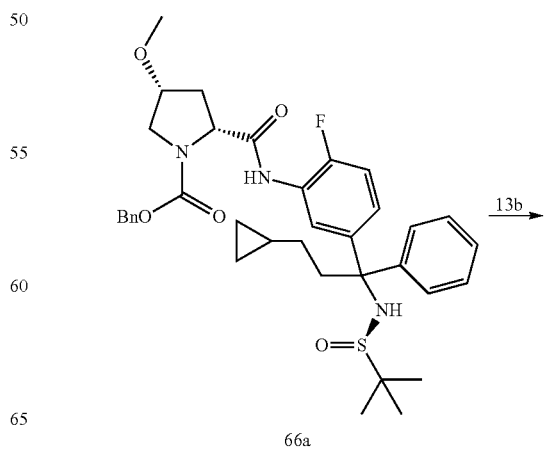

66a

231
-continued

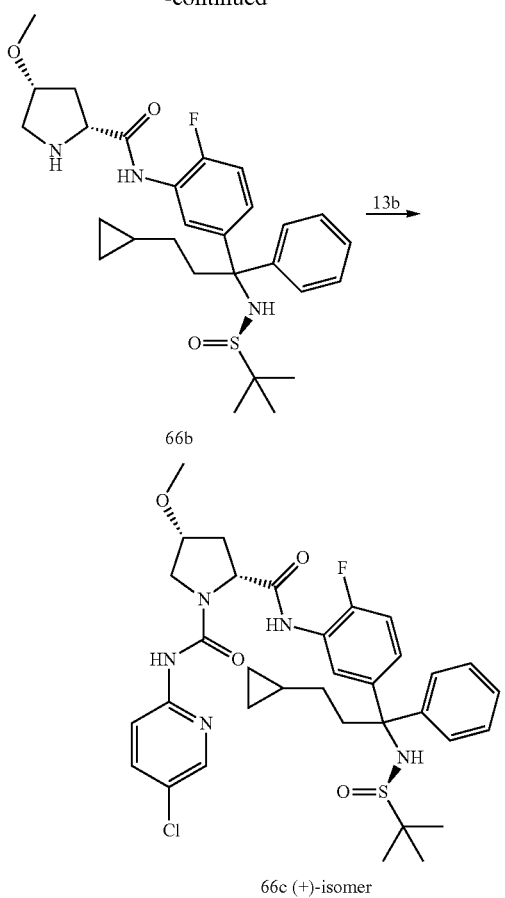

66b 66c (+)-isomer

Preparation of (2R,4R)-N1-(5-chloropyridin-2-yl)-N2-(5-((+)-3-cyclopropyl-1-((R)-1,1-dimethylethylsulfinamido)-1-phenylpropyl)-2-fluorophenyl)-4-methoxypyrrolidine-1,2-dicarboxamide (66c)

Step 1: Preparation of (2R,4R)-benzyl 2-(5-(3-cyclopropyl-1-((R)-1,1-dimethylethylsulfinamido)-1-phenylpropyl)-2-fluorophenylcarbamoyl)-4-methoxypyrrolidine-1-carboxylate (66a)

Reaction of (2R,4R)-1-(benzyloxycarbonyl)-4-methoxypyrrolidine-2-carboxylic acid (15b) (2 g, 7.16 mmol), (R)-N-((−)-(3-amino-4-fluorophenyl)(phenyl)methyl)-2-methylpropane-2-sulfinamide (1e) (2.41 g, 7.52 mmol) in tetrahydrofuran (50 mL) using ethyl 2-ethoxyquinoline-1(2H)-carboxylate (1.86 g, 7.52 mmol) using the reaction and workup conditions as reported in step 10 of Scheme 1 gave after purification by flash column chromatography (silica gel 40 g, eluting with CMA 80 in chloroform 0 to 100%) (2R,4R)-benzyl 2-(5-(3-cyclopropyl-1-((R)-1,1-dimethylethylsulfinamido)-1-phenylpropyl)-2-fluorophenylcarbamoyl)-4-methoxypyrrolidine-1-carboxylate (66a) (3.11 g, 75%) as a white solid; $^{1}$H NMR (300 MHz, DMSO-d$_{6}$) δ 9.54 (2s, 1H, rotamers), 7.81 (m, 1H), 7.45-7.09 (m, 12H), 6.00 (s, 1H), 5.47 (s, 1H), 5.17-4.93 (m, 2H), 4.44 (m, 1H), 3.99 (m, 1H), 3.69 (m, 1H), 3.50-3.36 (m, 1H), 3.18 (m, 3H), 2.11-1.98 (m, 2H), 1.13 (s, 9H); MS (ES+) 582.5 (M+1).

232

Step 2: Preparation of (2R,4R)-N-(5-(3-cyclopropyl-1-((R)-1,1-dimethylethylsulfinamido)-1-phenylpropyl)-2-fluorophenyl)-4-methoxypyrrolidine-2-carboxamide (66b)

Debenzylation by hydrogenation of (2R,4R)-benzyl 2-(5-(3-cyclopropyl-1-((R)-1,1-dimethylethylsulfinamido)-1-phenylpropyl)-2-fluorophenylcarbamoyl)-4-methoxypyrrolidine-1-carboxylate (66a) (3.0 g, 5.15 mmol) in ethanol (50 mL), using palladium on carbon 10% (0.3 g) as catalyst according to procedure reported in step 2 of Scheme 13 gave (2R,4R)-N-(5-(3-cyclopropyl-1-((R)-1,1-dimethylethylsulfinamido)-1-phenylpropyl)-2-fluorophenyl)-4-methoxypyrrolidine-2-carboxamide (66b) (1.45 g, 63% yield) as a white solid; MS (ES+) 448.4 (M+1), (ES−) 446.3 (M−1).

Step-3: Preparation of (2R,4R)-N1-(5-chloropyridin-2-yl)-N2-(5-((+)-3-cyclopropyl-1-((R)-1,1-dimethylethylsulfinamido)-1-phenylpropyl)-2-fluorophenyl)-4-methoxypyrrolidine-1,2-dicarboxamide (66c)

Reaction of (2R,4R)-N-(5-(3-cyclopropyl-1-((R)-1,1-dimethylethylsulfinamido)-1-phenylpropyl)-2-fluorophenyl)-4-methoxypyrrolidine-2-carboxamide (66b) (0.18 g, 0.4 mmol) in tetrahydrofuran (20 mL), phenyl (5-chloropyridin-2-yl)carbamate (13b) (0.13 g, 0.52 mmol), using triethylamine (0.08 g, 0.8 mmol) as base using reaction and workup conditions as reported in step 3 of Scheme 13 gave (2R,4R)-N1-(5-chloropyridin-2-yl)-N2-(5-((+)-3-cyclopropyl-1-((R)-1,1-dimethylethylsulfinamido)-1-phenylpropyl)-2-fluorophenyl)-4-methoxypyrrolidine-1,2-dicarboxamide (66c) (0.12 g, 52% yield) as a white solid; $^{1}$H NMR (300 MHz, DMSO-d$_{6}$) δ 9.78 (s, 1H), 9.45 (s, 1H), 8.60 (m, 1H), 8.25-8.03 (m, 3H), 7.72-7.43 (m, 7H), 6.29 (d, J=5.6 Hz, 1H), 5.77 (d, J=5.4 Hz, 1H), 4.88 (d, J=8.3 Hz, 1H), 4.34 (m, 1H), 4.02 (m, 2H), 3.50 (s, 3H), 2.75-2.59 (m, 1H), 2.39 (m, 1H), 1.42 (s, 9H); $^{19}$F NMR (282 MHz, DMSO-d$_{6}$) δ −127.17; MS (ES+) 624.5, 626.4 (M+Na), (ES−) 601.5.5, 602.5 (M−1); Optical rotation [α]$_{D}$=(+) 22.22 [0.135, MeOH].

Scheme 67

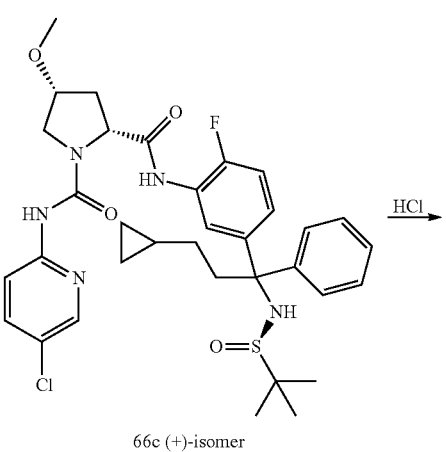

66c (+)-isomer

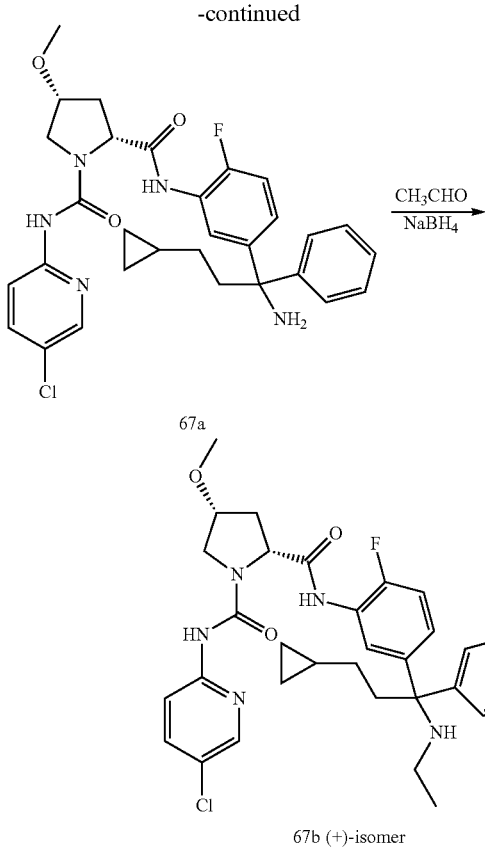

67a 67b (+)-isomer

Preparation of (2R,4R)-N1-(5-chloropyridin-2-yl)-N2-(5-((+)-3-cyclopropyl-1-(ethylamino)-1-phenylpropyl)-2-fluorophenyl)-4-methoxypyrrolidine-1,2-dicarboxamide (67b)

Step-1: Preparation of (2R,4R)-N2-(5-(1-amino-3-cyclopropyl-1-phenylpropyl)-2-fluorophenyl)-N1-(5-chloropyridin-2-yl)-4-methoxypyrrolidine-1,2-dicarboxamide (67a)

Reaction of (2R,4R)-N1-(5-chloropyridin-2-yl)-N2-(5-((+)-3-cyclopropyl-1-((R)-1,1-dimethylethylsulfinamido)-1-phenylpropyl)-2-fluorophenyl)-4-methoxypyrrolidine-1,2-dicarboxamide (66c) (0.8 g, 1.3 mmol) in ethanol (50 mL) using conc. HCl (1 mL) as reported in step 6 of Scheme 4 gave after purification by flash column chromatography (silica gel 12 g, eluting with CMA80 in chloroform 0 to 40%) (2R,4R)-N2-(5-(1-amino-3-cyclopropyl-1-phenylpropyl)-2-fluorophenyl)-N1-(5-chloropyridin-2-yl)-4-methoxypyrrolidine-1,2-dicarboxamide (67a) (0.32 g, 49%) as a white solid; $^1$H NMR (300 MHz, DMSO-$d_6$) δ 9.44 (s, 1H), 9.13 (s, 1H), 8.36-8.24 (m, 1H), 7.96-7.74 (m, 3H), 7.43-7.32 (m, 2H), 7.32-7.21 (m, 2H), 7.21-7.10 (m, 3H), 5.06 (s, 1H), 4.57 (d, J=8.2 Hz, 1H), 4.04 (s, 1H), 3.73 (m, 2H), 3.21 (m, 3H), 2.45-2.28 (m, 3H), 2.09 (m, 1H); 19F NMR (282 MHz, DMSO-$d_6$) δ −128.12; MS(ES+) 498.4 (M+1); MS (ES−) 532.4 (M+Cl).

Step 2: Preparation of (2R,4R)-N1-(5-chloropyridin-2-yl)-N2-(5-((+)-3-cyclopropyl-1-(ethylamino)-1-phenylpropyl)-2-fluorophenyl)-4-methoxypyrrolidine-1,2-dicarboxamide (67b)

Reductive amination of (2R,4R)-N2-(5-(1-amino-3-cyclopropyl-1-phenylpropyl)-2-fluorophenyl)-N1-(5-chloropyridin-2-yl)-4-methoxypyrrolidine-1,2-dicarboxamide (67a) (0.075 g, 0.15 mmol) in MeOH (3 mL) using acetaldehyde (0.02 g, 0.45 mmol) and sodium borohydride (0.017 g, 0.45 mmol) according to the procedure reported in Scheme 41 gave after workup and purification by flash column chromatography (silica gel 12 g, eluting with methanol in chloroform 0 to 10%) (2R,4R)-N1-(5-chloropyridin-2-yl)-N2-(5-((+)-3-cyclopropyl-1-(ethylamino)-1-phenylpropyl)-2-fluorophenyl)-4-methoxypyrrolidine-1,2-dicarboxamide (67b) (0.055 g, 69% yield) as a white solid; $^1$H NMR (300 MHz, DMSO-$d_6$) δ 9.51-9.42 (s, 1H), 9.16 (s, 1H), 8.30 (dd, J=2.7, 0.8 Hz, 1H), 7.94-7.85 (m, 2H), 7.81 (dd, J=9.0, 2.6 Hz, 1H), 7.38 (d, J=7.0 Hz, 2H), 7.27 (t, J=7.5 Hz, 2H), 7.22-7.09 (m, 4H), 4.76 (s, 1H), 4.58 (dd, J=9.2, 4.0 Hz, 1H), 4.09-3.97 (m, 2H), 3.84-3.63 (m, 1H), 3.22 (s, 3H), 2.46-2.27 (m, 3H), 2.09 (m, 1H), 1.03 (t, J=6.9 Hz, 3H); 19F NMR (282 MHz, DMSO-$d_6$) δ −128.09; MS(ES+) 526.4 (M+1), 548.4 (M+Na) MS (ES−) 524.4 (M−1), 560.4 (M+Cl); Optical rotation: $[α]_D$=(+) 72.31 [0.26, MeOH].

Scheme 68

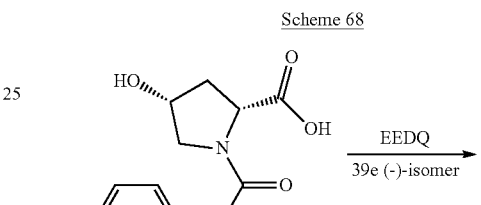

1o

68a

Preparation of (2R,4R)-N1-(4-chlorophenyl)-N2-(5-(3-cyclopropyl-1-((R)-1,1-dimethylethylsulfinamido)-1-(pyridin-4-yl)propyl)-2-fluorophenyl)-4-hydroxypyrrolidine-1,2-dicarboxamide (68a)

Reaction of (2R,4R)-1-(4-chlorophenylcarbamoyl)-4-hydroxypyrrolidine-2-carboxylic acid (0.095 g, 0.03 mmol), (R)-N-((−)-1-(3-amino-4-fluorophenyl)-3-cyclopropyl-1-(pyridin-4-yl)propyl)-2-methylpropane-2-sulfinamide (39e) (0.13 g, 0.3 mmol) in tetrahydrofuran (5 mL) using ethyl 2-ethoxyquinoline-1(2H)-carboxylate (0.085 g, 0.3 mmol) using the reaction and workup conditions as reported in step 10 of Scheme 1 gave (2R,4R)-N1-(4-chlorophenyl)-N2-(5-(3-cyclopropyl-1-((R)-1,1-dimethylethylsulfinamido)-1-(pyridin-4-yl)propyl)-2-fluorophenyl)-4-hydroxypyrrolidine-1,2-dicarboxamide (68a) (0.04 g, 21%) as a white solid; $^1$H NMR (300 MHz, DMSO-$d_6$) δ 9.67 (s, 1H), 8.56-8.44 (m, 3H), 8.09 (d, J=7.4 Hz, 1H), 7.61-7.48 (m, 2H), 7.34-7.24 (m, 4H), 7.24-7.14 (m, 1H), 7.10 (m, 1H), 5.51 (s, 1H), 5.33 (d, J=4.4 Hz, 1H), 4.51 (dd, J=9.1, 4.7 Hz, 1H), 4.34 (m, 1H), 3.68 (m, 1H), 3.54-3.45 (m, 1H), 2.42-2.27 (m, 3H), 1.25-1.16 (m, 1H), 1.14 (s, 9H), 0.89 (m, 1H), 0.63 (m, 1H), 0.34 (m, 2H), −0.07 (m, 2H); 19F NMR (282 MHz, DMSO-$d_6$) δ −128.49; MS (ES+) 656.5 (M+1), 678.5, 680.5 (M+Na) (ES−) 654.5, 655.5 (M−1), 690.5, 692.6 (M+Cl).

(m, 2H), −0.02−−0.15 (m, 2H); 19F NMR (282 MHz, DMSO-$d_6$) δ −129.12 (q, J=7.7 Hz); MS (ES+) 552.5 (M+1), 554.5 (M+2); Optical rotation: [α]$_D$=(+) 76.66 [0.06, MeOH].

Scheme 69

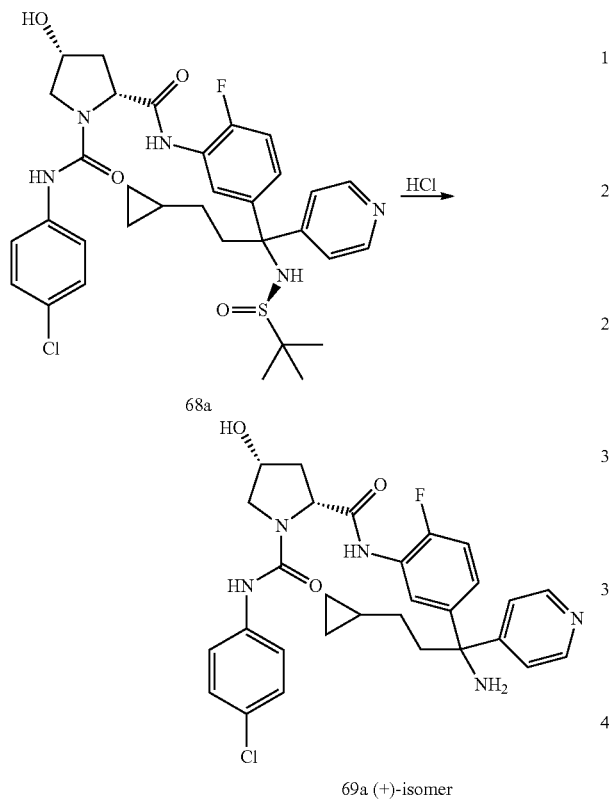

Scheme 70

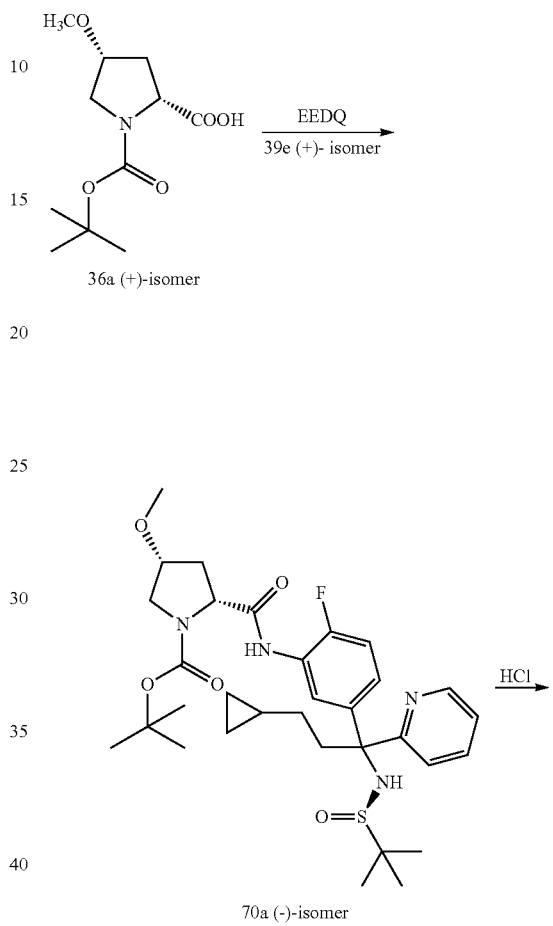

Preparation of (2R,4R)-N2-(5-((+)-1-amino-3-cyclopropyl-1-(pyridin-4-yl)propyl)-2-fluorophenyl)-N1-(4-chlorophenyl)-4-hydroxypyrrolidine-1,2-dicarboxamide (69a)

Reaction of (2R,4R)-N1-(4-chlorophenyl)-N2-(5-(3-cyclopropyl-1-((R)-1,1-dimethylethylsulfinamido)-1-(pyridin-4-yl)propyl)-2-fluorophenyl)-4-hydroxypyrrolidine-1,2-dicarboxamide (68a) (0.17 g, 0.26 mmol) in methanol (5 mL) using 3M HCl in methanol as reported in step 6 of Scheme 4 gave after purification by flash column chromatography (silica gel 12 g, eluting with CMA80 in chloroform 0 to 40%) (2R,4R)-N2-(5-((+)-1-amino-3-cyclopropyl-1-(pyridin-4-yl)propyl)-2-fluorophenyl)-N1-(4-chlorophenyl)-4-hydroxypyrrolidine-1,2-dicarboxamide (69a) (0.1 g, 70%) as a white solid; $^1$H NMR (300 MHz, DMSO-$d_6$) δ 9.61 (s, 1H), 8.50 (s, 1H), 8.47-8.40 (m, 2H), 8.05 (d, J=7.7 Hz, 1H), 7.59-7.49 (m, 2H), 7.38-7.31 (m, 2H), 7.31-7.23 (m, 2H), 7.13 (d, J=8.1 Hz, 2H), 5.30 (d, J=4.8 Hz, 1H), 4.50 (dd, J=9.0, 4.7 Hz, 1H), 4.40-4.26 (m, 1H), 3.68 (dd, J=10.0, 5.3 Hz, 1H), 3.51-3.41 (m, 1H), 2.39-2.12 (m, 5H), 1.96-1.81 (m, 1H), 1.12-0.92 (m, 2H), 0.72-0.54 (m, 1H), 0.41-0.26

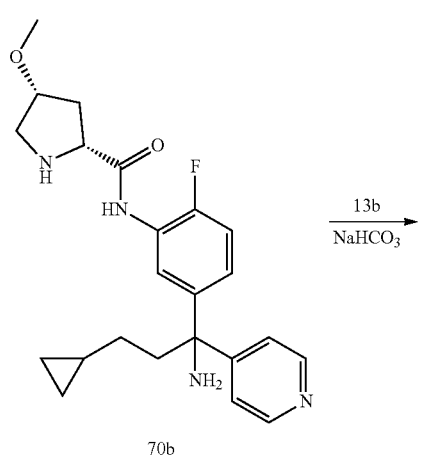

237

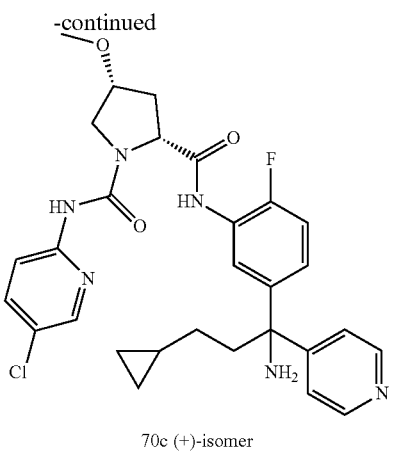

70c (+)-isomer

Preparation of (2R,4R)-N2-(5-((+)-1-amino-3-cyclopropyl-1-(pyridin-4-yl)propyl)-2-fluorophenyl)-N1-(5-chloropyridin-2-yl)-4-methoxypyrrolidine-1,2-dicarboxamide (70c)

Step-1 Preparation of (2R,4R)-tert-butyl 2-(5-((−)-3-cyclopropyl-1-((R)-1,1-dimethylethylsulfinamido)-1-(pyridin-4-yl)propyl)-2-fluorophenylcarbamoyl)-4-methoxypyrrolidine-1-carboxylate (70a)

Compound 70a was prepared from (2R,4R)-1-(tert-butoxycarbonyl)-4-methoxypyrrolidine-2-carboxylic acid (36a) (22 g, 90 mmol), (R)-N-((−)-1-(3-amino-4-fluorophenyl)-3-cyclopropyl-1-(pyridin-4-yl)propyl)-2-methylpropane-2-sulfinamide (39e) (34.2 g, 88 mmol) and ethyl 2-ethoxyquinoline-1(2H)-carboxylate (24.2 g, 98 mmol) using the reaction and workup conditions as reported in step 10 of Scheme 1 to afford after purification by flash column chromatography (silica gel, eluting with 0-100% 9:1 ethyl acetate/methanol in hexanes) (2R,4R)-tert-butyl 2-(5-((−)-3-cyclopropyl-1-((R)-1,1-dimethylethylsulfinamido)-1-(pyridin-4-yl)propyl)-2-fluorophenylcarbamoyl)-4-methoxypyrrolidine-1-carboxylate (70a) (38.8 g, 70%) as colorless foam. $^1$H NMR data showed product as rotamers; $^1$H NMR (300 MHz, DMSO-d$_6$) δ 9.52 (s, 1H), 8.54-8.45 (m, 2H), 7.89 (d, J=7.2 Hz, 1H), 7.36-7.27 (m, 2H), 7.20 (d, J=10.3 Hz, 2H), 5.47 (s, 1H), 4.39-4.21 (m, 1H), 4.01-3.89 (m, 1H), 3.63-3.50 (m, 1H), 3.27-3.12 (m, 3H), 2.64-2.53 (m, 4H), 1.94-1.83 (m, 1H), 1.47-1.06 (m, 19H), 1.00-0.79 (m, 1H), 0.73-0.55 (m, 1H), 0.42-0.26 (m, 2H), −0.02--0.16 (m, 2H); MS (ES+) 617.7 (M+1), MS(ES−) 615.6 (M−1), 651.6 (M+Cl); Optical Rotation [α]$_D$=(−) 48.2 [0.17, MeOH].

Step-2: Preparation of (2R,4R)-N-(5-(1-amino-3-cyclopropyl-1-(pyridin-4-yl)propyl)-2-fluorophenyl)-4-methoxypyrrolidine-2-carboxamide (70b)

Reaction of (2R,4R)-tert-butyl 2-(5-((−)-3-cyclopropyl-1-((R)-1,1-dimethylethylsulfinamido)-1-(pyridin-4-yl)propyl)-2-fluorophenylcarbamoyl)-4-methoxypyrrolidine-1-carboxylate (70a) (30 g, 48.7 mmol) in methanol (300 mL) with 3N HCl in methanol (130 mL, 400 mmol) gave after workup and purification as reported in step 6 of Scheme 4 (2R,4R)-N-(5-(1-amino-3-cyclopropyl-1-(pyridin-4-yl)propyl)-2-fluorophenyl)-4-methoxypyrrolidine-2-carboxamide

238

(70b) (25 g, 100% yield) as a hydrochloride salt which was pure enough to be used as such in next step.

Step-3: (2R,4R)-N2-(5-((+)-1-amino-3-cyclopropyl-1-(pyridin-4-yl)propyl)-2-fluorophenyl)-N1-(5-chloropyridin-2-yl)-4-methoxypyrrolidine-1,2-dicarboxamide (70c)

Reaction of (2R,4R)-N-(5-(1-amino-3-cyclopropyl-1-(pyridin-4-yl)propyl)-2-fluorophenyl)-4-methoxypyrrolidine-2-carboxamide (70b) (25.9 g, 48.7 mmol) in tetrahydrofuran/water (600/40 mL) with phenyl 5-chloropyridin-2-ylcarbamate (13b) (10.8 g, 43.8 mmol) using sodium bicarbonate (33 g, 400 mmol) as base according to procedure reported in step 3 of Scheme 13 gave after purification by flash column chromatography (silica gel, eluting with using 0-100% CMA-80 in Chloroform) to afford (2R,4R)-N2-(5-((+)-1-amino-3-cyclopropyl-1-(pyridin-4-yl)propyl)-2-fluorophenyl)-N1-(5-chloropyridin-2-yl)-4-methoxypyrrolidine-1,2-dicarboxamide (70c) (14 g, 47%) free base as a white solid; $^1$H NMR (300 MHz, DMSO-d$_6$) δ 9.45 (s, 1H), 9.15 (s, 1H), 8.48-8.40 (m, 2H), 8.30 (dd, J=2.6, 0.8 Hz, 1H), 7.95-7.85 (m, 2H), 7.81 (dd, J=9.0, 2.6 Hz, 1H), 7.38-7.30 (m, 2H), 7.19-7.10 (m, 2H), 4.57 (dd, J=9.2, 4.0 Hz, 1H), 4.03 (m, 1H), 3.72 (qd, J=10.8, 4.3 Hz, 2H), 3.20 (s, 3H), 2.40-2.24 (m, 2H), 2.19 (t, J=8.0 Hz, 2H), 2.09 (m, 1H), 1.03 (m, 2H), 0.62 (m, 1H), 0.40-0.28 (m, 2H), −0.07 (s, 2H). The free base (8.5 g, 15 mmol) was converted to hydrochloride salt using conc. HCl (2.87 mL) in ethanol (30 mL) to afford compound 70c (9.3 g) hydrochloride as a white solid; $^1$H NMR (300 MHz, DMSO-d$_6$) δ 9.76-9.69 (m, 1H), 9.63 (s, 4H), 9.23 (s, 1H), 8.85 (s, 2H), 8.31 (dd, J=2.6, 0.8 Hz, 1H), 8.01-7.92 (m, 1H), 7.85 (qd, J=9.0, 1.7 Hz, 2H), 7.72 (brs, 2H), 7.38 (dd, J=10.4, 8.8 Hz, 1H), 7.23 (s, 1H), 4.61 (dd, J=9.2, 4.2 Hz, 1H), 4.05 (d, J=4.8 Hz, 1H), 3.78 (dd, J=10.9, 5.2 Hz, 1H), 3.73-3.62 (m, 1H), 3.21 (s, 3H), 2.41 (m, 2H), 2.06 (m, 1H), 1.14 (m, 2H), 0.68 (m, 1H), 0.43-0.29 (m, 2H), 0.03 (m, 2H); $^{19}$F NMR (282 MHz, DMSO-d$_6$) δ −125.00; MS (ES+) 567.3 (M+1), 569.3 (M+2), MS (ES−) 601.2 (M+Cl); Optical Rotation [α]$_D$=(+) 96.4 [0.5, MeOH]; Analysis calculated for $C_{29}H_{32}ClFN_6O_3 \cdot 2.25HCl \cdot 2.0H_2O$: C, 50.84; H, 5.63; Cl, 16.82; N, 12.27. Found: C, 50.98; H, 5.67; Cl, 16.72; N, 12.12.

Scheme 71

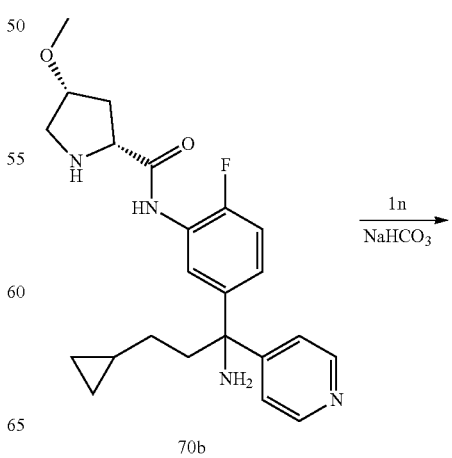

70b

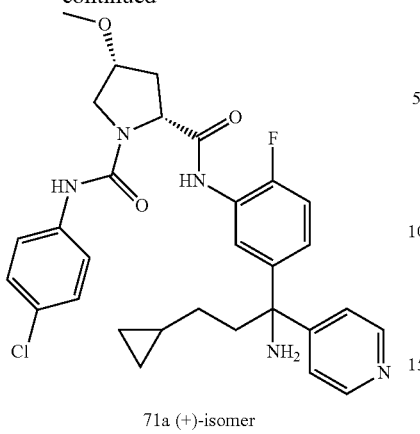

71a (+)-isomer

Preparation of (2R,4R)-N2-(5-((+)-1-amino-3-cyclopropyl-1-(pyridin-4-yl)propyl)-2-fluorophenyl)-N1-(4-chlorophenyl)-4-methoxypyrrolidine-1,2-dicarboxamide (71a)

Reaction of (2R,4R)-N-(5-(1-amino-3-cyclopropyl-1-(pyridin-4-yl)propyl)-2-fluorophenyl)-4-methoxypyrrolidine-2-carboxamide (70b) (0.5 g, 0.97 mmol) in tetrahydrofuran/water (20/2 mL) with 4-chlorophenyl isocyanate (1n) (0.13 g, 0.87 mmol) using sodium bicarbonate (0.33 g, 0.4 mmol) as base according to procedure reported in step 9 of Scheme 1 gave after purification by flash column chromatography (silica gel, eluting with using 0-30% CMA-80 in Chloroform) (2R,4R)-N2-(5-((+)-1-amino-3-cyclopropyl-1-(pyridin-4-yl)propyl)-2-fluorophenyl)-N1-(4-chlorophenyl)-4-methoxypyrrolidine-1,2-dicarboxamide (71a) (0.1 g, 18% yield) as a colorless foam; $^1$H NMR (300 MHz, DMSO-$d_6$) δ 9.60 (s, 1H), 8.62-8.50 (m, 3H), 7.94 (dd, J=7.4, 2.4 Hz, 1H), 7.61-7.49 (m, 2H), 7.38-7.22 (m, 5H), 7.16-7.06 (m, 1H), 4.55 (dd, J=9.2, 4.1 Hz, 1H), 4.07 (d, J=5.3 Hz, 1H), 3.79-3.69 (m, 1H), 3.61 (dd, J=10.3, 3.4 Hz, 1H), 3.22 (s, 3H), 2.48-2.23 (m, 3H), 2.14-2.02 (m, 1H), 1.08 (m, 2H), 0.67 (m, 1H), 0.44-0.30 (m, 2H), −0.03 (m, 2H); HPLC: 6.602 (98%); MS (ES+) 565.4 (M+), 567.4 (M+2), MS (ES−) 564.5 (M+), 600.5 (M+Cl); Analysis calculated for $C_{30}H_{33}ClFN_5O_3 \cdot 3H_2O$: C, 58.11; H, 6.34; N, 11.29. Found: C, 58.01; H, 5.98; N, 10.96.

The free base of compound 71a was converted to hydrochloride salt using conc. HCl in ethanol to afford compound 71a hydrochloride salt as a white solid; $^1$H NMR (300 MHz, DMSO-$d_6$) δ 9.71 (s, 1H), 9.55 (s, 3H), 8.81 (d, J=5.1 Hz, 2H), 8.59 (s, 1H), 7.98 (dd, J=7.3, 2.5 Hz, 1H), 7.64 (d, J=5.7 Hz, 1H), 7.60-7.50 (m, 2H), 7.38 (dd, J=10.5, 8.8 Hz, 1H), 7.32-7.25 (m, 2H), 7.21 (s, 1H), 4.57 (dd, J=9.2, 4.2 Hz, 1H), 4.07 (d, J=4.7 Hz, 1H), 3.81-3.69 (m, 1H), 3.62 (dd, J=10.3, 3.4 Hz, 1H), 3.23 (s, 3H), 2.45-2.35 (m, 3H), 2.14-2.00 (m, 1H), 1.30-0.98 (m, 2H), 0.69 (m, 1H), 0.38 (m, 2H), 0.07-0.01 (m, 2H); $^{19}$F NMR (282 MHz, DMSO-$d_6$) δ −125.33; MS (ES+) 565.4 (M+1), 567.4 (M+2), 588.4, 590.4 (M+Na), MS (ES−) 564.5 (M−1), 600.4 (M+Cl); Optical Rotation $[α]_D$=(+) 67.9 [0.28, MeOH]; Analysis calculated for $C_{30}H_{33}ClFN_5O_3 \cdot 2HCl \cdot 2.75H_2O$: C, 52.33; H, 5.93; Cl, 15.45; N, 10.17. Found: C, 52.68; H, 5.94; Cl, 15.30; N, 9.89.

Scheme 72

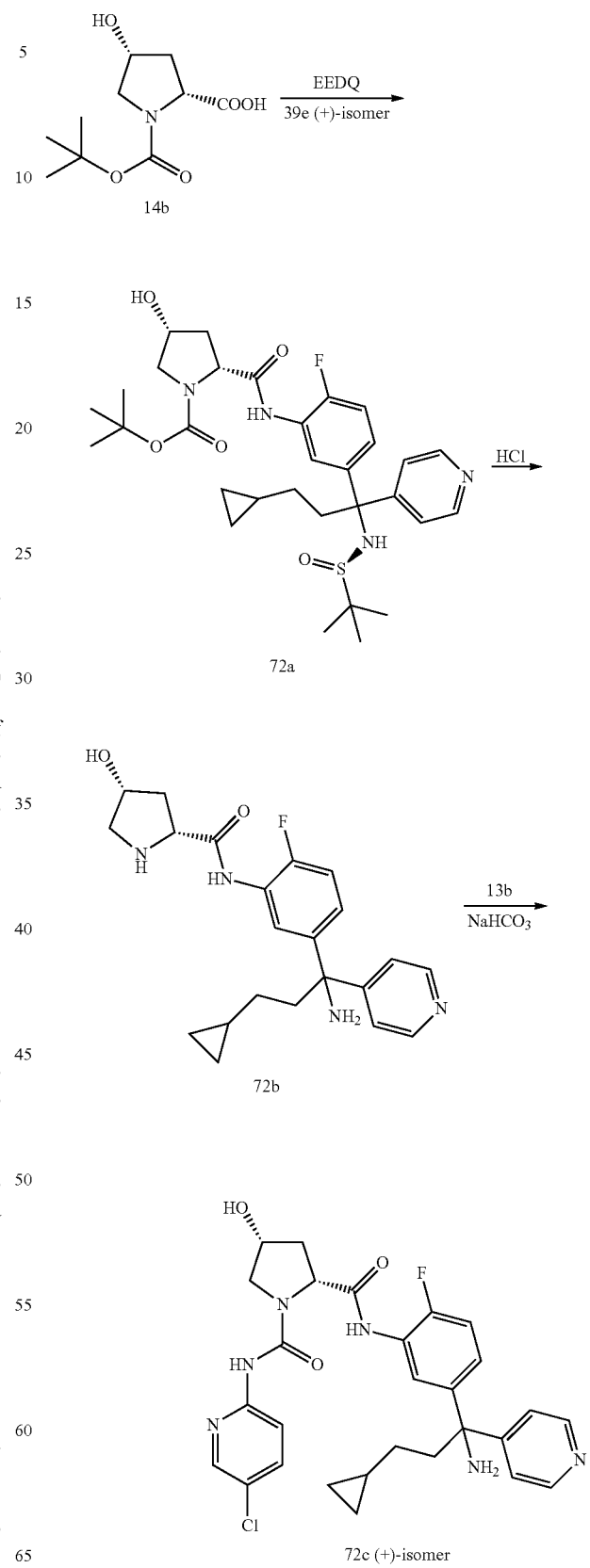

Preparation of (2R,4R)-N2-(5-((+)-1-amino-3-cyclo-propyl-1-(pyridin-4-yl)propyl)-2-fluorophenyl)-N1-(5-chloropyridin-2-yl)-4-hydroxypyrrolidine-1,2-dicarboxamide (72c)

Step-1: Preparation of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-hydroxypyrrolidine-1-carboxylate (72a)

Reaction of (2R,4R)-1-(tert-butoxycarbonyl)-4-hydroxy-pyrrolidine-2-carboxylic acid (14b) (0.16 g, 0.69 mmol), (R)-N-((−)-1-(3-amino-4-fluorophenyl)-3-cyclopropyl-1-(pyridin-4-yl)propyl)-2-methylpropane-2-sulfinamide (39e) (0.27 g, 0.69 mmol) in tetrahydrofuran (5 mL) using ethyl 2-ethoxyquinoline-1(2H)-carboxylate (0.17 g, 0.7 mmol) using the reaction and workup conditions as reported in step 10 of Scheme 1 gave (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-hydroxypyrrolidine-1-carboxylate (72a) (0.17 g, 40%) as a white solid; $^1$H NMR (300 MHz, DMSO-$d_6$) δ 9.80 (s, 1H), 8.48 (dt, J=6.1, 2.3 Hz, 2H), 7.98 (d, J=7.4 Hz, 1H), 7.35-7.26 (m, 2H), 7.20 (d, J=11.7 Hz, 2H), 5.49 (d, J=12.6 Hz, 1H), 5.36-5.17 (m, 1H), 4.35-4.15 (m, 2H), 3.57-3.42 (m, 1H), 3.29-3.16 (m, 1H), 2.44-2.30 (m, 1H), 1.89-1.73 (m, 1H), 1.46-1.01 (m, 19H), 0.97-0.79 (m, 1H), 0.70-0.50 (m, 1H), 0.43-0.27 (m, 2H), −0.03−−0.15 (m, 2H); MS (ES+) 603.5 (M+1), 625.5 (M+Na), MS (ES−) 601.5 (M−1).

Step-2: Preparation of (2R,4R)-N-(5-((S)-1-amino-3-cyclopropyl-1-(pyridin-4-yl)propyl)-2-fluorophenyl)-4-hydroxypyrrolidine-2-carboxamide (72b)

Reaction of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-hydroxypyrrolidine-1-carboxylate (72a) (0.17 g, 0.27 mmol) in methanol (10 mL) using 3N HCl in methanol (1 mL) followed by workup and purification as reported in step 6 of Scheme 4 gave (2R,4R)-N-(5-((S)-1-amino-3-cyclopropyl-1 (pyridin-4-yl)propyl)-2-fluorophenyl)-4-hydroxypyrrolidine-2-carboxamide (72b) as a yellow oil, which was used as such in next step without further purification.

Step-3: Preparation of (2R,4R)-N2-(5-((+)-1-amino-3-cyclopropyl-1-(pyridin-4-yl)propyl)-2-fluorophenyl)-N1-(5-chloropyridin-2-yl)-4-hydroxypyrrolidine-1,2-dicarboxamide (72c)

Reaction of (2R,4R)-N-(5-((S)-1-amino-3-cyclopropyl-1-(pyridin-4-yl)propyl)-2-fluorophenyl)-4-hydroxypyrrolidine-2-carboxamide (72b) obtained in above step 2 in tetrahydrofuran/water (8 mL/1 mL) with phenyl 5-chloropyridin-2-ylcarbamate (13b) (0.06 g, 0.25 mmol) using sodium bicarbonate (0.23 g, 2.7 mmol) as base according to procedure reported in step 3 of Scheme 13 gave after purification by flash column chromatography (silica gel 24 g, eluting with CMA-80 in chloroform 0-30%) (0.1 g, 74% yield) free base as a white solid; $^1$H NMR (300 MHz, DMSO-$d_6$) δ 9.67 (s, 1H), 9.17 (s, 1H), 8.47-8.38 (m, 2H), 8.32 (s, 1H), 8.29 (dd, J=2.6, 0.8 Hz, 1H), 8.01 (d, J=7.6 Hz, 1H), 7.88 (dd, J=9.1, 0.8 Hz, 1H), 7.79 (dd, J=9.0, 2.6 Hz, 1H), 7.39-7.30 (m, 2H), 7.13 (d, J=7.9 Hz, 1H), 5.31 (s, 1H), 4.54 (dd, J=9.0, 4.8 Hz, 1H), 4.30 (s, 1H), 3.72 (dd, J=10.4, 5.3 Hz, 1H), 3.50 (q, J=5.0, 4.1 Hz, 1H), 2.45-2.09 (m, 5H), 1.96-1.80 (m, 1H), 1.10-0.90 (m, 2H), 0.70-0.53 (m, 1H), 0.41-0.22 (m, 2H), −0.02−−0.16 (m, 2H); $^{19}$F NMR (282 MHz, DMSO-$d_6$) δ −125.05; MS (ES+) 553.5 (M+1), 555.4 (M+2), 575.4, 577.4 (M+Na), MS (ES−) 587.4 (M+Cl). The free base was converted into HCl salt using conc HCl in ethanol (5 mL) to afford compound 72c HCl salt as a white solid; 1H NMR (300 MHz, DMSO-$d_6$) δ 9.93 (s, 1H), 9.70 (s, 3H), 9.27 (s, 1H), 8.95-8.86 (m, 2H), 8.30 (dd, J=2.5, 0.9 Hz, 1H), 8.10 (dd, J=7.2, 2.5 Hz, 1H), 7.90-7.76 (m, 4H), 7.39 (dd, J=10.5, 8.8 Hz, 1H), 7.23 (dd, J=7.3, 4.5 Hz, 1H), 4.57 (dd, J=8.9, 5.1 Hz, 1H), 4.33 (t, J=5.1 Hz, 1H), 3.75 (dd, J=10.4, 5.4 Hz, 1H), 3.56-3.45 (m, 1H), 2.60-2.53 (m, 2H), 2.47-2.33 (m, 2H), 1.87 (m, 1H), 1.30-0.96 (m, 2H), 0.69 (m, 1H), 0.37 (m, 2H), 0.08-0.01 (m, 2H). $^{19}$F NMR (282 MHz, DMSO-$d_6$) δ −125.05; MS (ES+) 553.5 (M+1), 555.4 (M+2), 575.4, 577.4 (M+Na), MS (ES−) 587.4 (M+Cl); Optical rotation [α]$_D$=(+) 82.96 [0.27, MeOH].

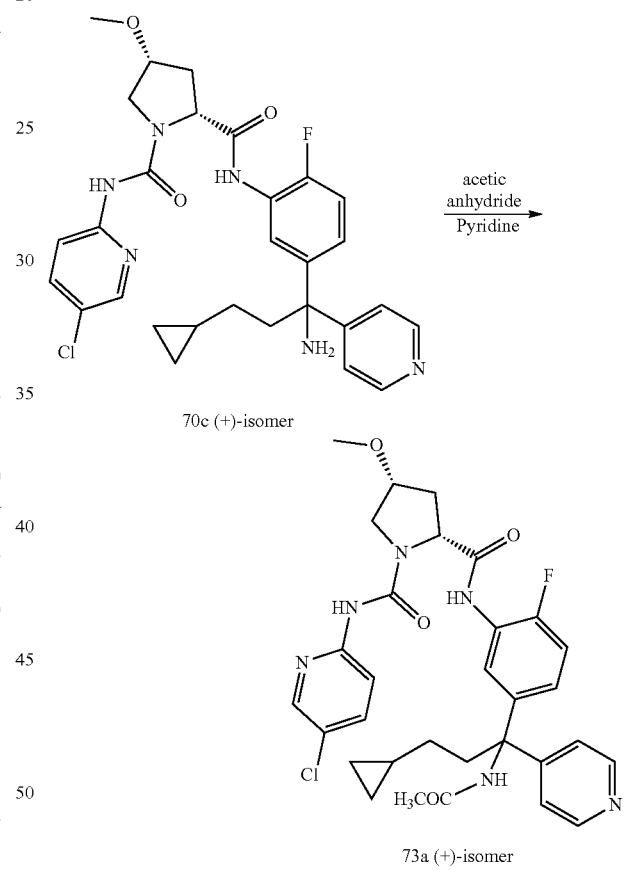

Scheme 73

70c (+)-isomer acetic anhydride
Pyridine 73a (+)-isomer

Preparation of (2R,4R)-N2-(5-((+)-1-acetamido-3-cyclopropyl-1-(pyridin-4-yl)propyl)-2-fluorophenyl)-N1-(5-chloropyridin-2-yl)-4-methoxypyrrolidine-1,2-dicarboxamide (73a)

Reaction of (2R,4R)-N2-(5-((+)-1-amino-3-cyclopropyl-1-(pyridin-4-yl)propyl)-2-fluorophenyl)-N1-(5-chloropyridin-2-yl)-4-methoxypyrrolidine-1,2-dicarboxamide (70c) (113 mg, 0.2 mmol) at 0° C. in dichloromethane (3 mL) using pyridine (126 mg, 1.6 mmol) and acetic anhydride (81 mg, 0.8 mmol) as reported in Scheme 55 gave (2R,4R)-N2-(5-((+)-1-acetamido-3-cyclopropyl-1-(pyridin-4-yl)propyl)-

2-fluorophenyl)-N1-(5-chloropyridin-2-yl)-4-methoxypyrrolidine-1,2-dicarboxamide (73a) (91 mg, 75%) free base as a white solid; $^1$H NMR (300 MHz, DMSO-d$_6$) δ 9.49 (s, 1H), 9.17 (s, 1H), 8.45 (d, J=5.8 Hz, 2H), 8.30 (dd, J=2.7, 0.8 Hz, 2H), 7.94-7.76 (m, 3H), 7.30-7.23 (m, 2H), 7.22-7.05 (m, 2H), 4.58 (dd, J=9.2, 4.0 Hz, 1H), 4.04 (d, J=5.4 Hz, 1H), 3.73 (td, J=11.3, 6.2 Hz, 3H), 3.21 (s, 3H), 2.43-2.23 (m, 2H), 2.10 (m, 1H), 1.90 (s, 3H), 0.91 (m, 2H), 0.62 (m, 1H), 0.38-0.33 (m, 2H), −0.13--0.13 (m, 2H). $^{19}$F NMR (282 MHz, DMSO-d$_6$) δ −128.00; MS (ES+) 609.4 (M+1), 631.4 (M+Na), MS (ES−) 607.4 (M−), 643.4 (M+Cl); The free base was converted to HCl salt to afford compound 73a HCl salt as a white solid; $^1$H NMR (300 MHz, DMSO-d$_6$) δ 9.60 (s, 1H), 9.22 (s, 1H), 8.75 (d, J=6.2 Hz, 2H), 8.69 (s, 1H), 8.30 (dd, J=2.6, 0.9 Hz, 1H), 7.97 (d, J=6.9 Hz, 1H), 7.94-7.88 (m, 3H), 7.86 (d, J=0.9 Hz, 1H), 7.81 (dd, J=9.0, 2.6 Hz, 1H), 7.31-7.18 (m, 2H), 4.59 (dd, J=9.2, 4.1 Hz, 1H), 4.10-4.00 (m, 1H), 3.73 (qd, J=10.8, 4.3 Hz, 2H), 3.22 (s, 3H), 2.78-2.53 (m, 2H), 2.47-2.32 (m, 1H), 2.15-2.00 (m, 1H), 1.94 (s, 3H), 1.09-0.93 (m, 2H), 0.74-0.57 (m, 1H), 0.34 (d, J=2.0 Hz, 1H), 0.04--0.14 (m, 2H); $^{19}$F NMR (282 MHz, DMSO-d$_6$) δ −127.10; MS (ES+) 609.3 (M+1) 631.3 (M+Na); MS (ES−) 643.3 (M+Cl); HPLC purity (87.9048%); Optical rotation [α]$_D$=(+) 105.84 [0.565, MeOH]; Analysis calculated for $C_{31}H_{34}ClFN_6O_4$·1.75HCl·2H$_2$O: C, 52.52; H, 5.65; Cl, 13.75; N, 11.85. Found: C, 52.28; H, 5.81; Cl, 13.92; N, 11.67.

Preparation of (2R,4R)-N1-(5-chloropyridin-2-yl)-N2-(5-((+)-3-cyclopropyl-1-(methylsulfonamido)-1-(pyridin-4-yl)propyl)-2-fluorophenyl)-4-methoxypyrrolidine-1,2-dicarboxamide (74a)

Reaction of (2R,4R)-N2-(5-((+)-1-amino-3-cyclopropyl-1-(pyridin-4-yl)propyl)-2-fluorophenyl)-N1-(5-chloropyridin-2-yl)-4-methoxypyrrolidine-1,2-dicarboxamide (70a) (57 mg, 0.1 mmol) at 0° C. in dichloromethane (3 mL) using pyridine (78 mg, 1 mmol) and methanesulfonic anhydride (68 mg, 0.4 mmol) according to the procedure as reported in Scheme 55 gave after purification by flash column chromatography (silica gel 12 g, eluting with MeOH in Chloroform 0 to 10%) (2R,4R)-N1-(5-chloropyridin-2-yl)-N2-(5-((+)-3-cyclopropyl-1-(methylsulfonamido)-1-(pyridin-4-yl)propyl)-2-fluorophenyl)-4-methoxypyrrolidine-1,2-dicarboxamide (74a) (25 mg, 40% yield) free base as a white solid; $^1$H NMR (300 MHz, DMSO-d$_6$) δ 9.58 (s, 1H), 9.18 (s, 1H), 8.42-8.25 (m, 2H), 8.01-7.75 (m, 5H), 7.33-7.17 (m, 1H), 7.08 (s, 1H), 4.68-4.53 (m, 1H), 4.04 (d, J=5.9 Hz, 1H), 3.89-3.61 (m, 2H), 3.19 (s, 3H), 2.61-2.31 (m, 3H), 2.28 (s, 3H), 2.10 (m, 1H), 1.14-0.96 (m, 1H), 0.86 (m, 1H), 0.65-0.49 (m, 1H), 0.43-0.22 (m, 2H), −0.01--0.23 (m, 2H); $^{19}$F NMR (282 MHz, DMSO-d$_6$) δ −126.45; MS (ES+) 645.3 (M+1), 667.3 (M+Na), (ES−) 643.4 (M−1). The free base was converted to HCl salt to furnish compound 74a hydrochloride as a white solid; $^1$H NMR (300 MHz, DMSO-d$_6$) δ 9.63 (s, 1H), 9.19 (s, 1H), 8.81 (d, J=6.2 Hz, 2H), 8.30 (d, J=2.6, Hz, 1H), 8.14 (s, 1H), 7.97 (d, J=7.9 Hz, 1H), 7.88 (q, J=4.1, 2.8 Hz, 3H), 7.82 (dd, J=9.0, 2.6 Hz, 1H), 7.29 (dd, J=10.3, 8.8 Hz, 1H), 7.11 (m, 1H), 4.61 (dd, J=9.2, 4.1 Hz, 1H), 4.05 (t, J=4.4 Hz, 1H), 3.78 (m, 1H), 3.21 (s, 3H), 2.78-2.59 (m, 1H), 2.42 (s, 3H), 2.40-2.34 (m, 1H), 2.17-2.02 (m, 1H), 1.37-0.95 (m, 2H), 0.91-0.70 (m, 2H), 0.60 (m, 1H), 0.33 (m, 2H), −0.03--0.13 (m, 2H); $^{19}$F NMR (282 MHz, DMSO-d$_6$) δ −125.93; MS (ES+) 645.3 (M+1), 667.3 (M+Na), MS (ES−) 679.4 (M+Cl); Optical rotation [α]$_D$= (+) 82.96 [0.27, MeOH].

Scheme 74

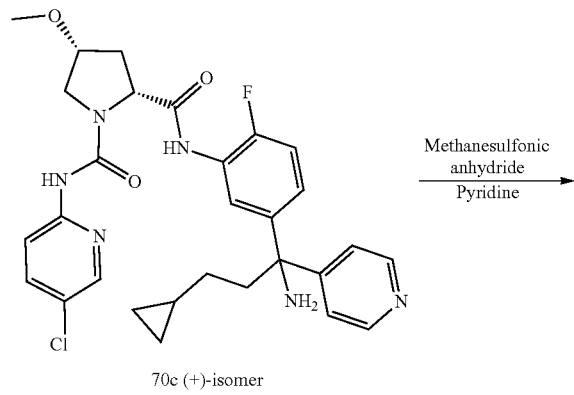

70c (+)-isomer

Methanesulfonic anhydride
Pyridine
→

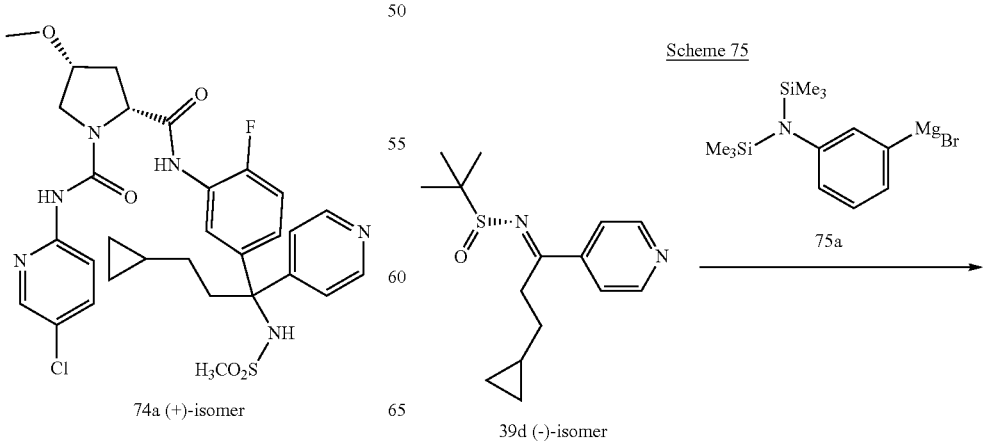

74a (+)-isomer

Scheme 75

39d (−)-isomer

75a

-continued

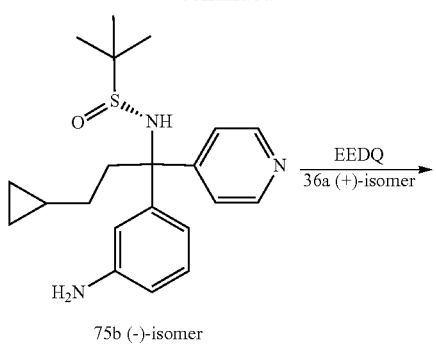

75b (−)-isomer

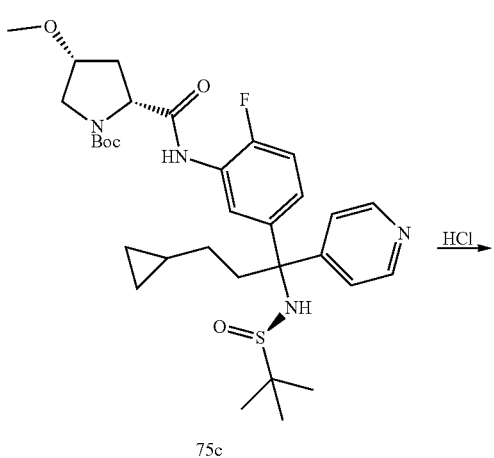

75c

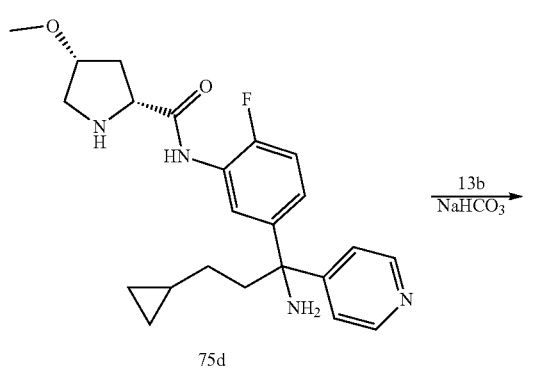

75d

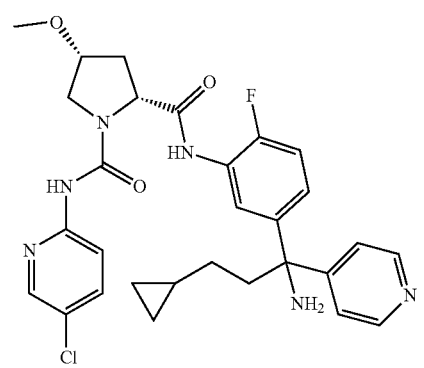

75e (+)-isomer

Preparation of (2R,4R)-N2-(3-((+)-1-amino-3-cyclopropyl-1-(pyridin-4-yl)propyl)phenyl)-N1-(5-chloropyridin-2-yl)-4-methoxypyrrolidine-1,2-dicarboxamide (75e)

Step-1 Preparation of (R)-N-((−)-1-(3-aminophenyl)-3-cyclopropyl-1-(pyridin-4-yl)propyl)-2-methylpropane-2-sulfinamide (75b)

Compound (75b) was prepared from (−)-N-(3-cyclopropyl-1-(pyridin-4-yl)propylidene)-2-methylpropane-2-sulfinamide (39d) (4.3 g, 15.5 mmol) and (3-(bis(trimethylsilyl)amino)phenyl)magnesium bromide (34 mL, 34 mmol, 1M solution in THF) using procedure as reported in step 4 of scheme 31 to afford (R)-N-((−)-1-(3-aminophenyl)-3-cyclopropyl-1-(pyridin-4-yl)propyl)-2-methylpropane-2-sulfinamide (75b) (1.9 g, 33%) as a white solid; $^1$H NMR (300 MHz, DMSO-$d_6$) δ 8.51-8.42 (m, 2H), 7.37-7.29 (m, 2H), 6.94 (t, J=7.8 Hz, 1H), 6.52 (t, J=2.0 Hz, 1H), 6.47 (dd, J=7.8, 1.4 Hz, 1H), 6.42-6.34 (m, 1H), 5.15 (s, 1H), 5.05 (s, 2H), 1.14 (s, 10H), 1.05-0.75 (m, 1H), 2.73-2.33 (m, 2H), 0.75-0.53 (m, 1H), 0.43-0.27 (m, 2H), −0.00--0.21 (m, 2H); Optical rotation $[α]_D$=(−) 90.34 [0.23, MeOH].

Step-2: Preparation of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methoxypyrrolidine-1-carboxylate (75c)

Compound 75c was prepared from (2R,4R)-1-(tert-butoxycarbonyl)-4-methoxypyrrolidine-2-carboxylic acid (36a) (245 mg, 1 mmol), (R)-N-((−)-1-(3-aminophenyl)-3-cyclopropyl-1-(pyridin-4-yl)propyl)-2-methylpropane-2-sulfinamide (75b) (0.37 g, 1 mmol) and ethyl 2-ethoxyquinoline-1(2H)-carboxylate (250 mg, 1 mmol) using the reaction and workup conditions as reported in step 10 of Scheme 1 to afford (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methoxypyrrolidine-1-carboxylate (75c) 0.44 g, 73% yield) as a white solid; $^1$H NMR (300 MHz, DMSO-$d_6$) δ 9.76 (2s, 1H, rotamers), 8.54-8.43 (m, 2H), 7.65-7.38 (m, 2H), 7.37-7.18 (m, 3H), 7.06 (2 dd, 1H, rotamers), 5.39 (2s, 1H, rotamers), 4.19 (m, 1H), 3.97 (m, 1H), 3.64 (dd, J=10.6, 6.1 Hz, 1H), 3.20 (2s, 3H, rotamers), 2.44 (m, 3H), 1.94-1.76 (m, 1H), 1.23 (2s, 9H, rotamers), 1.19-1.04 (m, 10H), 0.99-0.79 (m, 2H), 0.73-0.54 (m, 1H), 0.42-0.28 (m, 2H), 2.75-2.37 (m, 3H), −0.03--0.18 (m, 2H).

Step-3: Preparation of (2R,4R)-N-(3-(1-amino-3-cyclopropyl-1-(pyridin-4-yl)propyl)phenyl)-4-methoxypyrrolidine-2-carboxamide (75d)

Reaction of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methoxypyrrolidine-1-carboxylate (75c) (0.44 g, 0.73 mmol) in methanol (10 mL) with 3N HCl in MeOH (1 mL) gave after workup and purification as reported in step 6 of Scheme 4 (2R,4R)-N-(3-(1-amino-3-cyclopropyl-1-(pyridin-4-yl)propyl)phenyl)-4-methoxypyrrolidine-2-carboxamide (75d) as a hydrochloride salt which was used as such for next step.

Step-4: (2R,4R)-N2-(3-((+)-1-amino-3-cyclopropyl-1-(pyridin-4-yl)propyl)phenyl)-N1-(5-chloropyridin-2-yl)-4-methoxypyrrolidine-1,2-dicarboxamide (75e)

Reaction of (2R,4R)-N-(3-(1-amino-3-cyclopropyl-1-(pyridin-4-yl)propyl)phenyl)-4-methoxypyrrolidine-2-carboxamide (75d) (0.37 g, 0.73 mmol) in tetrahydrofuran/ water (25 mL/1 mL) with phenyl 5-chloropyridin-2-ylcarbamate (13b) (0.173 g, 0.7 mmol) using sodium bicarbonate (0.47 g, 5.6 mmol) as base according to procedure reported in step 3 of Scheme 13 gave after purification by flash column chromatography (silica gel 24 g, CMA80 in Chloroform 0 to 30%) (2R,4R)-N2-(3-((+)-1-amino-3-cyclopropyl-1-(pyridin-4-yl)propyl)phenyl)-N1-(5-chloropyridin-2-yl)-4-methoxypyrrolidine-1,2-dicarboxamide (75e) (0.31 g, 80%) free base as a white solid, which was converted to hydrochloride salt to furnish compound 75c HCl salt as a white solid; $^1$H NMR (300 MHz, DMSO-$d_6$) δ 9.99 (s, 1H), 9.41 (s, 3H), 9.18 (s, 1H), 8.80 (s, 2H), 8.30 (d, J=2.6 Hz, 1H), 7.92-7.75 (m, 2H), 7.71-7.54 (m, 4H), 7.39 (t, J=8.0 Hz, 1H), 7.08 (d, J=8.0 Hz, 1H), 4.50 (m, 1H), 4.04 (t, J=5.2 Hz, 1H), 3.85 (dd, J=10.7, 5.8 Hz, 1H), 3.58 (dd, J=10.6, 4.4 Hz, 1H), 3.20 (s, 3H), 2.44 (m, 3H), 1.97 (m, 1H), 1.12 (m, 2H), 0.70 (m, 1H), 0.38 (m, 2H), 0.00 (m, 2H); MS (ES+) 562.4 (M+Na), 549.6 (M+), (ES−) 583.5, (M+Cl); Optical rotation $[α]_D$=(+) 95.32 [0.235, MeOH]; Analysis calculated for $C_{29}H_{33}ClN_6O_3 \cdot 2.5HCl \cdot 3.25H_2O$: C, 49.85; H, 6.06; Cl, 17.76; N, 12.03. Found: C, 49.73; H, 5.89; Cl, 17.83; N, 11.88.

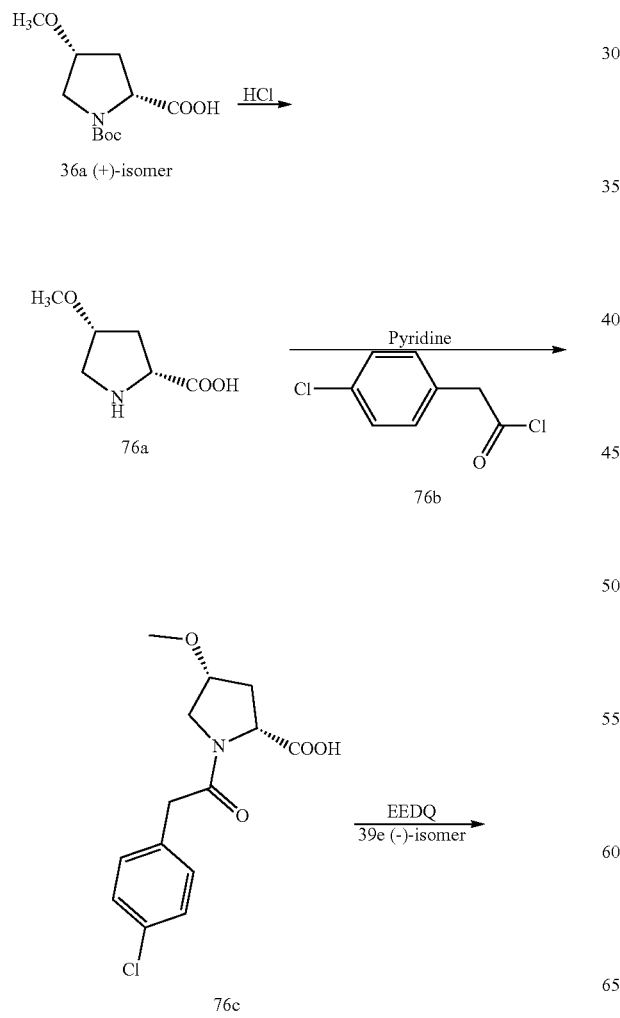

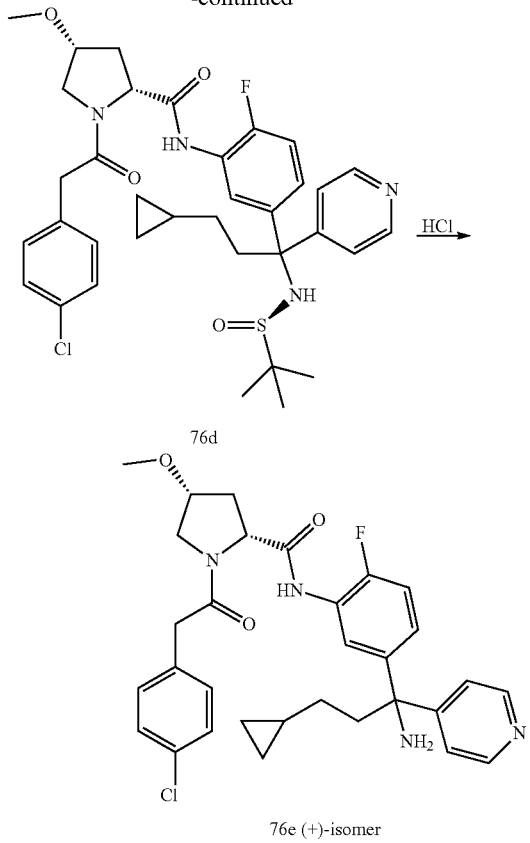

Preparation of (2R,4R)-N-(5-((+)-1-amino-3-cyclopropyl-1-(pyridin-4-yl)propyl)-2-fluorophenyl)-1-(2-(4-chlorophenyl)acetyl)-4-methoxypyrrolidine-2-carboxamide (76e)

Step-1 Preparation of (2R,4R)-4-methoxypyrrolidine-2-carboxylic acid (76a)

Compound 76a was prepared by hydrolysis of Boc protecting group on (2R,4R)-1-(tert-butoxycarbonyl)-4-methoxypyrrolidine-2-carboxylic acid (36a) (0.49 g, 2 mmol) in methanol (3 mL) with 3N HCl in MeOH (3 mL) as reported in step 6 of Scheme 4. This gave after workup (2R,4R)-4-methoxypyrrolidine-2-carboxylic acid (76a) hydrochloride salt as an off-white solid, which was used without further purification.

Step-2: Preparation of (2R,4R)-1-(2-(4-chlorophenyl)acetyl)-4-methoxypyrrolidine-2-carboxylic acid (76c)

To a solution of (2R,4R)-4-methoxypyrrolidine-2-carboxylic acid (76a) (2 mmol, obtained in step 1) in dichloromethane (20 mL) was added Pyridine (1 g, 12.5 mmol), 4-chloro phenyl acetyl chloride (76b) (0.38 g, 2 mmol) and stirred at room temperature overnight. The reaction was diluted with dichloromethane (20 mL), saturated aqueous NaHCO₃ (40 mL) solution and stirred for few mins. The aqueous layer was separated, acidified with 1N HCl (5 mL), and extracted with ethyl acetate (2×30 mL). The ethyl acetate layers were combined washed with brine, dried (MgSO₄), filtered and concentrated to afford (2R,4R)-1-(2-(4-chlorophenyl) acetyl)-4-methoxypyrrolidine-2-carboxylic acid (76c) (0.25 g, 42% yield) as a gummy solid; $^1$H NMR (300 MHz, DMSO-d$_6$) δ 12.38 (s, 1H), 7.43-7.17 (m, 4H), 4.34 (m, 1H), 4.05-3.95 (m, 1H), 3.87-3.77 (m, 2H), 3.68 (s, 2H), 3.52-3.42 (m, 2H), 3.17 (2s, 3H); MS (ES+) 320.2 (M+Na); (ES−) 296.2 (M−1), 332.2 (M+Cl).

Step-3: Preparation of (2R,4R)-1-(2-(4-chlorophenyl)acetyl)-N-(5-(3-cyclopropyl-1-((R)-1,1-dimethylethylsulfinamido)-1-(pyridin-4-yl)propyl)-2-fluorophenyl)-4-methoxypyrrolidine-2-carboxamide (76d)

Compound 76d was prepared from (2R,4R)-1-(2-(4-chlorophenyl)acetyl)-4-methoxypyrrolidine-2-carboxylic acid (76c) (80 mg, 0.27 mmol), (R)-N-((−)-1-(3-amino-4-fluorophenyl)-3-cyclopropyl-1-(pyridin-4-yl)propyl)-2-methylpropane-2-sulfinamide (39e) (0.1 g, 0.27 mmol) and ethyl 2-ethoxyquinoline-1(2H)-carboxylate (100 mg, 0.27 mmol) using the reaction and workup conditions as reported in step 10 of Scheme 1 to afford after purification by flash column chromatography (silica gel 24 g, CMA80 in Chloroform 0 to 30%) (2R,4R)-1-(2-(4-chlorophenyl)acetyl)-N-(5-(3-cyclopropyl-1-((R)-1,1-dimethylethylsulfinamido)-1-(pyridin-4-yl)propyl)-2-fluorophenyl)-4-methoxypyrrolidine-2-carboxamide (76d) (0.135 g, 75%) as a white solid; $^1$H NMR (300 MHz, DMSO-d$_6$) δ 9.42 (s, 1H), 8.55-8.44 (m, 2H), 7.89 (d, J=7.0 Hz, 1H), 7.41-7.05 (m, 8H), 5.54 (s, 1H), 4.57-4.42 (m, 1H), 4.07-3.77 (m, 3H), 3.78-3.68 (m, 2H), 3.65-3.55 (m, 1H), 3.18 (s, 3H), 2.61 (m, 3H), 2.40-2.22 (m, 2H), 1.18-1.08 (m, 10H), 1.01-0.81 (m, 1H), 0.70-0.54 (m, 1H), 0.42-0.29 (m, 2H), −0.02--0.14 (m, 2H); MS (ES+) 669.5 (M+), 691.5 (M+Na), MS (ES−) 667.5 (M−1).

Step-4: Preparation of (2R,4R)-N-(5-((+)-1-amino-3-cyclopropyl-1-(pyridin-4-yl)propyl)-2-fluorophenyl)-1-(2-(4-chlorophenyl)acetyl)-4-methoxypyrrolidine-2-carboxamide (76e)

Reaction of (2R,4R)-1-(2-(4-chlorophenyl)acetyl)-N-(5-(3-cyclopropyl-1-((R)-1,1-dimethylethylsulfinamido)-1-(pyridin-4-yl)propyl)-2-fluorophenyl)-4-methoxypyrrolidine-2-carboxamide (76d) (0.13 g, 0.19 mmol) in ethanol (10 mL) with conc HCl (0.2 mL) gave after workup and purification as reported in step 6 of Scheme 4 (2R,4R)-N-(5-((+)-1-amino-3-cyclopropyl-1-(pyridin-4-yl)propyl)-2-fluorophenyl)-1-(2-(4-chlorophenyl)acetyl)-4-methoxypyrrolidine-2-carboxamide (76e) (0.09 g, 86% yield) as a white solid; $^1$H NMR (300 MHz, DMSO-d$_6$, at 350 Kelvin) δ 9.07 (s, 1H), 8.49-8.40 (m, 2H), 7.92 (s, 1H), 7.40-7.22 (m, 6H), 7.20-7.05 (m, 3H), 4.58 (m, 1H), 4.04 (m, 1H), 3.90-3.46 (m, 4H), 3.23 (s, 3H), 2.42-2.10 (m, 5H), 1.21-1.01 (m, 2H), 0.77-0.55 (m, 1H), 0.43-0.24 (m, 2H), 0.01--0.16 (m, 2H); $^{19}$F NMR (282 MHz, DMSO-d$_6$) δ −128.37; MS (ES+) 565.4, 567.3 MS (ES−) 563.4, 599.3; Optical rotation [α]$_D$= (+) 60.3 [0.335, MeOH]; Analysis calculated for C$_{31}$H$_{34}$ClFN$_4$O$_3$.0.25H$_2$O: C; 65.37, H; 6.11, N; 9.84. Found: C; 65.18, H; 6.09, N; 9.63.

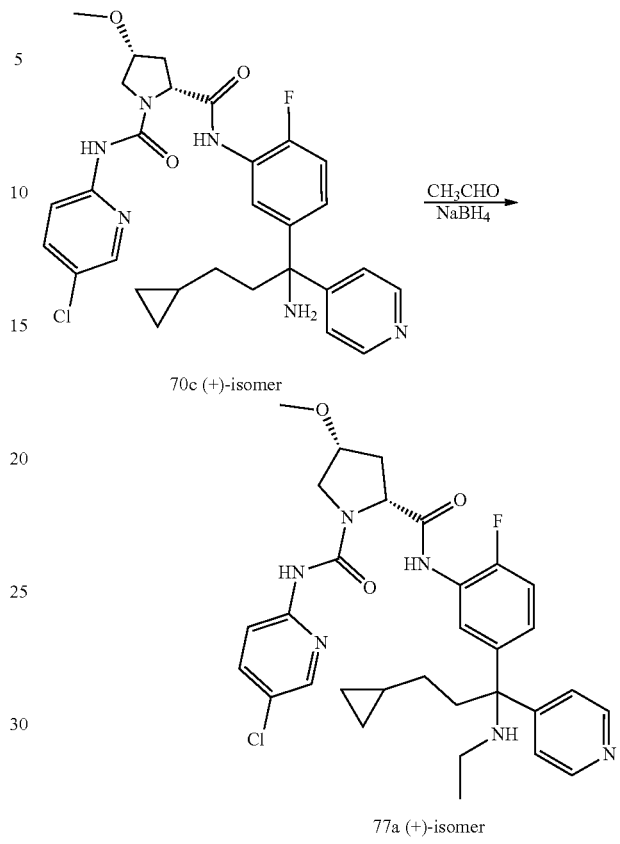

Scheme 77

70c (+)-isomer 77a (+)-isomer

Preparation of (2R,4R)-N1-(5-chloropyridin-2-yl)-N2-(5-((+)-3-cyclopropyl-1-(ethylamino)-1-(pyridin-4-yl)propyl)-2-fluorophenyl)-4-methoxypyrrolidine-1,2-dicarboxamide (77a)

Reductive amination of (2R,4R)-N2-(5-((S)-1-amino-3-cyclopropyl-1-(pyridin-4-yl)propyl)-2-fluorophenyl)-N1-(5-chloropyridin-2-yl)-4-methoxypyrrolidine-1,2-dicarboxamide (70c) (0.1 g, 0.17 mmol) in MeOH (3 mL) using acetaldehyde (0.1 mL, 1.7 mmol) and sodium borohydride (0.02 g, 0.53 mmol) according to the procedure reported in Scheme 41 gave after workup and purification (2R,4R)-N1-(5-chloropyridin-2-yl)-N2-(5-((+)-3-cyclopropyl-1-(ethylamino)-1-(pyridin-4-yl)propyl)-2-fluorophenyl)-4-methoxypyrrolidine-1,2-dicarboxamide (77a) (55 mg, 52.4% yield) free base as a white solid; $^1$H NMR (300 MHz, DMSO-d$_6$) δ 9.46 (s, 1H), 9.16 (s, 1H), 8.44 (d, J=6.0 Hz, 2H), 8.30 (dd, J=2.6, 0.8 Hz, 1H), 7.95-7.74 (m, 3H), 7.31 (d, J=6.0 Hz, 2H), 7.17-7.05 (m, 2H), 4.58 (d, J=5.6 Hz, 1H), 4.09-3.97 (m, 1H), 3.81-3.63 (m, 2H), 3.20 (s, 3H), 2.44-2.31 (m, 4H), 2.23 (t, J=8.1 Hz, 1H), 2.16-2.03 (m, 2H), 0.99 (t, J=7.0 Hz, 3H), 0.94-0.77 (m, 2H), 0.69-0.53 (m, 1H), 0.39-0.27 (m, 2H), −0.09--0.19 (m, 2H); The free base was converted to HCl salt using conc HCl in ethanol to afford compound 77a hydrochloride as a white solid; $^1$H NMR (300 MHz, DMSO-d$_6$) δ 9.99 (s, 1H), 9.74 (s, 1H), 9.24 (s, 1H), 8.81 (s, 3H), 8.31 (d, J=1.8 Hz, 1H), 8.00 (d, J=6.7 Hz, 1H), 7.92-7.79 (m, 2H), 7.79-7.63 (m, 1H), 7.49-7.33 (m, 1H), 7.33-7.19 (m, 1H), 4.61 (dd, J=8.8, 4.0 Hz, 1H), 4.13-3.98 (m, 1H), 3.87-3.61 (m, 2H), 3.21 (s, 3H), 2.96-

2.73 (m, 1H), 2.70-2.54 (m, 4H), 2.46-2.30 (m, 2H), 2.17-1.97 (m, 1H), 1.22 (t, J=6.6 Hz, 3H), 1.10-0.77 (m, 2H), 0.73-0.54 (m, 1H), 0.46-0.26 (m, 2H), 0.02--0.15 (m, 2H); $^{19}$F NMR (282 MHz, DMSO-d$_6$) δ -124.33; MS (ES+) 595.3 (M+1), 617.3 (M+Na), (ES-) 593.3 (M-1), 529.3 (M+Cl); Optical rotation [α]$_D$=(+) 77.78 [0.27, MeOH]; Analysis calculated for C$_{31}$H$_{36}$ClFN$_6$O$_3$.2.25HCl.2.5H$_2$O: C, 51.56; H, 6.04; Cl, 15.95; N, 11.64. Found: C, 51.48; H, 5.89; Cl, 16.23; N, 11.43.

Scheme 78

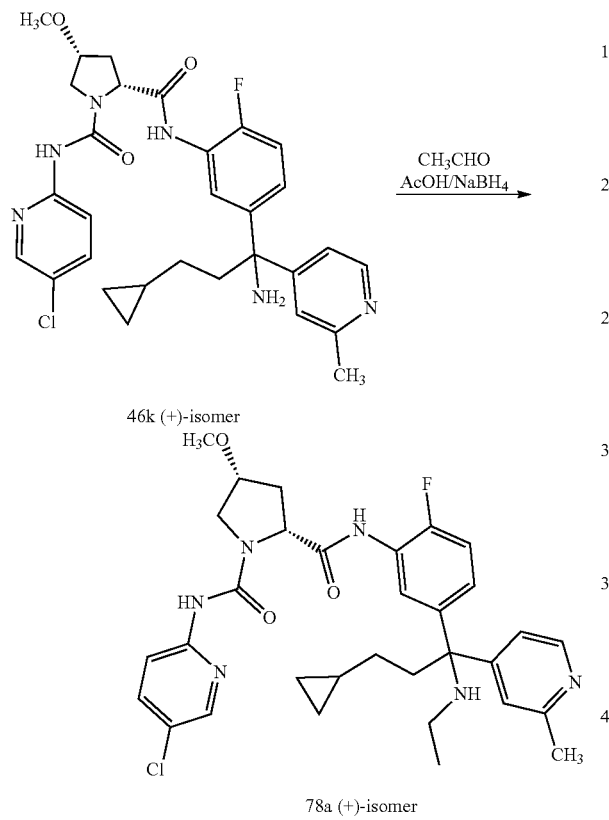

78a (+)-isomer

Preparation of (2R,4R)-N1-(5-chloropyridin-2-yl)-N2-(5-((+)-3-cyclopropyl-1-(ethylamino)-1-(2-methylpyridin-4-yl)propyl)-2-fluorophenyl)-4-methoxypyrrolidine-1,2-dicarboxamide (78a)

Reductive amination of (2R,4R)-N2-(5-((+)-1-amino-3-cyclopropyl-1-(2-methylpyridin-4-yl)propyl)-2-fluorophenyl)-N1-(5-chloropyridin-2-yl)-4-methoxypyrrolidine-1,2-dicarboxamide (46k) (0.68 g, 1.169 mmol) in THF/MeOH (25 mL, 4:1) using acetaldehyde (6.8 mL), acetic acid (1 mL) and sodium borohydride (0.619 g, 16.366 mmol) according to the procedure reported in Scheme 41 gave after workup and purification (2R,4R)-N1-(5-chloropyridin-2-yl)-N2-(5-((+)-3-cyclopropyl-1-(ethylamino)-1-(2-methylpyridin-4-yl)propyl)-2-fluorophenyl)-4-methoxypyrrolidine-1,2-dicarboxamide (78a) (120 mg, 16.79%) as a white solid; $^1$H NMR (300 MHz, DMSO-d$_6$) δ 9.45 (s, 1H), 9.15 (s, 1H), 8.42-8.09 (m, 2H), 7.98-7.64 (m, 3H), 7.34-6.98 (m, 4H), 4.68-4.47 (m, 1H), 4.13-3.90 (m, 1H), 3.84-3.60 (m, 2H), 3.21 (s, 3H), 2.49 (s, 2H), 2.41 (s, 3H), 2.27-2.17 (m, 2H), 2.14-2.01 (m, 3H), 0.99 (t, J=6.5 Hz, 3H), 0.93-0.78 (m, 2H), 0.70-0.50 (m, 1H), 0.42-0.18 (m, 2H), -0.04--0.24 (m, 2H); MS (ES+) 609.5, 610.5, 611.5 (M+1); Optical rotation [α]$_D$=(+) 74.87 [0.195, MeOH].

Scheme 79

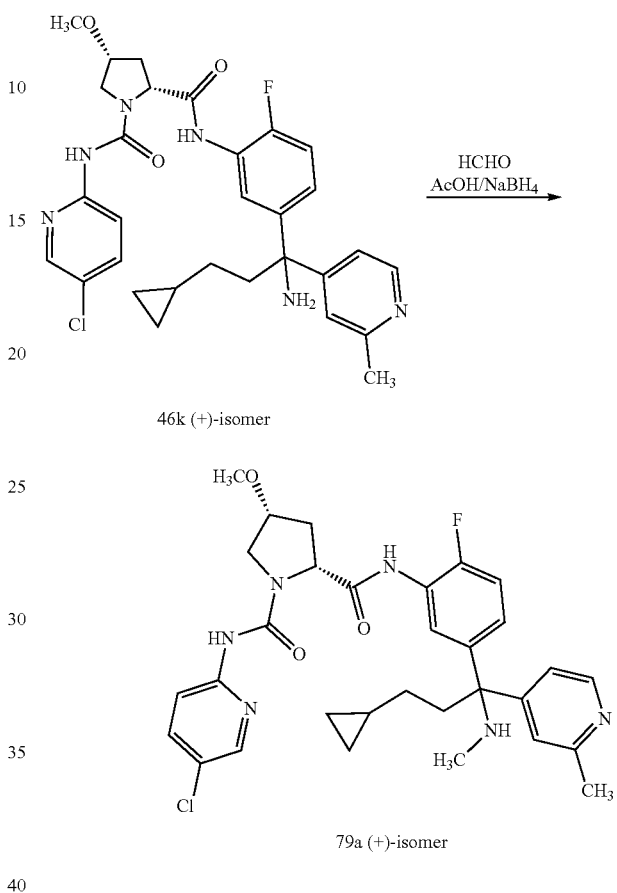

79a (+)-isomer

Preparation of (2R,4R)-N1-(5-chloropyridin-2-yl)-N2-(5-((+)-3-cyclopropyl-1-(methylamino)-1-(2-methylpyridin-4-yl)propyl)-2-fluorophenyl)-4-methoxypyrrolidine-1,2-dicarboxamide (79a)

Reductive amination of (2R,4R)-N2-(5-((+)-1-amino-3-cyclopropyl-1-(2-methylpyridin-4-yl)propyl)-2-fluorophenyl)-N1-(5-chloropyridin-2-yl)-4-methoxypyrrolidine-1,2-dicarboxamide (46k) (0.3 g, 0.516 mmol) in THF/MeOH (20 mL, 4:1) using paraformaldehyde (0.465 g, 5.16 mmol), acetic acid (0.5 mL) and sodium borohydride (0.195 g, 0.516 mmol) according to the procedure reported in Scheme 41 gave after workup and purification (2R,4R)-N1-(5-chloropyridin-2-yl)-N2-(5-((S)-3-cyclopropyl-1-(methylamino)-1-(2-methylpyridin-4-yl)propyl)-2-fluorophenyl)-4-methoxypyrrolidine-1,2-dicarboxamide (79a) (80 mg, 25.97%) as a white solid; $^1$H NMR (300 MHz, DMSO-d6) δ9.45 (s, 1H), 9.15 (s, 1H), 8.37-8.20 (m, 2H), 7.96-7.74 (m, 3H), 7.30-6.97 (m, 4H), 4.58 (dd, J=9.1, 3.9 Hz, 1H), 4.07-3.98 (m, 1H), 3.82-3.60 (m, 2H), 3.20 (s, 3H), 2.43-2.38 (m, 2H), 2.40 (s, 3H), 2.20 (t, J=8.1 Hz, 2H), 2.13-2.06 (m, 1H), 1.92 (s, 3H), 0.93-0.75 (m, 2H), 0.68-0.52 (m, 1H), 0.39-0.29 (m, 2H), -0.05--0.21 (m, 2H); MS (ES-) 593.5, 595.5 (M-1); Optical rotation [α]$_D$=(+) 29.19 [0.185, MeOH].

Scheme 80

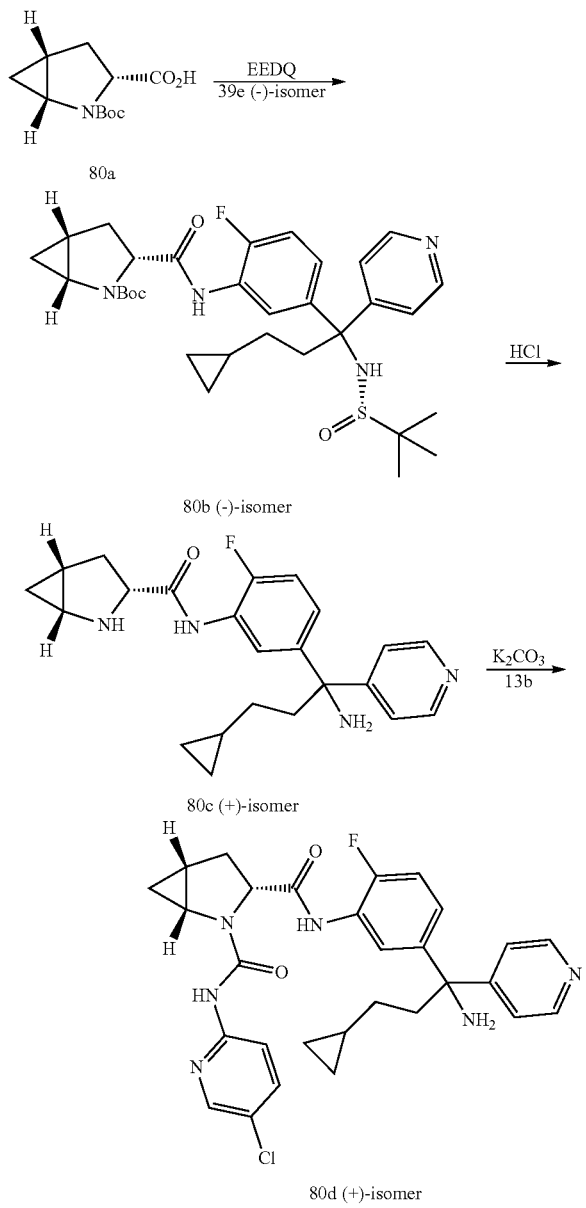

Preparation of (1R,3R,5R)-N3-(5-((+)-1-amino-3-cyclopropyl-1-(pyridin-4-yl)propyl)-2-fluorophenyl)-N2-(5-chloropyridin-2-yl)-2-azabicyclo[3.1.0]hexane-2,3-dicarboxamide (80d)

Step-1: Preparation of (1R,3R,5R)-tert-butyl 3-(5-(3-cyclopropyl-1-((−)-1,1-dimethylethylsulfinamido)-1-(pyridin-4-yl)propyl)-2-fluorophenylcarbamoyl)-2-azabicyclo[3.1.0]hexane-2-carboxylate (80b)

Reaction of (1R,3R,5R)-2-(tert-butoxycarbonyl)-2-azabicyclo[3.1.0]hexane-3-carboxylic acid (80a) (98 mg, 0.431 mmol), (R)-N-((−)-1-(3-amino-4-fluorophenyl)-3-cyclopropyl-1-(pyridin-4-yl)propyl)-2-methylpropane-2-sulfinamide (39e) (168 mg, 0.431 mmol) in tetrahydrofuran (15 mL) using ethyl 2-ethoxyquinoline-1(2H)-carboxylate (107 mg, 0.431 mmol) using the reaction and workup conditions as reported in step 10 of Scheme 1 gave (1R,3R,5R)-tert-butyl 3-(5-(3-cyclopropyl-1-((−)-1,1-dimethylethylsulfinamido)-1-(pyridin-4-yl)propyl)-2-fluorophenylcarbamoyl)-2-azabicyclo[3.1.0]hexane-2-carboxylate (80b) (132 mg, 51% yield) as a white solid; $^1$H NMR (300 MHz, DMSO-d6) δ 9.80 (s, 1H), 8.49 (d, J=6.0 Hz, 2H), 7.99-7.82 (m, 1H), 7.32 (d, J=5.8 Hz, 2H), 7.24-7.03 (m, 2H), 5.51 (s, 1H), 4.80-4.61 (m, 1H), 1.97-1.79 (m, 1H), 1.55-1.47 (m, 1H), 1.44-1.37 (m, 3H), 1.26 (s, 9H), 1.13 (s, 9H), 1.03-0.84 (m, 4H), 0.70-0.56 (m, 2H), 0.41-0.29 (m, 2H), −0.02−−0.12 (m, 2H); MS (ES$^+$) 599.7 (M+1), 621.7 (M+Na); Optical rotation $[\alpha]_D$=(−) 30.0 [0.08, MeOH].

Step-2: Preparation of (1R,3R,5R)-N-(5-((+)-1-amino-3-cyclopropyl-1-(pyridin-4-yl)propyl)-2-fluorophenyl)-2-azabicyclo[3.1.0]hexane-3-carboxamide (80c)

Reaction of (1R,3R,5R)-tert-butyl 3-(5-(3-cyclopropyl-1-((−)-1,1-dimethylethylsulfinamido)-1-(pyridin-4-yl)propyl)-2-fluorophenylcarbamoyl)-2-azabicyclo[3.1.0]hexane-2-carboxylate (80b) (132 mg, 0.220 mmol) in ethanol (10 mL) using conc. HCl in methanol (0.033 mL, 1.102 mmol) followed by workup and purification as reported in step 6 of Scheme 4 gave (1R,3R,5R)-N-(5-((+)-1-amino-3-cyclopropyl-1-(pyridin-4-yl)propyl)-2-fluorophenyl)-2-azabicyclo[3.1.0]hexane-3-carboxamide (80c) (111 mg, 0.224 mmol, 100% yield) hydrochloride salt as a yellow solid, which was used in the next step without further purification; $^1$H NMR (300 MHz, DMSO-d6) δ 10.63 (s, 2H), 9.74 (s, 2H), 9.02-8.76 (m, 3H), 7.81-7.68 (m, 3H), 7.48-7.30 (m, 2H), 4.78 (s, 1H), 3.37 (s, 2H), 2.75-2.55 (m, 2H), 2.18 (d, J=10.8 Hz, 1H), 1.84-1.72 (m, 1H), 1.22 (d, J=7.2 Hz, 1H), 0.87 (d, J=7.3 Hz, 1H), 0.73 (d, J=20.9 Hz, 2H), 0.39 (d, J=7.8 Hz, 2H), 0.04 (s, 2H); $^{19}$F NMR (282 MHz, DMSO) δ −122.43; MS (ES$^+$) 395.5 (M+1); Optical rotation $[\alpha]_D$=(+) 6.67 [0.09, MeOH].

Step-3: Preparation of (1R,3R,5R)-N3-(5-((+)-1-amino-3-cyclopropyl-1-(pyridin-4-yl)propyl)-2-fluorophenyl)-N2-(5-chloropyridin-2-yl)-2-azabicyclo[3.1.0]hexane-2,3-dicarboxamide (80d)

Reaction of (1R,3R,5R)-N-(5-((+)-1-amino-3-cyclopropyl-1-(pyridin-4-yl)propyl)-2-fluorophenyl)-2-azabicyclo[3.1.0]hexane-3-carboxamide (80c) obtained in above step 2 (49.3 mg, 0.198 mmol) in tetrahydrofuran (10 mL) with phenyl 5-chloropyridin-2-ylcarbamate (13b) (49.3 mg, 0.198 mmol) using potassium carbonate (76 mg, 0.551 mmol) as base according to procedure reported in step 3 of Scheme 13 gave after purification by flash column chromatography (silica gel 24 g, eluting with CMA-80 in chloroform 0-40%) (1R,3R,5R)-N3-(5-((+)-1-amino-3-cyclopropyl-1-(pyridin-4-yl)propyl)-2-fluorophenyl)-N2-(5-chloropyridin-2-yl)-2-azabicyclo[3.1.0]hexane-2,3-dicarboxamide (80d) (52 mg, 0.095 mmol, 47.8% yield) as a white solid; $^1$H NMR (300 MHz, DMSO-d$_6$) δ 9.77 (s, 1H), 9.23 (s, 1H), 8.52-8.34 (m, 2H), 8.29 (s, 1H), 7.98-7.72 (m, 3H), 7.44-7.21 (m, 2H), 7.13 (d, J=7.3 Hz, 2H), 4.93 (d, J=11.2 Hz, 1H), 3.83 (s, 1H), 2.68-2.55 (m, 1H), 2.45-2.30 (m, 1H), 2.27-2.07 (m, 2H), 1.95 (d, J=13.3 Hz, 1H), 1.76-1.55 (m, 1H), 1.24 (s, 1H), 1.16-0.95 (m, 2H), 0.91-0.76 (m, 1H), 0.75-0.53 (m, 2H), 0.43-0.22 (m, 2H), −0.04−−0.24 (m, 2H); $^{19}$F NMR (282 MHz, DMSO) δ −122.43; $^{19}$F NMR (282 MHz, DMSO) δ −127.55; MS (ES+) 549.6 (M+1); Optical rotation [α]_D=(+) 68.46 [0.26, MeOH].

Scheme 81

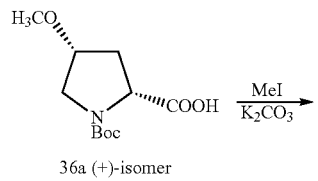

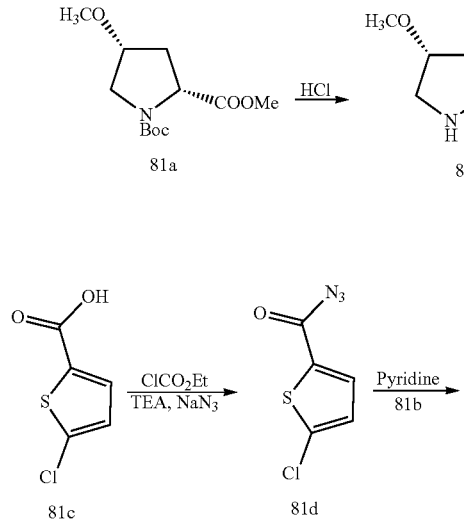

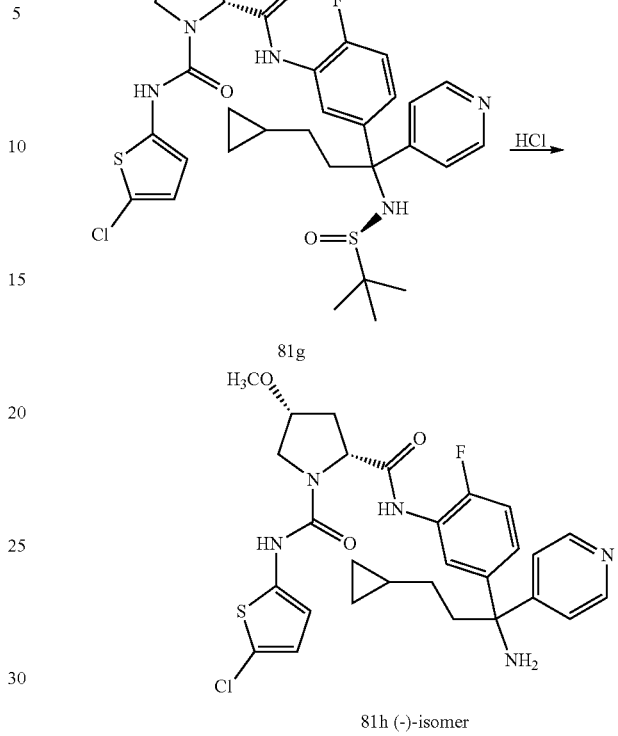

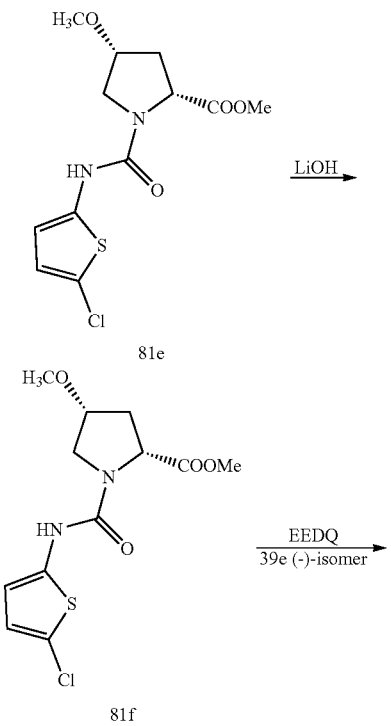

Preparation of (2R,4R)-N2-(5-((−)-1-amino-3-cyclopropyl-1-(pyridin-4-yl)propyl)-2-fluorophenyl)-N1-(5-chlorothiophen-2-yl)-4-methoxypyrrolidine-1,2-dicarboxamide (81h)

Step-1 Preparation of (2R,4R)-1-tert-butyl 2-methyl 4-methoxypyrrolidine-1,2-dicarboxylate (81a)

To a solution of (2R,4R)-1-(tert-butoxycarbonyl)-4-methoxypyrrolidine-2-carboxylic acid (36a) (2.45 g, 9.99 mmol) in DMF (30 mL) was added K$_2$CO$_3$ (1.381 g, 9.99 mmol), CH$_3$I (1.249 mL, 19.98 mmol), stirred at room temperature for 48 h, diluted with water (200 mL) and EtOAc (100 mL). Aqueous layer was extracted with EtOAc (100 mL) and combined organic layers were washed with water (100 mL), brine, dried (MgSO4), filtered, concentrated in vacuum to afford (2R,4R)-1-tert-butyl 2-methyl 4-methoxypyrrolidine-1,2-dicarboxylate (81a) (2.5 g, 9.64 mmol, 97%) as light orange colored thick syrup; $^1$H NMR (300 MHz, DMSO-d$_6$) δ 4.34-4.17 (m, 1H), 3.99-3.84 (m, 1H), 3.67-3.57 (m, 3H), 3.56-3.45 (m, 1H), 3.29-3.19 (m, 1H), 3.19-3.10 (2s, 3H, rotamers), 2.45-2.23 (m, 1H), 2.08-1.94 (m, 1H), 1.45-1.28 (2s, 9H, rotamers).

Step-2: Preparation of (2R,4R)-methyl 4-methoxypyrrolidine-2-carboxylate (81b)

Reaction of (2R,4R)-1-tert-butyl 2-methyl 4-methoxypyrrolidine-1,2-dicarboxylate (81a) (2.4 g, 9.26 mmol) in methanol (40 mL) with 3N HCl in methanol (9.26 mL, 27.8 mmol) gave after workup as reported in step 6 of Scheme 4

(2R,4R)-methyl 4-methoxypyrrolidine-2-carboxylate (81b) (1.75 g, 8.94 mmol, 97% yield) as an off-white solid; MS (ES+) 160.2 (M+1).

Step-3: Preparation of 5-chlorothiophene-2-carbonyl azide (81d)

To a solution of 5-chlorothiophene-2-carboxylic acid (81c) (0.5 g, 3.08 mmol) in acetone (20 mL) cooled to 0° C. was added triethylamine (0.471 mL, 3.38 mmol), ethyl chloroformate (0.325 mL, 3.38 mmol) and stirred at 0° C. for 1 h. Sodium azide (0.360 g, 5.54 mmol) was added to reaction mixture and continued stirring at 0° C. for 2 h. the reaction mixture was poured into 50 mL of ice water and extracted with $CH_2Cl_2$ (2×40). The combined organic layers were washed with water (2×30) and brine, dried, filtered and concentrated in vacuum to afford 5-chlorothiophene-2-carbonyl azide (81d) (0.35 g, 1.866 mmol, 60.7% yield) as a white semi solid; $^1$H NMR (300 MHz, $CDCl_3$,) δ 7.67 (d, 1H), 6.99 (d, 1H).

Step-4: Preparation of (2R,4R)-methyl 1-(5-chlorothiophen-2-ylcarbamoyl)-4-methoxypyrrolidine-2-carboxylate (81e)

A solution of 5-chlorothiophene-2-carbonyl azide (81d) (0.35 g, 1.866 mmol) in toluene was heated at 100° C. for 2 h, cooled to room temperature and added a solution of (2R,4R)-methyl 4-methoxypyrrolidine-2-carboxylate hydrochloride (0.365 g, 1.866 mmol) in dichloromethane (15 mL) and pyridine (0.754 mL, 9.33 mmol). The reaction mixture was stirred at room temperature for 16 h poured into water (50 mL) and separated aqueous layer was extracted with dichloromethane (2×30 mL). The dichloromethane layers were combined washed with brine, dried, filtered and concentrated in vacuum. The residue obtained was purified by flash chromatography [silica gel 24 g, eluting with MeOH-EtOAc (9:1) in hexane 0 to 100%] to afford (2R, 4R)-methyl 1-(5-chlorothiophen-2-ylcarbamoyl)-4-methoxypyrrolidine-2-carboxylate (81e) as a light pink foam (0.24 g, 0.753 mmol, 40.4% yield); $^1$H NMR (300 MHz, DMSO-$d_6$) δ 9.78 (s, 1H), 6.77 (d, J=4.1 Hz, 1H), 6.39 (d, J=4.1 Hz, 1H), 4.52 (d, J=8.4 Hz, 1H), 4.01 (s, 1H), 3.61 (s, 4H), 3.49-3.38 (m, 1H), 3.17 (s, 3H), 2.35-2.11 (m, 2H); MS (ES+) 341.2 (M+Na), MS (ES−) 317.3 (M−1).

Step-5: Preparation of (2R,4R)-1-(5-chlorothiophen-2-ylcarbamoyl)-4-methoxypyrrolidine-2-carboxylic acid (81f)

Compound (81f) was prepared by hydrolysis of (2R,4R)-methyl 1-(5-chlorothiophen-2-ylcarbamoyl)-4-methoxypyrrolidine-2-carboxylate (81e) (0.24 g, 0.753 mmol) in THF (5 mL) using LiOH (0.018 g, 0.753 mmol) in water (3 mL) at room temperature according to the procedure reported in scheme 54 step 3 to afford after workup (2R,4R)-1-(5-chlorothiophen-2-ylcarbamoyl)-4-methoxypyrrolidine-2-carboxylic acid (81f) (0.205 g, 0.673 mmol, 89% yield) as a purple foam; MS(ES+) 305.4 (M+1), 327.4 (M+Na), MS(ES−) 303.3 (M−1).

Step-6: Preparation of (2R,4R)-N1-(5-chlorothiophen-2-yl)-N2-(5-(3-cyclopropyl-1-((R)-1,1-dimethylethylsulfinamido)-1-(pyridin-4-yl)propyl)-2-fluorophenyl)-4-methoxypyrrolidine-1,2-dicarboxamide (81g)

Compound 81g was prepared from (2R,4R)-1-(5-chlorothiophen-2-ylcarbamoyl)-4-methoxypyrrolidine-2-carboxylic acid (81f) (0.1 g, 0.328 mmol), (R)-N-((−)-1-(3-amino-4-fluorophenyl)-3-cyclopropyl-1-(pyridin-4-yl)propyl)-2-methylpropane-2-sulfinamide (39e) (0.128 g, 0.328 mmol) and ethyl 2-ethoxyquinoline-1(2H)-carboxylate (0.089 g, 0.361 mmol) using the reaction and workup conditions as reported in step 10 of Scheme 1 to afford after purification by flash column chromatography (silica gel 12 g, eluting with 0-100% 9:1 ethyl acetate/methanol in hexanes) (2R, 4R)-N1-(5-chlorothiophen-2-yl)-N2-(5-(3-cyclopropyl-1-((R)-1,1-dimethylethylsulfinamido)-1-(pyridin-4-yl)propyl)-2-fluorophenyl)-4-methoxypyrrolidine-1,2-dicarboxamide (81g) (0.037 g, 0.055 mmol, 16.67% yield) as off white solid; $^1$H NMR (300 MHz, DMSO-$d_6$) δ 9.88 (s, 1H), 9.51 (s, 1H), 8.56 (d, J=5.5 Hz, 2H), 7.88 (d, J=7.4 Hz, 1H), 7.45 (d, J=5.4 Hz, 2H), 7.19 (q, J=10.8, 9.8 Hz, 2H), 6.78 (d, J=4.1 Hz, 1H), 6.44 (d, J=4.1 Hz, 1H), 5.62 (s, 1H), 4.57-4.46 (m, 1H), 4.15-4.01 (m, 1H), 3.75-3.62 (m, 1H), 3.62-3.48 (m, 1H), 3.21 (s, 3H), 2.66-2.53 (m, 3H), 2.16-2.04 (m, 1H), 1.14 (s, 9H), 1.01-0.78 (m, 2H), 0.72-0.56 (m, 1H), 0.41-0.28 (m, 2H), −0.04-−0.14 (m, 2H); MS (ES+) 676.6 (M+1), 698.6 (M+Na).

Step-7: Preparation of (2R,4R)-N2-(5-((−)-1-amino-3-cyclopropyl-1-(pyridin-4-yl)propyl)-2-fluorophenyl)-N1-(5-chlorothiophen-2-yl)-4-methoxypyrrolidine-1,2-dicarboxamide (81h)

Reaction of (2R,4R)-N1-(5-chlorothiophen-2-yl)-N2-(5-(3-cyclopropyl-1-((R)-1,1-dimethylethylsulfinamido)-1-(pyridin-4-yl)propyl)-2-fluorophenyl)-4-methoxypyrrolidine-1,2-dicarboxamide (81g) (0.03 g, 0.044 mmol) in methanol (3 mL) with 3N HCl in methanol (0.074 mL, 0.222 mmol) gave after workup and purification as reported in step 6 of Scheme 4 (2R,4R)-N2-(5-((−)-1-amino-3-cyclopropyl-1-(pyridin-4-yl)propyl)-2-fluorophenyl)-N1-(5-chlorothiophen-2-yl)-4-methoxypyrrolidine-1,2-dicarboxamide (81h) (0.015 g, 0.026 mmol, 59.1% yield) as a white solid; $^1$H NMR (300 MHz, DMSO-$d_6$) δ 9.86 (s, 1H), 9.46 (s, 1H), 8.44 (d, J=4.9 Hz, 2H), 7.85 (d, J=7.3 Hz, 1H), 7.39-7.31 (m, 2H), 7.23-7.10 (m, 2H), 6.78 (dd, J=4.1, 1.3 Hz, 1H), 6.44 (dd, J=4.2, 1.3 Hz, 1H), 4.51 (dd, J=9.2, 3.7 Hz, 1H), 4.06 (d, J=5.7 Hz, 1H), 3.69 (dd, J=10.5, 5.4 Hz, 1H), 3.53 (s, 1H), 3.20 (s, 3H), 2.25 (m, 6H), 1.17-0.92 (m, 2H), 0.72-0.56 (m, 1H), 0.41-0.30 (m, 2H), −0.04-−0.10 (m, 2H); MS 572.6 (M+1); 570.5 (M−1); Optical Rotation [α]$_D$=(−) 27.42 [0.175, MeOH].

Scheme 82

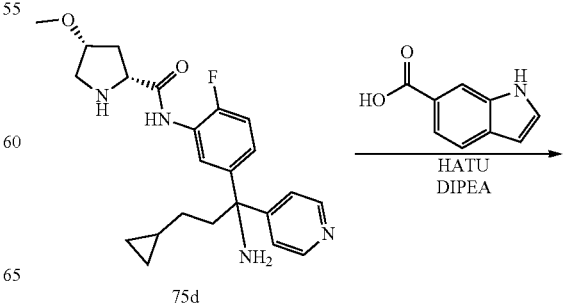

75d

259

-continued

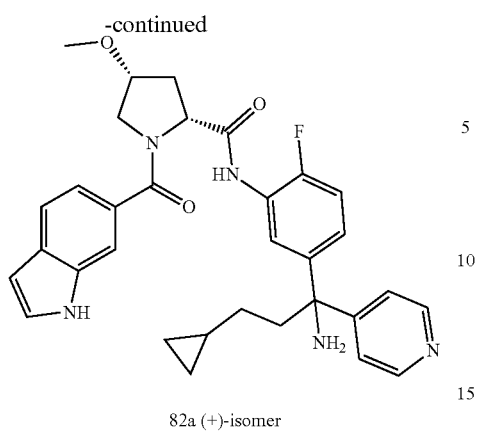

82a (+)-isomer

260

-continued

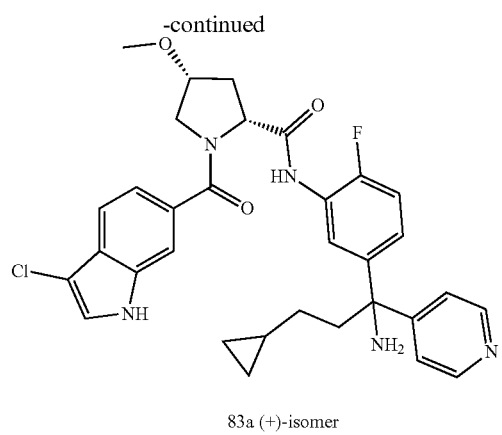

83a (+)-isomer

Preparation of (2R,4R)-N-(5-(-(+)-1-amino-3-cyclopropyl-1-(pyridin-4-yl)propyl)-2-fluorophenyl)-1-(1H-indole-6-carbonyl)-4-methoxypyrrolidine-2-carboxamide (82a)

To a solution of (2R,4R)-N-(3-(1-amino-3-cyclopropyl-1-(pyridin-4-yl)propyl)phenyl)-4-methoxypyrrolidine-2-carboxamide (75d) (0.2 g, 0.41 mmol) in DMF (3.0 mL) was added DIPEA (0.3 mL); HATU (0.15 g, 0.41 mmol) and 1H-indole-6-carboxylic acid (0.72 g, 0.37 mmol). The reaction mixture was stirred at room temperature overnight, quenched with water (40 mL) and extracted with ethyl acetate (2×40 mL). The organic layers were combined washed with brine, dried, filtered and concentrated in vacuum to dryness. The residue obtained was purified by flash column chromatography (silica gel, 12 g, eluting with 0-10% methanol in ethyl acetate) to afford (2R,4R)-N-(5-(-(+)-1-amino-3-cyclopropyl-1-(pyridin-4-yl)propyl)-2-fluorophenyl)-1-(1H-indole-6-carbonyl)-4-methoxypyrrolidine-2-carboxamide (82a) (0.02 g, 10% yield) as white solid; $^1$H NMR (300 MHz, DMSO-$d_6$) δ 11.32 (s, 1H), 9.64 (s, 1H), 8.50-8.36 (m, 2H), 7.96 (s, 1H), 7.71-7.41 (m, 3H), 7.41-7.29 (m, 2H), 7.19 (m, 3H), 6.48 (s, 1H), 4.84-4.66 (m, 1H), 4.09-3.88 (m, 1H), 3.88-3.68 (m, 1H), 3.68-3.50 (m, 1H), 3.20 (s, 3H), 2.37-2.06 (m, 4H), 2.06-1.85 (m, 1H), 1.02 (m, 2H), 0.64 (m, 1H), 0.34 (m, 2H), −0.03-−0.14 (m, 2H); MS (ES+) 556.7 (M+1), 578.6 (M+Na), MS (ES−) 554.6 (M−1); Optical rotation [α]$_D$=(+) 54.19 [0.155, MeOH].

Preparation of (2R,4R)-N-(5-((+)-1-amino-3-cyclopropyl-1-(pyridin-4-yl)propyl)-2-fluorophenyl)-1-(3-chloro-1H-indole-6-carbonyl)-4-methoxypyrrolidine-2-carboxamide (83a)

Reaction of (2R,4R)-N-(3-(1-amino-3-cyclopropyl-1-(pyridin-4-yl)propyl)phenyl)-4-methoxypyrrolidine-2-carboxamide (75d) (0.2 g, 0.41 mmol) in DMF (3.0 mL) using DIPEA (0.3 mL); HATU (0.15 g, 0.41 mmol) and 3-chloro-1H-indole-6-carboxylic acid (0.72 g, 0.37 mmol) according to the procedure as reported in Scheme 82 gave (2R,4R)-N-(5-((+)-1-amino-3-cyclopropyl-1-(pyridin-4-yl)propyl)-2-fluorophenyl)-1-(3-chloro-1H-indole-6-carbonyl)-4-methoxypyrrolidine-2-carboxamide (83a) (0.05 g, 28% yield) as white solid; $^1$H NMR (300 MHz, DMSO-$d_6$) δ 11.61 (s, 1H), 9.66 (s, 1H), 8.44 (d, J=5.2 Hz, 2H), 7.97 (d, J=7.6 Hz, 1H), 7.68 (d, J=5.4 Hz, 2H), 7.54 (d, J=8.4 Hz, 1H), 7.37 (m, 3H), 7.16 (d, J=7.8 Hz, 2H), 4.75 (t, J=6.9 Hz, 1H), 3.99 (m, 2H), 3.76 (m, 1H), 3.65-3.49 (m, 1H), 3.19 (s, 3H), 2.32-2.09 (m, 4H), 2.06-1.87 (m, 1H), 1.13-0.92 (m, 2H), 0.71-0.56 (m, 1H), 0.42-0.25 (m, 2H), −0.02-−0.13 (m, 2H); $^{19}$F NMR (282 MHz, DMSO-$d_6$) δ −128.16; MS (ES+) 590.7 (M+1), 612.6 (M+Na), MS(ES−) 588.6 (M−1); Optical rotation [α]$_D$=(+) 51.43 [0.21, MeOH].

Scheme 83

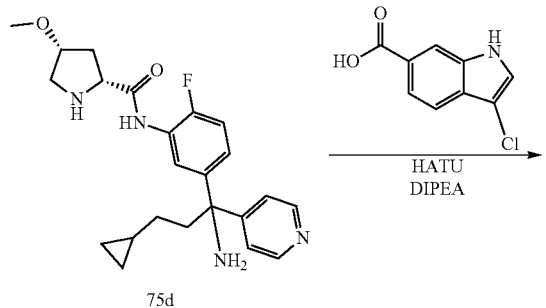

75d

HATU
DIPEA

Scheme 84

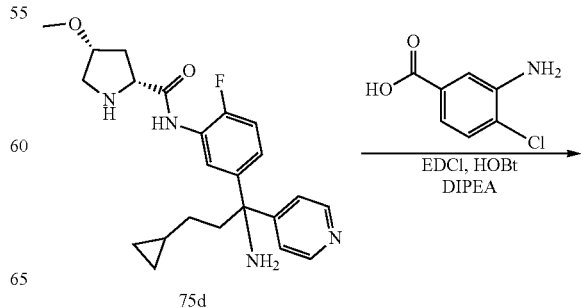

75d

EDCl, HOBt
DIPEA

261
-continued

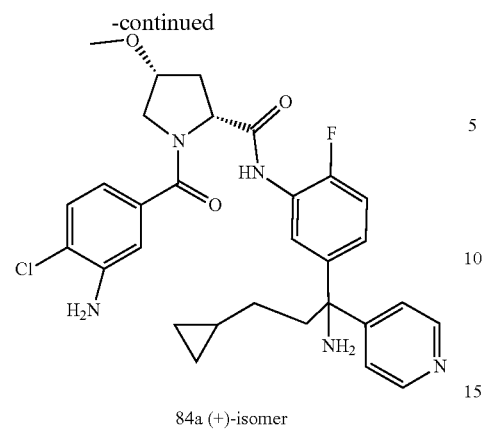

84a (+)-isomer

Preparation of (2R,4R)-N-(5-((+)-1-amino-3-cyclopropyl-1-(pyridin-4-yl)propyl)-2-fluorophenyl)-1-(3-amino-4-chlorobenzoyl)-4-methoxypyrrolidine-2-carboxamide (84a)

Reaction of (2R,4R)-N-(3-(1-amino-3-cyclopropyl-1-(pyridin-4-yl)propyl)phenyl)-4-methoxypyrrolidine-2-carboxamide (75d) (0.44 g, 0.852 mmol) in DMF (5.0 mL) using DIPEA (0.7 mL, 3.99 mmol); EDCI (0.197 g, 1.275 mmol), HOBt (0.195 g, 1.275 mmol) and 3-amino-4-chlorobenzoic acid (0.184 g, 1.064 mmol) according to the procedure as reported in Scheme 82 gave (2R,4R)-N-(5-((+)-1-amino-3-cyclopropyl-1-(pyridin-4-yl)propyl)-2-fluorophenyl)-1-(3-amino-4-chlorobenzoyl)-4-methoxypyrrolidine-2-carboxamide (84a) (0.06 g, 12% yield) as off white solid; $^1$H NMR (300 MHz, DMSO-d$_6$) δ 9.64 (s, 1H), 8.53-8.37 (m, 2H), 7.97 (d, J=7.7 Hz, 1H), 7.42-7.32 (m, 2H), 7.25 (d, J=8.2 Hz, 1H), 7.15 (d, J=7.9 Hz, 2H), 6.98 (d, J=2.0 Hz, 1H), 6.72 (dd, J=8.2, 1.9 Hz, 1H), 5.57 (s, 2H), 4.69 (t, J=7.7 Hz, 1H), 4.05-3.90 (m, 1H), 3.80-3.65 (m, 1H), 3.54-3.41 (m, 1H), 3.20 (s, 3H), 2.35-2.10 (m, 5H), 2.00-1.84 (m, 1H), 1.12-0.89 (m, 2H), 0.72-0.52 (m, 1H), 0.34 (d, J=7.6 Hz, 2H), −0.07 (s, 2H); $^{19}$F NMR (282 MHz, DMSO-d$_6$) δ −128.56; MS (ES+) 589.8 (M+Na), MS (ES−) 601.7 (M+Cl); Optical rotation [α]$_D$=(+) 57.23 [0.325, MeOH].

262
-continued

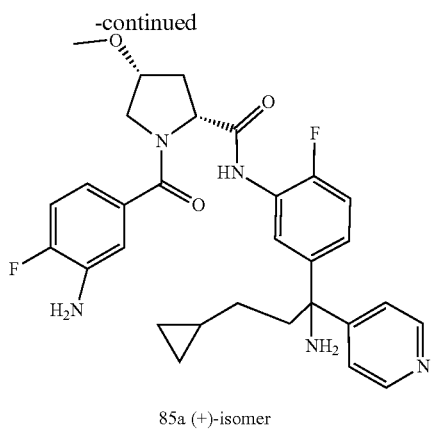

85a (+)-isomer

Preparation of (2R,4R)-N-(5-((+)-1-amino-3-cyclopropyl-1-(pyridin-4-yl)propyl)-2-fluorophenyl)-1-(3-amino-4-fluorobenzoyl)-4-methoxypyrrolidine-2-carboxamide (85a)

Reaction of (2R,4R)-N-(3-(1-amino-3-cyclopropyl-1-(pyridin-4-yl)propyl)phenyl)-4-methoxypyrrolidine-2-carboxamide (75d) (0.44 g, 0.852 mmol) in DMF (5.0 mL) using DIPEA (0.7 mL, 3.99 mmol); EDCI (0.198 g, 1.276 mmol), HOBt (0.195 g, 1.276 mmol) and 3-amino-4-fluorobenzoic acid (0.165 g, 1.064 mmol) according to the procedure as reported in Scheme 82 gave (2R,4R)-N-(5-((+)-1-amino-3-cyclopropyl-1-(pyridin-4-yl)propyl)-2-fluorophenyl)-1-(3-amino-4-fluorobenzoyl)-4-methoxypyrrolidine-2-carboxamide (85a) (0.05 g, 10.7% yield) as off white solid; $^1$H NMR (300 MHz, DMSO-d$_6$) δ 9.61 (s, 1H), 8.52-8.38 (m, 2H), 7.98 (s, 1H), 7.48-7.29 (m, 2H), 7.23-6.92 (m, 4H), 6.73 (s, 1H), 5.30 (s, 2H), 4.76-4.60 (m, 1H), 4.06-3.87 (m, 1H), 3.80-3.64 (m, 1H), 3.58-3.34 (m, 1H), 3.20 (s, 3H), 2.37-2.10 (m, 5H), 2.03-1.82 (m, 1H), 1.11-0.90 (m, 2H), 0.73-0.53 (m, 1H), 0.42-0.25 (m, 2H), −0.03-−0.16 (m, 2H); $^{19}$F NMR (282 MHz, DMSO-d$_6$) δ −128.63, −132.44; MS (ES+) 550.7 (M+1), 572.7 (M+Na), MS (ES−) 548.6 (M−1), 584.5 (M+Cl); Optical rotation [α]$_D$=(+) 55.43 [0.35, MeOH].

Scheme 85

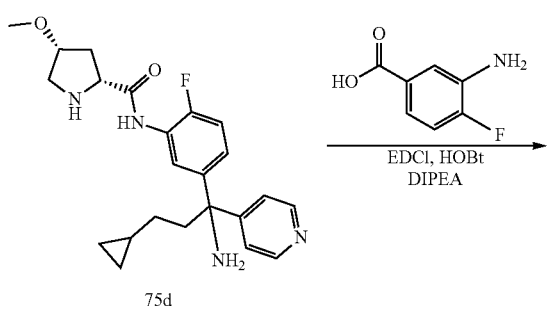

75d

Scheme 86

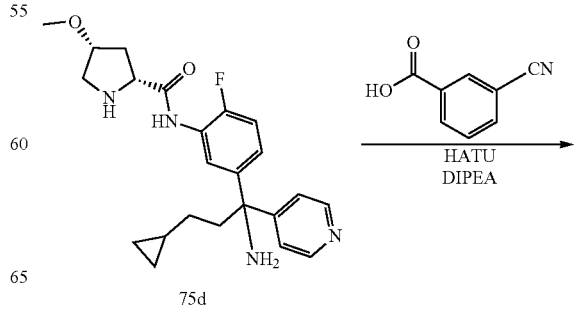

75d

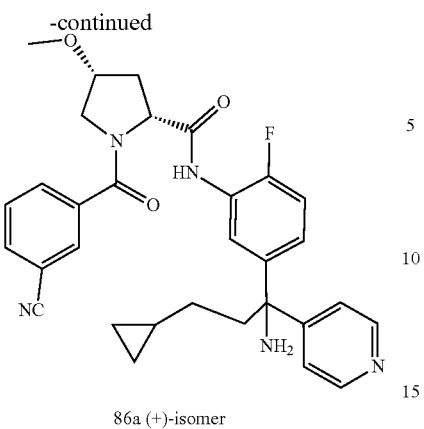

86a (+)-isomer

Preparation of (2R,4R)-N-(5-((+)-1-amino-3-cyclopropyl-1-(pyridin-4-yl)propyl)-2-fluorophenyl)-1-(3-cyanobenzoyl)-4-methoxypyrrolidine-2-carboxamide (86a)

Reaction of (2R,4R)-N-(3-(1-amino-3-cyclopropyl-1-(pyridin-4-yl)propyl)phenyl)-4-methoxypyrrolidine-2-carboxamide (75d) (0.7 g, 1.355 mmol) in DMF (10.0 mL) using DIPEA (0.7 mL, 3.99 mmol); HATU (0.772 g, 2.032 mmol) and 3-cyanobenzoic acid (0.25 g, 1.693 mmol) according to the procedure as reported in Scheme 82 gave (2R,4R)-N-(5-((+)-1-amino-3-cyclopropyl-1-(pyridin-4-yl)propyl)-2-fluorophenyl)-1-(3-cyanobenzoyl)-4-methoxypyrrolidine-2-carboxamide (86a) (0.07 g, 22.4% yield) as on off white solid; $^1$H NMR (300 MHz, DMSO-$d_6$) δ 9.62 (s, 1H), 8.44 (d, J=5.7 Hz, 2H), 8.08 (s, 1H), 7.98 (d, J=7.7 Hz, 1H), 7.94-7.80 (m, 3H), 7.69 (t, J=7.8 Hz, 1H), 7.40-7.29 (m, 2H), 7.17 (d, J=9.3 Hz, 2H), 4.82-4.65 (m, 1H), 3.99 (t, J=5.7 Hz, 1H), 3.69 (dd, J=10.5, 5.9 Hz, 1H), 3.55 (dd, J=10.3, 5.6 Hz, 1H), 3.19 (d, J=1.1 Hz, 3H), 2.33-1.90 (m, 5H), 1.13-0.93 (m, 2H), 0.64 (s, 1H), 0.34 (d, J=7.5 Hz, 2H), −0.07 (s, 2H); $^{19}$F NMR (282 MHz, DMSO-$d_6$) δ −127.51; MS (ES+) 542.7 (M+1), MS (ES−) 540.7 (M−1), 576.6 (M+Cl); Optical rotation $[α]_D$=(+) 49.70 [0.33, MeOH].

Scheme 87

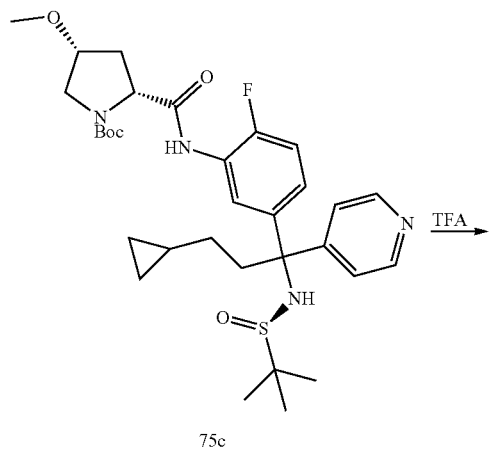

75c

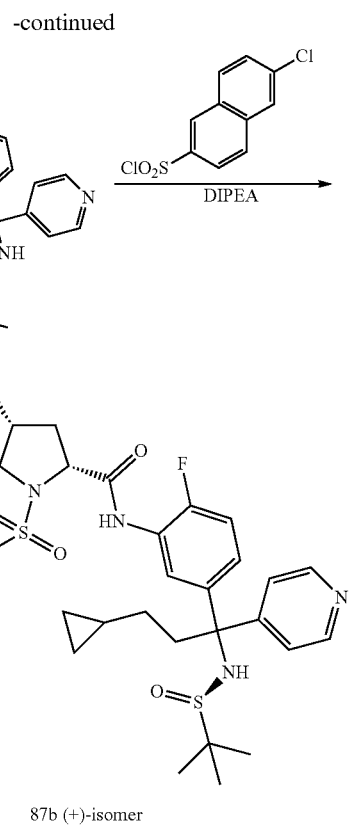

87a 87b (+)-isomer

Preparation of (2R,4R)-1-(6-chloronaphthalen-2-yl sulfonyl)-N-(5-((S)-3-cyclopropyl-1-((R)-1,1-dimethylethylsulfinamido)-1-(pyridin-4-yl)propyl)-2-fluorophenyl)-4-methoxypyrrolidine-2-carboxamide (87b)

Step-1 Preparation of (2R,4R)-N-(5-(3-cyclopropyl-1-((R)-1,1-dimethylethylsulfinamido)-1-(pyridin-4-yl)propyl)-2-fluorophenyl)-4-methoxypyrrolidine-2-carboxamide (87a)

To a stirred solution of (2R,4R)-tert-butyl 2-(5-(3-cyclopropyl-1-((R)-1,1-dimethylethylsulfinamido)-1-(pyridin-4-yl)propyl)-2-fluorophenylcarbamoyl)-4-methoxypyrrolidine-1-carboxylate (75c) (1 g, 1.623 mmol) in DCM (20 mL) was added TFA (3 mL) stirred at room temperature for 3 h and concentrated under vacuum to afford (2R,4R)-N-(5-(3-cyclopropyl-1-((R)-1,1-dimethylethylsulfinamido)-1-(pyridin-4-yl)propyl)-2-fluorophenyl)-4-methoxypyrrolidine-2-carboxamide (87a) 1.3 g TFA salt as an off-white solid, which was used as such in next step; MS (ES+) 517.3 (M+1), MS (ES−) 515.2 (M−1).

Step-2: Preparation of (2R,4R)-1-(5-chloronaphthalen-1-ylsulfonyl)-N-(5-((+)-3-cyclopropyl-1-((R)-1,1-dimethylethylsulfinamido)-1-(pyridin-4-yl)propyl)-2-fluorophenyl)-4-methoxypyrrolidine-2-carboxamide (87b)

To a stirred solution of (2R,4R)-N-(5-(3-cyclopropyl-1-((R)-1,1-dimethylethylsulfinamido)-1-(pyridin-4-yl)propyl)-2-fluorophenyl)-4-methoxypyrrolidine-2-carboxamide (87a) (0.7 g, 1.355 mmol) in DCM (20 mL) was added N, N-diisopropylethylamine (1.2 mL, 6.775 mmol) followed by 5-chloronaphthalene-1-sulfonyl chloride (0.354 g, 1.355 mmol) under nitrogen. The reaction mixture was stirred at room temperature for 3 h and concentrated in vacuum. The residue obtained was purified by flash column chromatography (silica gel, eluting with 0-2% methanol in Ethyl acetate) to afford (2R,4R)-1-(6-chloronaphthalen-2-yl sulfonyl)-N-(5-((S)-3-cyclopropyl-1-((R)-1,1-dimethylethylsulfinamido)-1-(pyridin-4-yl)propyl)-2-fluorophenyl)-4-methoxypyrrolidine-2-carboxamide (87b) (0.06 g, 6.96%) as an off white solid. $^1$H NMR (300 MHz, DMSO-d$_6$) δ 9.44-9.29 (m, 1H), 8.64 (d, J=2.0 Hz, 1H), 8.49 (d, J=5.2 Hz, 2H), 8.32-8.21 (m, 2H), 8.17 (d, J=8.7 Hz, 1H), 8.07-7.95 (m, 2H), 7.73 (dd, J=8.8, 2.2 Hz, 1H), 7.45-7.33 (m, 2H), 7.25-7.11 (m, 2H), 4.39 (dd, J=9.6, 2.9 Hz, 1H), 3.87-3.72 (m, 1H), 3.58 (dd, J=10.5, 2.1 Hz, 1H), 3.11 (s, 3H), 2.34-2.07 (m, 3H), 1.97-1.77 (m, 1H), 1.36-1.14 (m, 9H), 1.10-1.03 (m, 3H), 0.93-0.59 (m, 2H), 0.49-0.26 (m, 2H), −0.01−−0.10 (m, 2H). $^{19}$F NMR (282 MHz, DMSO-d$_6$) δ −130.08; MS (ES+): 637.7 (M+1, loss of sulfinamine group); (ES−) 635.7 (M−1, loss of sulfinamine group), 671.6 (M+Cl, loss of sulfinamine group); Optical rotation: [α]$_D$= (+) 83.28 [0.305, MeOH].

Example 88

Plasma Kallikrein Activity Assay.

The effect of compounds of the invention on human plasma kallikrein activity was determined using the chromogenic substrates (DiaPharma Group, Inc., West Chester, Ohio, USA). In these experiments, 2 nM kallikrein (Enzyme Research Laboratories, South Bend, Ind., USA) was incubated with 80 μM S2302 (H-D-Pro-Phe-Arg-p-nitroaniline) in the absence or presence of increasing concentrations of compounds of the invention in a final volume of 200 μL Tris-HCl buffer (200 mM NaCl; 2.5 mM CaCl$_2$; 50 mM Tris-HCl, pH 7.8).

After incubation at 30° C., the activity of kallikrein was measured as a change in absorbance at OD 405 nm using BioTek PowerWave X340 Microplate Reader (Winooski, Vt., USA). Data were analyzed using SigmaPlot software (Systat Software, Inc., San Jose, Calif., USA) (Four Parameter Logistic Curve). Ki values for the inhibitors were determined using the Cheng-Prusoff equation (*Biochem. Pharmacol.* 1973, 22, 3099).

The compounds disclosed in this application have Ki values less than 1 micromolar (μM) for the plasma kallikrein enzyme. See Table 1.

TABLE 1

Measured Ki values for compounds.

| Compound | Ki (nM) | Compound | Ki (nM) | Compound | Ki (nM) |
|---|---|---|---|---|---|
| 1p | >100 | 17b | 50-100 | 61b | <50 |
| 2a | >100 | 18b | <50 | 30b | 50-100 |
| 3a | 50-100 | 18a | <50 | 62c | <50 |
| 4g | 50-100 | 19c | >100 | 63g | 50-100 |
| 5e | >100 | 33d | >100 | 64g | <50 |
| 6f | >100 | 20b | >100 | 65b | <50 |
| 6e | >100 | 21d | >100 | 37d | <50 |
| 7c | >100 | 22b | >100 | 36d | >100 |
| 8c | >100 | 23b | 50-100 | 31i | <50 |
| 9c | >100 | 24b | >100 | 32a | <50 |
| 10c | >100 | 25b | >100 | 32b | >100 |
| 11e | >100 | 26b | >100 | 34d | <50 |
| 13e | >100 | 27b | >100 | 35a | 50-100 |
| 14h | <50 | 28b | >100 | 66c | >100 |
| 15f | >100 | 29e | <50 | 68a | <50 |
| 14g | >100 | 30a | <50 | 69a | <50 |
| 16h | >100 | 60a | >100 | 72c | <50 |
| 70c | <50 | 76e | >100 | 10b | >100 |
| 71a | <50 | 55a | <50 | 4f | 50-100 |
| 67b | >100 | 56a | <50 | 9b | >100 |
| 38d | <50 | 77a | <50 | 11d | >100 |
| 39h | <50 | 57d | <50 | 12b | >100 |
| 40a | <50 | 41a | <50 | 27a | >100 |
| 47d | 50-100 | 58j | <50 | 29d | >100 |
| 48d | <50 | 59d | <50 | 33b | >100 |
| 49d | 50-100 | 44e | >100 | 34b | >100 |
| 52d | <50 | 43m | 50-100 | 81h | <50 |
| 53d | <50 | 45c | >100 | 79a | <50 |
| 51b | <50 | 46k | <50 | 78a | <50 |
| 73a | <50 | 5d | >100 | 80c | 50-100 |
| 74a | <50 | 6d | >100 | 82a | >100 |
| 54g | <50 | 6c | >100 | 83a | >100 |
| 42l | <50 | 7b | >100 | 84a | >100 |
| 75e | <50 | 8b | >100 | 85a | >100 |
|  |  |  |  | 86a | >100 |
|  |  |  |  | 87b | >100 |

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by Formula (I), or a pharmaceutically acceptable salt thereof:

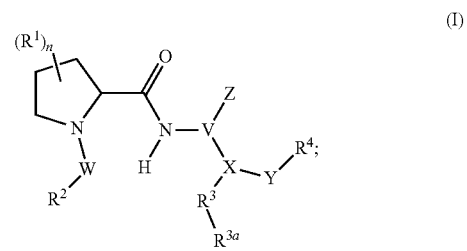

(I)

wherein, independently for each occurrence:

R$^1$ represents —OH, —OR$^c$, —NH$_2$, —NHR$^c$, —NR$^c$R$^d$, alkyl, aryl, aralkyl, heteroaryl, heteroaralkyl, halo, haloalkyl, cycloalkyl, (cycloalkyl)alkyl, —C(O)R$^c$, —C(O)OH, —C(O)OR$^c$, —OC(O)R$^c$, —C(O)NH$_2$, —C(O)NHR$^c$, —C(O)NR$^c$R$^d$, —NHC(O)R$^c$, or —NR$^c$C(O)R$^d$; or two geminal occurrences of R$^1$ taken together with the carbon to which they are attached represent —C(O)—; or two vicinal or geminal occurrences of R$^1$ taken together form an optionally substituted fused or spirocyclic carbocyclic or heterocyclic ring;

W is —C(O)NH- or —C(O)N($R^c$)—;

$R^2$ represents optionally substituted aryl or heteroaryl;

Z is absent or represents one or more substituents independently selected from the group consisting of halo, haloalkyl, -$NO_2$, —CN, —C(O)$R^c$, —C(O)OH, —C(O)O$R^c$, —OC(O)$R^c$, —C(O)$NH_2$, —C(O)NH$R^c$, —C(O)N$R^cR^d$, —NHC(O)$R^c$, -N($R^c$)C(O)$R^d$, -OS(O)$_p$($R^c$), —NHS(O)$_p$($R^c$), and —N$R^c$S(O)$_p$($R^c$);

X represents —C($NH_2$)—, —C(NH($R^c$))—, —C(N$R^cR^d$)—, —C(NHS(O)$_p R^c$)—, —C(NHC(O)$R^c$)—, —C(NHC(O)$NH_2$)—, —C(NHC(O)NH$R^c$)—, —C(NHC(O)N$R^cR^d$)—, —C(OH)—, —C(O(alkyl))-, —C($N_3$)—, —C(CN)—, —C($NO_2$)—, —C(S(O)$_n R^a$)—, —C[—C(=O)$R^c$]—, —C[—C(=O)N$R^cR^d$]-, —C[—C(=O)S$R^c$]—, —C[—S(O)$R^c$]-, —C[—S(O)$_2 R^c$]—, —C[S(O)(O$R^c$)]—, —C[—S(O)$_2$(O$R^c$)]—, —C[—$SO_2$N$R^cR^d$]—, —C(halogen)-, —C(alkyl), —C((cycloalkyl)alkyl), —C(alkenyl)-, —C(alkynyl)-, or —C(aralkyl)-;

$R^3$ represents optionally substituted aryl, heteroaryl, cycloalkyl, or heterocycloalkyl;

$R^{3a}$ is absent or represents one or more substituents independently selected from the group consisting of halo, hydroxy, alkyl, —$CF_3$, —$OCF_3$, alkoxy, aryl, heteroaryl, aryloxy, amino, aminoalkyl, —C(O)$NH_2$, cyano, —NHC(O)alkyl, —$SO_2$alkyl, —$SO_2NH_2$, cycloalkyl, —($CH_2$)$_r$O$R^a$, —$NO_2$, —($CH_2$)$_r$N$R^aR^b$, —($CH_2$)$_r$C(O)$R^a$, —N$R^a$C(O)$R^b$, —C(O)N$R^cR^d$, —N$R^a$C(O)N$R^cR^d$, —C(=N$R^a$)N$R^cR^d$, —NHC(=N$R^a$)N$R^cR^d$, —N$R^aR^b$, —$SO_2$N$R^cR^d$, —N$R^aSO_2$N$R^cR^d$, —N$R^aSO_2$alkyl, —N$R^aSO_2R^a$, —S(O)$_p R^a$, —($CF_2$)$_r CF_3$, —NHC$H_2R^a$, —OC$H_2R^a$, —SC$H_2R^a$, —NH($CH_2$)$_2$($CH_2$)$_r R^a$, —O($CH_2$)$_2$($CH_2$)$_r R^a$, or —S($CH_2$)$_2$($CH_2$)$_r R^a$;

Y represents a bond; or —Y—$R^4$ represents optionally substituted -alkylene-$R^4$, —$CH_2$C(O)—$R^4$, —$CH_2$NH—$R^4$, —$CH_2$N(alkyl)-$R^4$, —C$R^aR^b$—$R^4$, —NH—$R^4$, —NHC$H_2$—$R^4$, —NHC(O)—$R^4$, —N(alkyl)-$R^4$, —N(alkyl)C$H_2$-$R^4$, —N(($CH_2$)$_2$OH)—$R^4$, —N((cycloalkyl)alkyl)$R^4$, -heterocyclyl-$R^4$, —O$R^4$, —OC$H_2$—$R^4$, —OC(O)—$R^4$, —OC(O)N$R^aR^b$, —SC$H_2R^4$, or —S$R^4$;

$R^4$ represents hydrogen, hydroxy, optionally substituted alkyl, cycloalkyl, (heterocycloalkyl)alkyl, (cycloalkyl)alkyl, —$CH_2$OH, —CH(alkyl)OH, —CH($NH_2$)CH(alkyl)$_2$, aryl, aralkyl, heteroaryl, heteroaralkyl, —$CH_2$S(alkyl), amino, or cyano; or —(C$R^aR^b$)$_r$(C$R^aR^b$)$_p$— fused to the 4-position of the ring bearing Z to form a 5- to 7-membered heterocyclic ring with optional substituents; or, when $R^3$ is phenyl, $R^4$ can represent —N$R^a$— fused to the position ortho to X on that phenyl;

each $R^a$ and $R^b$ is independently H, alkyl, alkenyl, alkynyl, aralkyl, (cycloalkyl)alkyl, —C(=O)$R^c$, —C(=O)O$R^c$, —C(=O)N$R^cR^d$, —C(=O)S$R^c$, —S(O)$R^c$, —S(O)$_2R^c$, —S(O)(O$R^c$), or —$SO_2$N$R^cR^d$;

$R^c$ and $R^d$ represent, independently for each occurrence, optionally substituted alkyl, alkenyl, alkynyl, haloalkyl, aryl, aralkyl, heteroaryl, heteroaralkyl, cycloalkyl, (cycloalkyl)alkyl, heterocycloalkyl, (heterocycloalkyl)alkyl, —C(O)alkyl, or —S(O)$_p$(alkyl); or $R^c$ and $R^d$ can be taken together to form an optionally substituted heterocyclic ring;

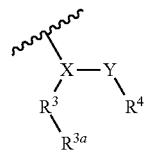

can represent

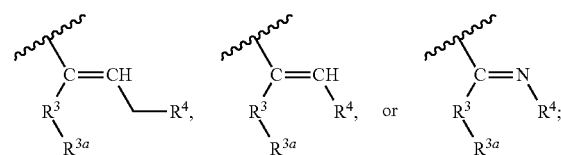

r is 0, 1, 2, or 3;
n is an integer from 0 to 6; and
p is 0, 1, or 2.

2. The compound of claim 1, wherein $R^1$ represents —OH, —O$R^c$, —$NH_2$, —NH$R^c$, —N$R^cR^d$, alkyl, aryl, heteroaryl, halo, haloalkyl, cycloalkyl, —OC(O)$R^c$, —NHC(O)$R^c$, or —N$R^c$C(O)$R^d$; or two geminal occurrences of $R^1$ taken together with the carbon to which they are attached represent —C(O)—; or two vicinal or geminal occurrences of $R^1$ taken together form an optionally substituted fused or spirocyclic carbocyclic or heterocyclic ring.

3. The compound of claim 2, wherein $R^1$ represents —OH, —O$R^c$, —$NH_2$, alkyl, aryl, halo, haloalkyl, cycloalkyl, or —OC(O)R; and n is 1 or 2.

4. The compound of claim 3, wherein n is 1; and
$R^1$ represents —OH, -O(($C_1$-$C_6$)alkyl), —OC(O)(($C_1$-$C_6$)alkyl), —$NH_2$, or ($C_1$-$C_6$)alkyl.

5. The compound of claim 3, wherein n is 2; and
the two occurrences of $R^1$ are geminal.

6. The compound of claim 5, wherein:
(a) one occurrence of $R^1$ represents —OH or —O$R^c$; and the other occurrence of $R^1$ represents aryl or heteroaryl;
(b) one occurrence of $R^1$ represents —OH or —O$R^c$; and the other occurrence of $R^1$ represents haloalkyl;
(c) both occurrences of $R^1$ are halo; or
(d) the two geminal occurrences of $R^1$ taken together with the carbon to which they are attached represent —C(O)—.

7. The compound of claim 3, wherein n is 2; the two occurrences of $R^1$ are vicinal; and the two vicinal occurrences of $R^1$ taken together form an optionally substituted fused carbocyclic ring.

8. The compound of claim 1, wherein $R^2$ represents aryl or heteroaryl, substituted by one or more substituents selected from the group consisting of —OH, halo, —$NH_2$, —NH(($C_1$-$C_6$)alkyl), —N(($C_1$-$C_6$)alkyl)$_2$, —CN, —$NO_2$, ($C_1$-$C_6$)alkyl, ($C_1$-$C_6$)haloalkyl, ($C_1$-$C_6$)alkoxy, —C(O)OH, —C(O)O($C_1$-$C_6$)alkyl, —C(O)$NH_2$, —C(O)NH($C_1$-$C_6$)alkyl, and —C(O)N(($C_1$-$C_6$)alkyl)$_2$.

9. The compound of claim 1, wherein V represents optionally substituted aryl.

10. The compound of claim 1, wherein Z is absent, or wherein Z represents one or more substituents independently selected from the group consisting of halo, haloalkyl, —$NO_2$, and —CN.

11. The compound of claim 10, wherein Z represents one instance of halo.

12. The compound of claim 1, wherein X represents —C(NH$_2$)—, —C(NH(R$^c$))—, —C(NR$^c$R$^d$)—, —C(NHS(O)$_p$R$^c$)—, —C(NHC(O)R$^c$)—, —C(NHC(O)NH$_2$)—, —C(NHC(O)NHR$^c$)—, or —C(NHC(O)NR$^c$R$^d$)—.

13. The compound of claim 12, wherein X represents —C(NH$_2$)—; —C(NH(cycloalkyl)alkyl)-; —C(NH(C$_1$-C$_6$)alkyl)-; —C(NHS(O)$_p$(C$_1$-C$_6$)alkyl)-, wherein p is 1 or 2; optionally substituted —C(NHC(O)NH(aryl))-; optionally substituted C(NHC(O)NH(heteroaryl))-; or —C(NHC(O)((C$_1$-C$_6$)alkyl))-.

14. The compound of claim 1, wherein R$^3$ represents optionally substituted aryl or optionally substituted heteroaryl.

15. The compound of claim 14, wherein R$^3$ represents phenyl, optionally substituted by one or more substituents selected from the group consisting of —CN, halo, —NO$_2$, (C$_1$-C$_6$)alkyl, and (C$_1$-C$_6$)haloalkyl; or wherein R$^3$ represents pyridyl.

16. The compound of claim 1, wherein R$^{3a}$ is absent or represents halo, alkyl, —CF$_3$, —OCF$_3$, aryl, heteroaryl, —C(O)NH$_2$, cyano, —NHC(O)alkyl, —SO$_2$alkyl, —SO$_2$NH$_2$, —NO$_2$, —NR$^a$C(O)R$^b$, —C(O)NR$^c$R$^d$, —NR$^a$C(O)NR$^c$R$^d$, —C(=NR$^a$)NR$^c$R$^d$, —NHC(=NR$^a$)NR$^c$R$^d$, —SO$_2$NR$^c$R$^d$, —NR$^a$SO$_2$NR$^c$R$^d$, —NR$^a$SO$_2$alkyl, —NR$^a$SO$_2$R$^a$, —S(O)$_p$R$^a$, or —(CF$_2$)$_r$CF$_3$.

17. The compound of claim 1, wherein Y represents a bond.

18. The compound of claim 1, wherein R$^4$ represents H, (cycloalkyl)alkyl, or (cyclopropyl)(C$_1$-C$_6$)alkyl.

19. The compound of claim 1, selected from the following table:

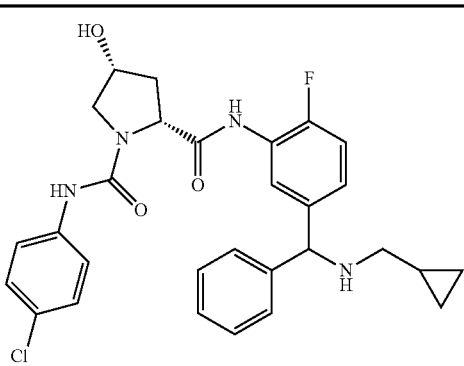

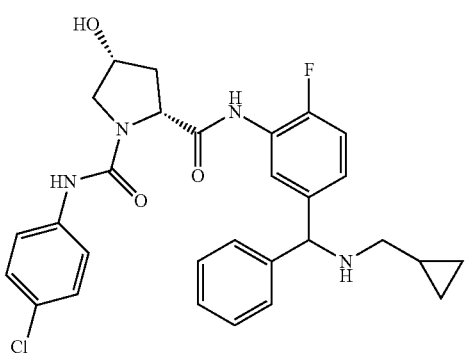 [SMILES: O=C(Nc1cc(C(NCC2CC2)c2ccccc2)ccc1F)[C@H]1C[C@@H](O)CN1C(=O)Nc1ccc(Cl)cc1]

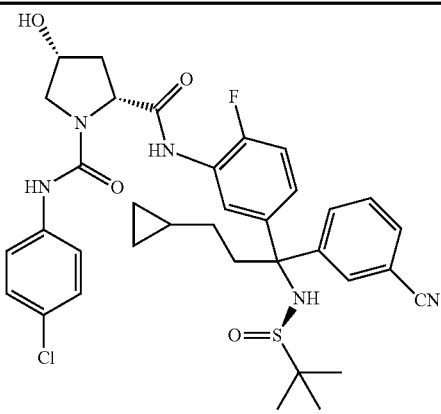

-continued

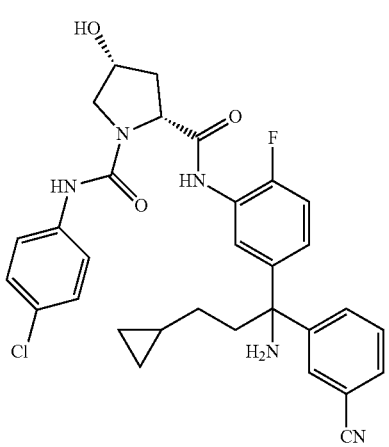 [SMILES: N#Cc1cccc(C(N)(CCC2CC2)c2ccc(F)c(NC(=O)[C@H]3C[C@@H](O)CN3C(=O)Nc3ccc(Cl)cc3)c2)c1]

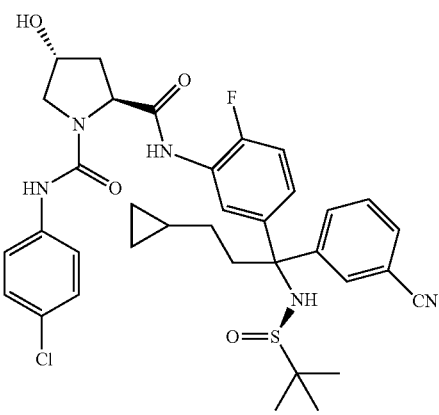 [SMILES: CC(C)(C)[S@@](=O)NC(CCC1CC1)(c1cccc(C#N)c1)c1ccc(F)c(NC(=O)[C@@H]2C[C@@H](O)CN2C(=O)Nc2ccc(Cl)cc2)c1]

| 271 | 272 |
|---|---|
| 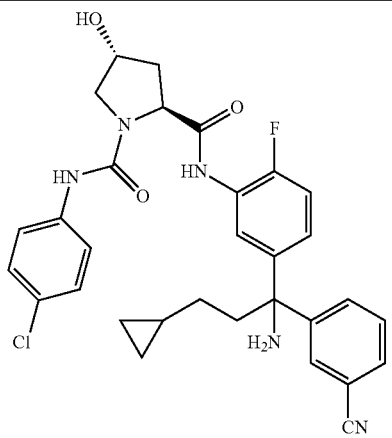 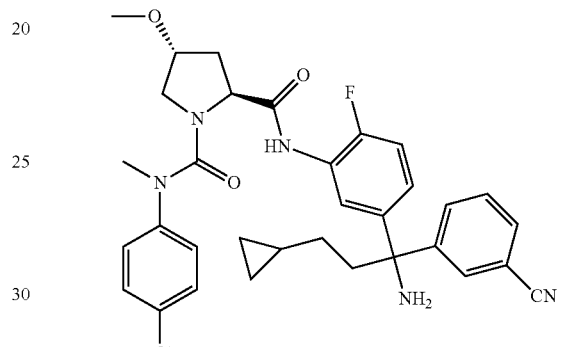 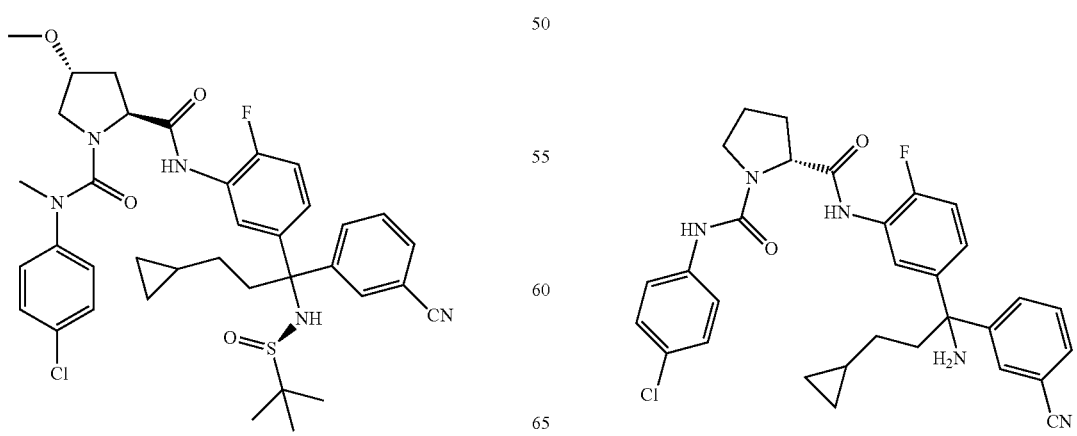 | 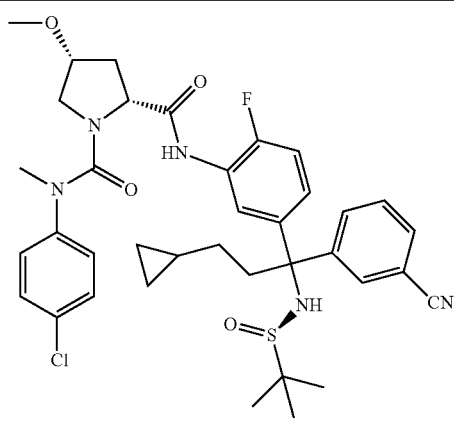 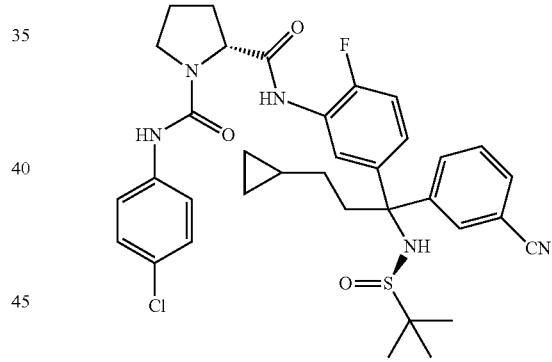 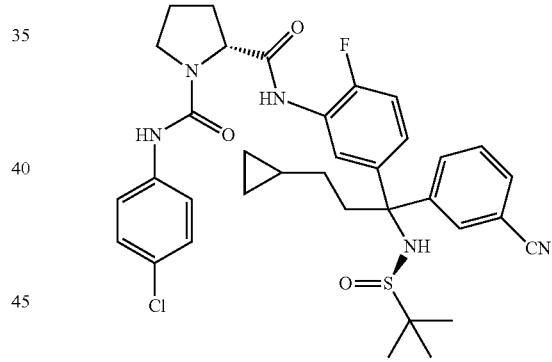 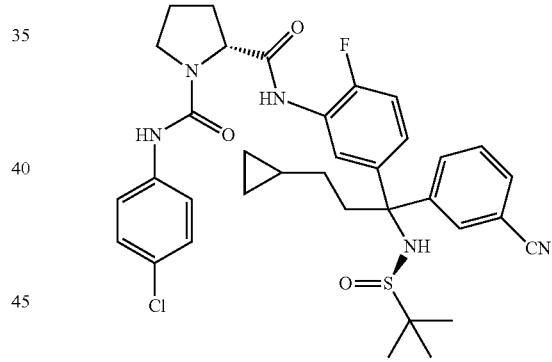 |

273
-continued
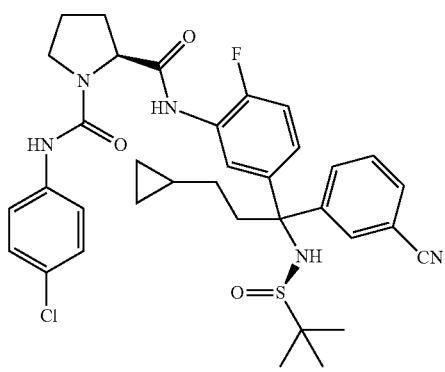 [SMILES: CC(C)(C)[S@@](=O)NC(CCC1CC1)(c1cccc(C#N)c1)c1ccc(F)c(NC(=O)[C@@H]2CCCN2C(=O)Nc2ccc(Cl)cc2)c1]
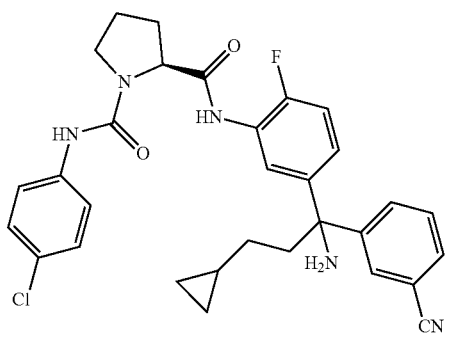 [SMILES: N#Cc1cccc(C(N)(CCC2CC2)c2ccc(F)c(NC(=O)[C@@H]3CCCN3C(=O)Nc3ccc(Cl)cc3)c2)c1]
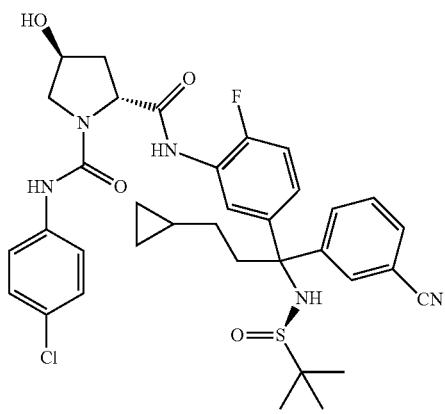 [SMILES: CC(C)(C)[S@@](=O)NC(CCC1CC1)(c1cccc(C#N)c1)c1ccc(F)c(NC(=O)[C@H]2C[C@H](O)CN2C(=O)Nc2ccc(Cl)cc2)c1]
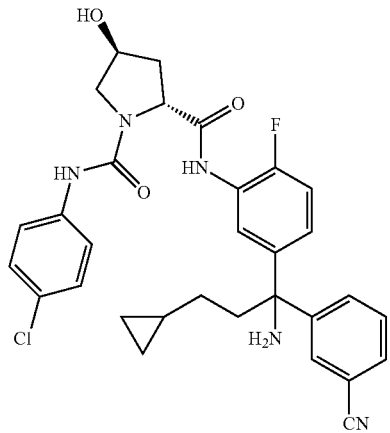 [SMILES: N#Cc1cccc(C(N)(CCC2CC2)c2ccc(F)c(NC(=O)[C@H]3C[C@H](O)CN3C(=O)Nc3ccc(Cl)cc3)c2)c1]
274
-continued
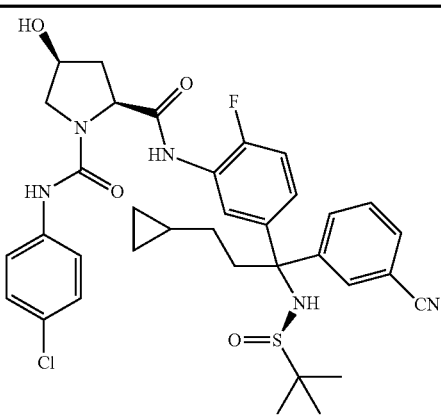
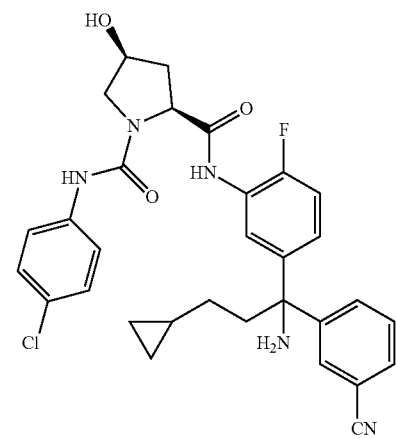 [SMILES: N#Cc1cccc(C(N)(CCC2CC2)c2ccc(F)c(NC(=O)[C@@H]3C[C@H](O)CN3C(=O)Nc3ccc(Cl)cc3)c2)c1]
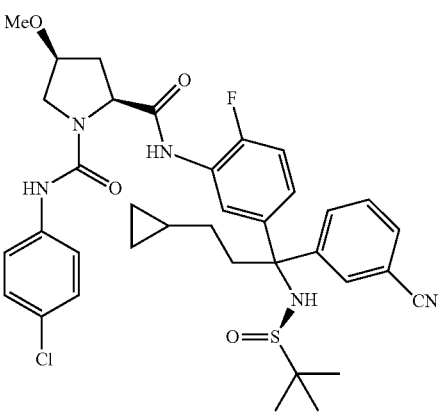 [SMILES: CO[C@H]1C[C@@H](C(=O)Nc2cc(C(CCC3CC3)(N[S@](=O)C(C)(C)C)c3cccc(C#N)c3)ccc2F)N(C(=O)Nc2ccc(Cl)cc2)C1]

275
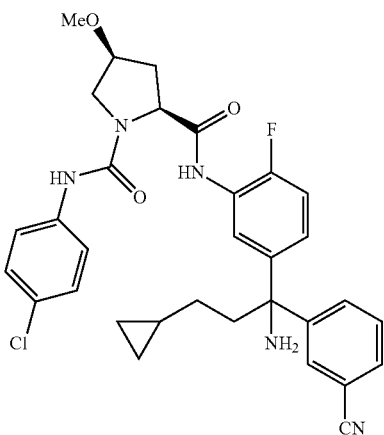 [SMILES: CO[C@H]1C[C@@H](C(=O)Nc2cc(C(N)(CCC3CC3)c3cccc(C#N)c3)ccc2F)N(C(=O)Nc2ccc(Cl)cc2)C1]
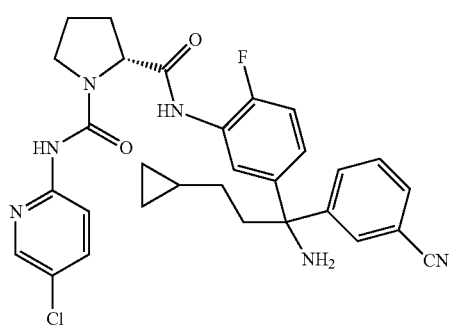 [SMILES: N#Cc1cccc(C(N)(CCC2CC2)c2ccc(F)c(NC(=O)[C@H]3CCCN3C(=O)Nc3ccc(Cl)cn3)c2)c1]
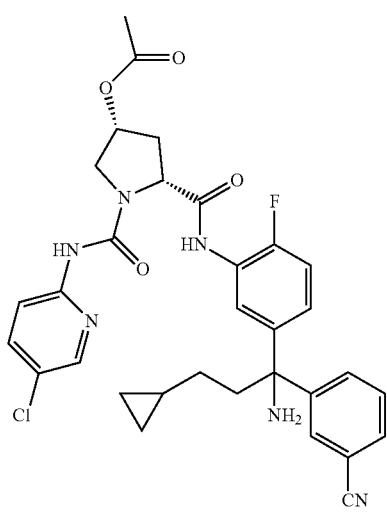 [SMILES: CC(=O)O[C@@H]1C[C@H](C(=O)Nc2cc(C(N)(CCC3CC3)c3cccc(C#N)c3)ccc2F)N(C(=O)Nc2ccc(Cl)cn2)C1]
276
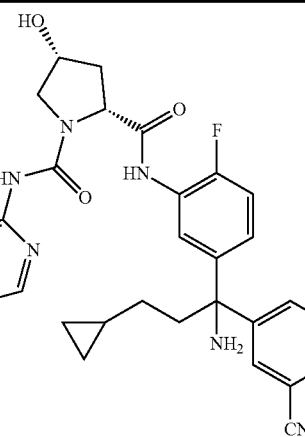
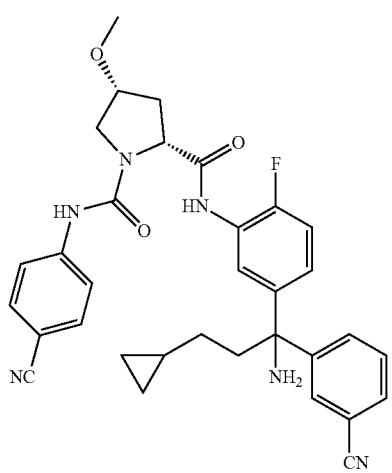 [SMILES: CO[C@@H]1C[C@H](C(=O)Nc2cc(C(N)(CCC3CC3)c3cccc(C#N)c3)ccc2F)N(C(=O)Nc2ccc(C#N)cc2)C1]
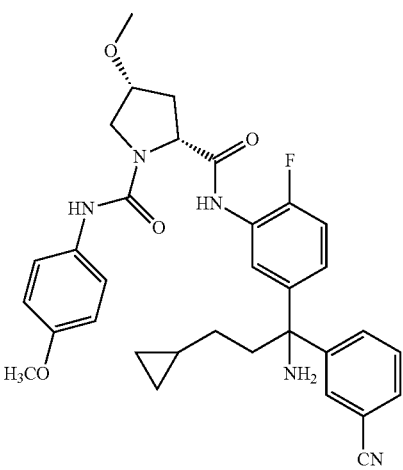 [SMILES: COc1ccc(NC(=O)N2C[C@H](OC)C[C@@H]2C(=O)Nc2cc(C(N)(CCC3CC3)c3cccc(C#N)c3)ccc2F)cc1]

| 277 -continued | 278 -continued |
|---|---|
| 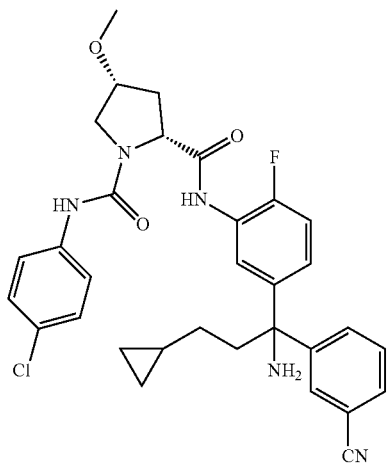 [SMILES: CO[C@@H]1C[C@H](C(=O)Nc2cc(C(N)(CCC3CC3)c3cccc(C#N)c3)ccc2F)N(C(=O)Nc2ccc(Cl)cc2)C1] | 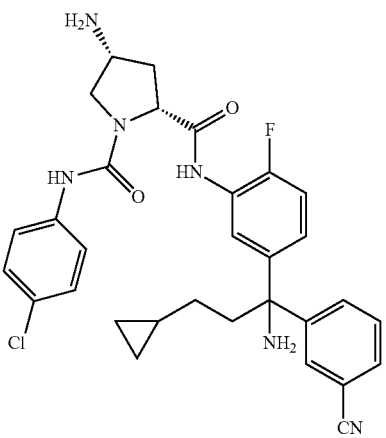 |
| 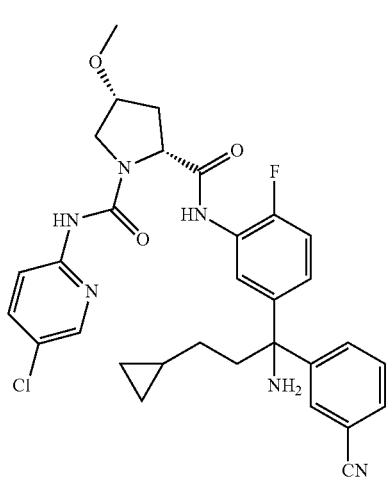 [SMILES: CO[C@@H]1C[C@H](C(=O)Nc2cc(C(N)(CCC3CC3)c3cccc(C#N)c3)ccc2F)N(C(=O)Nc2ccc(Cl)cn2)C1] | 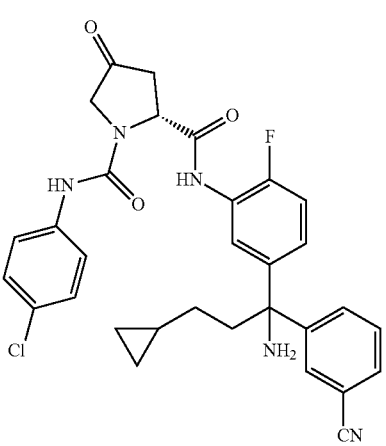 |
| 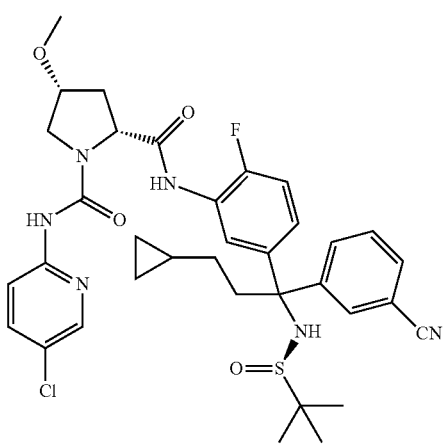 [SMILES: CO[C@@H]1C[C@H](C(=O)Nc2cc(C(CCC3CC3)(N[S@](=O)C(C)(C)C)c3cccc(C#N)c3)ccc2F)N(C(=O)Nc2ccc(Cl)cn2)C1] | 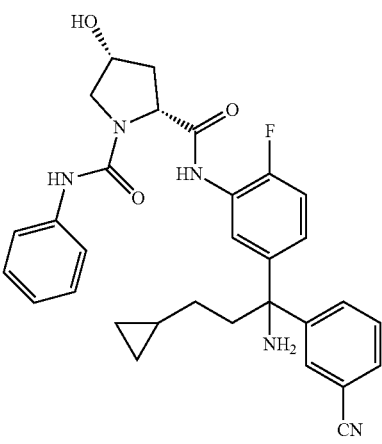 [SMILES: N#Cc1cccc(C(N)(CCC2CC2)c2ccc(F)c(NC(=O)[C@H]3C[C@@H](O)CN3C(=O)Nc3ccccc3)c2)c1] |

| 279 -continued | 280 -continued |
|---|---|
| 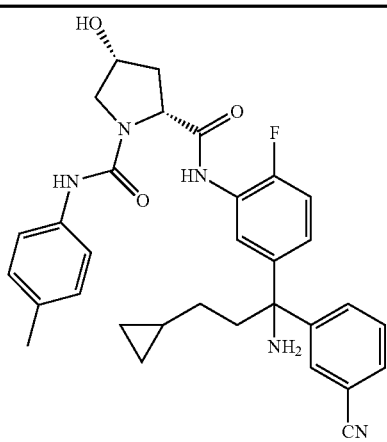 | 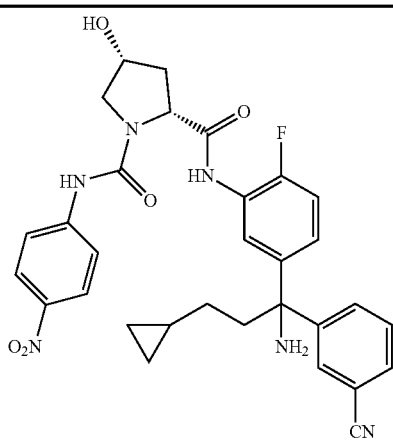 |
| 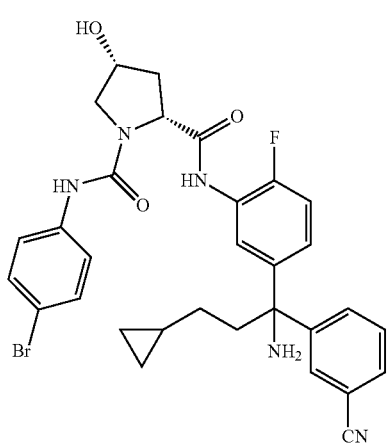 [SMILES: N#Cc1cccc(C(N)(CCC2CC2)c2ccc(F)c(NC(=O)[C@H]3C[C@@H](O)CN3C(=O)Nc3ccc(Br)cc3)c2)c1] | 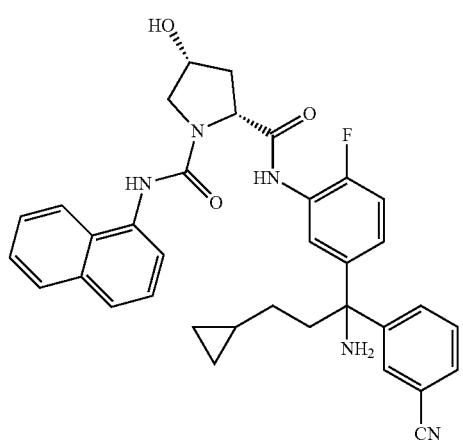 |
| 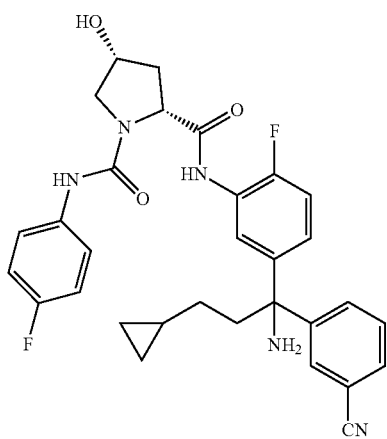 [SMILES: N#Cc1cccc(C(N)(CCC2CC2)c2ccc(F)c(NC(=O)[C@H]3C[C@@H](O)CN3C(=O)Nc3ccc(F)cc3)c2)c1] | 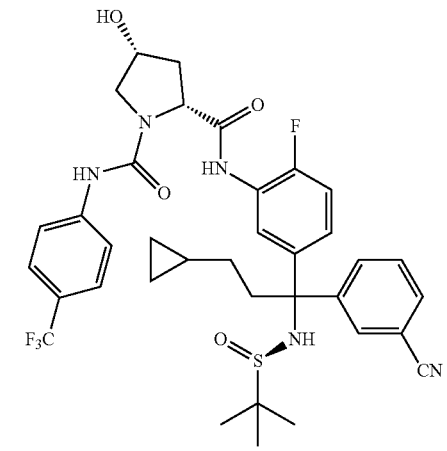 [SMILES: CC(C)(C)[S@@](=O)NC(CCC1CC1)(c1cccc(C#N)c1)c1ccc(F)c(NC(=O)[C@H]2C[C@@H](O)CN2C(=O)Nc2ccc(C(F)(F)F)cc2)c1] |

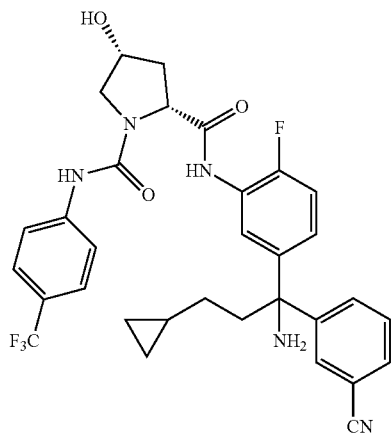 [SMILES: N#Cc1cccc(C(N)(CCC2CC2)c2ccc(F)c(NC(=O)[C@H]3C[C@@H](O)CN3C(=O)Nc3ccc(C(F)(F)F)cc3)c2)c1]
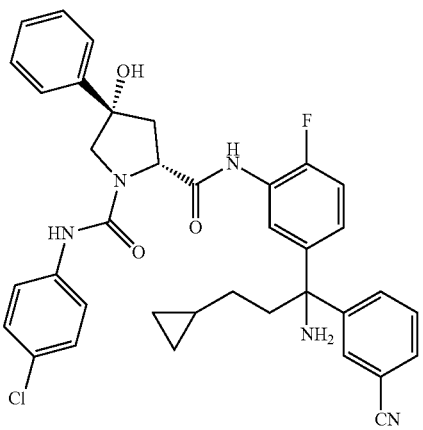 [SMILES: N#Cc1cccc(C(N)(CCC2CC2)c2ccc(F)c(NC(=O)[C@H]3C[C@](O)(c4ccccc4)CN3C(=O)Nc3ccc(Cl)cc3)c2)c1]
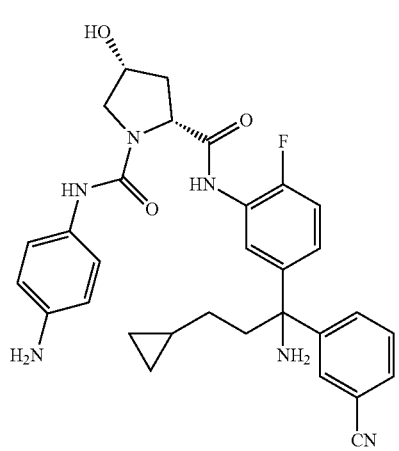
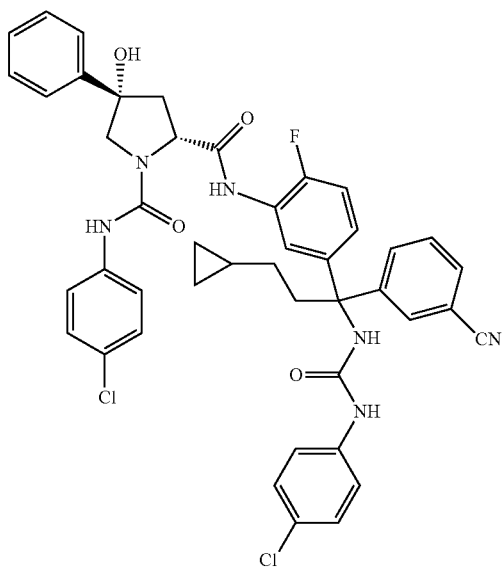 [SMILES: N#Cc1cccc(C(CCC2CC2)(NC(=O)Nc2ccc(Cl)cc2)c2ccc(F)c(NC(=O)[C@H]3C[C@](O)(c4ccccc4)CN3C(=O)Nc3ccc(Cl)cc3)c2)c1]
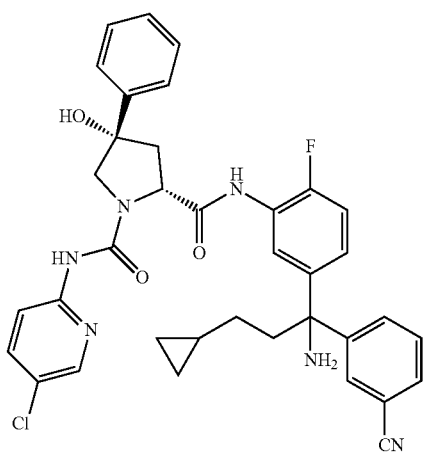
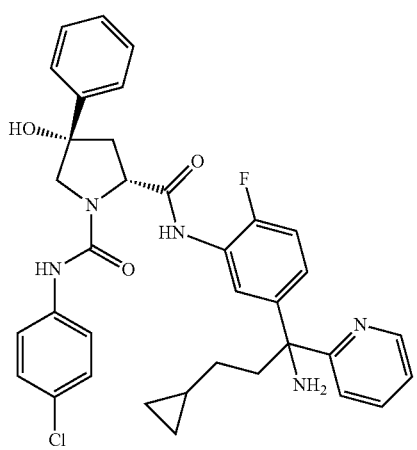 [SMILES: NC(CCC1CC1)(c1ccc(F)c(NC(=O)[C@H]2C[C@](O)(c3ccccc3)CN2C(=O)Nc2ccc(Cl)cc2)c1)c1ccccn1]

| 283 -continued | 284 -continued |
|---|---|
| 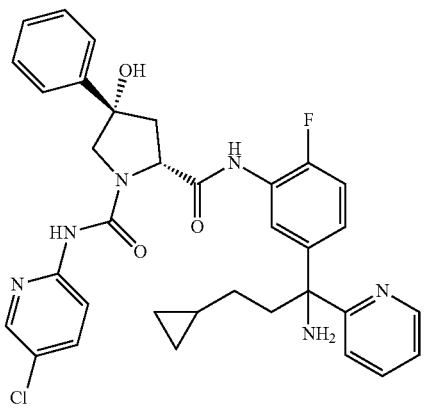 [SMILES: NC(CCC1CC1)(c1ccc(F)c(NC(=O)[C@H]2C[C@](O)(c3ccccc3)CN2C(=O)Nc2ccc(Cl)cn2)c1)c1ccccn1] | 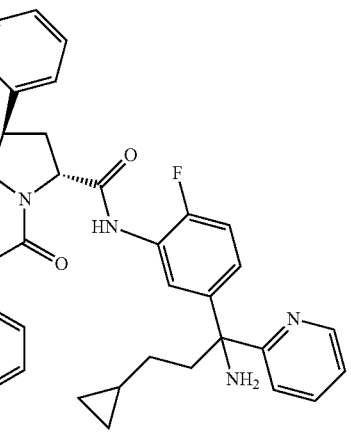 |
| 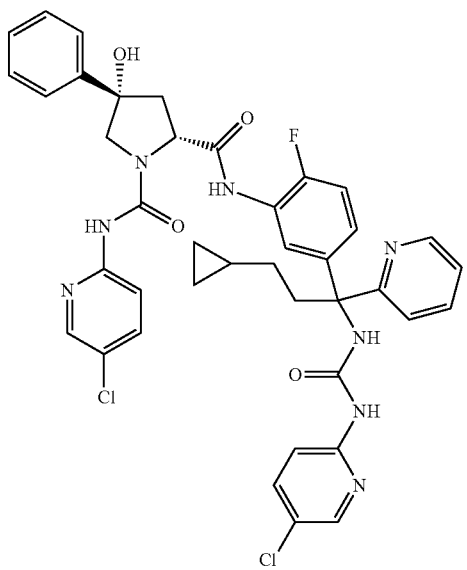 [SMILES: O=C(Nc1ccc(Cl)cn1)NC(CCC1CC1)(c1ccc(F)c(NC(=O)[C@H]2C[C@](O)(c3ccccc3)CN2C(=O)Nc2ccc(Cl)cn2)c1)c1ccccn1] | 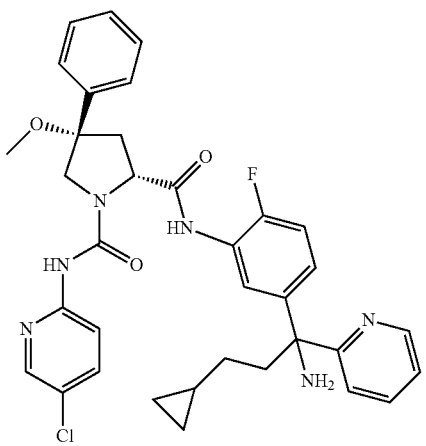 |
| 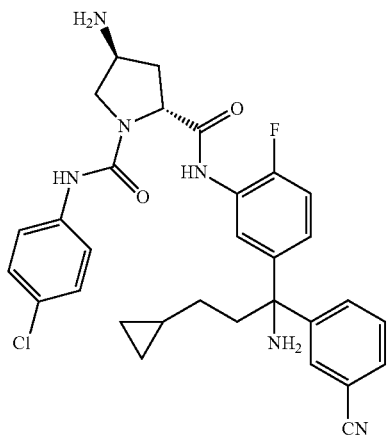 [SMILES: N#Cc1cccc(C(N)(CCC2CC2)c2ccc(F)c(NC(=O)[C@H]3C[C@H](N)CN3C(=O)Nc3ccc(Cl)cc3)c2)c1] | 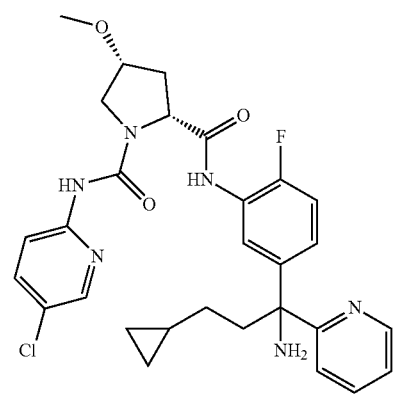 [SMILES: CO[C@@H]1C[C@H](C(=O)Nc2cc(C(N)(CCC3CC3)c3ccccn3)ccc2F)N(C(=O)Nc2ccc(Cl)cn2)C1] |

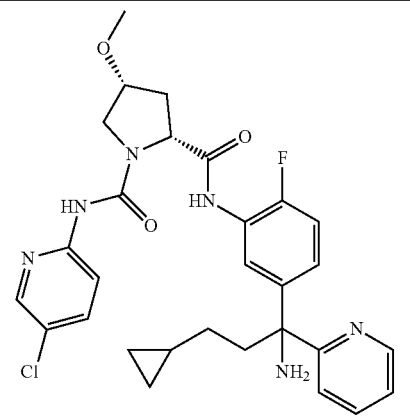
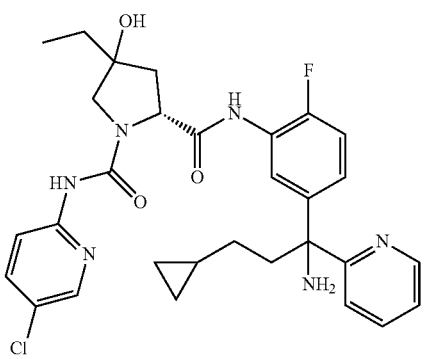 [SMILES: CCC1(O)C[C@H](C(=O)Nc2cc(C(N)(CCC3CC3)c3ccccn3)ccc2F)N(C(=O)Nc2ccc(Cl)cn2)C1]
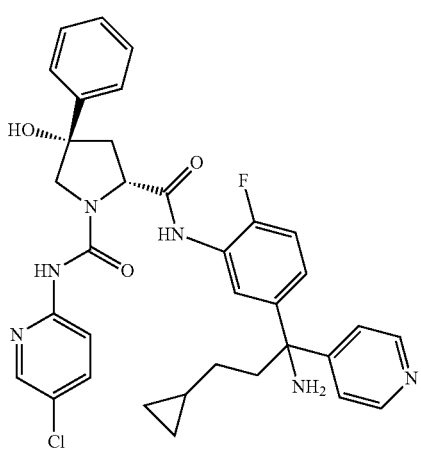 [SMILES: NC(CCC1CC1)(c1ccncc1)c1ccc(F)c(NC(=O)[C@H]2C[C@](O)(c3ccccc3)CN2C(=O)Nc2ccc(Cl)cn2)c1]
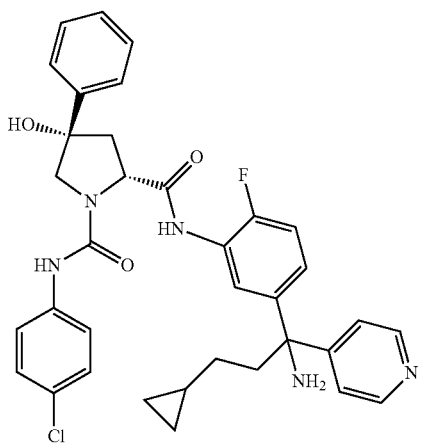 [SMILES: NC(CCC1CC1)(c1ccncc1)c1ccc(F)c(NC(=O)[C@H]2C[C@](O)(c3ccccc3)CN2C(=O)Nc2ccc(Cl)cc2)c1]
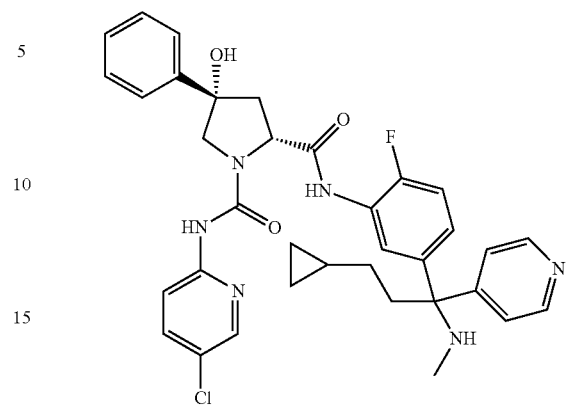
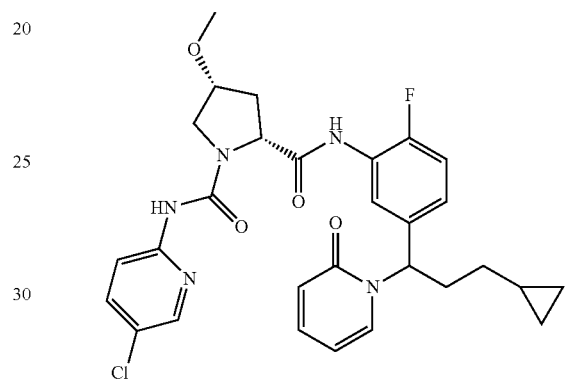
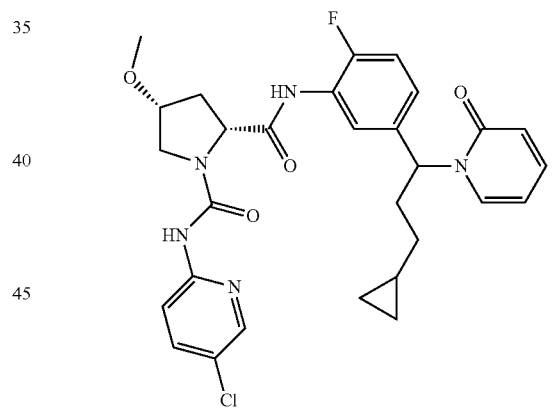
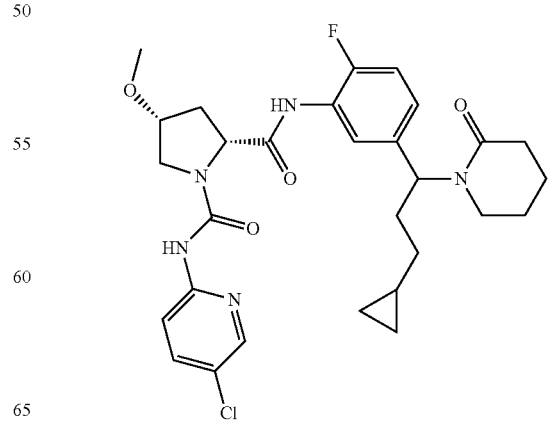

287
-continued
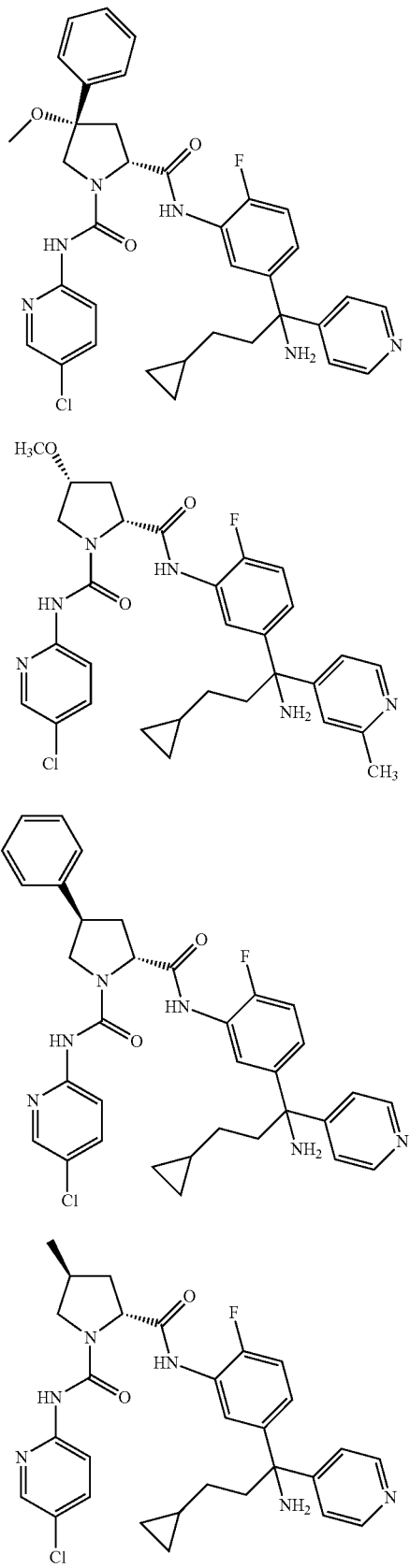
288
-continued
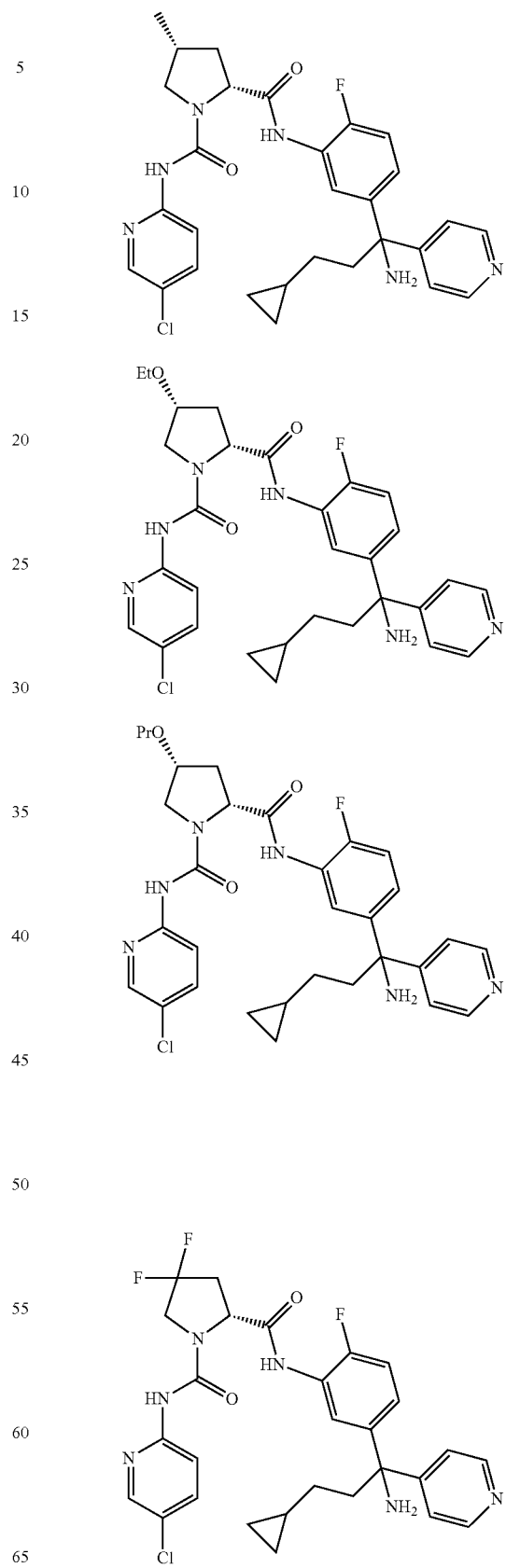

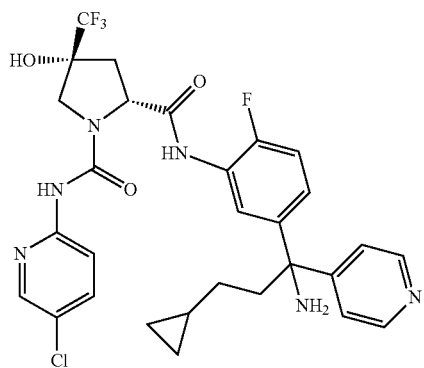 [SMILES: NC(CCC1CC1)(c1ccncc1)c1ccc(F)c(NC(=O)[C@H]2C[C@](O)(C(F)(F)F)CN2C(=O)Nc2ccc(Cl)cn2)c1]
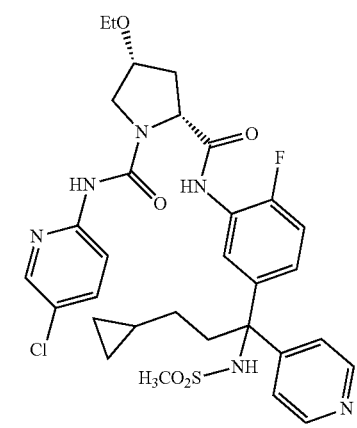
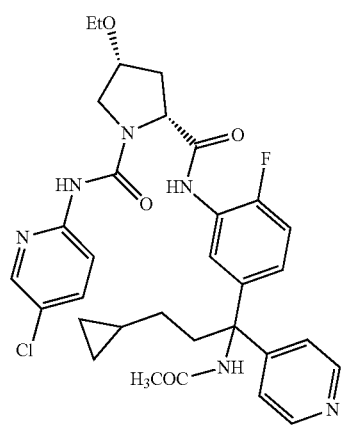
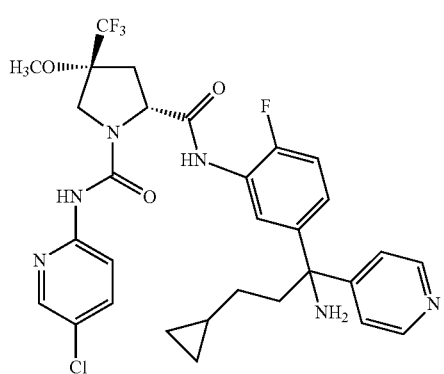 [SMILES: CO[C@]1(C(F)(F)F)C[C@H](C(=O)Nc2cc(C(N)(CCC3CC3)c3ccncc3)ccc2F)N(C(=O)Nc2ccc(Cl)cn2)C1]
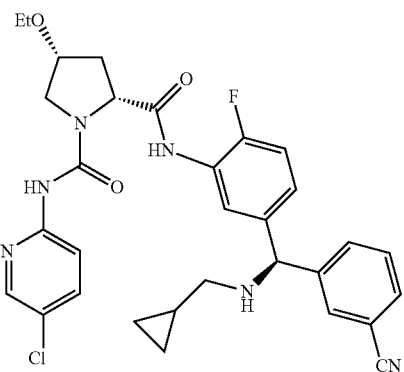 [SMILES: CCO[C@@H]1C[C@H](C(=O)Nc2cc([C@H](NCC3CC3)c3cccc(C#N)c3)ccc2F)N(C(=O)Nc2ccc(Cl)cn2)C1]
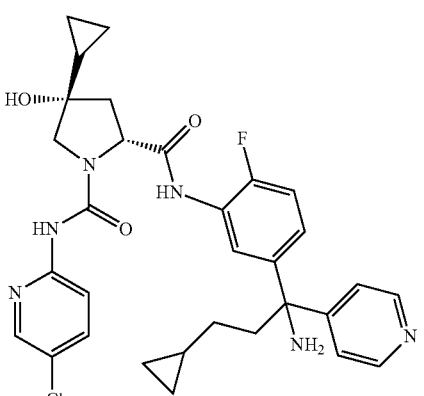
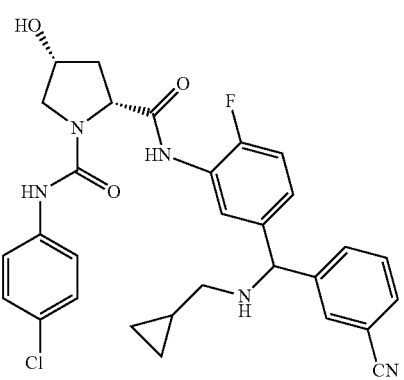 [SMILES: N#Cc1cccc(C(NCC2CC2)c2ccc(F)c(NC(=O)[C@H]3C[C@@H](O)CN3C(=O)Nc3ccc(Cl)cc3)c2)c1]
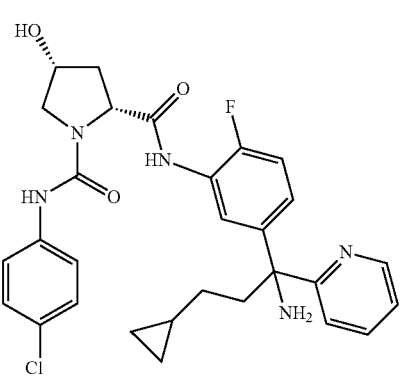 [SMILES: NC(CCC1CC1)(c1ccc(F)c(NC(=O)[C@H]2C[C@@H](O)CN2C(=O)Nc2ccc(Cl)cc2)c1)c1ccccn1]

291
-continued
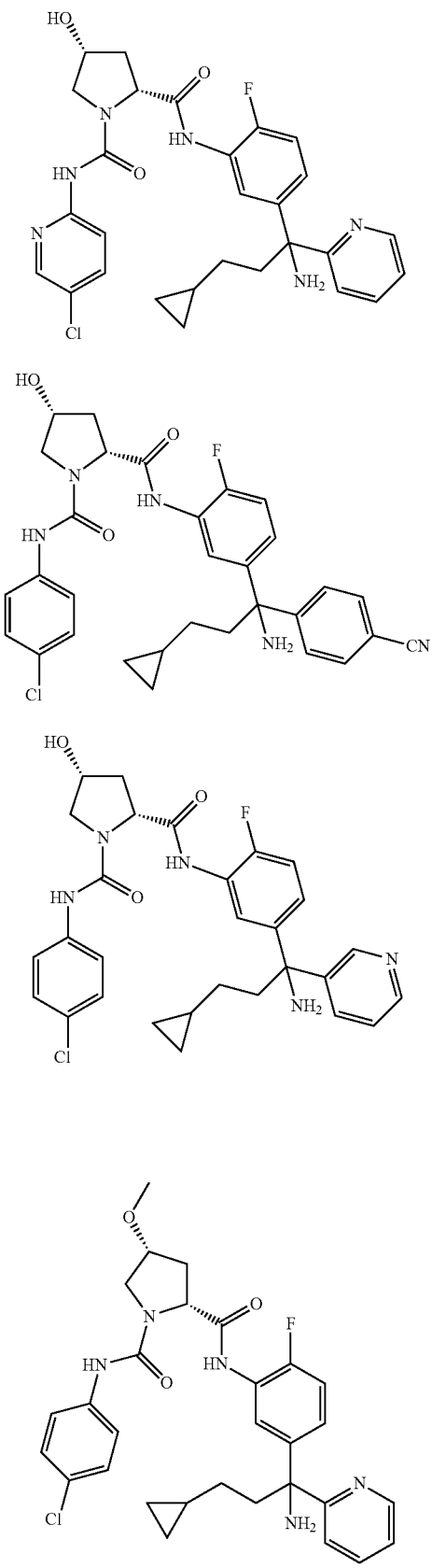
292
-continued
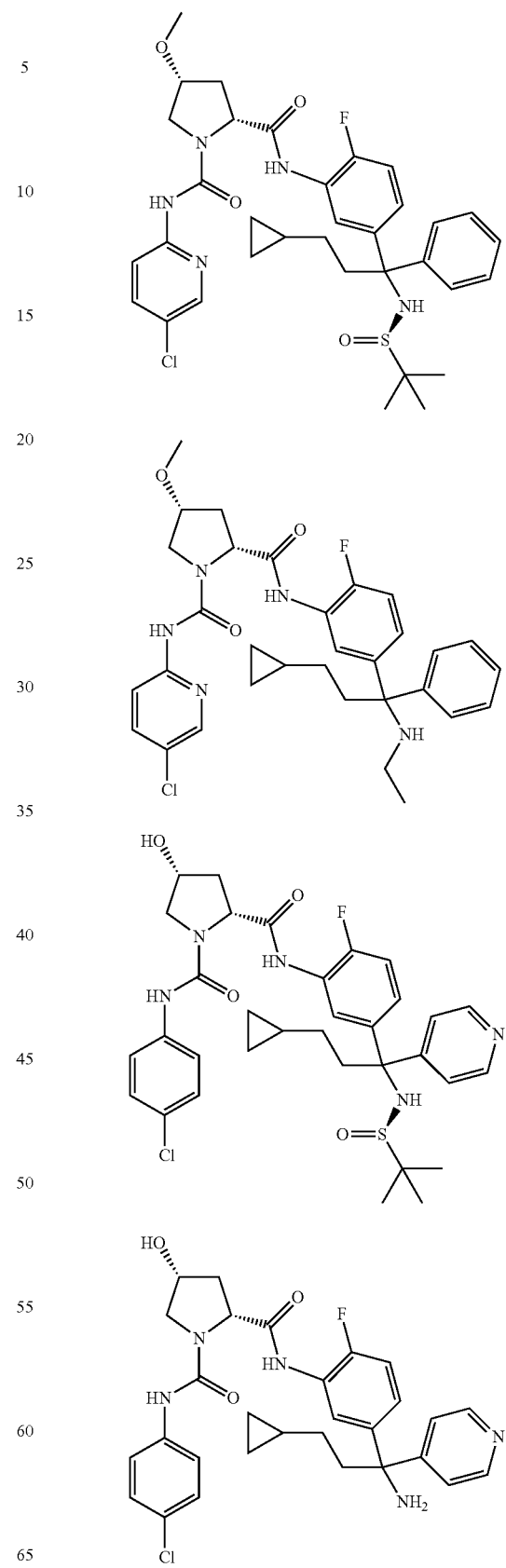

293
-continued
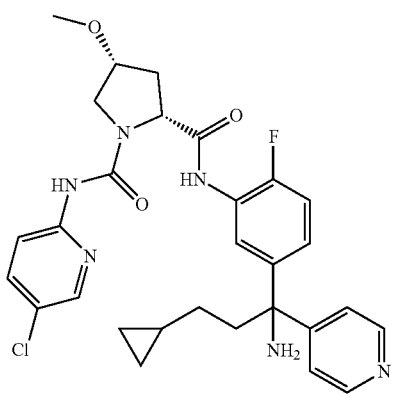 [SMILES: CO[C@@H]1C[C@H](C(=O)Nc2cc(C(N)(CCC3CC3)c3ccncc3)ccc2F)N(C(=O)Nc2ccc(Cl)cn2)C1]
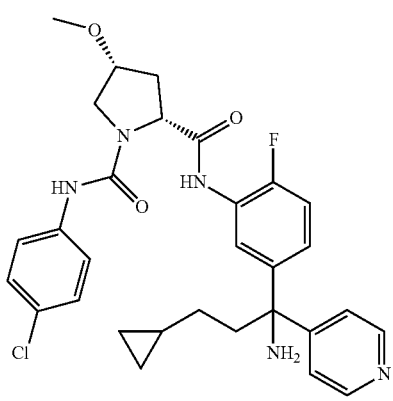 [SMILES: CO[C@@H]1C[C@H](C(=O)Nc2cc(C(N)(CCC3CC3)c3ccncc3)ccc2F)N(C(=O)Nc2ccc(Cl)cc2)C1]
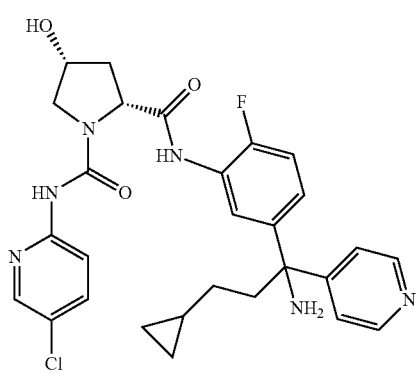
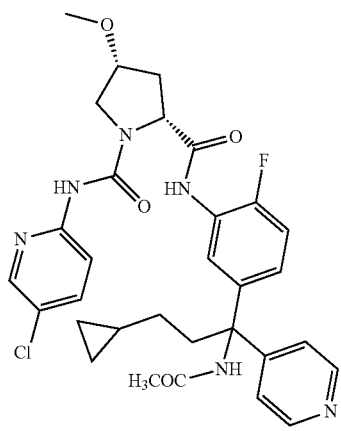
294
-continued
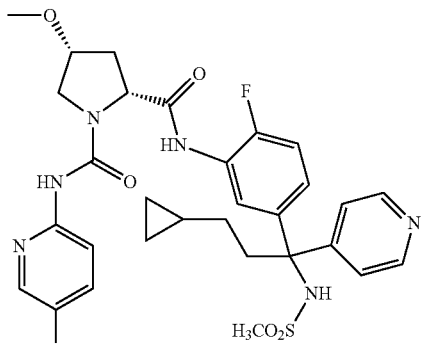
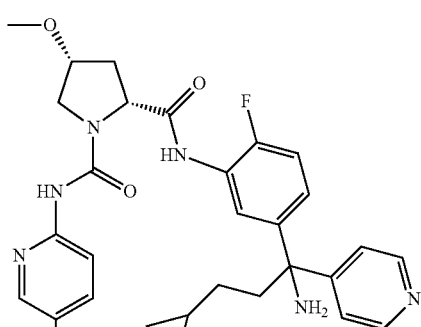
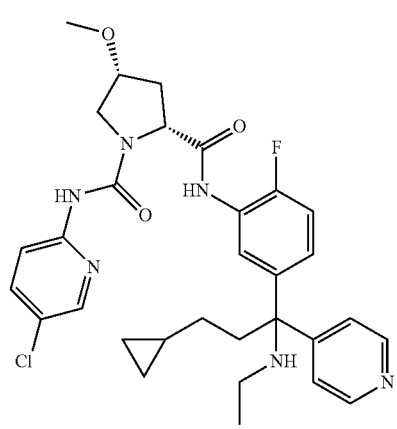 [SMILES: CCNC(CCC1CC1)(c1ccncc1)c1ccc(F)c(NC(=O)[C@H]2C[C@@H](OC)CN2C(=O)Nc2ccc(Cl)cn2)c1]
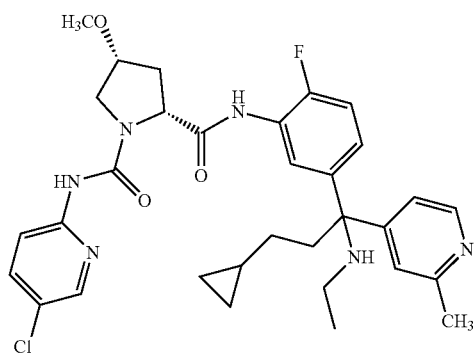 [SMILES: CCNC(CCC1CC1)(c1ccnc(C)c1)c1ccc(F)c(NC(=O)[C@H]2C[C@@H](OC)CN2C(=O)Nc2ccc(Cl)cn2)c1]

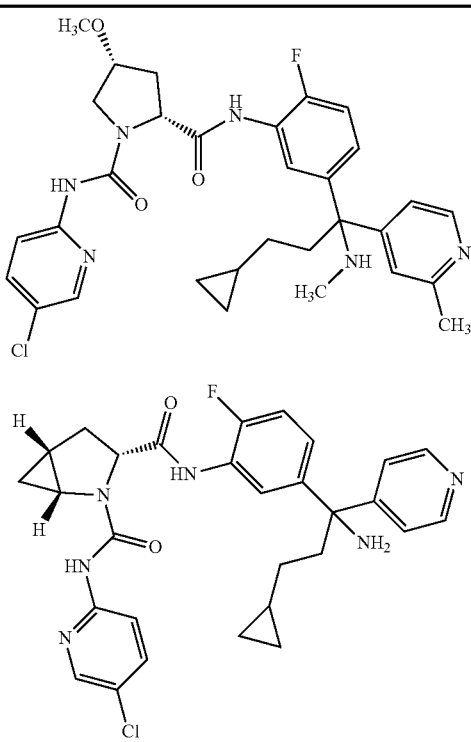

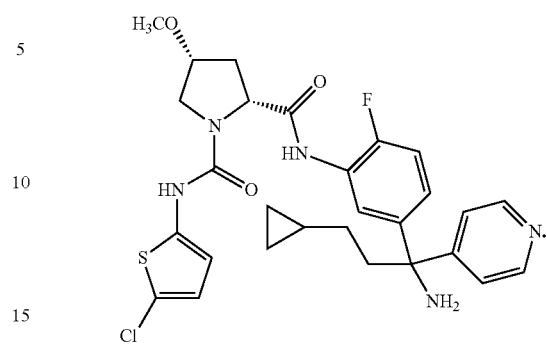

20. A pharmaceutical composition, comprising a compound of claim 1, or a pharmaceutically acceptable salt thereof; and a pharmaceutically acceptable carrier.

21. A pharmaceutical composition, comprising a compound of claim 19, or a pharmaceutically acceptable salt thereof; and a pharmaceutically acceptable carrier.

22. The compound of claim 8 wherein R2 represents (halo)aryl or (halo)heteroaryl.

23. The compound of claim 11 wherein Z represents one instance of fluoro.

* * * * *

UNITED STATES PATENT AND TRADEMARK OFFICE
CERTIFICATE OF CORRECTION

PATENT NO. : 10,562,850 B2
APPLICATION NO. : 15/764071
DATED : February 18, 2020
INVENTOR(S) : Pravin L. Kotian et al.

Page 1 of 1

It is certified that error appears in the above-identified patent and that said Letters Patent is hereby corrected as shown below:

In the Claims

In Claim 1, at Column 267, after Line number 2 insert:
-- V represents optionally substituted aryl or heteroaryl; --.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*